United States Patent
Ihn et al.

(10) Patent No.: US 11,569,452 B2
(45) Date of Patent: *Jan. 31, 2023

(54) ORGANIC LIGHT-EMITTING DEVICE

(71) Applicant: Samsung Electronics Co., Ltd., Suwon-si (KR)

(72) Inventors: Sooghang Ihn, Hwaseong-si (KR); Daun Jeong, Anyang-si (KR); Myungsun Sim, Suwon-si (KR); Hasup Lee, Seoul (KR); Eunsuk Kwon, Suwon-si (KR); Sangmo Kim, Hwaseong-si (KR); Minsik Min, Suwon-si (KR); Sangho Park, Anyang-si (KR); Soonok Jeon, Suwon-si (KR); Yeonsook Chung, Seoul (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 627 days.

This patent is subject to a terminal disclaimer.

(21) Appl. No.: 16/564,265

(22) Filed: Sep. 9, 2019

(65) Prior Publication Data

US 2020/0091439 A1 Mar. 19, 2020

(30) Foreign Application Priority Data

Sep. 19, 2018 (KR) .................. 10-2018-0112382

(51) Int. Cl.
*H01L 51/00* (2006.01)
*C07D 209/88* (2006.01)
*C09K 11/06* (2006.01)
*H01L 51/50* (2006.01)

(52) U.S. Cl.
CPC ........ *H01L 51/0072* (2013.01); *C07D 209/88* (2013.01); *C09K 11/06* (2013.01); *C09K 2211/1018* (2013.01); *H01L 51/5016* (2013.01); *H01L 2251/5384* (2013.01)

(58) Field of Classification Search
CPC ............. H01L 2251/5384; H01L 51/52; H01L 51/5024; H01L 51/5016; H01L 51/5012; H01L 51/0072; H01L 51/0067; H01L 51/0058; H01L 51/0052; C09K 2211/1018; C09K 11/06; C07D 209/88
USPC ........................................................ 428/690
See application file for complete search history.

(56) References Cited

U.S. PATENT DOCUMENTS

| 10,833,276 B2 * | 11/2020 | Zeng | H01L 51/0067 |
| 10,957,863 B2 * | 3/2021 | Lee | H01L 51/0072 |
| 2017/0141323 A1 | 5/2017 | Miyazaki | |
| 2017/0358755 A1 | 12/2017 | Jung et al. | |
| 2017/0365796 A1 | 12/2017 | Kim et al. | |
| 2017/0369439 A1 | 12/2017 | Jung et al. | |
| 2018/0145262 A1 * | 5/2018 | Zeng | H01L 51/0072 |
| 2019/0157570 A1 * | 5/2019 | Sim | C09K 11/06 |
| 2020/0002315 A1 | 1/2020 | Chung et al. | |
| 2020/0028094 A1 * | 1/2020 | Sim | H01L 51/0054 |
| 2020/0194681 A1 * | 6/2020 | Miyazaki | H01L 51/0072 |

FOREIGN PATENT DOCUMENTS

| CN | 106749243 A | 5/2017 |
| EP | 3369728 A1 | 9/2018 |
| KR | 1020170056951 A | 5/2017 |
| WO | 2017101675 A1 | 6/2017 |

OTHER PUBLICATIONS

CAS reg. No. 2170586-97-5, Jan. 18, 2018. (Year: 2018).*
CAS reg. No. 2226739-10-0, Jun. 11, 2018. (Year: 2018).*
E. L i p p e r t, "Conversion of electron excitation energy", Angew. Chem. 173. Jahrg. 1961 Nr. 21, 695-706.
Christine L. Kalcic, et al., "Controlling the Excited State Charge Transfer in DMABN Using Shaped Femtosecond Pulses", 2007 Optical Society of America, OCIS codes: (300.2530) Fluorescence, laser-induced; (320.5540) Pulse Shaping, 2 pp.
Huaning Zhu, et al., "Ultrafast Investigation of Intramolecular Charge Transfer and Solvation Dynamics of Tetrahydro [5]-helicene-Based Imide Derivatives", Scientific Reports | 6:24313 | DOI: 10.1038/srep24313, Published Apr. 14, 2016, pp. 1-12.
José M. López-de-Luzuriaga, "The effect of gold(I) coordination on the dual fluorescence of 4-(dimethylamino) pyridine". The Royal Society of Chemistry 2015, DOI: 10.1039/c5dt00584a, 11 pp.
Shunsuke Sasaki, et al., "Recent advances in twisted intramolecular charge transfer (TICT) fluorescence and related phenomena in materials chemistry", J. Mater. Chem. C, 2016, 4, 2731-2743.
Yong Joo Cho, et al. "Donor Interlocked Molecular Design for Fluorescence-like NarrowEmission in Deep Blue Thermally Activated Delayed FluorescentEmitters", DOI: 10.1021/acs.chemmater. 6b01484, Chem. Mater. 2016, 28, 5400-5405.
Yujie Dong, "Supramolecular interactions induced fluorescent organic nanowires with high quantum yield based on 9,10-distyrylanthracene", CrystEngComm, 2012, 14, 6593-6598.

* cited by examiner

*Primary Examiner* — Douglas J McGinty
(74) *Attorney, Agent, or Firm* — Cantor Colburn LLP

(57) ABSTRACT

An organic light-emitting device including a predetermined host and a thermally activated delayed fluorescence emitter.

19 Claims, 1 Drawing Sheet

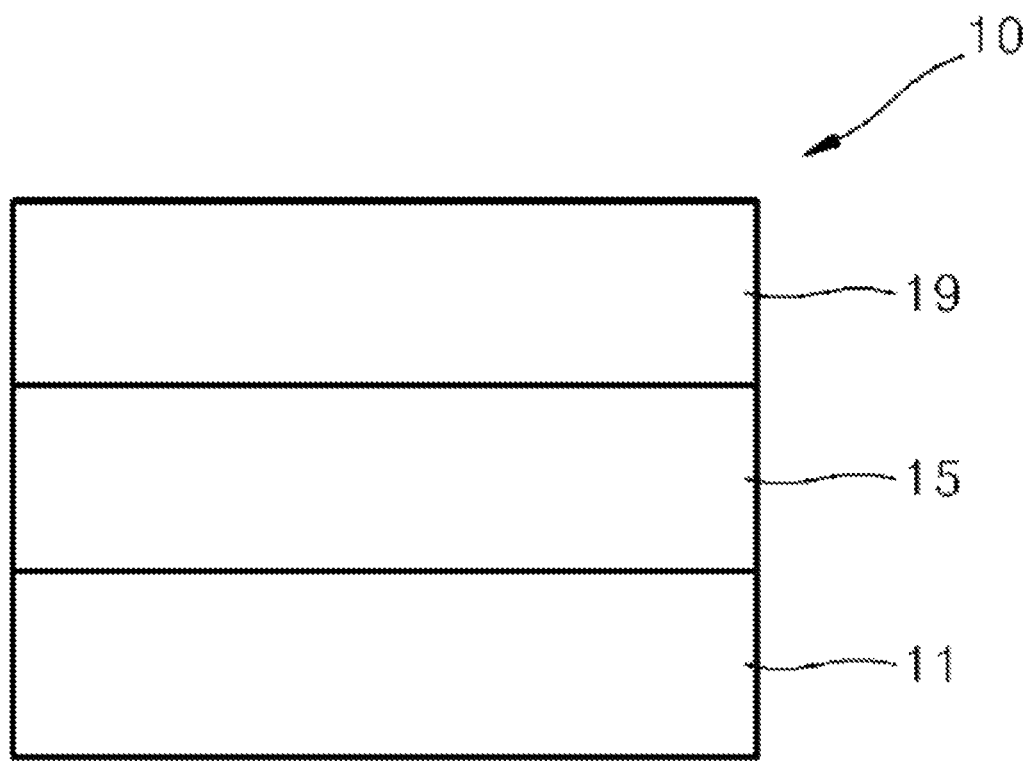

ORGANIC LIGHT-EMITTING DEVICE

CROSS-REFERENCE TO RELATED APPLICATION

This application claims priority to and the benefit of Korean Patent Application No. 10-2018-0112382, filed on Sep. 19, 2018, in the Korean Intellectual Property Office, and all of the benefits accruing therefrom under 35 U.S.C. § 119, the disclosure of which is incorporated herein in its entirety by reference.

BACKGROUND

1. Field

One or more embodiments relate to an organic light-emitting device.

2. Description of the Related Art

Organic light-emitting devices are self-emission devices that produce full-color images, and also have wide viewing angles, high contrast ratios, short response times, and excellent characteristics in terms of brightness, driving voltage, and response speed, compared to devices in the art.

In an example, an organic light-emitting device includes an anode, a cathode, and an organic layer that is disposed between the anode and the cathode and includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in an emission layer region to produce excitons. These excitons transit from an excited state to a ground state, thereby generating light.

SUMMARY

Provided is an organic light-emitting device having a high efficiency and a long lifespan.

Additional aspects will be set forth in part in the description which follows and, in part, will be apparent from the description, or may be learned by practice of the presented embodiments.

According to an aspect of an embodiment, an organic light-emitting device includes:

a first electrode;

a second electrode facing the first electrode; and an emission layer disposed between the first electrode and the second electrode, wherein the emission layer includes a host and a thermally activated delayed fluorescence emitter, and the host includes a compound represented by Formula 1, a compound represented by Formula 2, or a combination thereof:

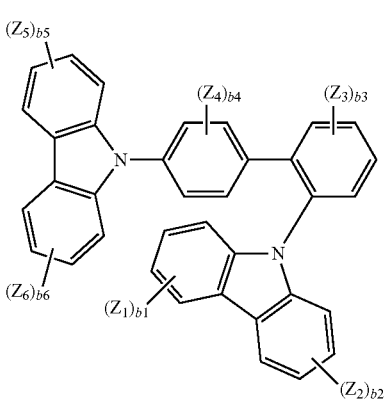

Formula 1

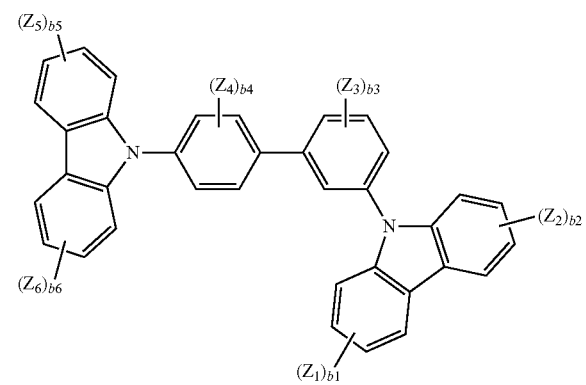

Formula 2

In Formulae 1 and 2, $Z_1$ to $Z_6$ may each independently be:

hydrogen, deuterium, —F, —Cl, —Br, —I, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof, b1 to b6 may each independently be 1, 2, 3, or 4, and in Formulae 1 and 2, at least one of, i) $Z_1$ in the number of b1, ii) $Z_2$ in the number of b2, iii) $Z_3$ in the number of b3, iv) $Z_4$ in the number of b4, v) $Z_5$ in the number of b5, and vi) $R_6$ in the number of b6 may be a cyano group.

BRIEF DESCRIPTION OF THE DRAWINGS

These and/or other aspects will become apparent and more readily appreciated from the following description of the embodiments, taken in conjunction with FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an embodiment, an organic light-emitting device includes a first electrode, a second electrode facing the first electrode, and an emission layer located between the first electrode and the second electrode, wherein the emission layer includes a host and a thermally activated delayed fluorescence emitter.

In one embodiment, the host may include a compound represented by Formula 1, a compound represented by Formula 2, or a combination thereof:

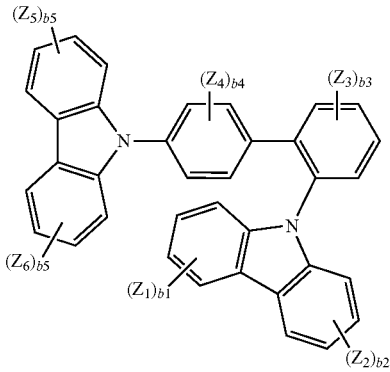

Formula 1

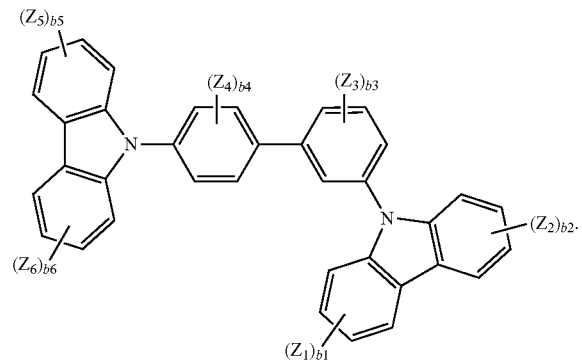

Formula 2

In Formulae 1 and 2, $Z_1$ to $Z_6$ may each independently be:

hydrogen, deuterium, —F, —Cl, —Br, —I, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof.

In an exemplary embodiment, $Z_1$ to $Z_6$ may each independently be:

hydrogen, deuterium, or a cyano group; or a $C_1$-$C_{10}$ alkyl group, a phenyl group, a biphenyl group, a terphenyl group, a dibenzofuranyl group, or a dibenzothiophenyl group, each unsubstituted or substituted with deuterium, a cyano group, a $C_1$-$C_{10}$ alkyl group, a phenyl group, a biphenyl group, or any combination thereof.

In one embodiment, $Z_1$ to $Z_6$ may each independently be:

hydrogen, deuterium, or a cyano group; or a $C_3$-$C_{10}$ alkyl group, a phenyl group, a biphenyl group, a terphenyl group, a dibenzofuranyl group, or a dibenzothiophenyl group, each unsubstituted or substituted with deuterium, a cyano group, a $C_3$-$C_{10}$ alkyl group, a phenyl group, a biphenyl group, or any combination thereof.

In one or more embodiments, $Z_1$ to $Z_6$ may each independently be:

hydrogen, deuterium, or a cyano group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, or a terphenyl group, each unsubstituted or substituted with deuterium, a cyano group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, or any combination thereof, but embodiments of the present disclosure are not limited thereto.

In Formula 1, b1 to b6 each indicate the number of $Z_1$ to the number of $Z_6$, respectively, and may each independently be 1, 2, 3, or 4. When b1 to b6 are each independently two or more, two or more of each of $Z_1$ to $Z_6$ may be identical to or different from each other.

In an exemplary embodiment, b1 to b6 may each independently be 0, 1, or 2, but embodiments of the present disclosure are not limited thereto.

In Formulae 1 and 2, at least one of, i) $Z_1$ in the number of b1, ii) $Z_2$ in the number of b2, iii) $Z_3$ in the number of b3, iv) $Z_4$ in the number of b4, v) $Z_5$ in the number of b5, and vi) $R_6$ in the number of b6 may be a cyano group. That is, Formulae 1 and 2 may each independently include at least one cyano group.

In one embodiment, the number of cyano group(s) included in the compound represented by Formula 1 and the number of cyano group(s) included in the compound represented by Formula 2 may each independently be 1, 2, 3, or 4, but embodiments of the present disclosure are not limited thereto.

In one or more embodiments, in Formulae 1 and 2, at least one (for example, 1, 2, 3, or 4) of, i) $Z_1$ in the number of b1 and ii) $Z_2$ in the number of b2 may be a cyano group;

at least one (for example, 1, 2, 3, or 4) of, i) $Z_3$ in the number of b3 and ii) $Z_4$ in the number of b4 may be a cyano group;

at least one (for example, 1, 2, 3, or 4) of, i) $Z_5$ in the number of b5 and ii) $Z_6$ in the number of b6 may be a cyano group;

at least one (for example, 1 or 2) of, i) $Z_1$ in the number of b1 and ii) $Z_2$ in the number of b2 may be a cyano group, and at least one (for example, 1 or 2) of, i) $Z_3$ in the number of b3 and ii) $Z_4$ in the number of b4 may be a cyano group;

at least one (for example, 1 or 2) of, i) $Z_1$ in the number of b1 and ii) $Z_2$ in the number of b2 may be a cyano group, and at least one (for example, 1 or 2) of, i) $Z_5$ in the number of b5 and ii) $Z_6$ in the number of b6, may be a cyano group;

at least one (for example, 1 or 2) of, i) $Z_3$ in the number of b3 and ii) $Z_4$ in the number of b4 may be a cyano group, and at least one (for example, 1 or 2) of, i) $Z_5$ in the number of b5 and ii) $Z_6$ in the number of b6 may be a cyano group; or at least one (for example, 1 or 2) of i) $Z_1$ in the number of b1 and ii) $Z_2$ in the number of b2 may be a cyano group, at least one (for example, 1 or 2) of, i) $Z_3$ in the number of b3 and ii) $Z_4$ in the number of b4 may be a cyano group, and at least one (for example, 1 or 2) of, i) $Z_5$ in the number of b5 and ii) $Z_6$ in the number of b6 may be a cyano group.

In one embodiment, a group represented by

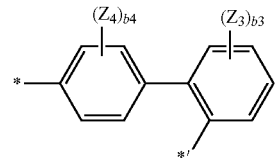

in Formula 1 may be a group represented by one of Formulae PO1 to PO25, and/or a group represented by

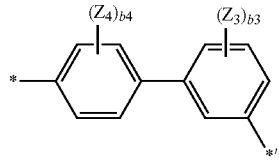

in Formula 2 may be a group represented by one of Formulae PM1 to PM25:

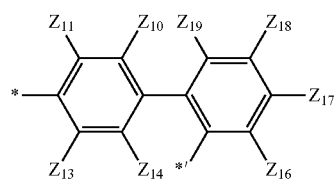

PO1

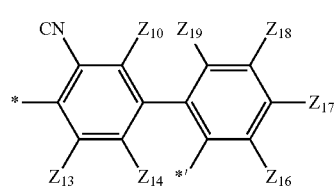

PO2

PO3
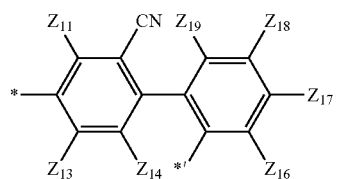
PO4
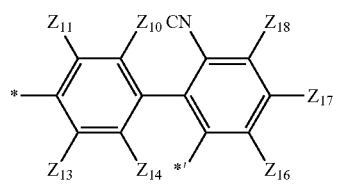
PO5
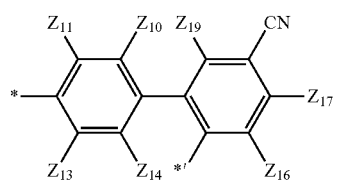
PO6
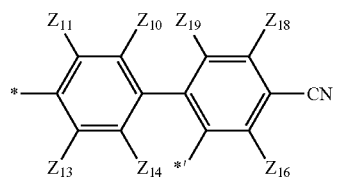
PO7
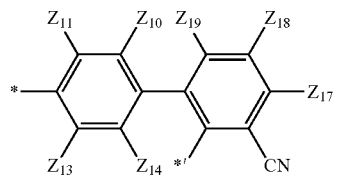
PO8
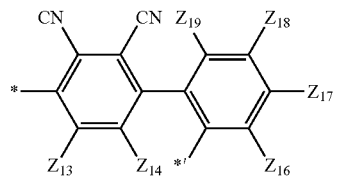
PO9
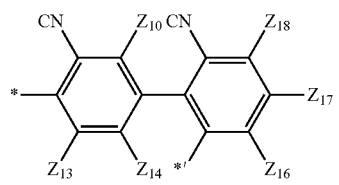
PO10
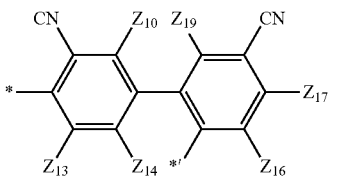
PO11
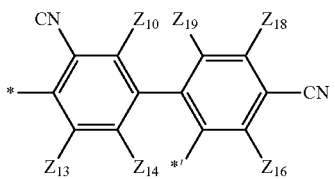
PO12
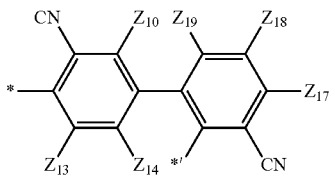
PO13
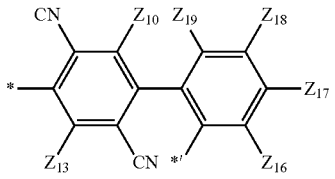
PO14
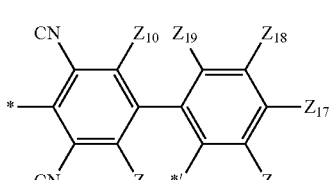
PO15
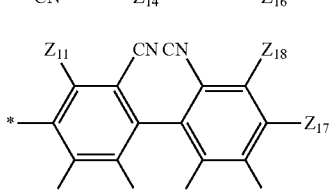
PO16
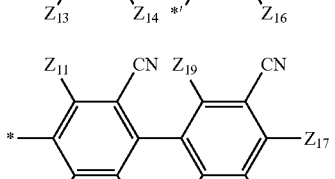
PO17
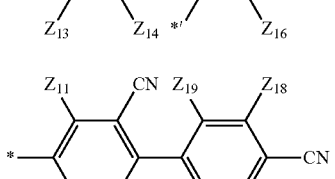
PO18
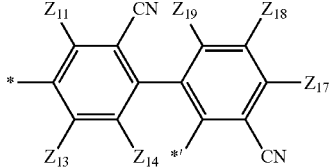

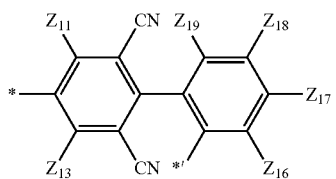 PO19
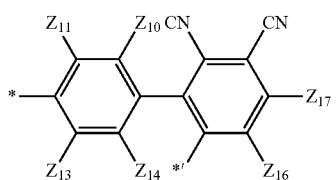 PO20
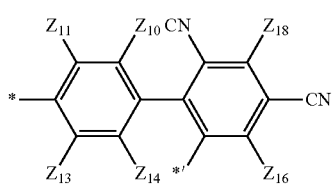 PO21
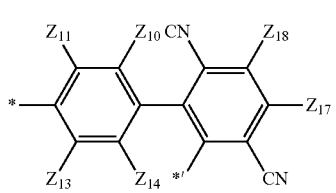 PO22
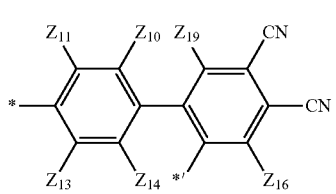 PO23
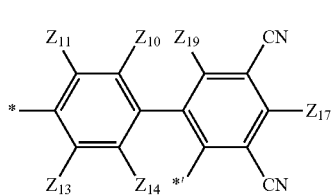 PO24
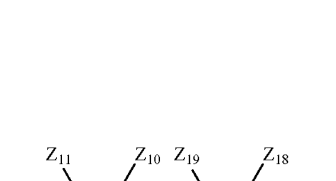 PO25
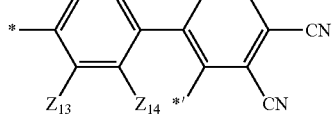 PM1
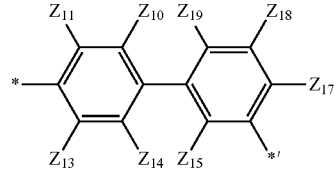
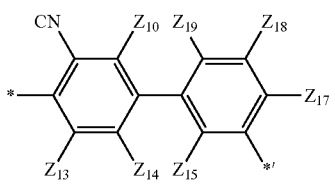 PM2
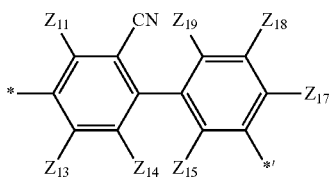 PM3
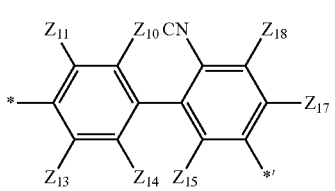 PM4
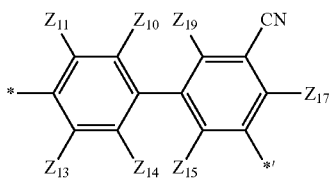 PM5
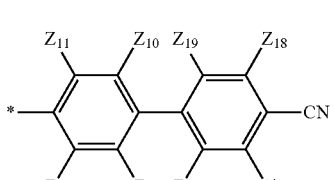 PM6
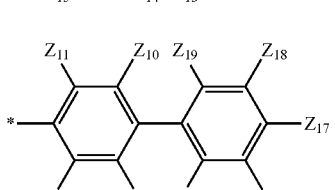 PM7
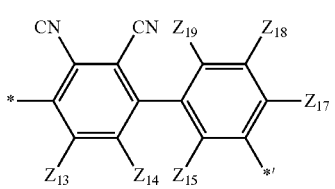 PM8
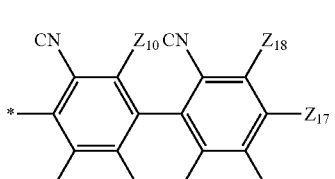 PM9

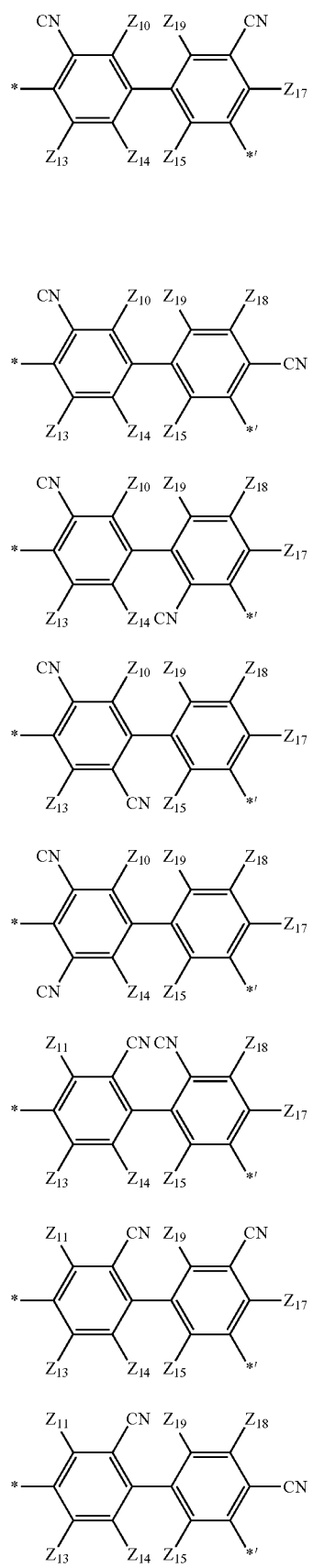
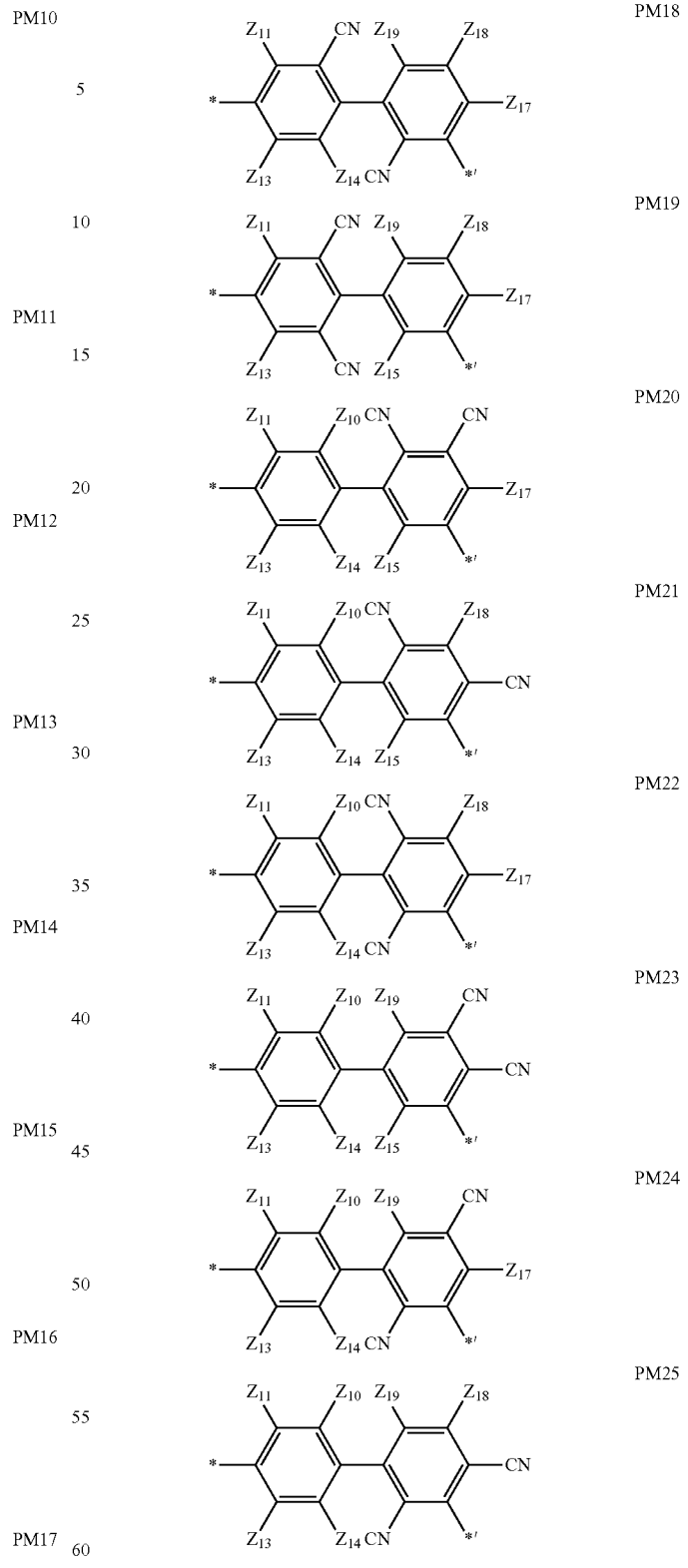
In Formulae PO1 to PO25 and PM1 to PM25, $Z_{10}$ to $Z_{19}$ are each defined the same as $Z_3$ and $Z_4$, and * and *' each indicate a binding site to a neighboring nitrogen atom.
In one embodiment, in Formulae PO1 to PO25 and PM1 to PM25, $Z_{10}$ to $Z_{19}$ may not be a cyano group.

In one or more embodiments, in Formulae PO1 to PO25 and PM1 to PM25, $Z_{10}$ to $Z_{19}$ may each independently be:

hydrogen, deuterium, —F, —Cl, —Br, —I, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof.

In one or more embodiments, in Formulae PO1 to PO25 and PM1 to PM25, $Z_{10}$ to $Z_{19}$ may each independently be:

hydrogen, deuterium, or a cyano group; or an-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, or a terphenyl group, each unsubstituted or substituted with deuterium, a cyano group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, or any combination thereof.

In one or more embodiments, a group represented by

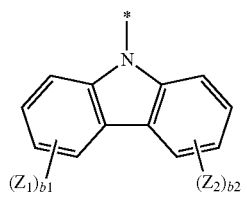

in Formulae 1 and 2 may be a group represented by one of Formulae A1-1 to A1-3, and/or a group represented by

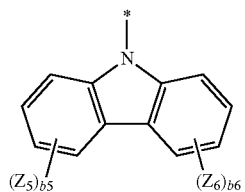

in Formulae 1 and 2 may be a group represented by one of Formulae A2-1 to A2-3:

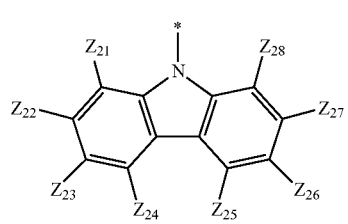

A1-1

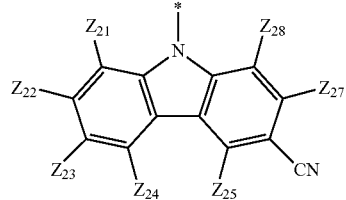

A1-2

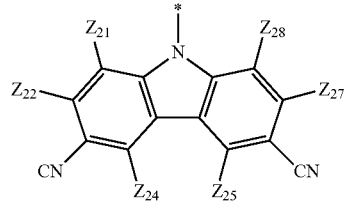

A1-3

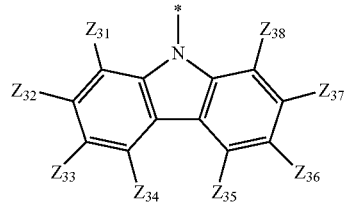

A2-1

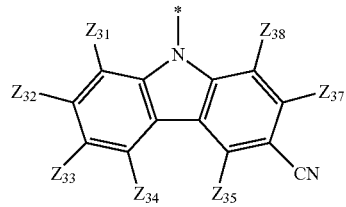

A2-2

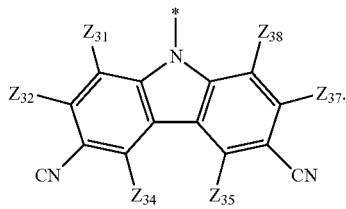

A2-3

In Formulae A1-1 to A1-3 and A2-1 to A2-3, $Z_{21}$ to $Z_{28}$ and $Z_{31}$ to $Z_{38}$ may each independently be:

hydrogen, deuterium, —F, —Cl, —Br, —I, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof, and

* and *' each indicate a binding site to a neighboring carbon atom.

In an exemplary embodiment, in Formulae A1-1 to A1-3 and A2-1 to A2-3, $Z_{21}$ to $Z_{28}$ and $Z_{31}$ to $Z_{38}$ may not a cyano group.

In one or more embodiments, the host may include at least one of Compounds EH1 to EH15:

EH1 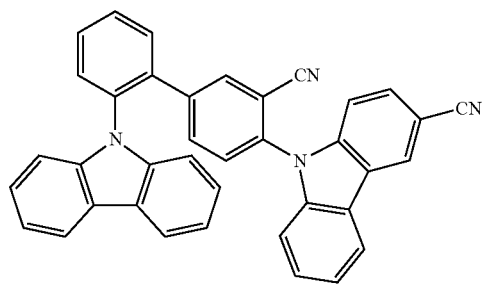
EH6 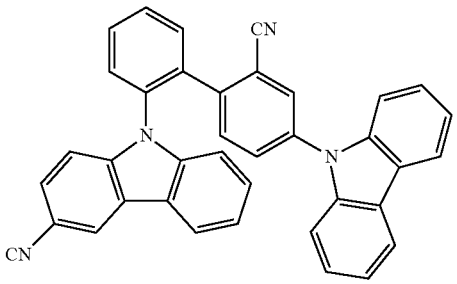
EH2 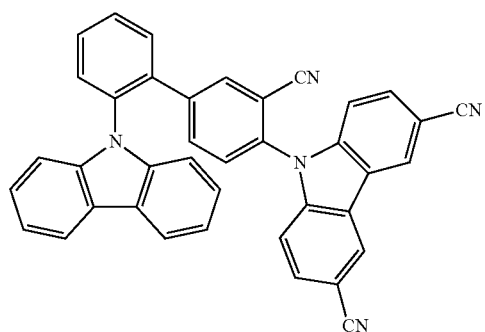
EH7 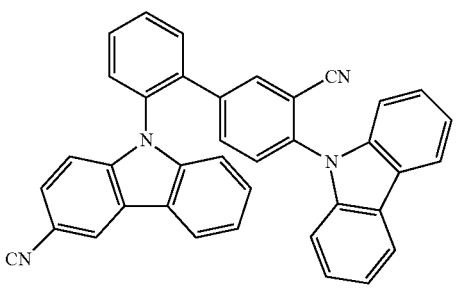
EH3 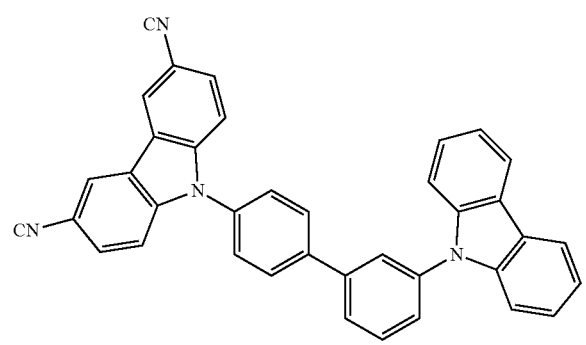
EH8 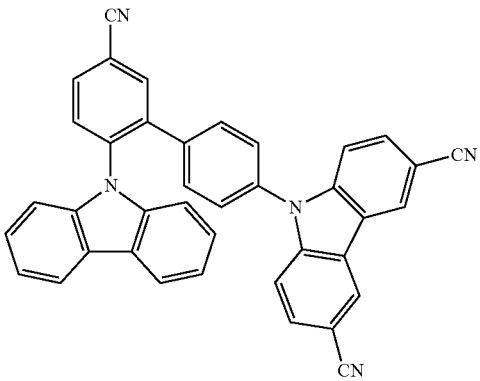
EH4 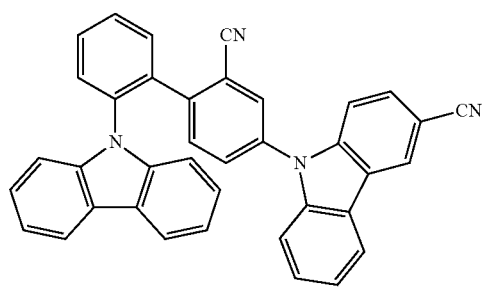
EH9 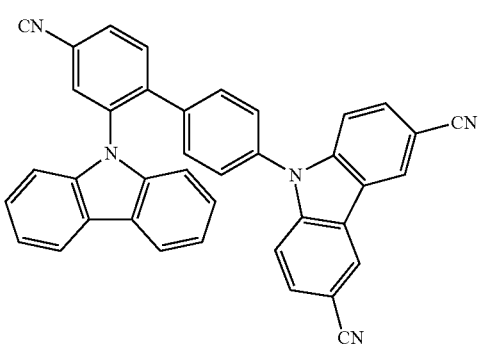
EH5 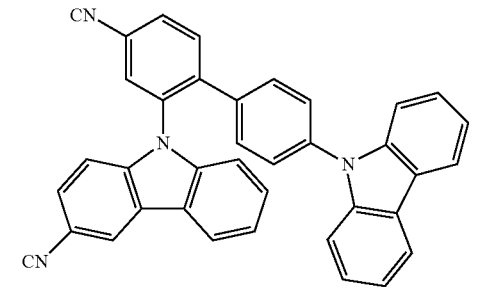

EH10

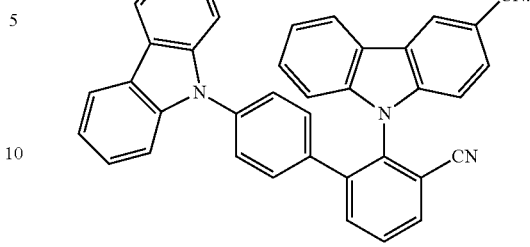

EH11

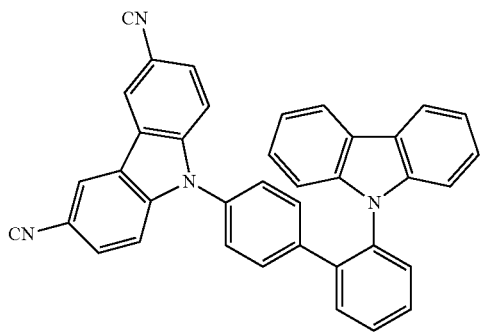

EH12

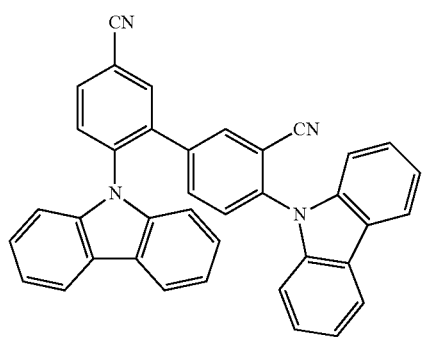

EH13

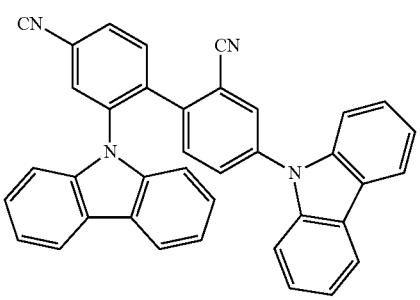

EH14

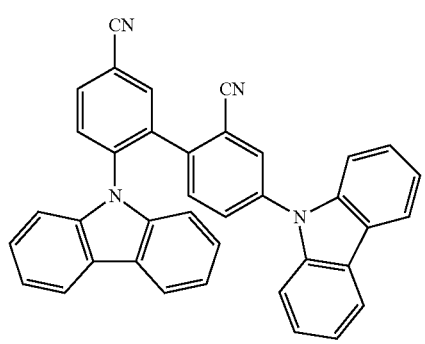

EH15

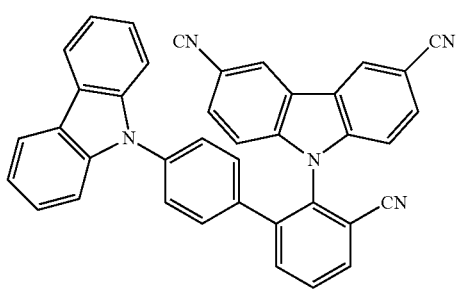

Two carbazole rings included in each of Formulae 1 and 2 may be linked to each other via a biphenylene linking group. Here, one of the two carbazole rings is linked to a carbon atom at a "para" position with respect to carbon atoms to which two benzene rings of the biphenylene linking group are linked, whereas the other one of the two carbazole rings is linked to a carbon atom at an "ortho" position (see Formula 1) or a "meta" position (See Formula 2), with respect to carbon atoms to which two benzene rings of the biphenylene linking group are linked. In this regard, Formulae 1 and 2 may each have an asymmetric structure in which two carbazole rings are linked to each other via the biphenylene linking group, and accordingly, Formulae 1 and 2 may each have a high dipole moment. Thus, an electronic device, for example, an organic light-emitting device, including the compound represented by Formula 1, the compound represented by Formula 2, or a combination thereof, may have excellent luminescence efficiency.

In an exemplary embodiment, the dipole moment of each of the compound represented by Formula 1 and the compound represented by Formula 2 may be about 6.4 debye or more, and for example, may be in a range of about 7.0 debye to about 15.0 debye (for example, in a range of about 9.0 debye to about 13.0 debye), but embodiments of the present disclosure are not limited thereto.

To evaluate the dipole moment, the electrostatic potential fitting (ESP) charge of each atom of the relevant compounds and the distance between atoms are obtained by using a Density Functional Theory (DFT) method of a Jaguar program (that is structurally optimized at a level of B3LYP, 6-31G(d,p), and then, the dipole moment of the relevant compounds may be calculated therefrom.

The compound represented by Formula 1 and the compound represented by 2 may each have a high dipole moment as described above, and at the same time, may not include a group represented by *=o (where * indicates a binding site to a neighboring atom) (for example, a phosphine oxide-containing compound may include a group represented by *=o). In this regard, the compound represented by Formula 1 and the compound represented by 2 may stabilize the charge transfer excited state of the thermally activated delayed fluorescence emitter, thereby significantly increasing a delayed fluorescence component in the emission layer. Therefore, use of the emission layer including the host and the thermally activated delayed fluorescence emitter, wherein the host includes the compound represented by Formula 1, the compound represented by 2, or a combination thereof may achieve a high luminescence efficiency. Also, when storing and/or driving an organic light-emitting device, a material for the emission layer may be substantially prevented from being decomposed by the group represented by *=o, thereby realizing an organic light-emitting device having a high luminescence efficiency and a long lifespan "at the same time".

In addition, the compound represented by Formula 1 and the compound represented by 2 may each include at least one cyano group, and accordingly, may each have excellent electron transport characteristics and relatively high triplet energy levels.

A difference between a triplet energy level of the host and a triplet energy level of the thermally activated delayed fluorescence emitter may be greater than or equal to about 0.2 electron volts (eV) to less than or equal to about 0.5 eV. When the difference of the triplet energy levels between the host and the thermally activated delayed fluorescence emitter is within the range above, the energy of triplet excitons generated in the thermally activated delayed fluorescence emitter may be prevented from leaking to the host in the emission layer, thereby realizing efficient light emission. In addition, due to a suppressed activation exciton energy level of the host, the long lifespan of the organic light-emitting device may be realized.

The triplet energy level may be evaluated by using a DFT method of a Gaussian program that is structurally optimized at a level of B3LYP/6-31G(d,p).

The thermally activated delayed fluorescence emitter may be a compound capable of emitting delayed fluorescence according to an emission mechanism of the thermally activated delayed fluorescence emitter.

In one embodiment, a difference between a triplet energy level of the thermally activated delayed fluorescence emitter and a singlet energy level of the thermally activated delayed fluorescence emitter may be greater than or equal to about 0 eV to less than or equal to about 0.5 eV. When the difference between the triplet energy level of the thermally activated delayed fluorescence emitter and the singlet energy level of the thermally activated delayed fluorescence emitter is within the range above, the up-conversion from the triplet state to the singlet state may be efficiently performed, so that the thermally activated delayed fluorescence emitter may be able to emit delayed fluorescence with a high efficiency.

The triplet energy level and the singlet energy level may each be evaluated by using a DFT method of a Gaussian program that is structurally optimized at a level of B3LYP/6-31G (d,p).

In one embodiment, the thermally activated delayed fluorescence emitter may include a compound represented by Formula 11:

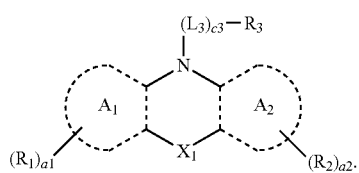

Formula 11

In Formula 11, $X_1$ may be a single bond, $N-[(L_4)_{c4}-R_4]$, $C(R_5)(R_6)$, O, or S.

In an exemplary embodiment, $X_1$ may be a single bond, but embodiments of the present disclosure are not limited thereto.

In Formula 11, $A_1$ and $A_2$ may each independently be a benzene group, a naphthalene group, an indene group, an indole group, a benzofuran group, a benzothiophene group, a benzosilole group, a fluorene group, a carbazole group, a dibenzofuran group, a dibenzothiophene group, a dibenzosilole group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, or a benzothienodibenzothiophene group.

In an exemplary embodiment, $A_1$ and $A_2$ may each independently be a benzene group, a fluorene group, a carbazole group, a dibenzofuran group, a dibenzothiophene group, or a dibenzosilole group, and $A_1$, $A_2$, or a combination thereof may each independently be a benzene group. However, embodiments of the present disclosure are not limited thereto.

$L_3$ and $L_4$ may each independently be a substituted or unsubstituted cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group.

In an exemplary embodiment, $L_3$ and $L_4$ may each independently be:

a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, a dibenzothiophenylene group, or an indolocarbazolylene group; or a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, a dibenzothiophenylene group, or an indolocarbazolylene group, each substituted with deuterium, a $C_1$-$C_{10}$ alkyl group, a alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, $-Si(Q_{31})(Q_{32})(Q_{33})$, $-N(Q_{34})(Q_{35})$, or any combination thereof, and $Q_{31}$ to $Q_{35}$ may each independently be a $C_1$-$C_{10}$ alkyl group, a $C_1$-$C_{10}$ alkoxy group, a phenyl group, a biphenyl group, a terphenyl group, or a naphthyl group. However, embodiments of the present disclosure are not limited thereto.

In one embodiment, at least one of $L_3$(s) in the number of c3 in Formula 11 may be a group represented Formulae L-1 or L-2, but embodiments of the present disclosure are not limited thereto:

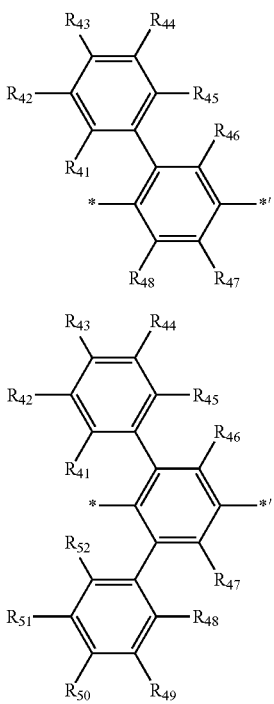

L-1

L-2

In Formulae L-1 and L-2, $R_{41}$ to $R_{52}$ may each independently be hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, —Si($Q_{31}$)($Q_{32}$)($Q_{33}$), or —N($Q_{34}$)($Q_{35}$), $Q_{31}$ to $Q_{35}$ are each independently the same as described herein, * indicates a binding site to a neighboring atom, and *' indicates a binding site to $L_3$ or $R_3$.

In one embodiment, c3 and c4 each indicate the number of $L_3$ and the number of $L_4$, respectively, and may each independently be an integer from 0 to 4. When c3 is two or more, two or more $L_3$ may be identical to or different from each other, and when c4 is two or more, two or more $L_4$ may be identical to or different from each other. In an exemplary embodiment, c3 and c4 may each independently be 0, 1, or 2, but embodiments of the present disclosure are not limited thereto.

In Formula 11, $R_1$ to $R_5$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), and $Q_1$ to $Q_7$ are each independently the same as described herein.

In one embodiment, $R_3$ in Formula 11 may include at least one π electron-depleted nitrogen-containing cyclic group.

In the present specification, the term "π electron-depleted nitrogen-containing cyclic group" as used herein indicates a group including a cyclic group having at least one of *—N=*' moiety. In an exemplary embodiment, the π electron-depleted nitrogen-containing cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, or an azadibenzosilole group.

In one or more embodiments, $R_3$ in Formula 11 may be:
a phenyl group, an indenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, an isoindolyl group, an indolyl group, a furanyl group, a thiophenyl group, a silolyl group, a benzofuranyl group, a benzothiophenyl group, a benzosilolyl group, a carbazolyl group, a dibenzofuranyl group, a dibenzothiophenyl group, a dibenzosilolyl group, an indeno carbazolyl group, an indolocarbazolyl group, a benzofuracarbazolyl group, a benzothienocarbazolyl group, a benzosilolocarbazolyl group, an imidazolyl group, a pyrazolyl group, a thiazolyl group, an isothiazolyl group, an oxazolyl group, an isoxazolyl group, a pyridinyl group, a pyrazinyl group, a pyridazinyl group, a pyrimidinyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, an azaindenyl group, an azaindolyl group, an azabenzofuranyl group, an azabenzothiophenyl group, an azabenzosilolyl group, an azafluorenyl group, an azacarbazolyl group, an azadibenzofuranyl group, an azadibenzothiophenyl group, or an azadibenzosilolyl group, each unsubstituted or substituted with deuterium, a $C_1$-$C_{10}$ alkyl group, a $C_1$-$C_{10}$ alkoxy group, a phenyl group, a ($C_1$-$C_{10}$ alkyl)phenyl group, a di($C_1$-$C_{10}$ alkyl)phenyl group, a biphenyl group, a terphenyl group, a di(phenyl)phenyl group, a di(biphenyl)phenyl group, a (pyridinyl)phenyl group, a di(pyridinyl)phenyl group, a (pyrimidinyl)phenyl group, a di(pyrimidinyl)phenyl group, a (triazinyl)phenyl group, a di(triazinyl)phenyl group, a pyridinyl group, a ($C_1$-$C_{10}$ alkyl)pyridinyl group, a di($C_1$-$C_{10}$ alkyl)pyridinyl group, a (phenyl)pyridinyl group, a di(phenyl)pyridinyl group, a (biphenyl)pyridinyl group, a di(biphenyl)pyridinyl group, a (terphenyl)pyridinyl group, a bi(terphenyl)pyridinyl group, a (pyridinyl)pyridinyl group, a di(pyridinyl)pyridinyl group, a (pyrimidinyl)pyridinyl group, a di(pyrimidinyl)pyridinyl group, a (triazinyl)pyridinyl group, a di(triazinyl)pyridinyl group, a pyrimidinyl group, a ($C_1$-$C_{10}$ alkyl)pyrimidinyl group, a di($C_1$-$C_{10}$ alkyl) pyrimidinyl group, a (phenyl)pyrimidinyl group, a di(phenyl)pyrimidinyl group, a (biphenyl)pyrimidinyl group, a di(biphenyl)pyrimidinyl group, a (terphenyl)pyrimidinyl group, a bi(terphenyl)pyrimidinyl group, a (pyridinyl)pyrimidinyl group, a di(pyridinyl)pyrimidinyl group, a (pyrimidinyl)pyrimidinyl group, a di(pyrimidinyl)pyrimidinyl group, a (triazinyl)pyrimidinyl group, a di(triazinyl)pyrimidinyl group, a triazinyl group, a ($C_1$-$C_{10}$ alkyl)triazinyl group, a di($C_1$-$C_{10}$ alkyl)triazinyl group, a (phenyl)triazinyl group, a di(phenyl)triazinyl group, a (biphenyl)triazinyl group, a di(biphenyl)triazinyl group, a (terphenyl)triazinyl group, a bi(terphenyl)triazinyl group, a (pyridinyl)triazinyl group, a di(pyridinyl)triazinyl group, a (pyrimidinyl)triazinyl group, a di(pyrimidinyl)triazinyl group, a (triazinyl) triazinyl group, a di(triazinyl)triazinyl group, a fluorenyl group, a di($C_1$-$C_{10}$ alkyl)fluorenyl group, a di(phenyl)fluorenyl group, a di(biphenyl)fluorenyl group, a carbazolyl group, a ($C_1$-$C_{10}$ alkyl)carbazolyl group, a (phenyl)carbazolyl group, a (biphenyl)carbazolyl group, a dibenzofuranyl group, a ($C_1$-$C_{10}$ alkyl)dibenzofuranyl group, a (phenyl) dibenzofuranyl group, a (biphenyl)dibenzofuranyl group, a dibenzothiophenyl group, a ($C_1$-$C_{10}$ alkyl)dibenzothiophenyl group, a (phenyl)dibenzothiophenyl group, a (biphenyl) dibenzothiophenyl group, or any combination thereof, but embodiments of the present disclosure are not limited thereto.

In one or more embodiments, in $R_3$ in Formula 11 may be:

a group represented by Formula 13(1) or a group represented by Formula 13(2);

a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group; or a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group, each substituted with deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, —Si($Q_{31}$)($Q_{32}$)($Q_{33}$), or any combination thereof, and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group:

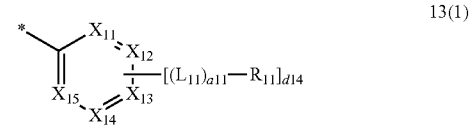

13(1)

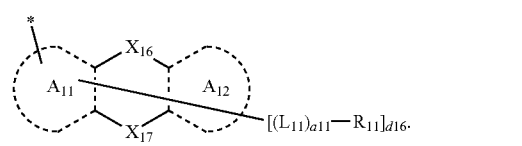

13(2)

In Formula 13(1), $X_{11}$ to $X_{15}$ may each independently be C or N, and at least one of $X_{11}$ to $X_{15}$ may be N.

In an exemplary embodiment, two or three of $X_{11}$ to $X_{15}$ may each independently be N.

In Formula 13(2), $A_{11}$ and $A_{12}$ may each independently be a benzene group, a naphthalene group, a pyridine group, a pyrazine group, a pyrimidine group, a pyridazine group, a quinoline group, an isoquinoline group, a quinoxaline group, or a quinazoline group, and $A_{11}$, $A_{12}$, or a combination thereof may each independently be a pyridine group, a pyrazine group, a pyrimidine group, a pyridazine group, a quinoline group, an isoquinoline group, a quinoxaline group, a quinazoline group, or a combination thereof.

In an exemplary embodiment, $A_{11}$ may be a pyridine group, a pyrimidine group, a quinoline group, an isoquinoline group, a quinoxaline group, or a quinazoline group, and $A_{12}$ may be a benzene group or a naphthalene group, but embodiments of the present disclosure are not limited thereto.

In Formula 13(2), $X_{16}$ may be N-[($L_{12}$)$_{a12}$-$R_{12}$], C($R_{14}$)($R_{15}$), O, or S, and $X_{17}$ may be a single bond, N-[($L_{13}$)$_{a13}$-$R_{13}$], C($R_{16}$)($R_{17}$), O or S.

In an exemplary embodiment, $X_{16}$ may be O or S, and $X_{17}$ may be a single bond, but embodiments of the present disclosure are not limited thereto.

In Formulae 13(1) and 13(2), $L_{11}$ to $L_{13}$ are each independently defined the same as $L_3$, a11 to a13 are each independently defined the same as c3, and $R_{11}$ to $R_{17}$ are each independently defined the same as $R_1$.

In Formula 13(2), d16 may be an integer from 0 to 6. In Formula 13(1), d14 may be an integer from 0 to 4.

In Formulae 13(1) and 13(2), * indicates a binding site to a neighboring atom.

In one embodiment, $R_3$ in Formula 11 may be a group represented by one of Formulae 13-1 to 13-20, but embodiments of the present disclosure are not limited thereto:

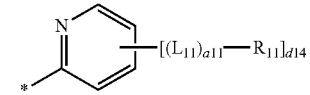

13-1

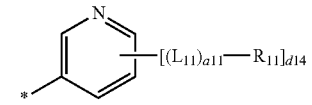

13-2

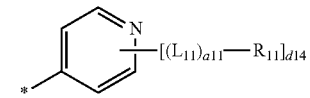

13-3

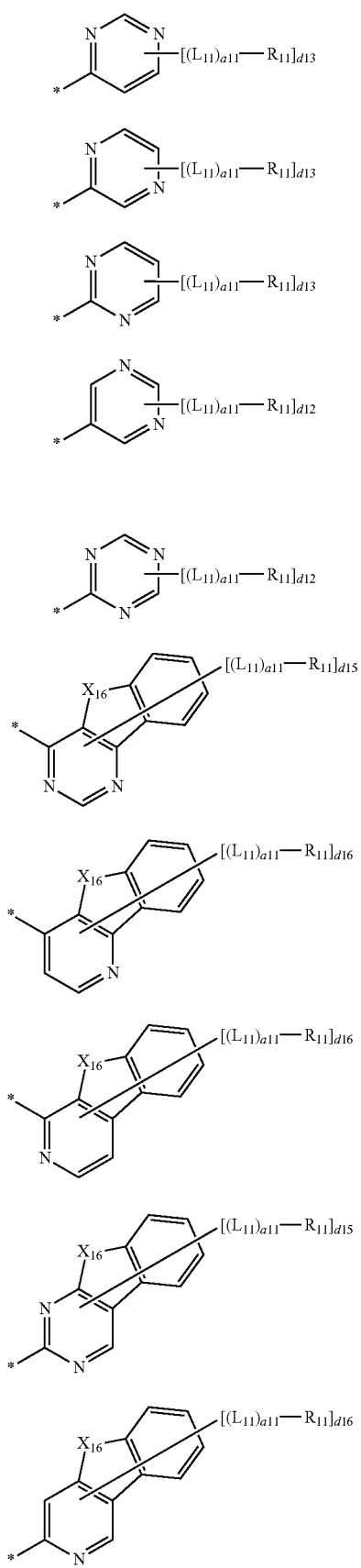
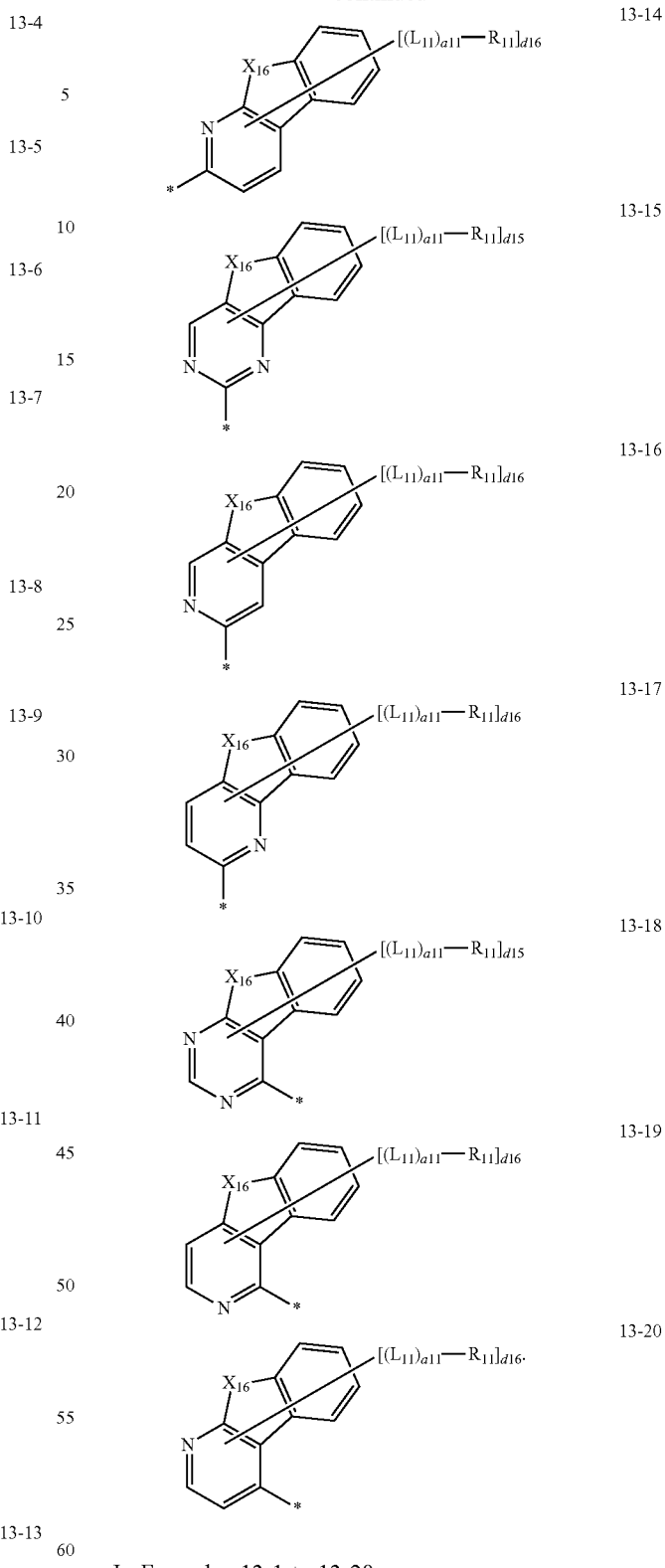
In Formulae 13-1 to 13-20,
X$_{16}$ may be N-[(L$_{12}$)$_{a12}$-R$_{12}$], C(R$_{14}$)(R$_{15}$), O, or S,
L$_{11}$ and L$_{12}$ are each independently defined the same as L$_3$,
a11 and a12 are each independently defined the same as c3, $R_{11}$, $R_{12}$, $R_{14}$, and $R_{15}$ are each independently defined the same as $R_1$, d16 may be an integer from 0 to 6,
d15 may be an integer from 0 to 5,
d14 may be an integer from 0 to 4,
d13 may be an integer from 0 to 3,
d12 may be an integer from 0 to 2, and
* indicates a binding site to a neighboring atom.

In one embodiment, in Formula 11, $R_1$, $R_2$, $R_5$, and $R_6$ may each independently be hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a carbazolyl group, a dibenzofuranyl group, a dibenzothiophenyl group, an indolocarbazolyl group, —Si($Q_1$)($Q_2$)($Q_3$), or —N($Q_4$)($Q_5$), $Q_1$ to $Q_5$ may each independently be a $C_1$-$C_{10}$ alkyl group, a $C_1$-$C_{10}$ alkoxy group, a phenyl group, a biphenyl group, a terphenyl group, or a naphthyl group.

In Formula 11, a1 and a2 each indicate the number of $R_1$ and the number of $R_2$, respectively, and may each independently be an integer from 0 to 10. When a1 is two or more, two or more $R_1$ may be identical to or different from each other, and when a2 is two or more, two or more $R_2$ may be identical to or different from each other.

In one embodiment, the thermally activated delayed fluorescence emitter may include a compound represented by one of Formulae 11-1 to 11-7, but embodiments of the present disclosure are not limited thereto:

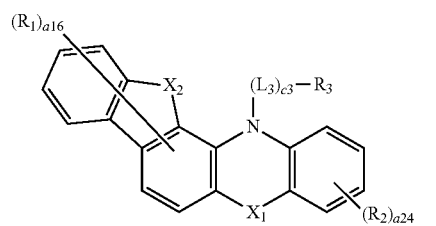

11-1

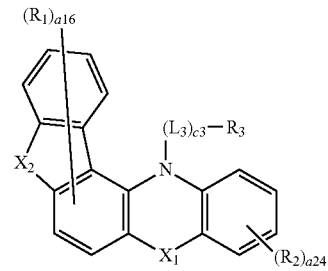

11-2

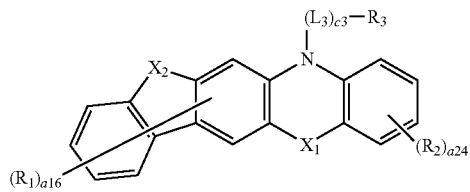

11-3

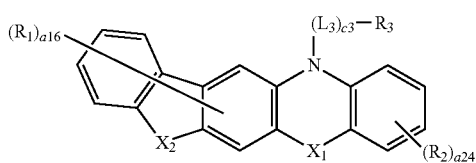

11-4

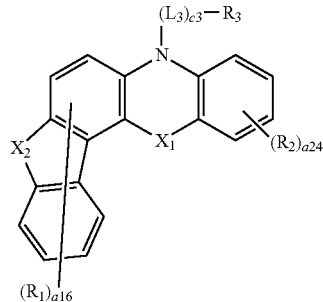

11-5

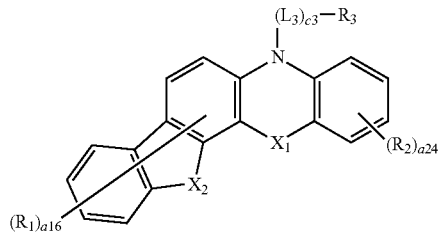

11-6

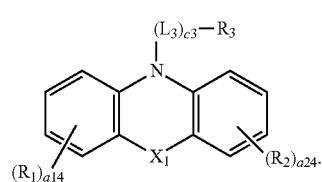

11-7

In Formulae 11-1 to 11-7, $X_1$, $L_3$, c3, and $R_1$ to $R_3$ are each independently the same described herein, $X_2$ may be N-[($L_5$)$_{c5}$-$R_7$], C($R_8$)($R_9$), O, or S, $L_5$ and c5 are each independently defined the same as $L_3$ and c3, respectively, $R_7$ is defined the same as $R_3$, $R_8$ and $R_9$ are each independently defined the same as $R_5$ and $R_6$, respectively, a16 may be an integer from 0 to 6, and a14 and a24 may each independently be an integer from 0 to 4.

In one embodiment, in Formulae 11-1 to 11-17, 1) $R_3$ in the case where $X_2$ is C($R_8$)($R_9$), O, or S, and 2) $R_3$, $R_7$, or a combination thereof, in the case where $X_2$ is N-[($L_5$)$_{c5}$-$R_7$] may each independently include at least one π electron-depleted nitrogen-containing cyclic group described above.

In one or more embodiments, in Formulae 11-1 to 11-17, 1) $R_3$ in the case where $X_2$ is C($R_8$)($R_9$), O, or S, and 2) $R_3$ and $R_7$ in the case where $X_2$ is N-[($L_5$)$_{c5}$-$R_7$] may each independently be:

a group represented by Formula 13(1) or a group represented by Formula 13(2) (for example, one of the groups represented by Formulae 13-1 to 13-20);

a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group; and a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group, each substituted with deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, —Si($Q_{31}$)($Q_{32}$)($Q_{33}$), or any combination thereof, and 1) $R_3$ in the case where $X_2$ is C($R_8$)($R_9$), O, or S, $R_3$ and
2) $R_3$, $R_7$, or a combination thereof in the case where $X_2$ is N-[($L_5$)$_{c5}$-$R_7$] may each independently be a group represented by Formula 13(1) or a group represented by Formula 13(2) (for example, one of the groups represented by Formulae 13-1 to 13-20).

In one embodiment, the thermally activated delayed fluorescence emitter may include a compound represented by Formula 14A:

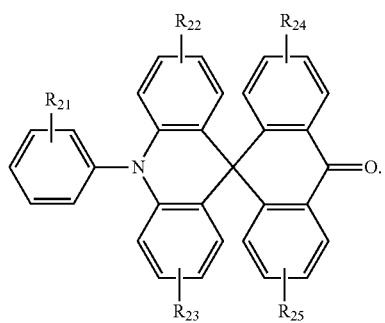

Formula 14A

In Formula 14A, $R_{21}$ to $R_{25}$ may each independently be hydrogen, deuterium, a cyano group, a $C_1$-$C_{10}$ alkyl group, a phenyl group, a biphenyl group, or a terphenyl group.

In one embodiment, the thermally activated delayed fluorescence emitter may not include a cyano group.

The thermally activated delayed fluorescence emitter may include at least one of Compounds D1-1 to D1-83, D2-1 to D2-81, D3-1 to D3-81, D201 to D211, 1 to 1030, and TD1 to TD4, but embodiments of the present disclosure are not limited thereto:

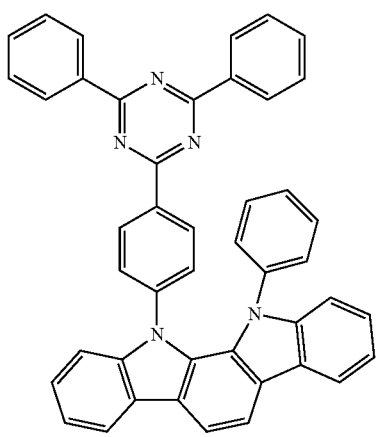

D1-1

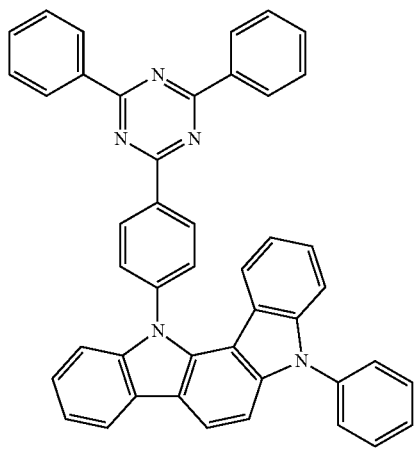

D1-2

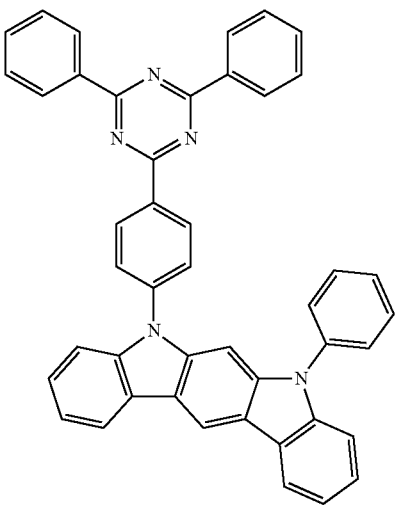

D1-3

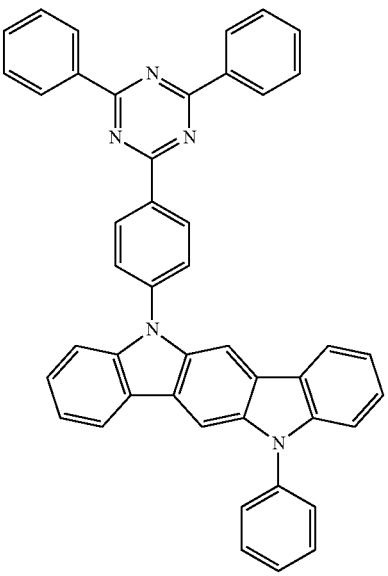

D1-4

-continued
D1-5
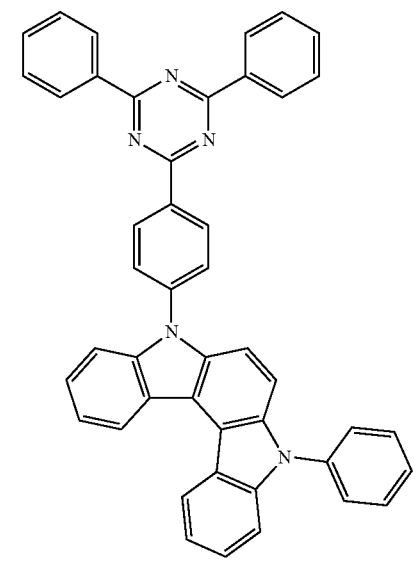
D1-6
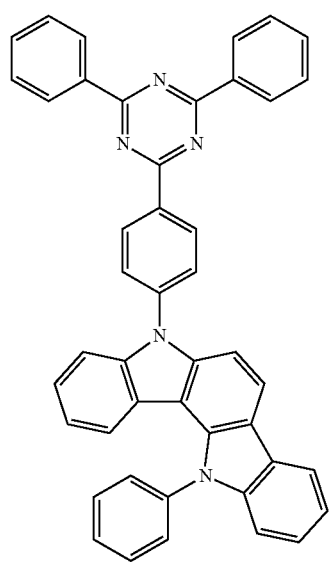
D1-7
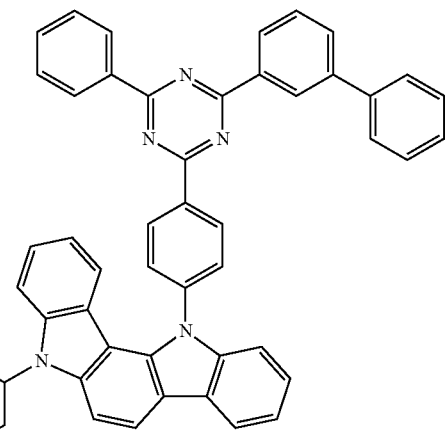
-continued
D1-8
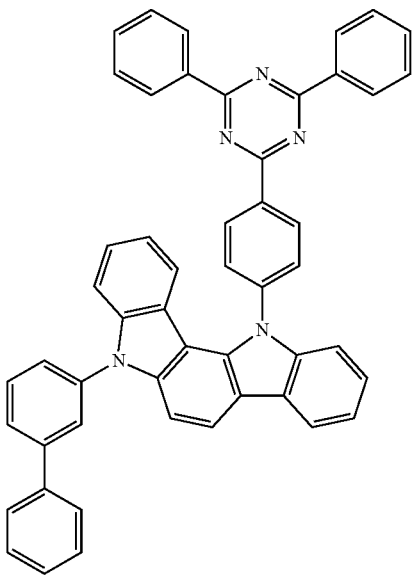
D1-9
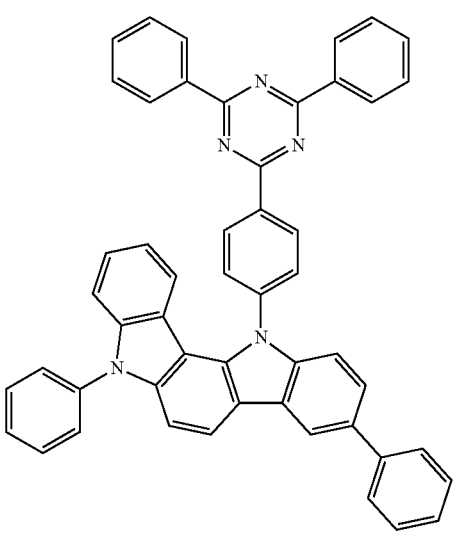
D1-10
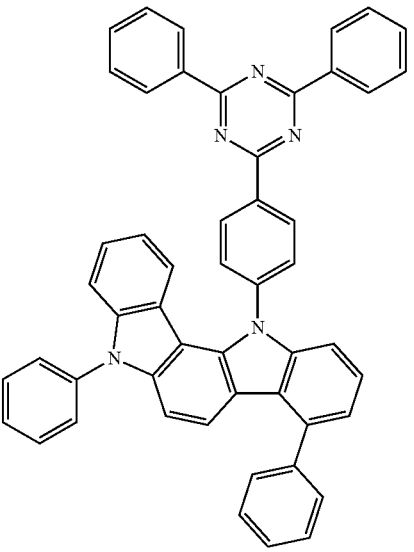

-continued
D1-11
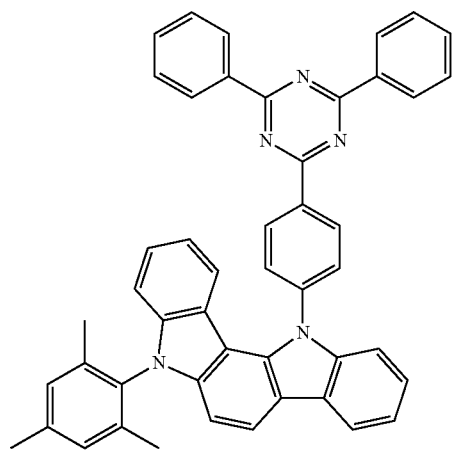
D1-14
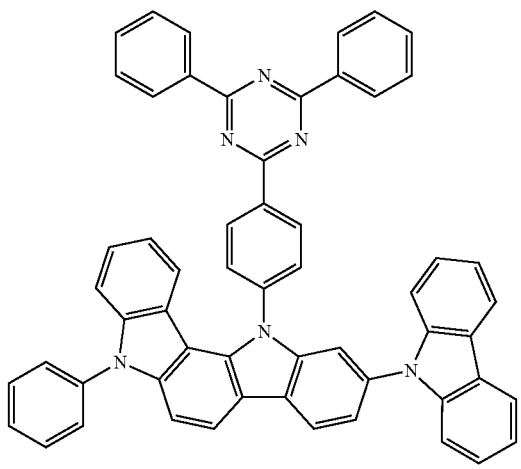
D1-12
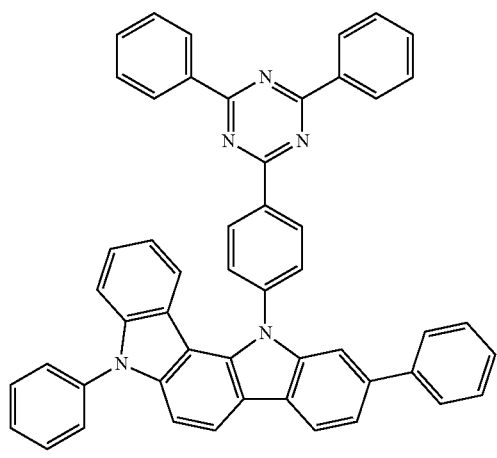
D1-15
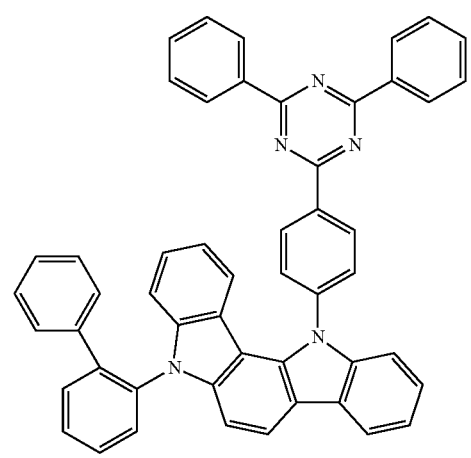
D1-13
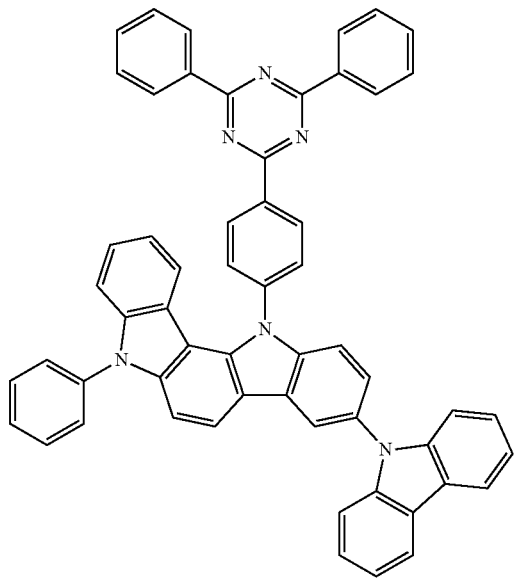
D1-16
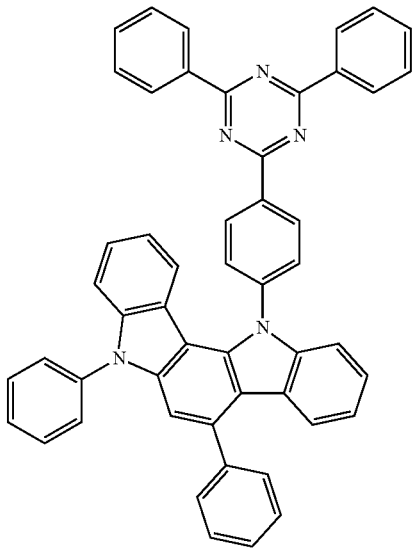

-continued
D1-17
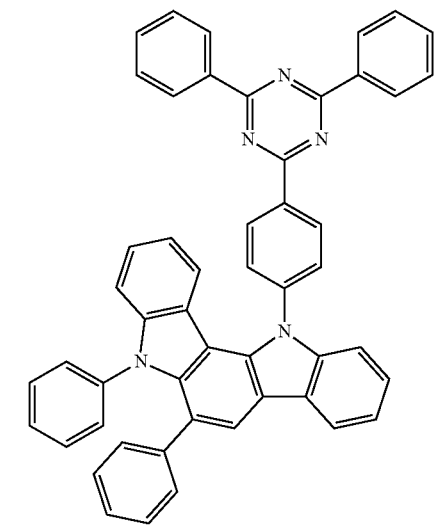
D1-18
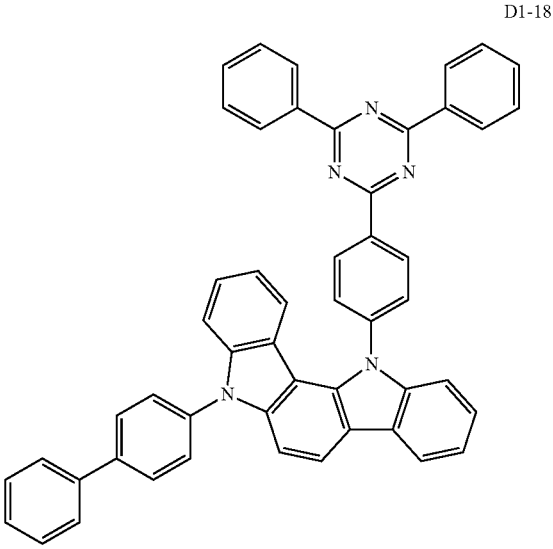
D1-19
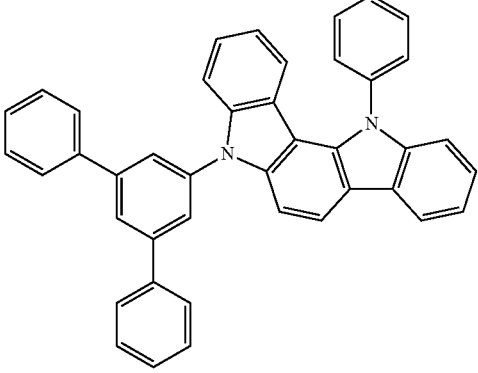
-continued
D1-20
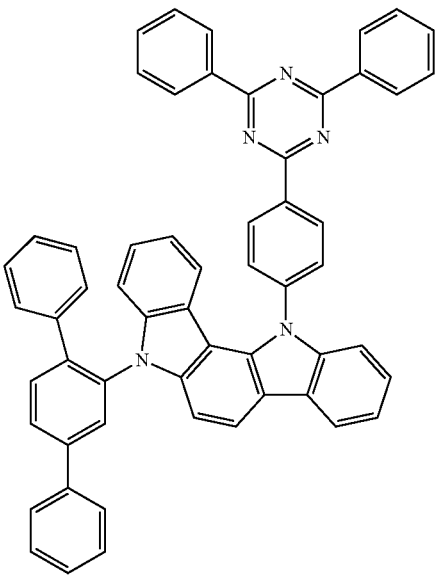
D1-21
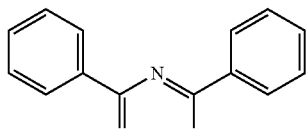
D1-22
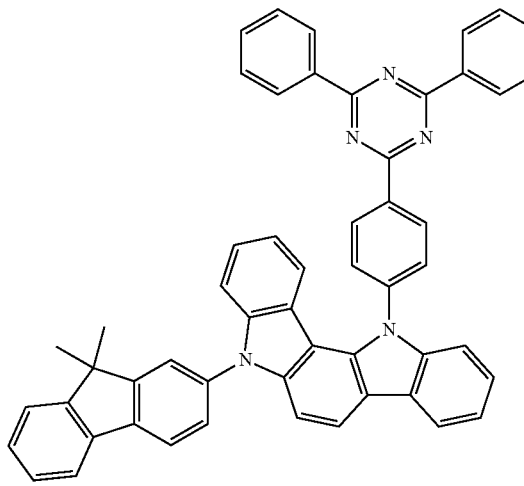

D1-23
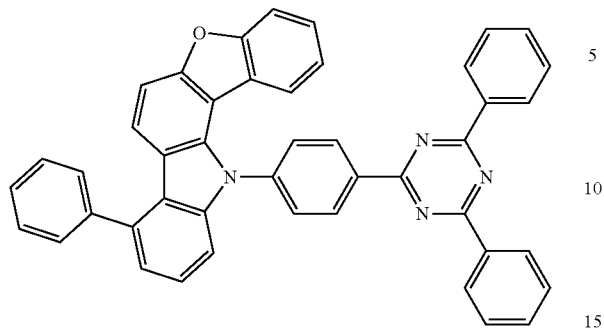
D1-24
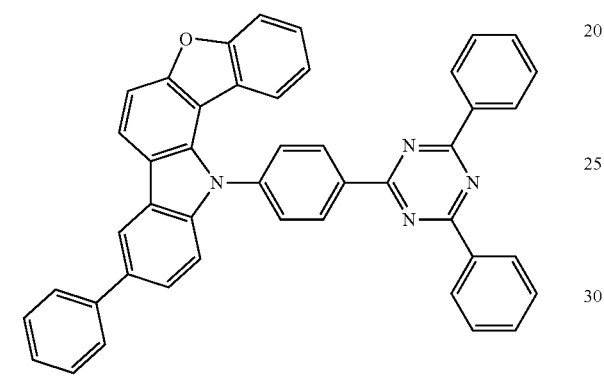
D1-25
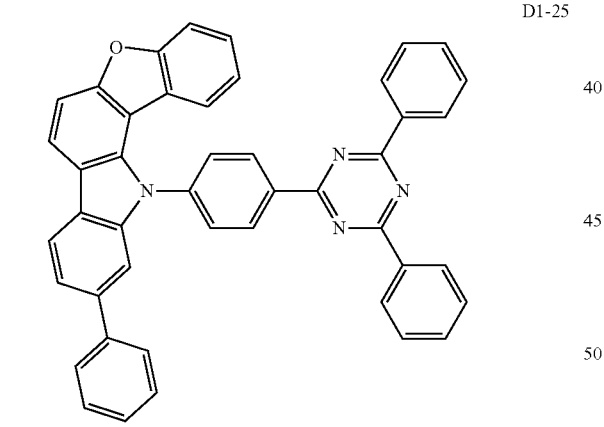
D1-26
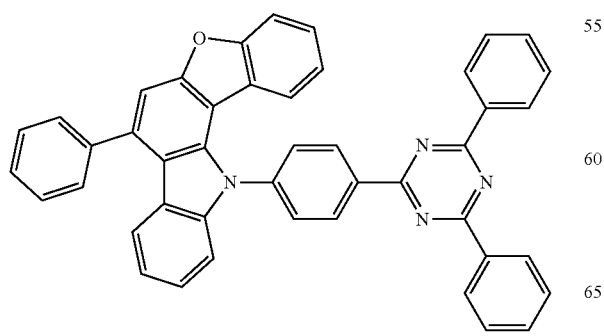
D1-27
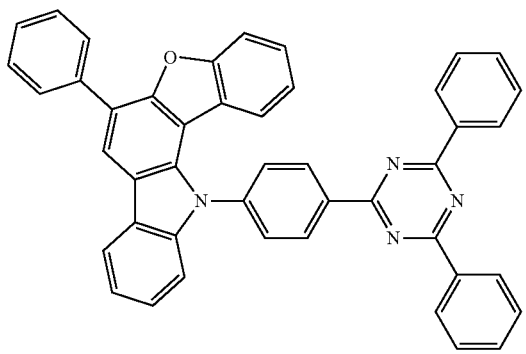
D1-28
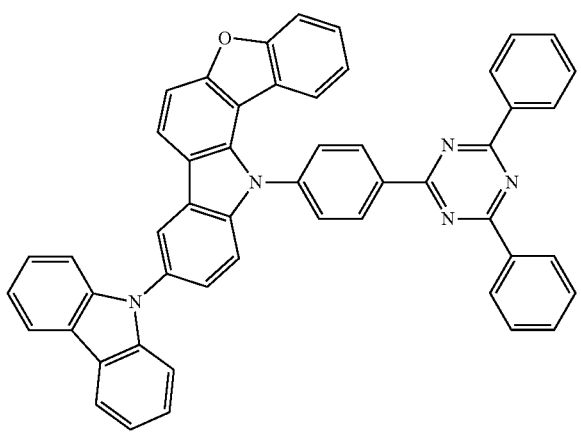
D1-29
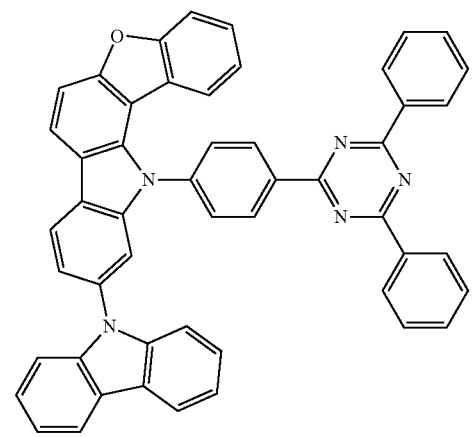

D1-30
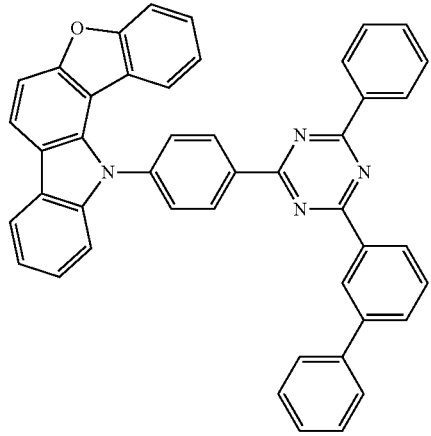
D1-31
D1-32
D1-33
D1-34
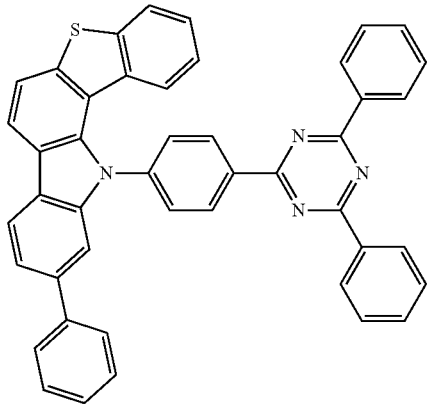
D1-35
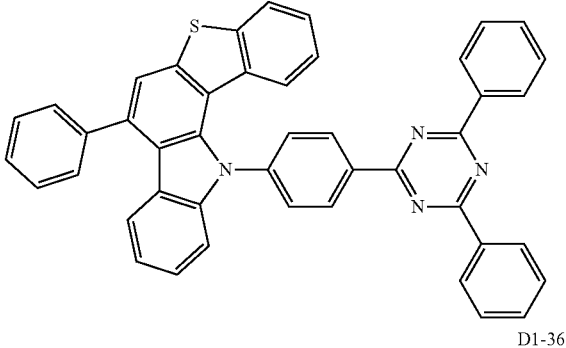
D1-36
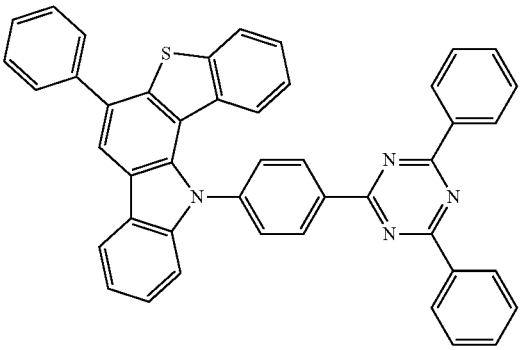
D1-37
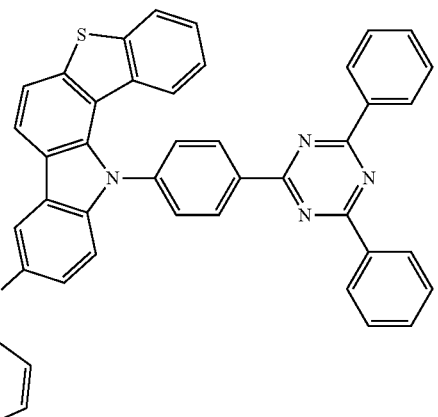

D1-38
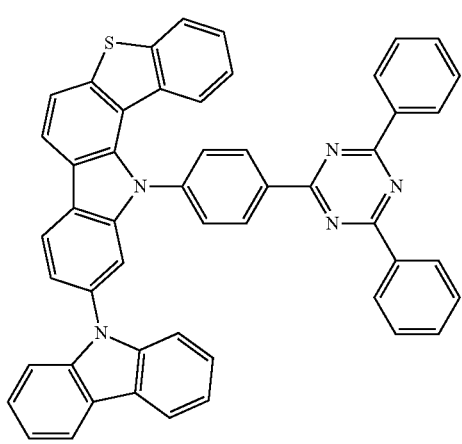
D1-39
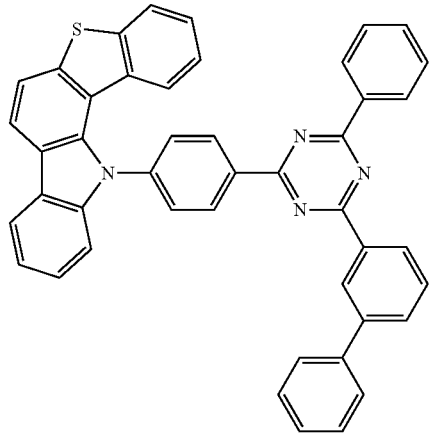
D1-40
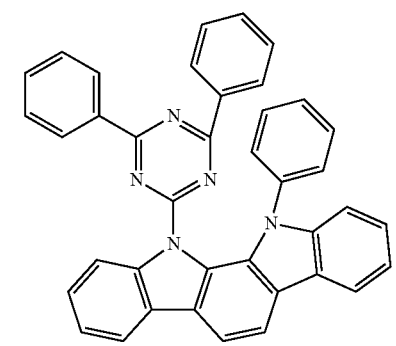
D1-41
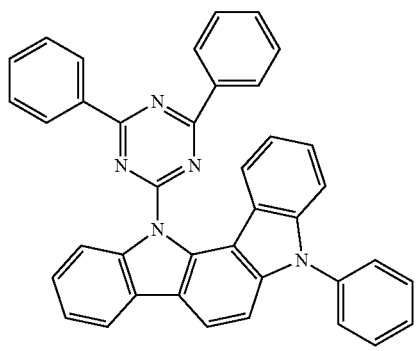
D1-42
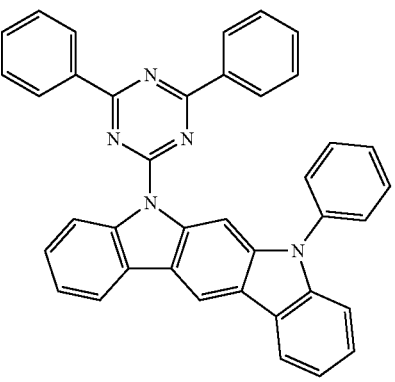
D1-43
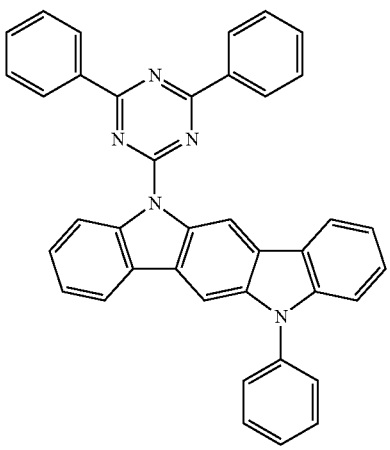
D1-44
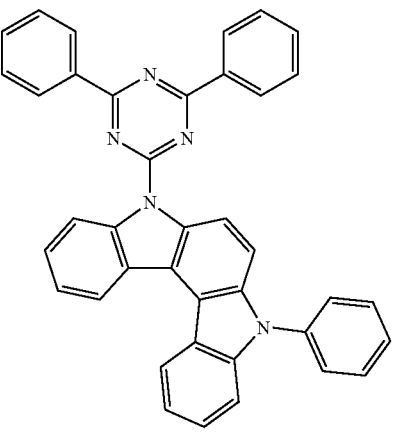

-continued
D1-45
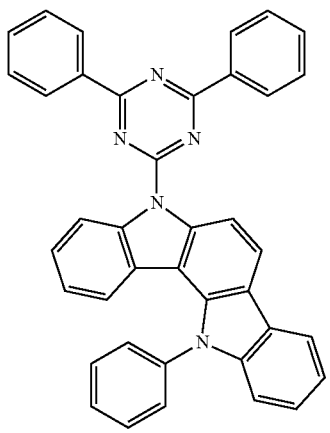
D1-46
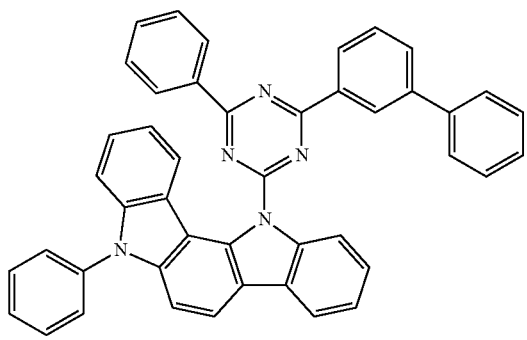
D1-47
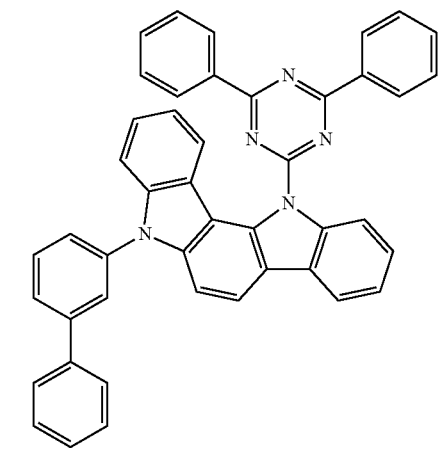
D1-48
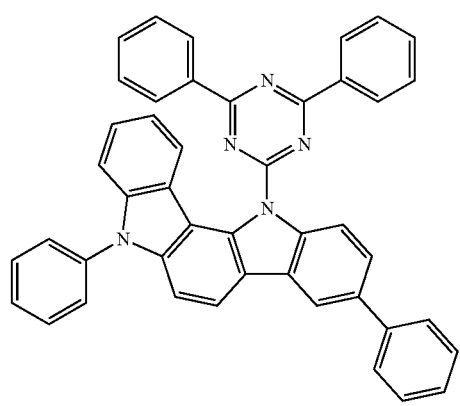
D1-49
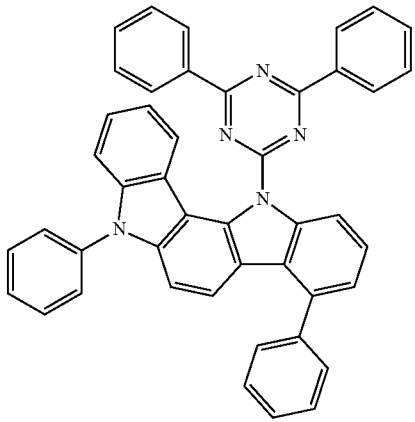
D1-50
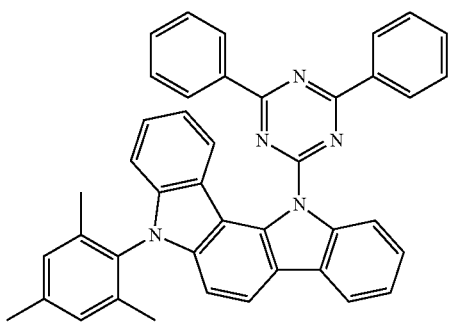
D1-51
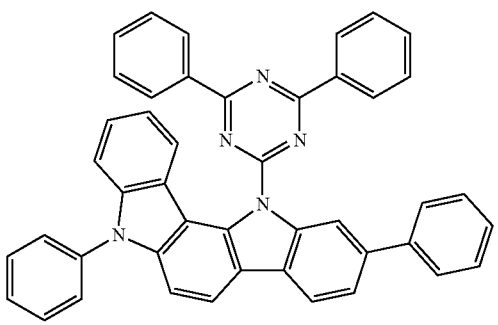
D1-52
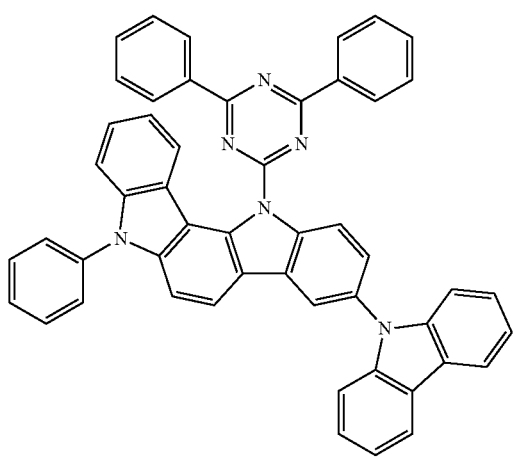

D1-53
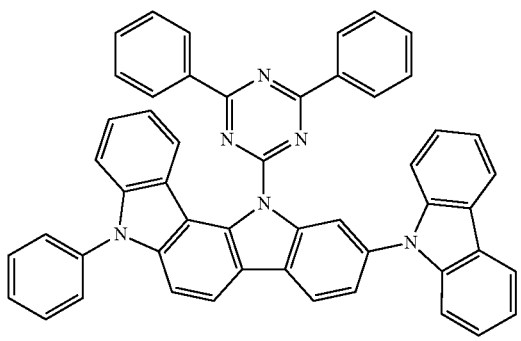
D1-54
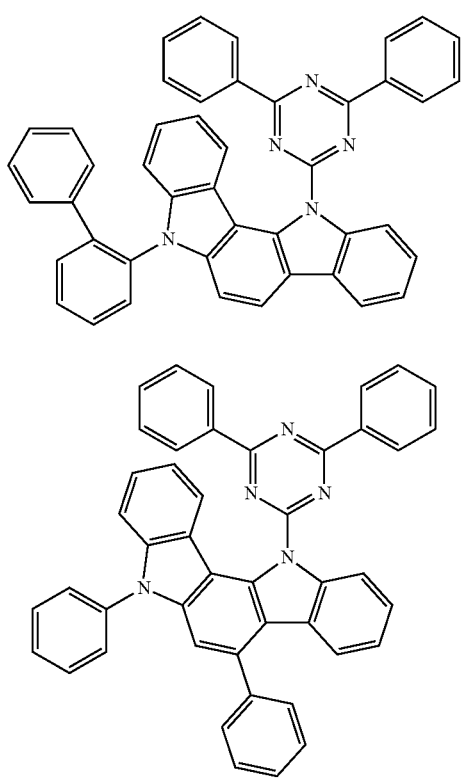
D1-55
D1-56
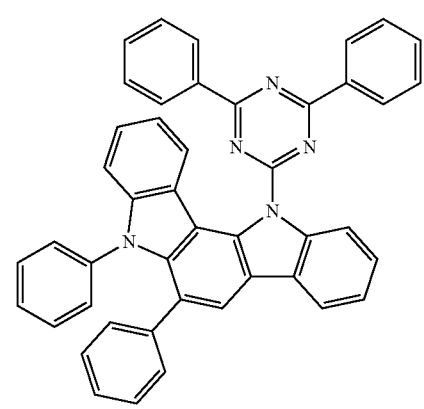
D1-57
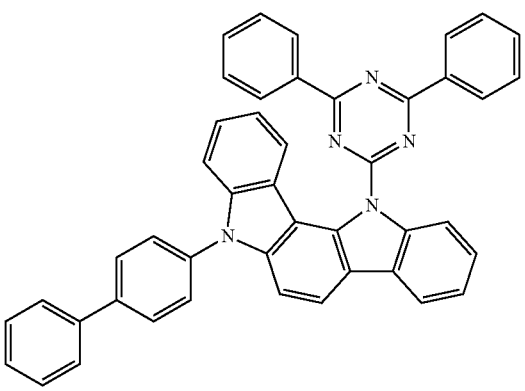
D1-58
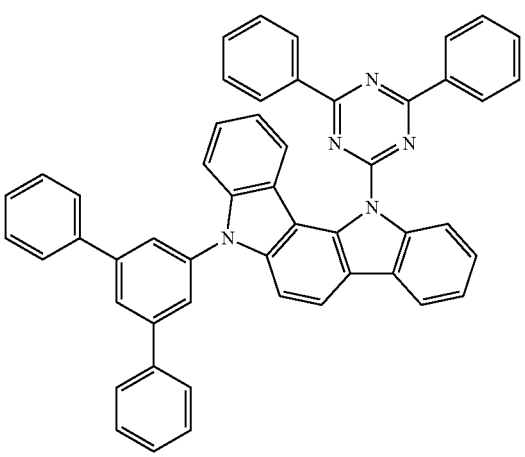
D1-59
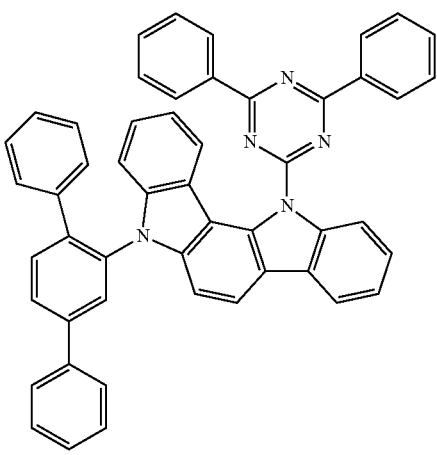

-continued
D1-60
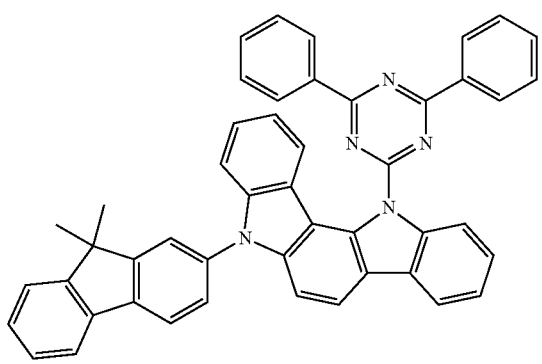
D1-61
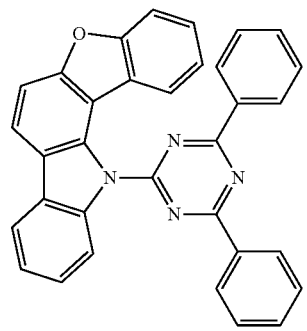
D1-62
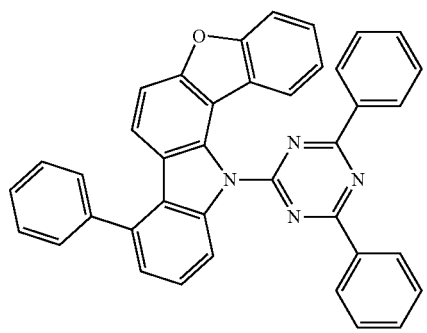
D1-63
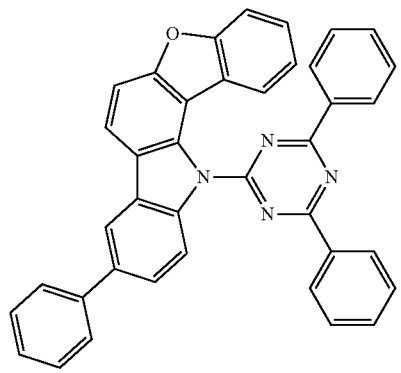
-continued
D1-64
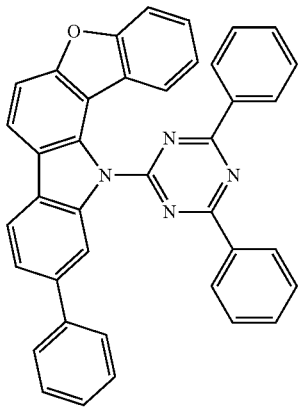
D1-65
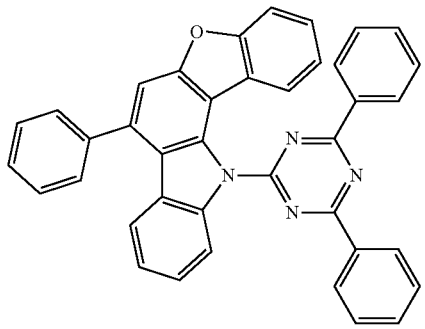
D1-66
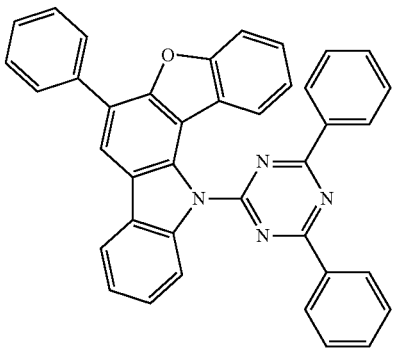
D1-67
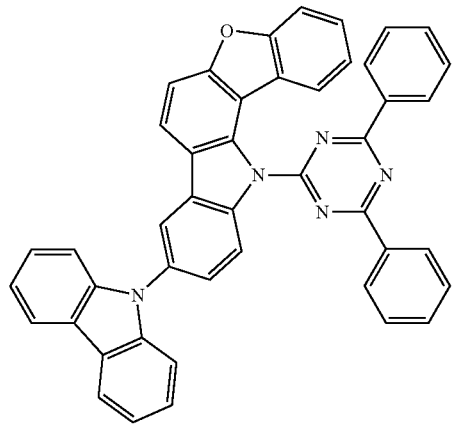

-continued
D1-68
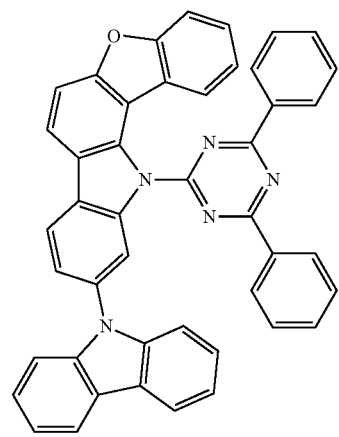
D1-69
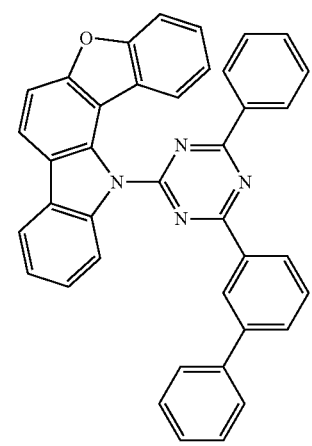
D1-70
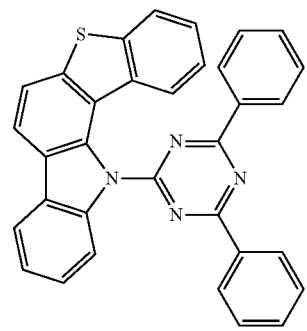
D1-71
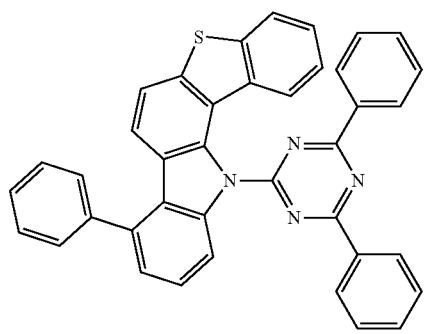
-continued
D1-72
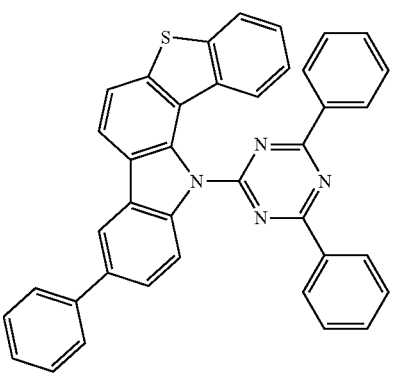
D1-73
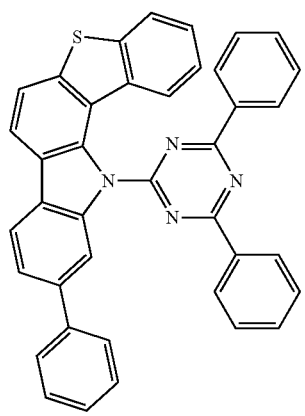
D1-74
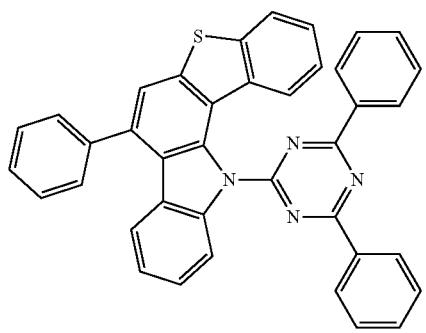
D1-75
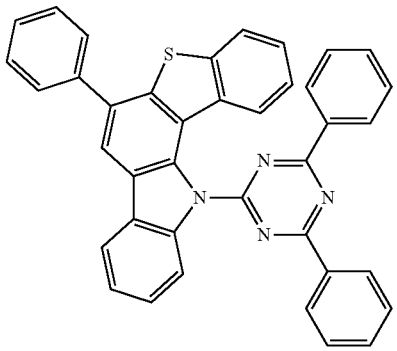

D1-76
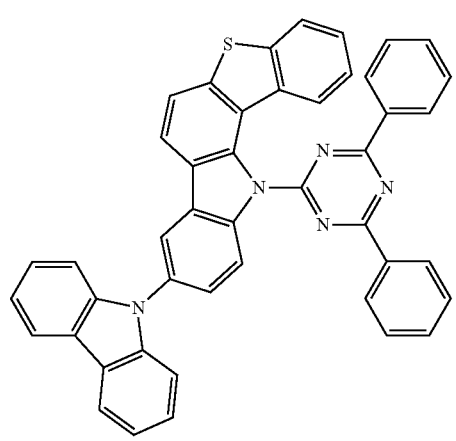
D1-79
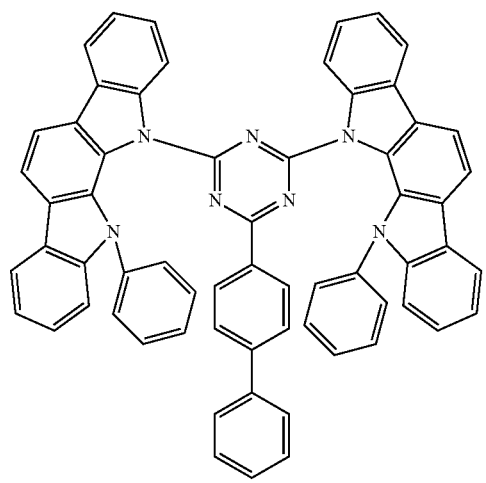
D1-77
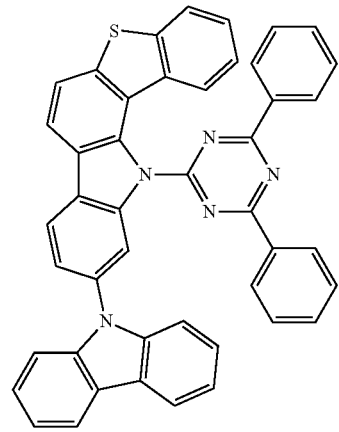
D1-80
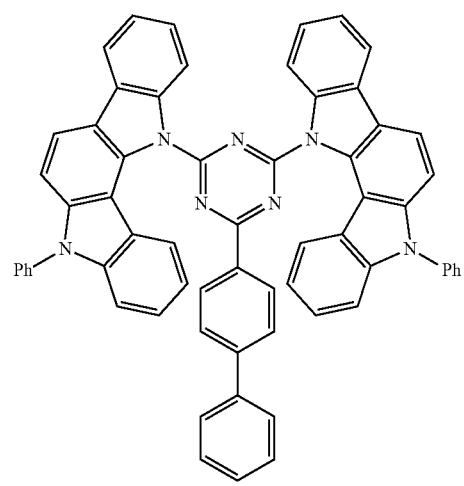
D1-78
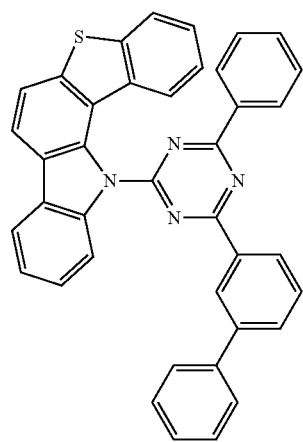
D1-81
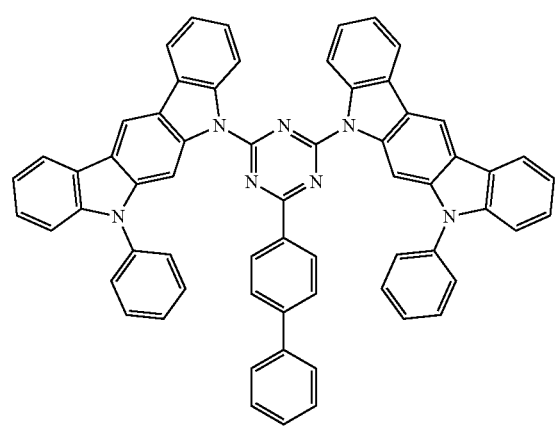

D1-82
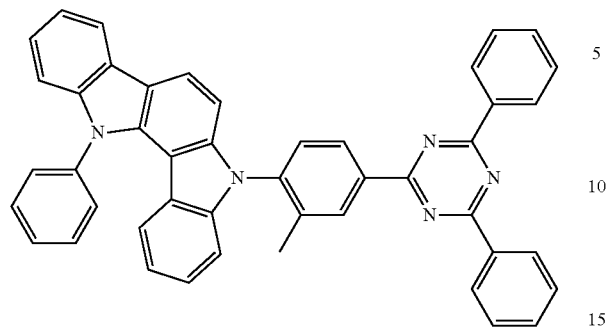
D1-83
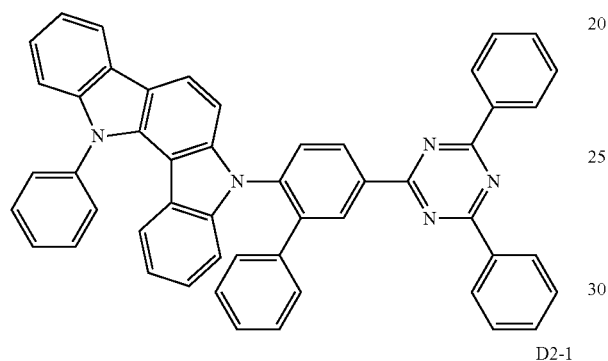
D2-1
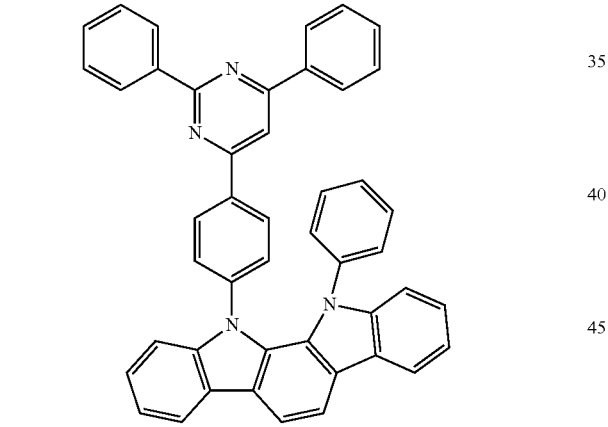
D2-2
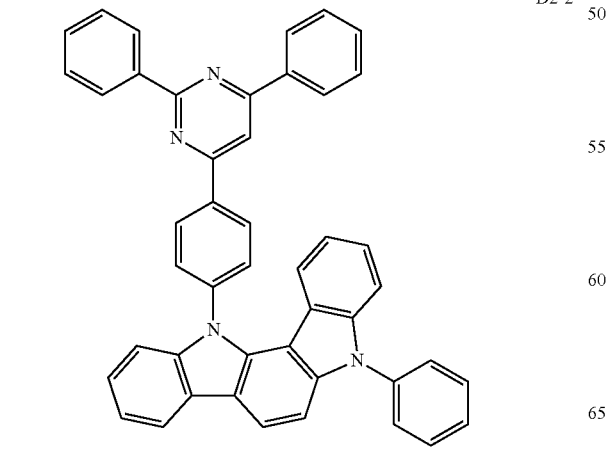
D2-3
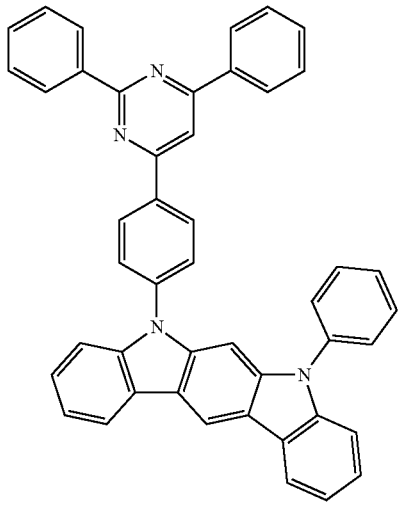
D2-4
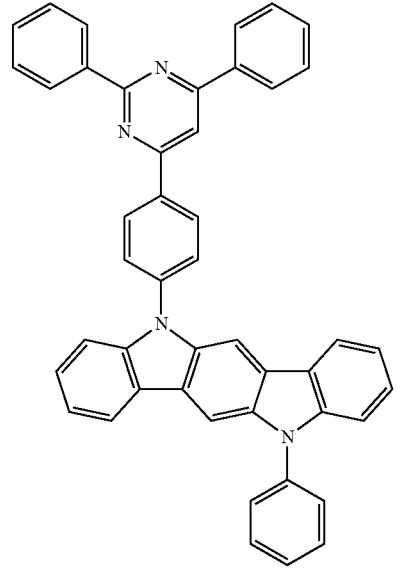
D2-5
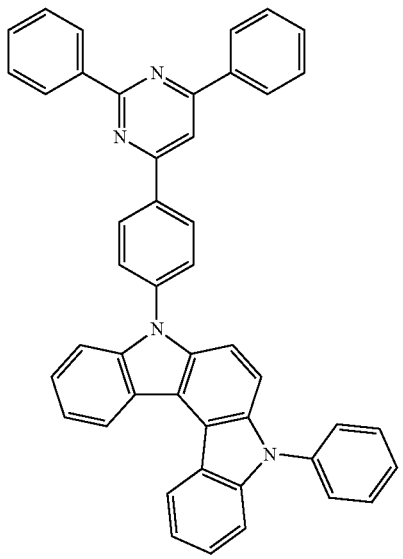

D2-6
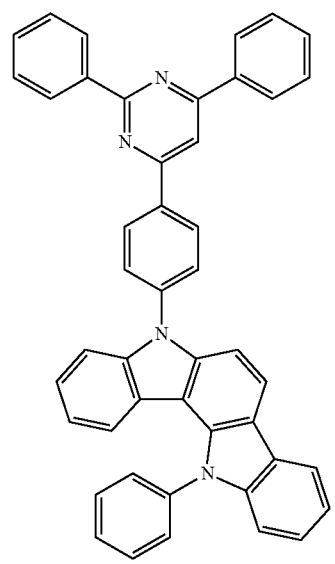
D2-9
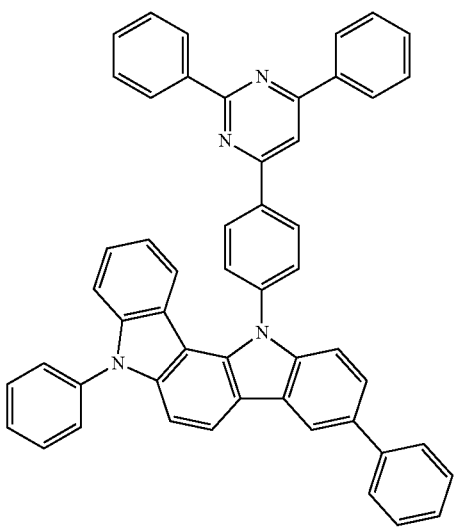
D2-7
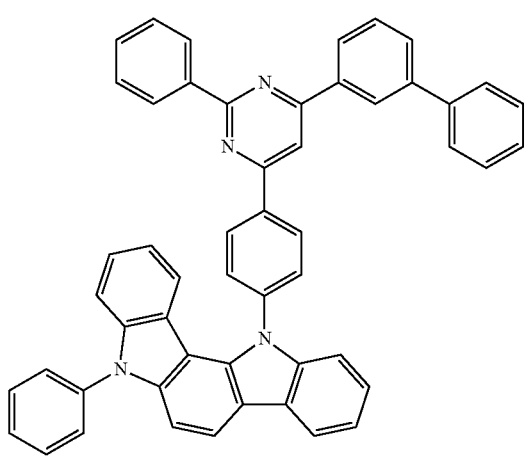
D2-10
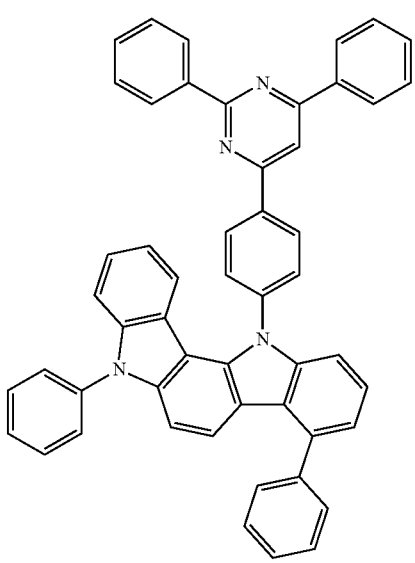
D2-8
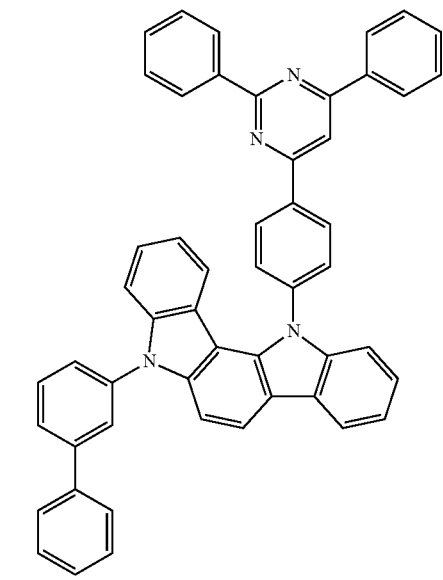
D2-11
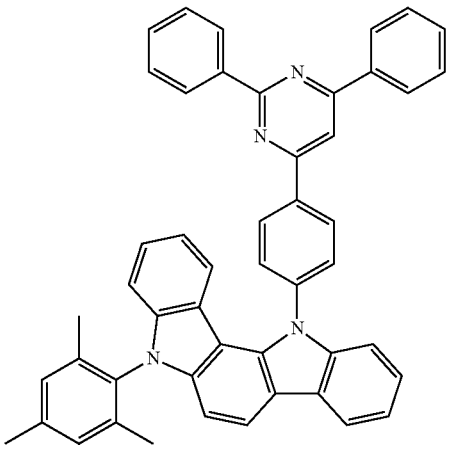

-continued
D2-12
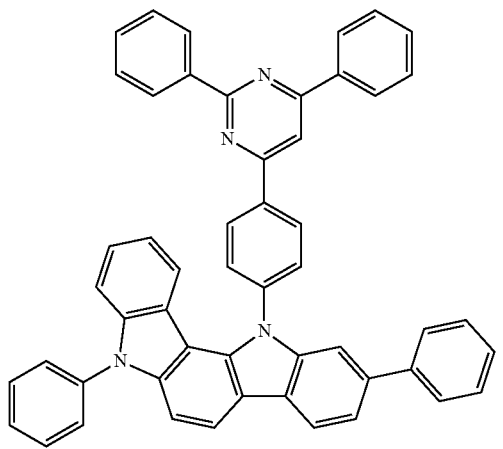
D2-13
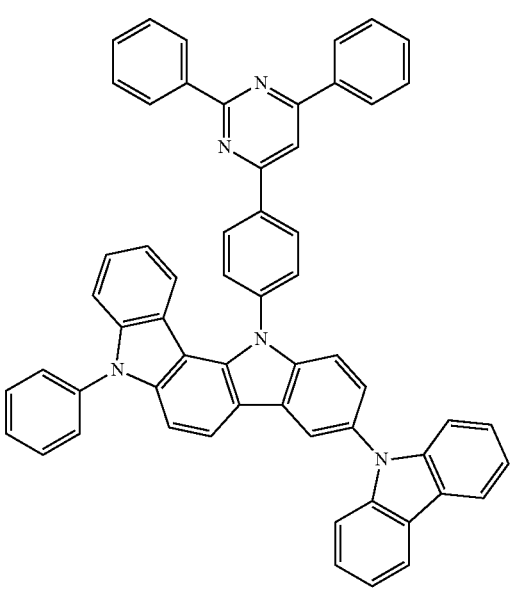
D2-14
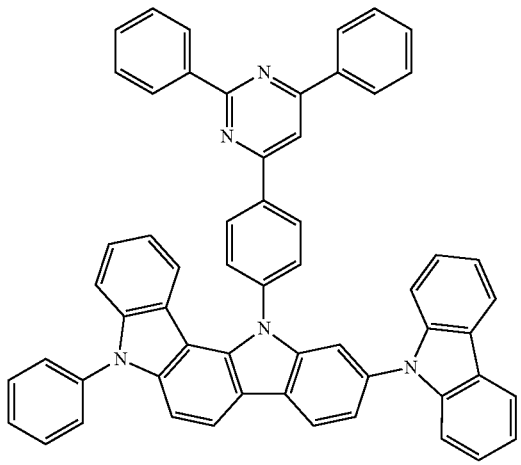
-continued
D2-15
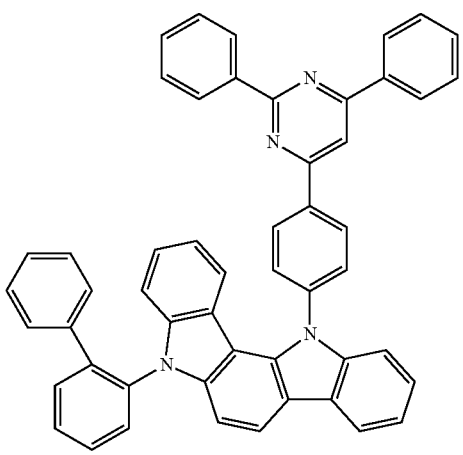
D2-16
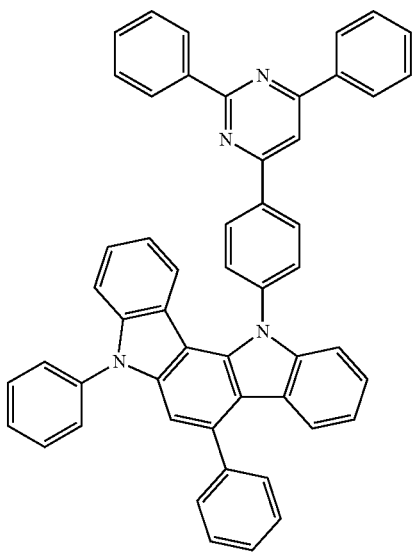
D2-17
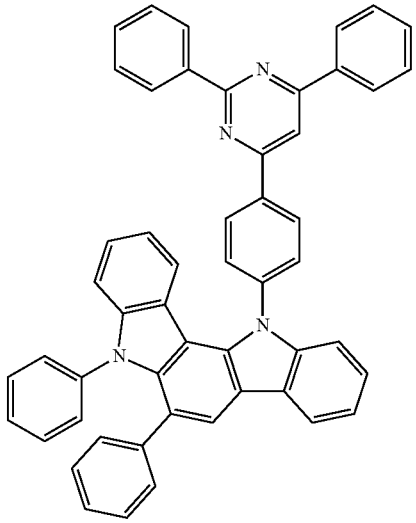

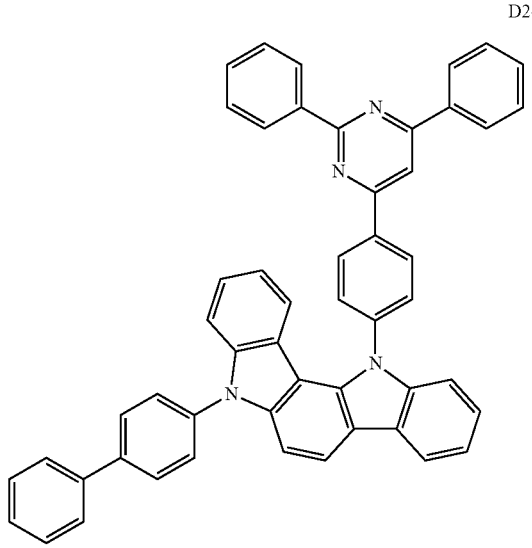
D2-18
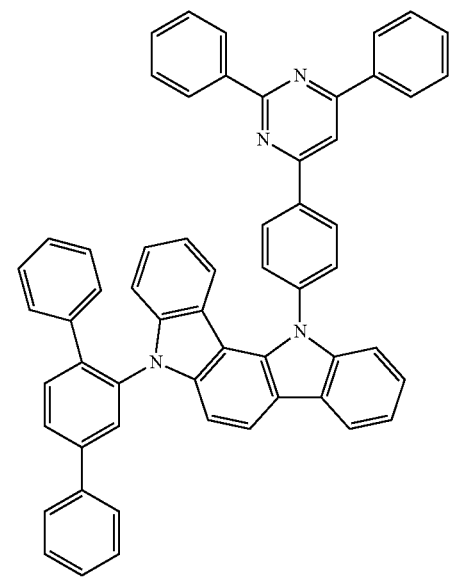
D2-20
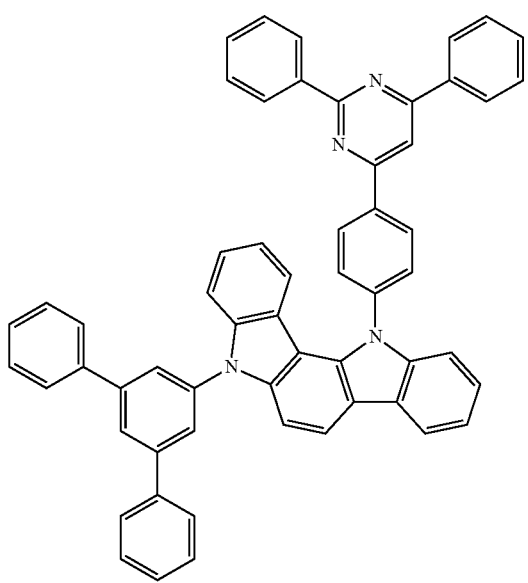
D2-19
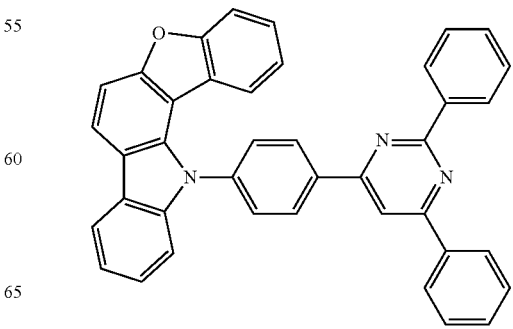
D2-21
D2-22

-continued
D2-23
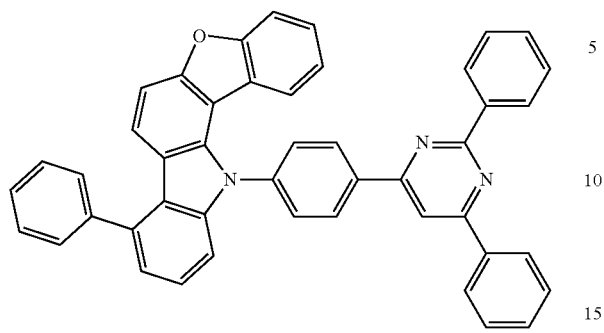
D2-24
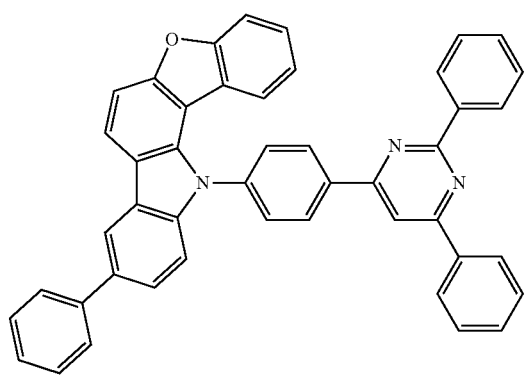
D2-25
D2-26
-continued
D2-27
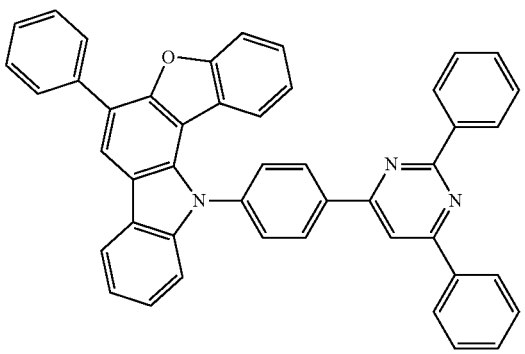
D2-28
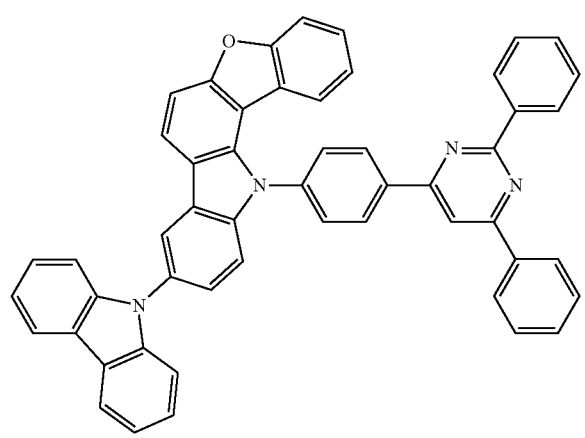
D2-29
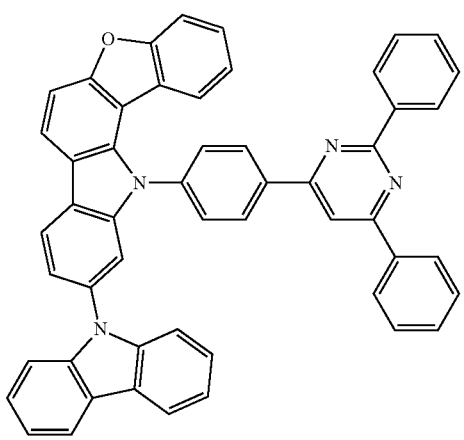

-continued
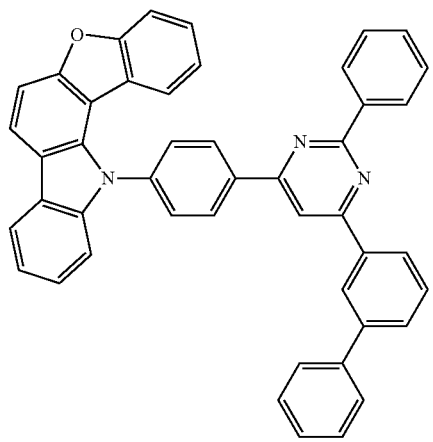
D2-30
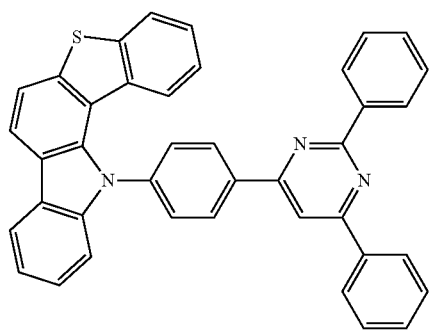
D2-31
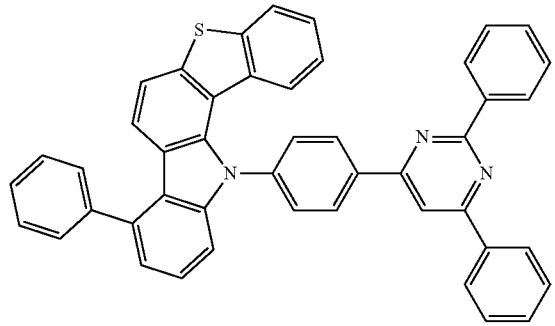
D2-32
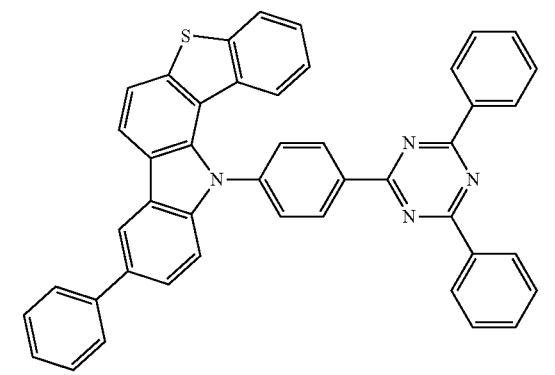
D2-33
-continued
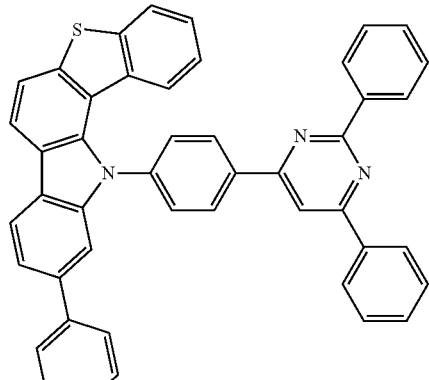
D2-34
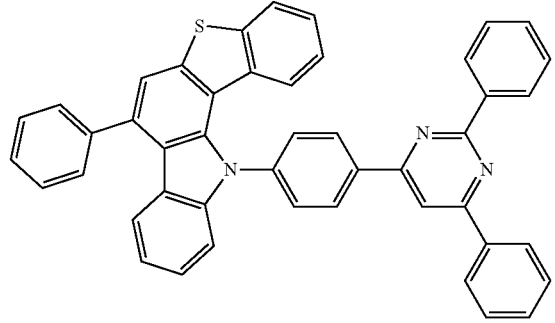
D2-35
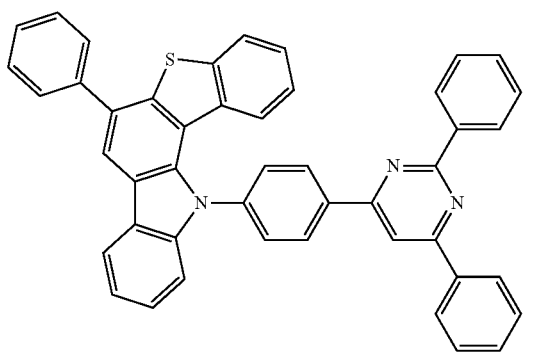
D2-36
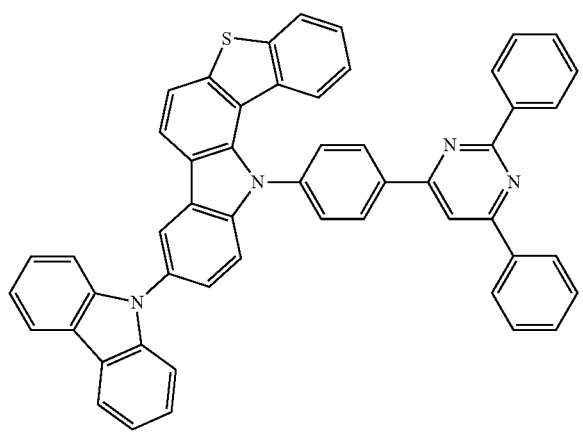
D2-37

D2-38
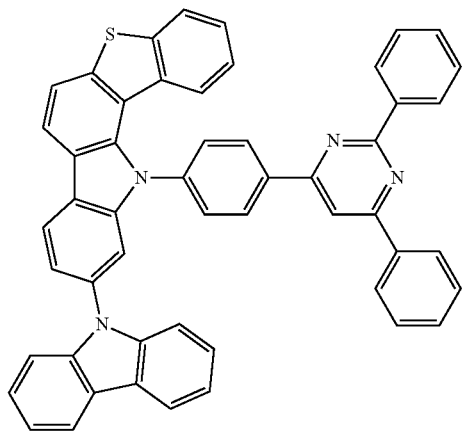
D2-39
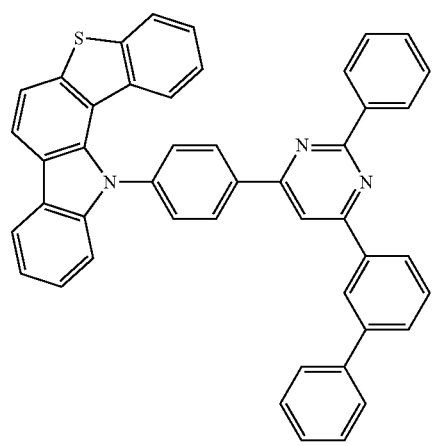
D2-40
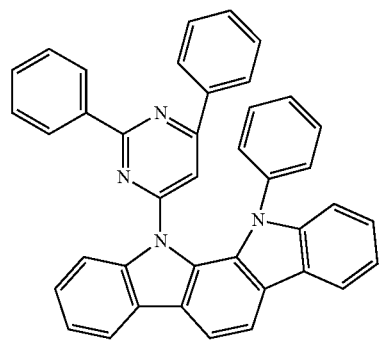
D2-41
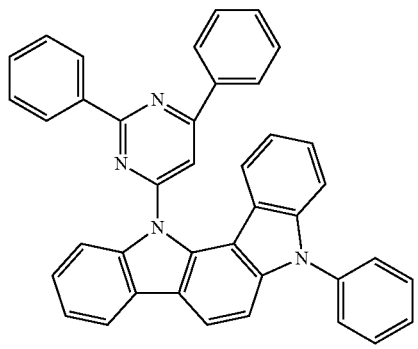
D2-42
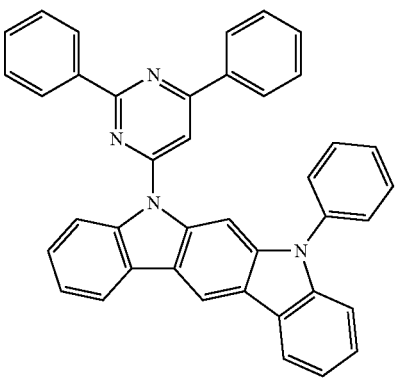
D2-43
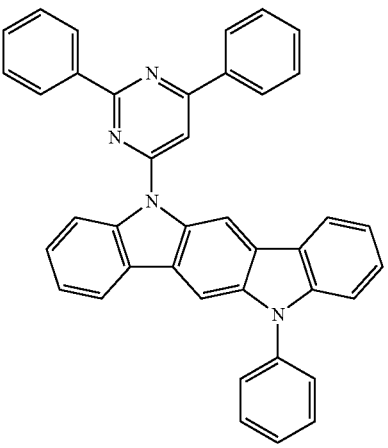
D2-44
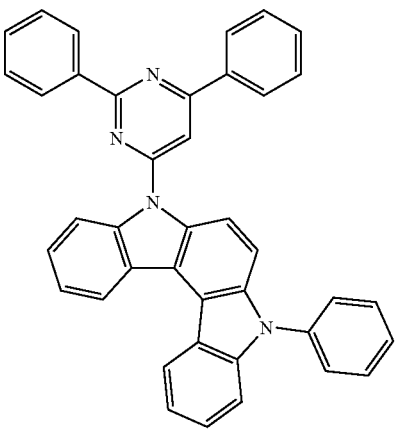

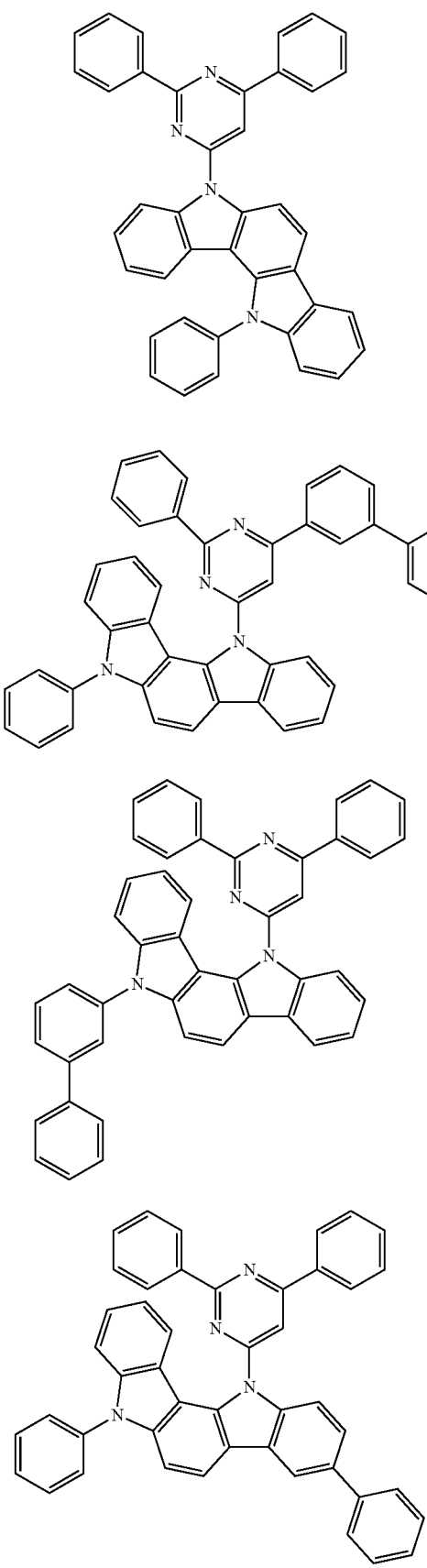
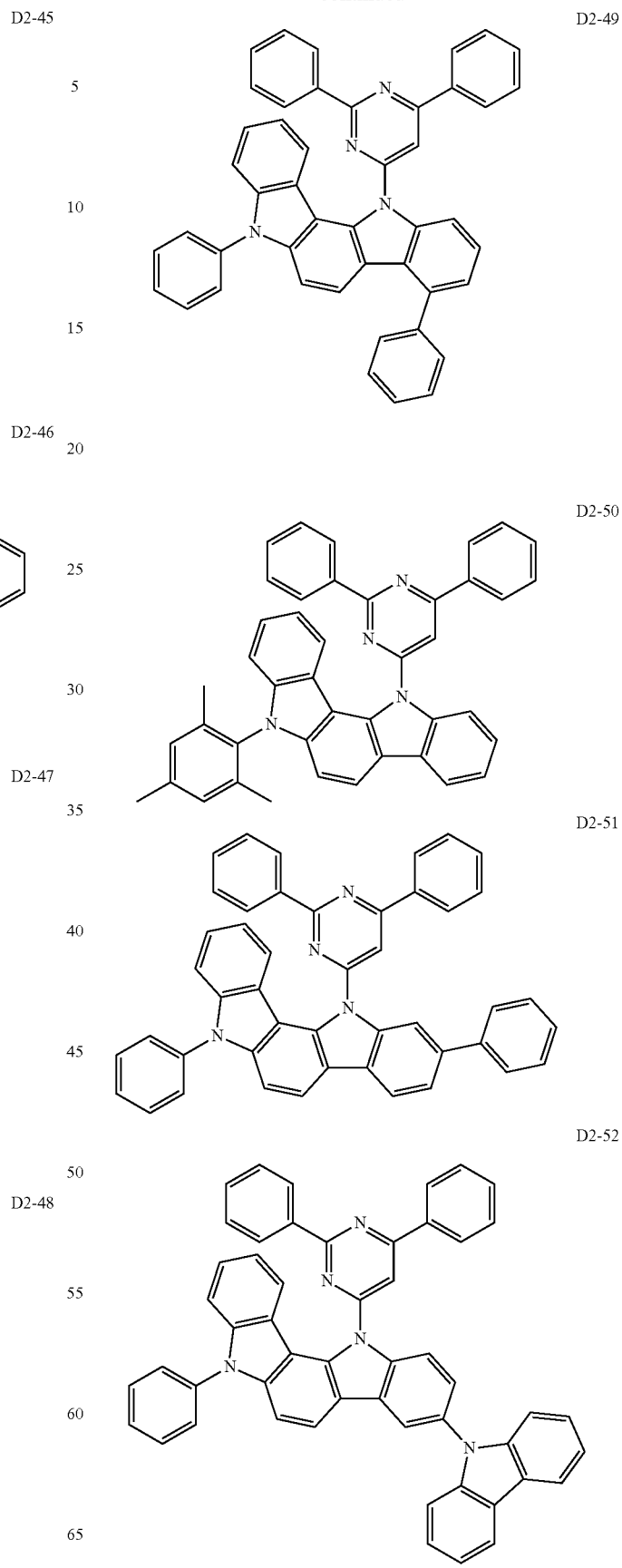

-continued
D2-53
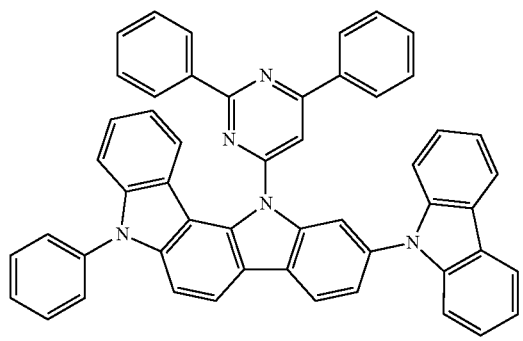
D2-54
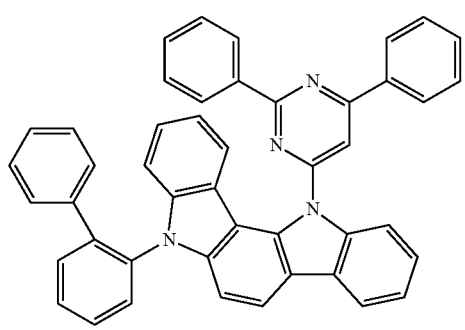
D2-55
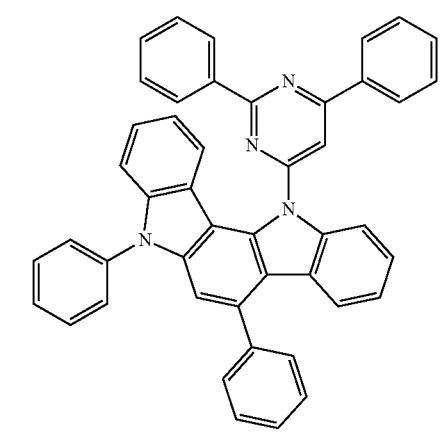
D2-56
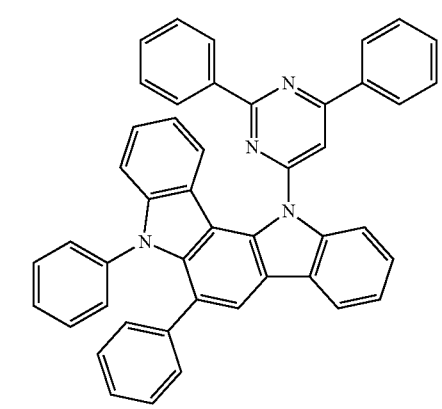
-continued
D2-57
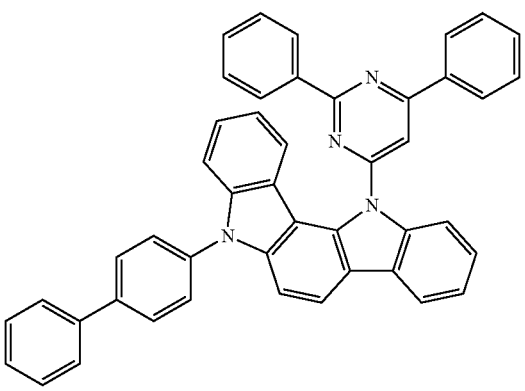
D2-58
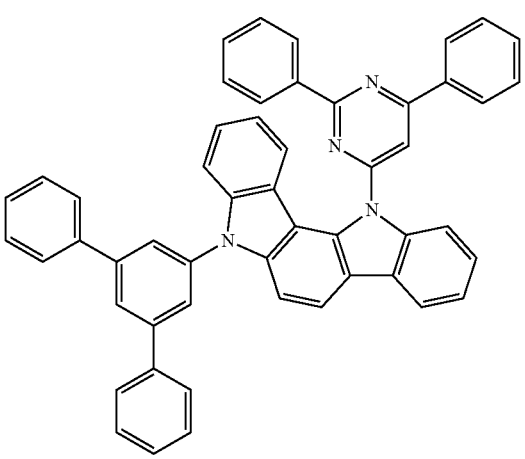
D2-59
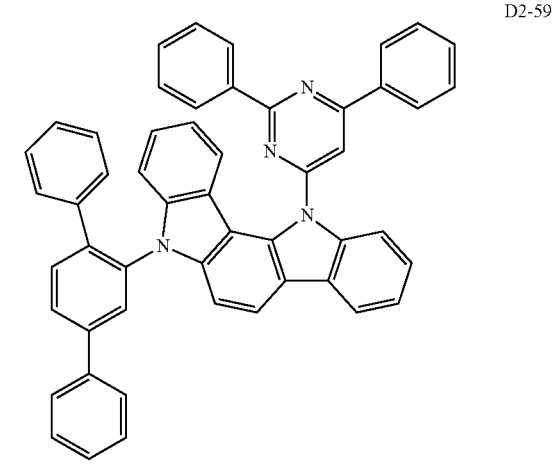

D2-60
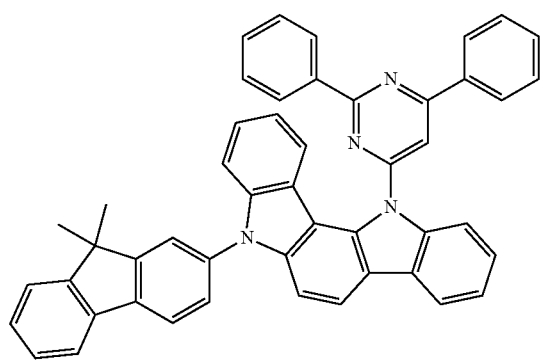
D2-61
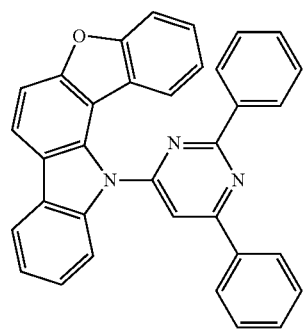
D2-62
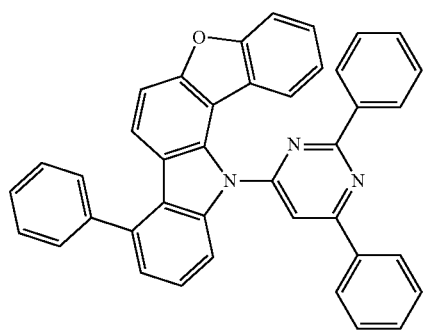
D2-63
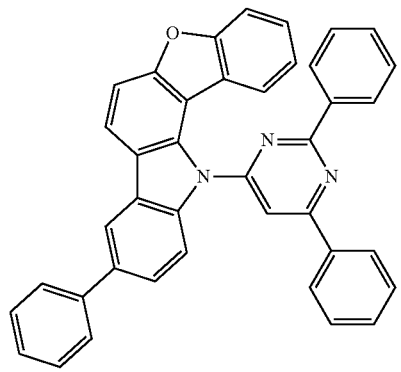
D2-64
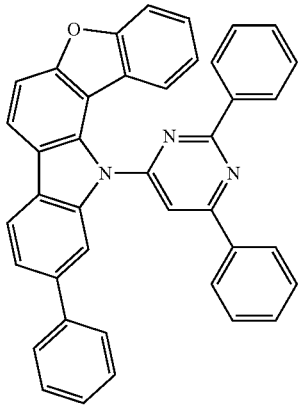
D2-65
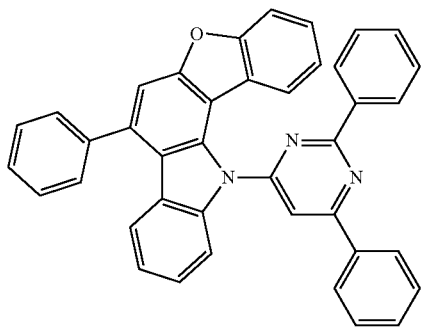
D2-66
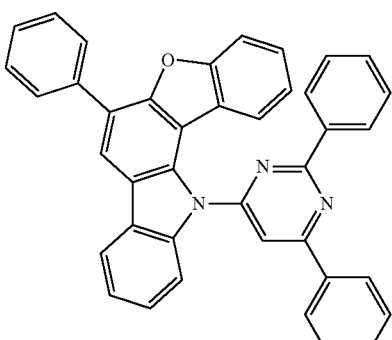
D2-67
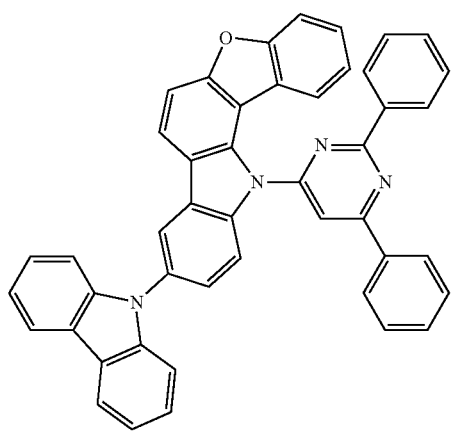

-continued
D2-68
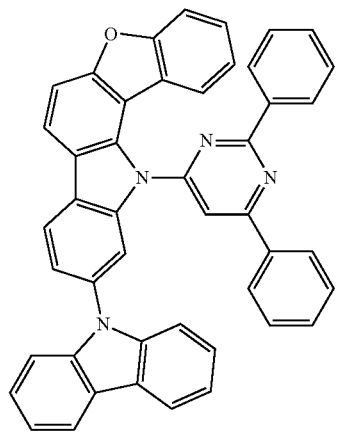
D2-69
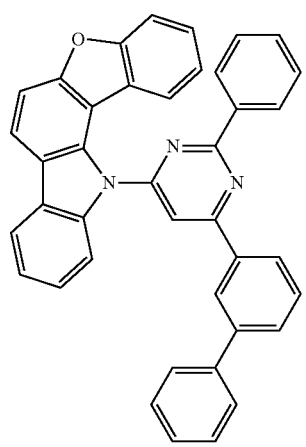
D2-70
D2-71
-continued
D2-72
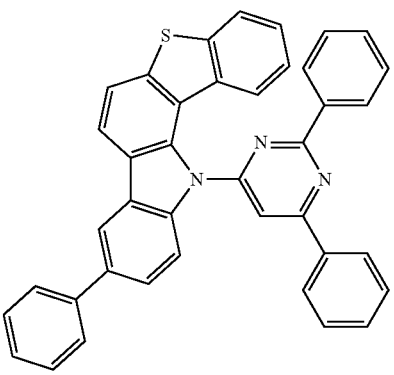
D2-73
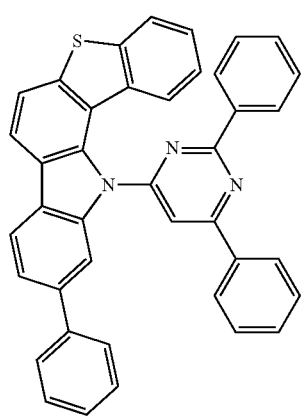
D2-74
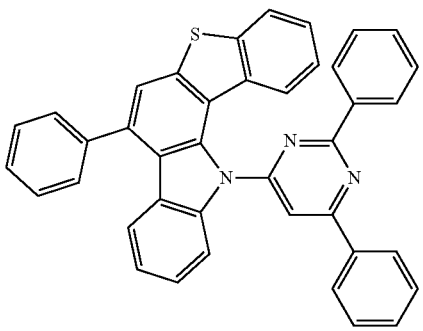
D2-75
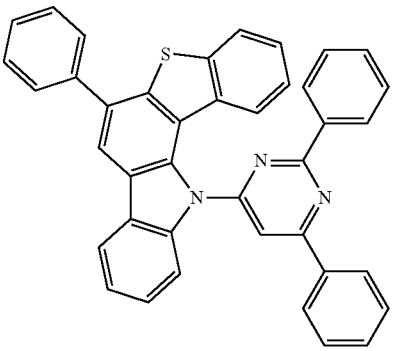

D2-76
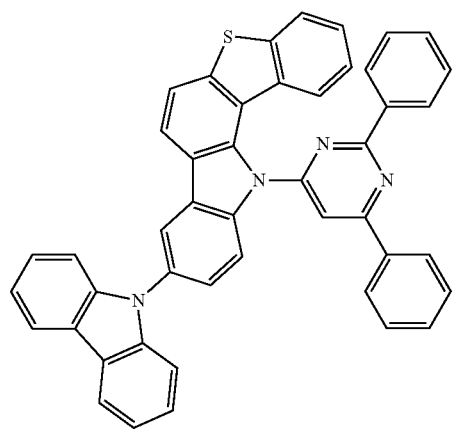
D2-77
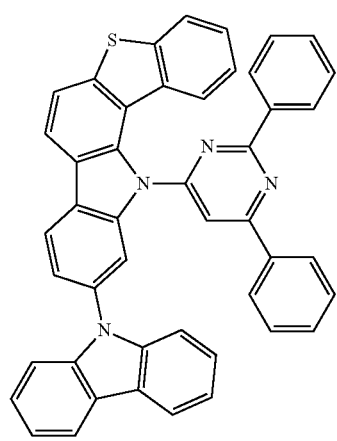
D2-78
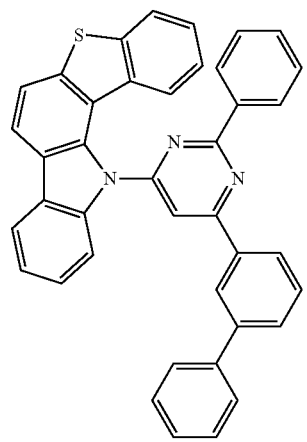
D2-79
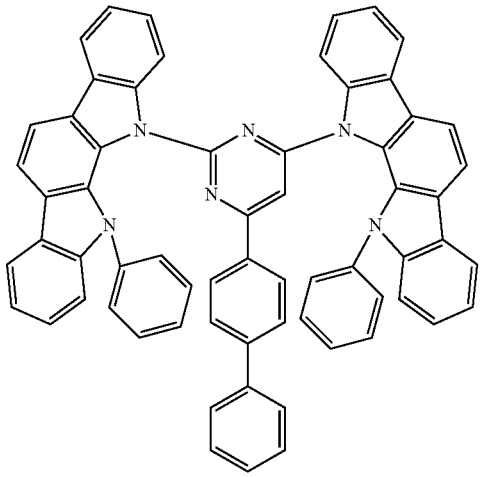
D2-80
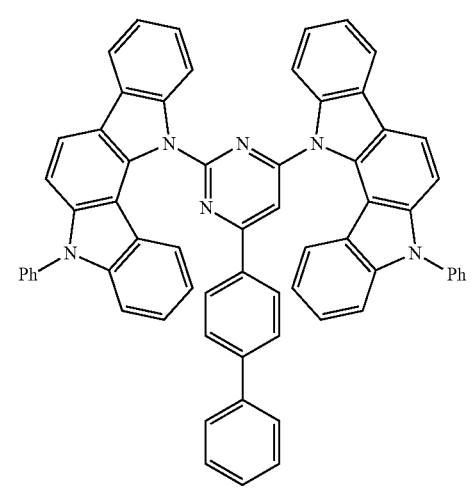
D2-81
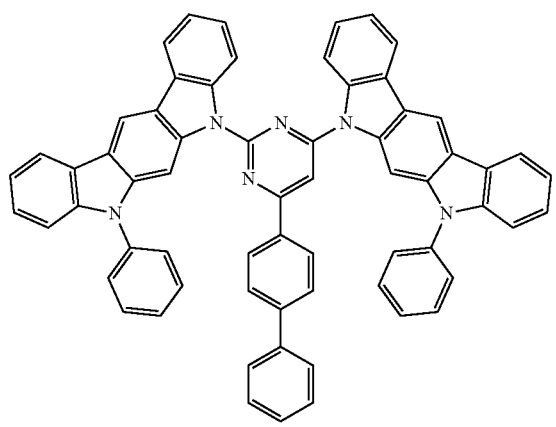

D3-1
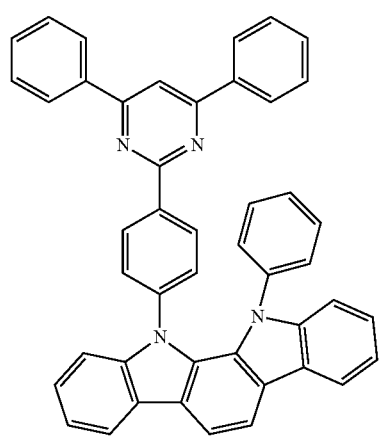
D3-2
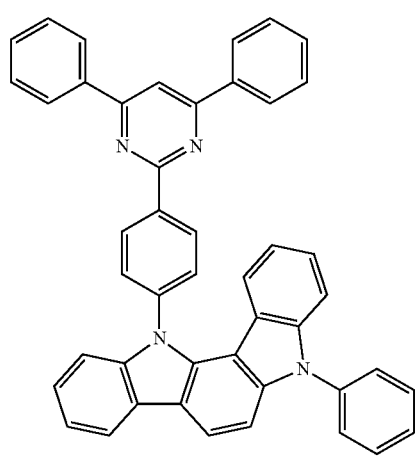
D3-3
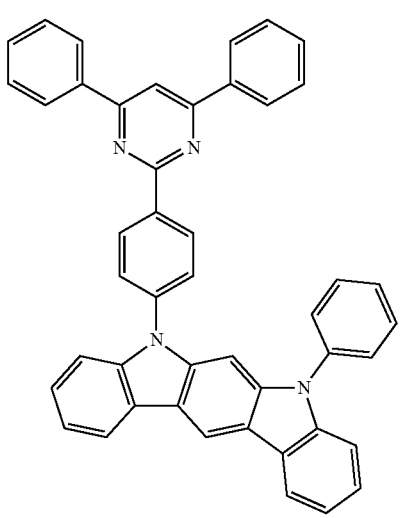
D3-4
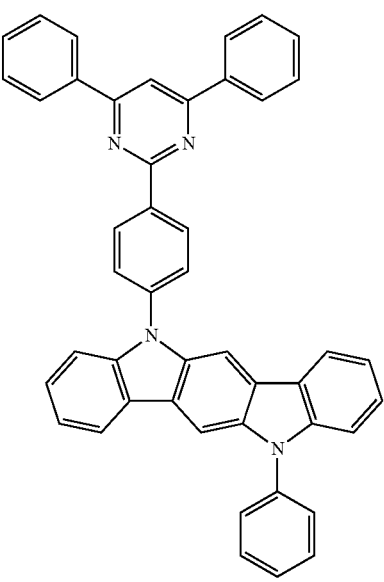
D3-5
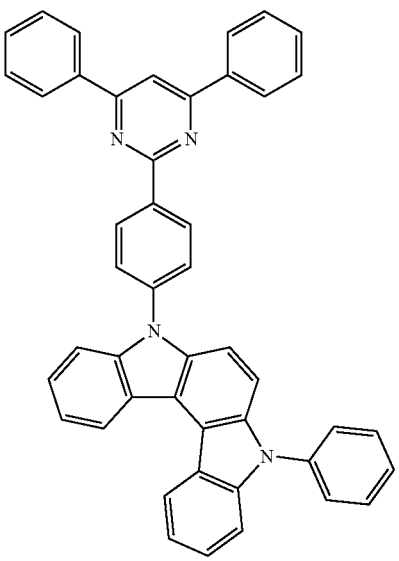

D3-6
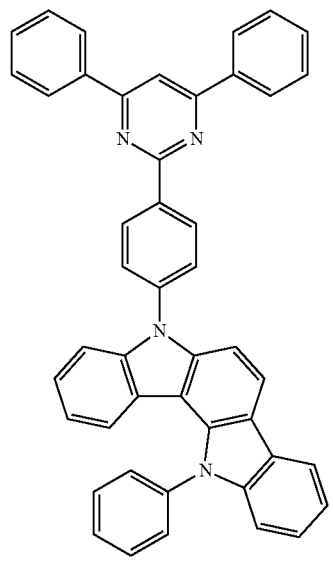
D3-7
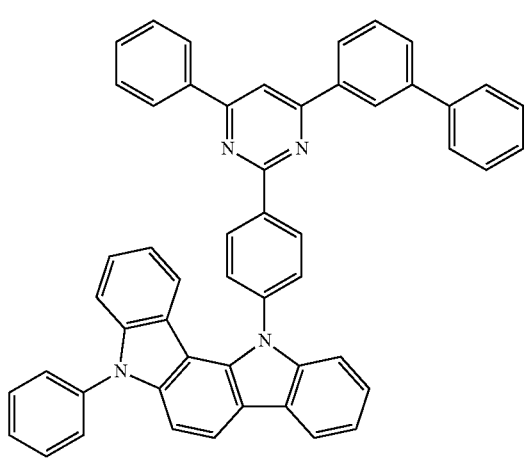
D3-8
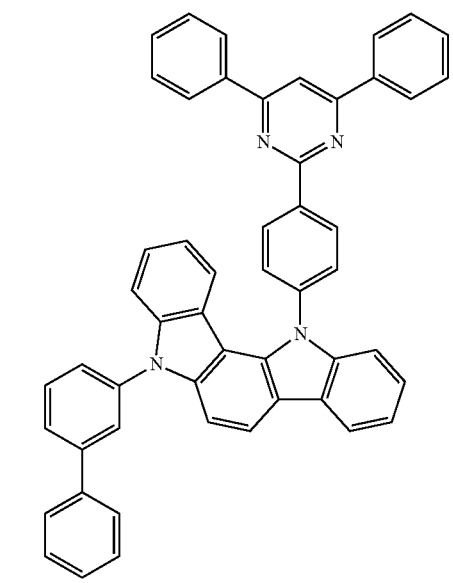
D3-9
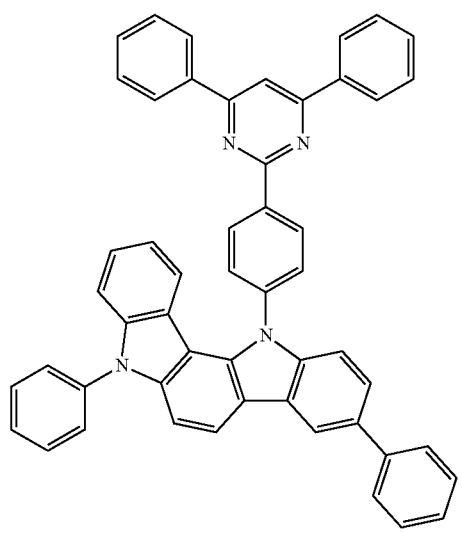
D3-10
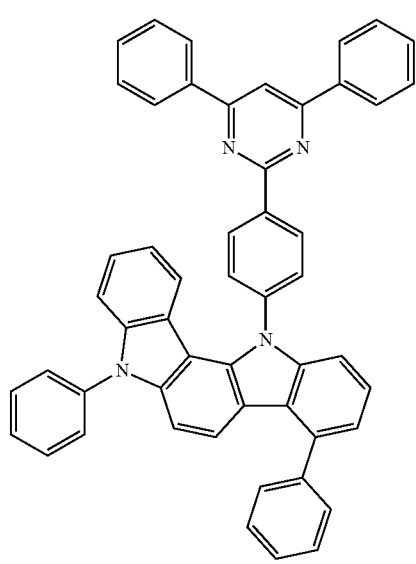
D3-11
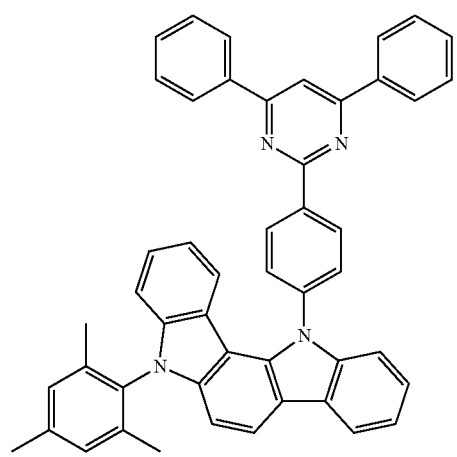

-continued
D3-12
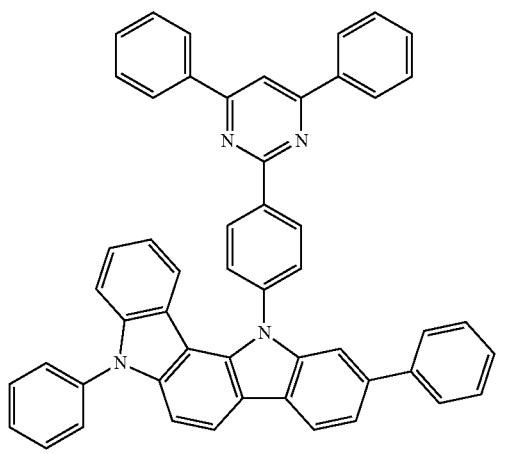
D3-13
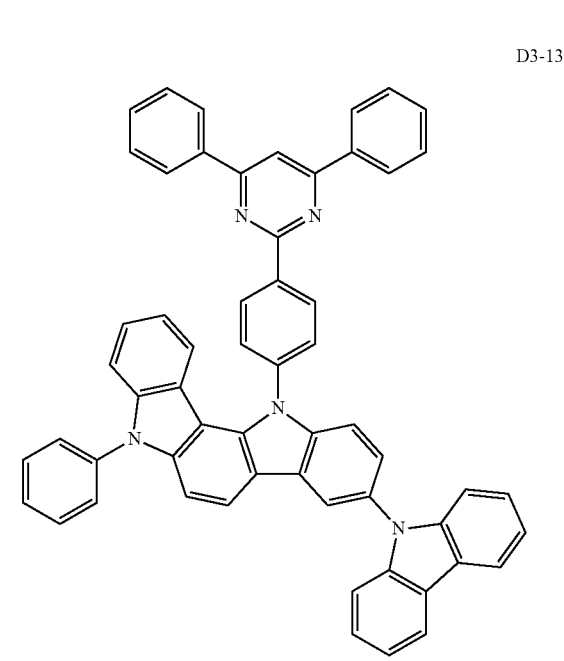
D3-14
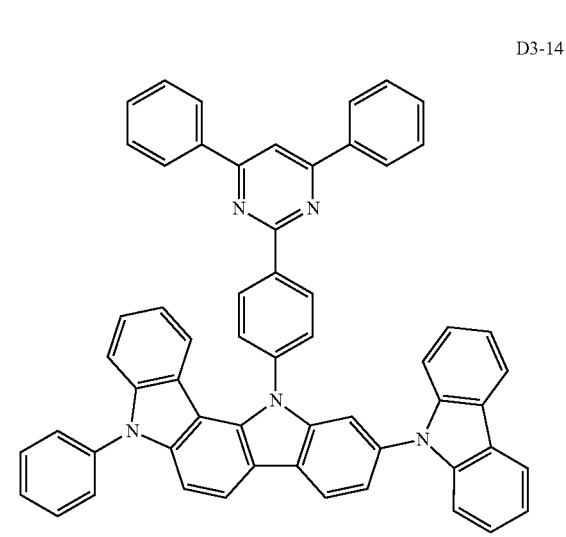
-continued
D3-15
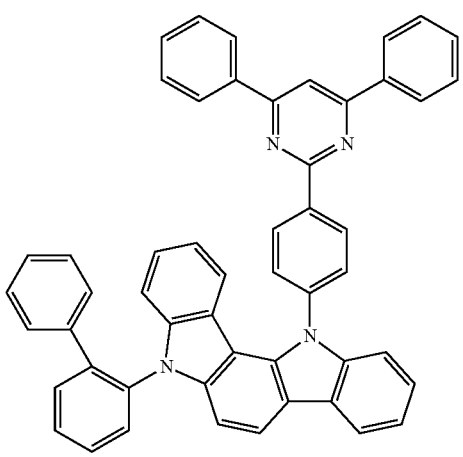
D3-16
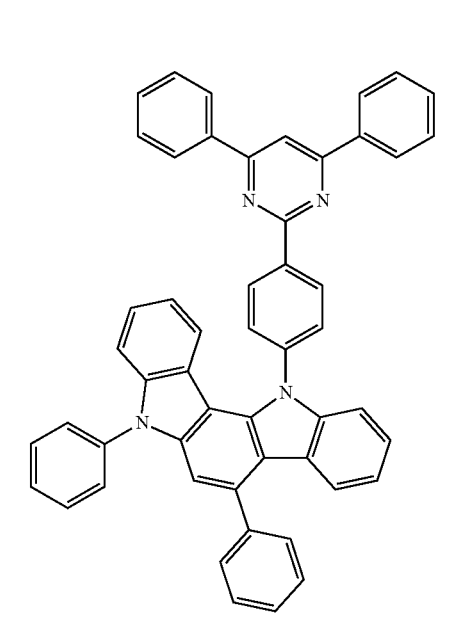
D3-17
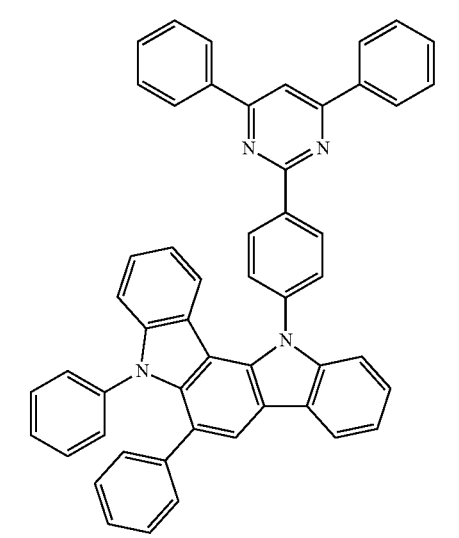

-continued
D3-18
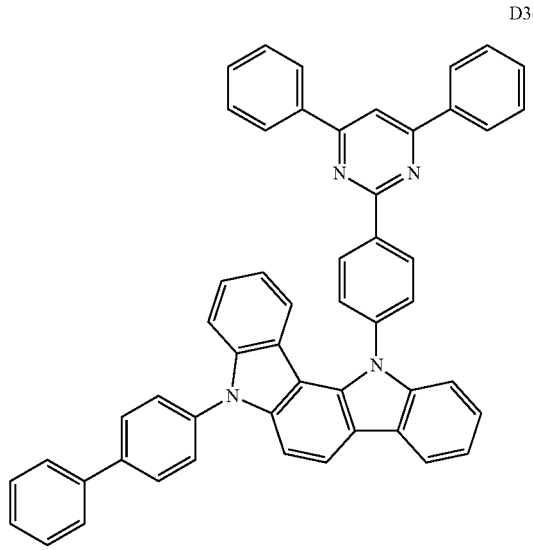
D3-20
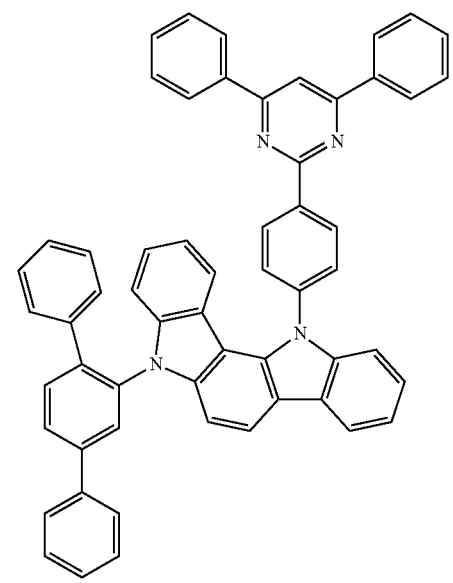
D3-21
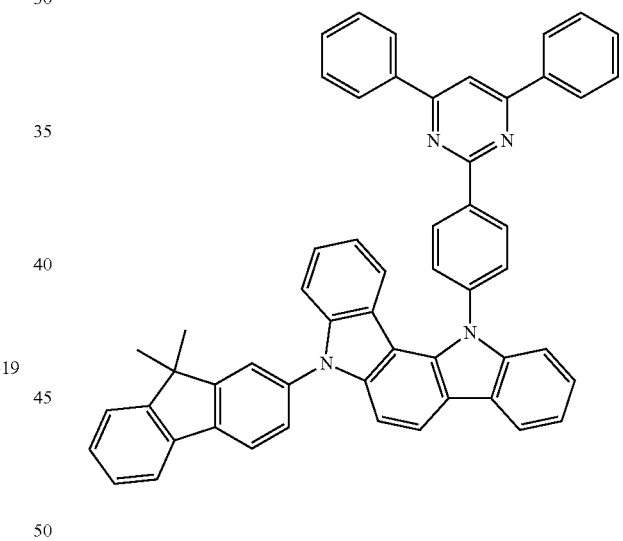
D3-19
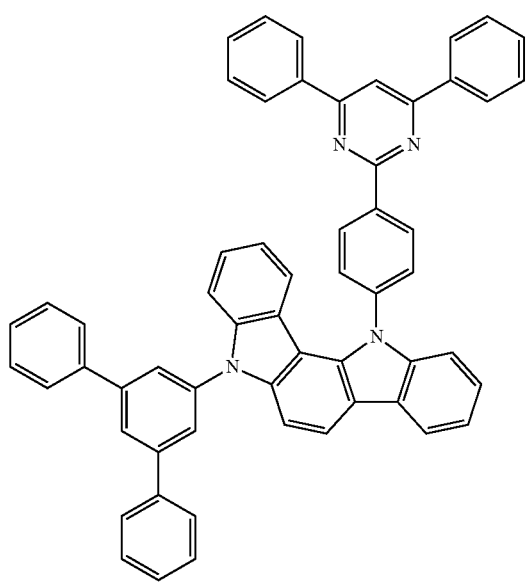
D3-22
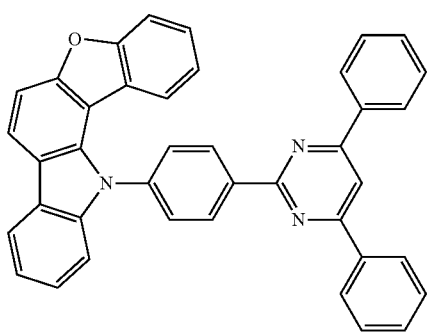

D3-23
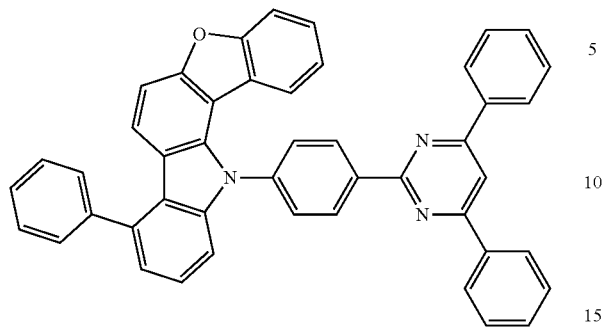
D3-24
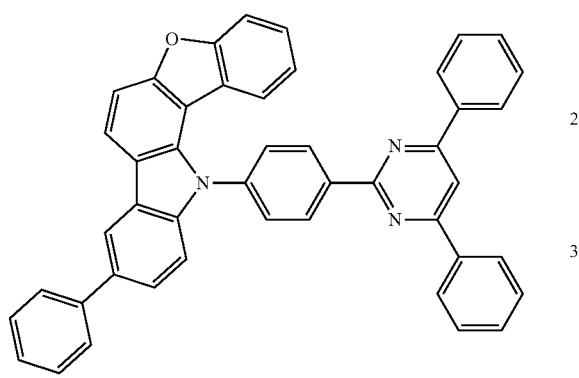
D3-25
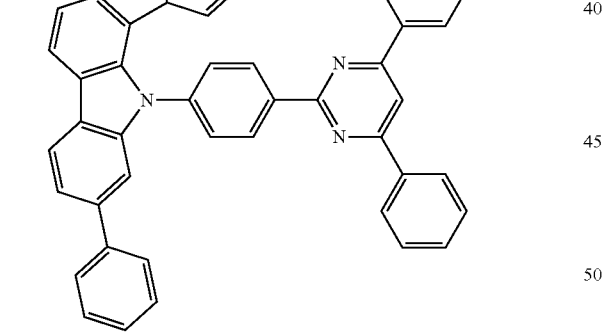
D3-26
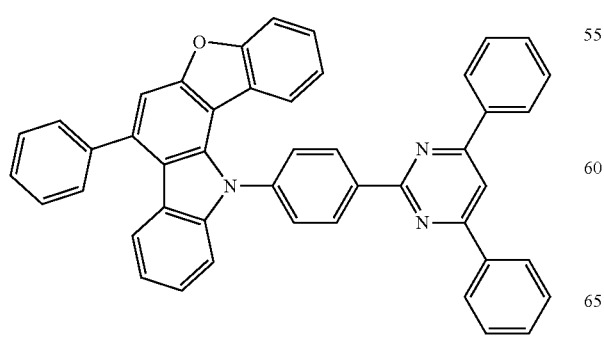
D3-27
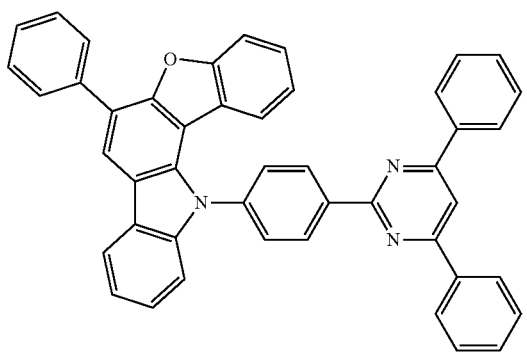
D3-28
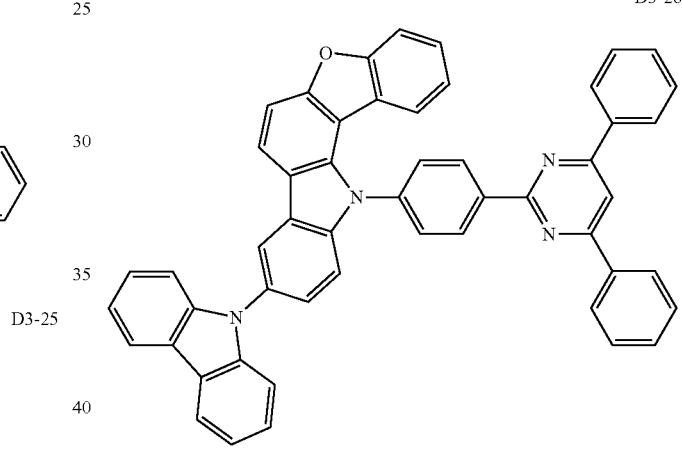
D3-29
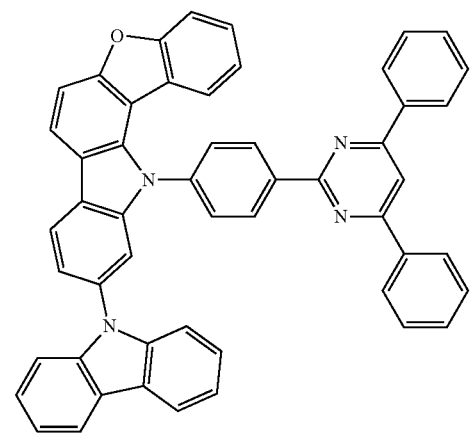

D3-30
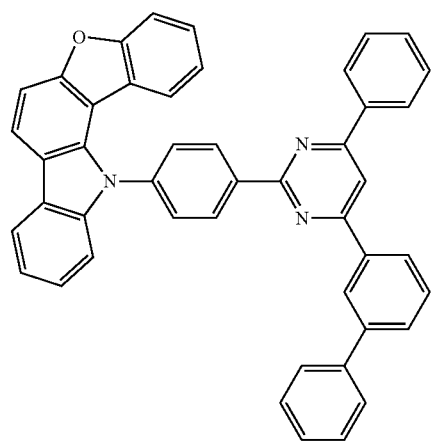
D3-34
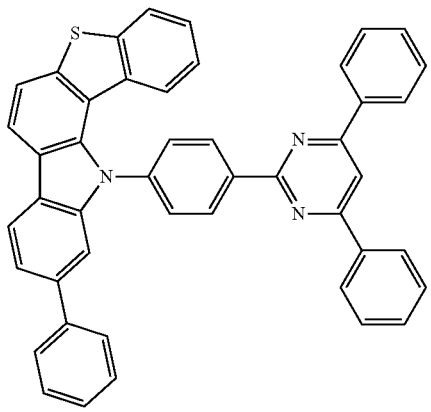
D3-31
D3-35
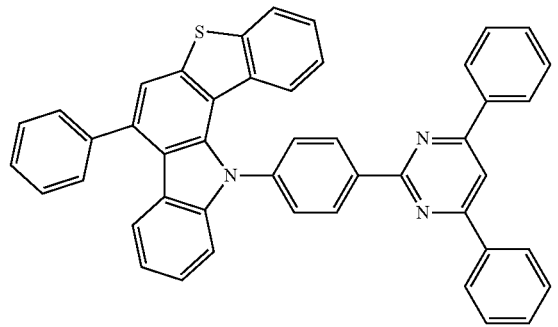
D3-32
D3-36
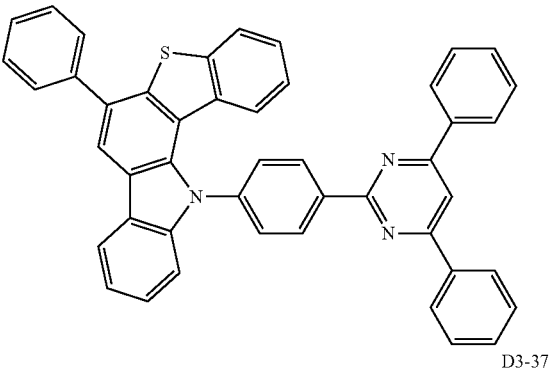
D3-33
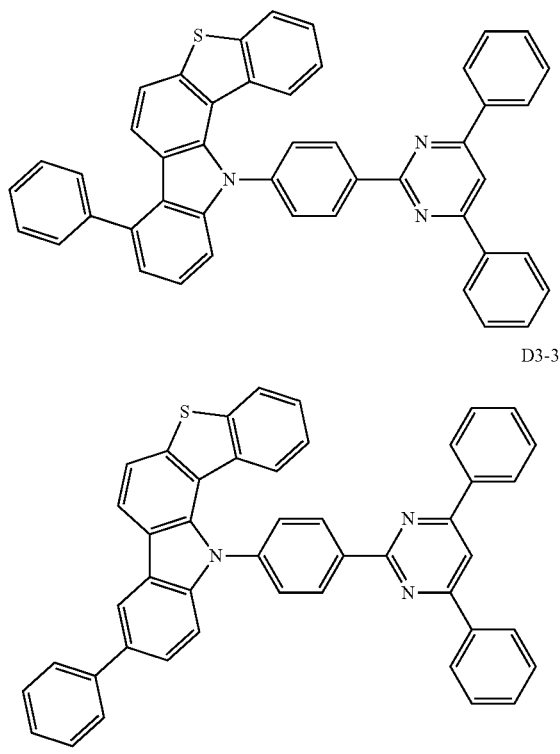
D3-37

D3-38
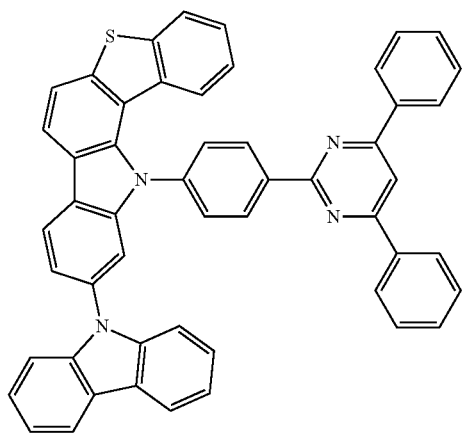
D3-39
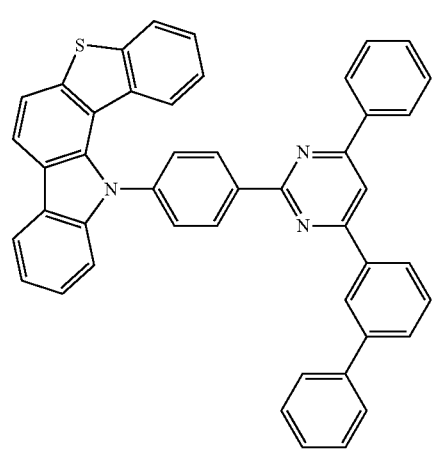
D3-40
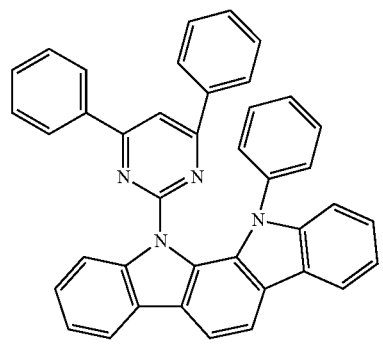
D3-41
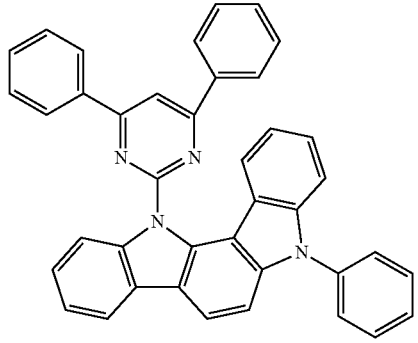
D3-42
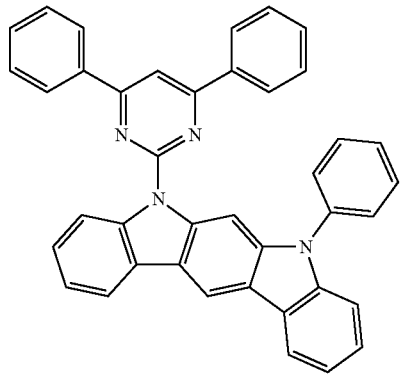
D3-43
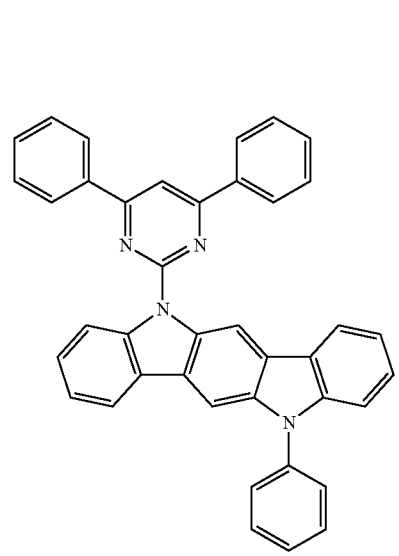
D3-44
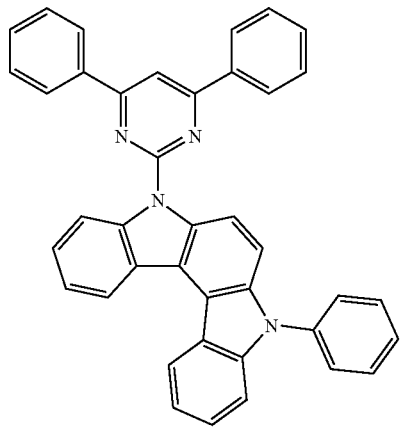

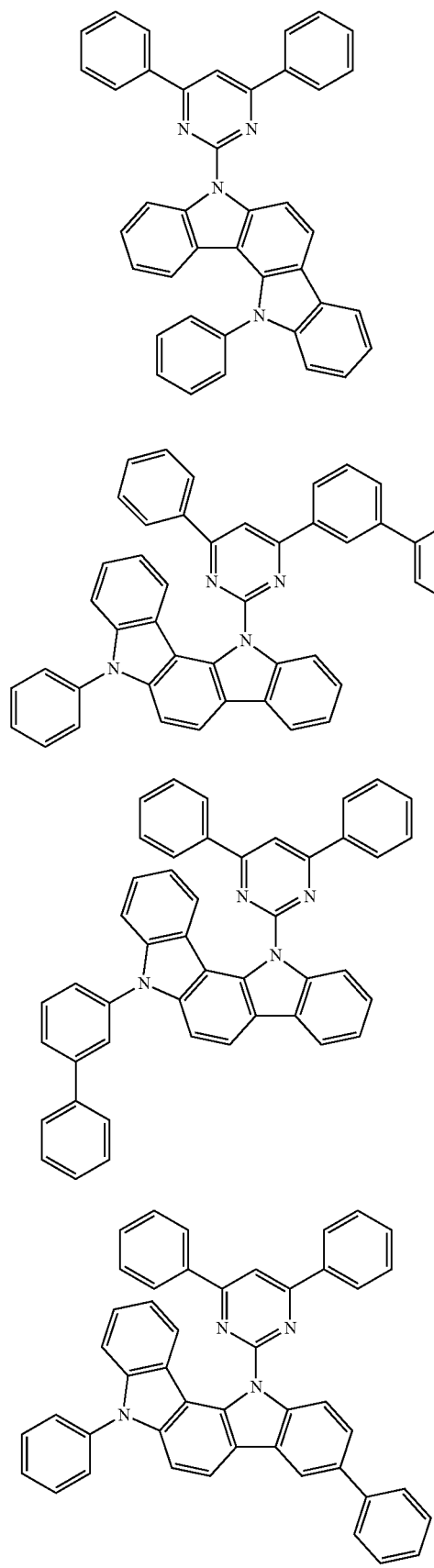
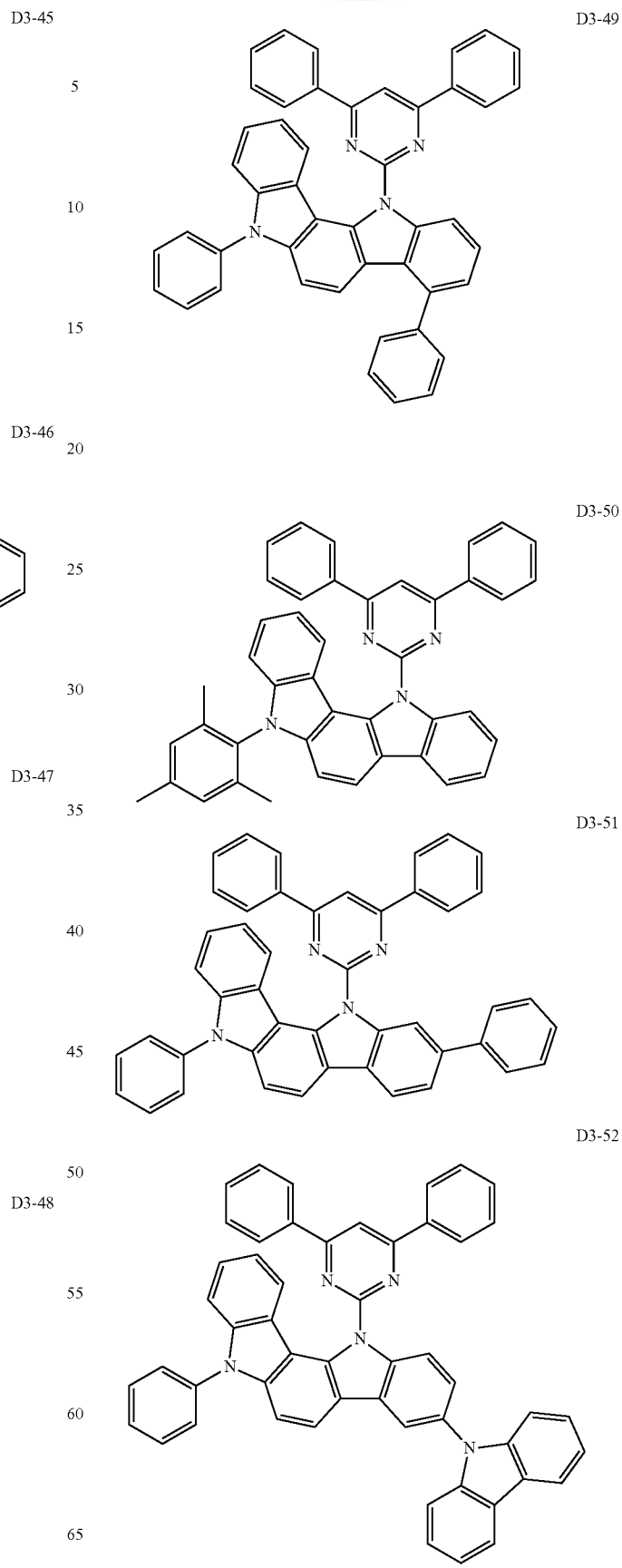

D3-53
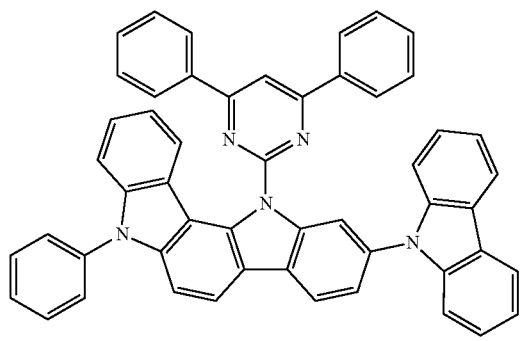
D3-54
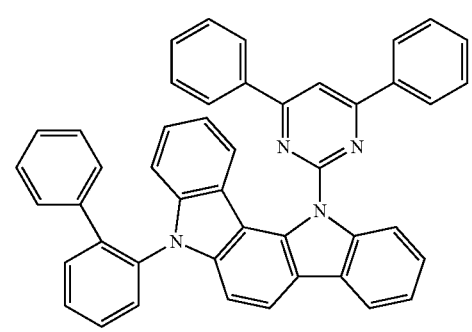
D3-55
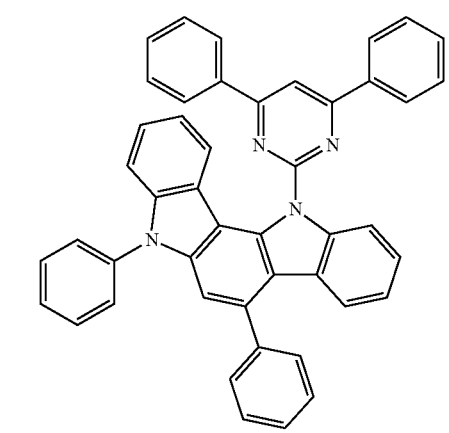
D3-56
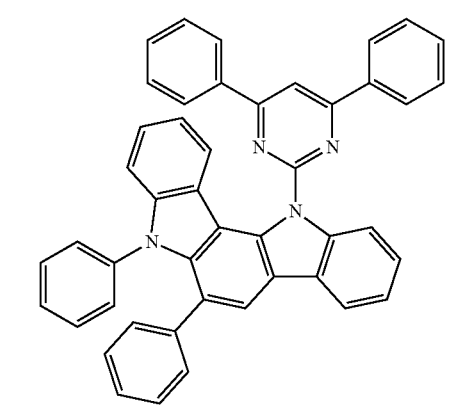
D3-57
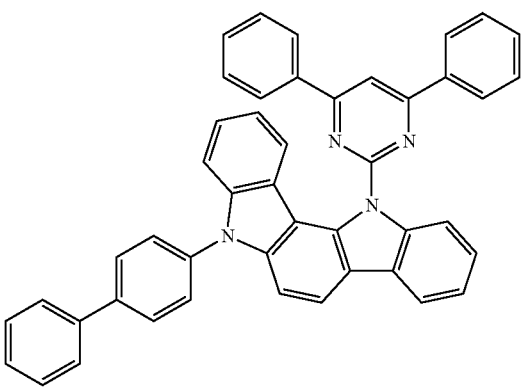
D3-58
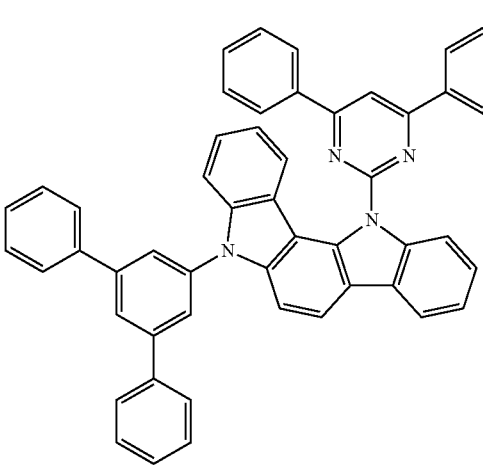
D3-59
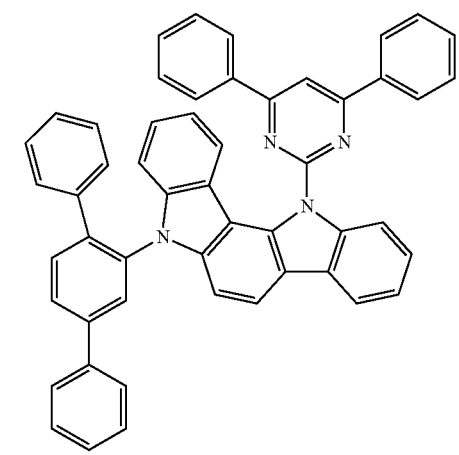

-continued
D3-60
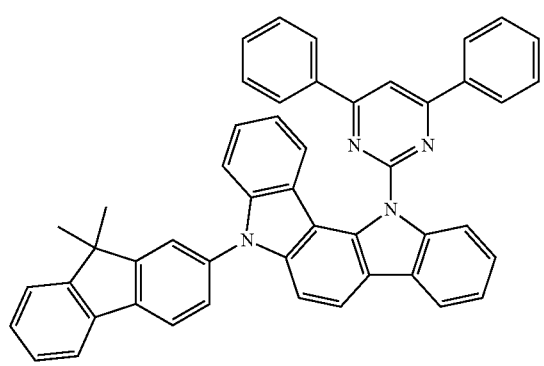
D3-61
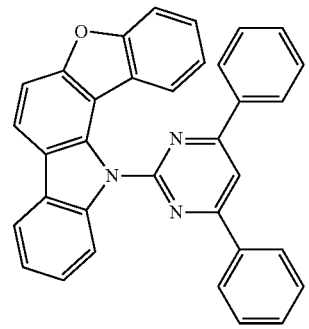
D3-62
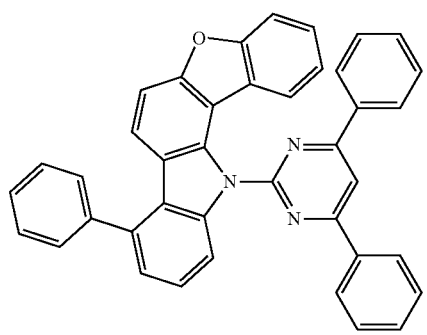
D3-63
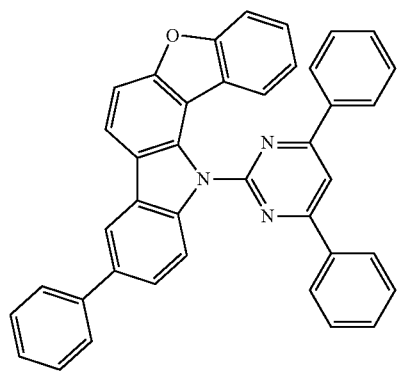
-continued
D3-64
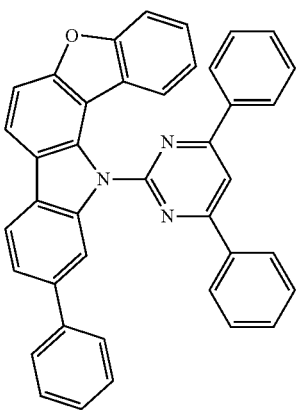
D3-65
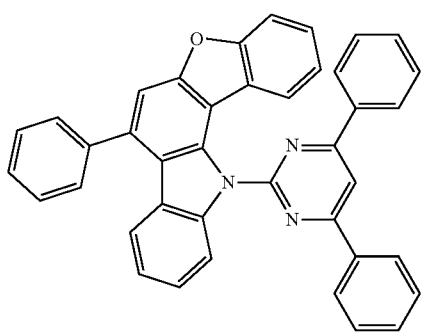
D3-66
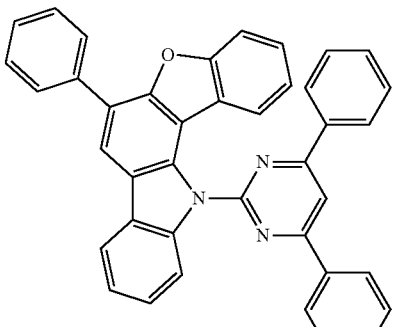
D3-67
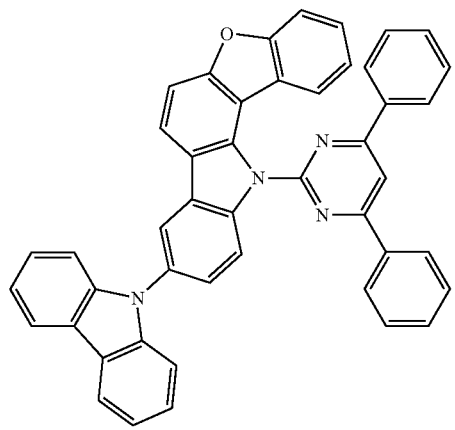

D3-68
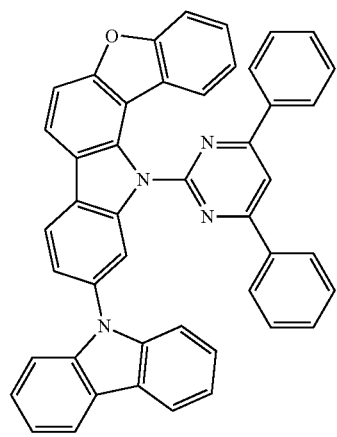
D3-69
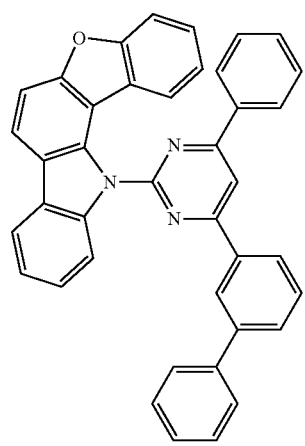
D3-70
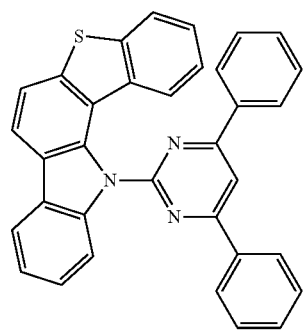
D3-71
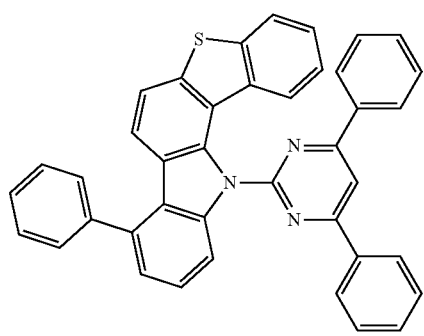
D3-72
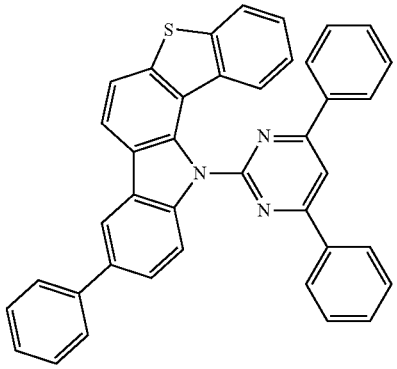
D3-73
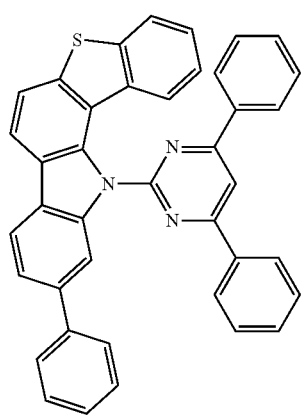
D3-74
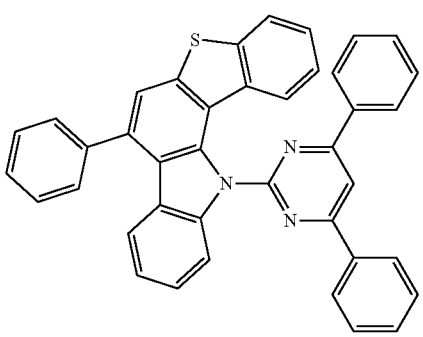
D3-75
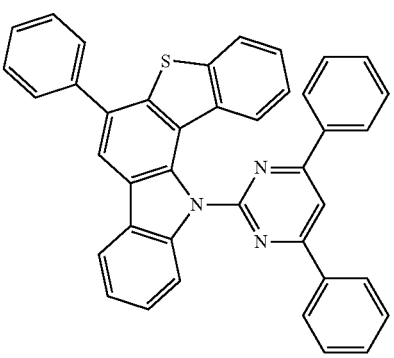

-continued
D3-76
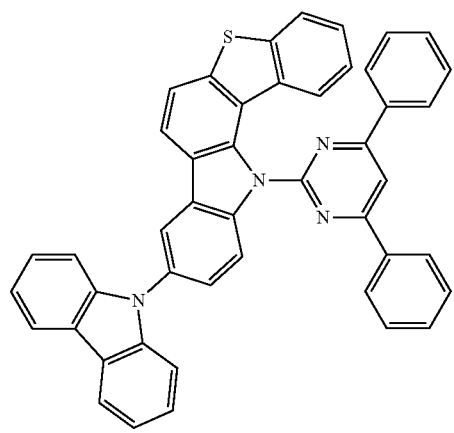
D3-77
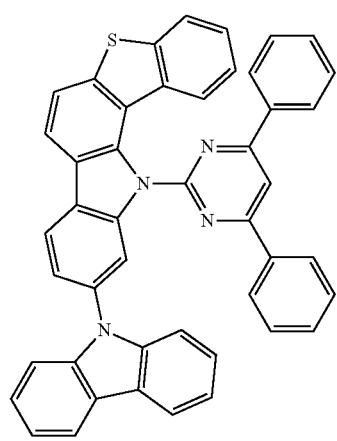
D3-78
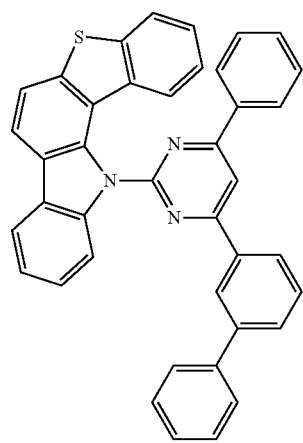
D3-79
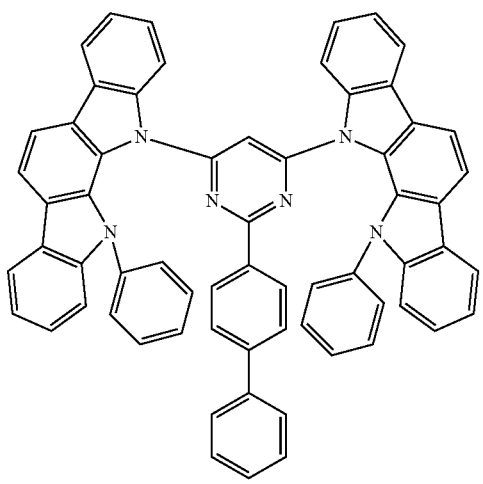
D3-80
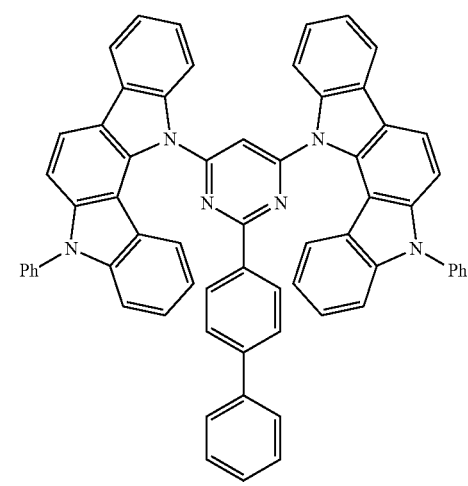
D3-81
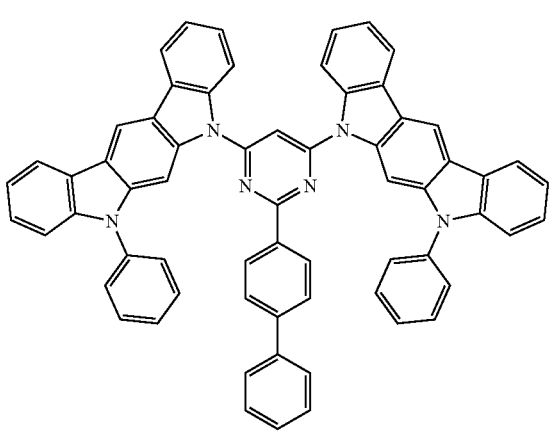
D201
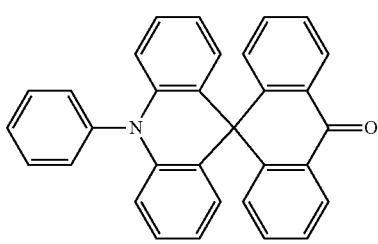

-continued
D202
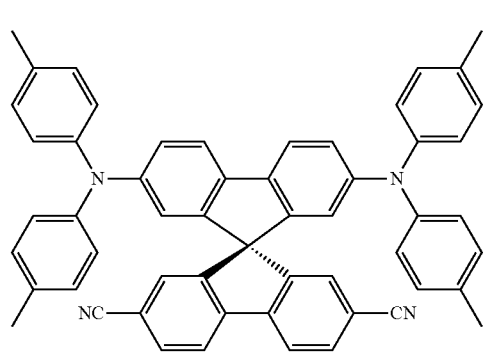
D203
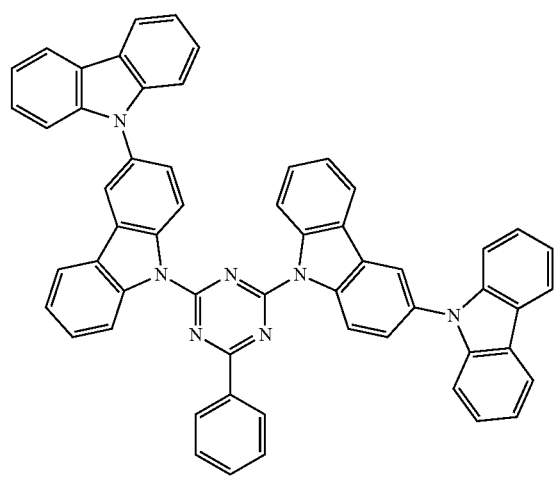
D204
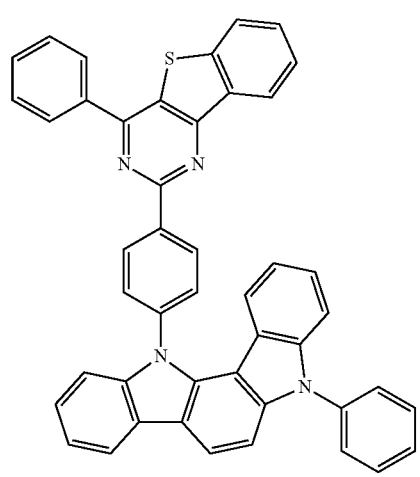
D205
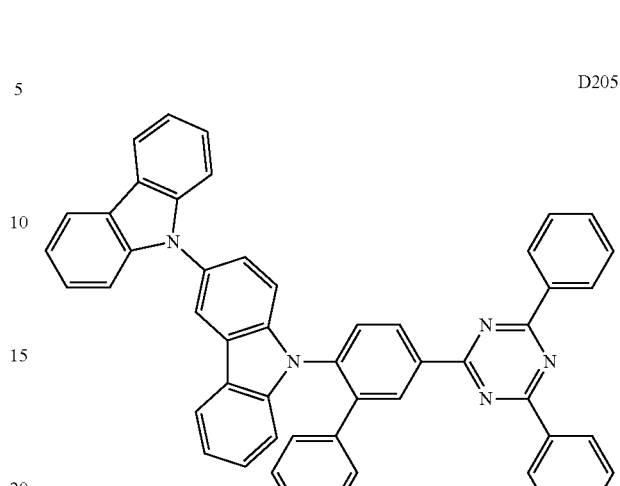
D206
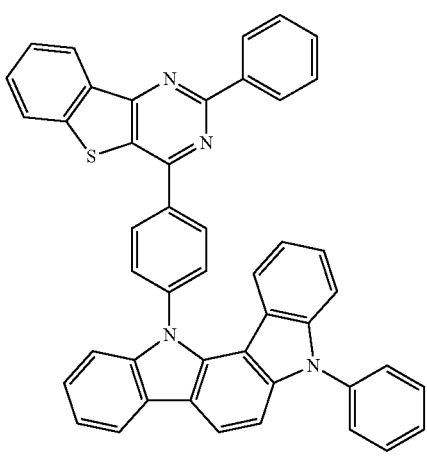

D207
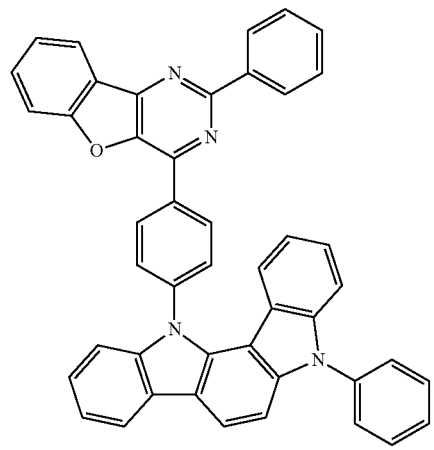
D208
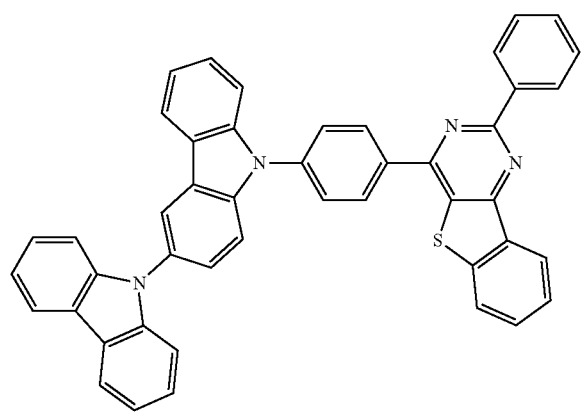
D209
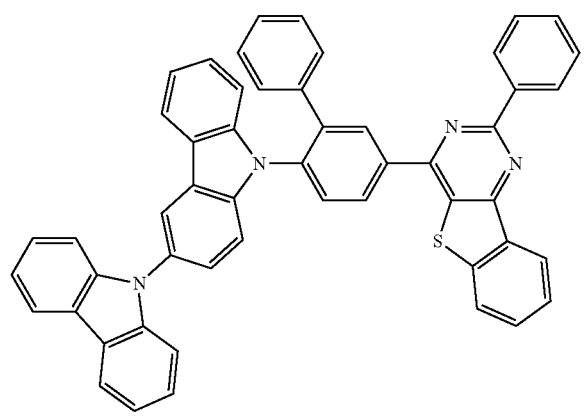

D210
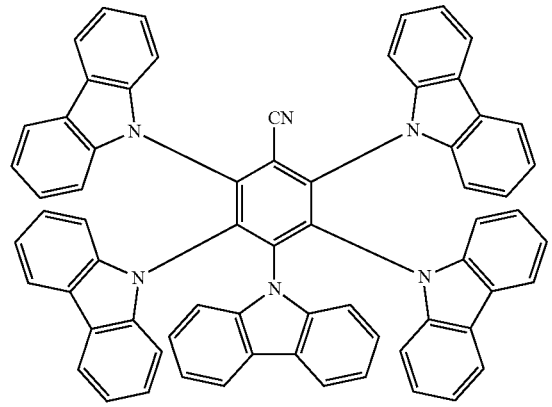
D211
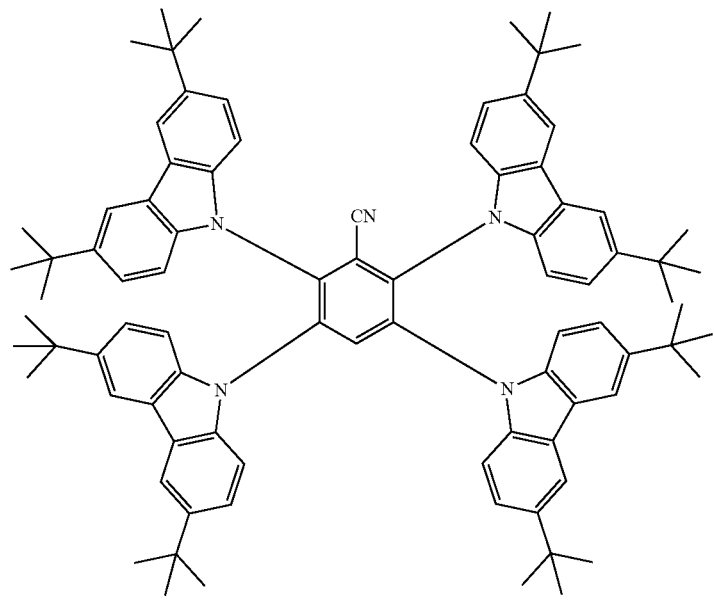
1
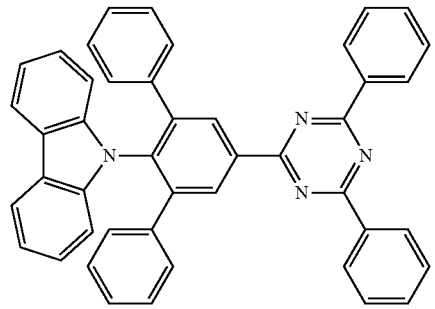
2
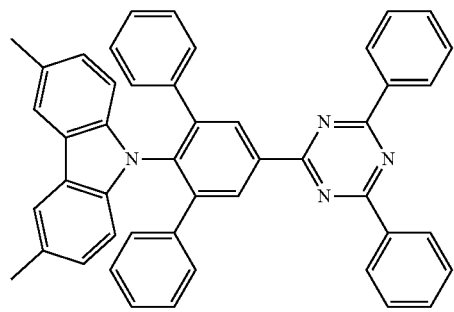

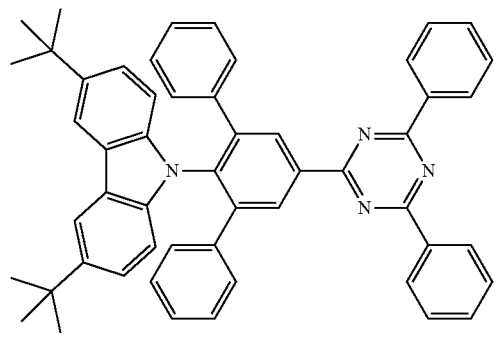
3
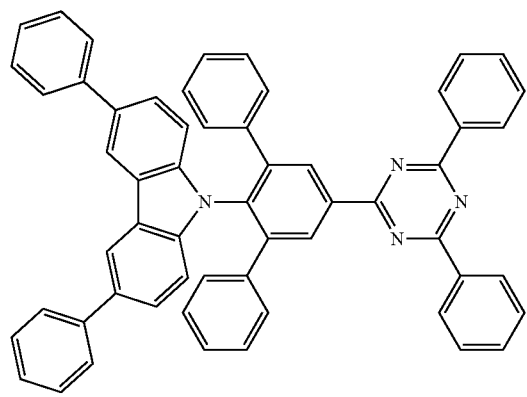
4
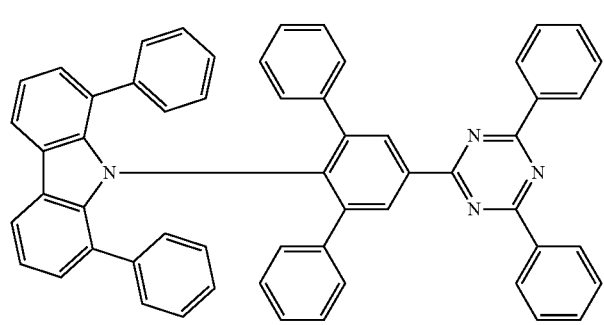
5
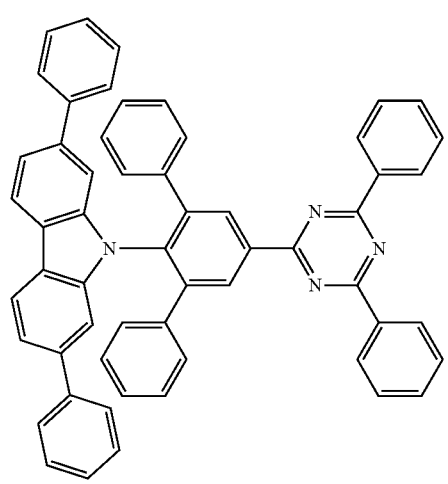
6

7
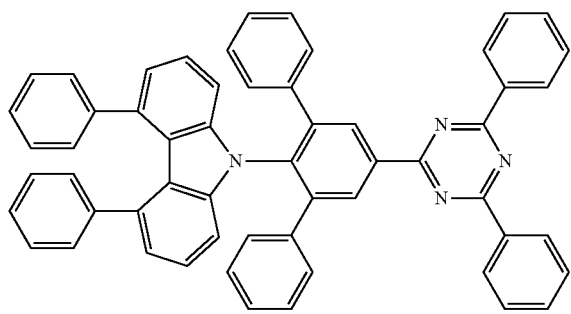
8
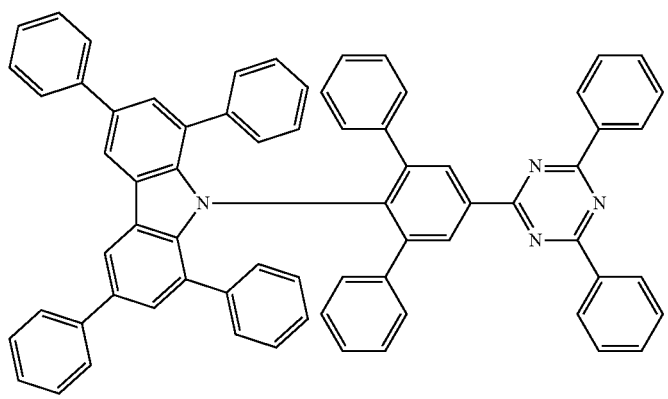
9
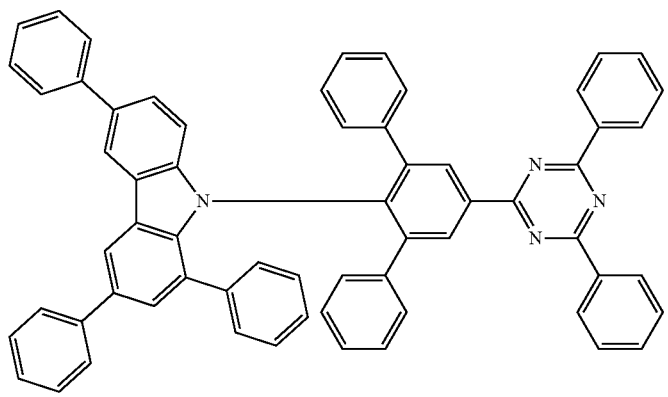
10
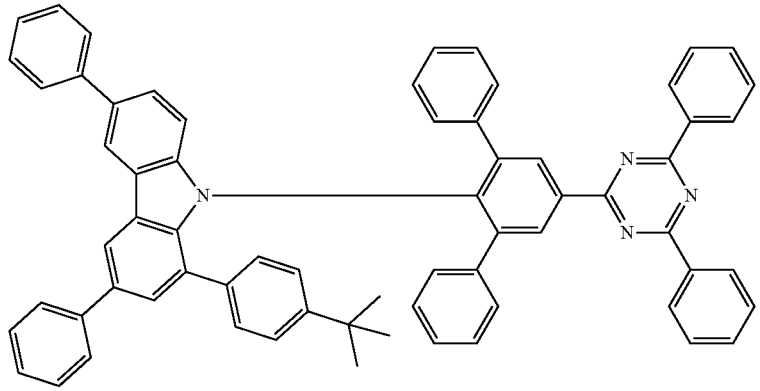

11
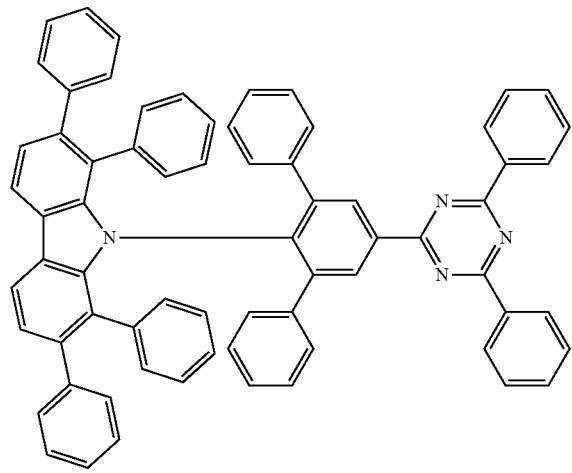
12
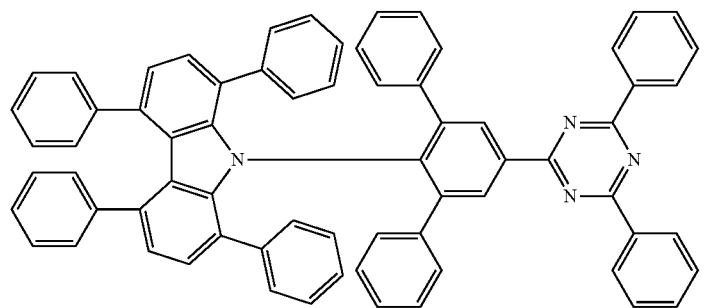
13
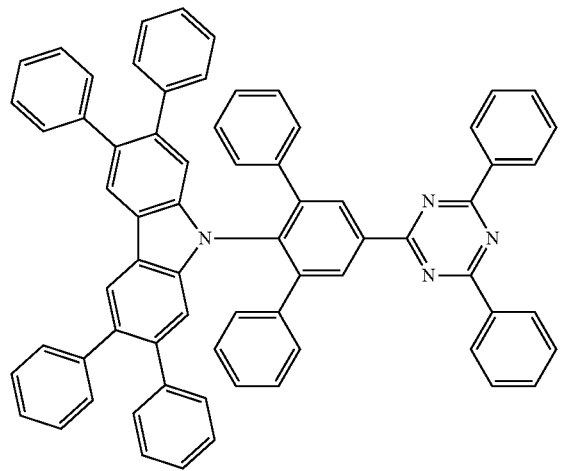

14
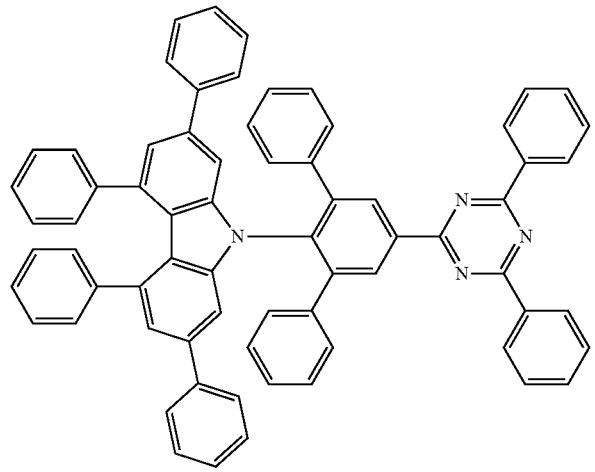
15
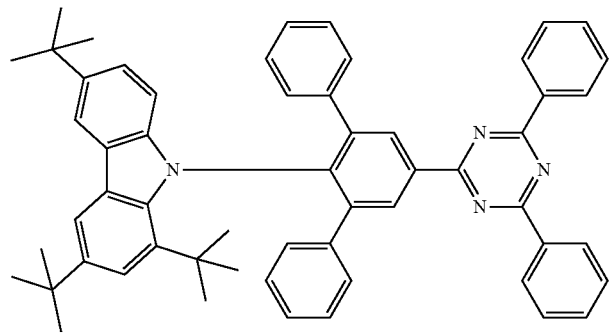
16
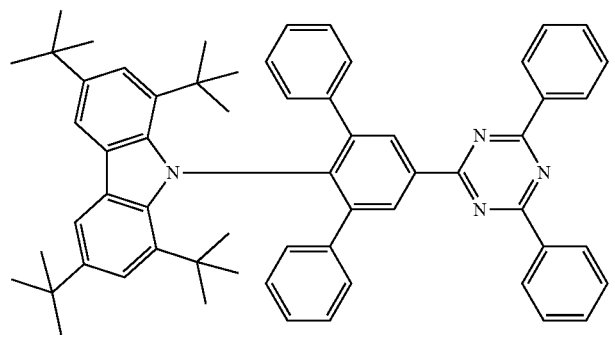
17
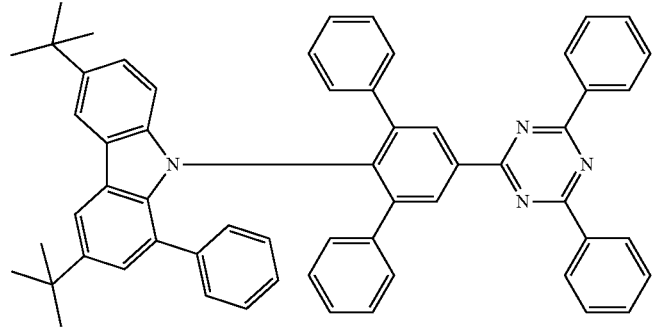

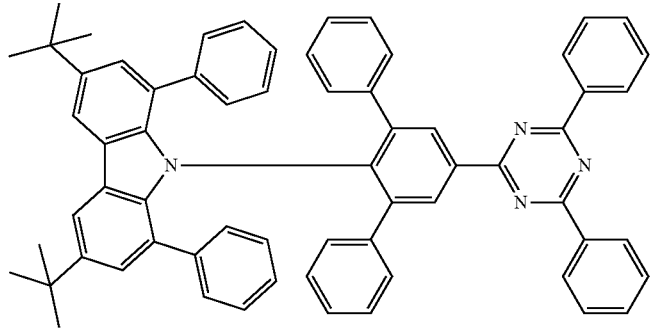
18

19
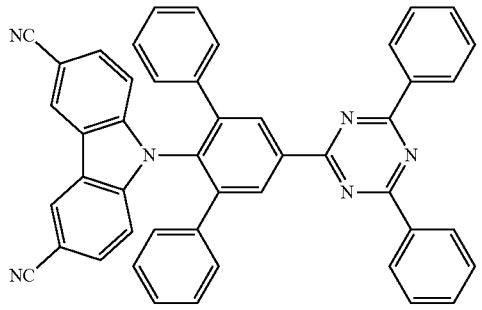
20
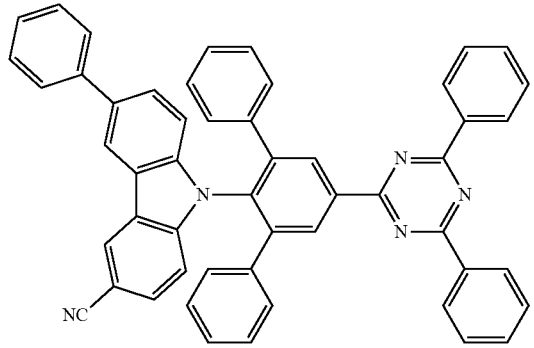
21
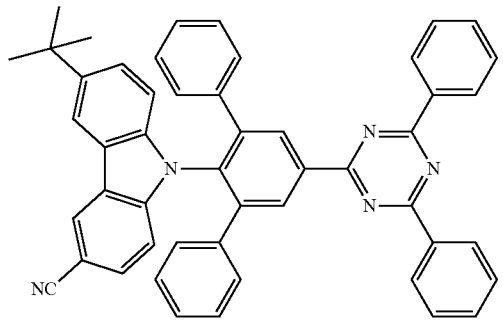
22

-continued
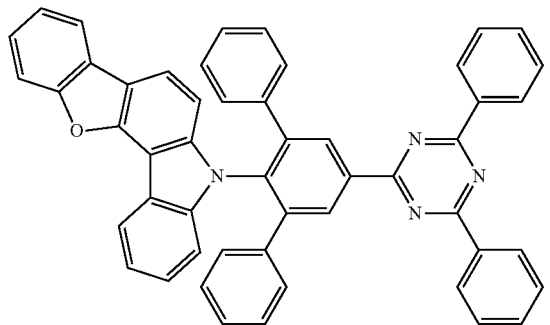
23
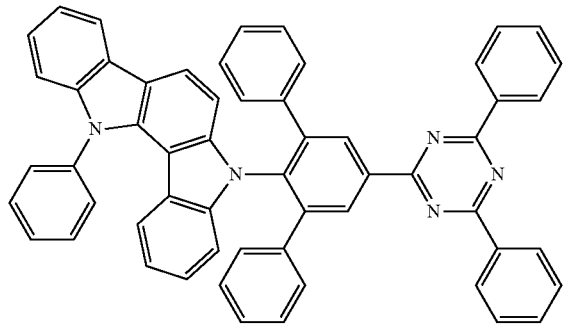
24
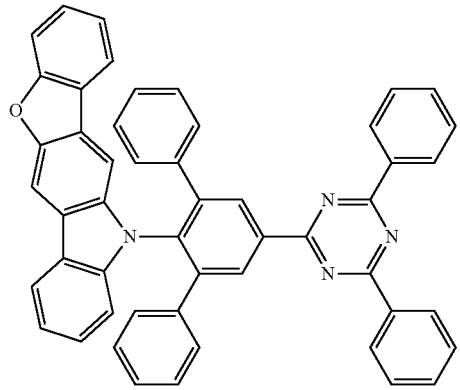
25
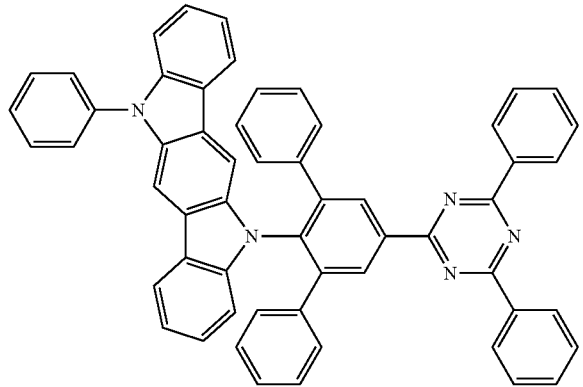
26

-continued
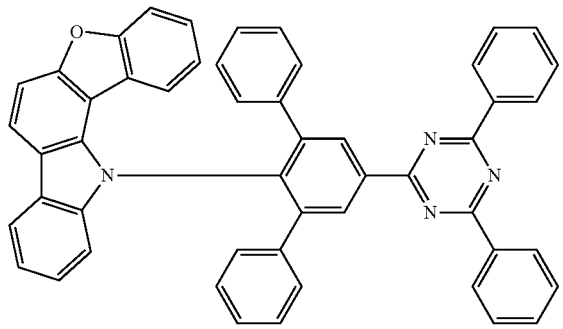
27
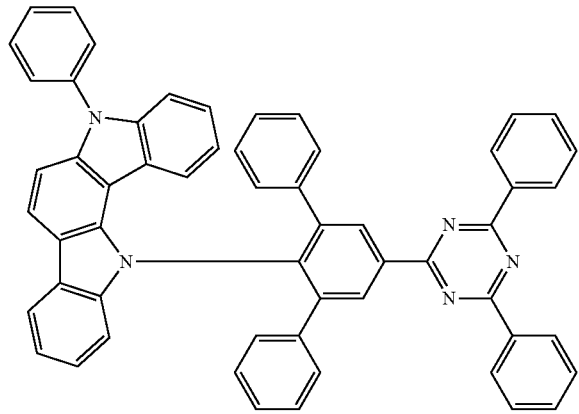
28
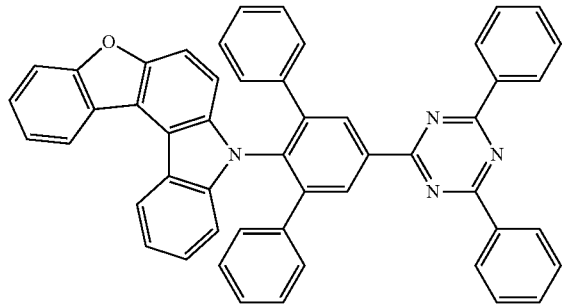
29
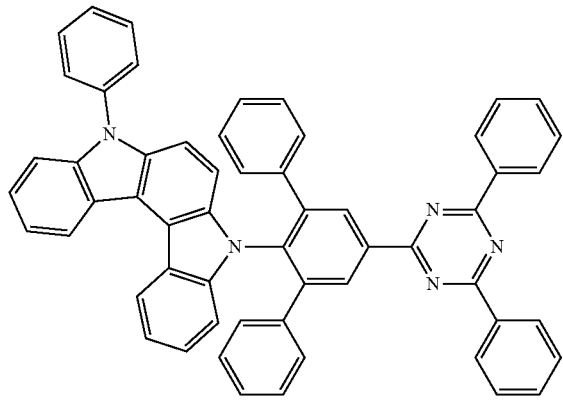
30

31
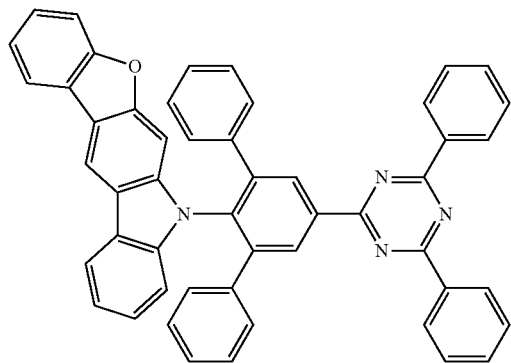
32
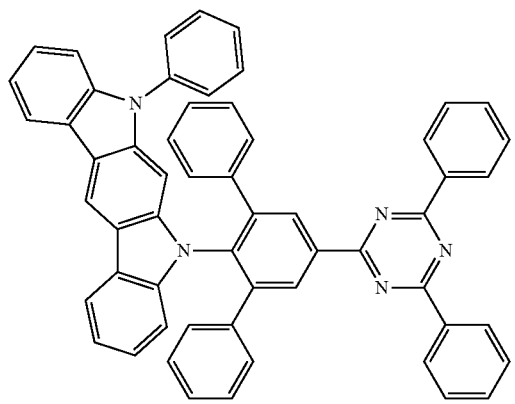
33
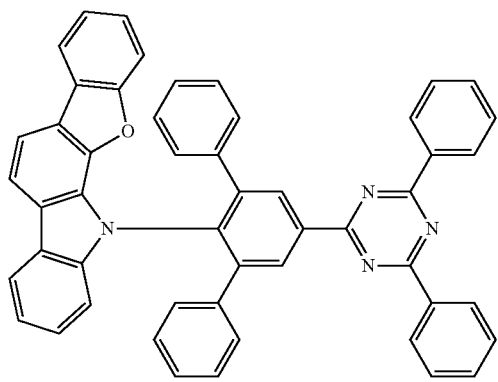
34
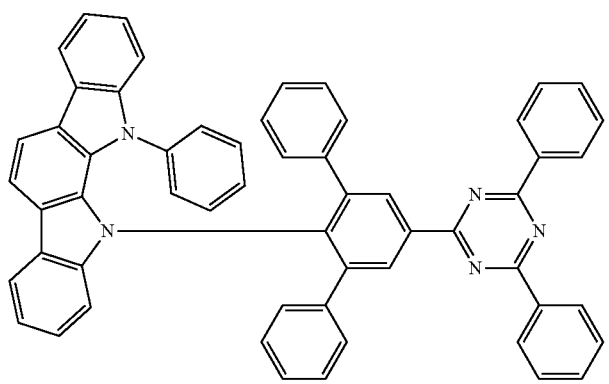

35
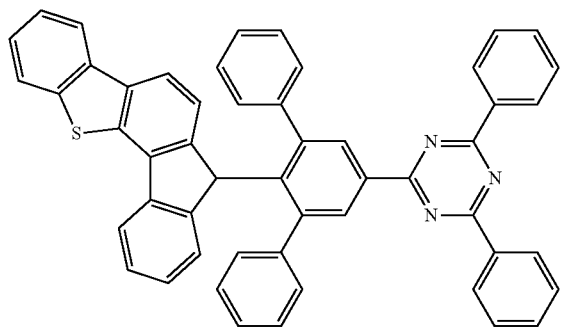
36
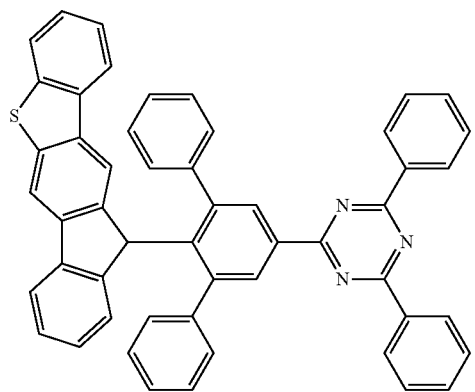
37
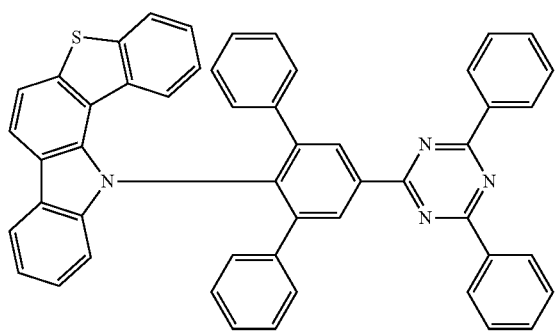
38
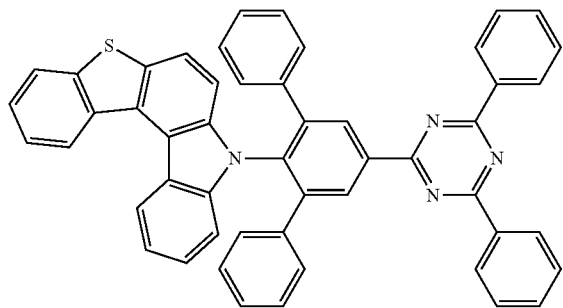

39
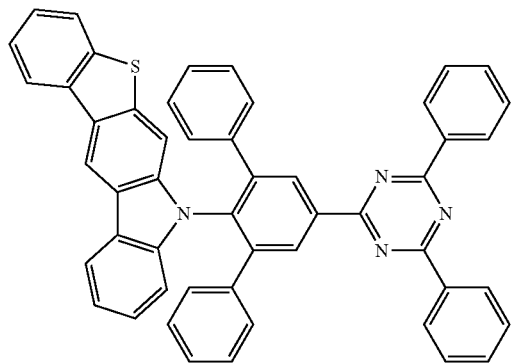
40
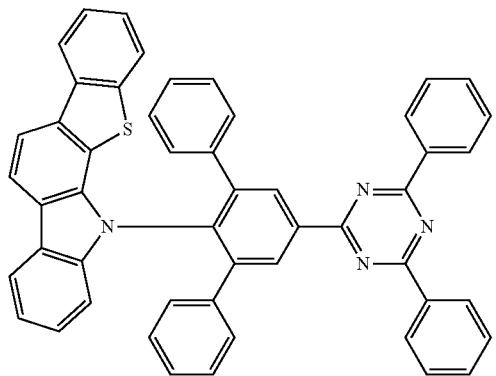
41
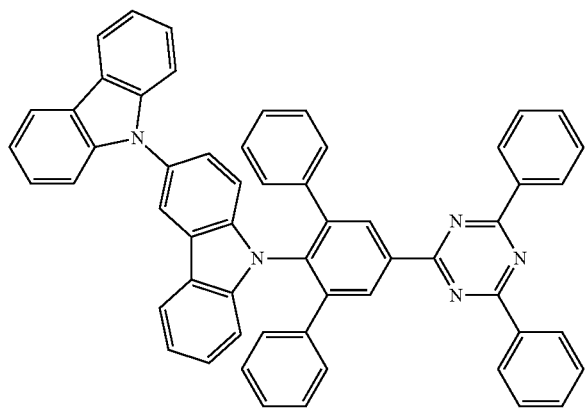
42
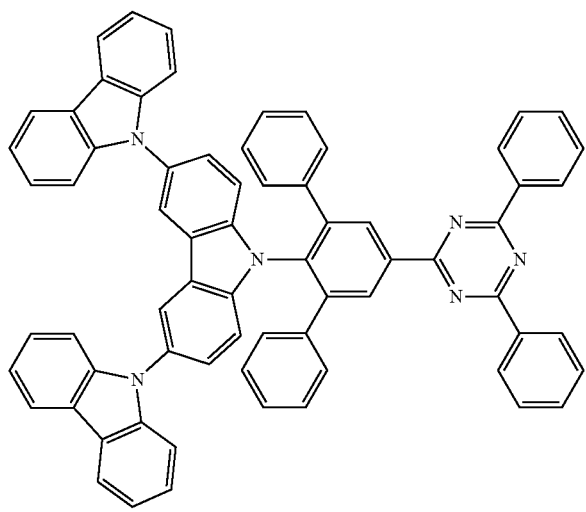

43
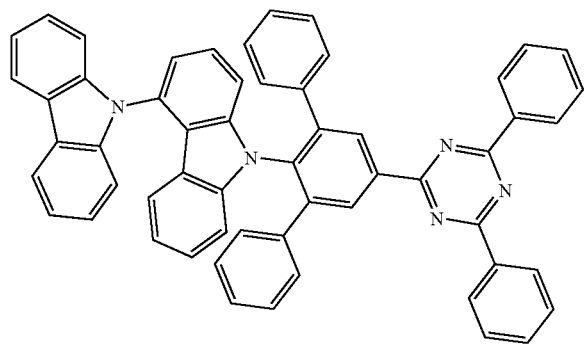
44
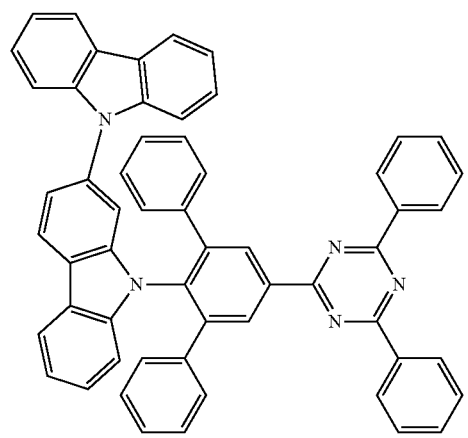
45
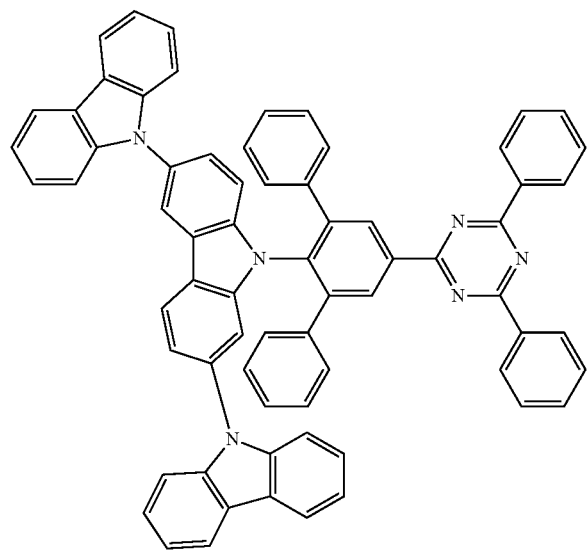

-continued
46
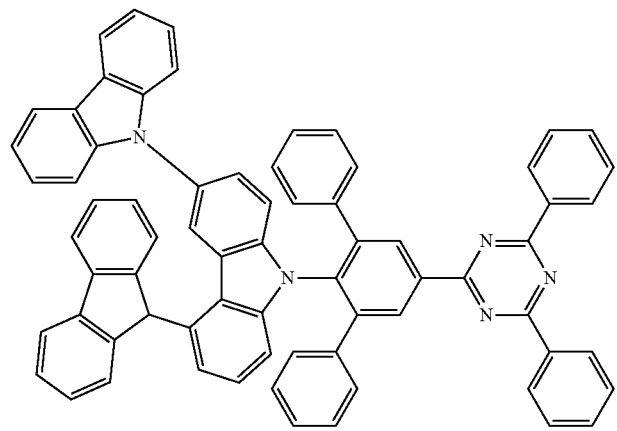
47
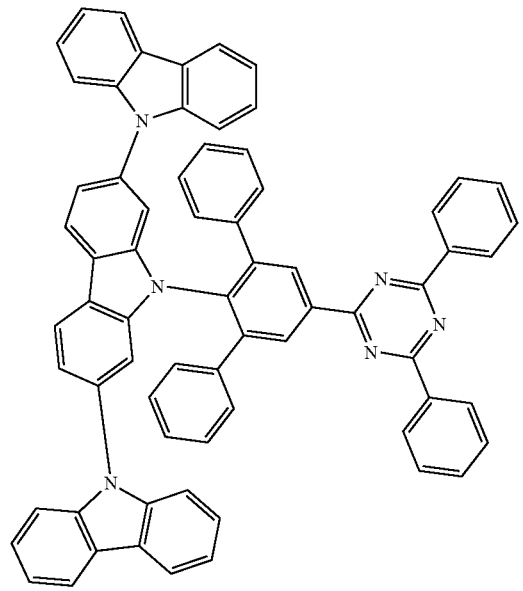
48
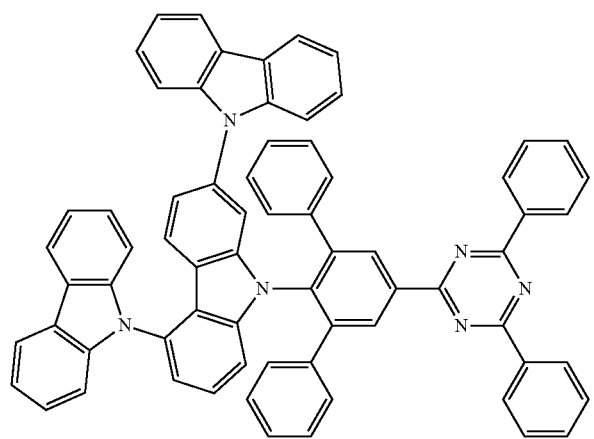

49
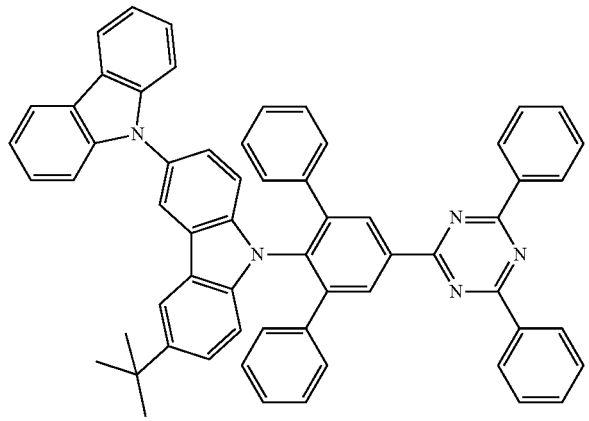
50
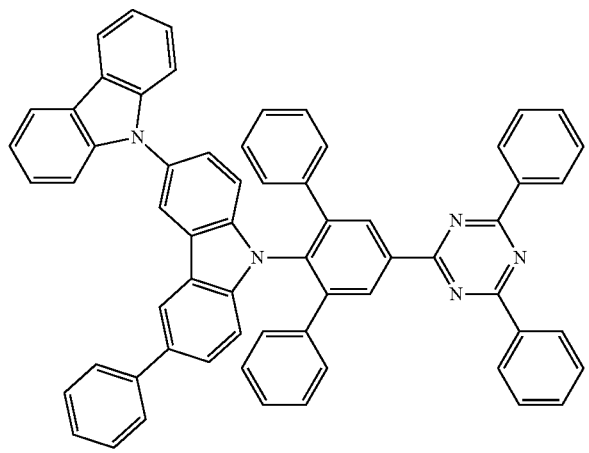
51
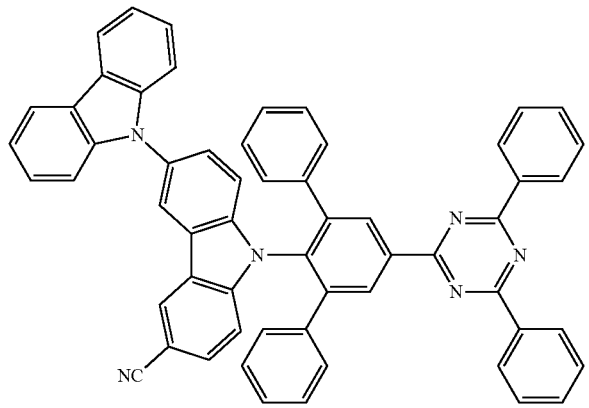

52
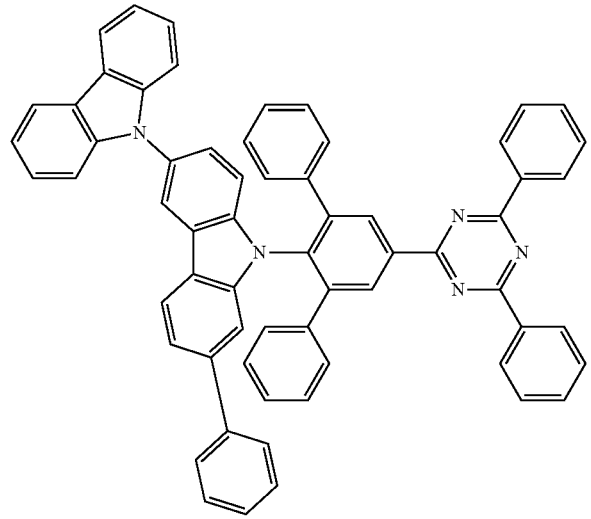
53
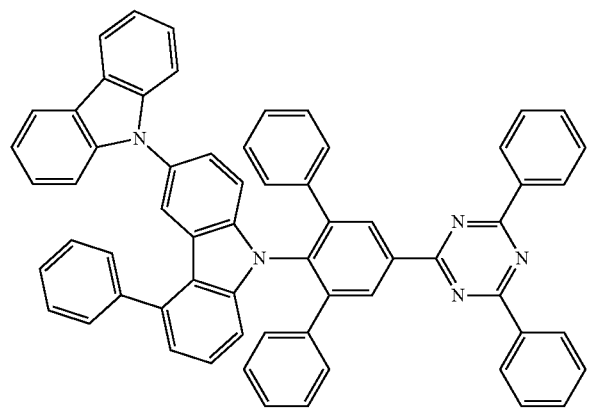
54
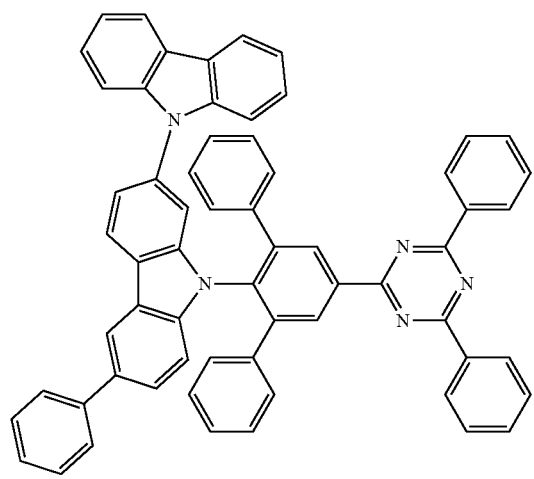

-continued
55
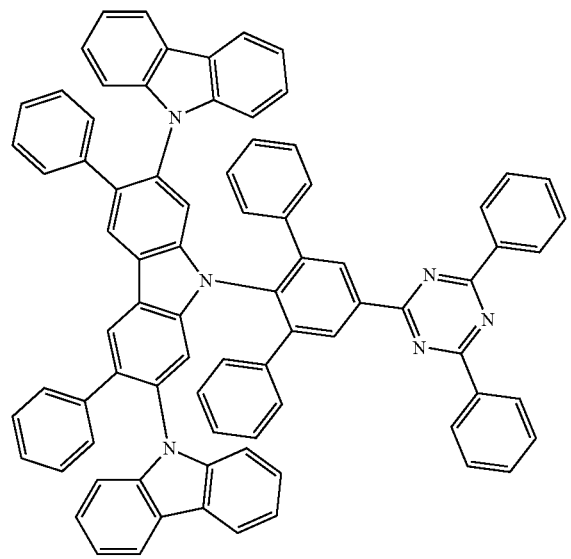
56
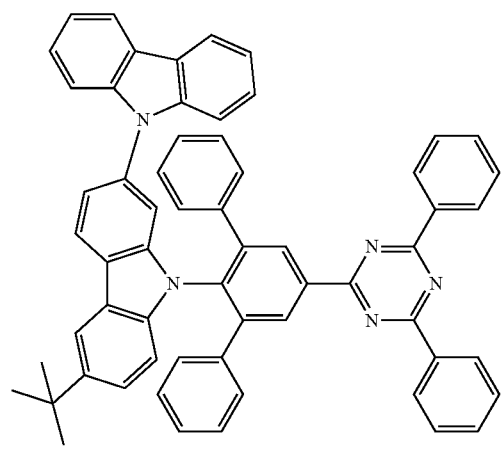
57
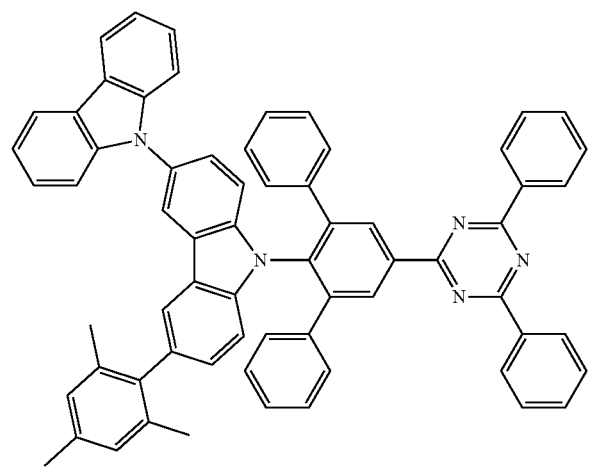

58
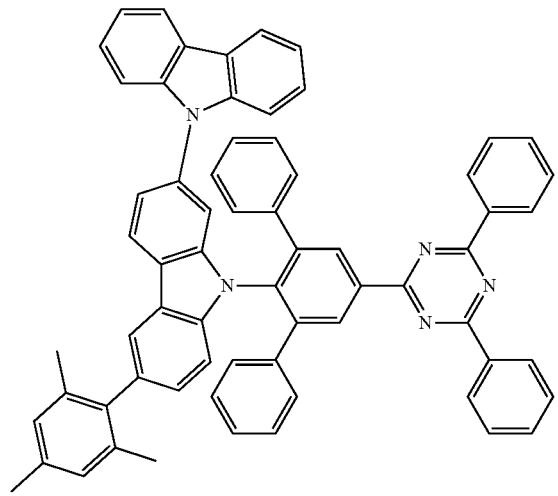
59
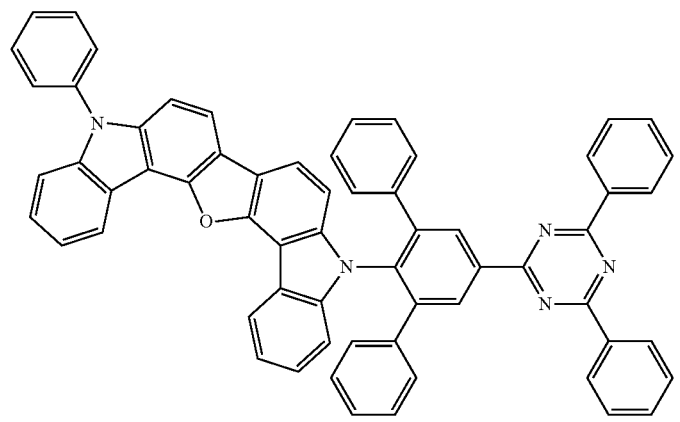
60
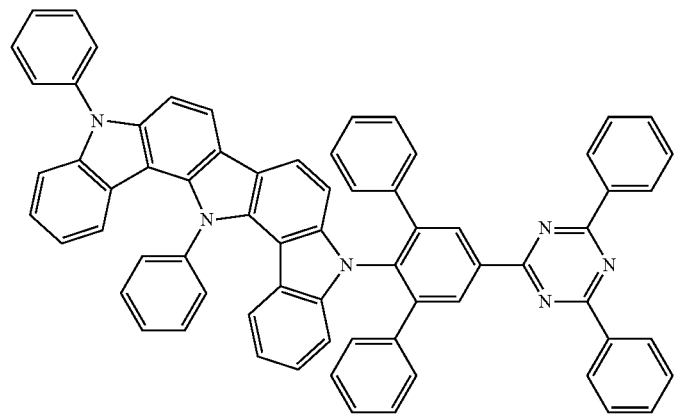

61
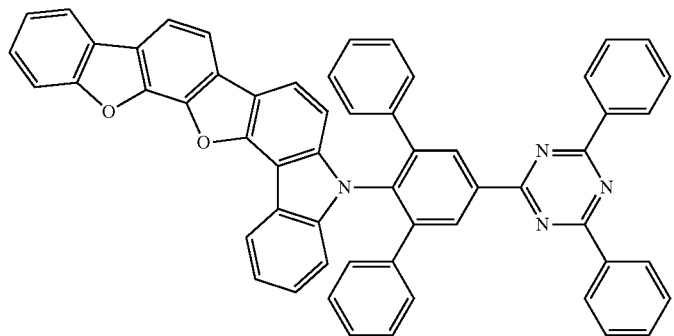
62
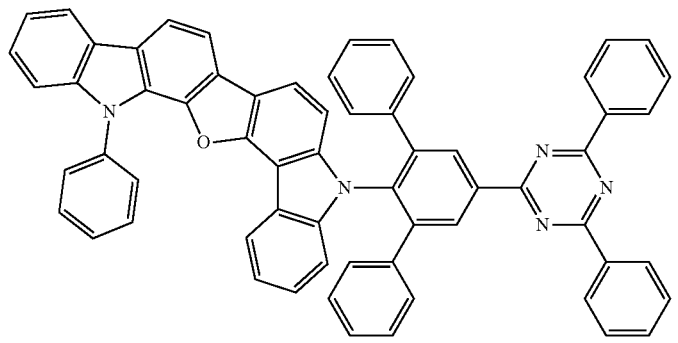
63
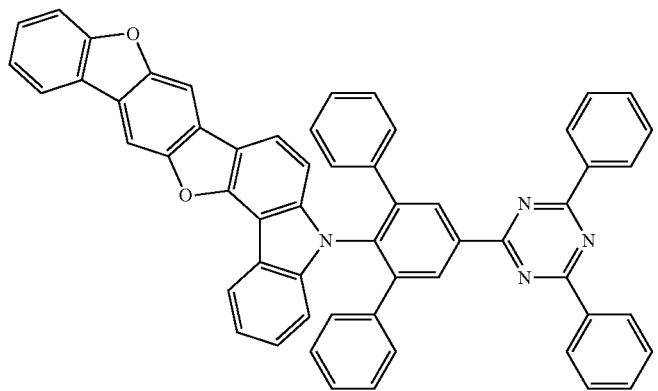
64
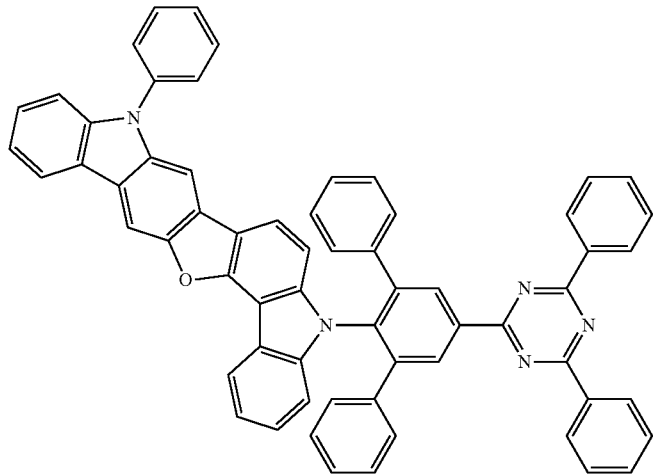

-continued
65
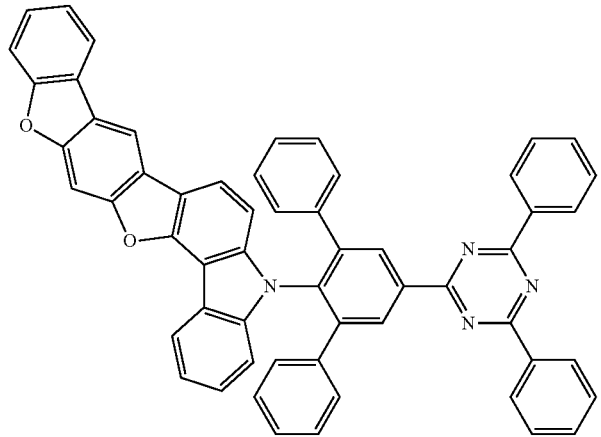
66
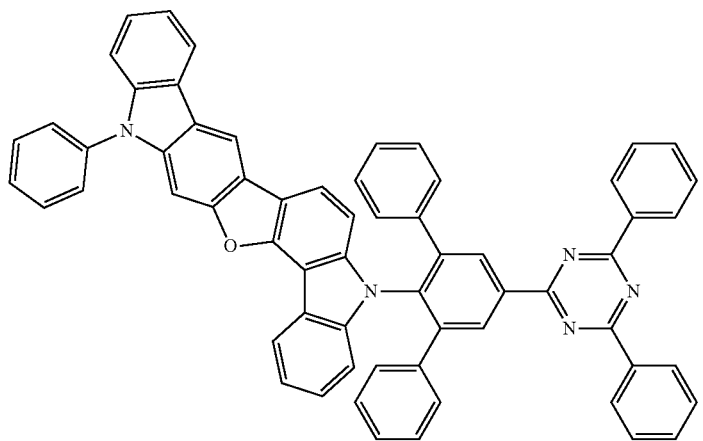
67
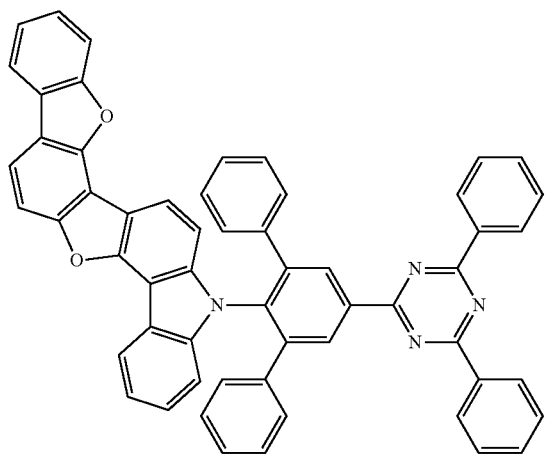

-continued
68
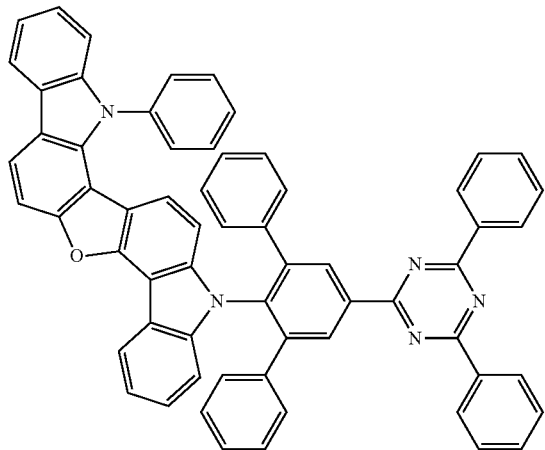
69
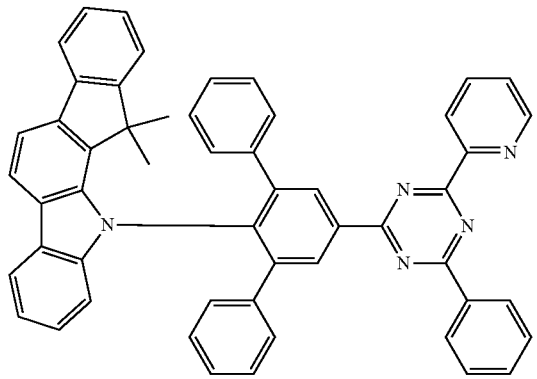
70
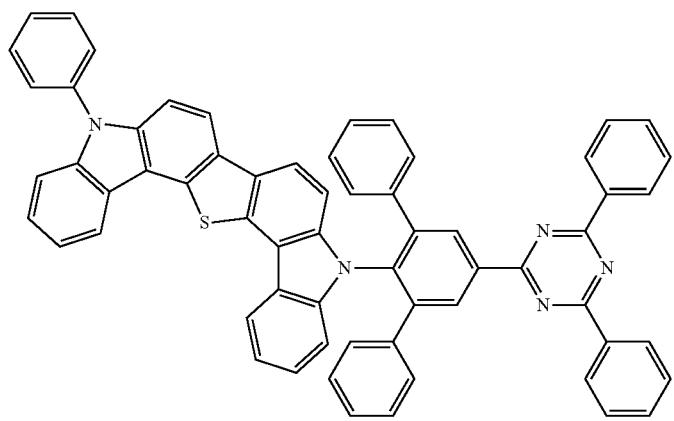
71
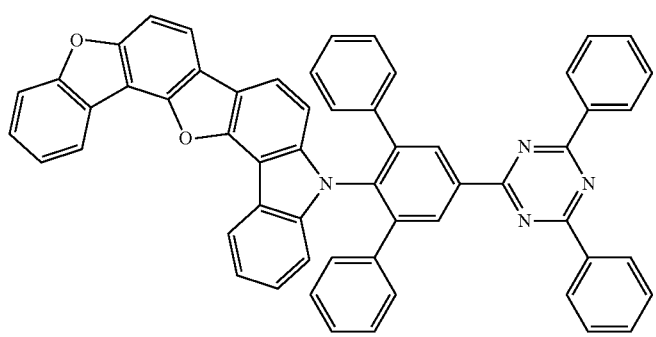

-continued
72
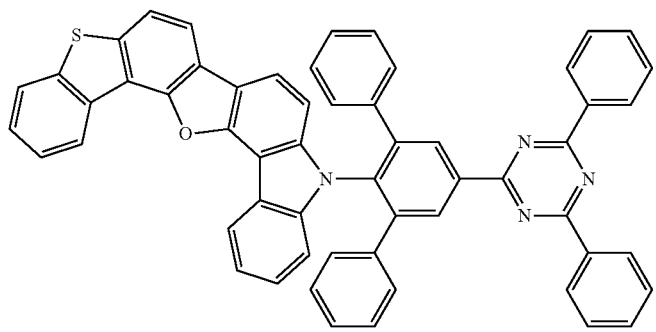
73
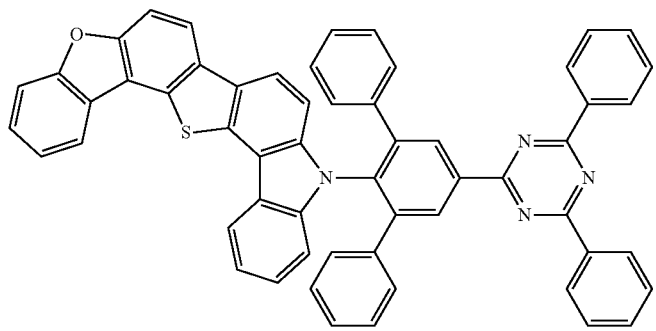
74
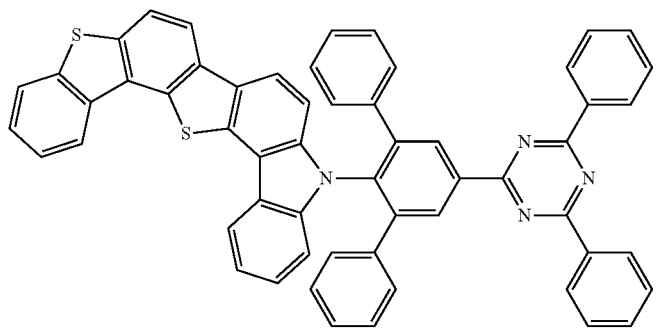
75
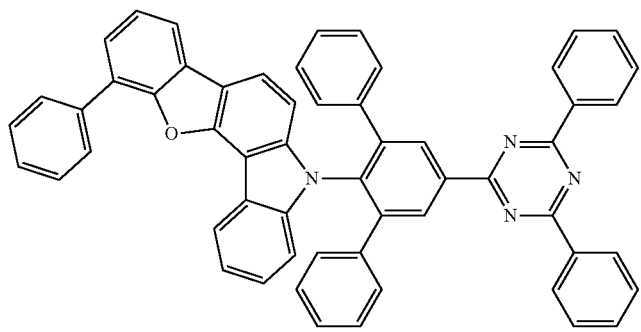
76
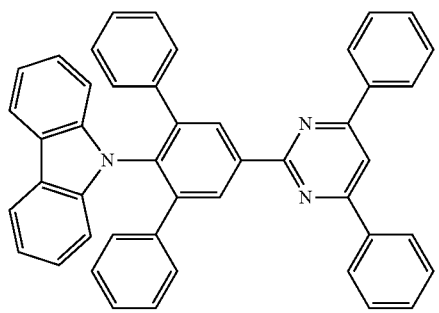

77
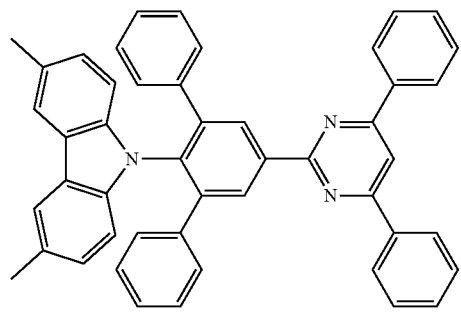
78
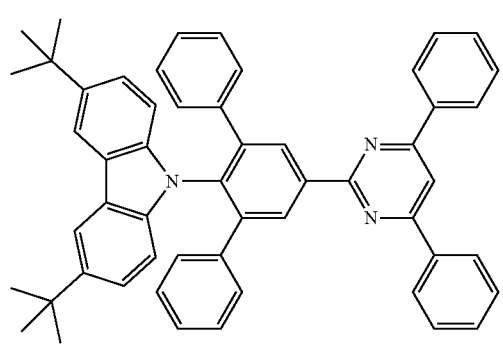
79
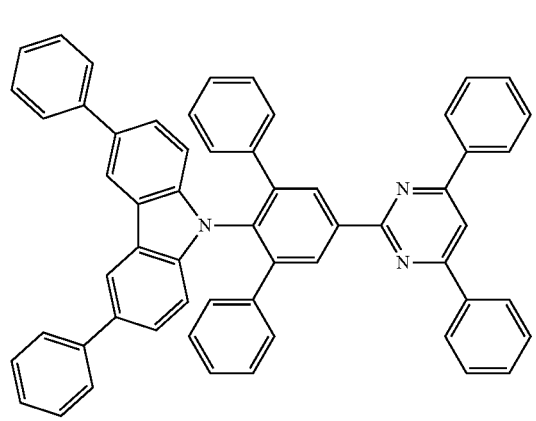
80
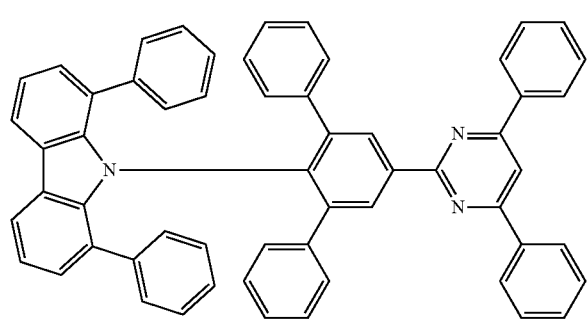

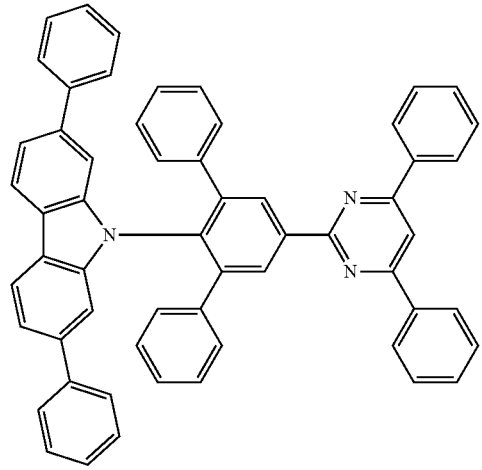
81
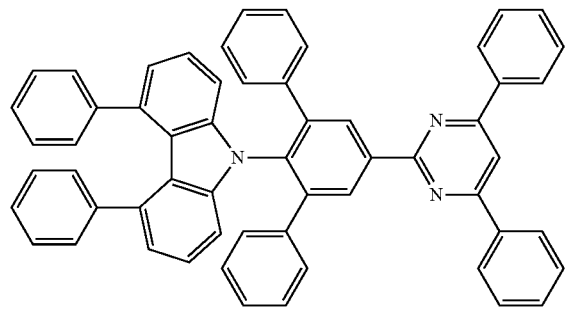
82
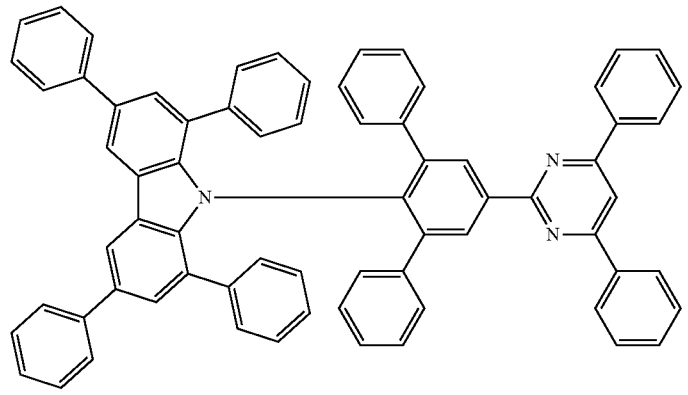
83

84

85
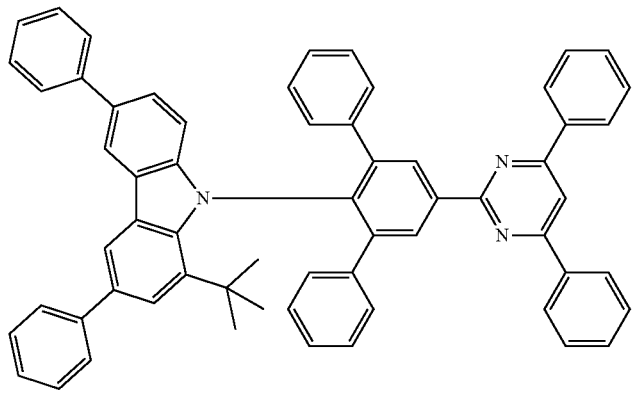
86
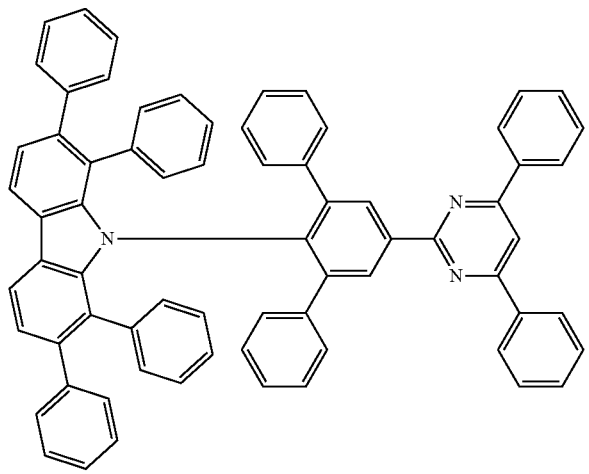
87
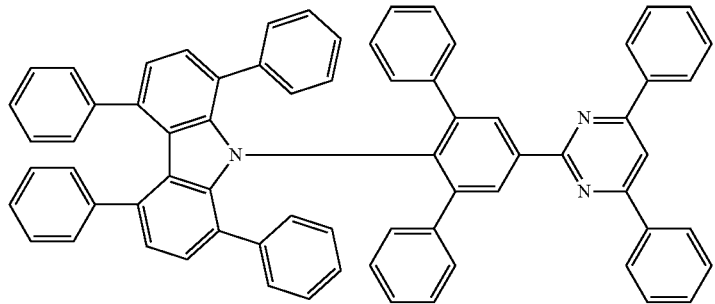
88
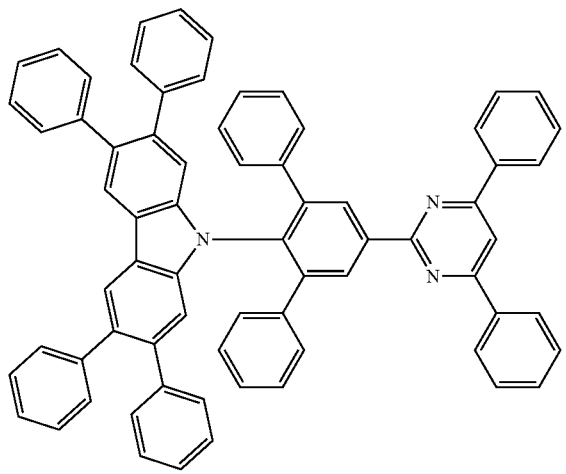

89
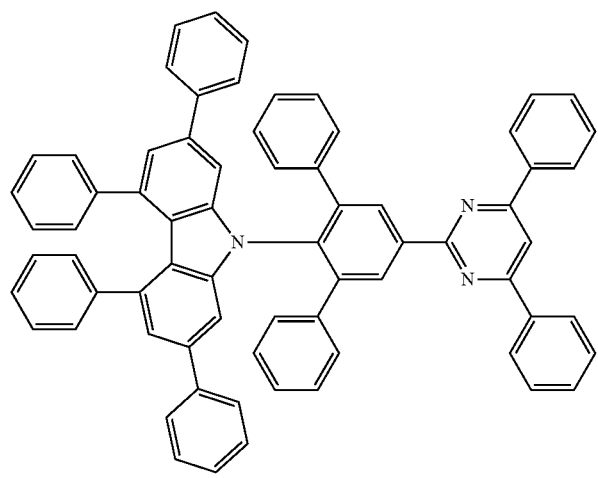
90
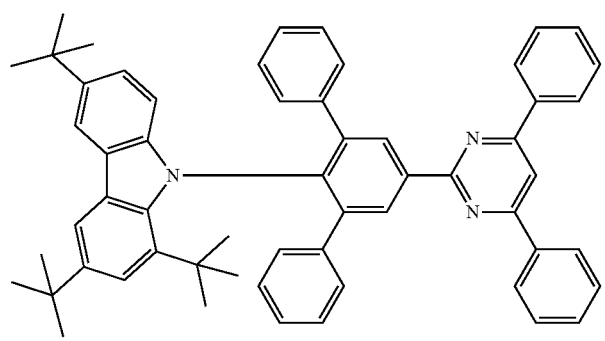
91
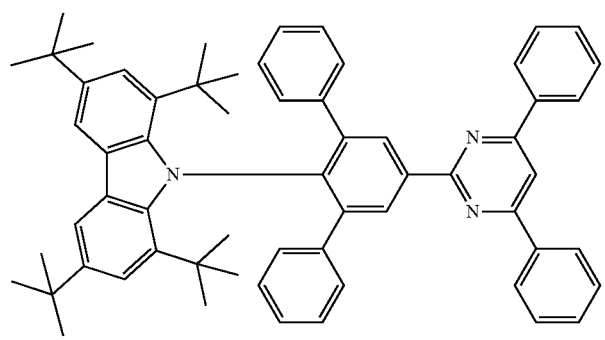
92
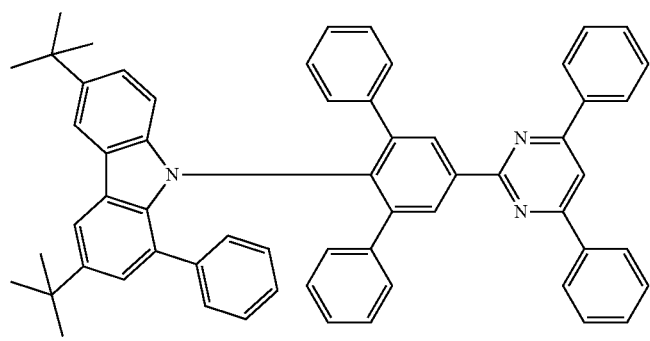

93
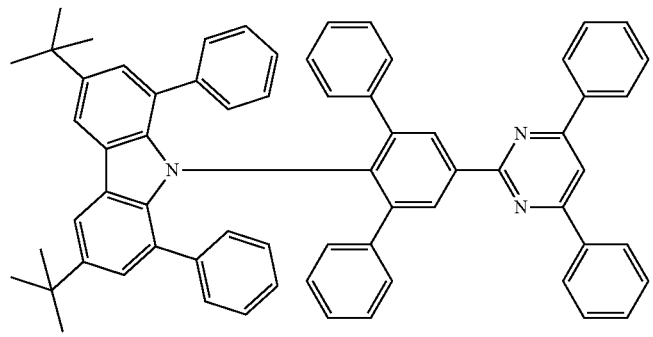
94
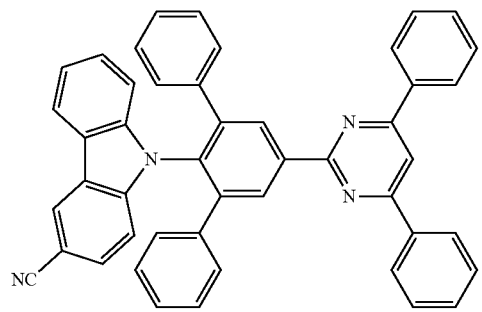
95
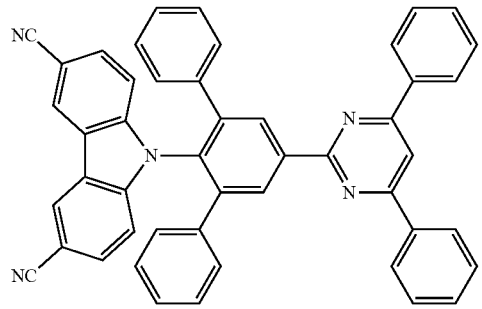
96
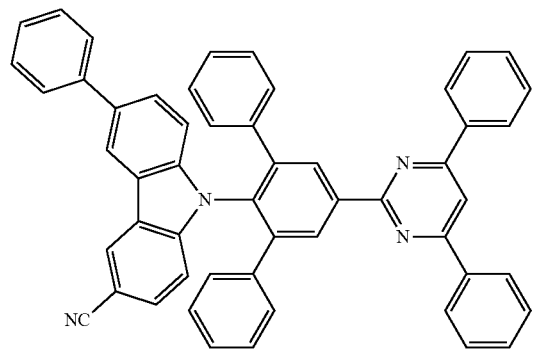
97
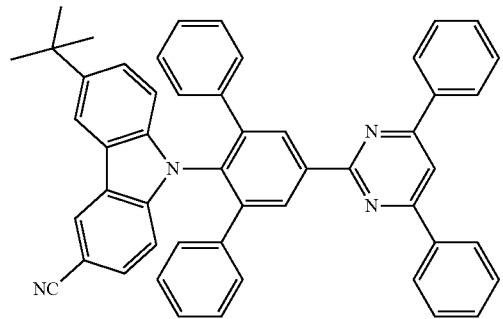

-continued
98
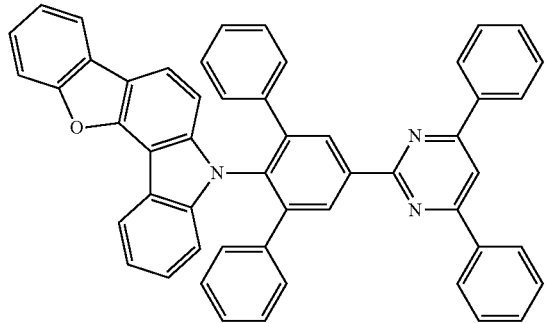
99
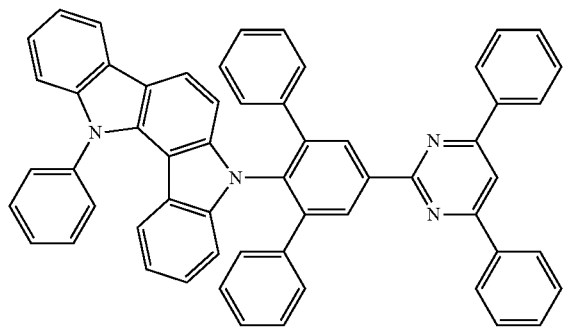
100
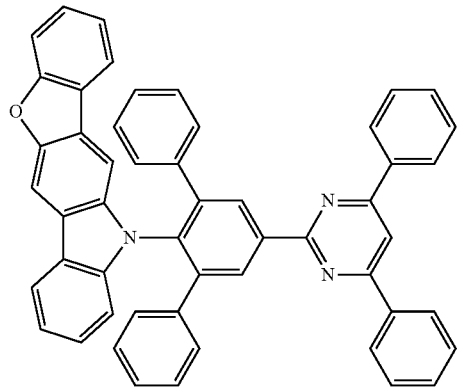
101
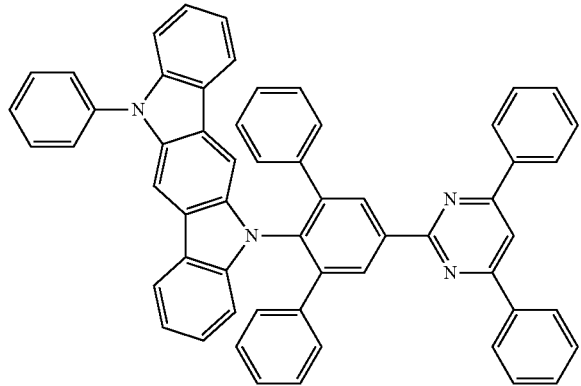

-continued
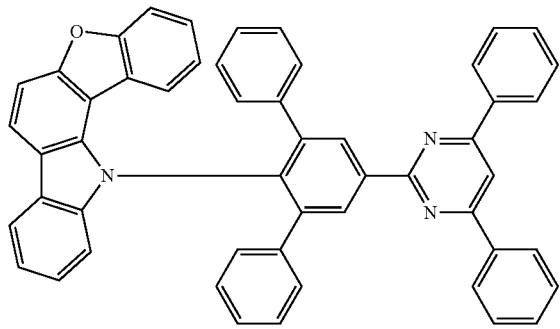
102
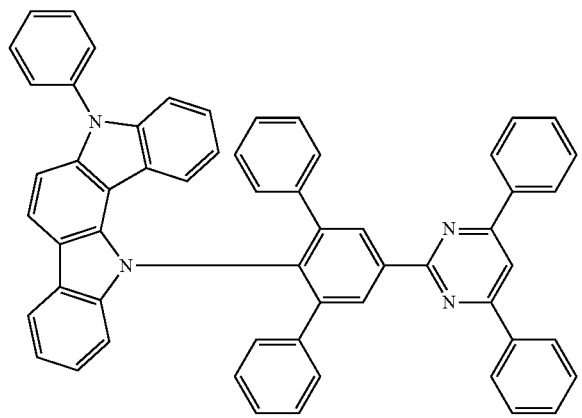
103
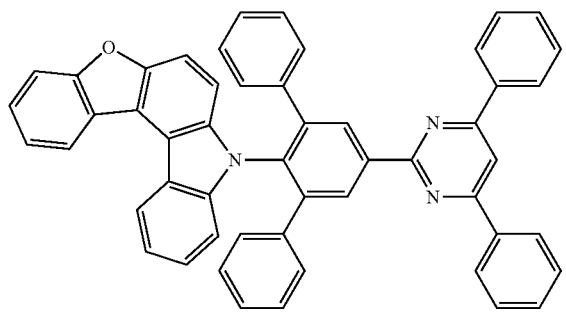
104
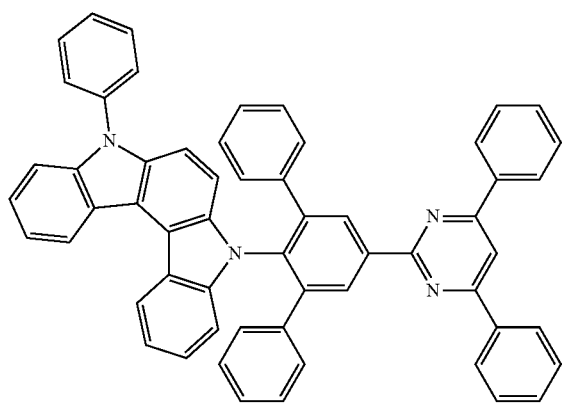
105

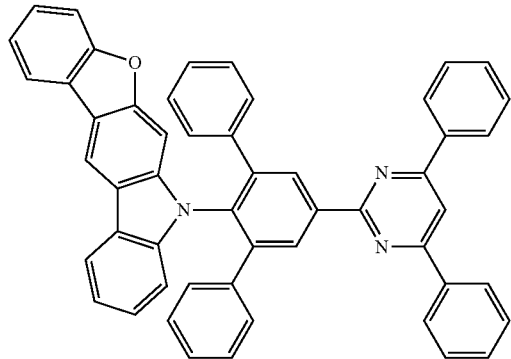
106
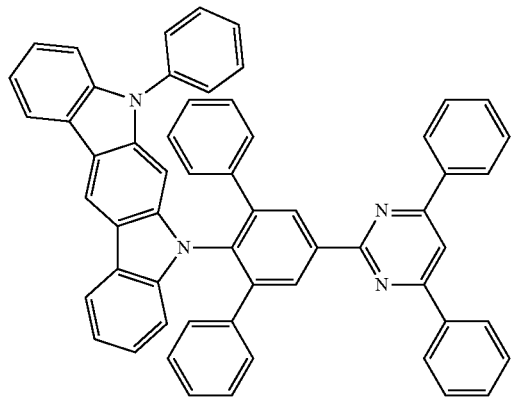
107
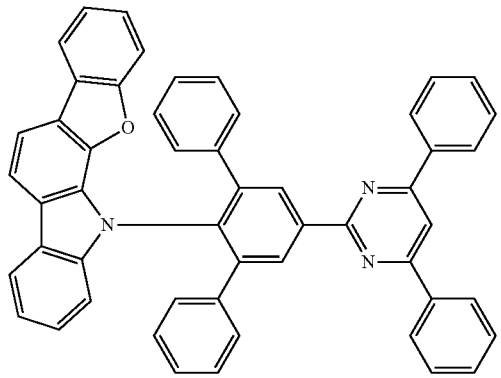
108
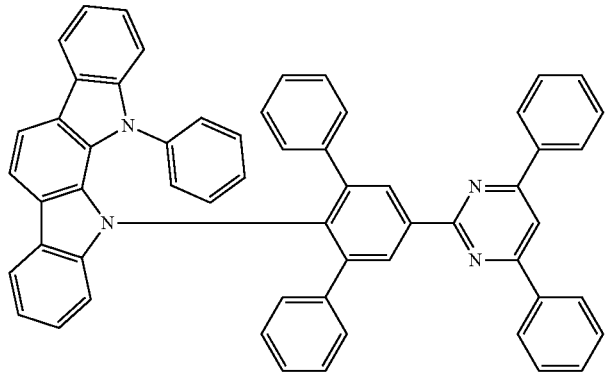
109

-continued
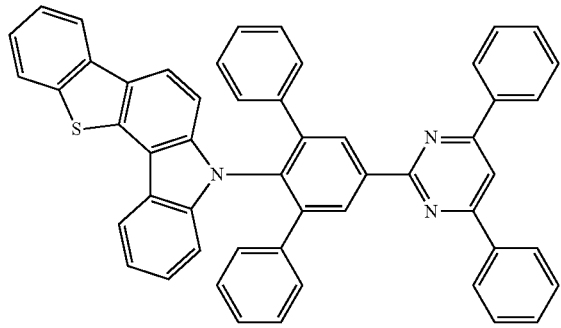
110
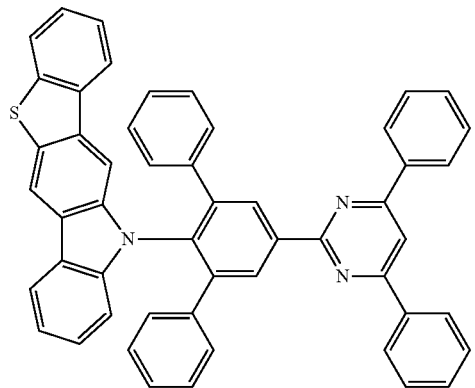
111
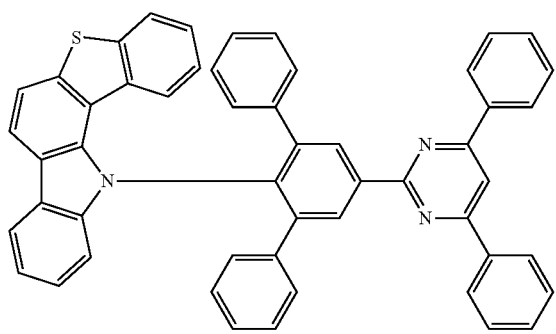
112
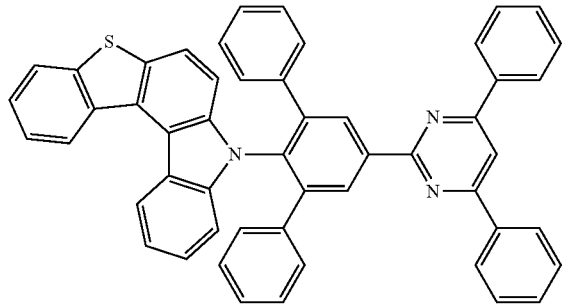
113

-continued
114
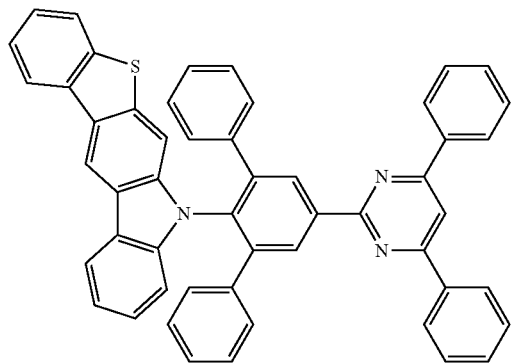
115
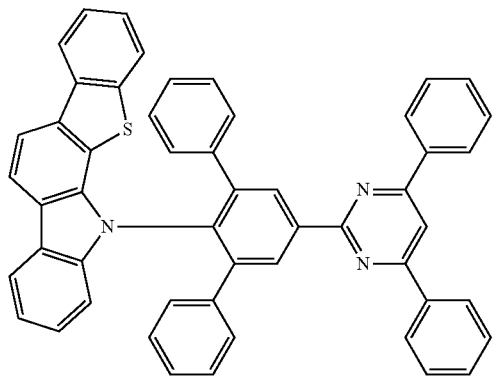
116
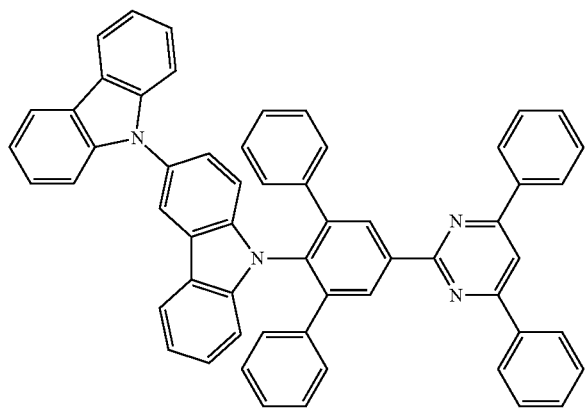
117
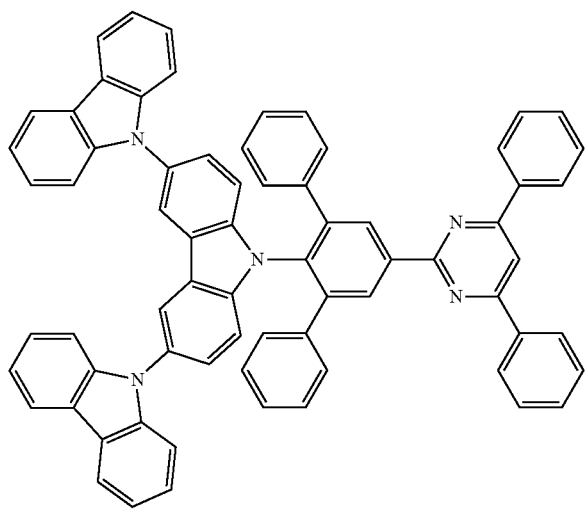

118
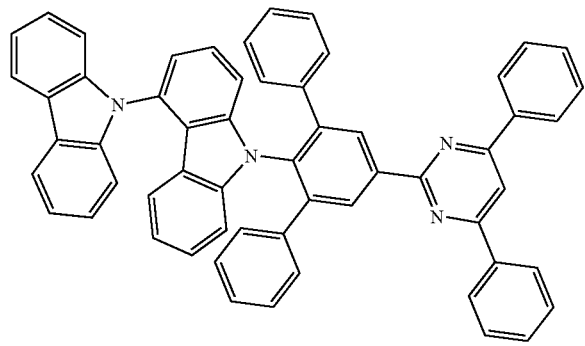
119
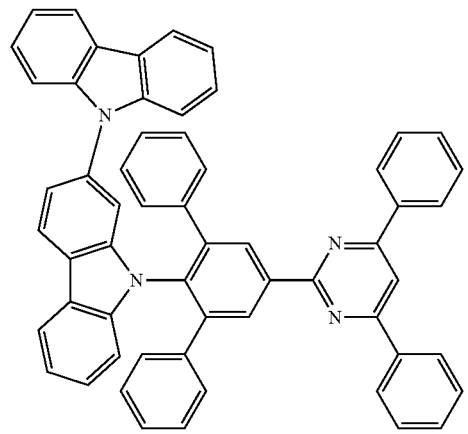
120
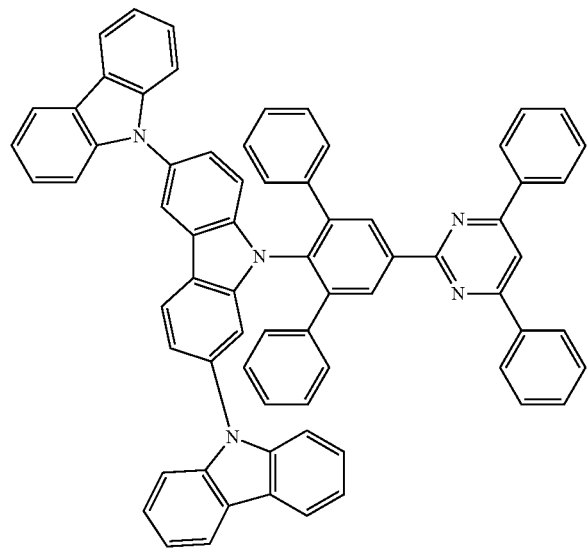

121
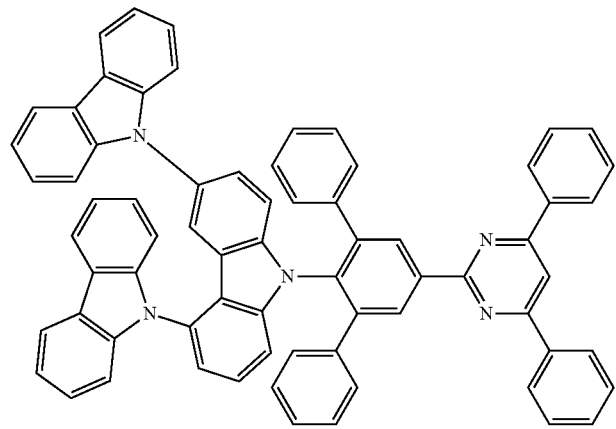
122
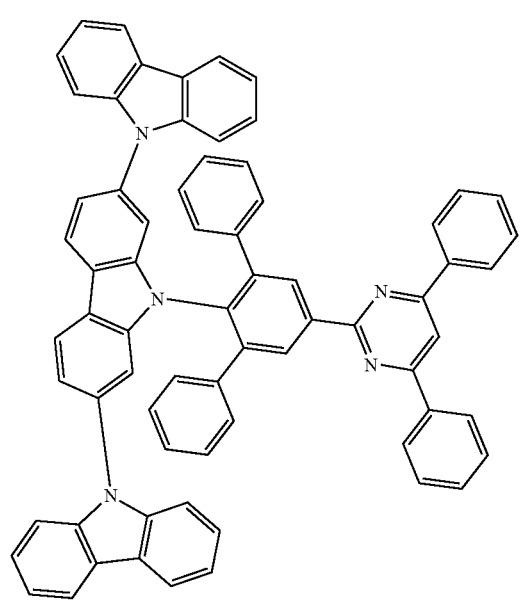
123
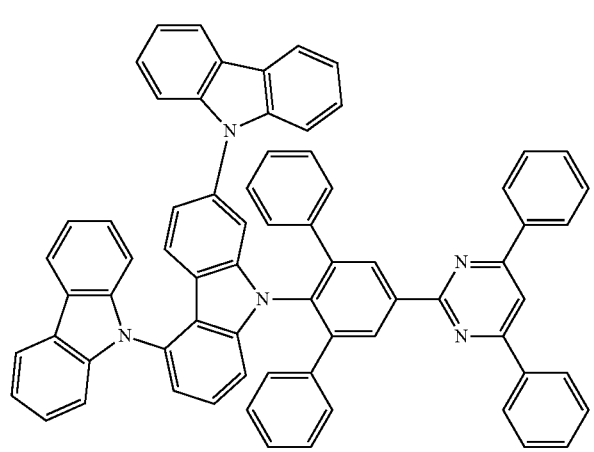

124
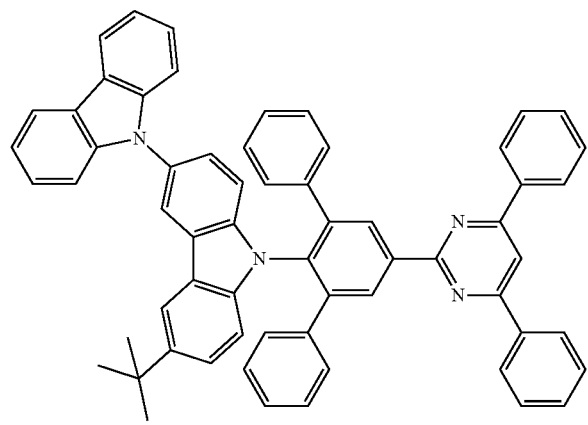
125
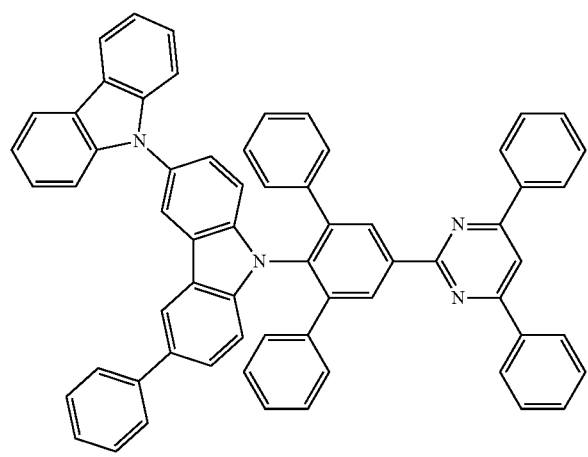
126
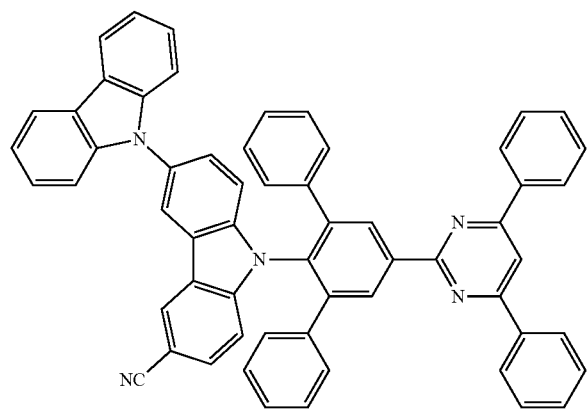

127
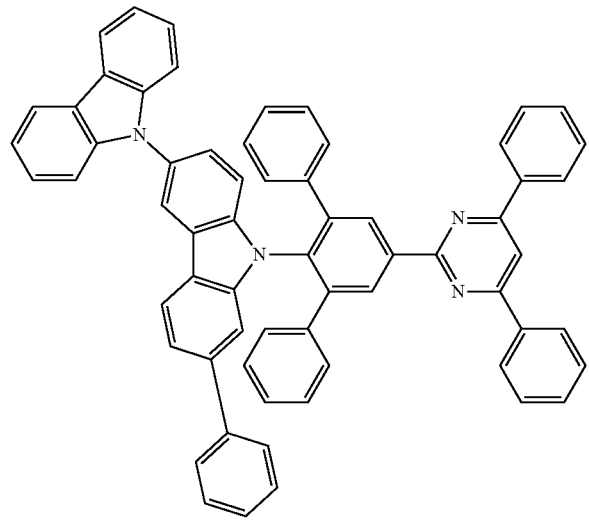
128
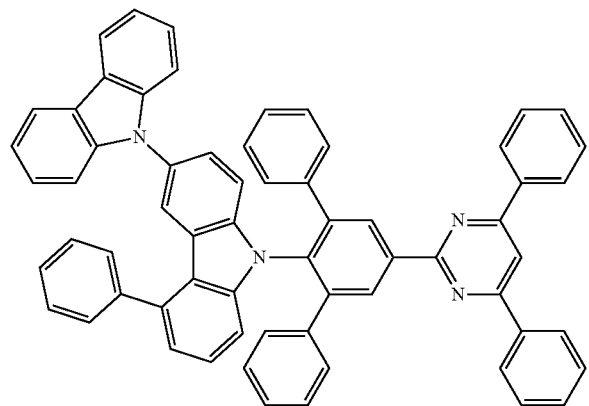
129
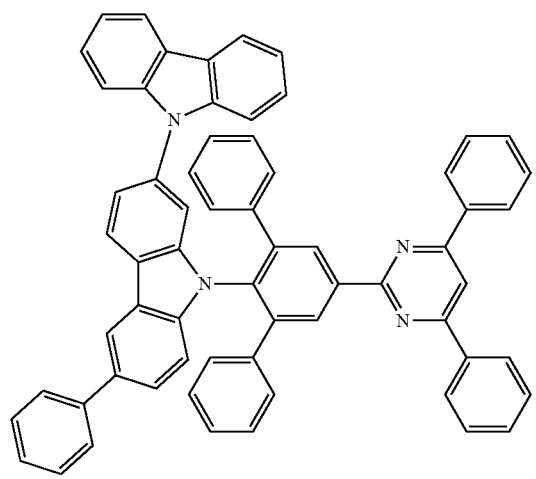

-continued
130
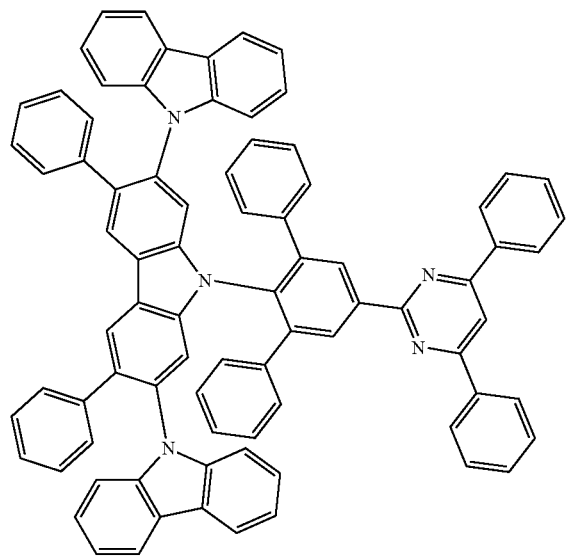
131
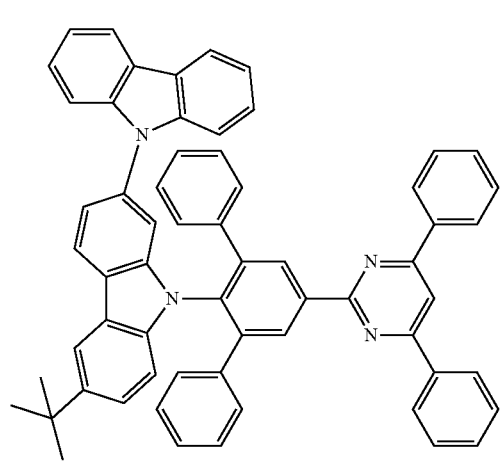
132
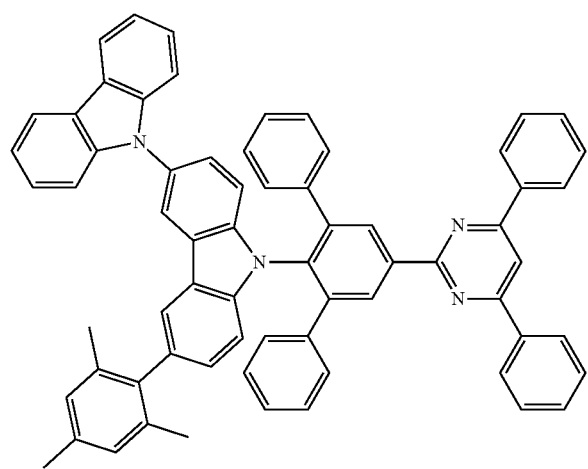

133
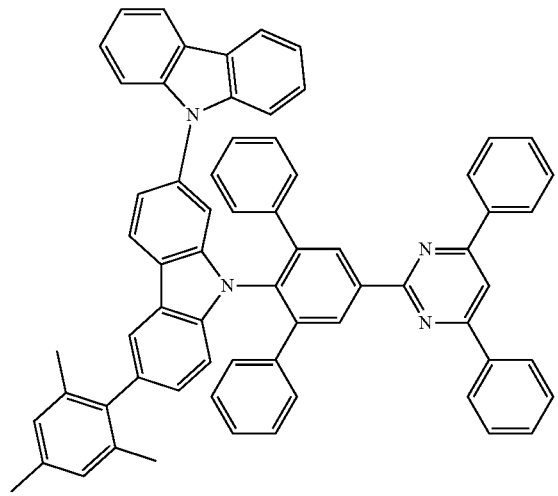
134
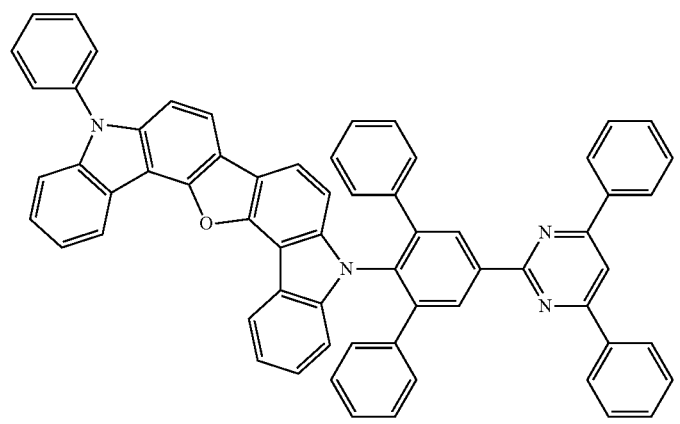
135
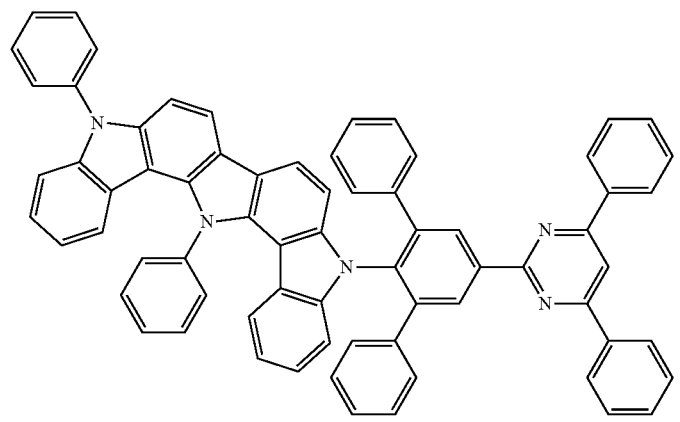

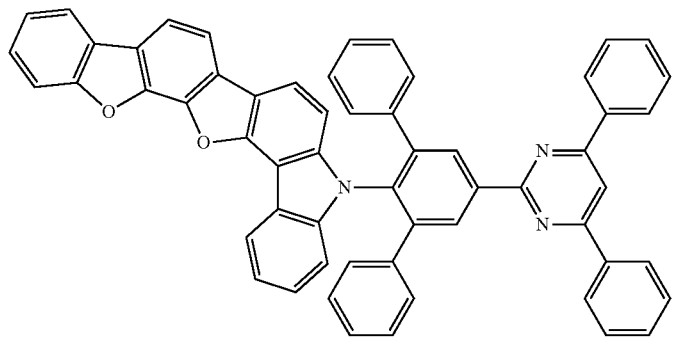
136

137
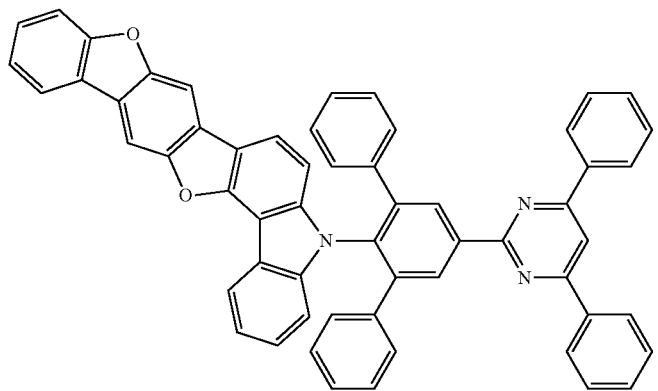
138
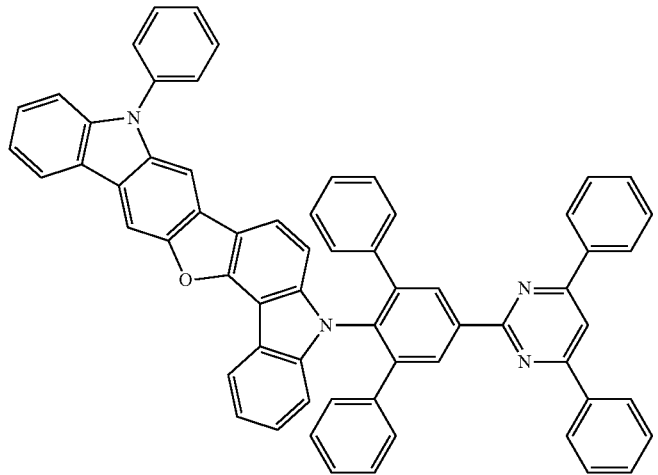
139

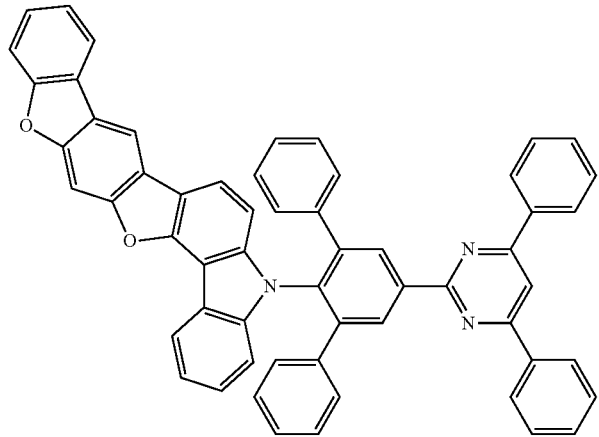
140
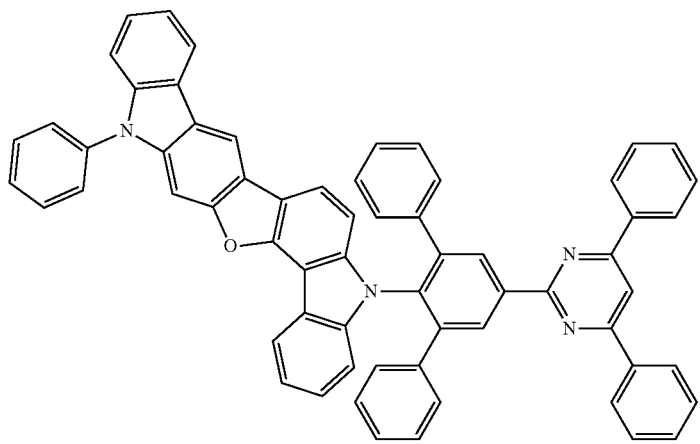
141
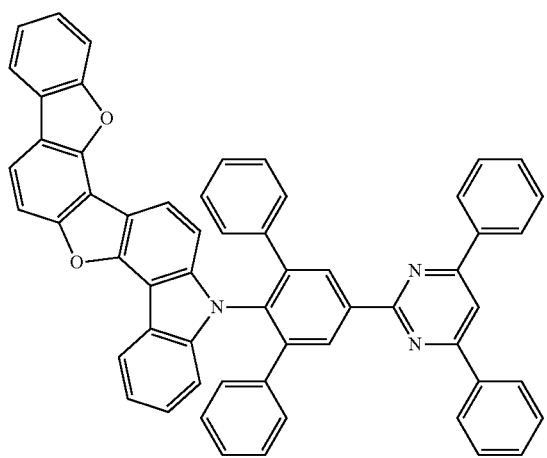
142

143
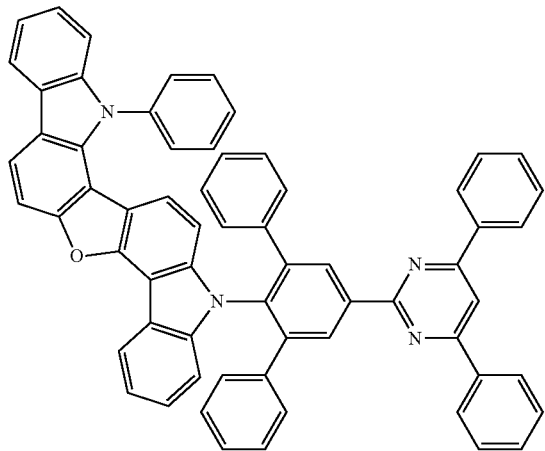
144
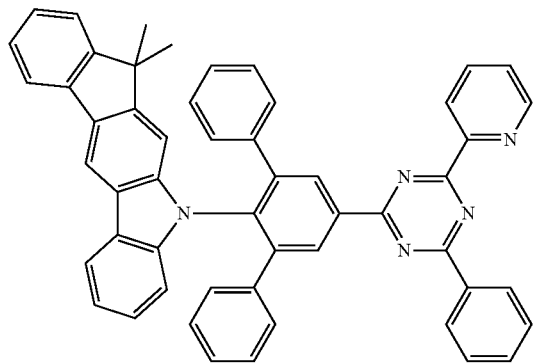
145
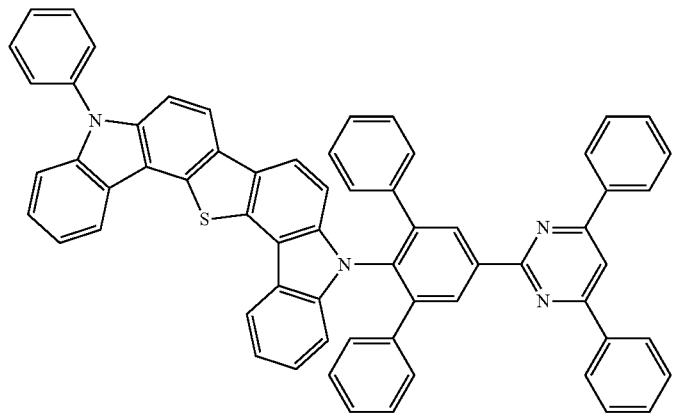
146
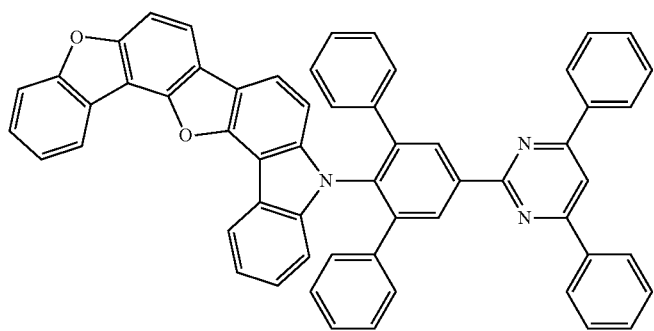

147
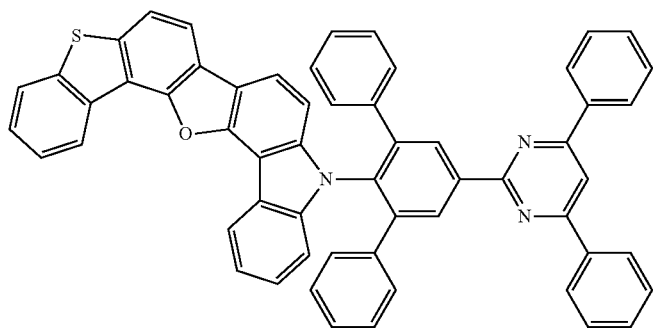
148
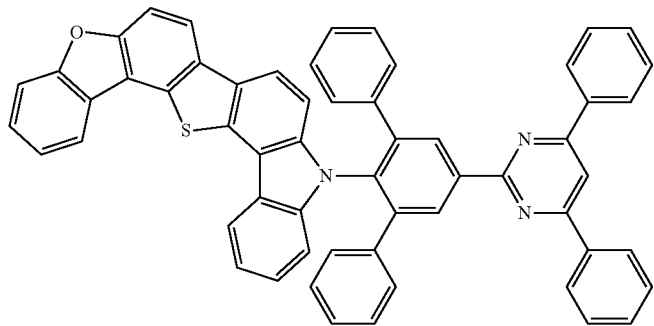
149
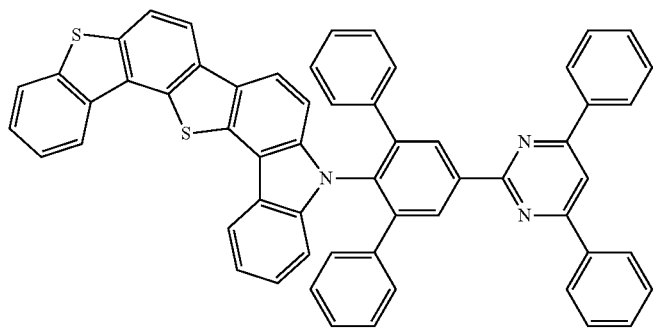
150
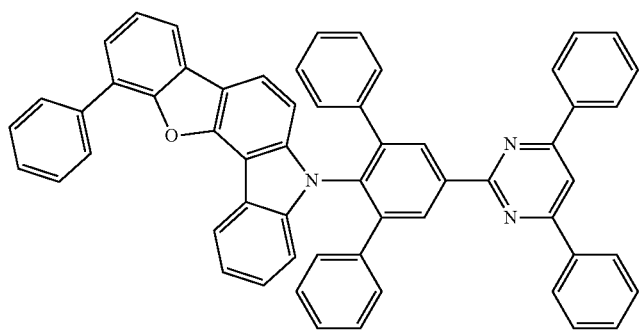
151
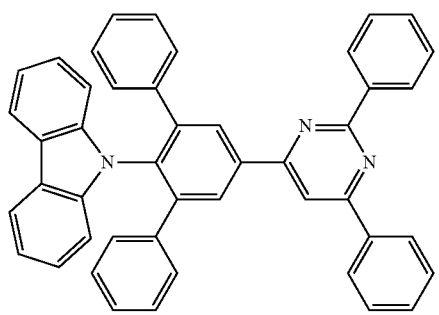

152
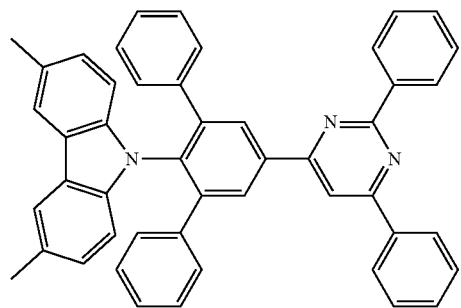
153
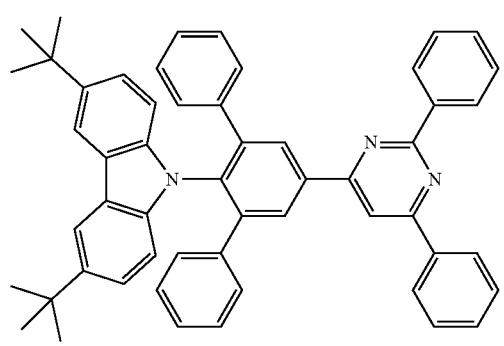
154
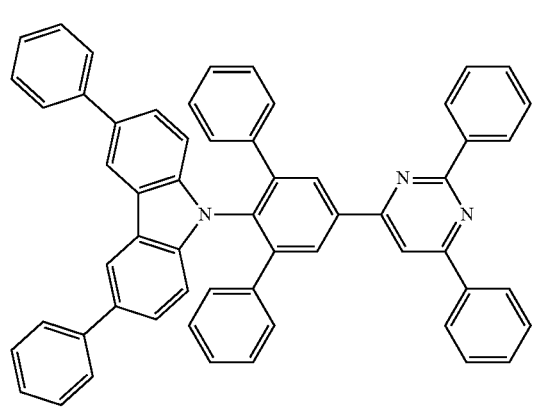
155
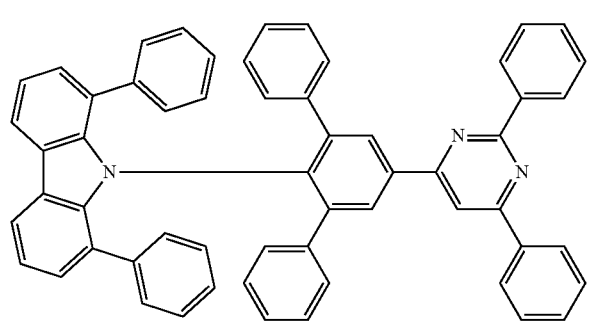

-continued
156
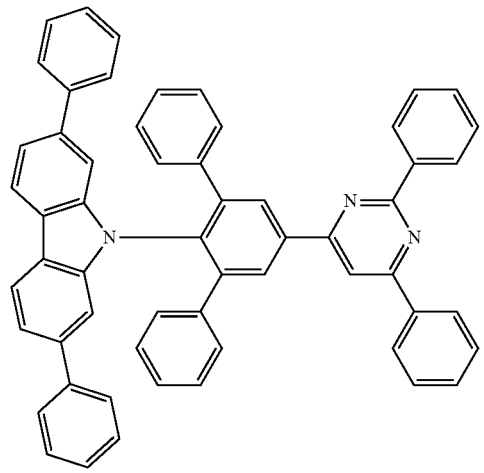
157
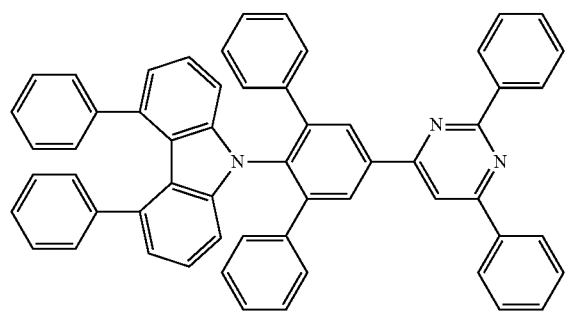
158
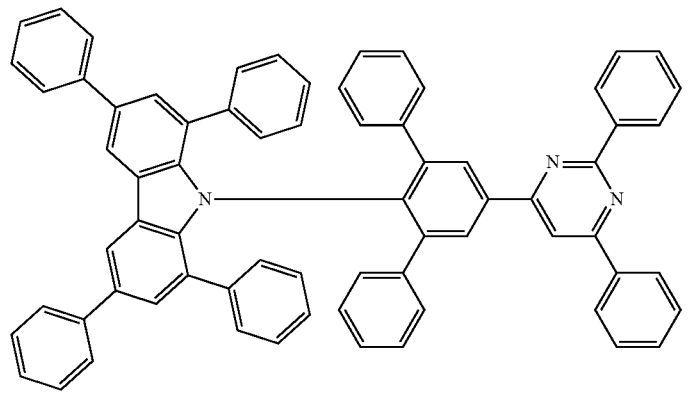
159
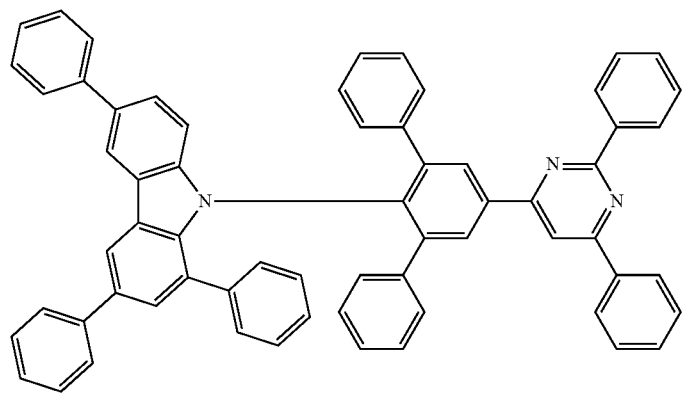

-continued
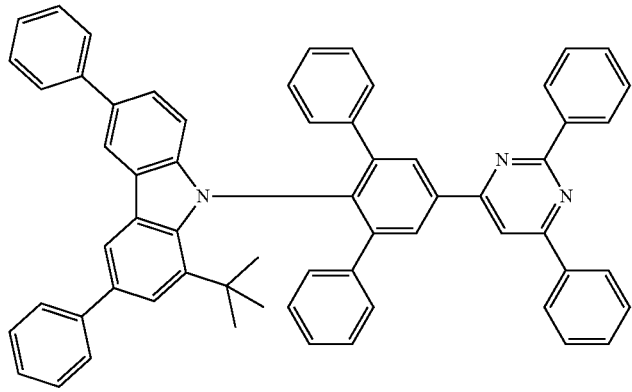
160
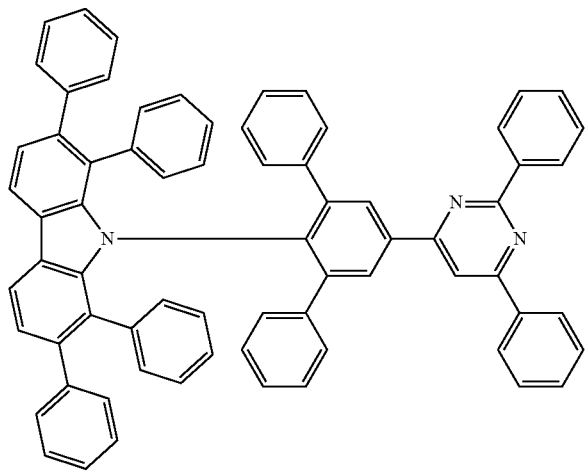
161
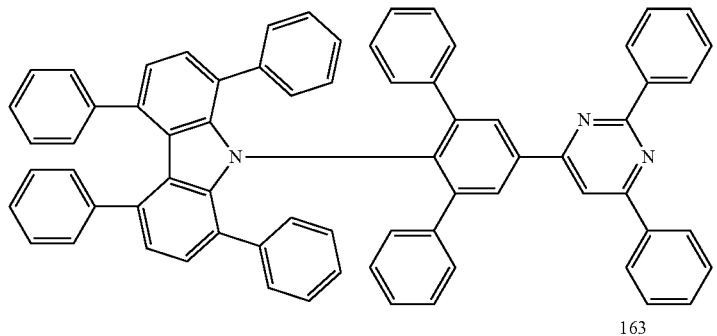
162
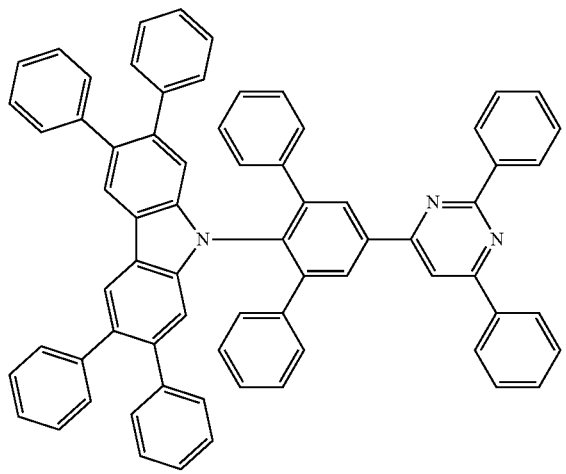
163

-continued
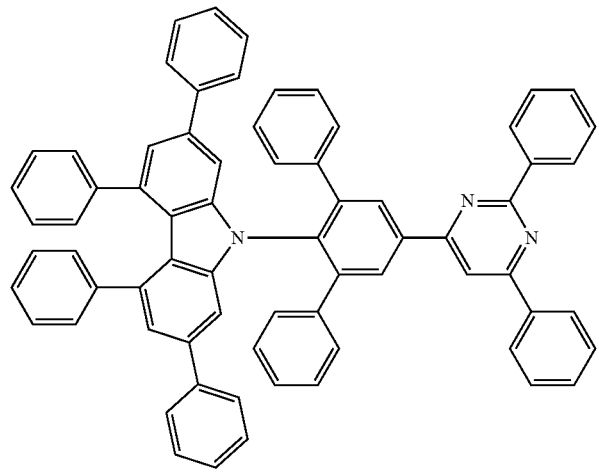
164
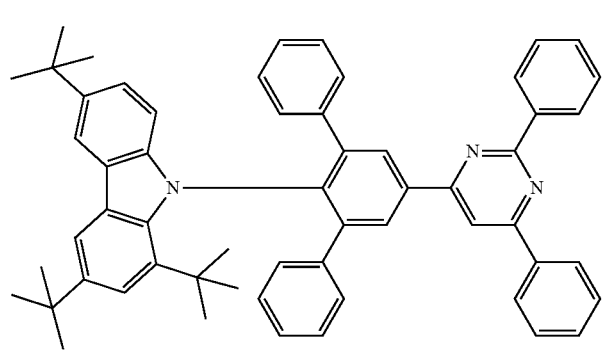
165
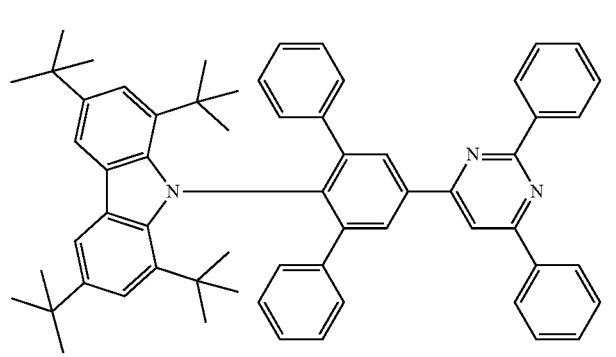
166
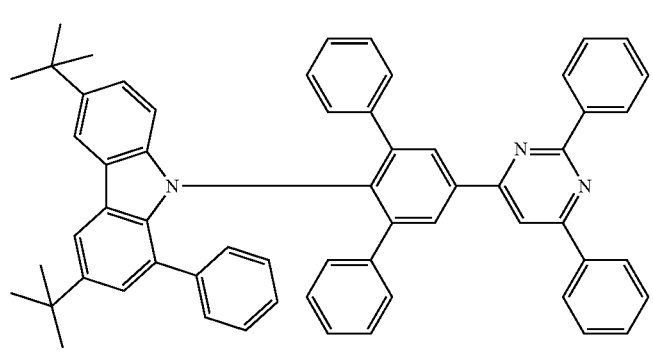
167

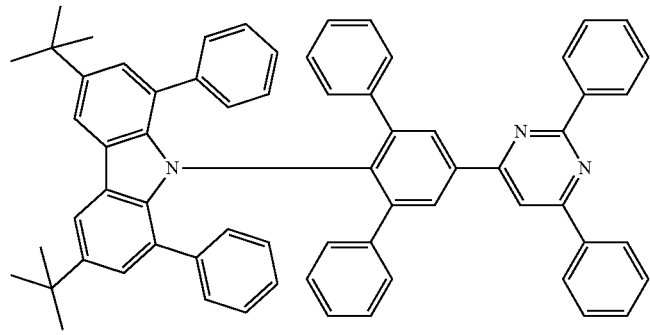
168
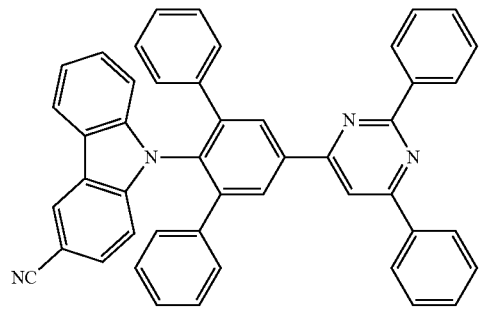
169
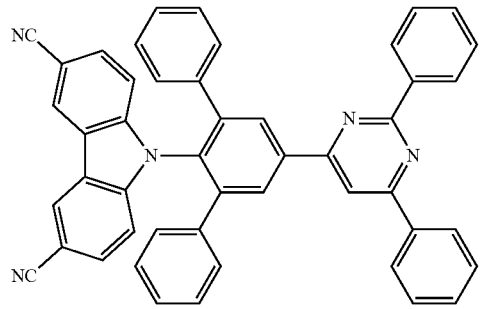
170
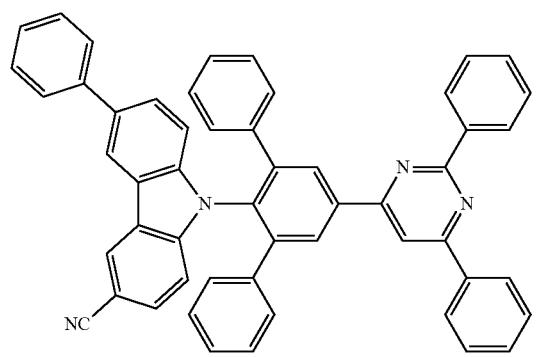
171
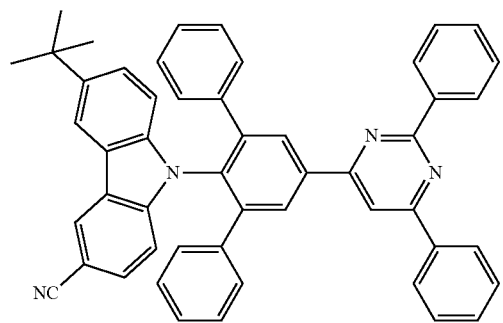
172

-continued
173
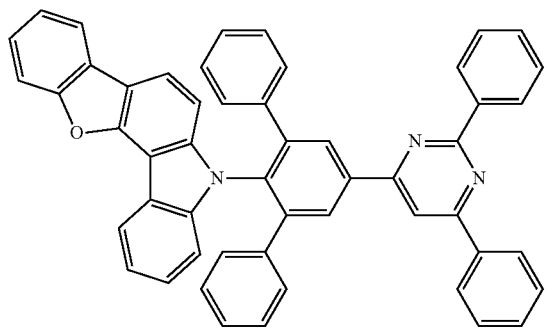
174
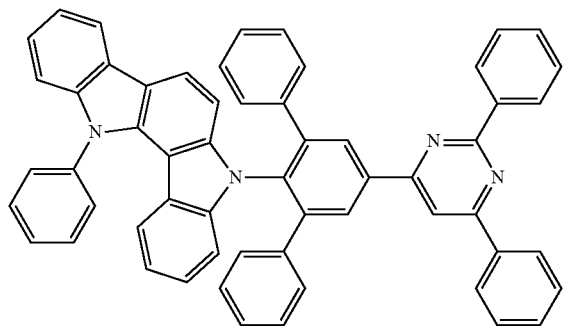
175
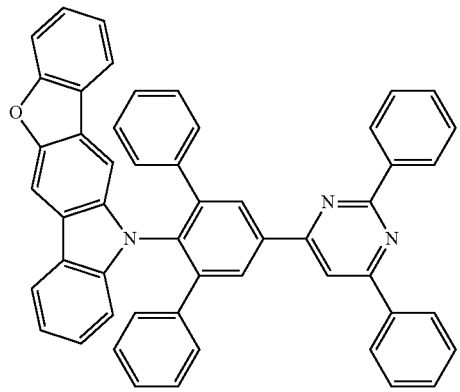
176
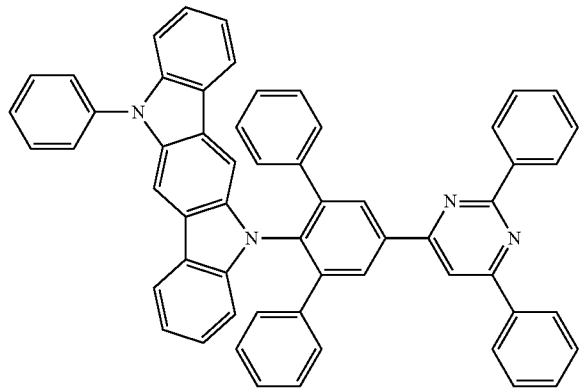

177
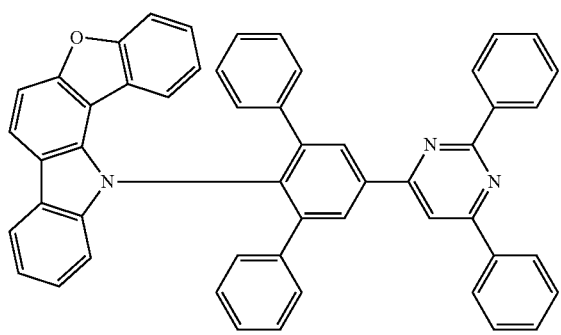
178
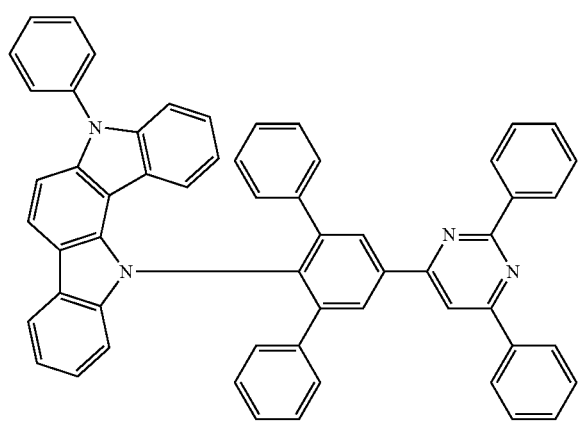
179
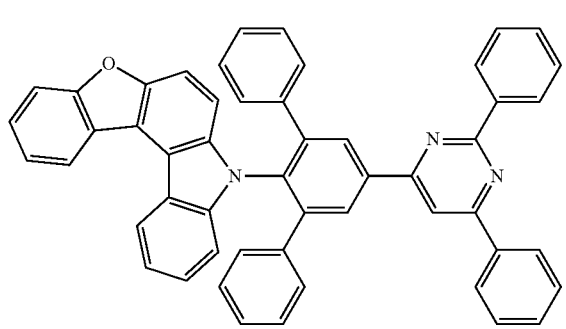
180
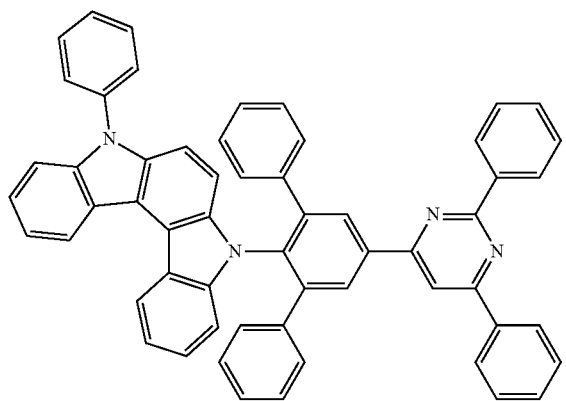

181
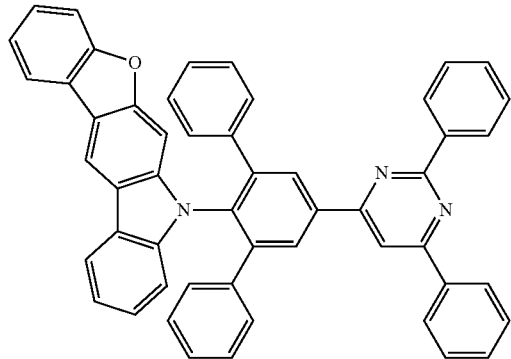
182
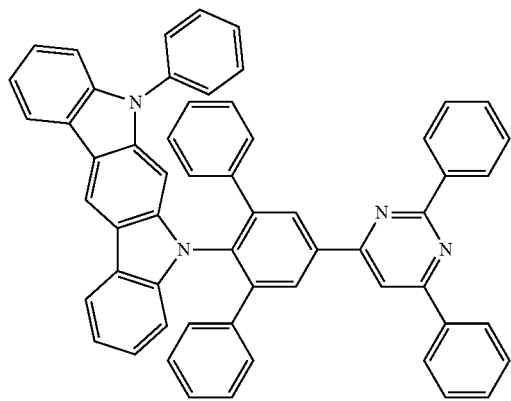
183
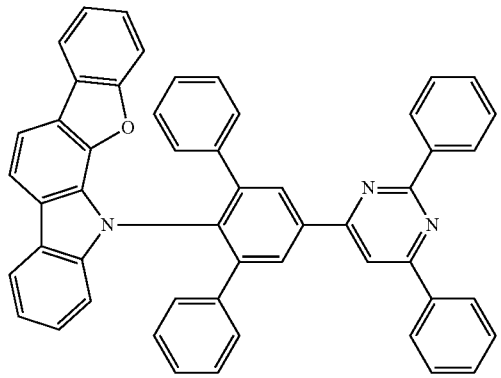
184
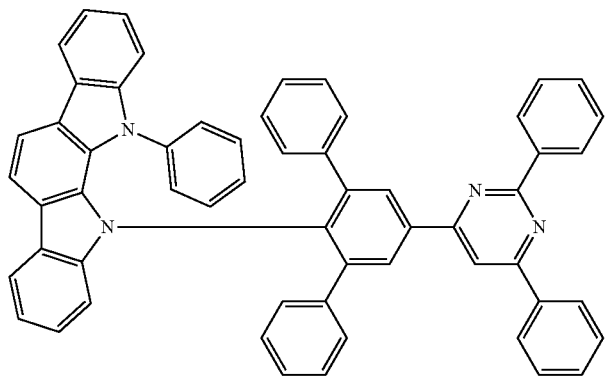

185
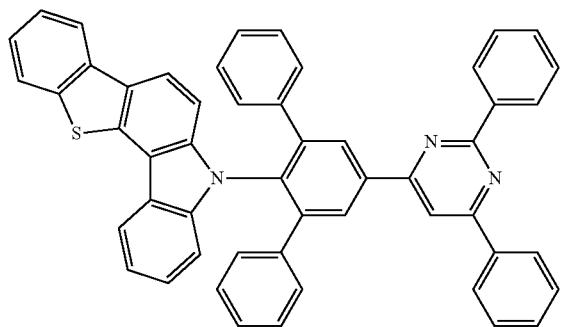
186
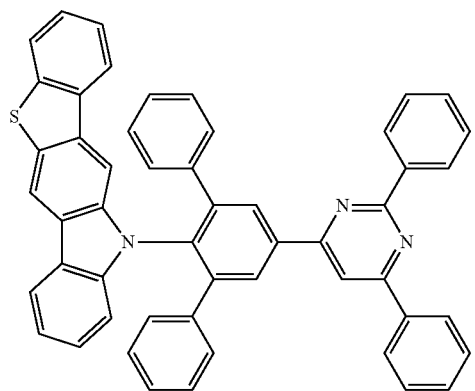
187
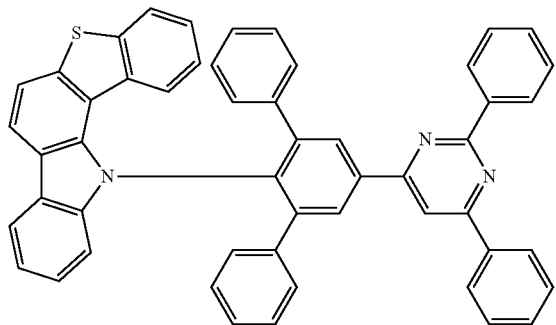
188
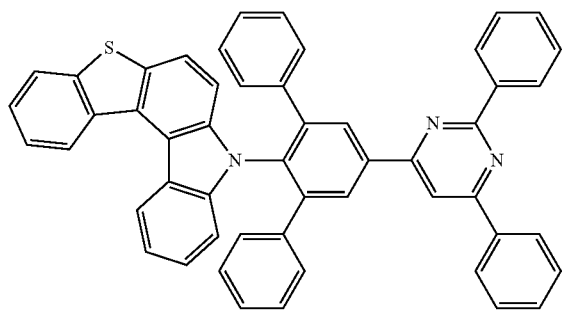

-continued
189
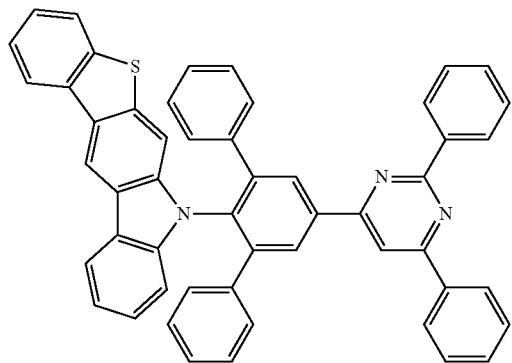
190
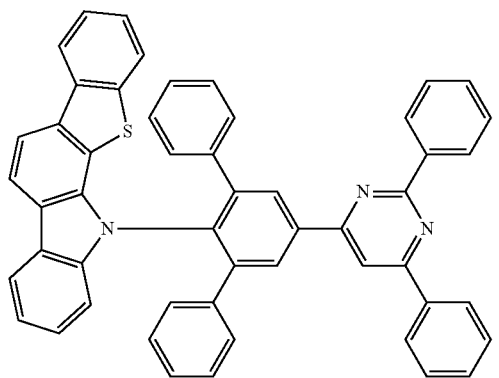
191
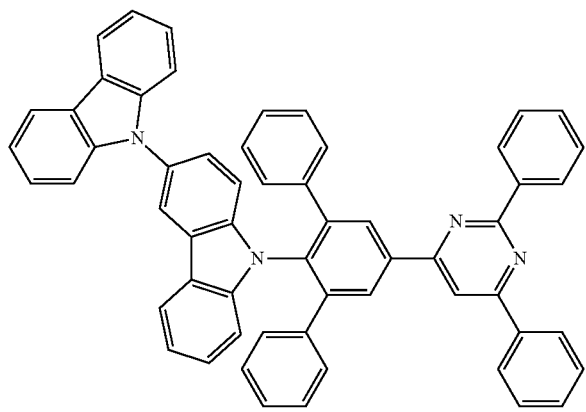
192
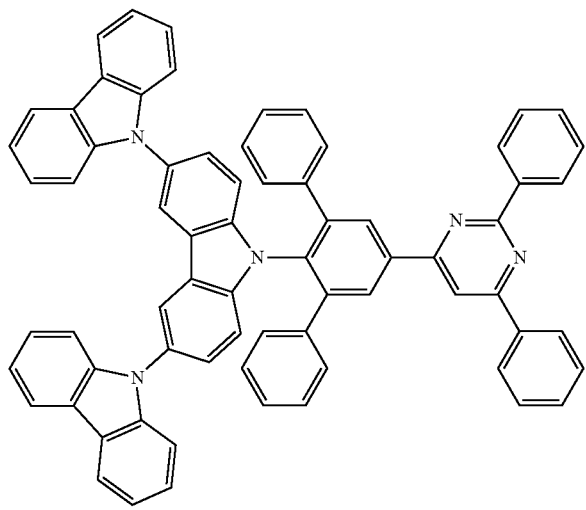

-continued
193
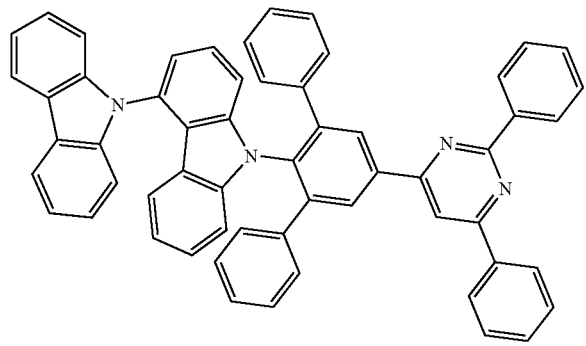
194
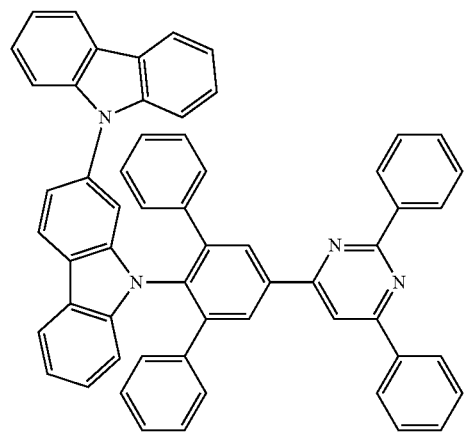
195
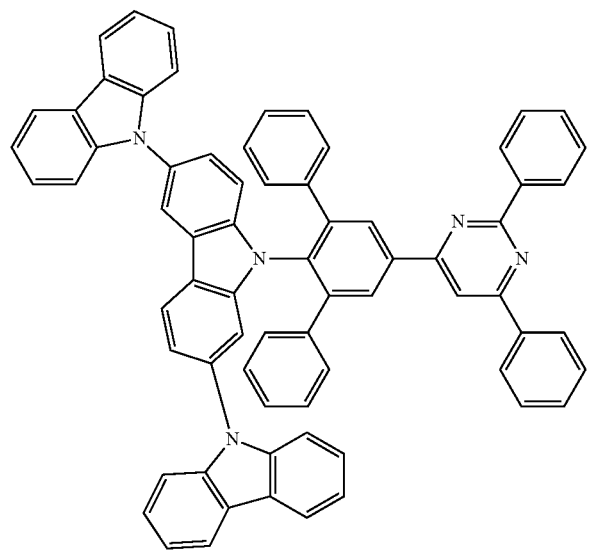

-continued
196
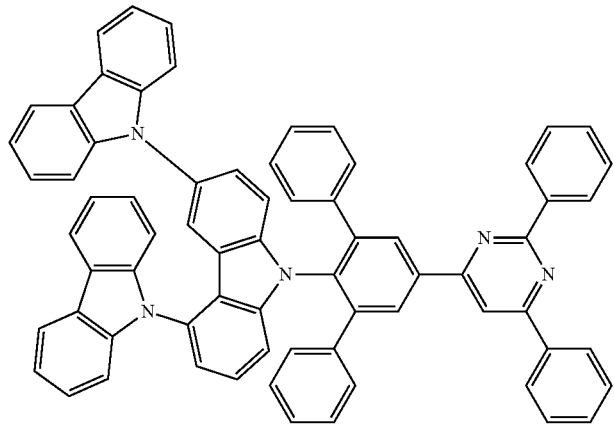
197
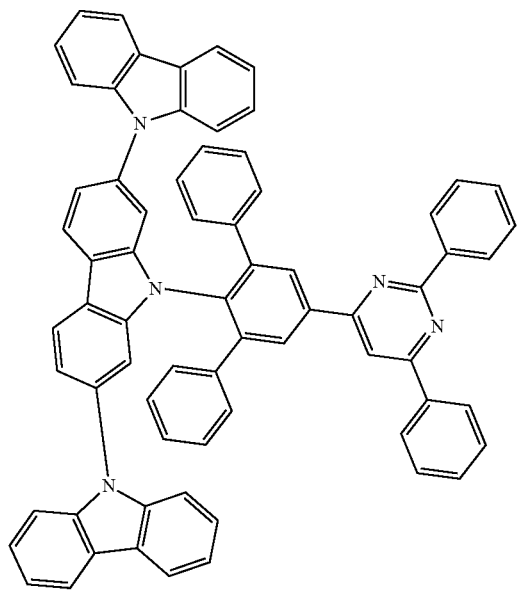
198
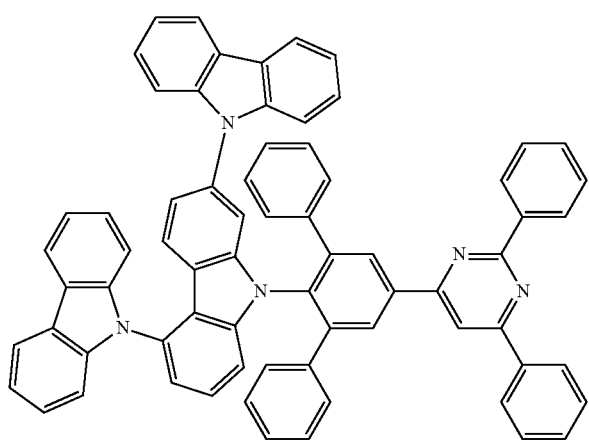

-continued
199
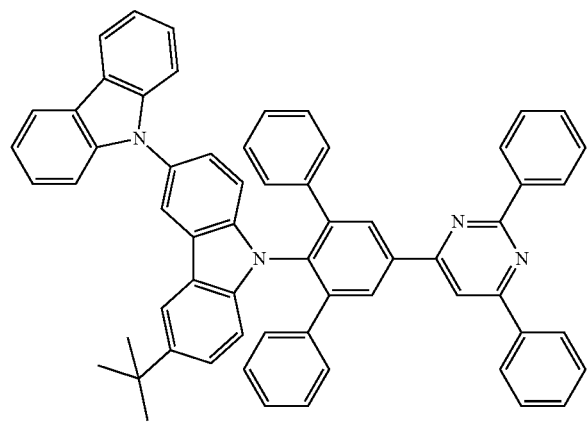
200
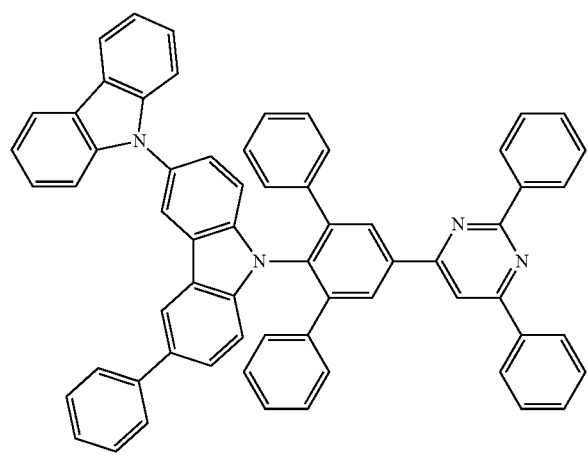
201
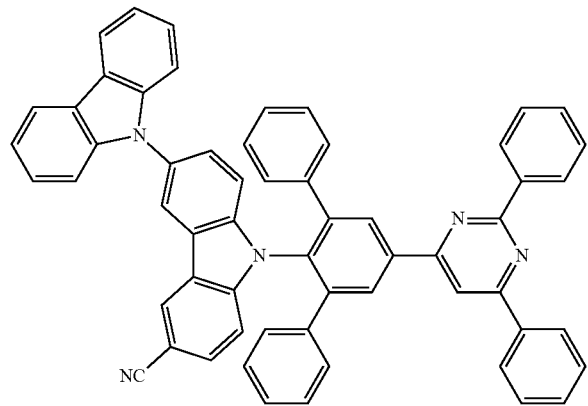

-continued
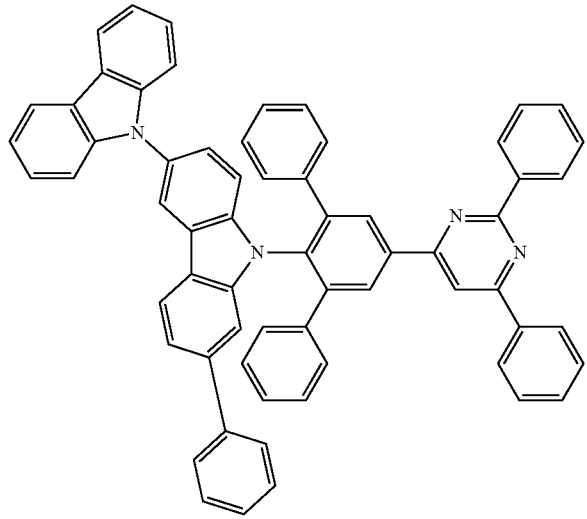
202
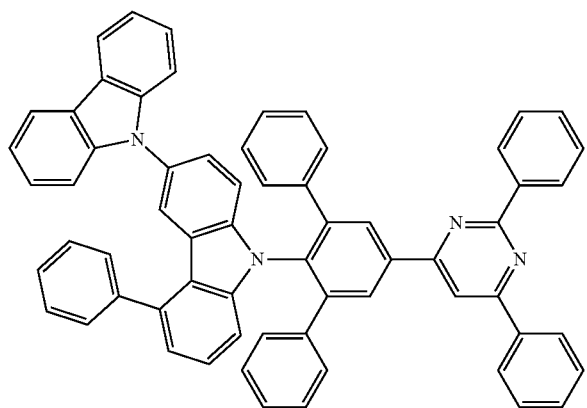
203
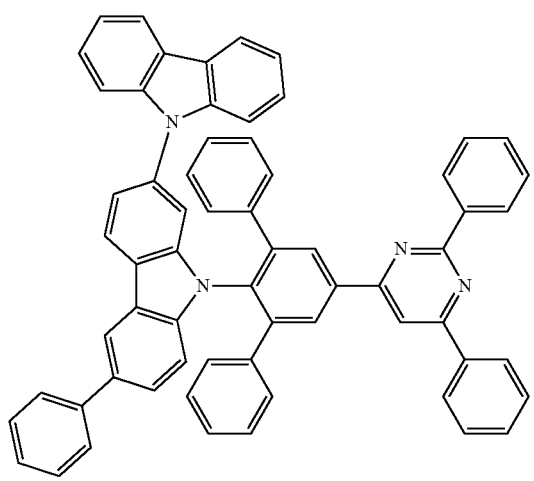
204

205
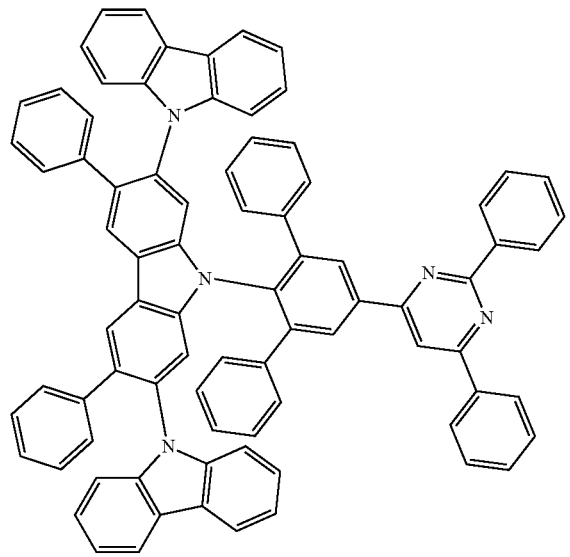
206
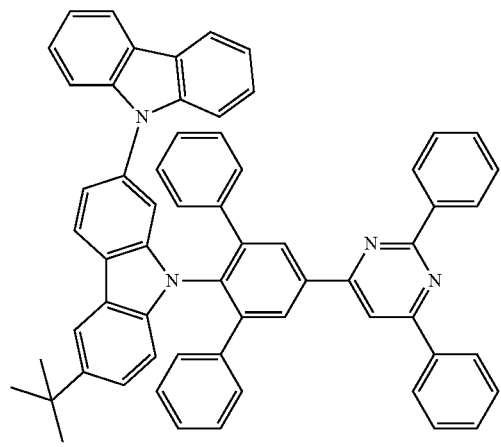
207
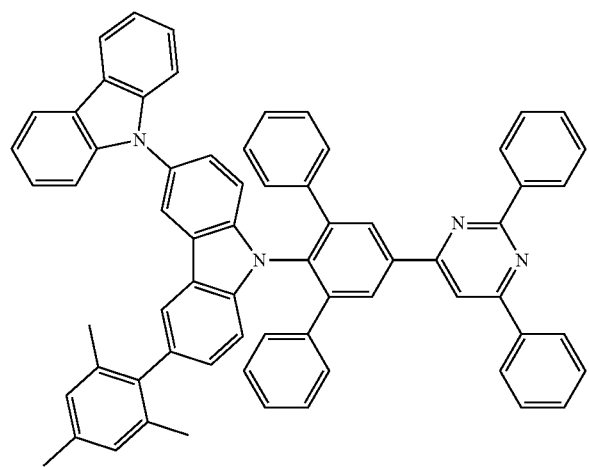

208
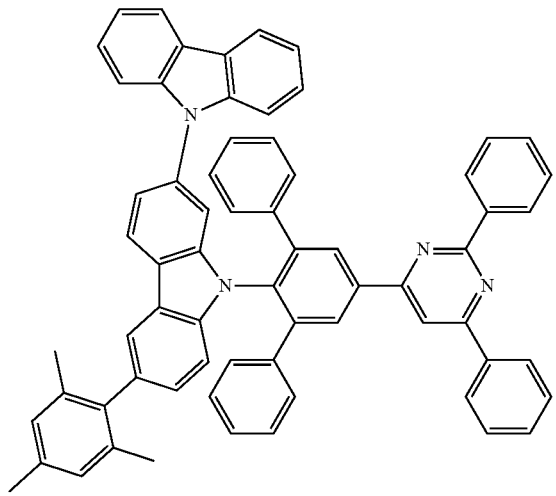
209
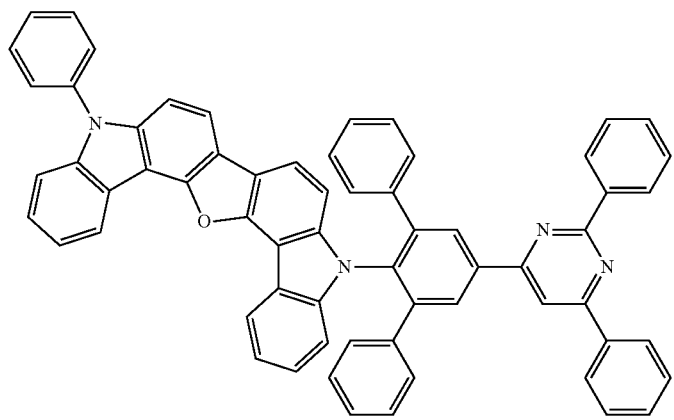
210
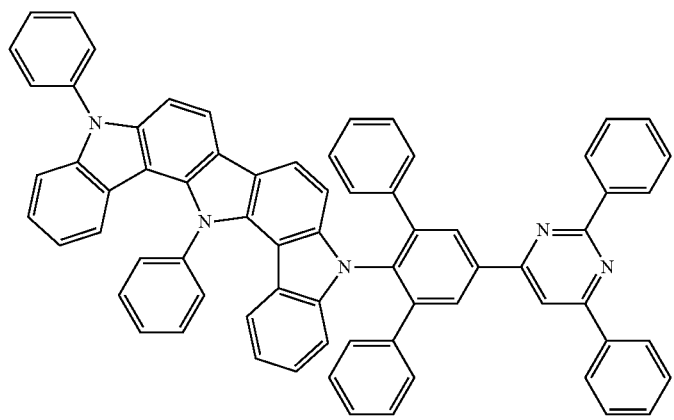

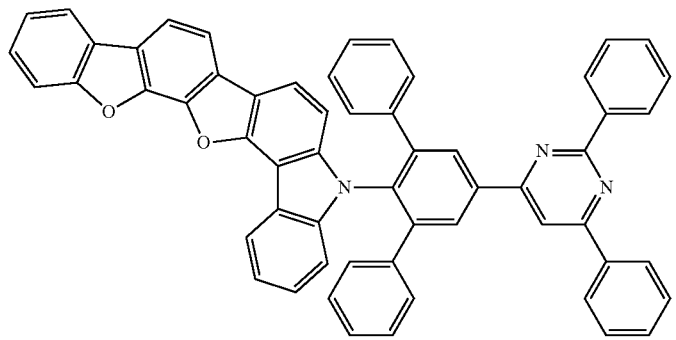
211
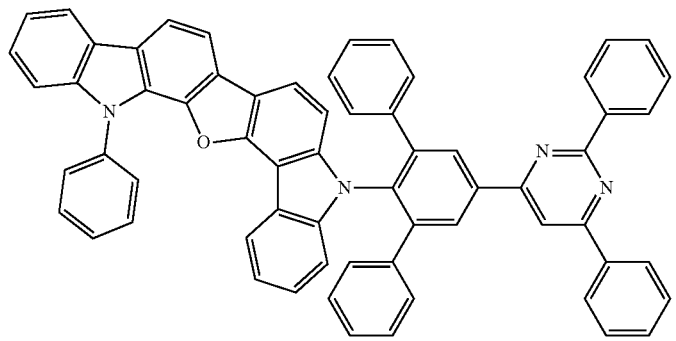
212
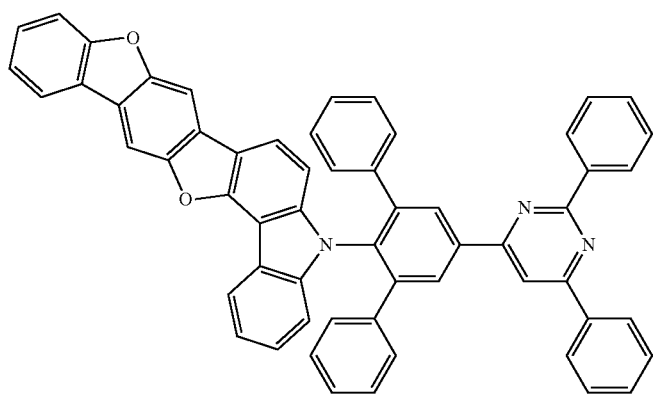
213
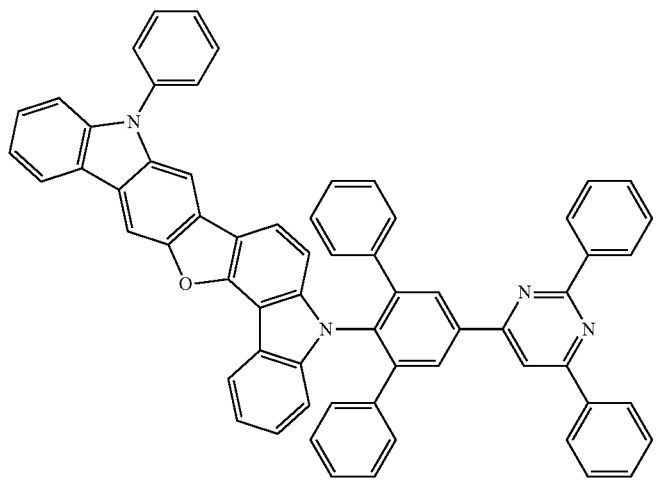
214

215
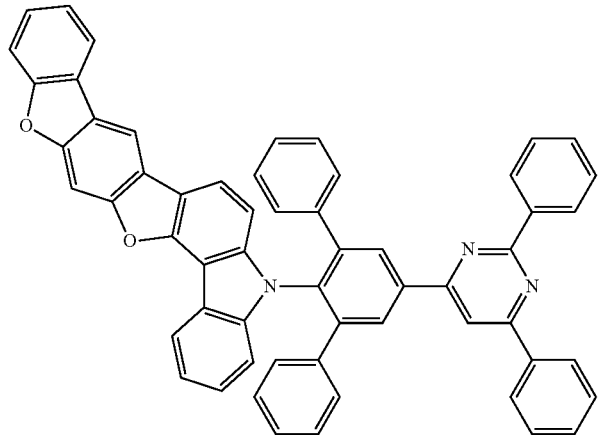
216
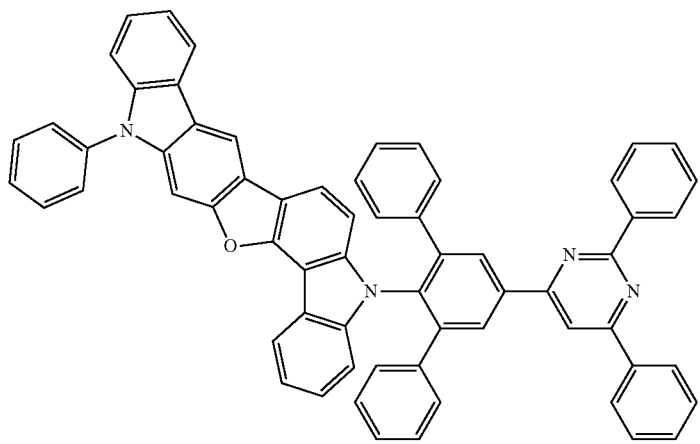
217
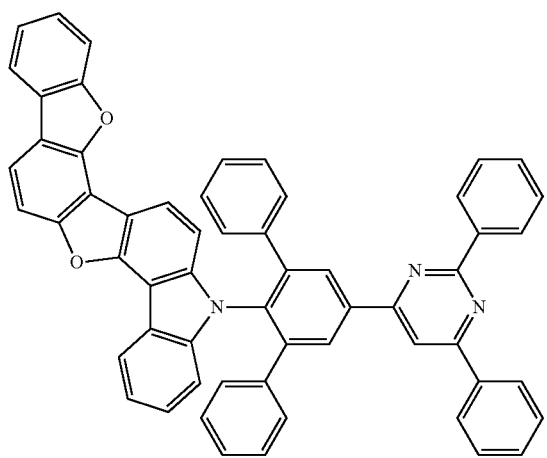

218
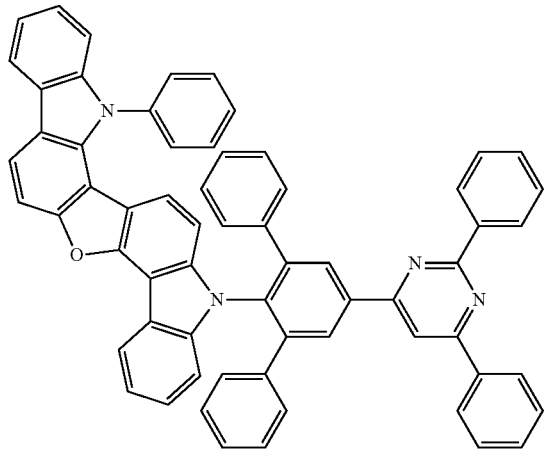
219
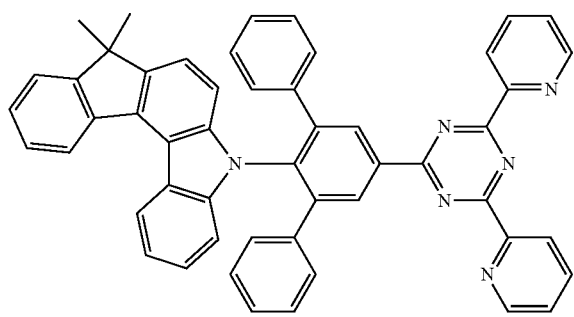
220
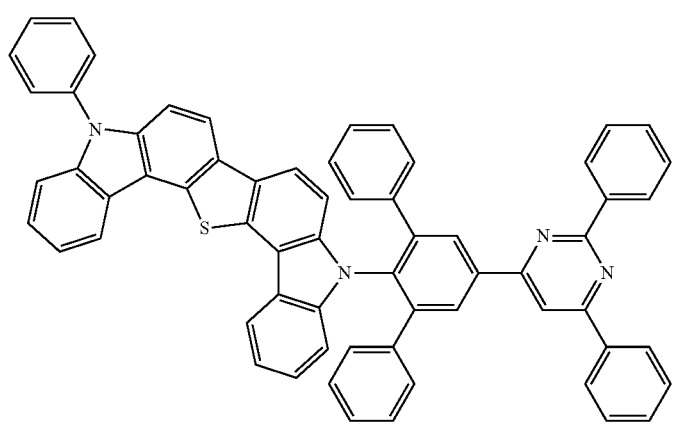
221
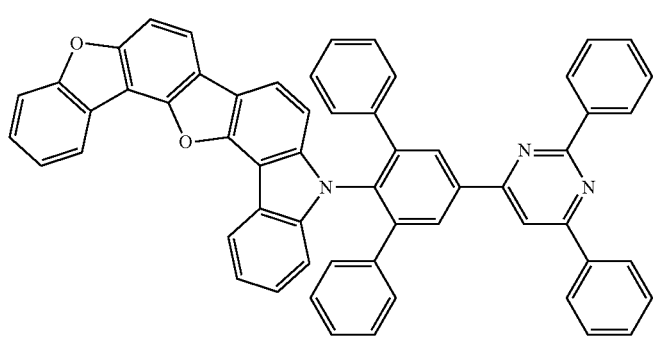

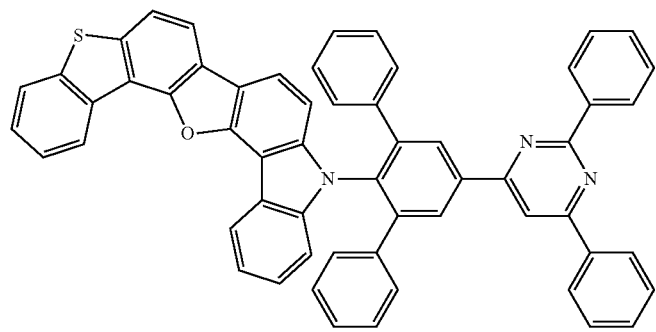
222
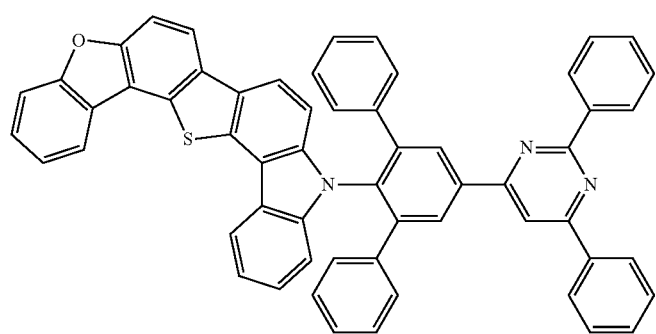
223
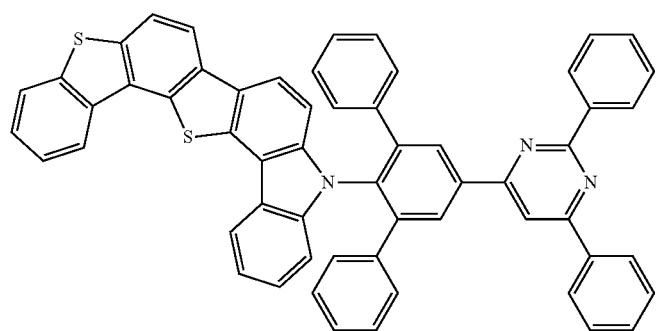
224
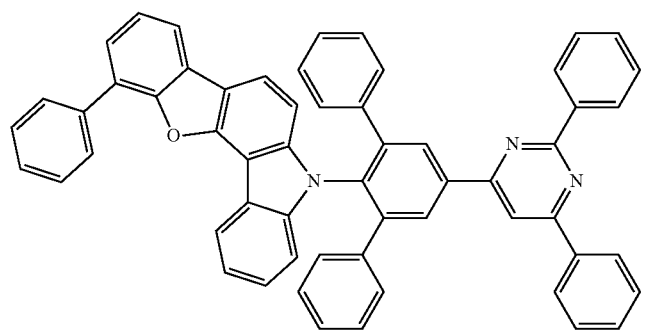
225

226
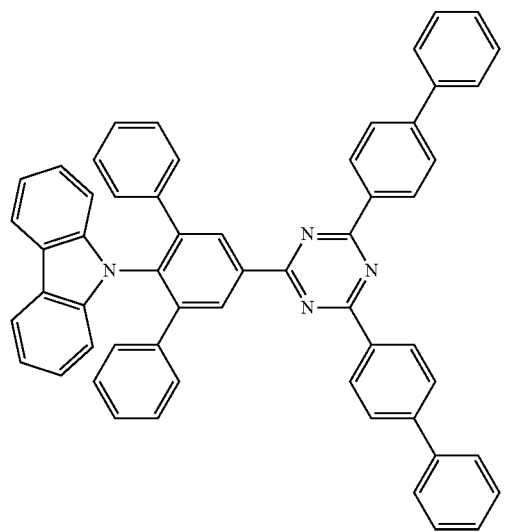
227
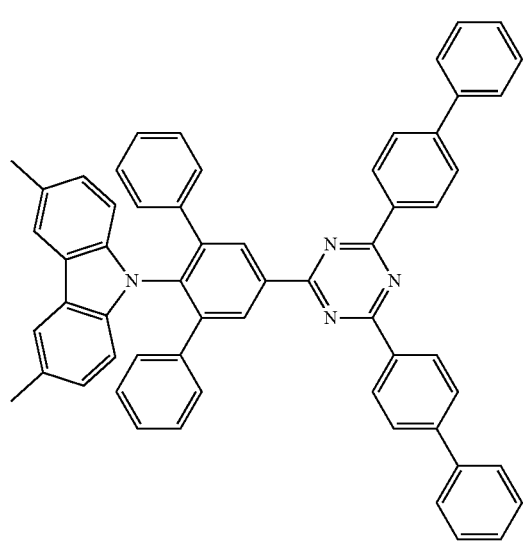
228
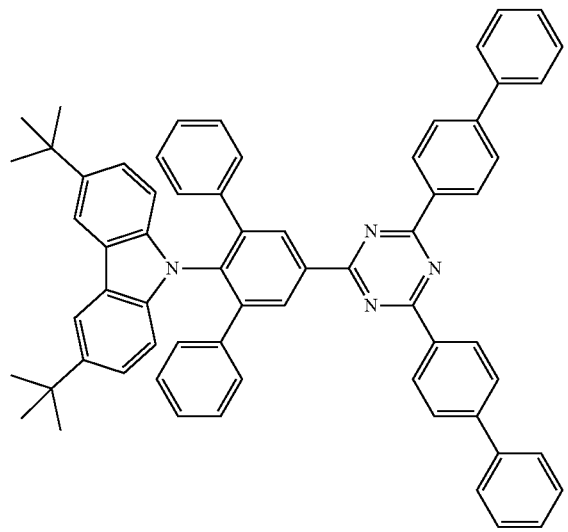

229
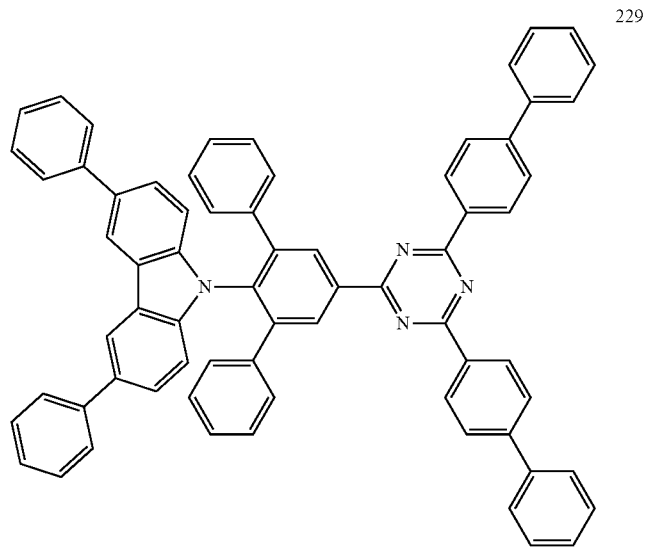 [SMILES: c1ccc(-c2ccc(-c3nc(-c4ccc(-c5ccccc5)cc4)nc(-c4cc(-c5ccccc5)c(-n5c6ccc(-c7ccccc7)cc6c6cc(-c7ccccc7)ccc65)c(-c5ccccc5)c4)n3)cc2)cc1]
230
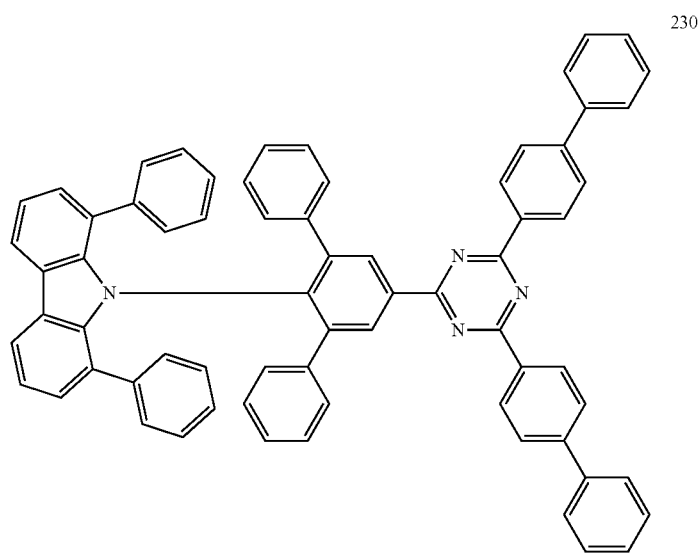
231
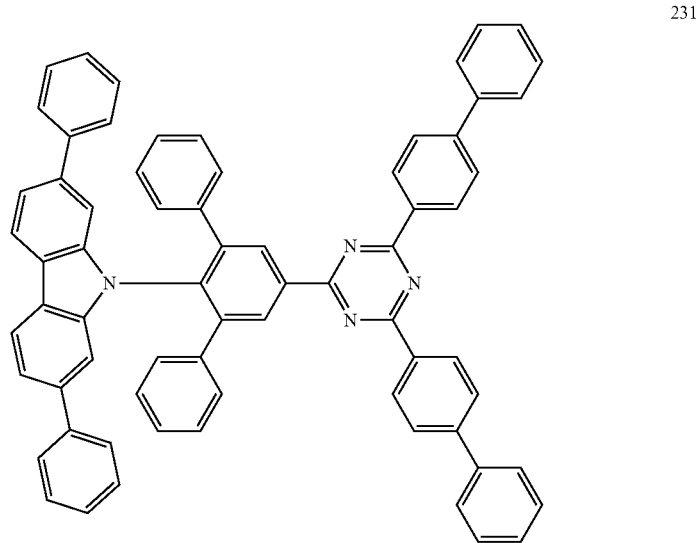

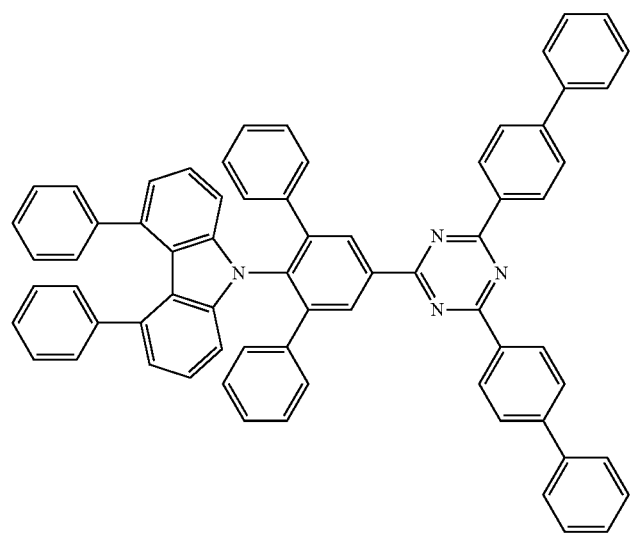
232
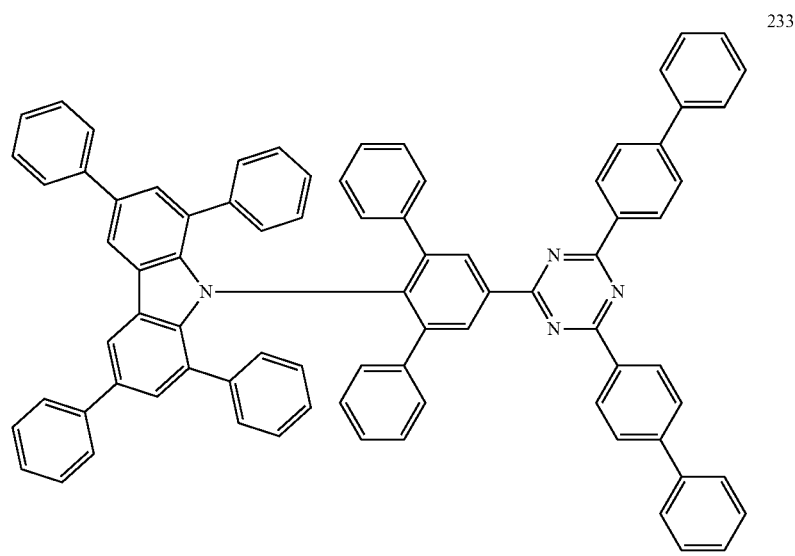 [SMILES: c1ccc(-c2ccc(-c3nc(-c4ccc(-c5ccccc5)cc4)nc(-c4cc(-c5ccccc5)c(-n5c6c(-c7ccccc7)cc(-c7ccccc7)cc6c6cc(-c7ccccc7)cc(-c7ccccc7)c65)c(-c5ccccc5)c4)n3)cc2)cc1]
233
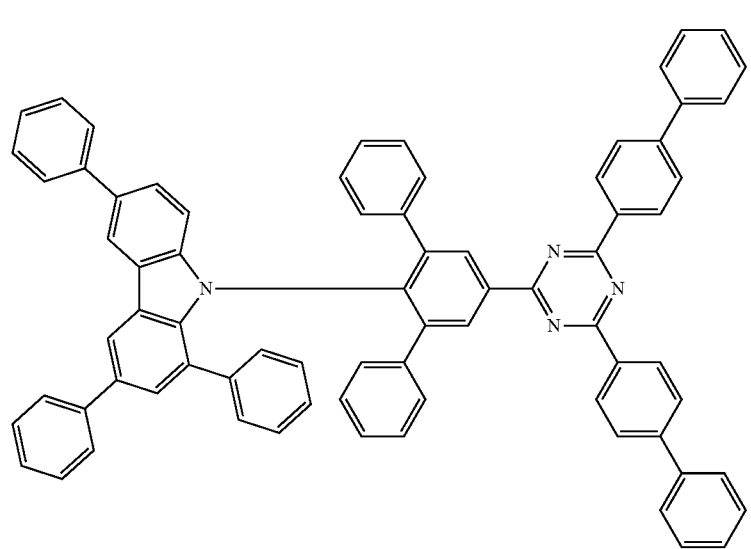
234

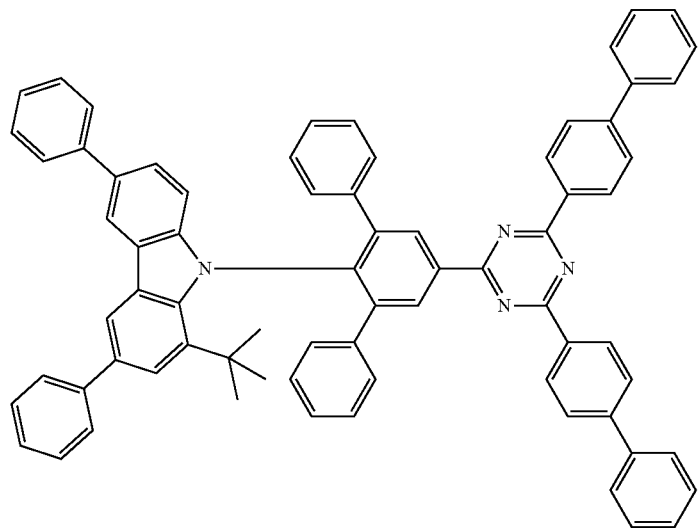
235
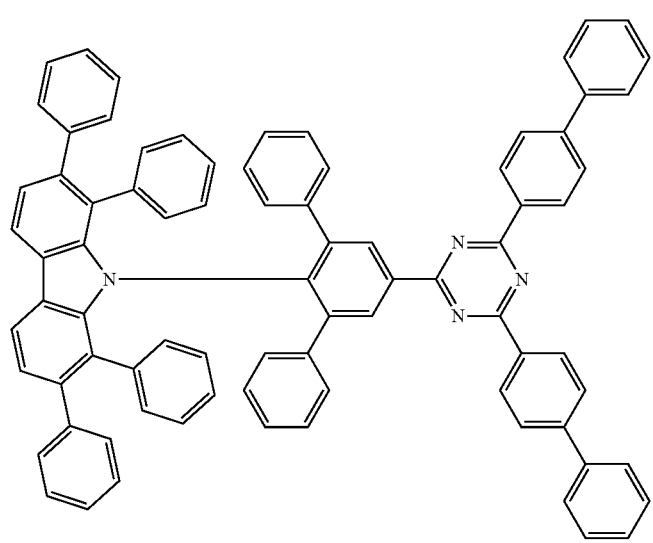
236
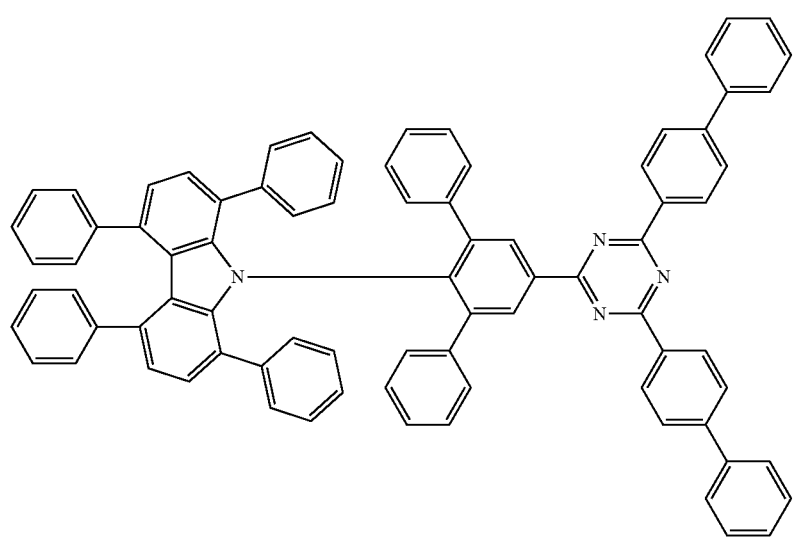
237

-continued
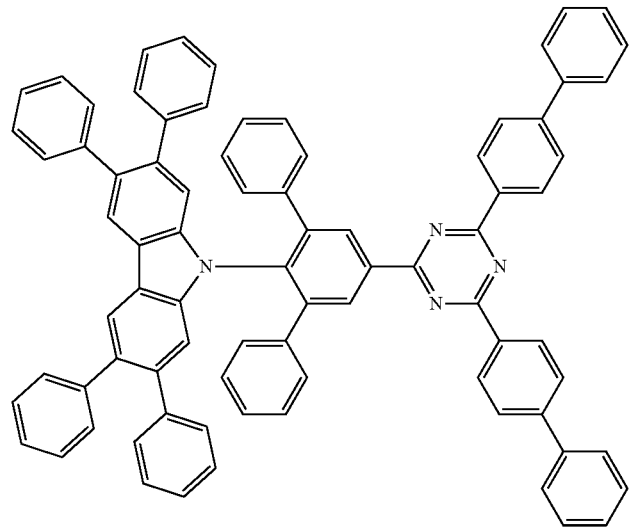
238
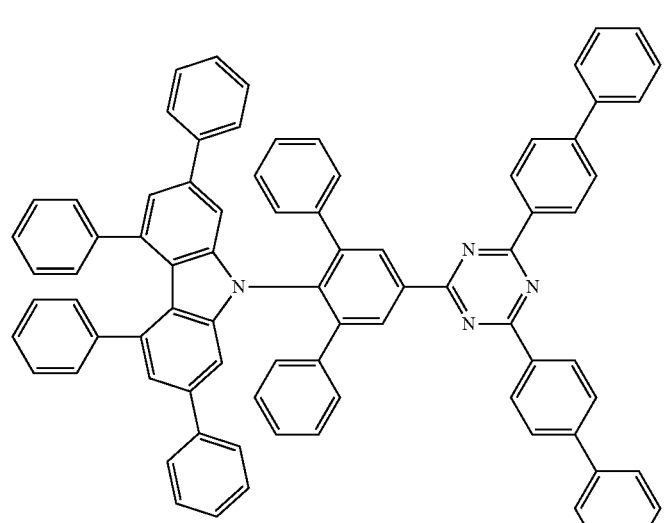
239
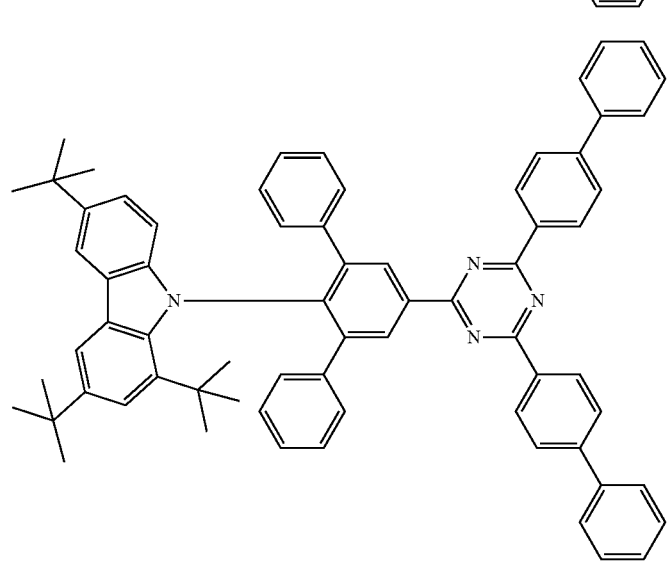
240

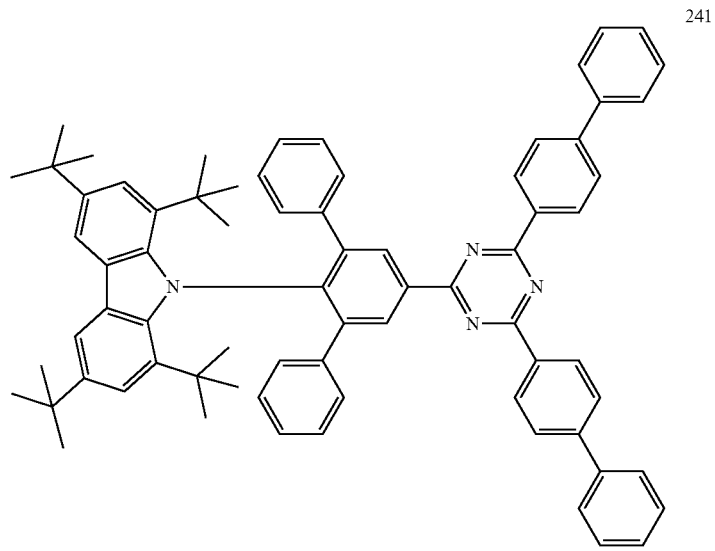 [SMILES: CC(C)(C)c1cc(C(C)(C)C)c2c(c1)c1cc(C(C)(C)C)cc(C(C)(C)C)c1n2-c1c(-c2ccccc2)cc(-c2nc(-c3ccc(-c4ccccc4)cc3)nc(-c3ccc(-c4ccccc4)cc3)n2)cc1-c1ccccc1]
241
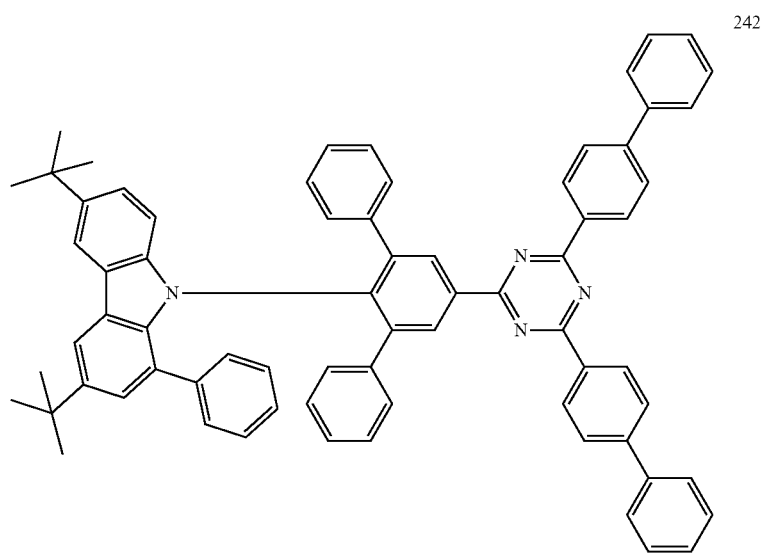
242
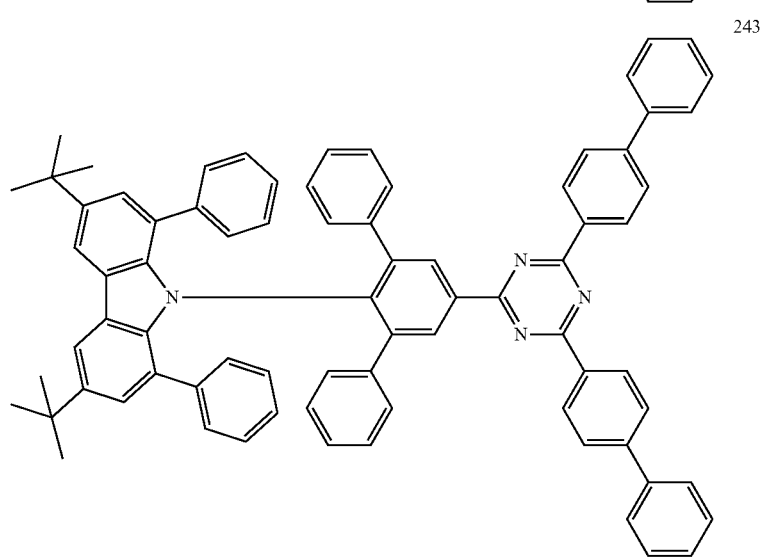
243

-continued
244
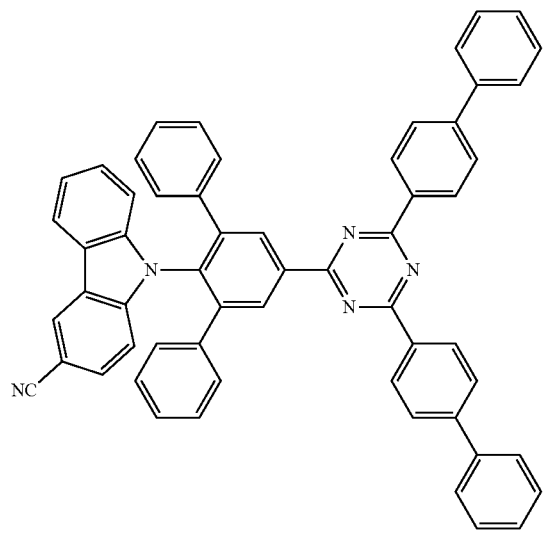
245
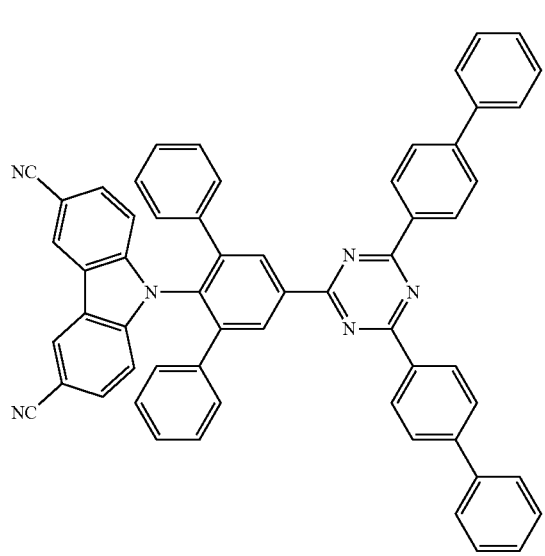
246
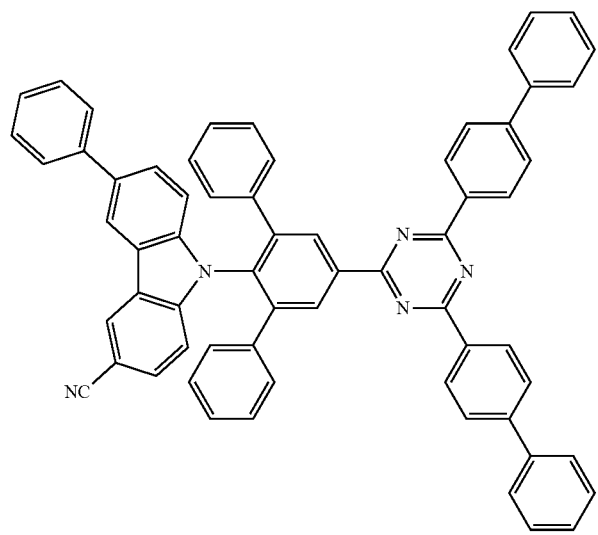

-continued
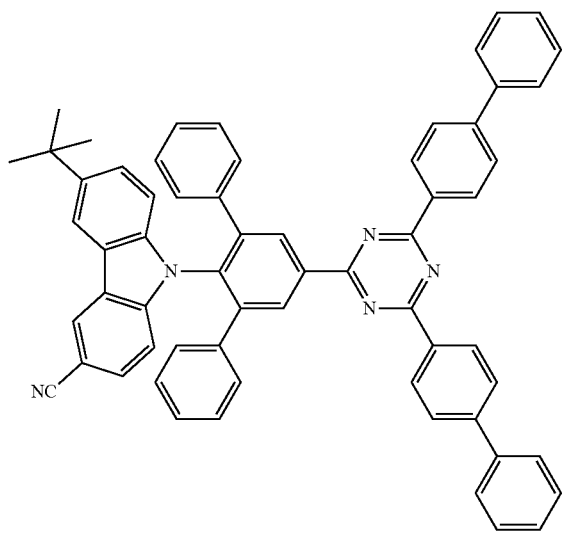
247
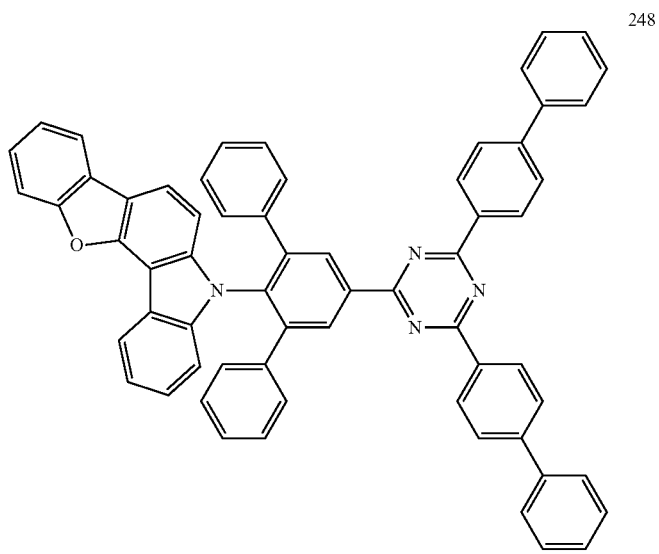
248
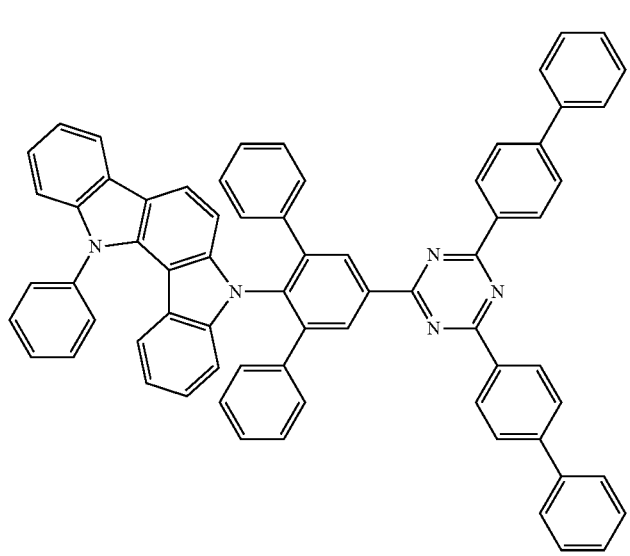
249

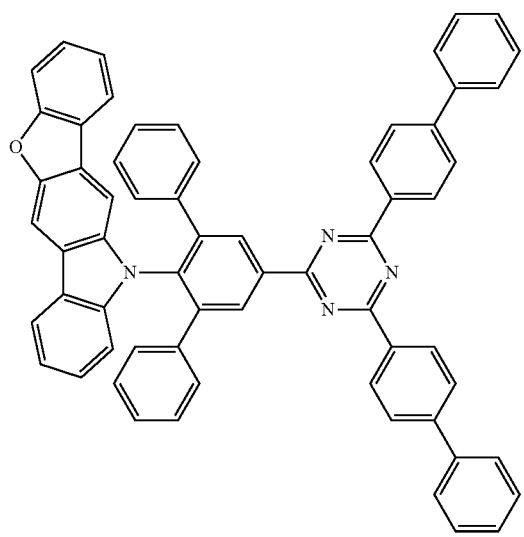
250
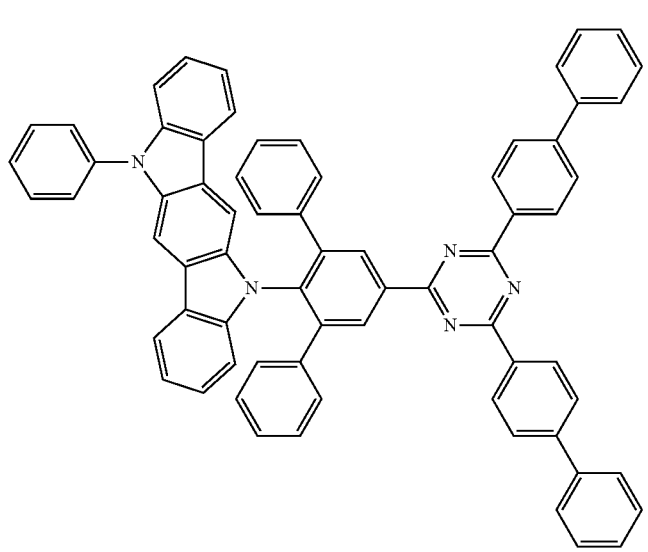
251
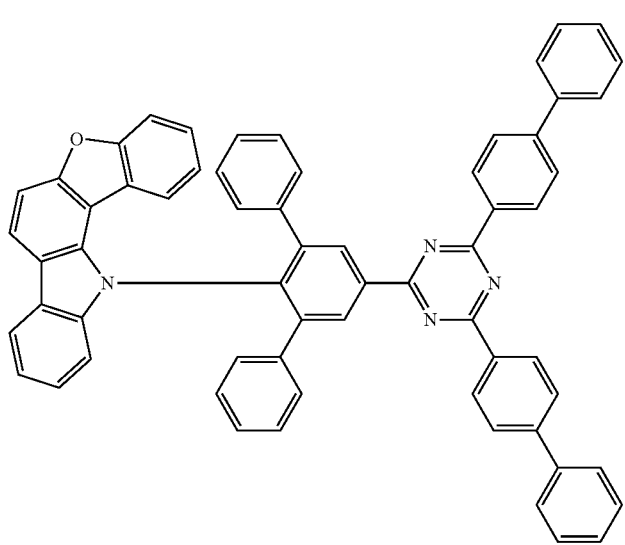
252

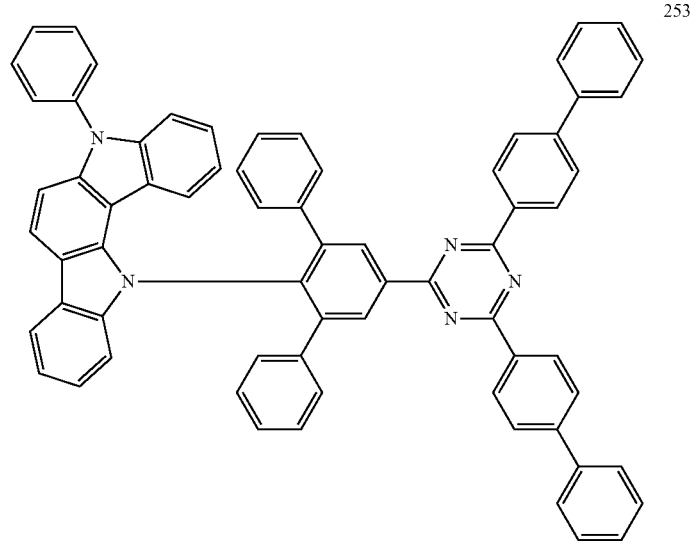 [SMILES: c1ccc(-c2ccc(-c3nc(-c4ccc(-c5ccccc5)cc4)nc(-c4cc(-c5ccccc5)c(-n5c6ccccc6c6ccc7c(c8ccccc8n7-c7ccccc7)c65)c(-c5ccccc5)c4)n3)cc2)cc1]
253
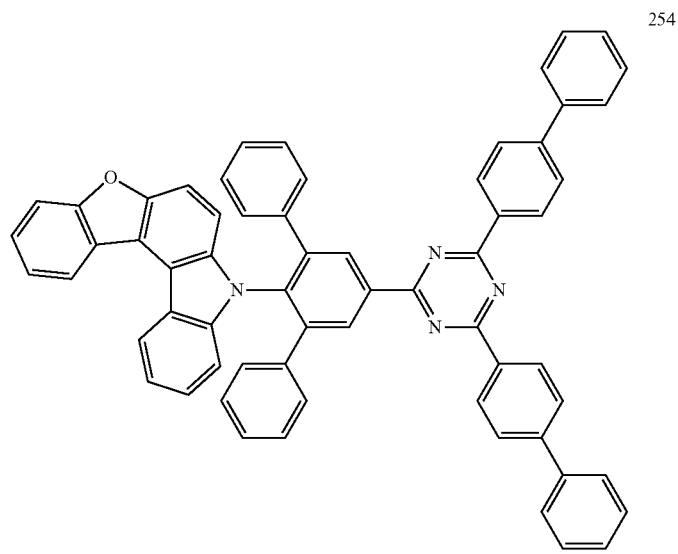
254
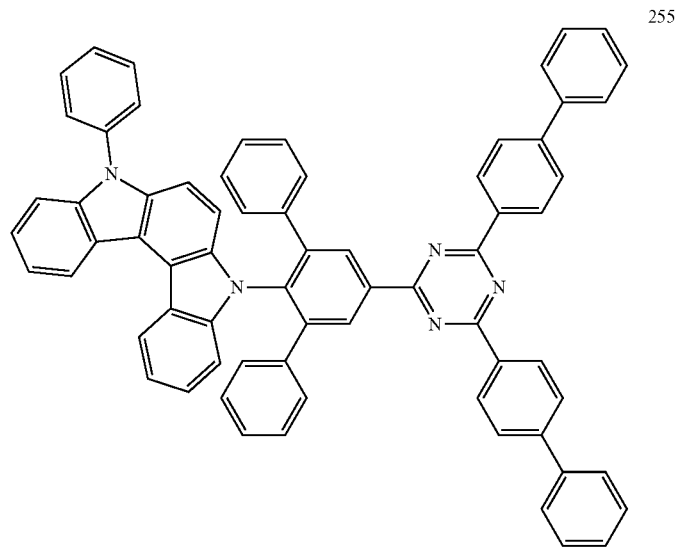
255

-continued
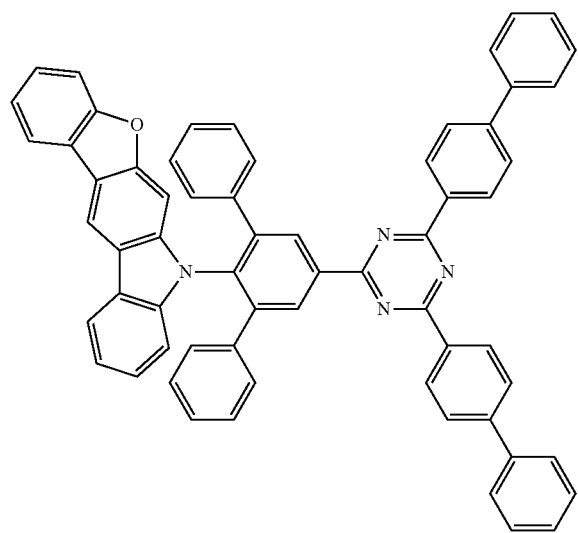
256
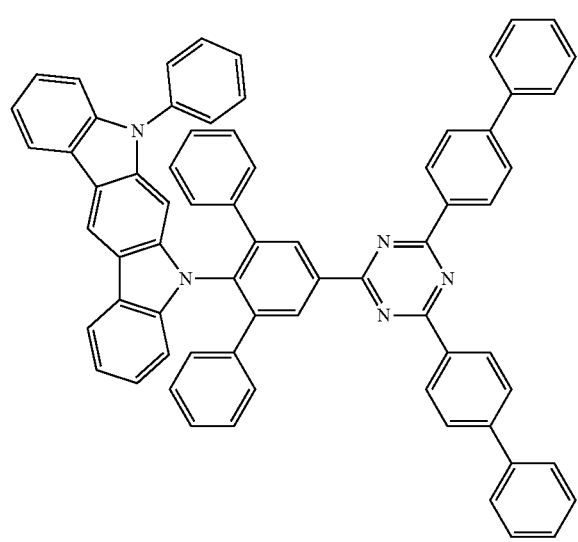
257
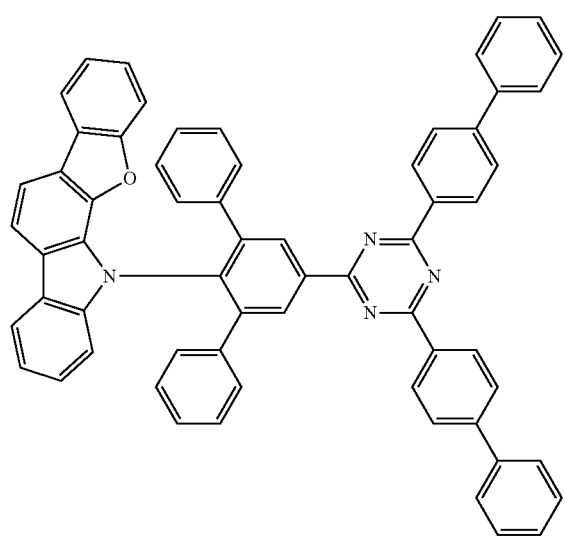
258

-continued
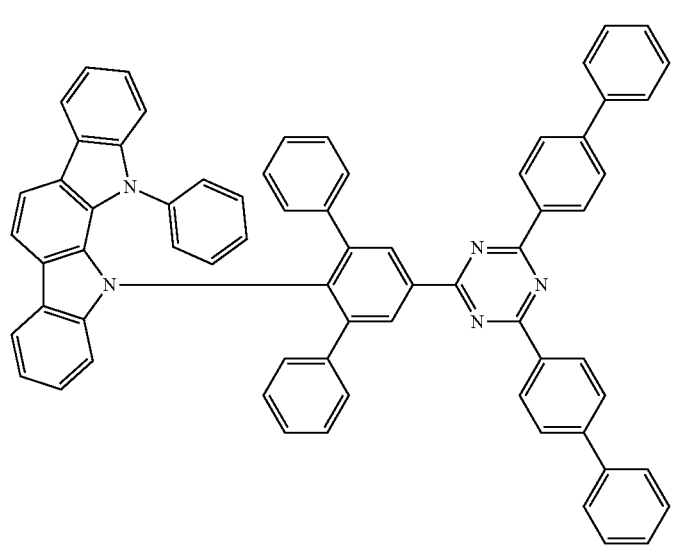
259
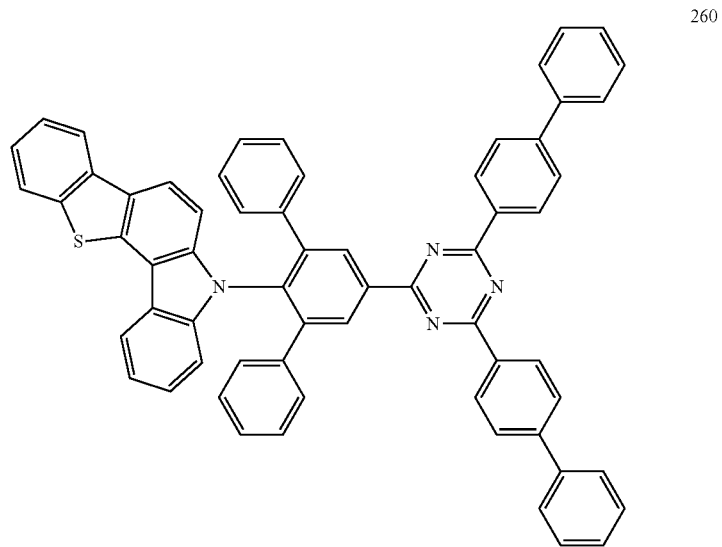
260
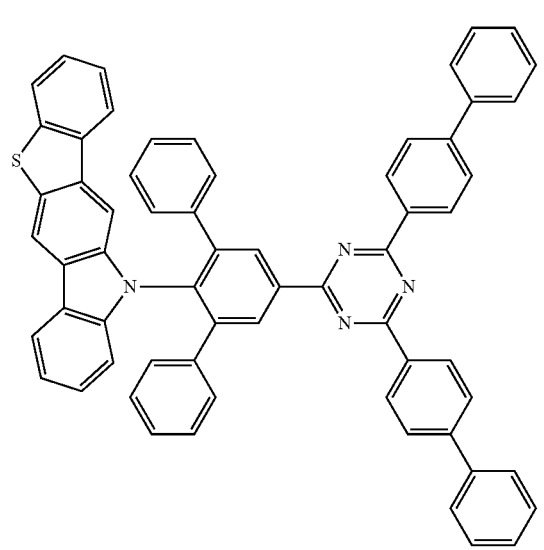
261

-continued
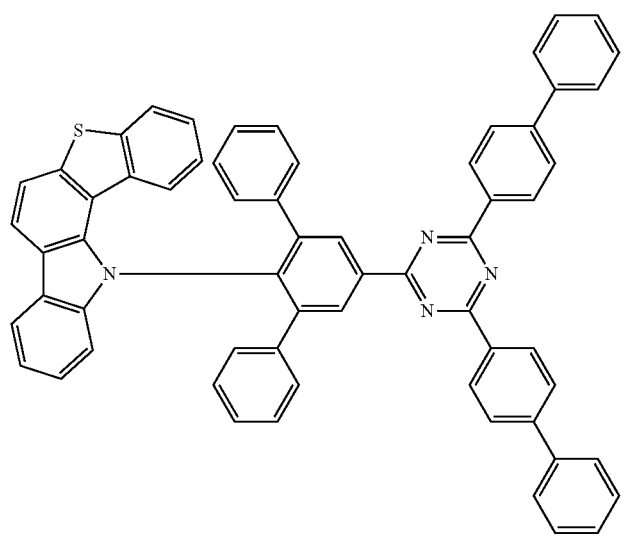
262
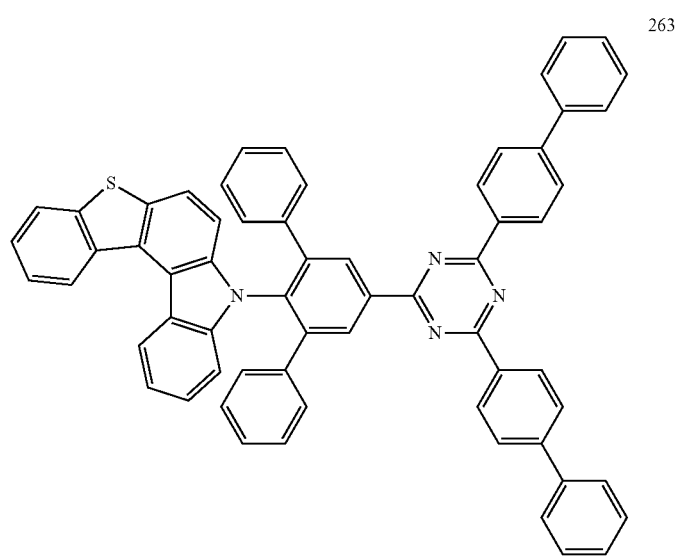
263
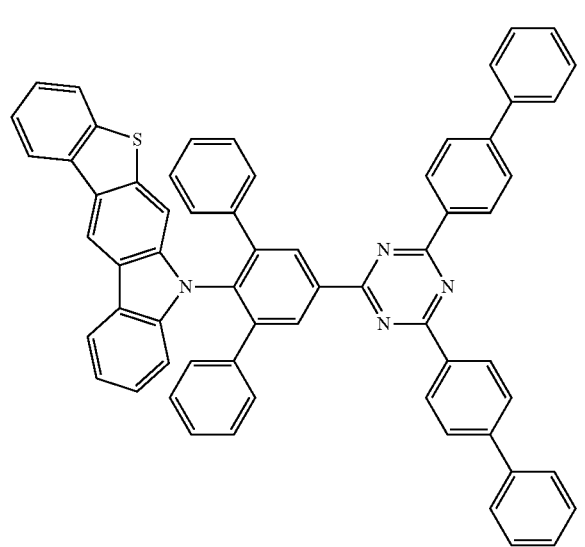
264

-continued
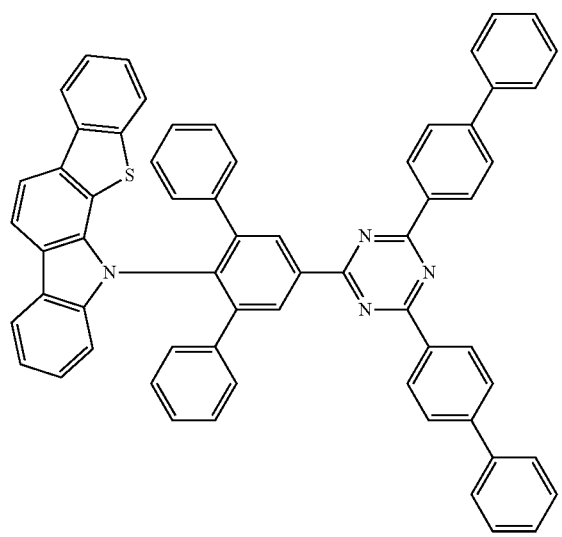
265
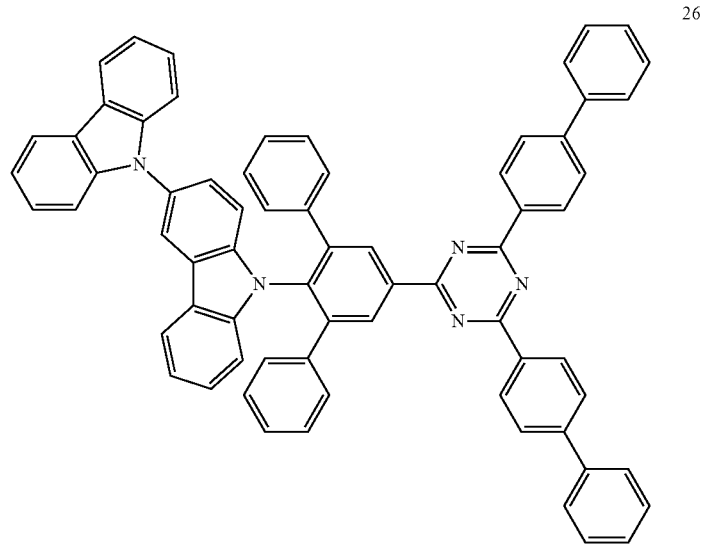
266
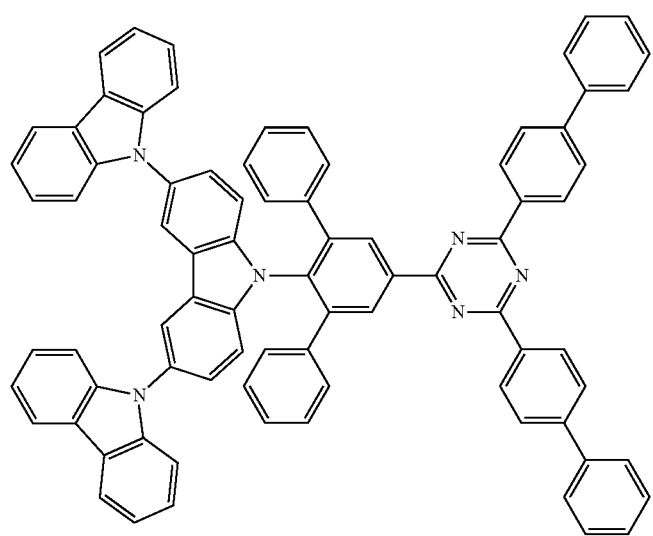
267

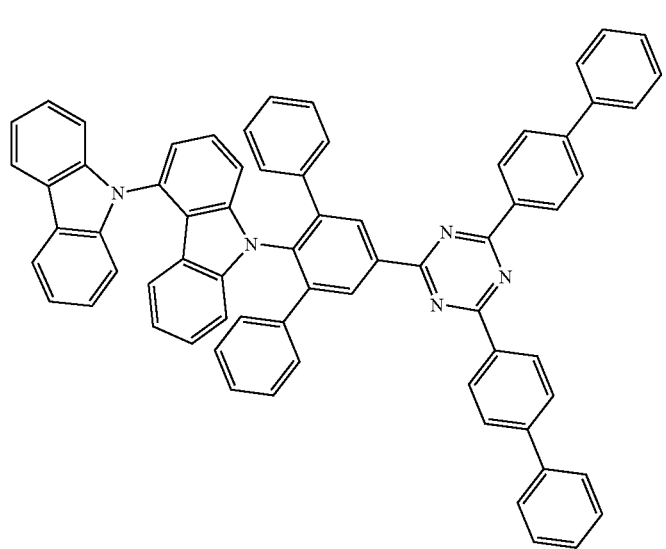
268
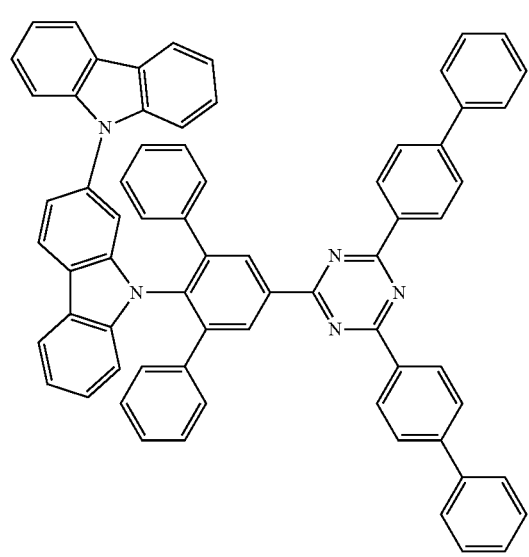
269
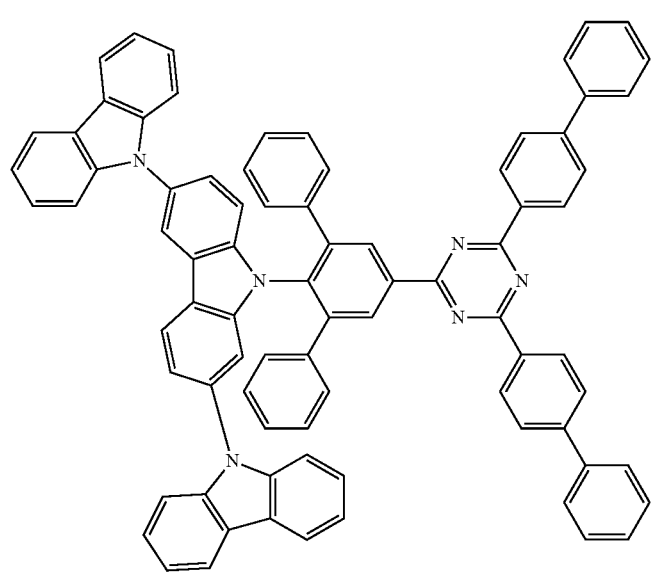
270

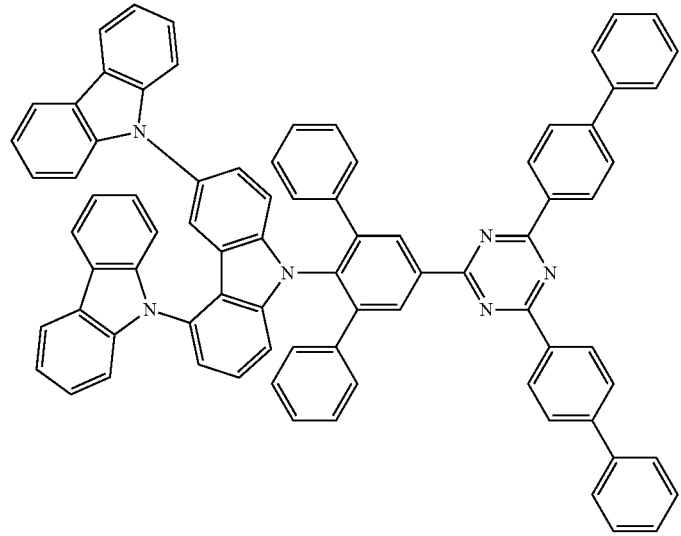
271
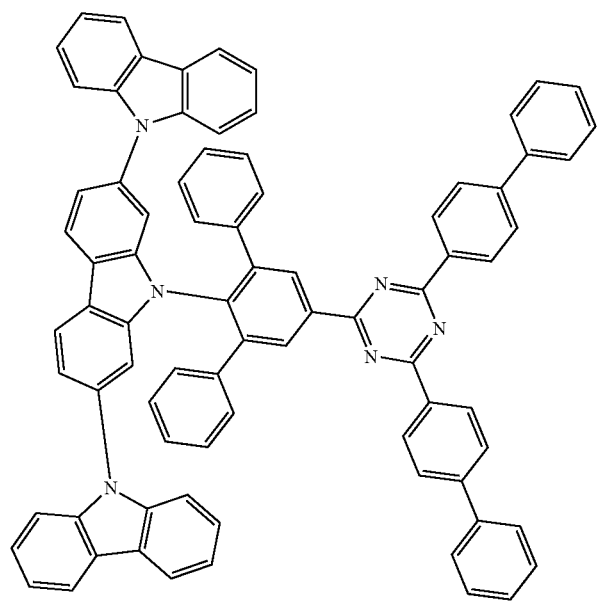
272

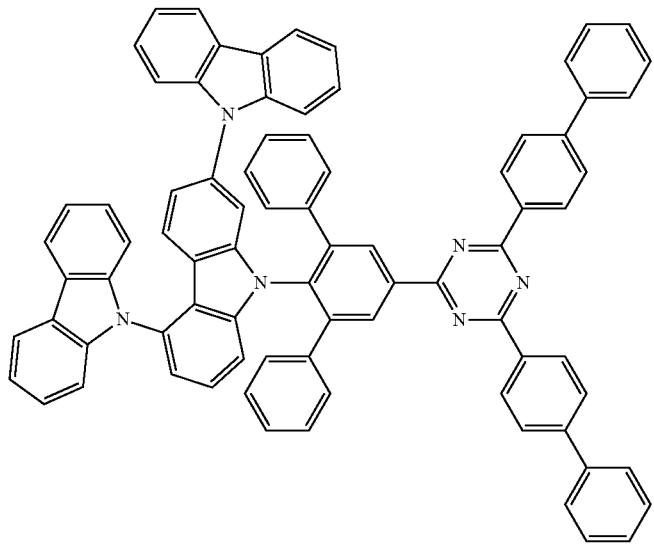
273
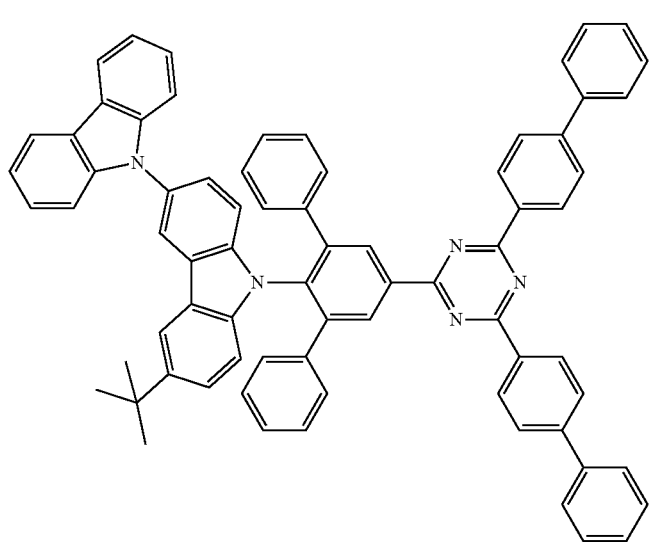
274
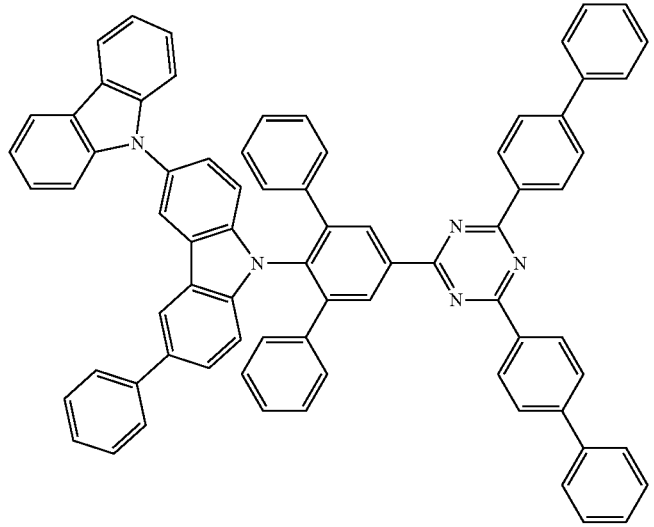
275

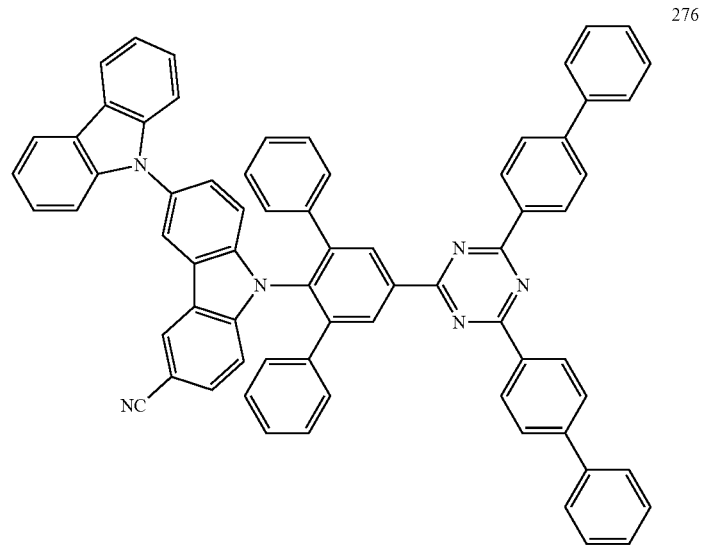 [SMILES: c1ccc(-c2ccc(-c3nc(-c4ccc(-c5ccccc5)cc4)nc(-c4cc(-c5ccccc5)c(-n5c6ccc(-n7c8ccccc8c8ccccc87)cc6c6ccc(-c7ccccc7)cc65)c(-c5ccccc5)c4)n3)cc2)cc1]
276
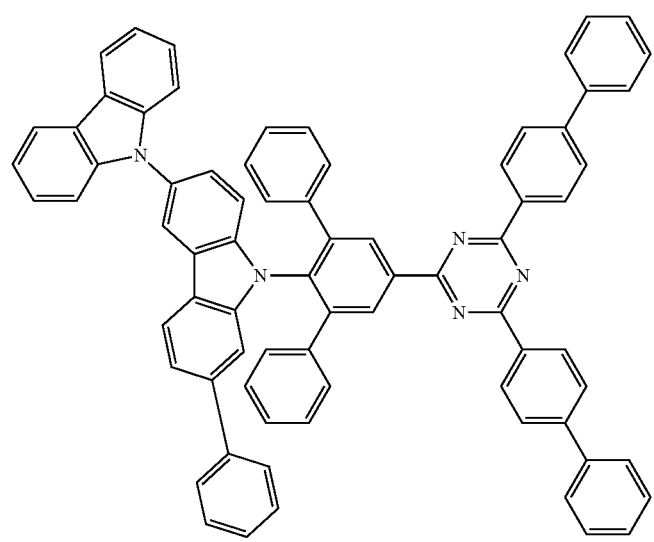
277

263
264
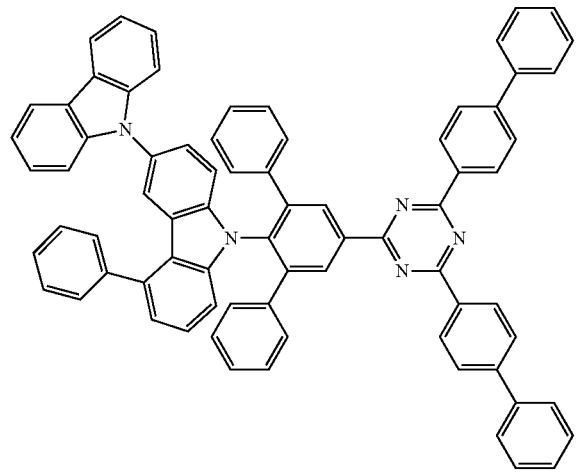
278
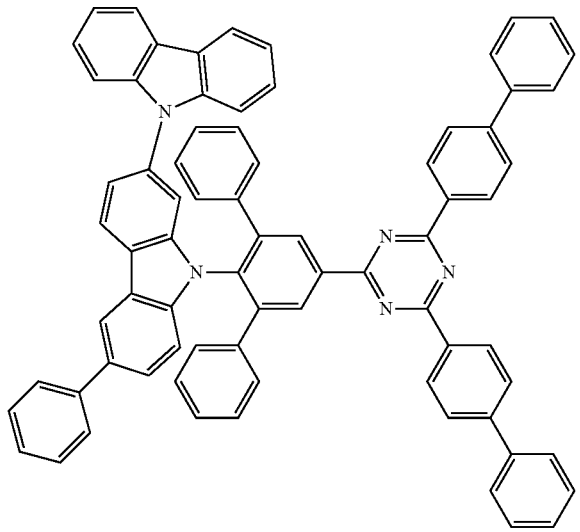
279
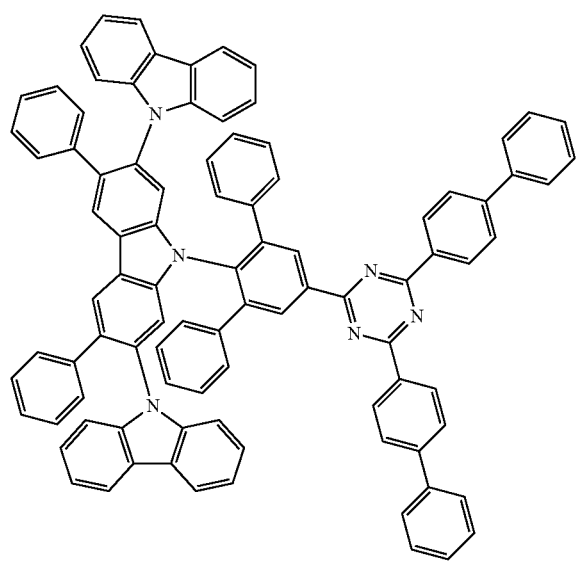
280
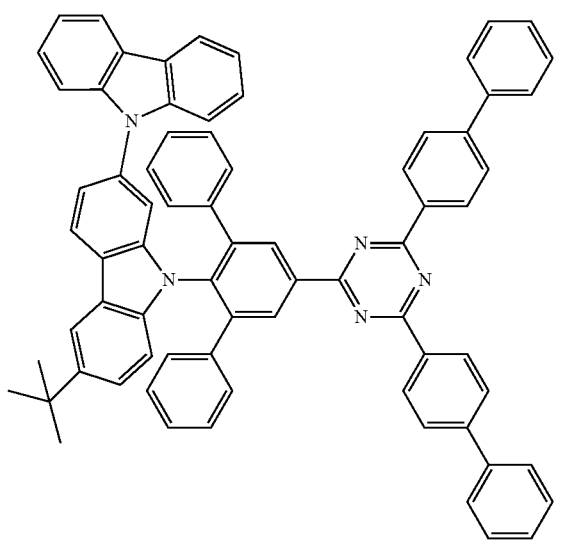
281

282
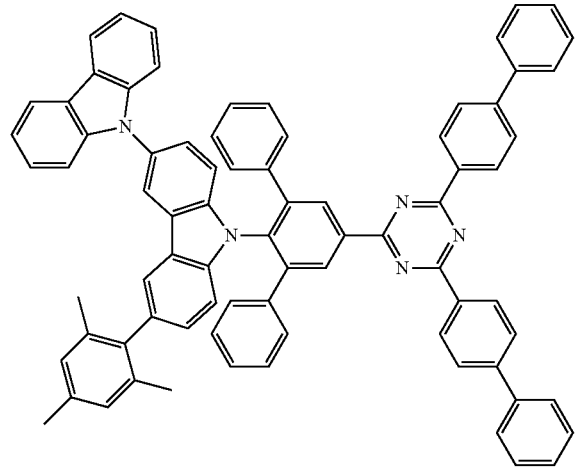
283
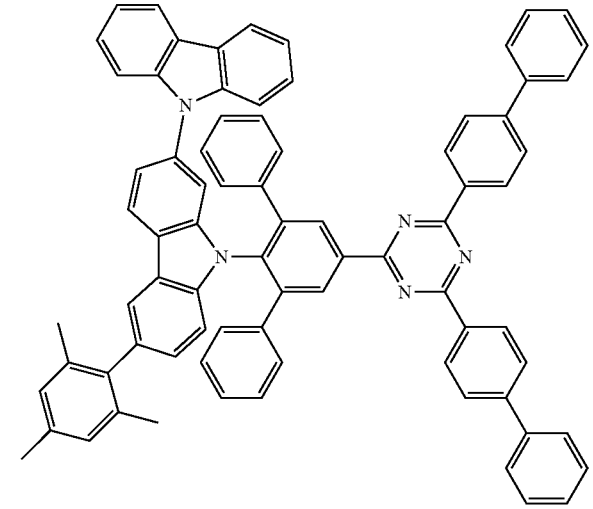
284
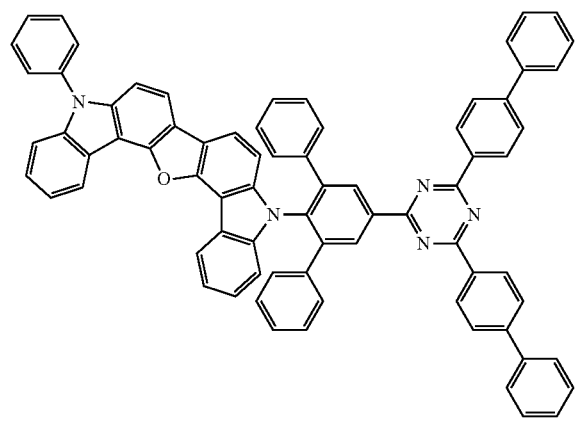
285
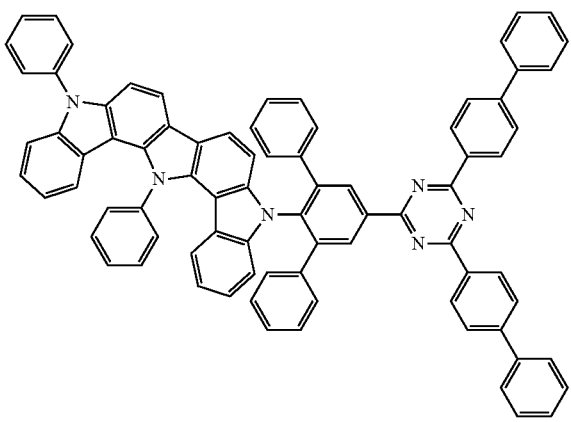
286
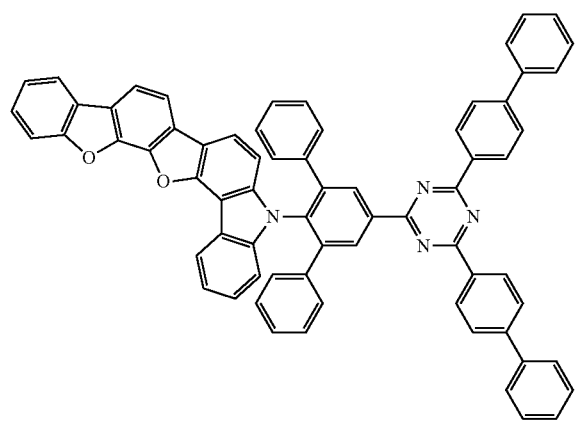
287
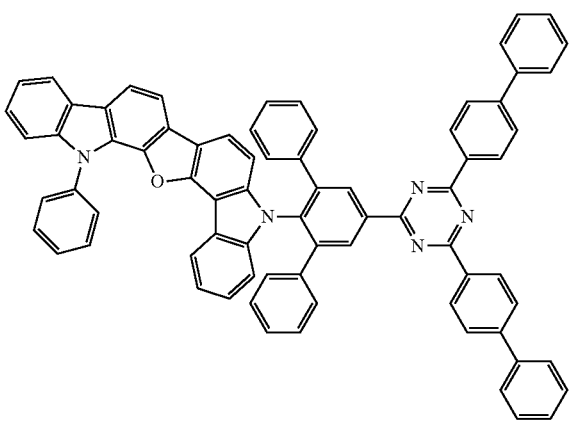

-continued
288
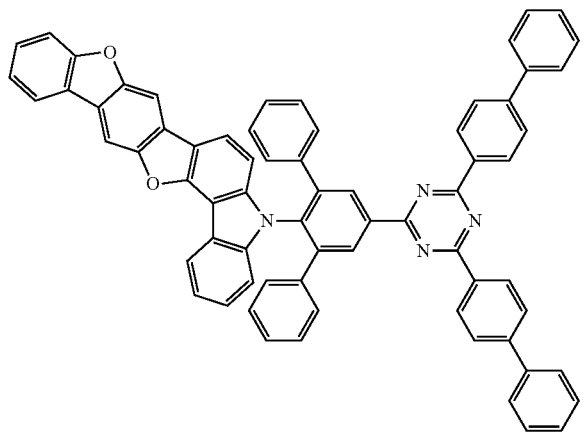
289
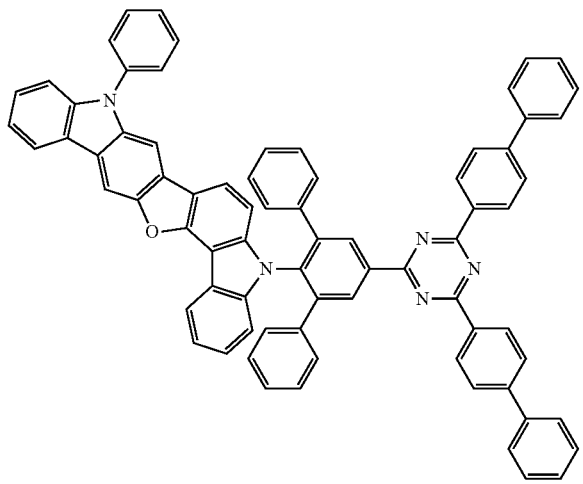
290
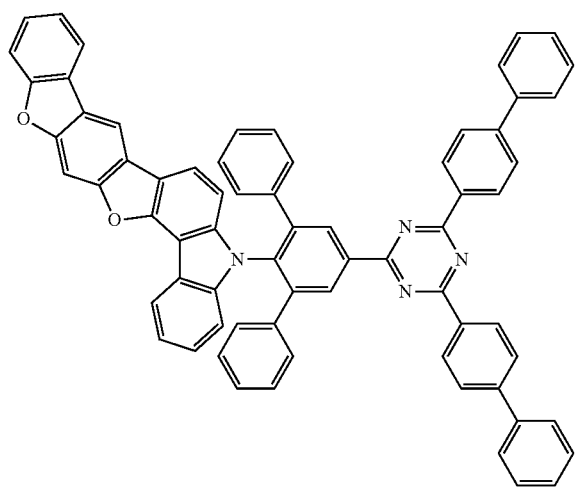
291
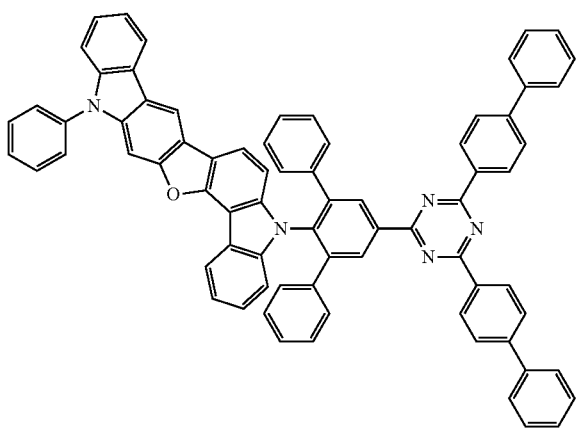
292
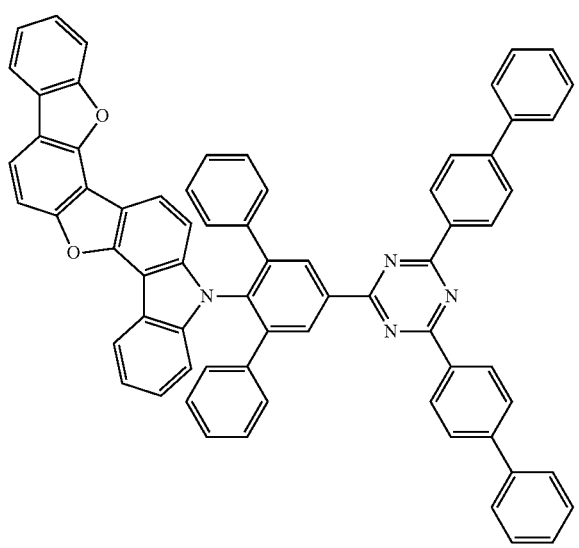
293
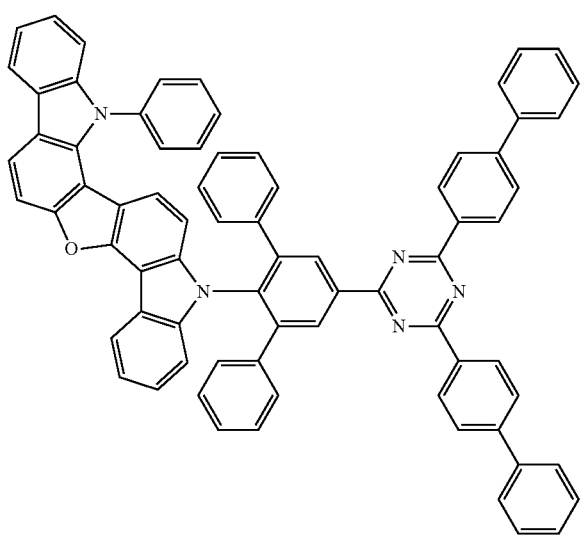

-continued
294
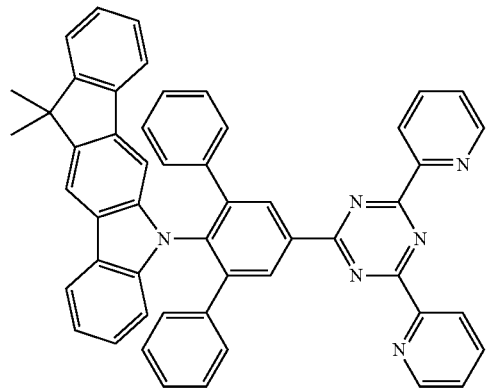
295
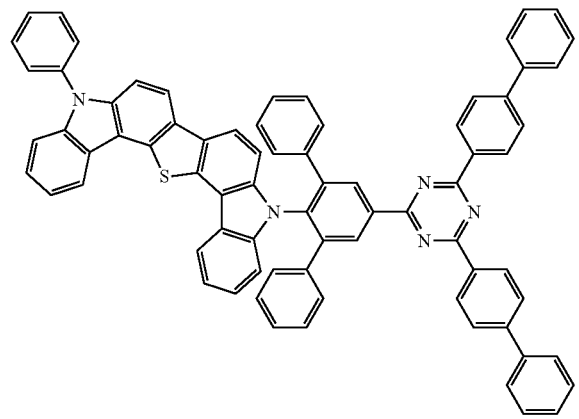
296
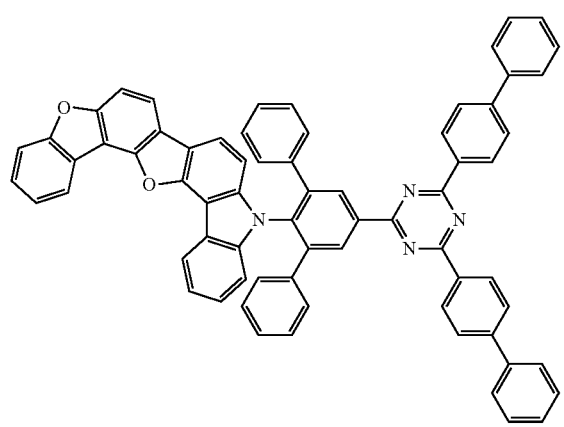
297
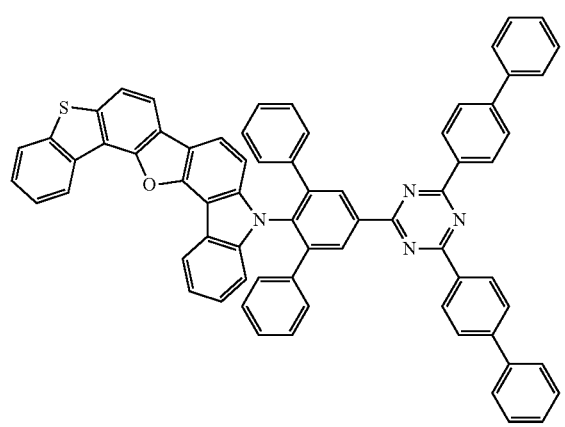
298
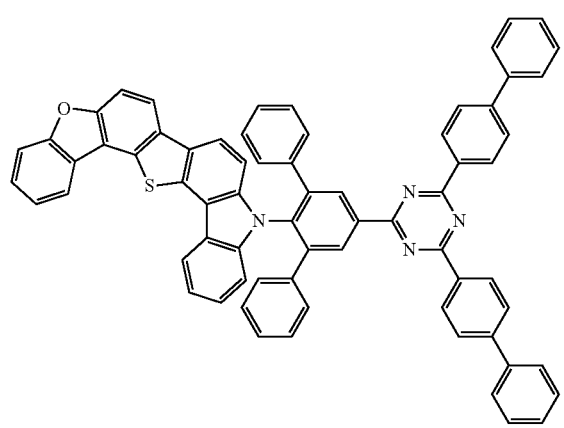
299
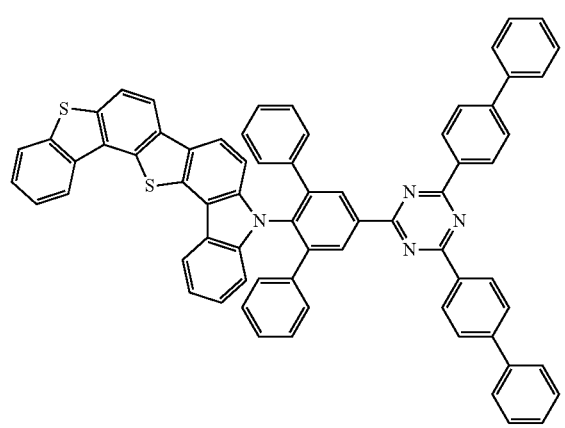

-continued
300
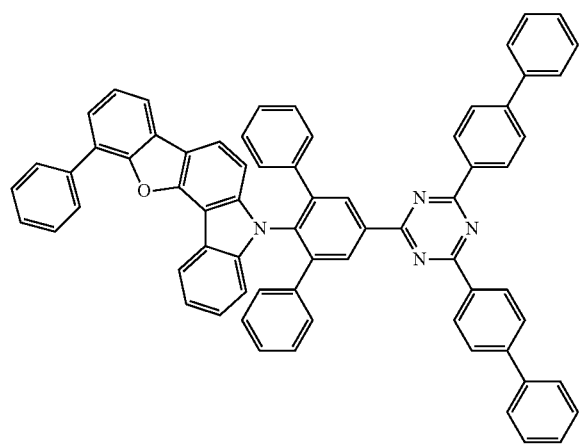
301
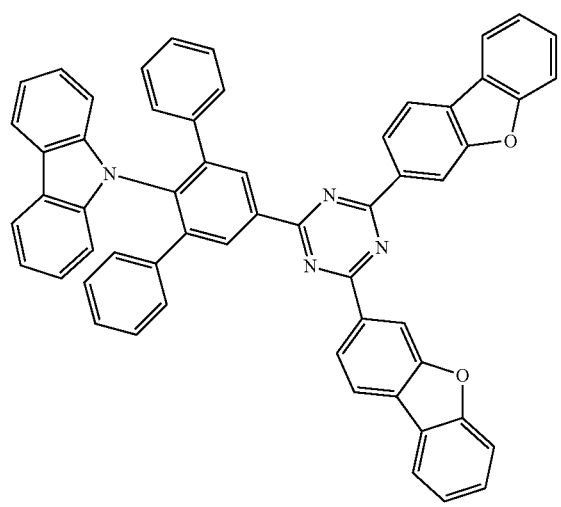
302
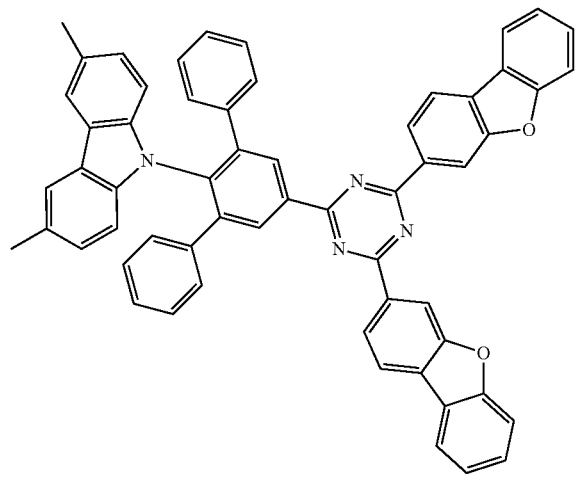
303
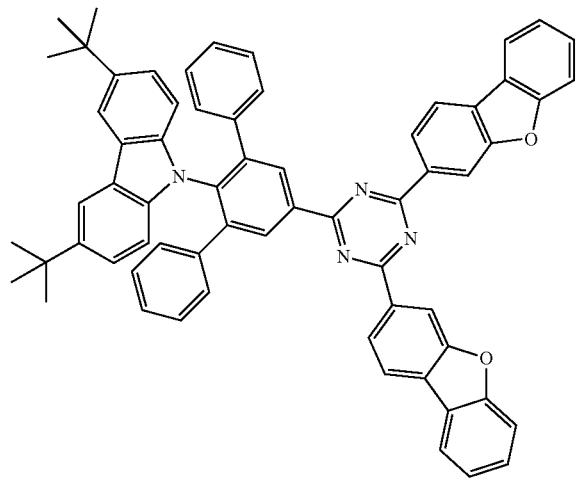
304
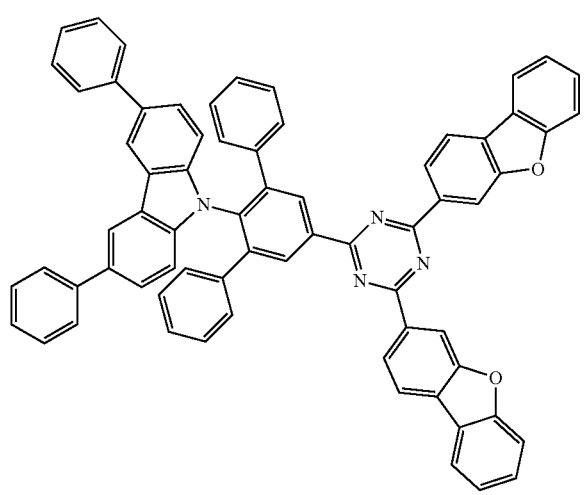
305
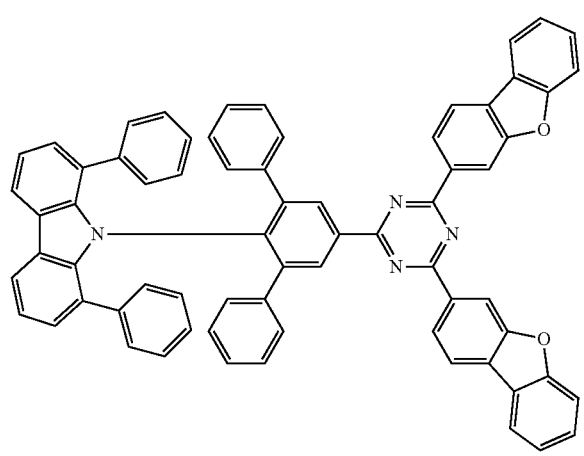

306
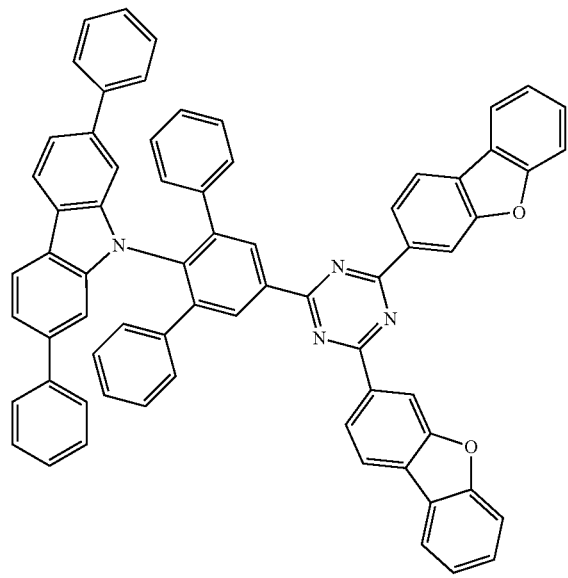
307
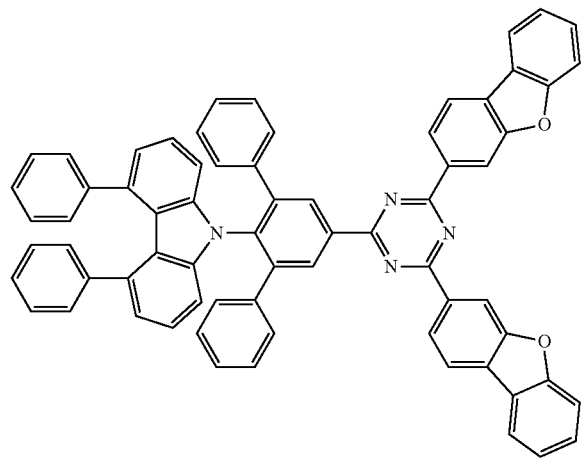
308
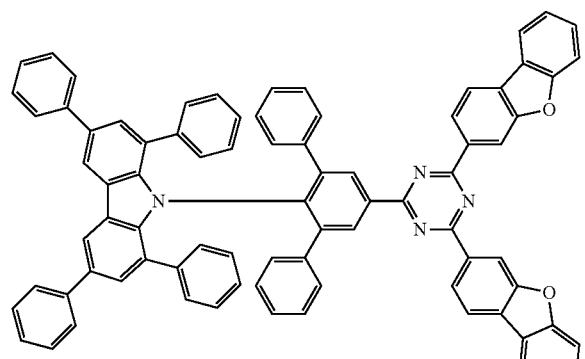
309
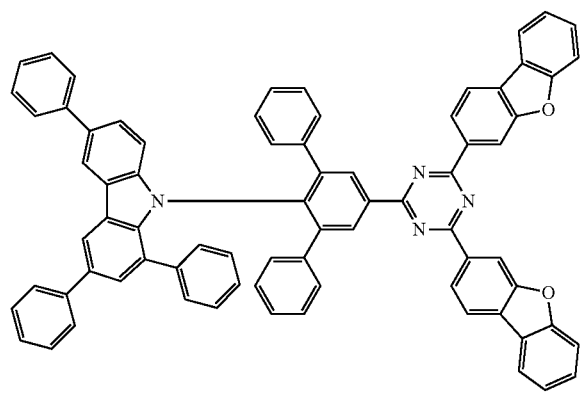
310
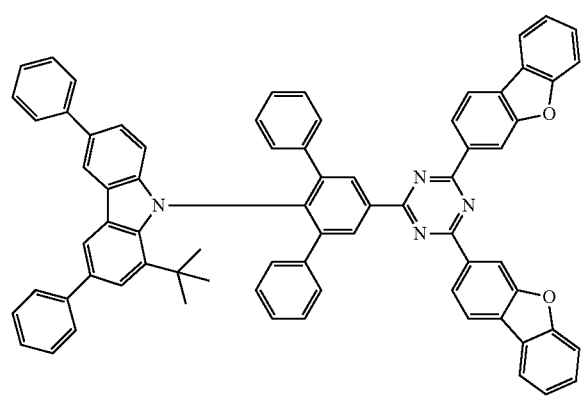
311
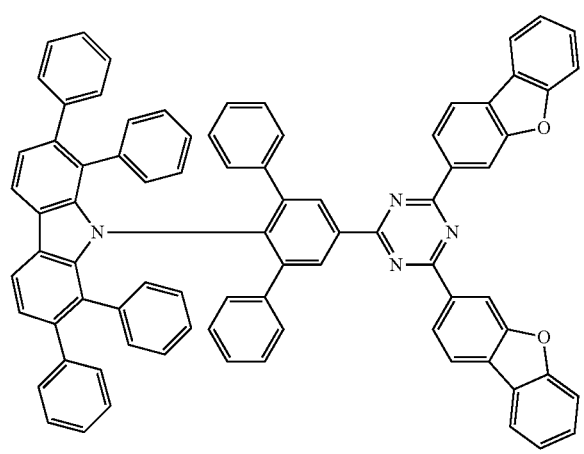

-continued
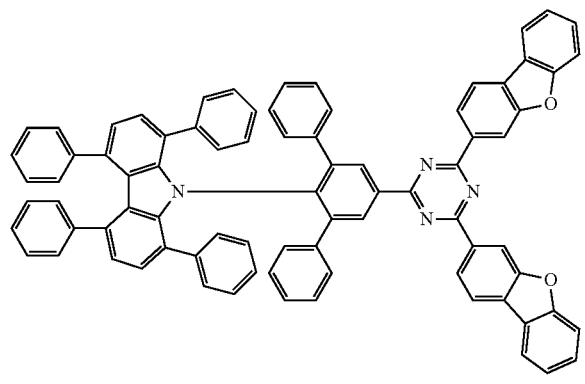
312
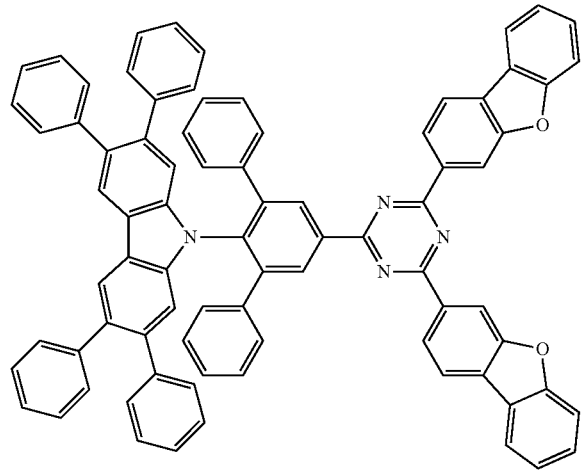
313
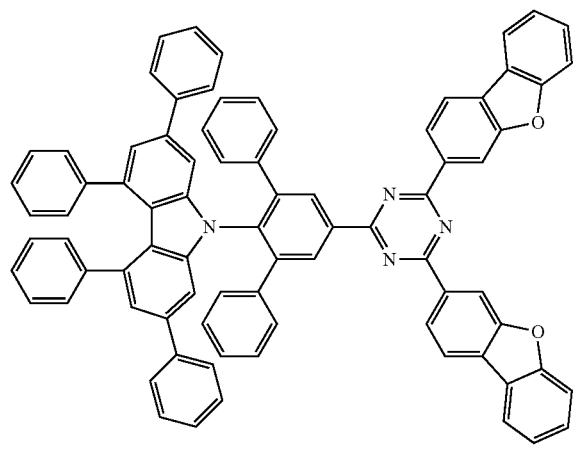
314
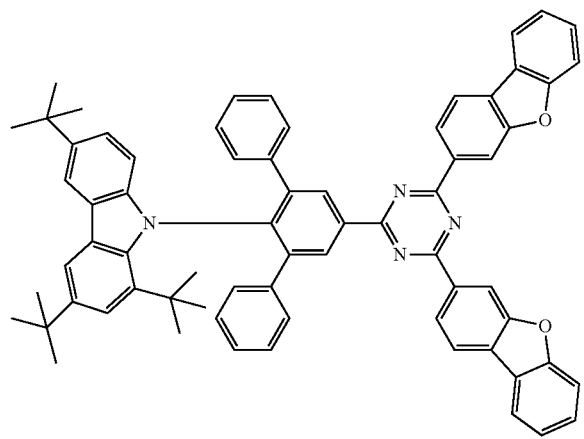
315
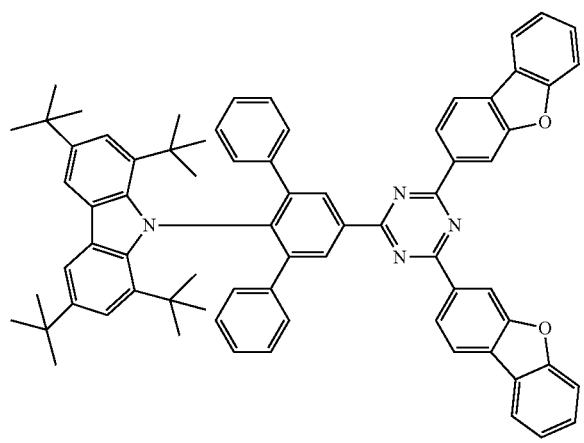
316
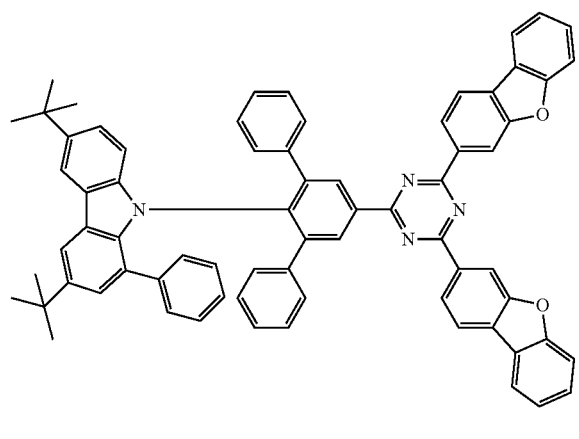
317

-continued
318
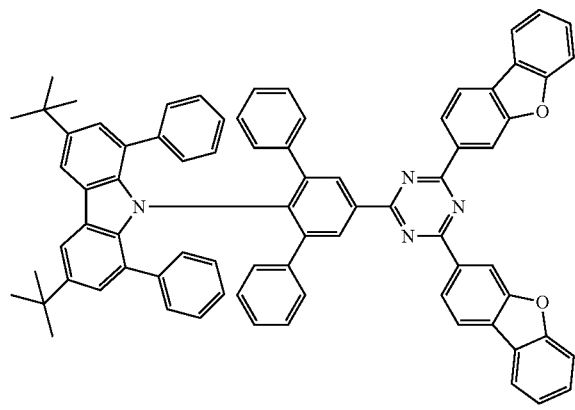
319
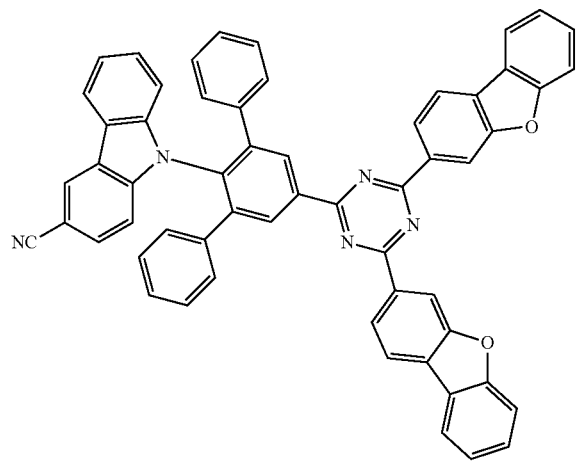
320
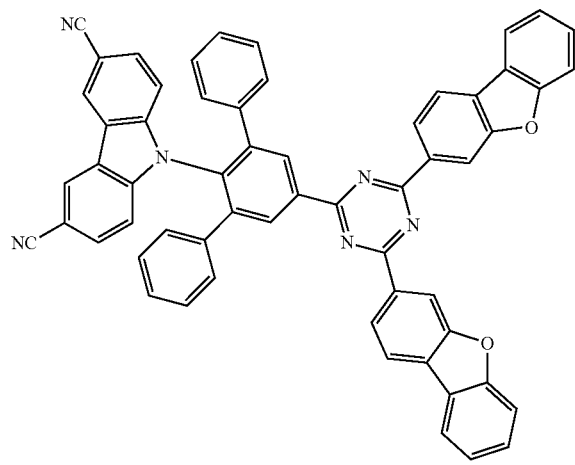
321
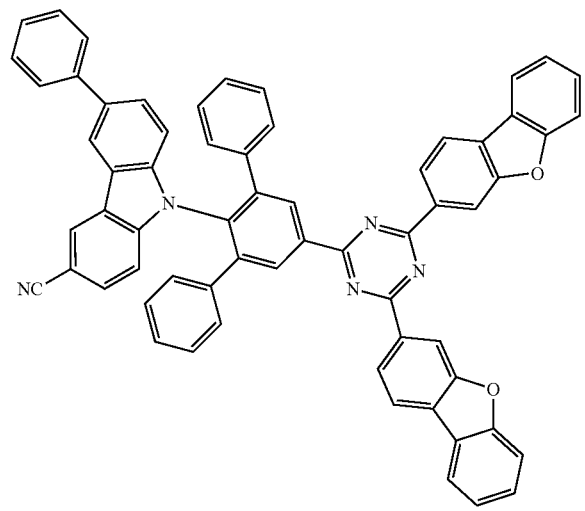
322
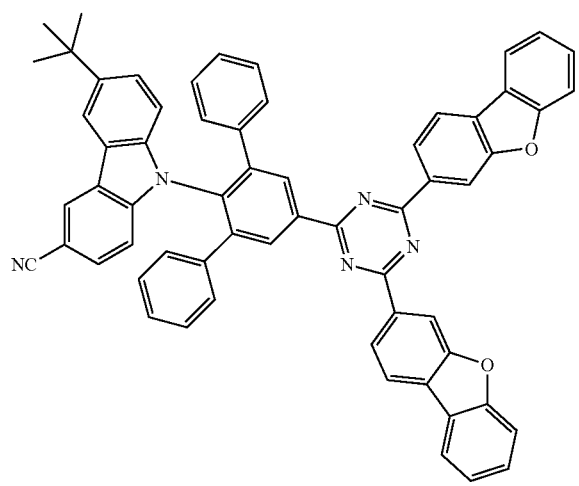
323
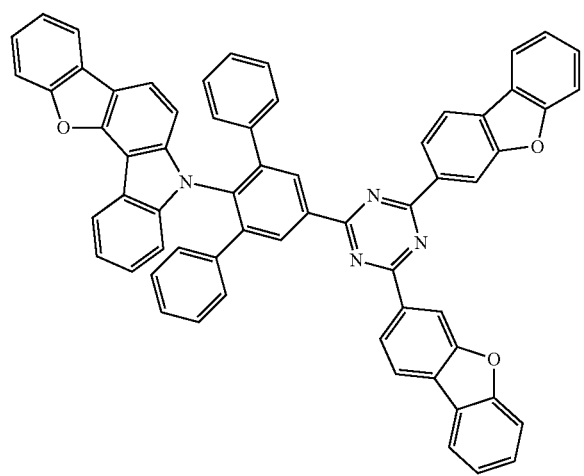

-continued
324
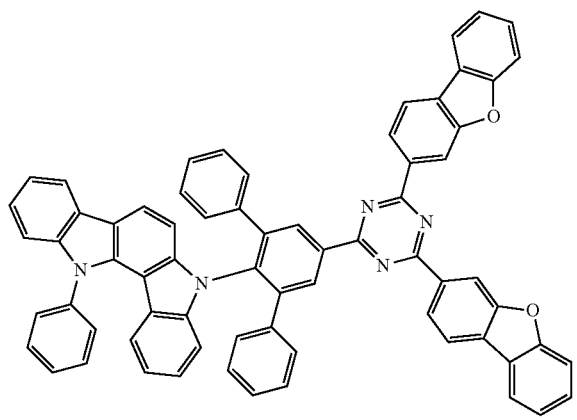
325
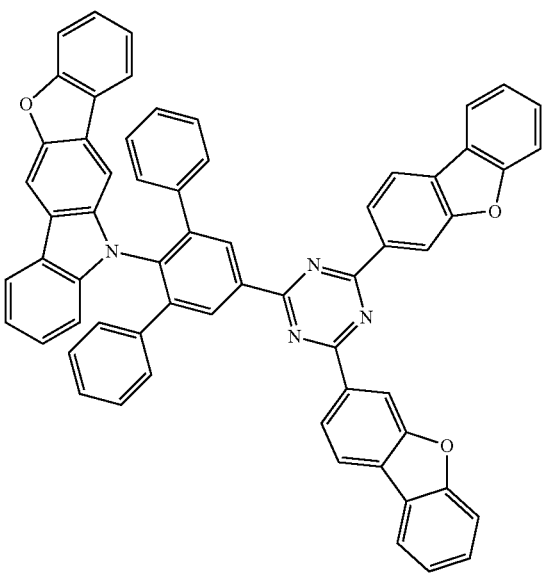
326
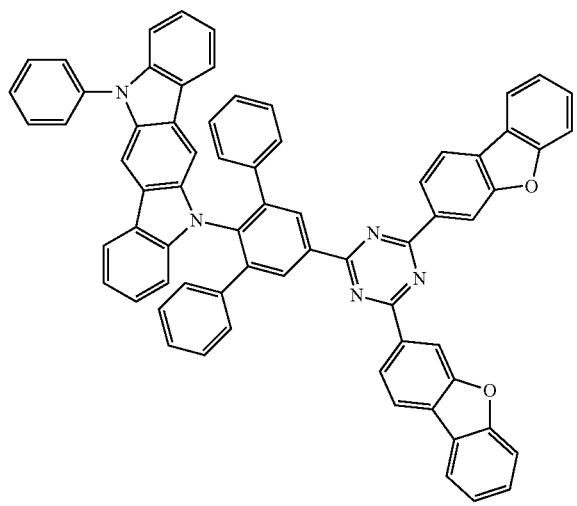
327
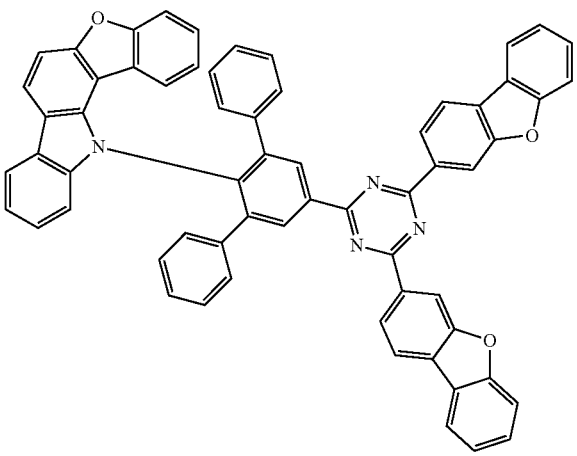
328
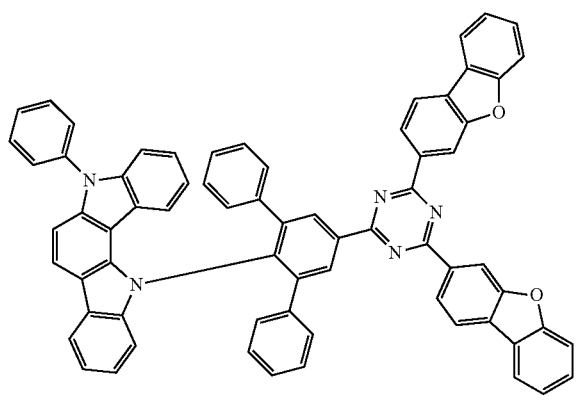
329
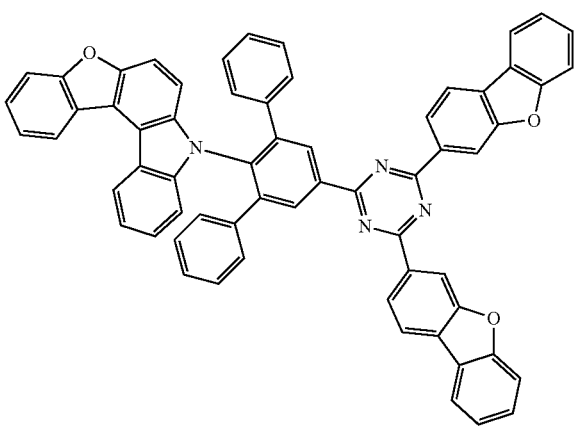

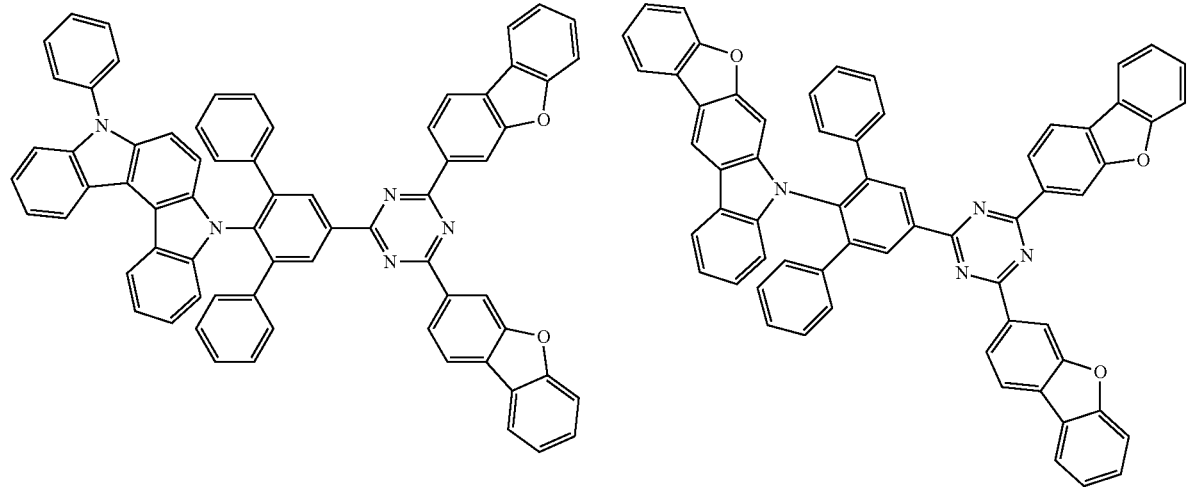
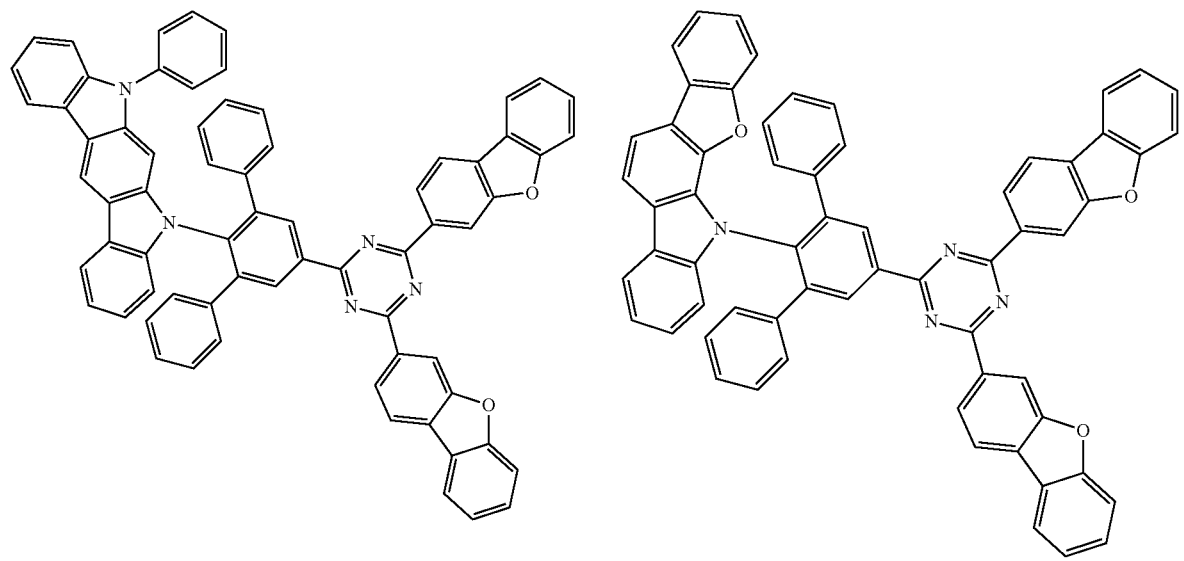
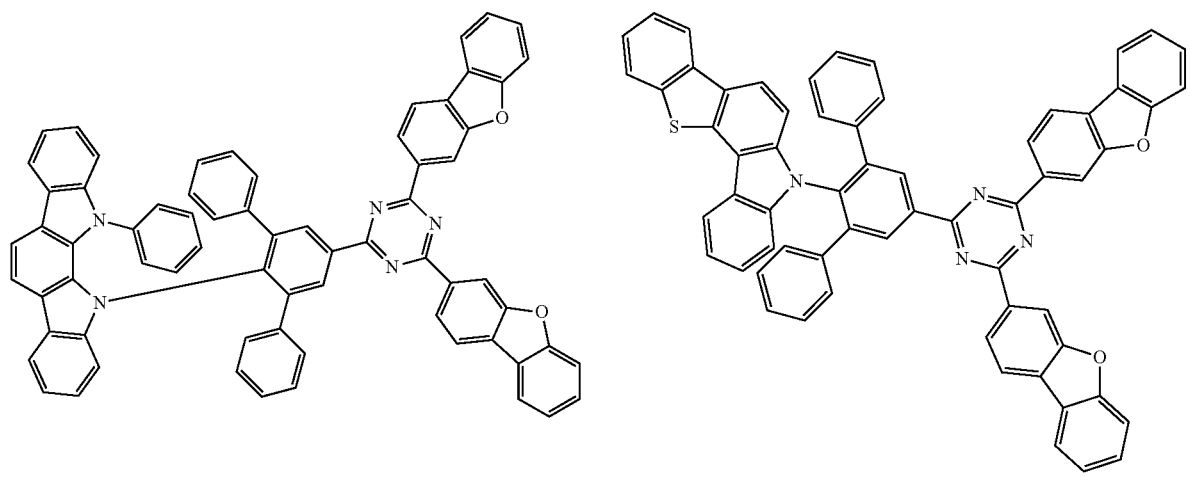

336
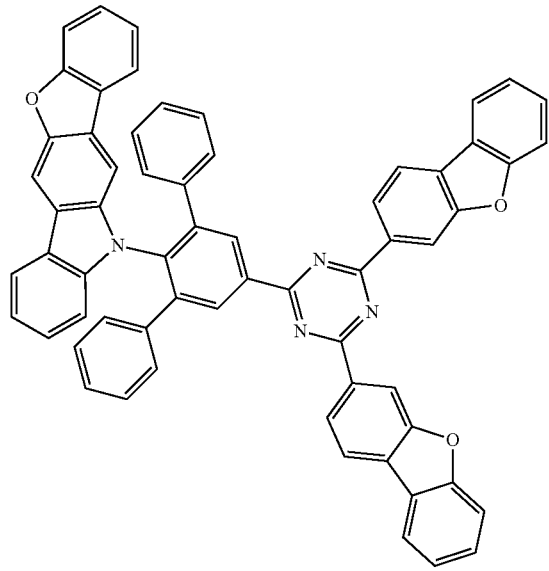
337
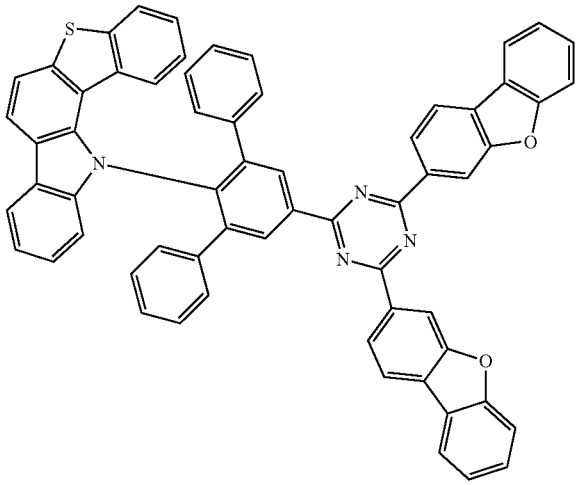
338
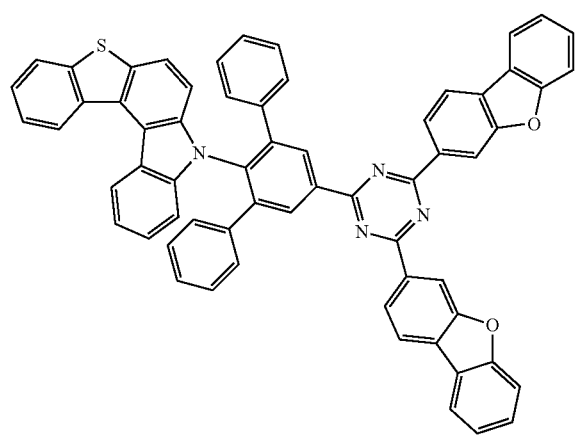
339
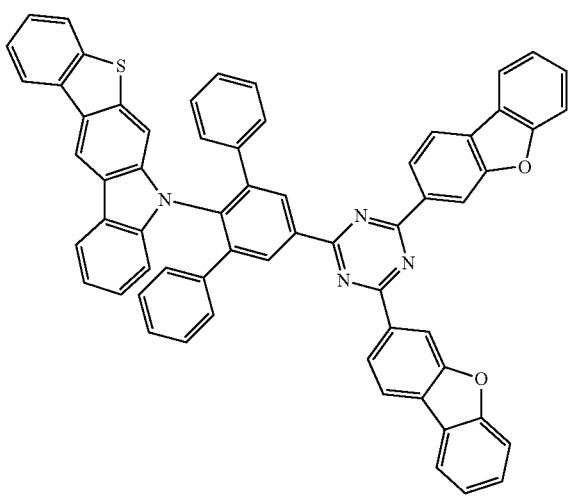

340
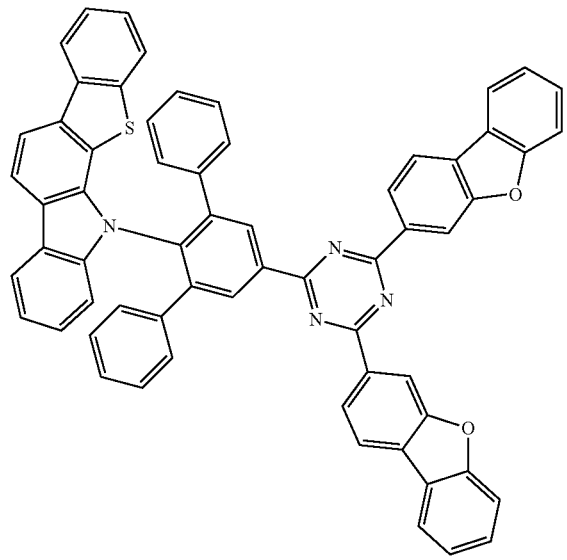
341
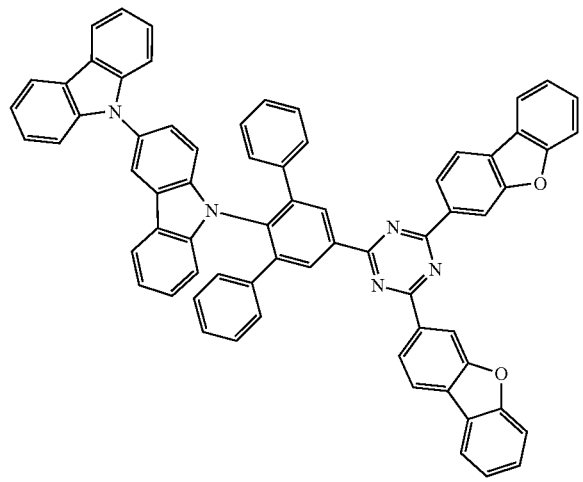
342
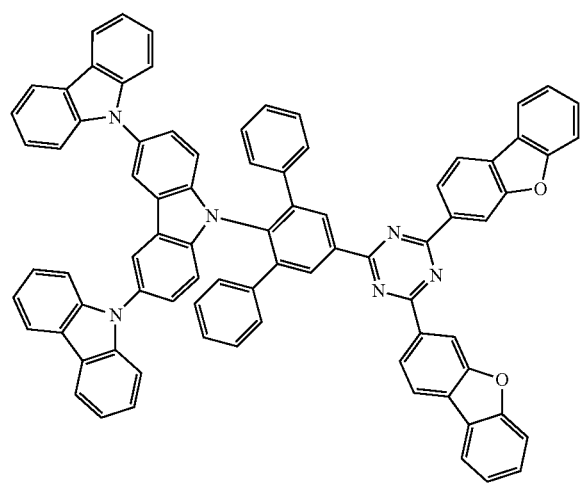
343
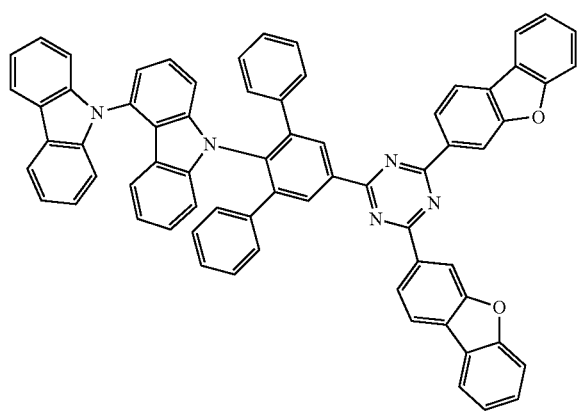

-continued
344
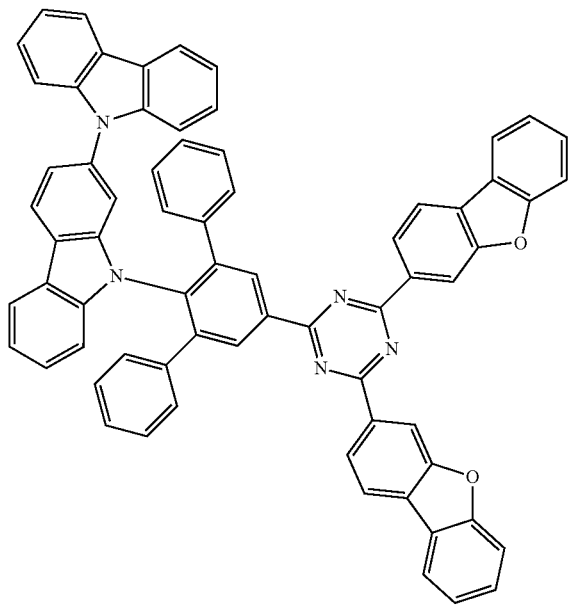
345
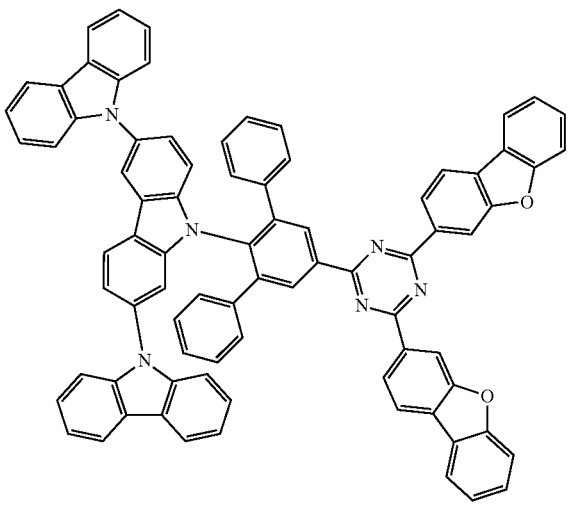
346
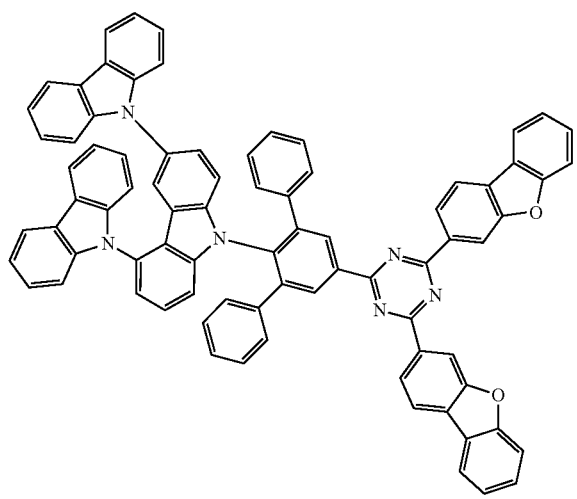
347
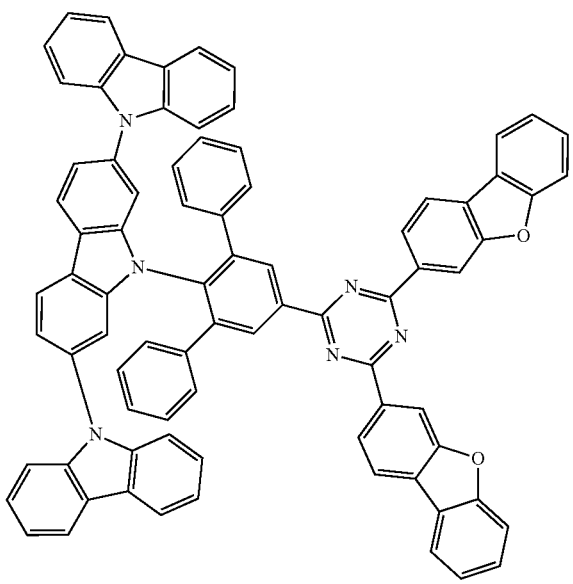

-continued
348
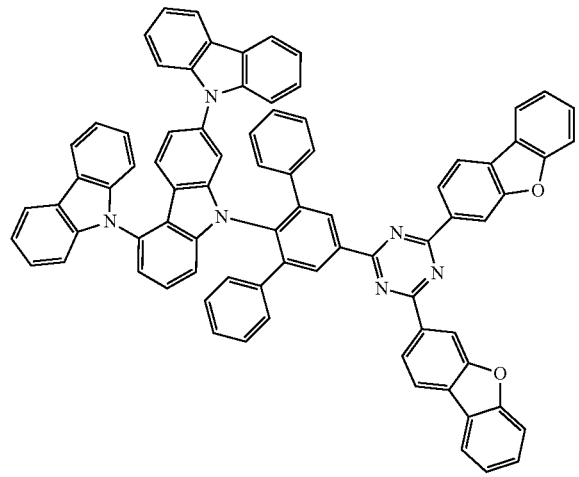
349
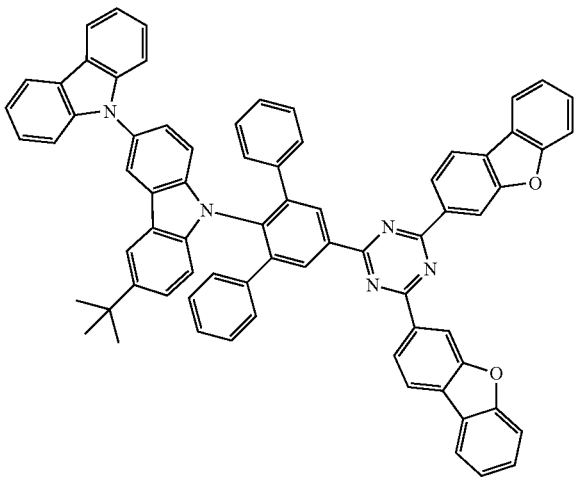
350
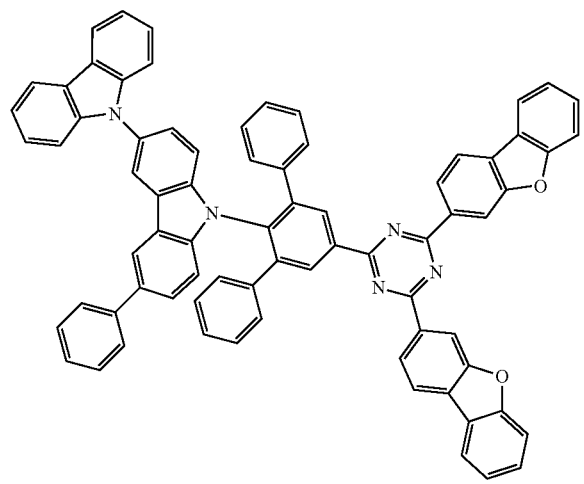
351
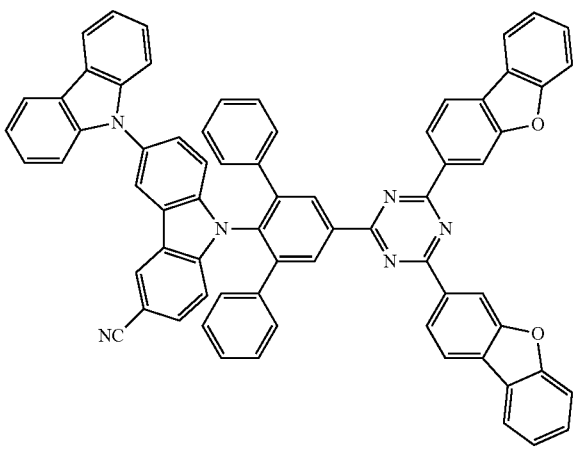
352
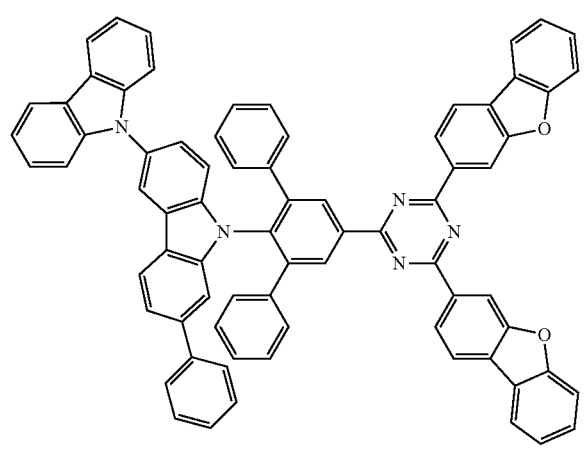
353
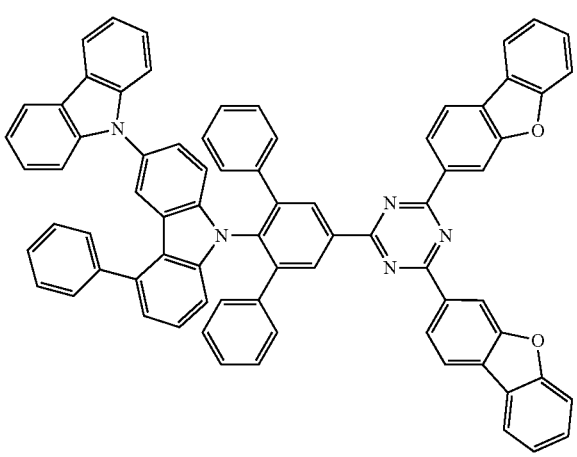

354
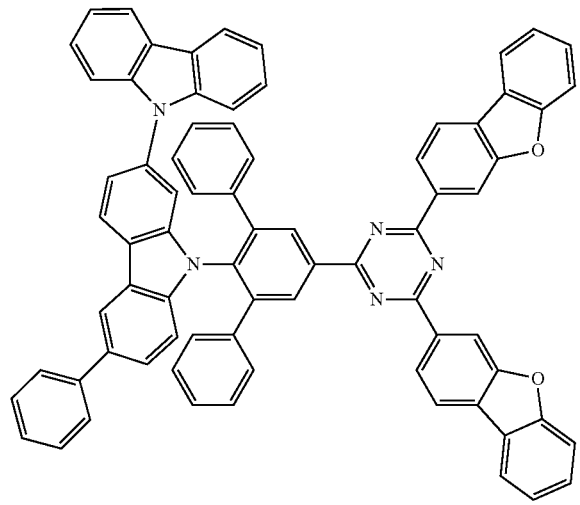
355
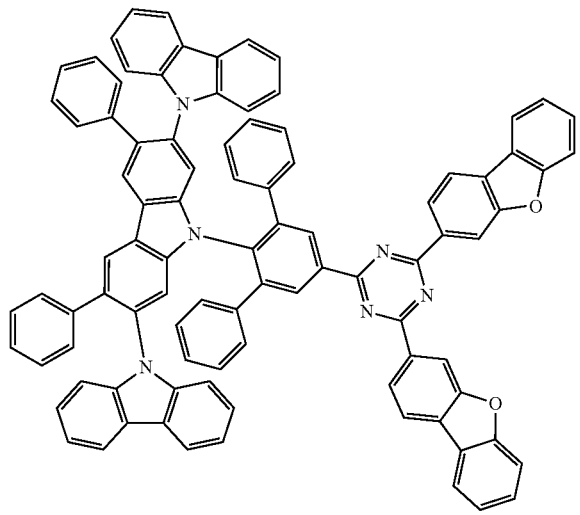
356
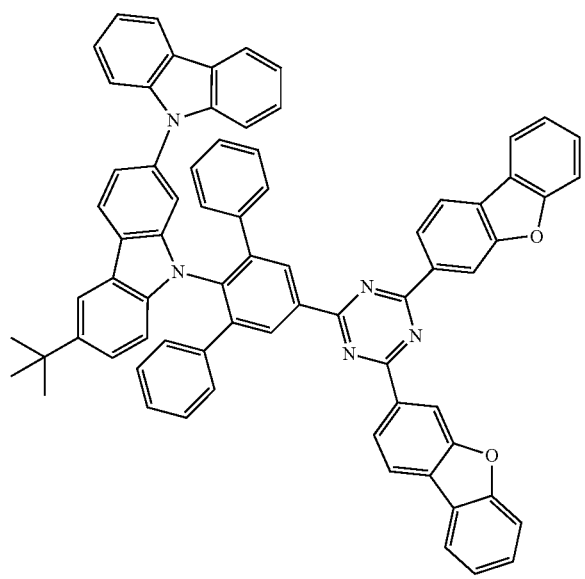
357
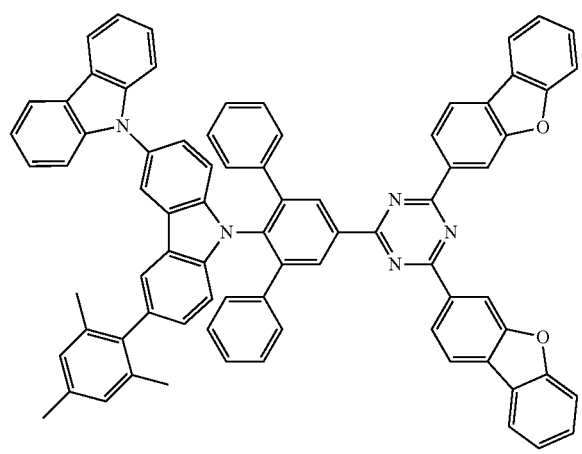
358
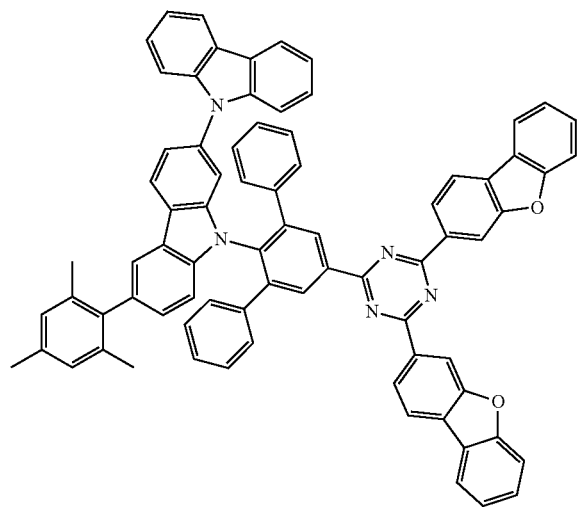
359
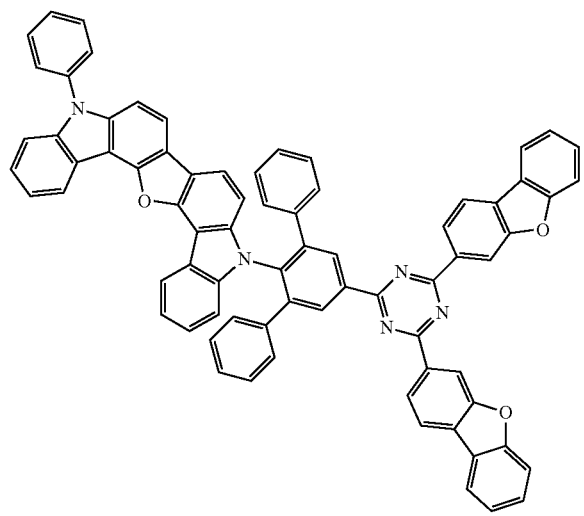

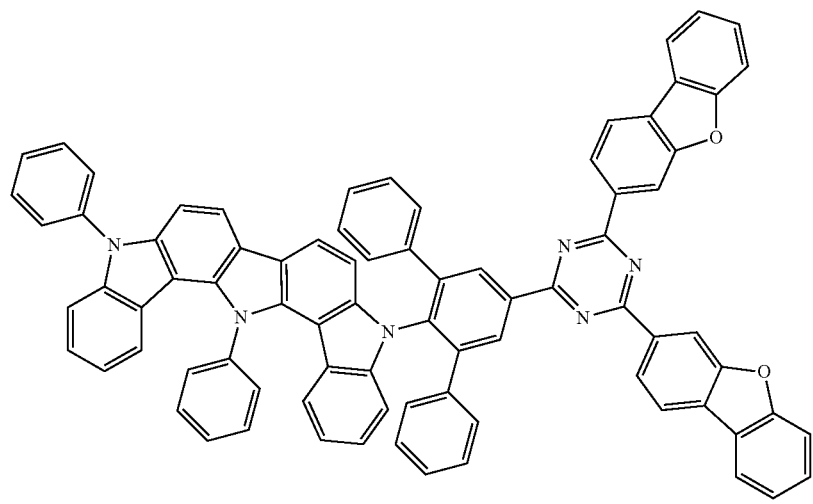
360
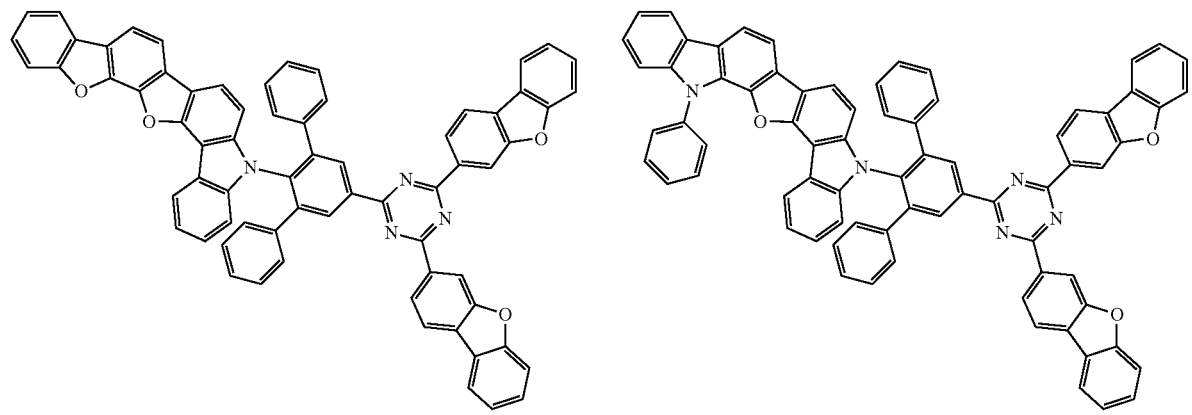
361
362
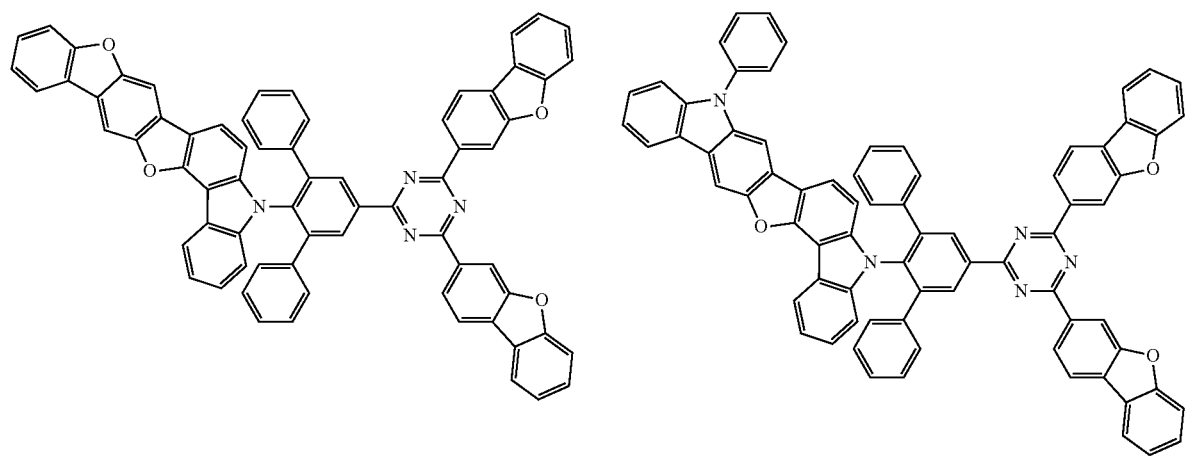
363
364

-continued
365
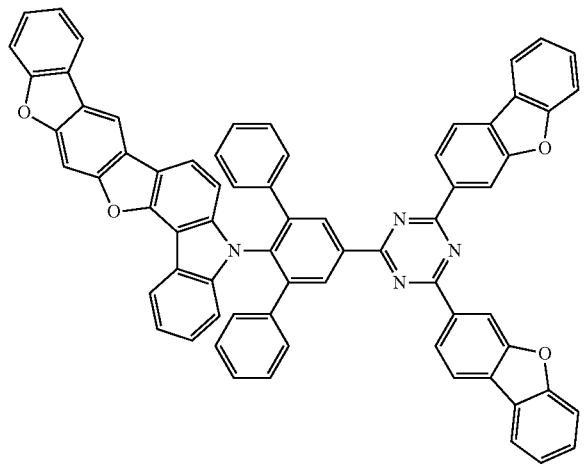
366
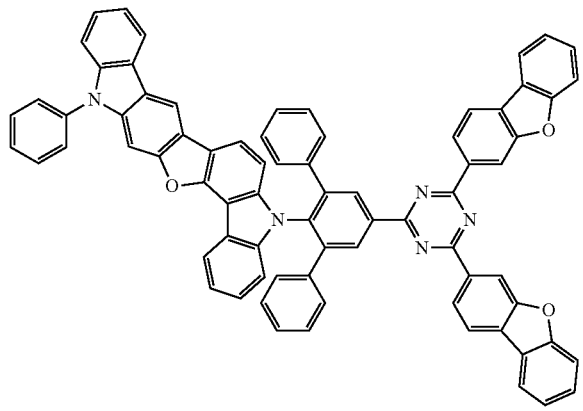
367
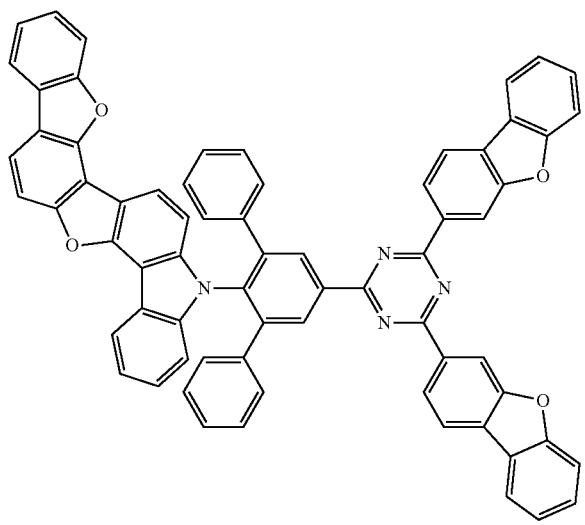
368
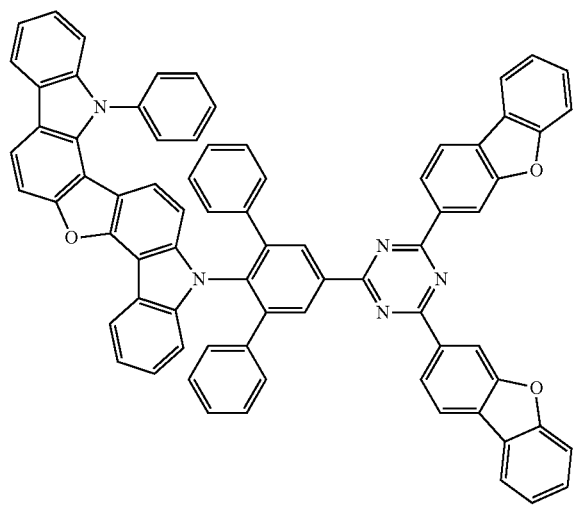
369
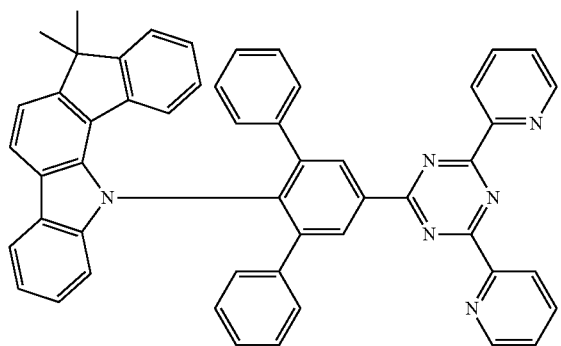
370
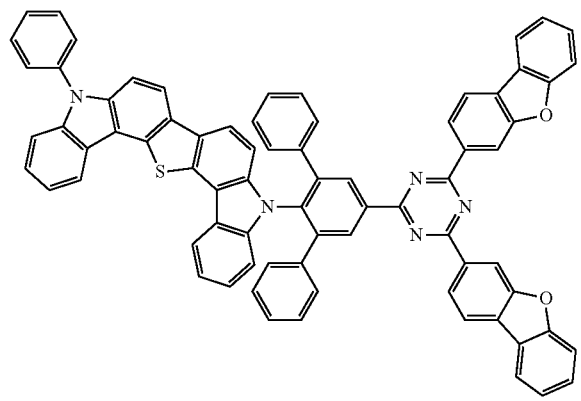

-continued
371
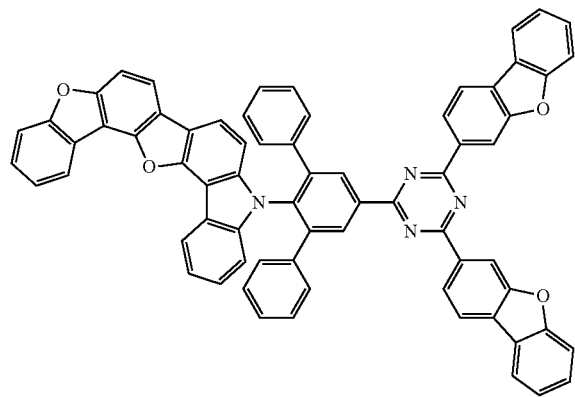
372
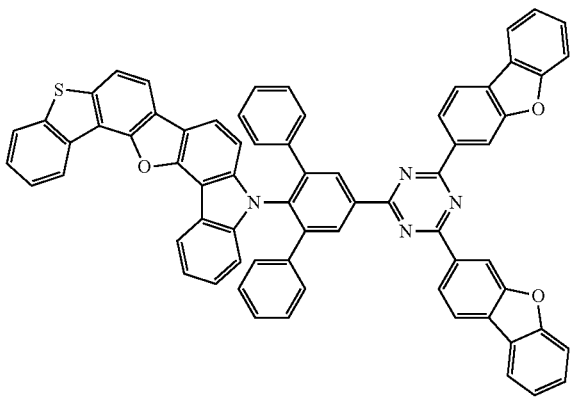
373
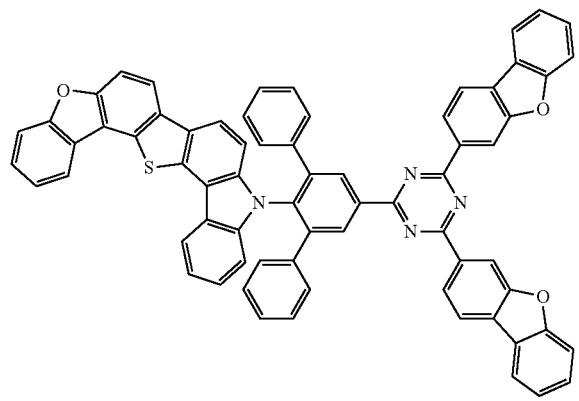
374
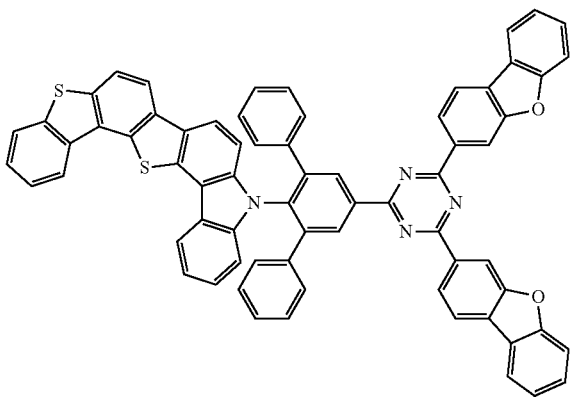
375
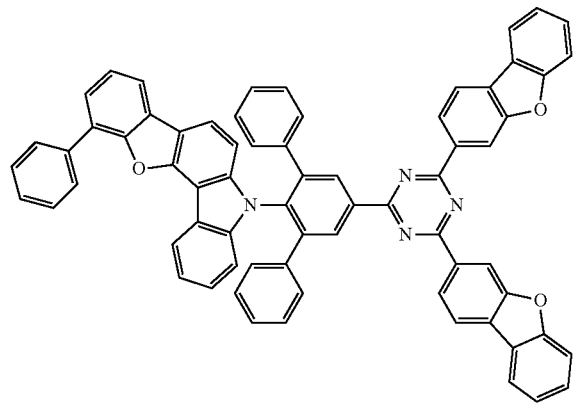
376
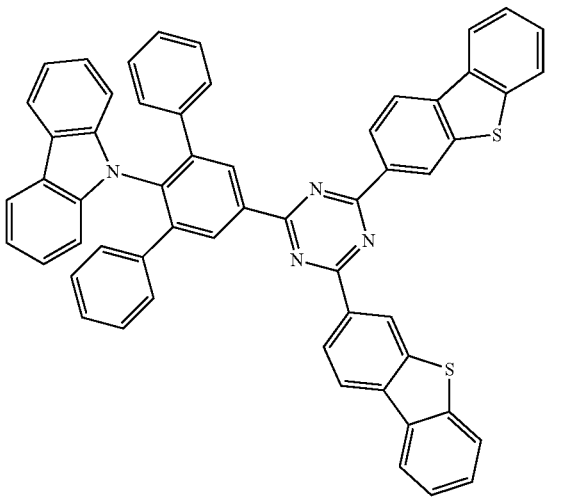

-continued
377
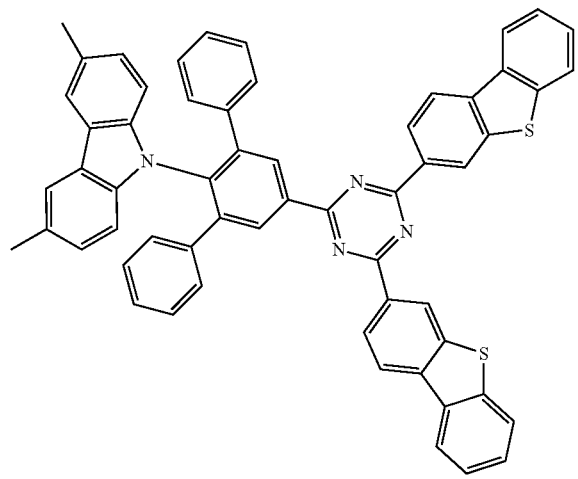
378
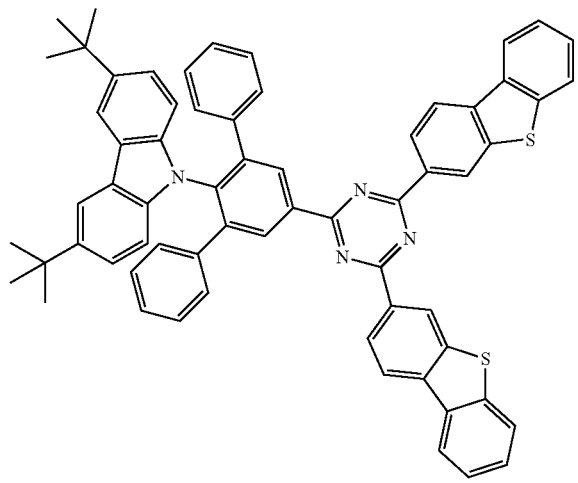
379
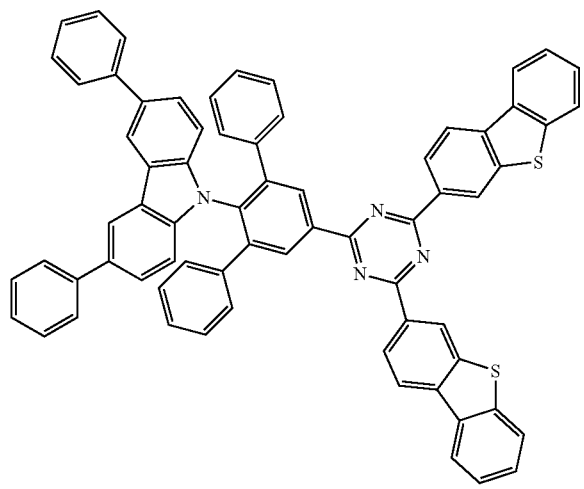
380
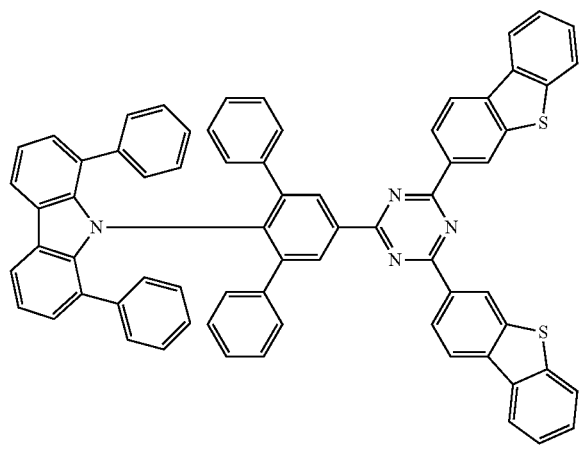
381
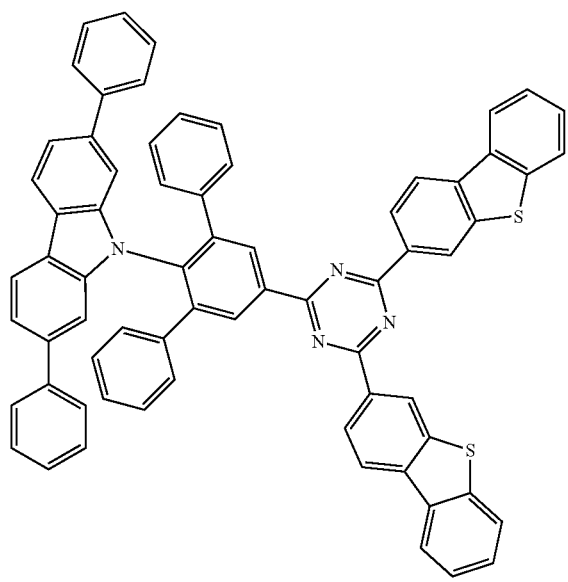
382
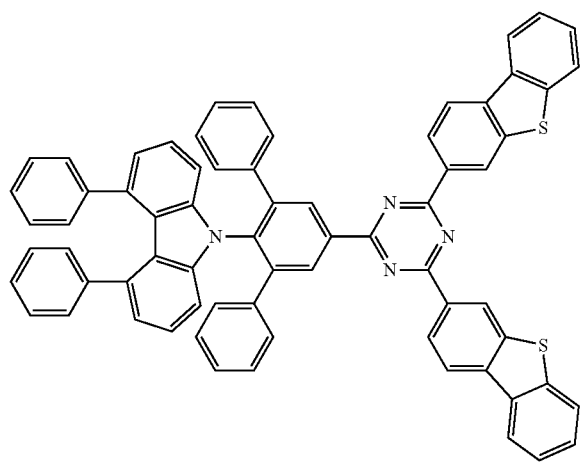

-continued
383
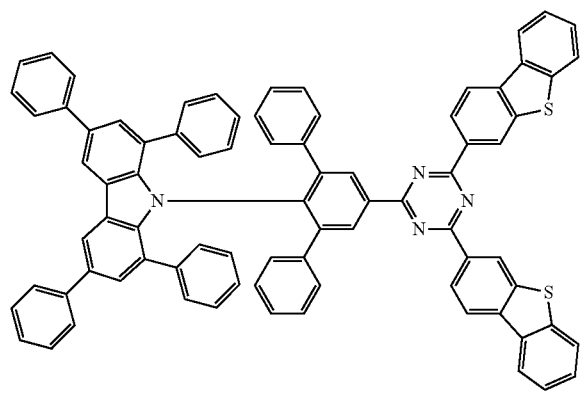
384
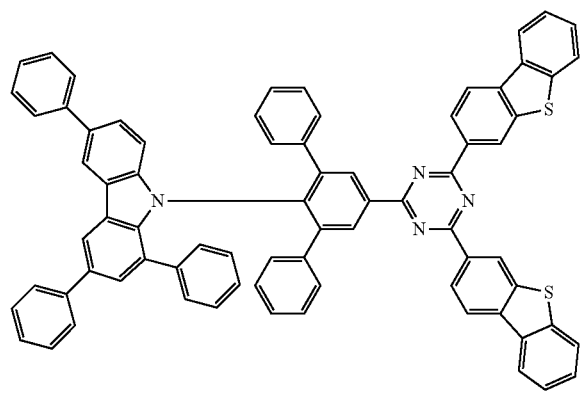
385
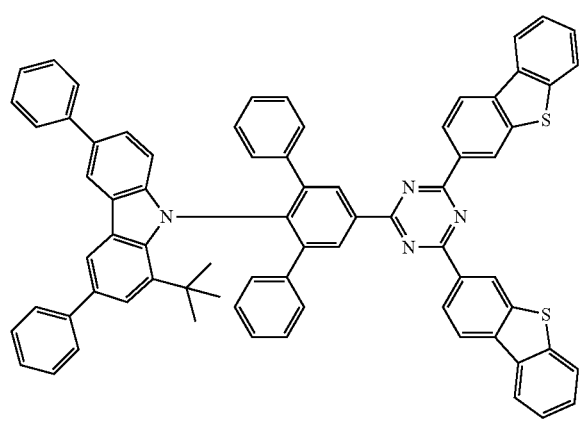
3866
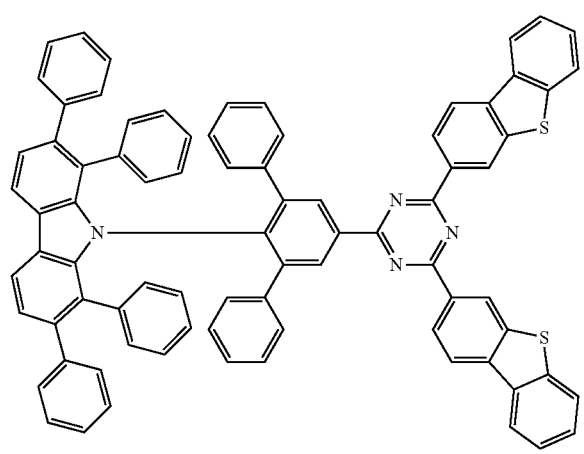
387
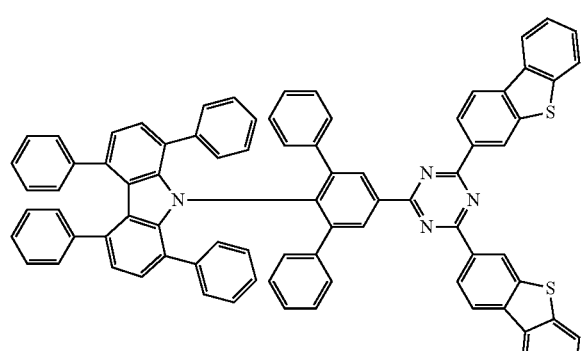
388
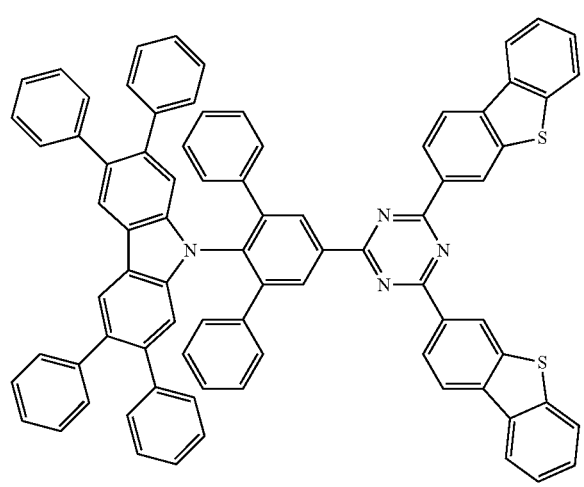

-continued
389
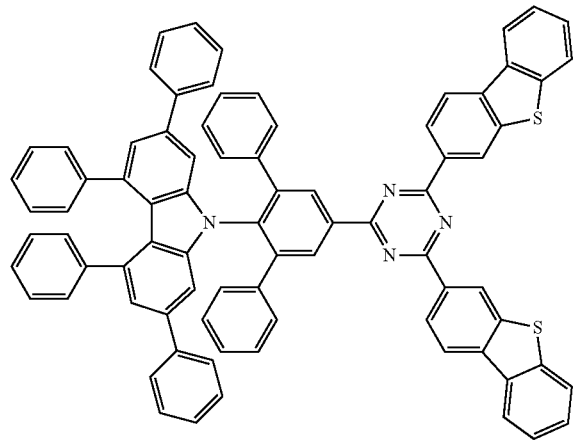
390
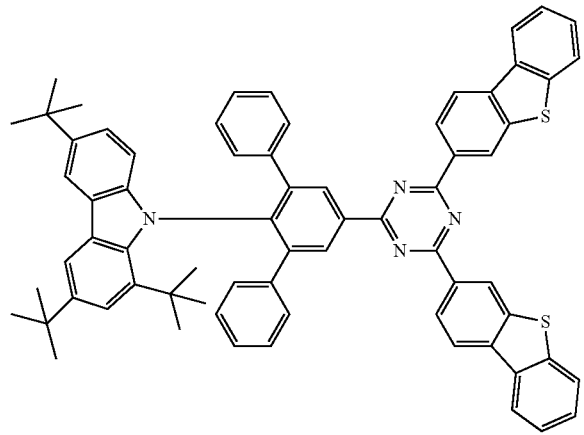
391
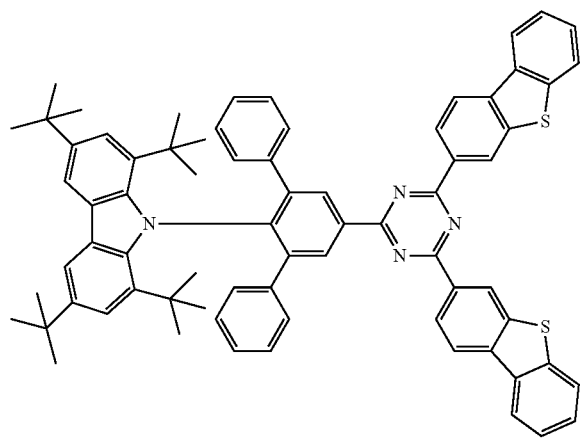
392
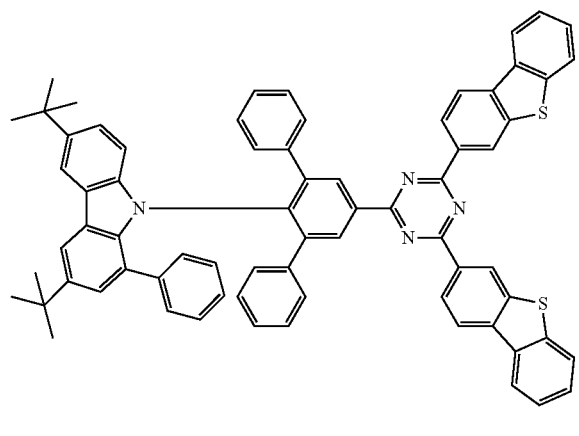
393
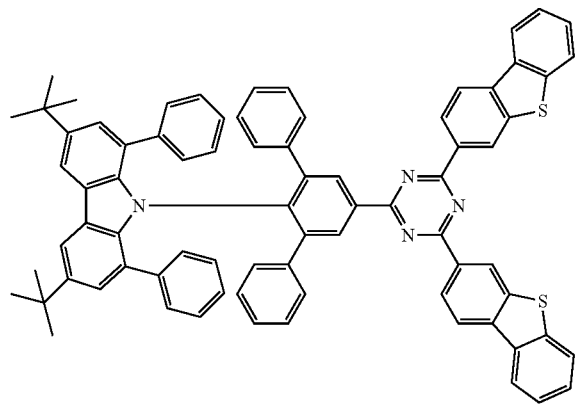
394
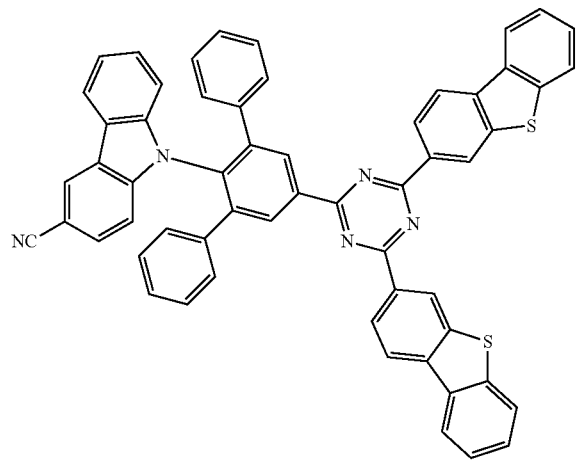

-continued
395
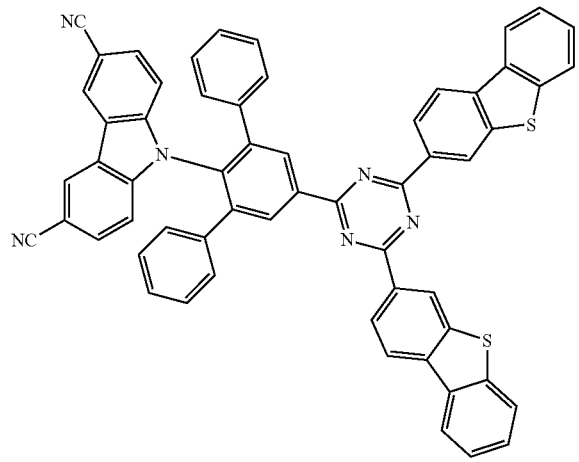
396
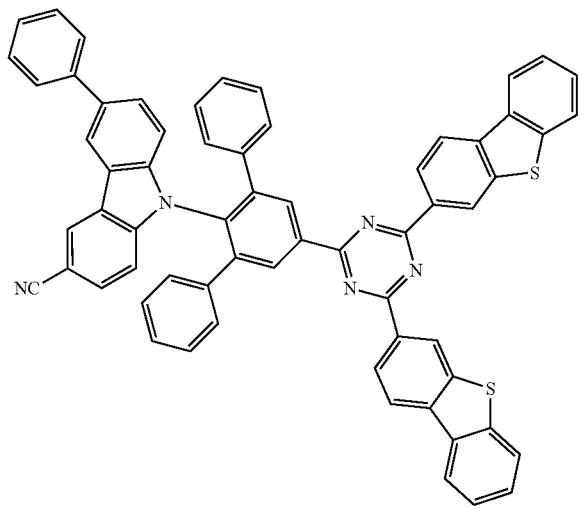
397
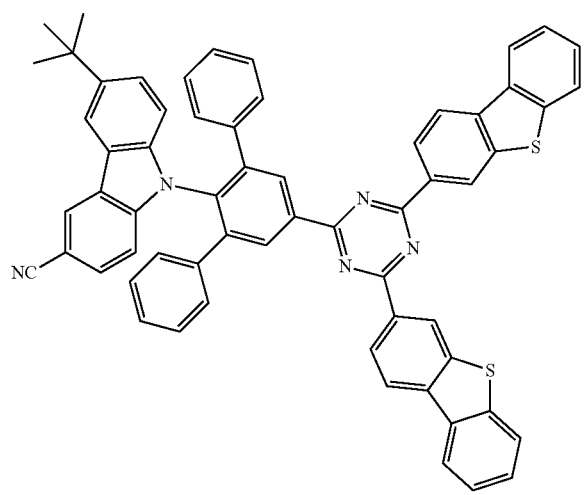
398
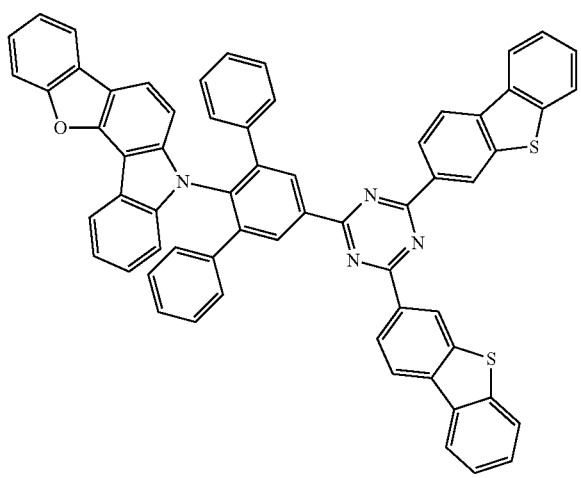
399
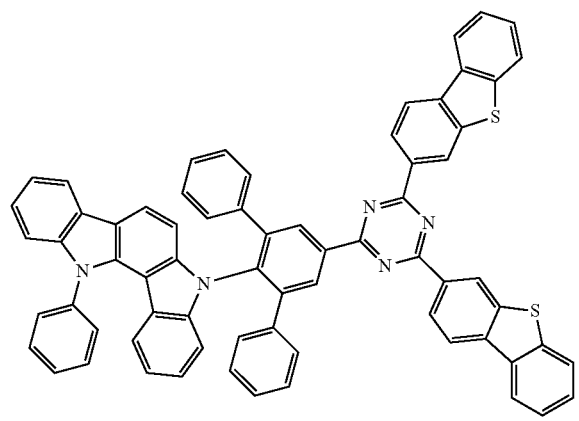
400
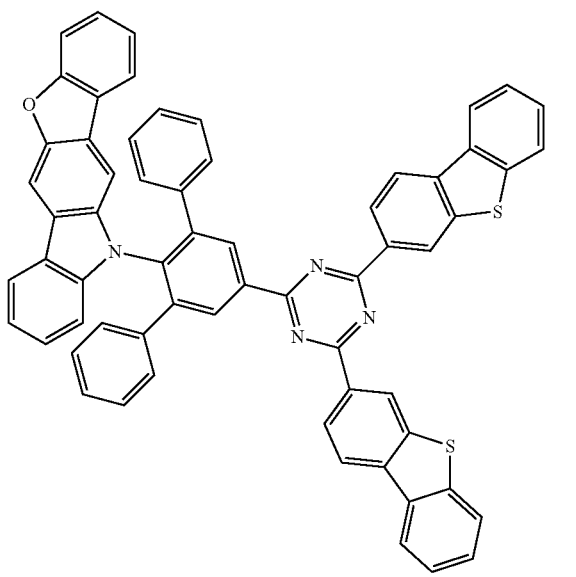

-continued
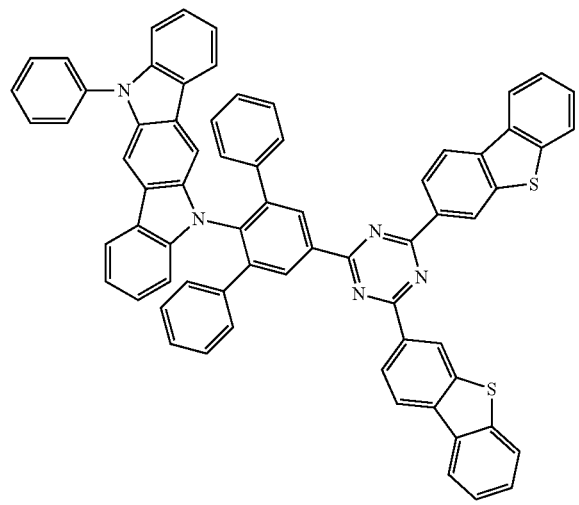
401
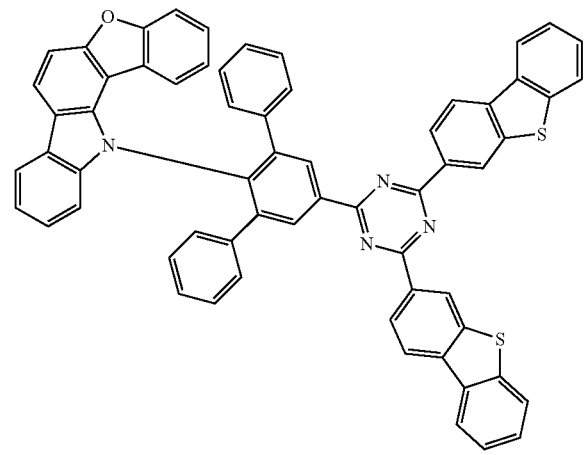
402
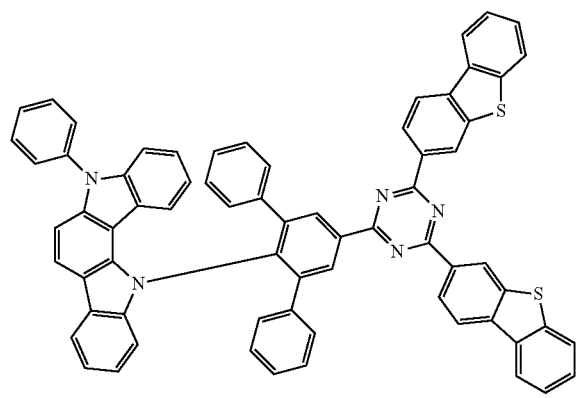
403
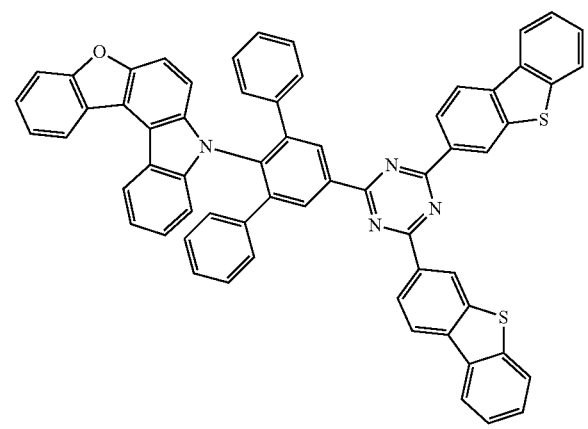
404
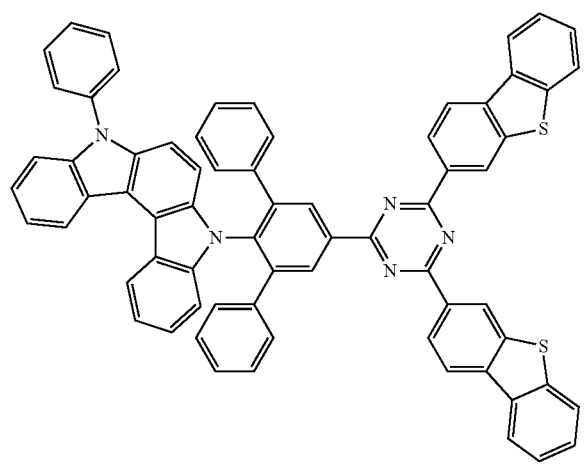
405
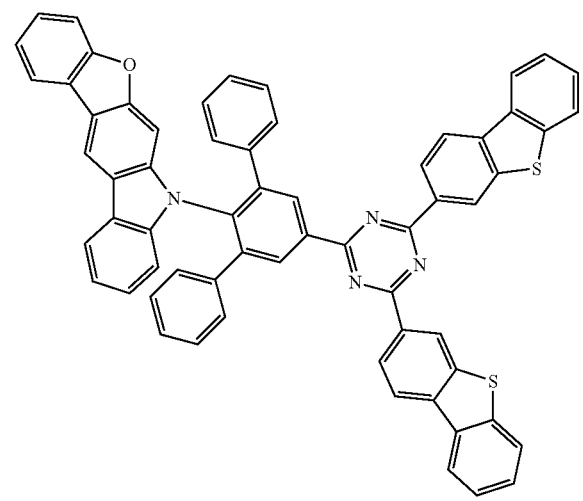
406

-continued
407
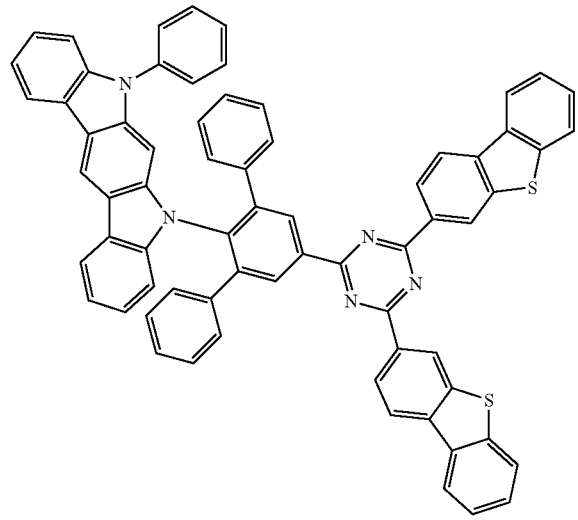
408
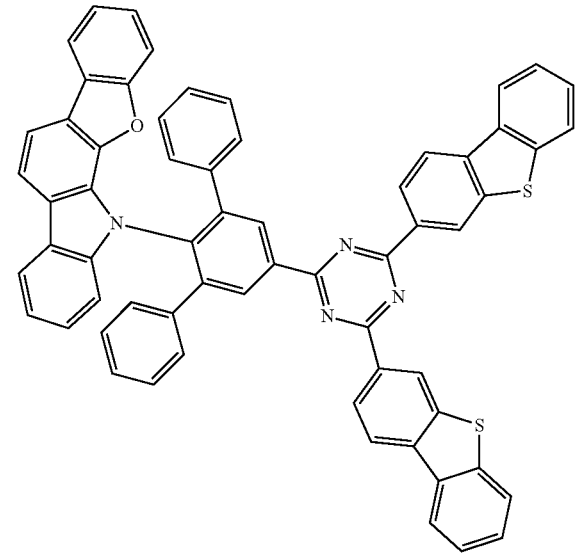
409
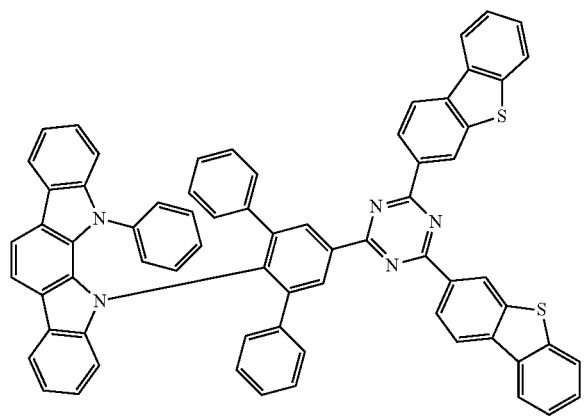
410
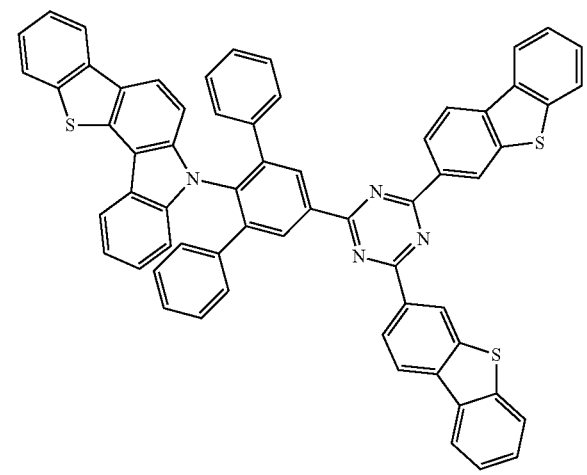
411
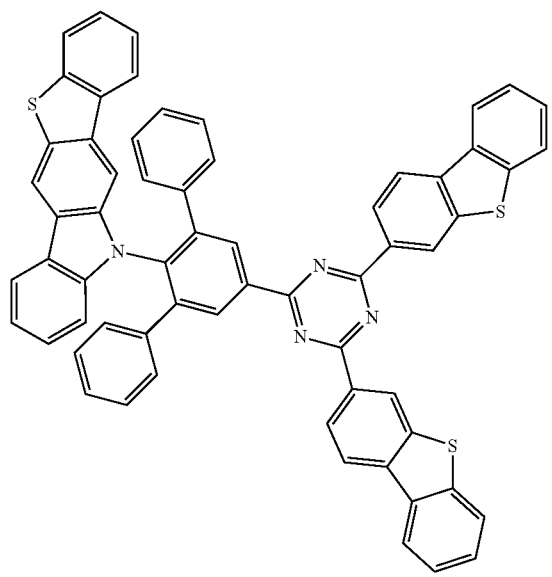
412
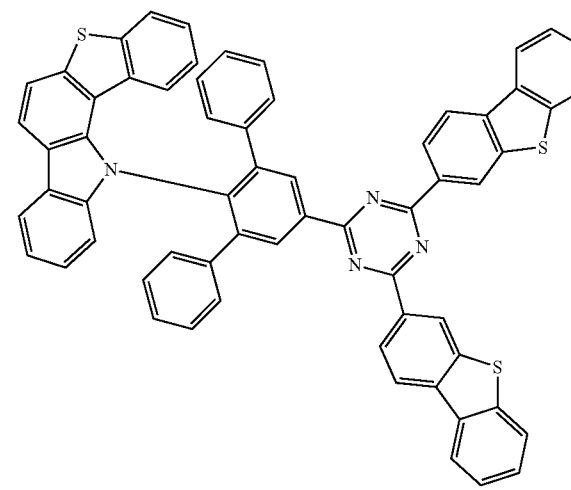

-continued
413
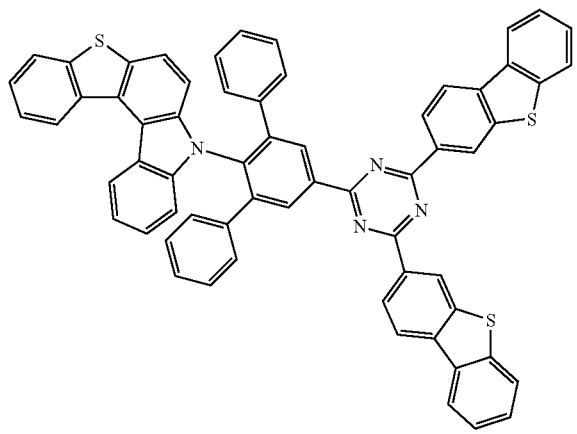
414
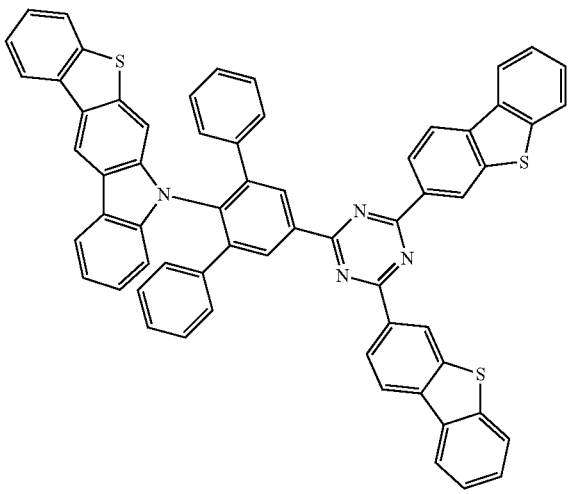
415
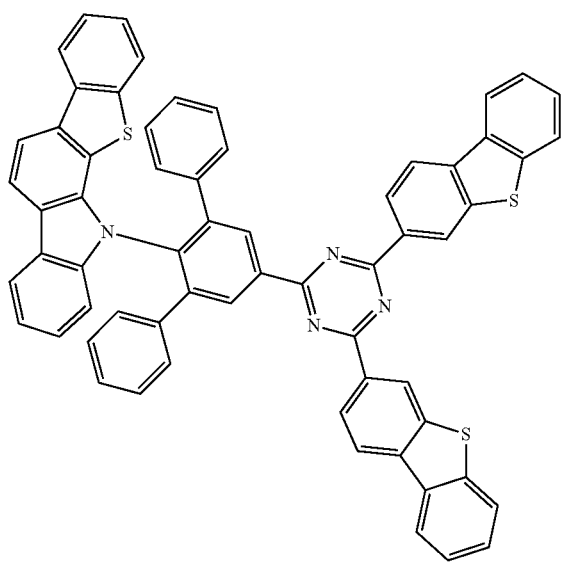
416
417
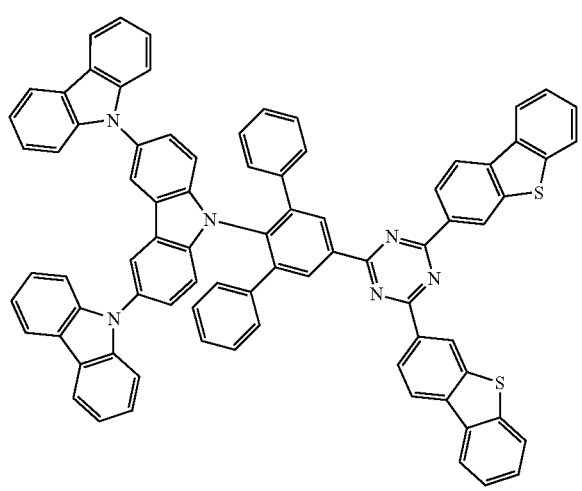
418
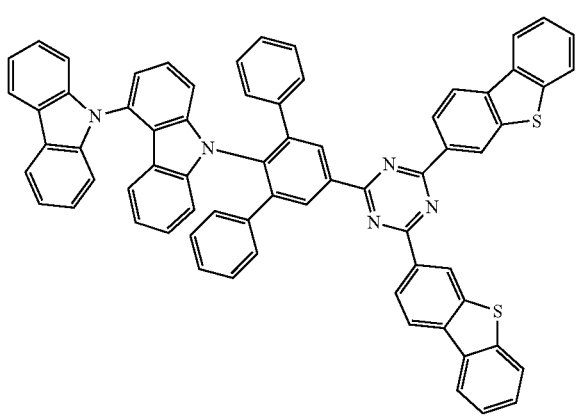

-continued
419
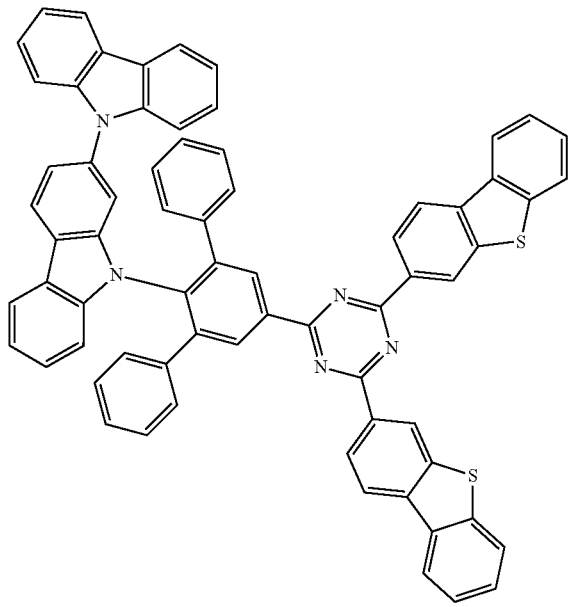
420
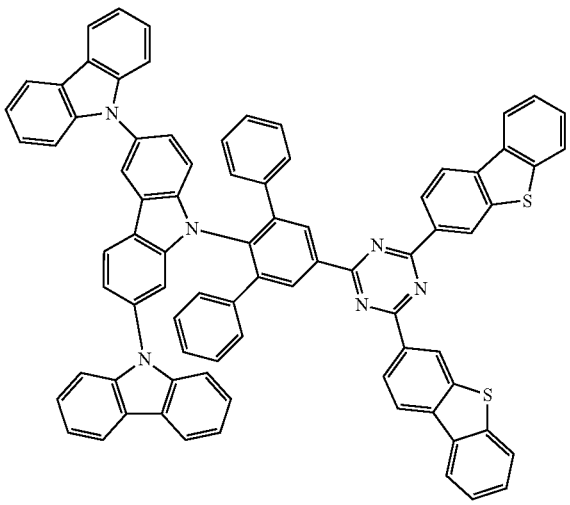
421
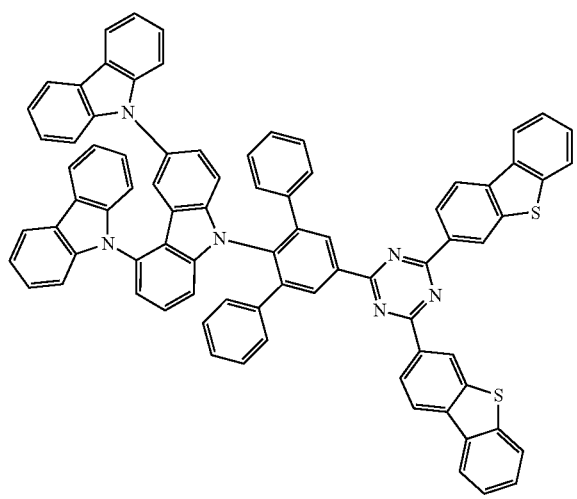
422
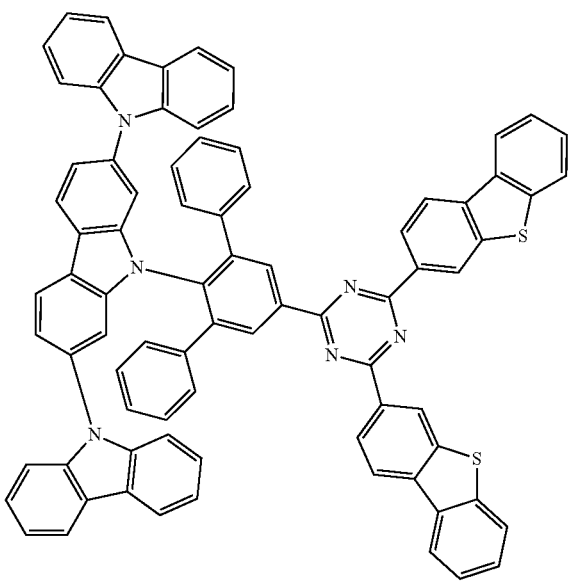

-continued
423
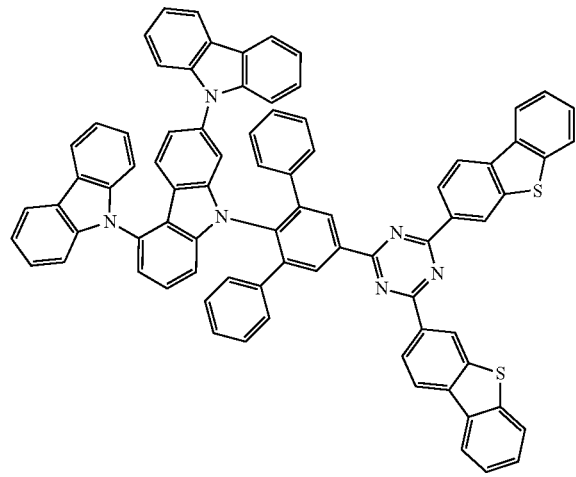
424
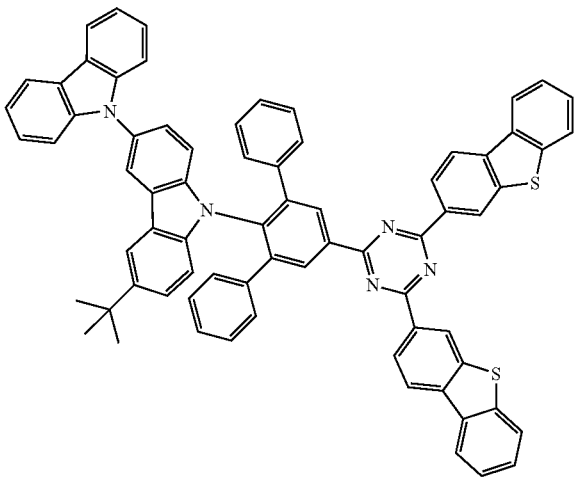
425
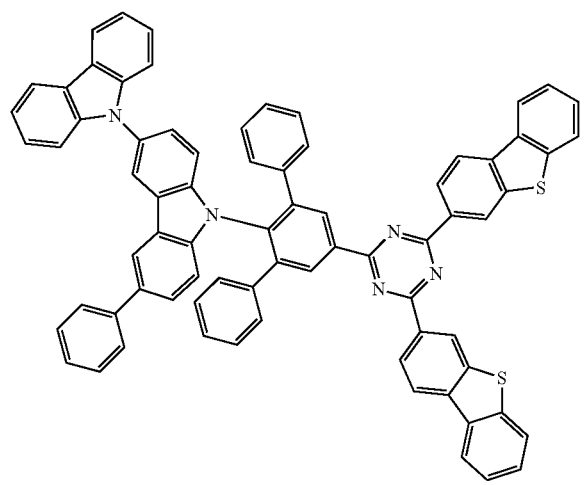
426
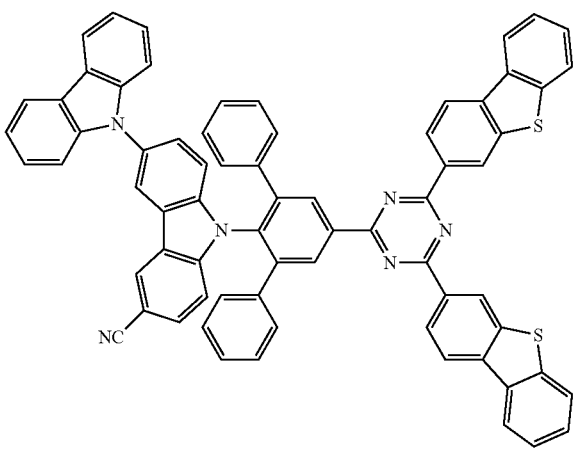
427
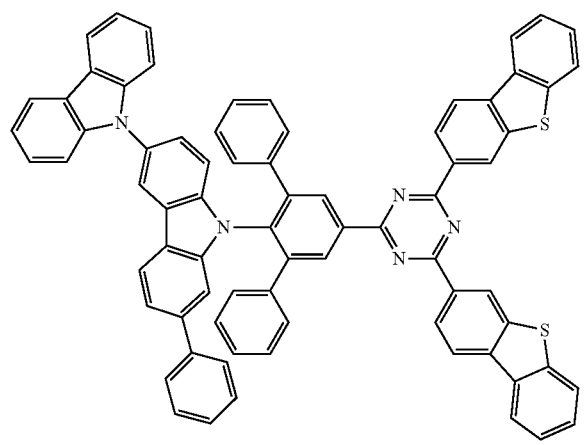
428
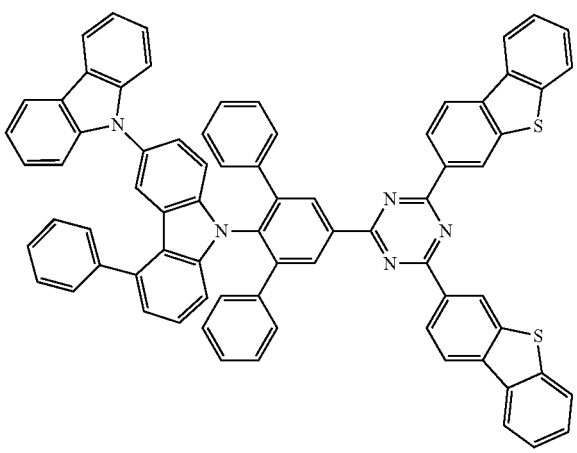

-continued
429
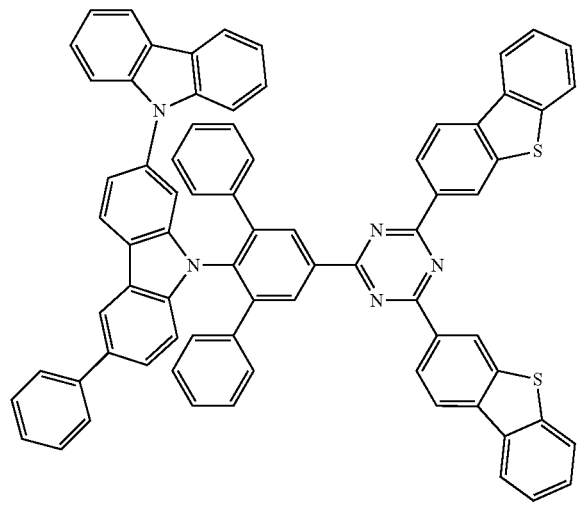
430
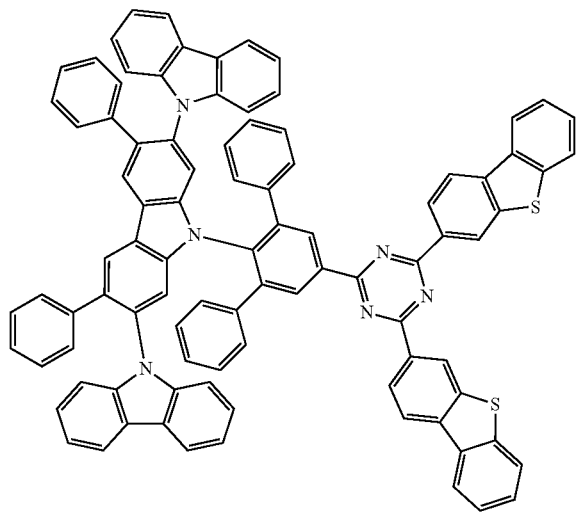
431
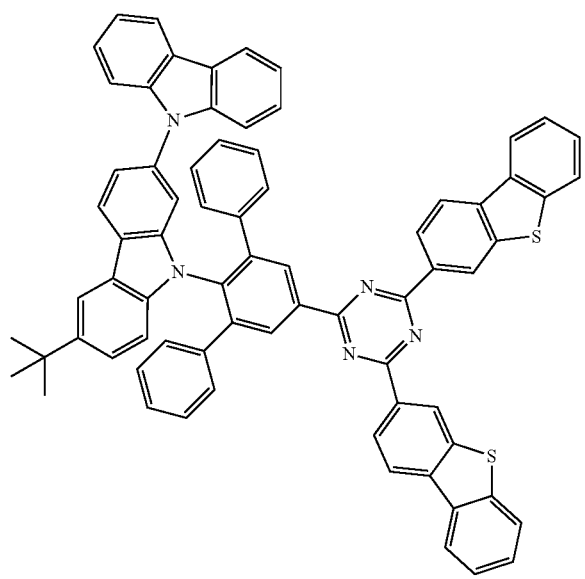
432
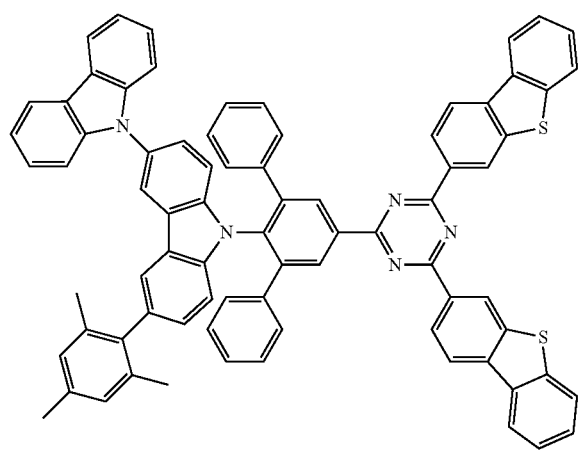
433
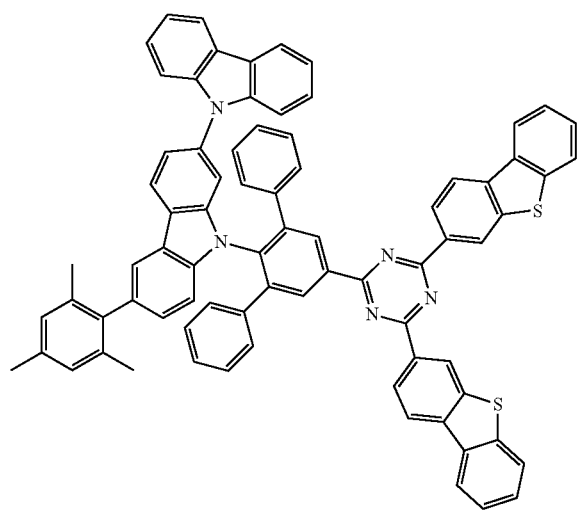
434
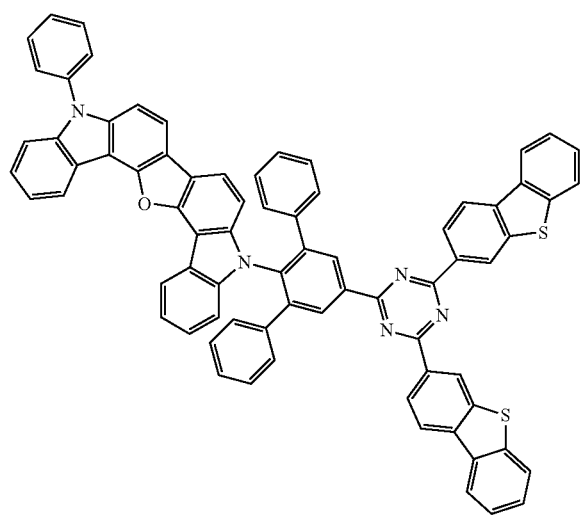

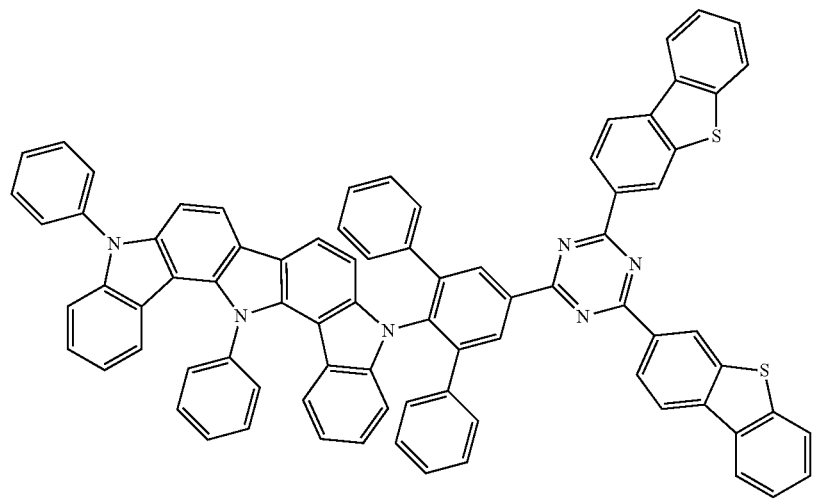
435
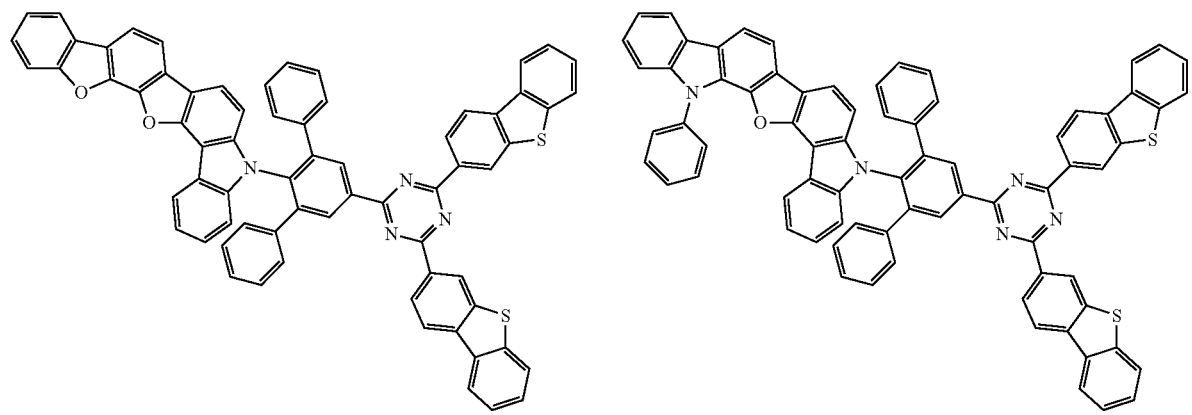
436    437
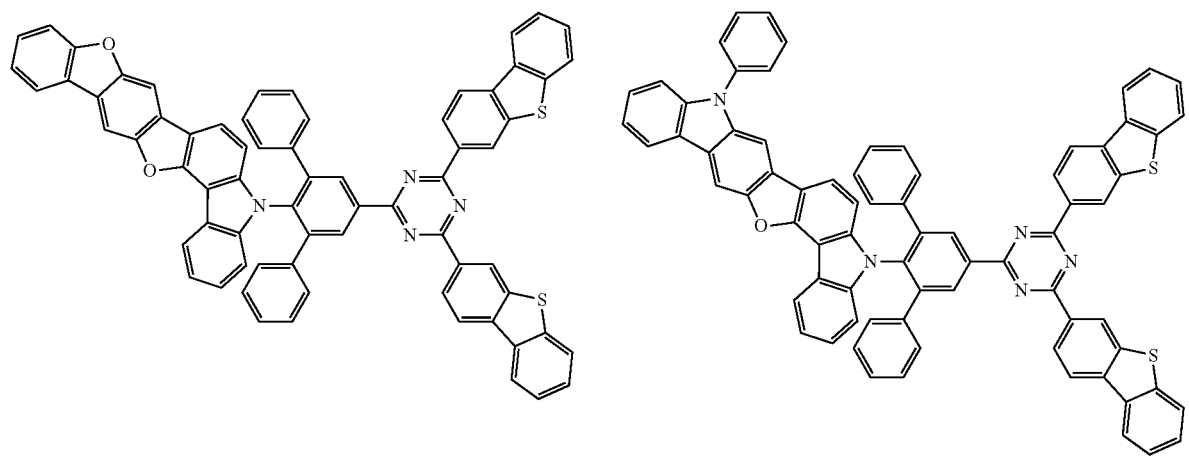
438    439

-continued
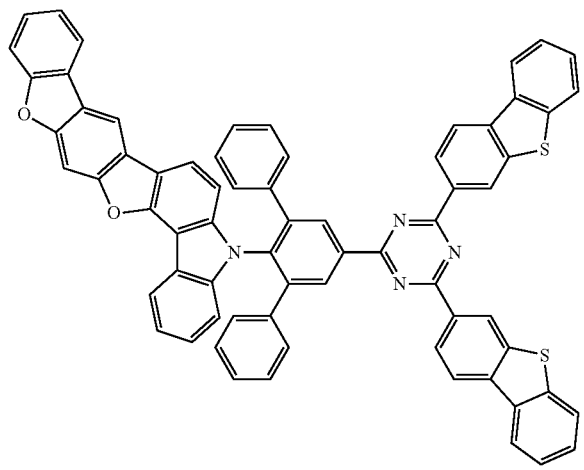
440
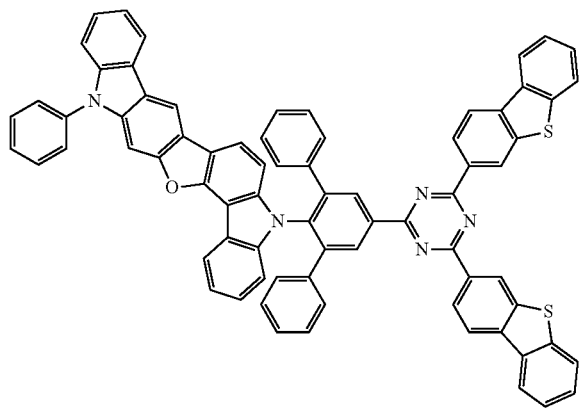
441
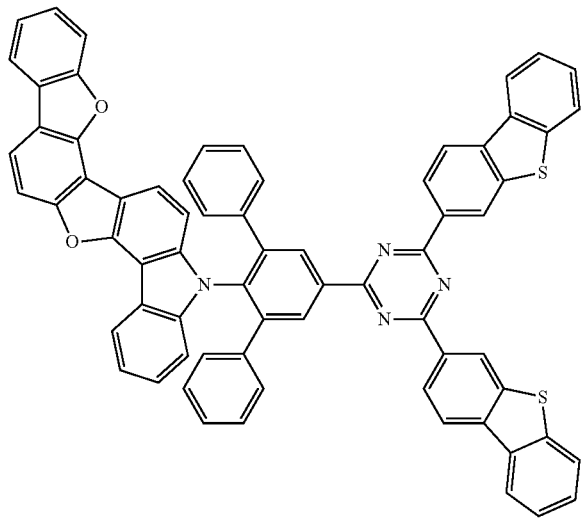
442
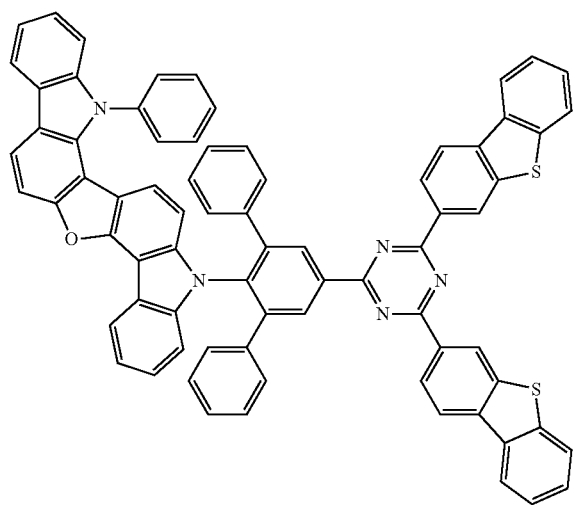
443
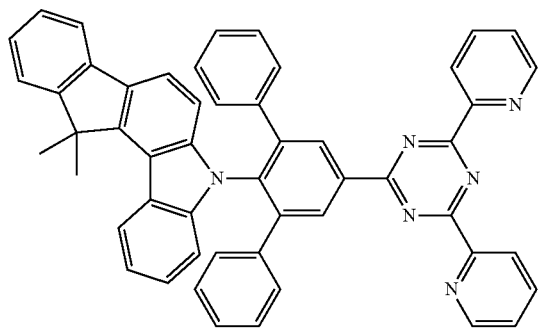
444
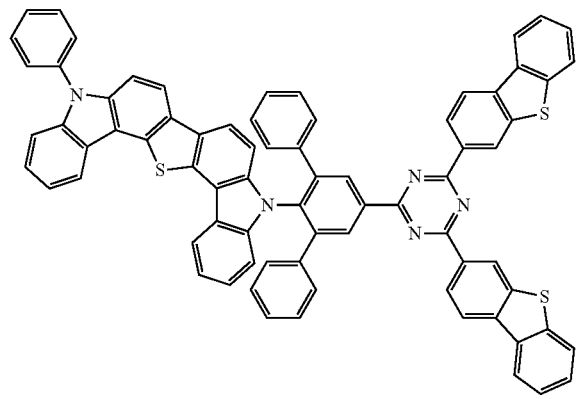
445

-continued
446
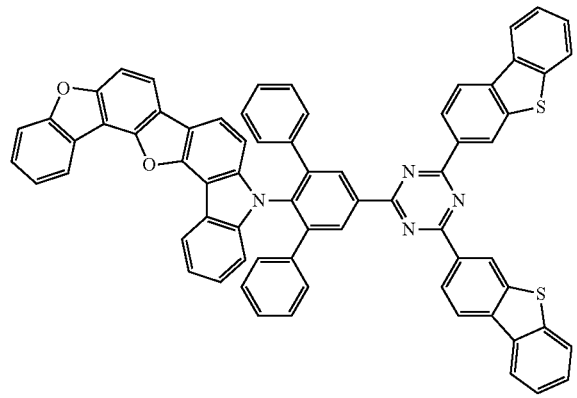
447
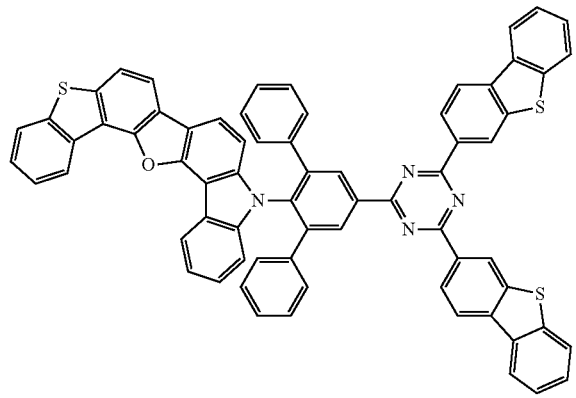
448
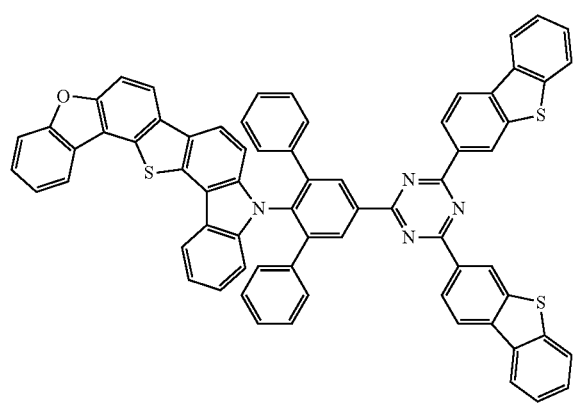
449
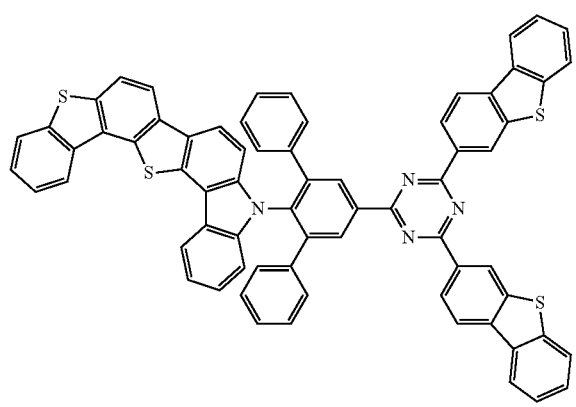
450
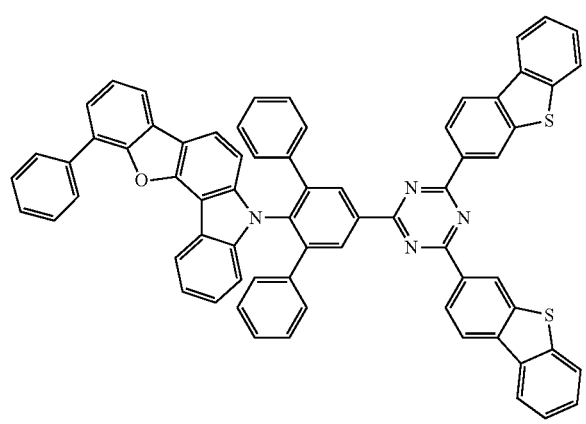
451
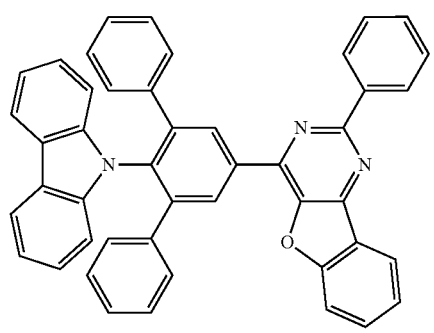
452
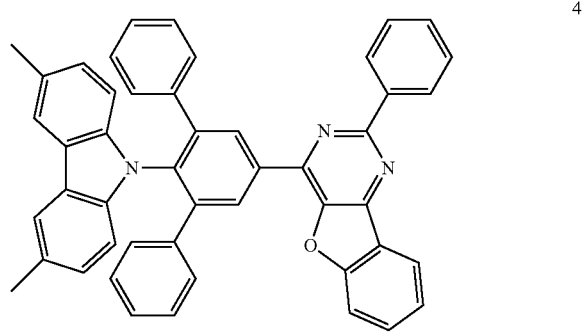
453
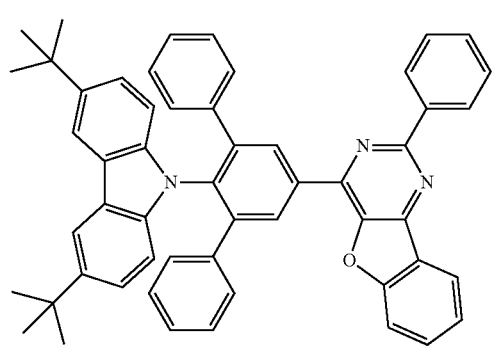

-continued
454
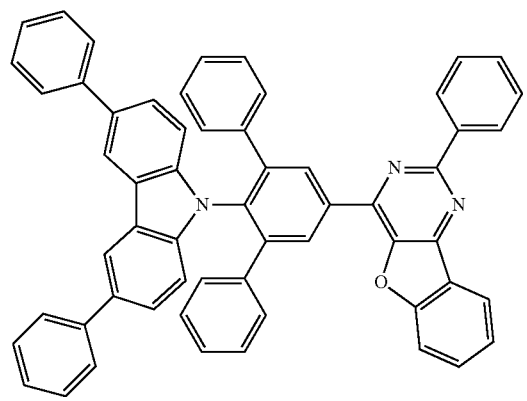
455
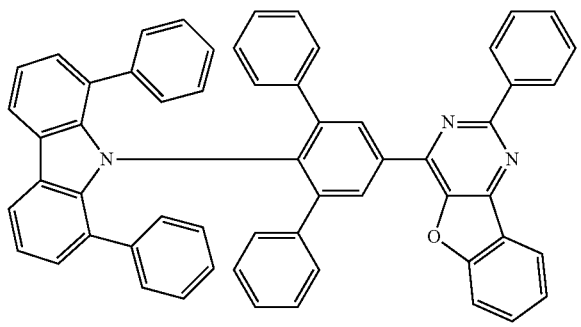
456
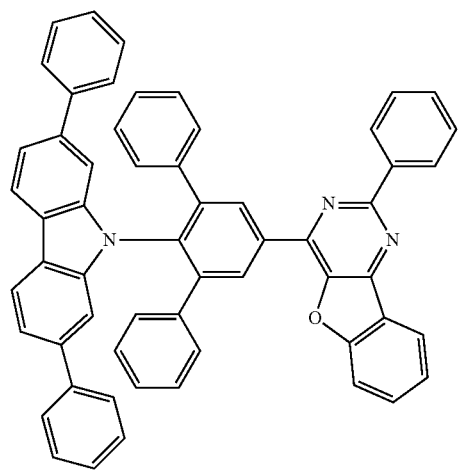
457
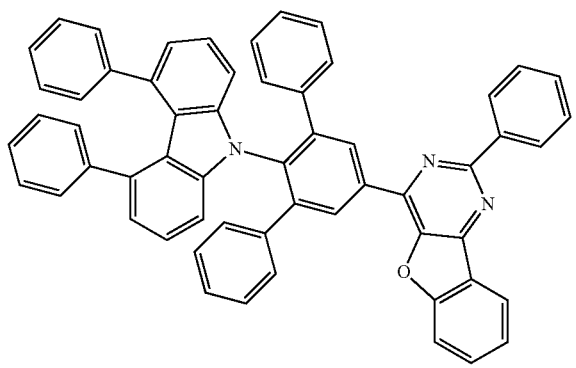
458
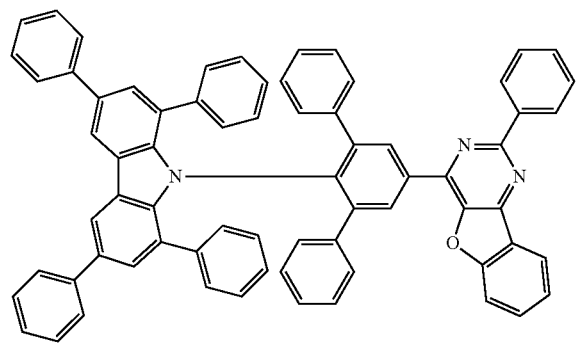
459
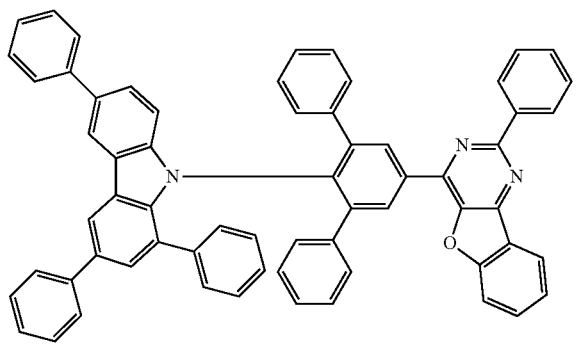

460
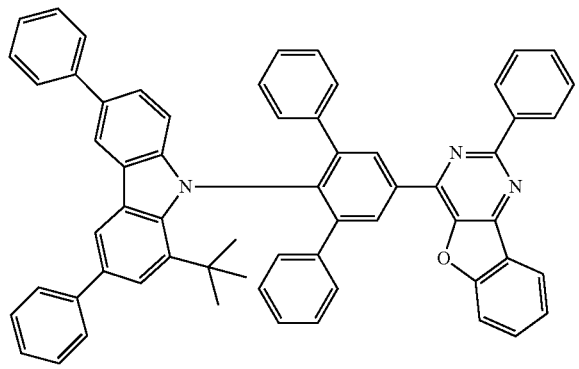
461
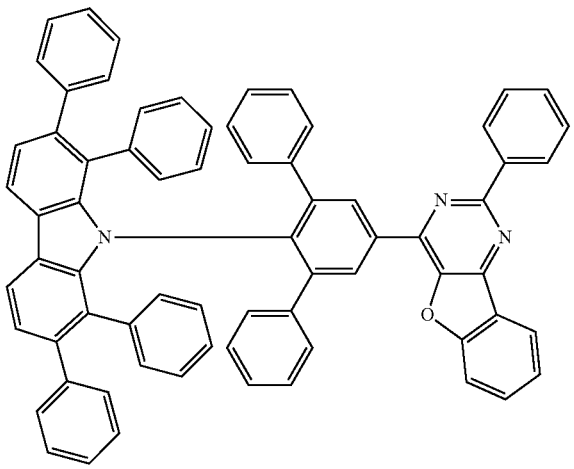
462
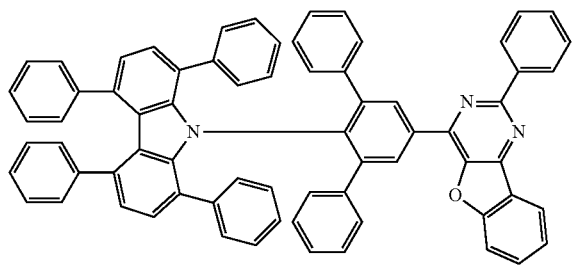
463
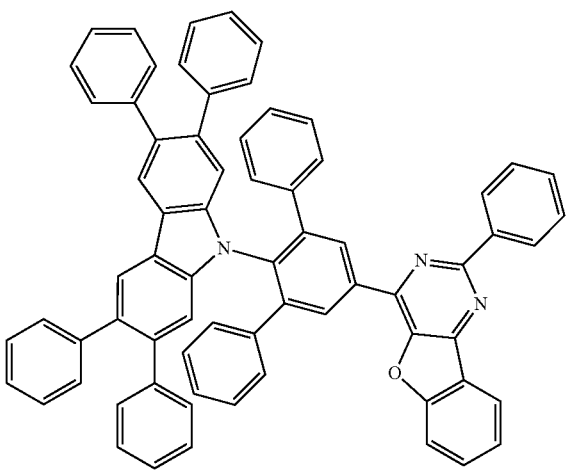
464
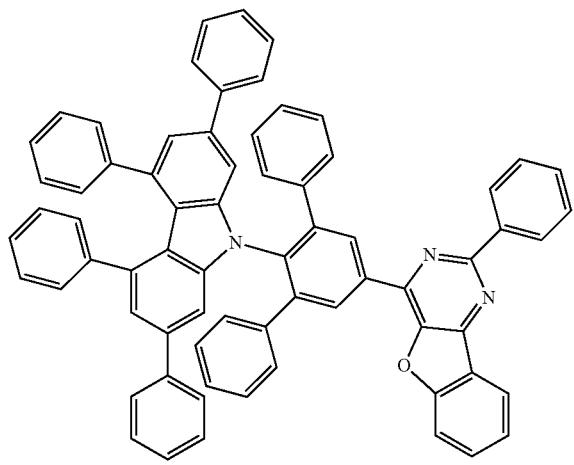
465
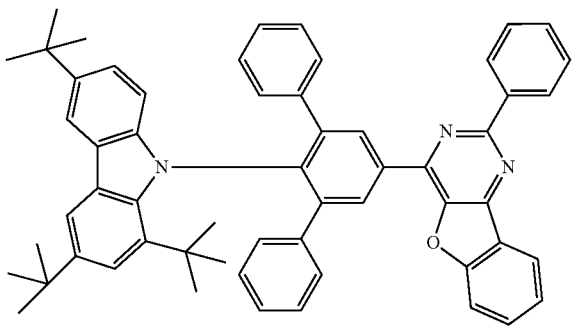

-continued
466
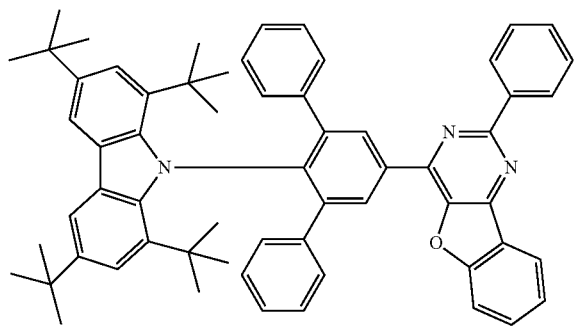
467
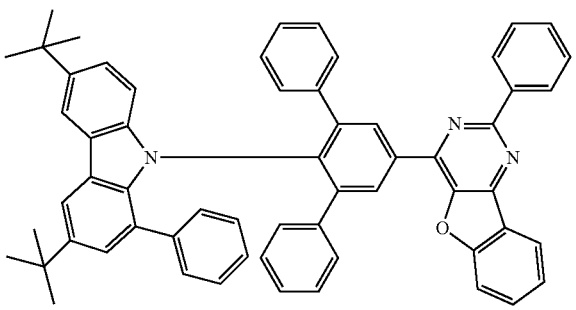
468
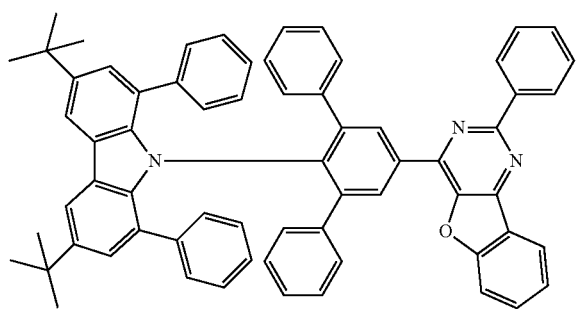
469
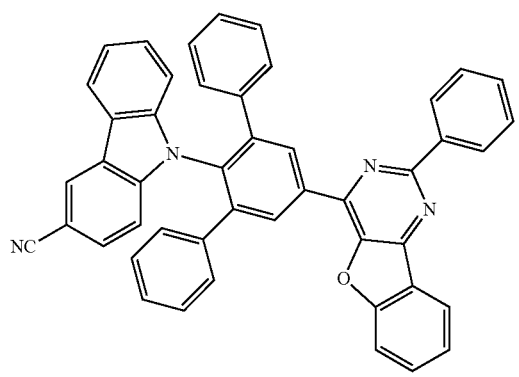
470
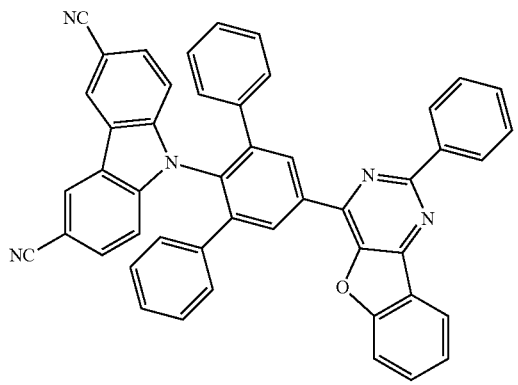
471
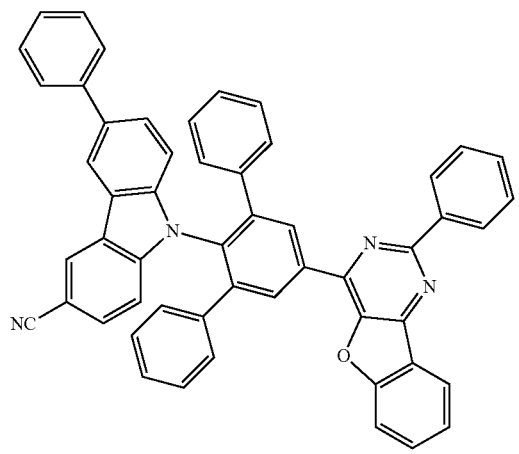
472
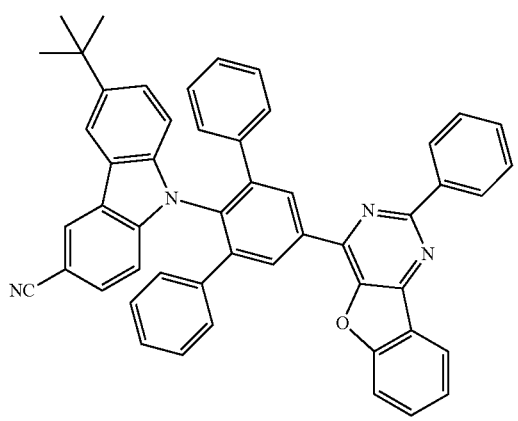
473
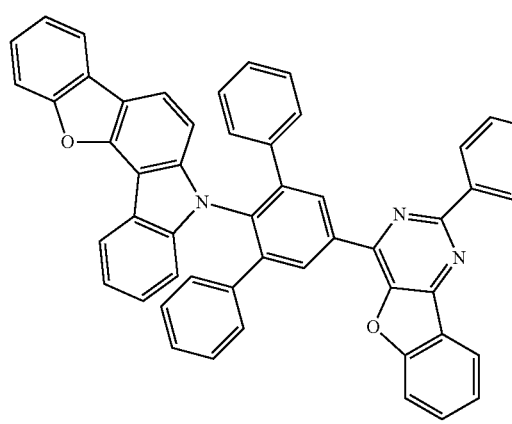

-continued
474
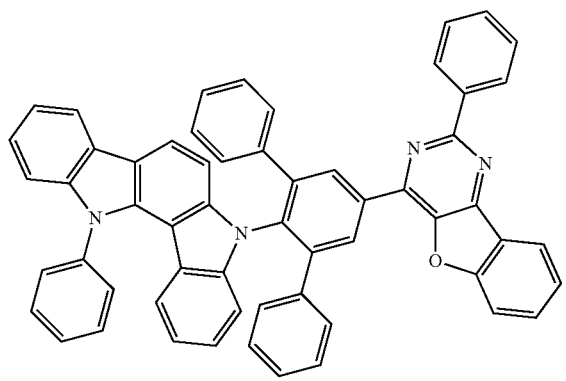
475
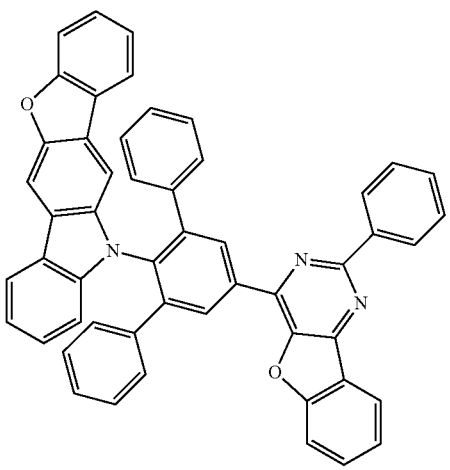
476
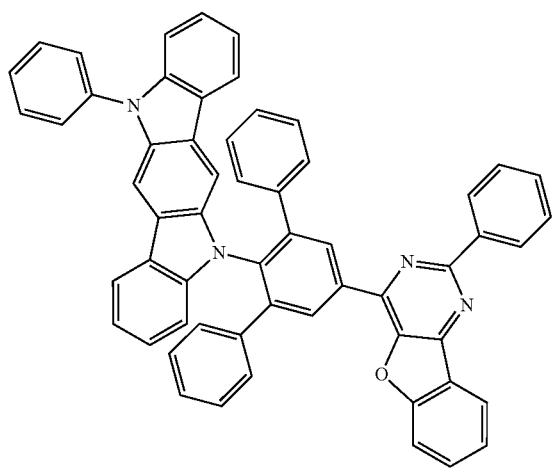
477
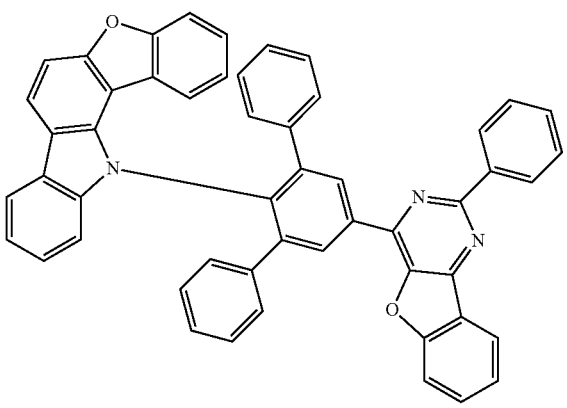
478
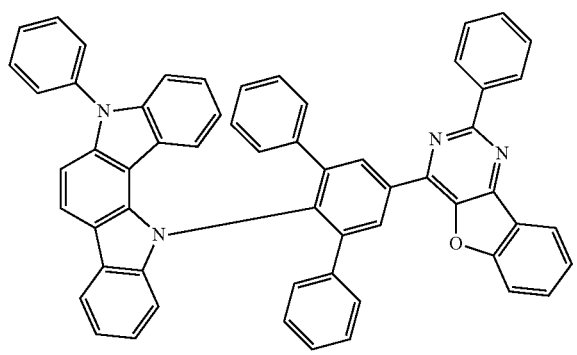
479
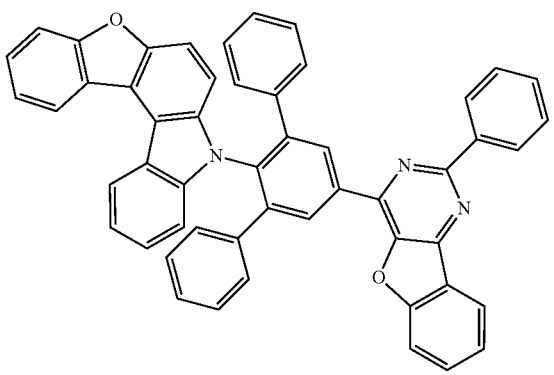

480
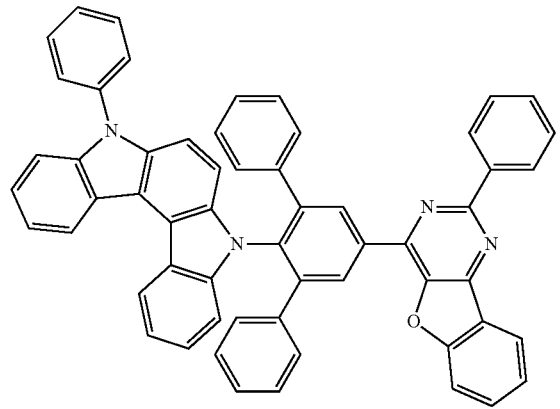
481
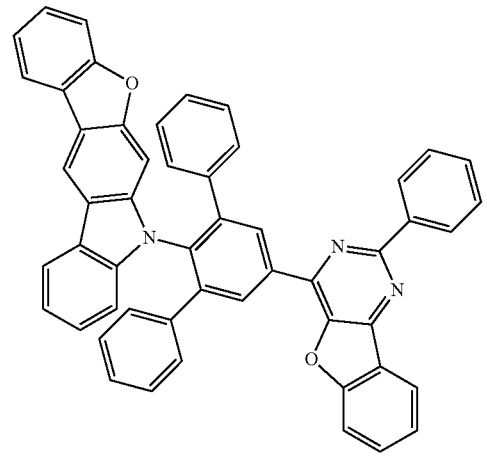
482
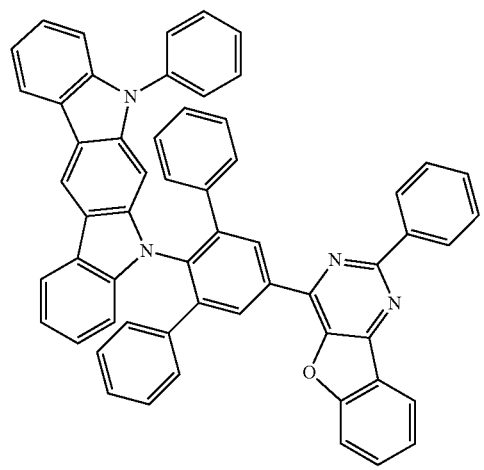
483
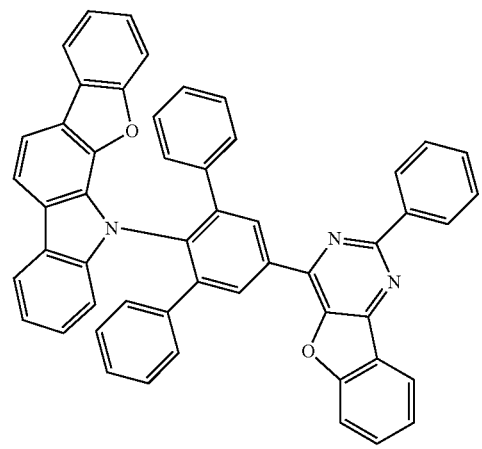
484
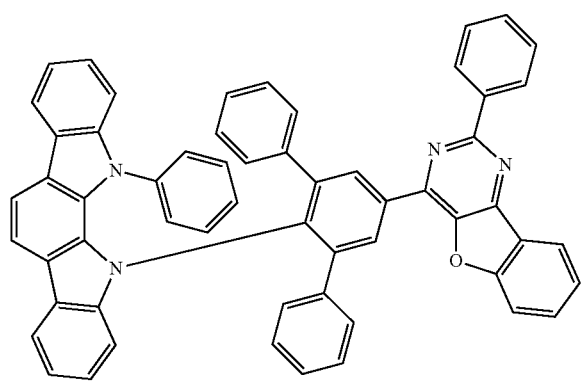
485
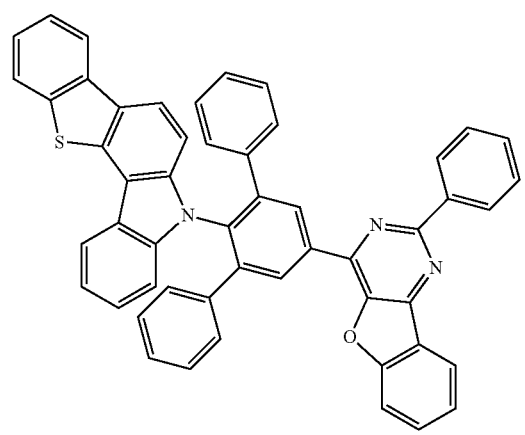

-continued
486
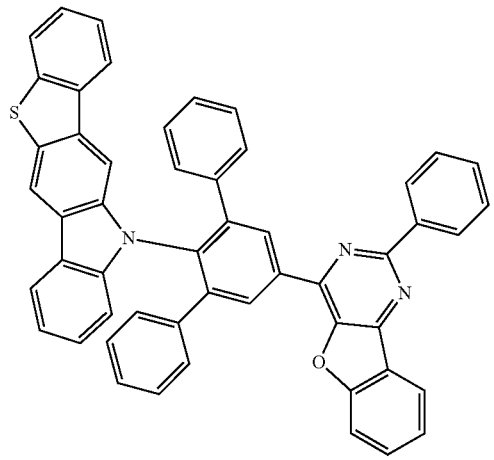
487
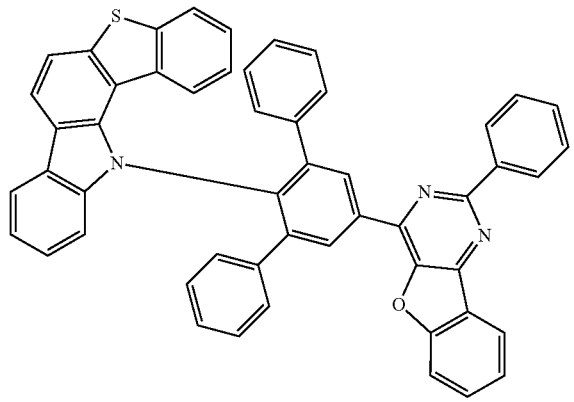
488
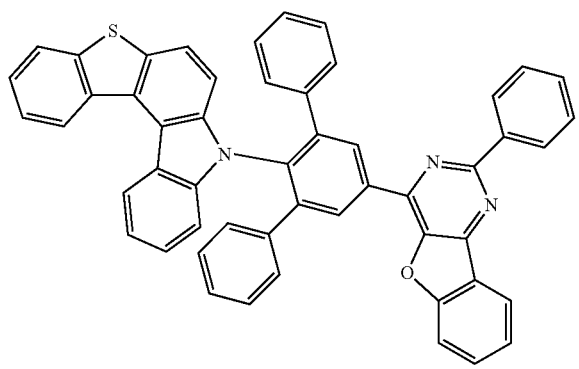
489
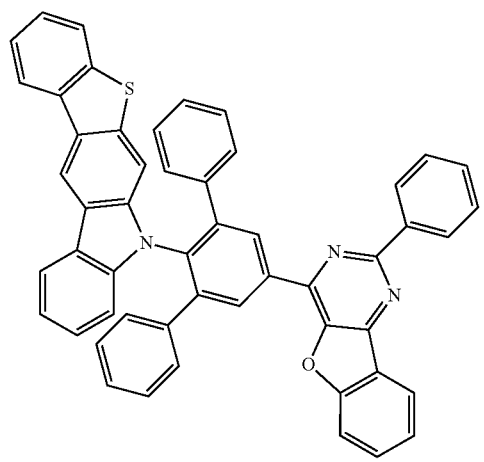
490
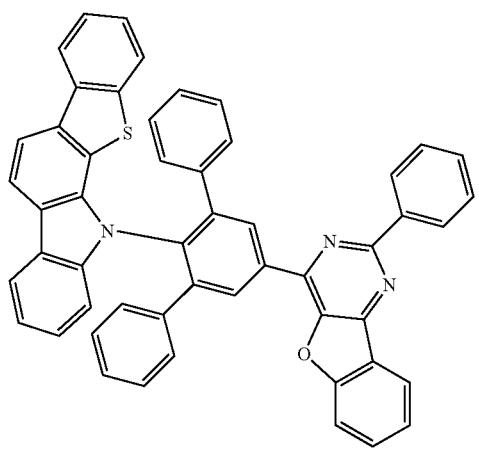
491
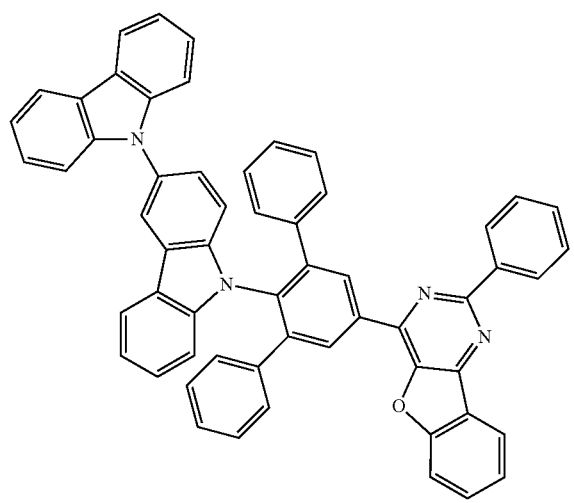

-continued
492
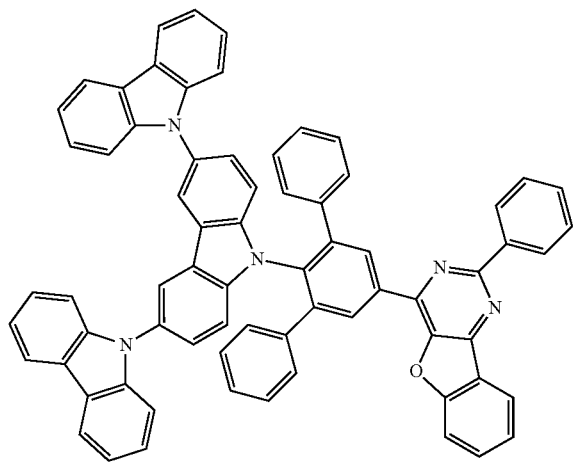
493
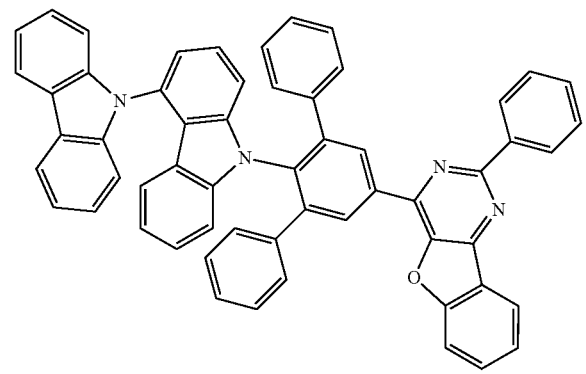
494
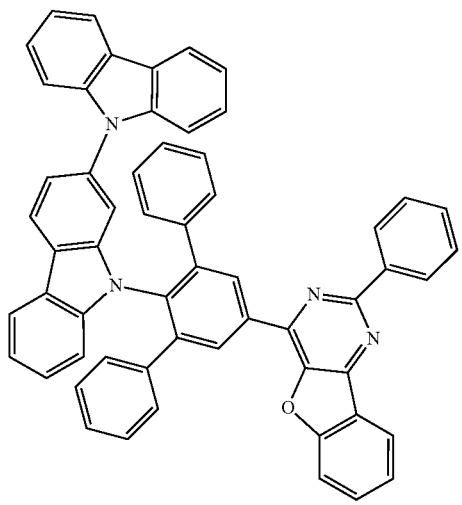
495
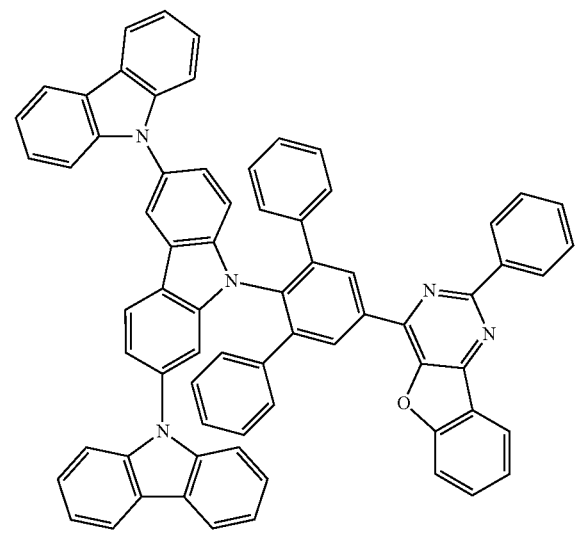
496
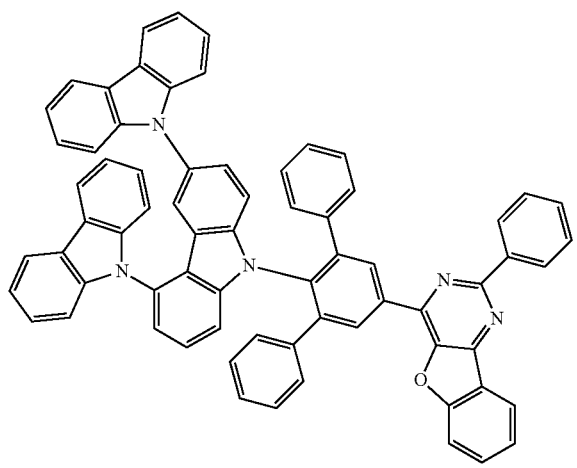
497
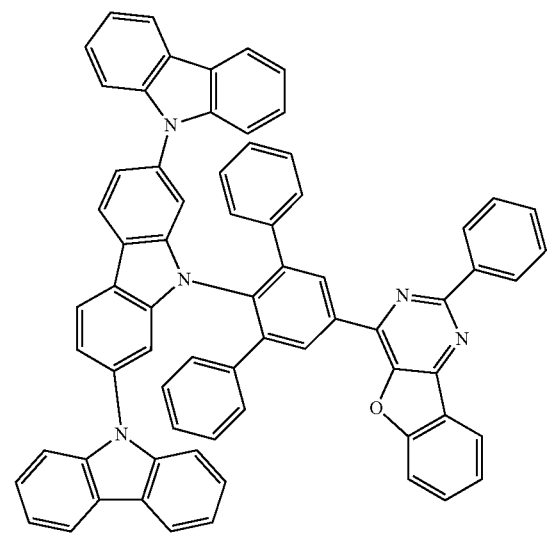

-continued
498
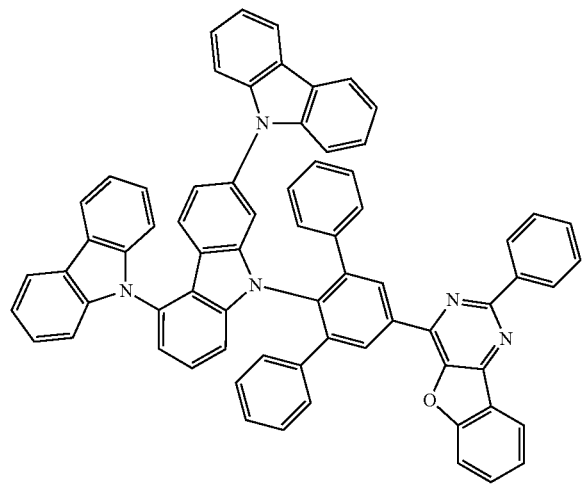
499
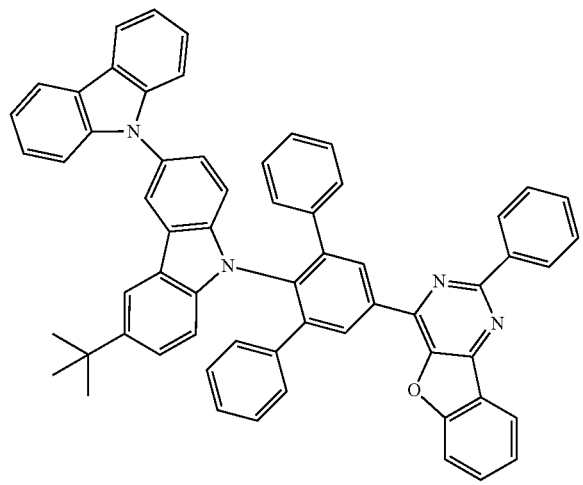
500
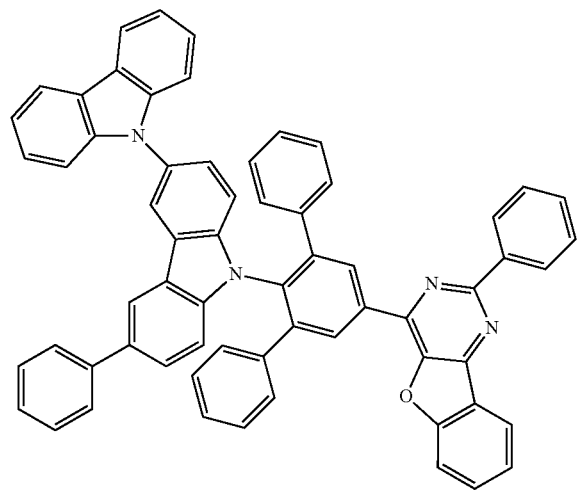
501
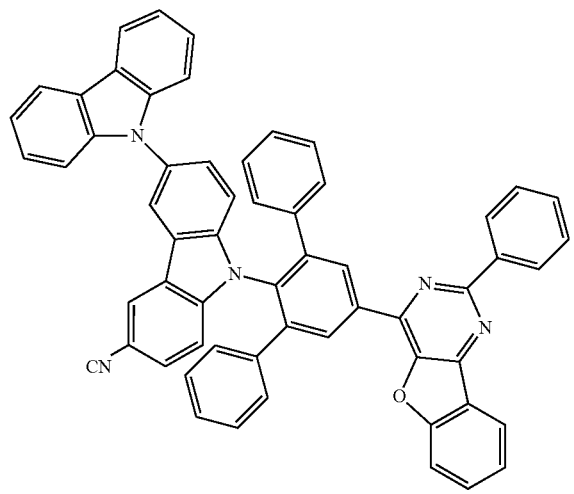
502
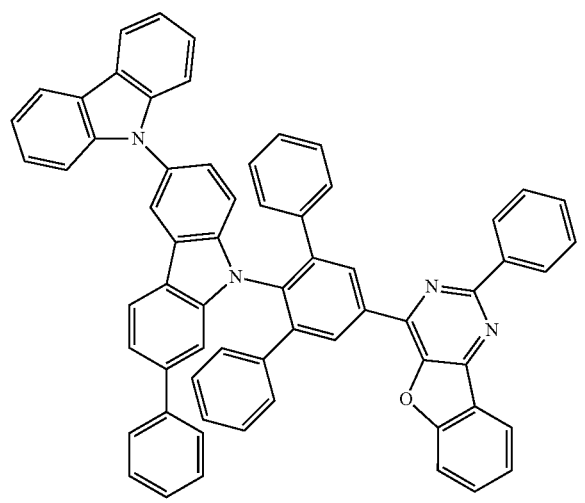
503
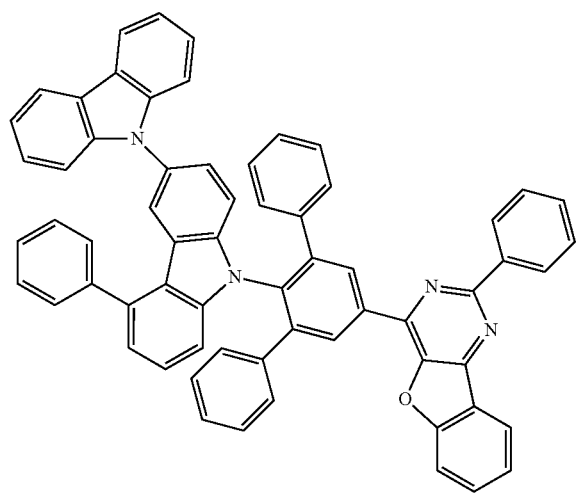

-continued
504
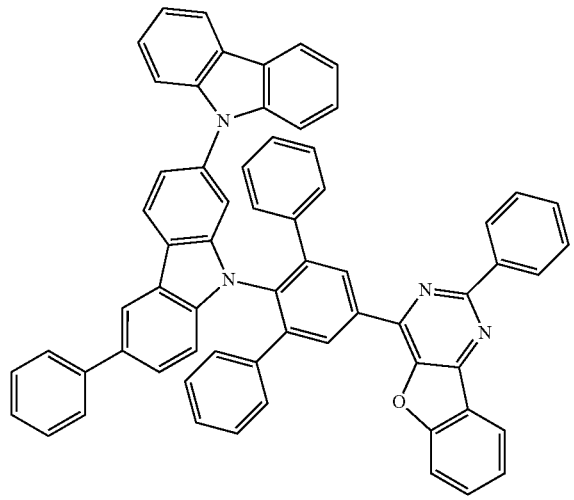
505
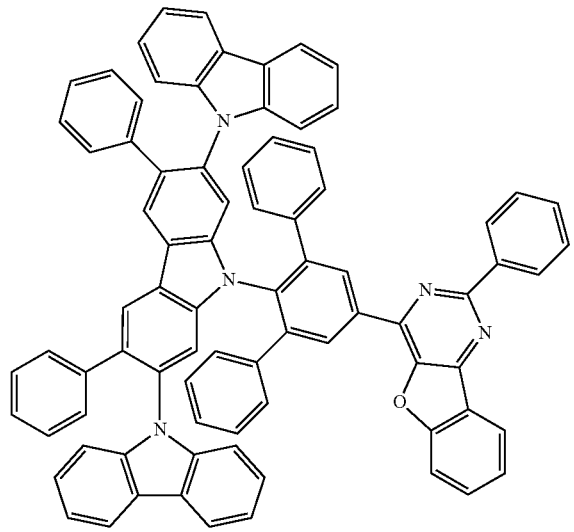
506
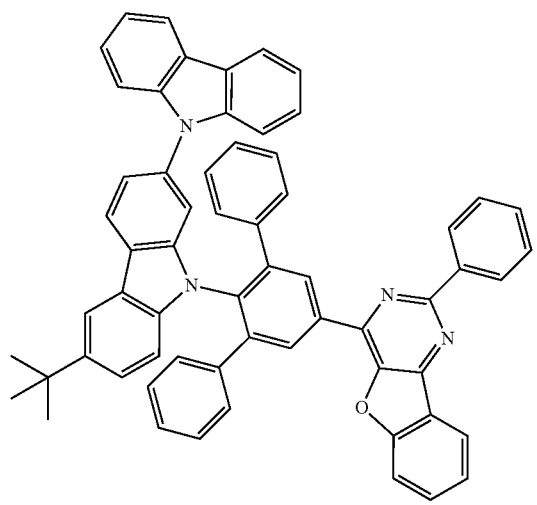
507
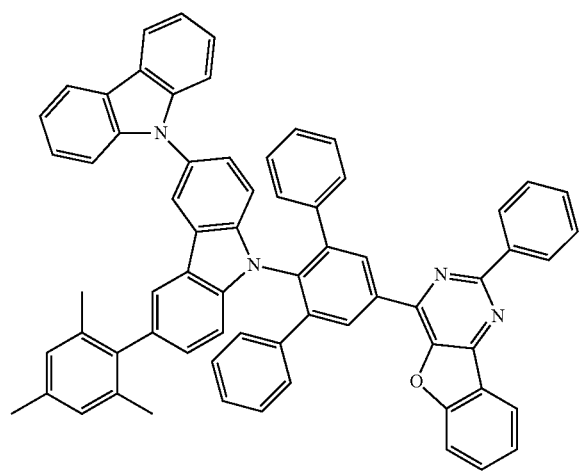
508
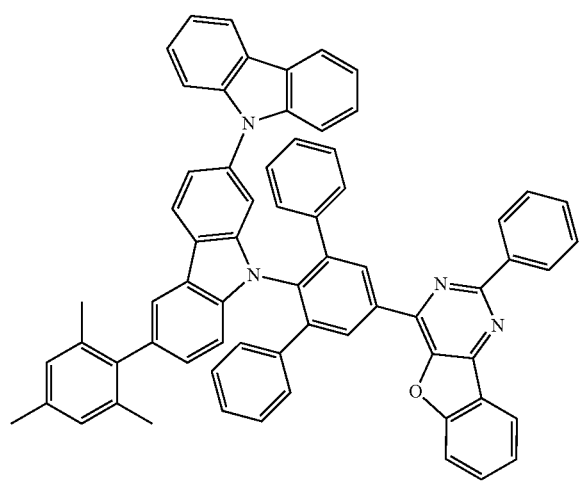
509
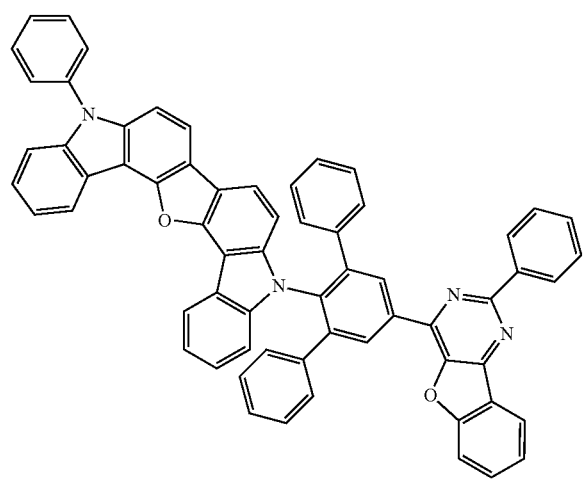

-continued
510
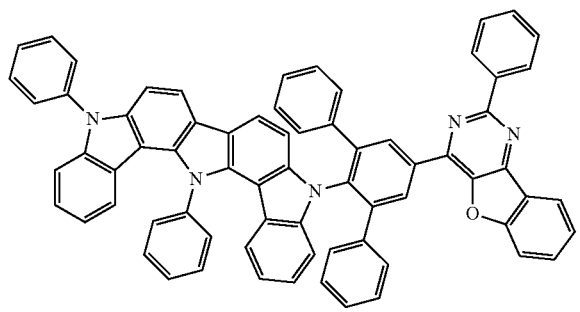
511
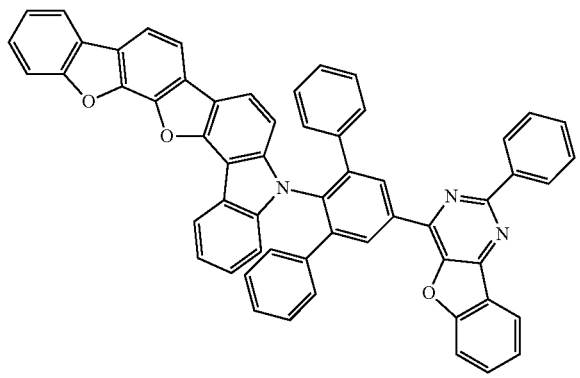
512
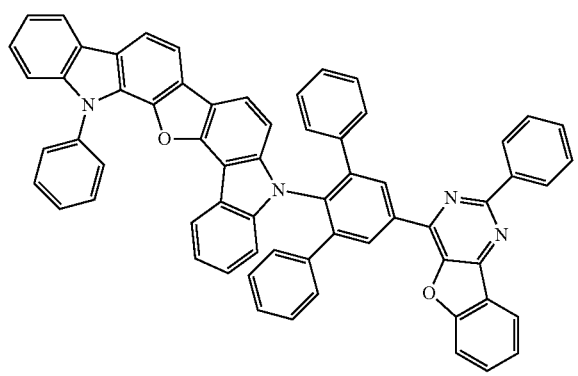
513
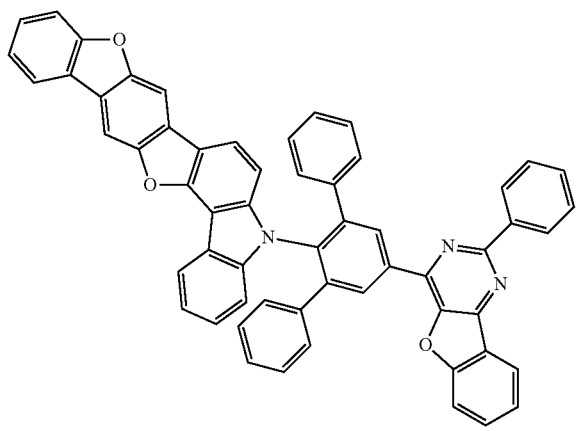
514
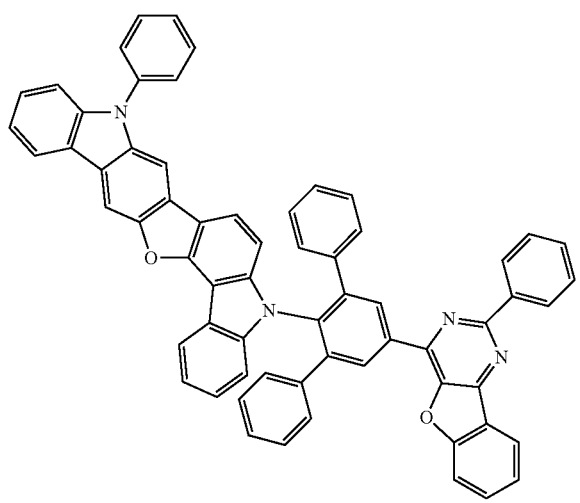
515
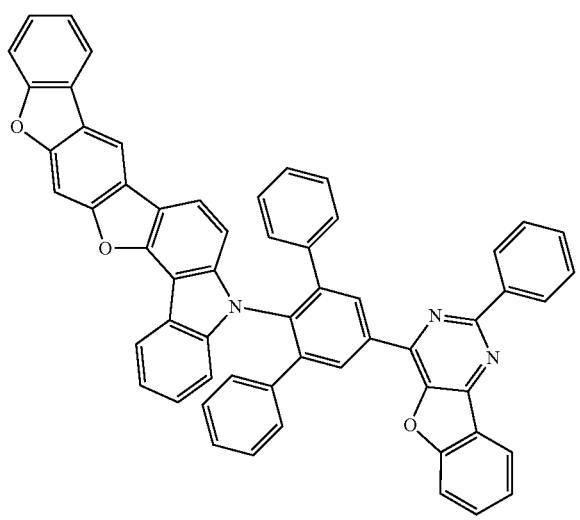

-continued
516
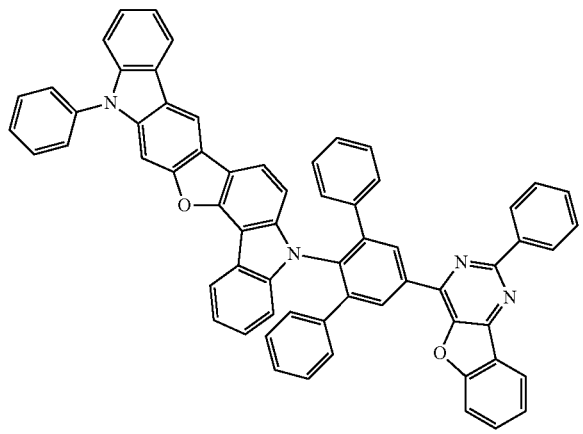
517
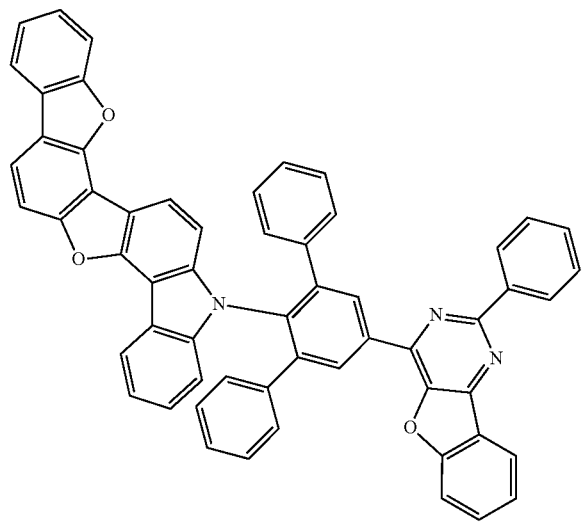
518
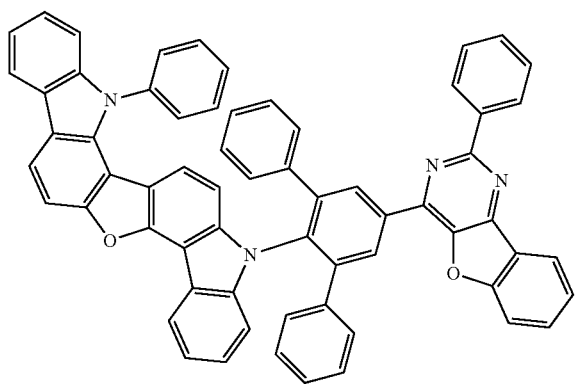
519
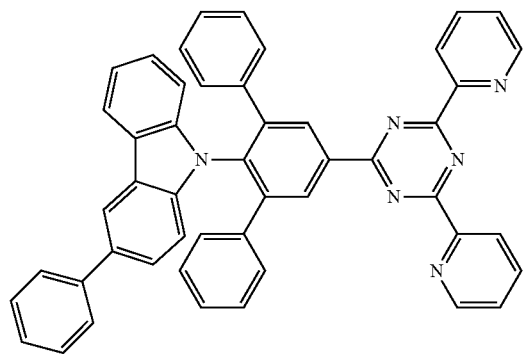
520
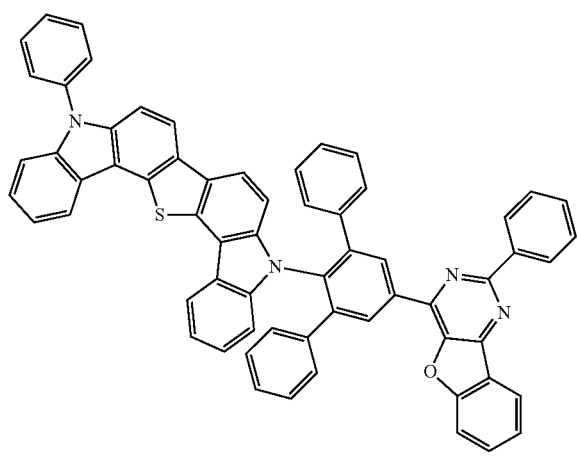
521
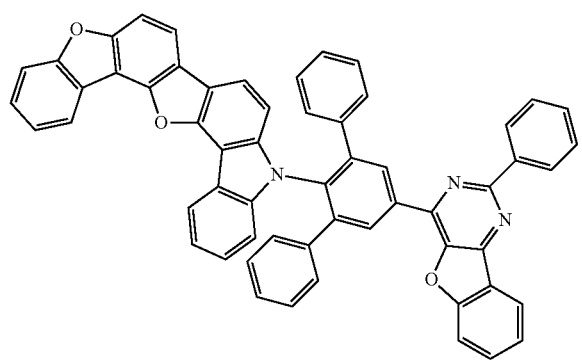

-continued
522
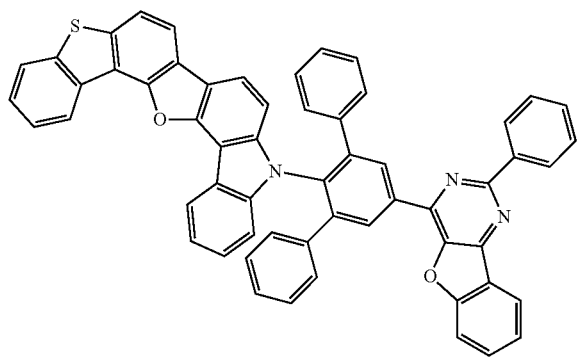
523
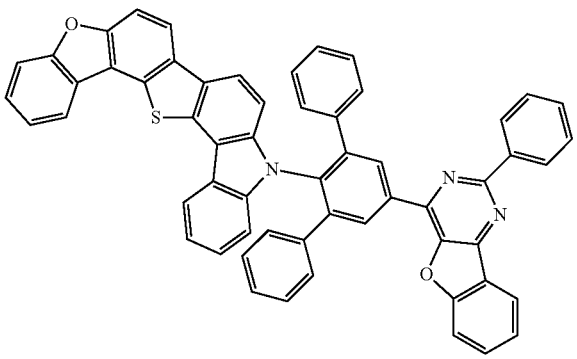
524
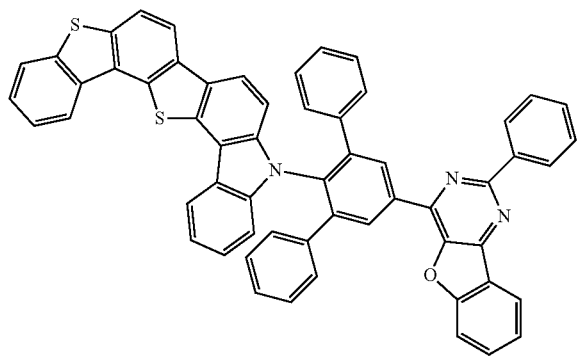
525
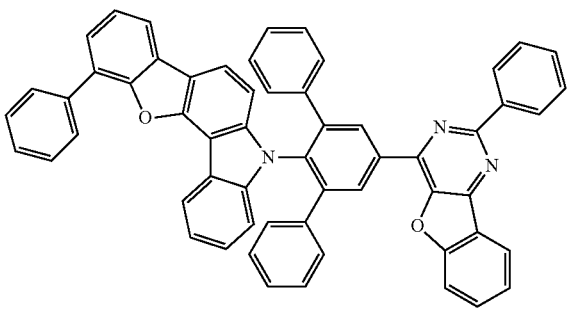
526
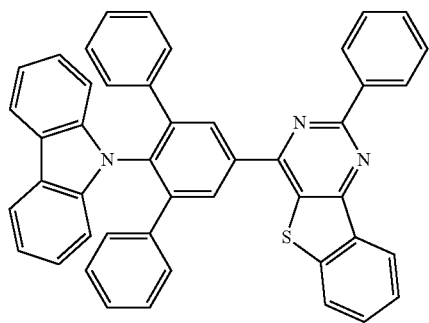
527
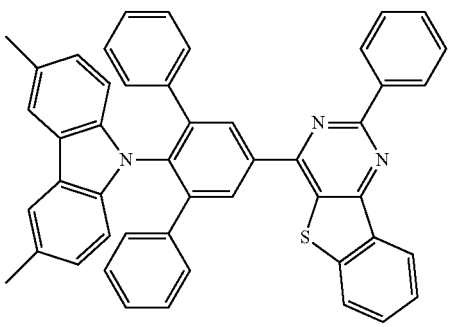
528
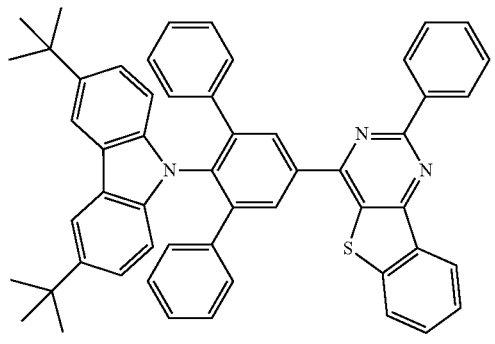
529
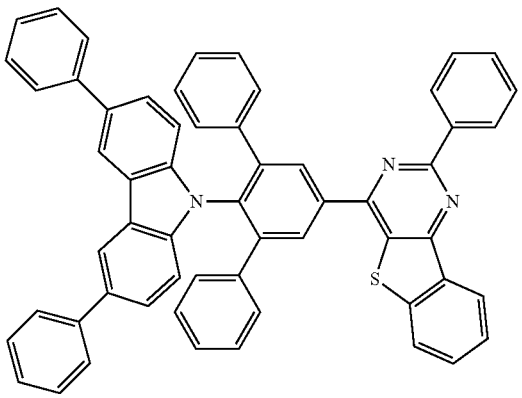

-continued
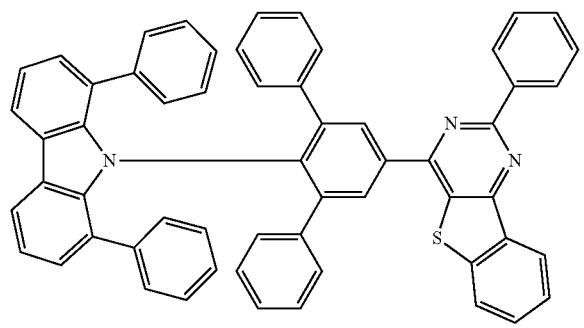 530
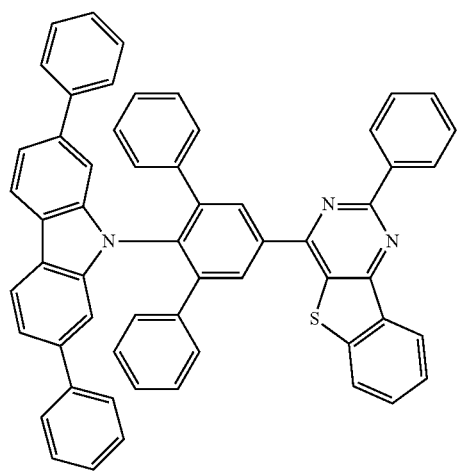 531
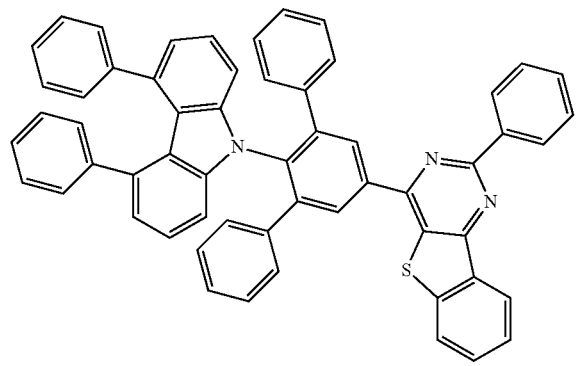 532
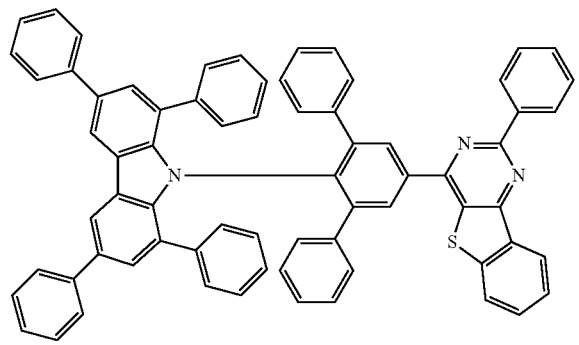 533
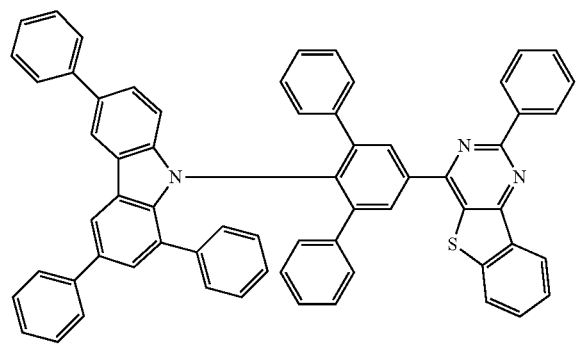 534
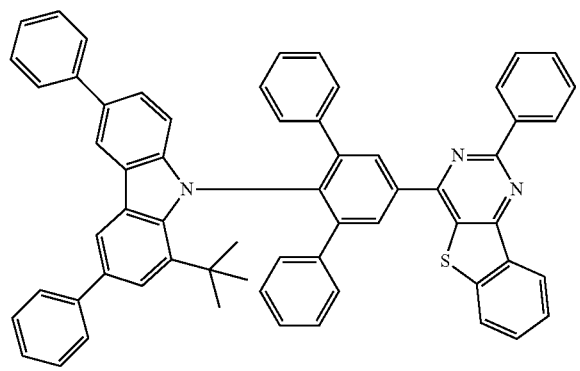 535

-continued
536
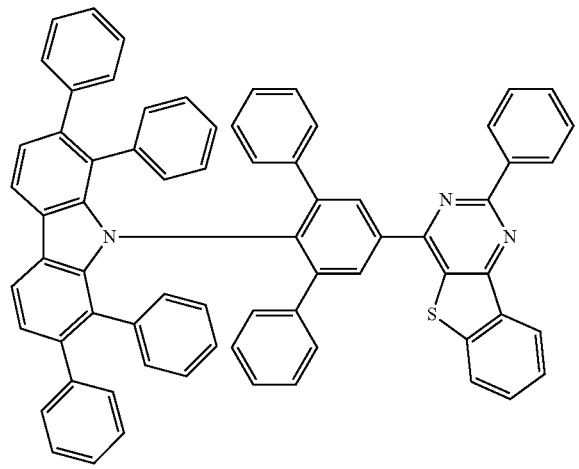
537
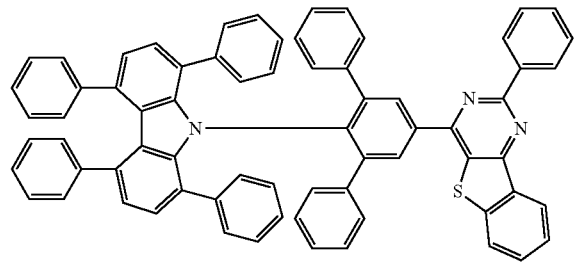
538
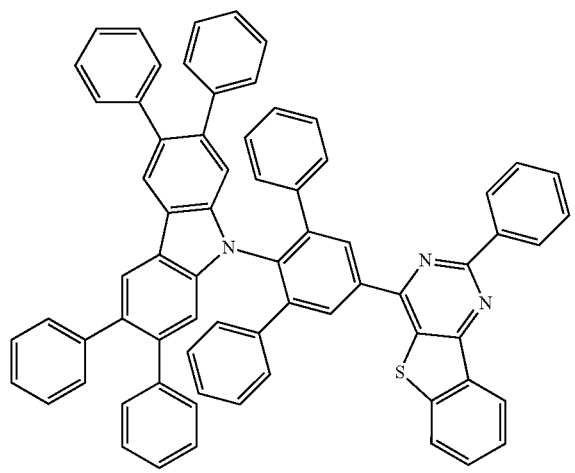
539
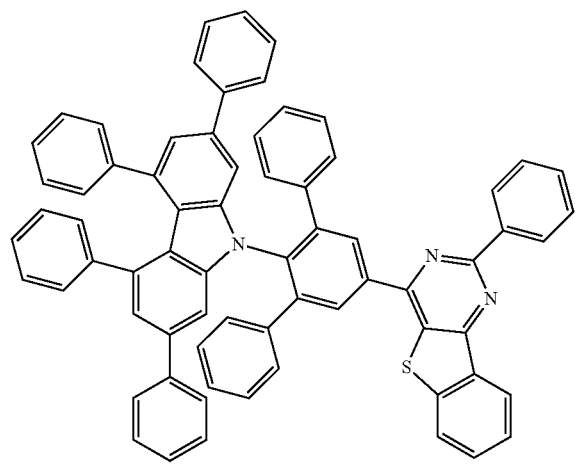
540
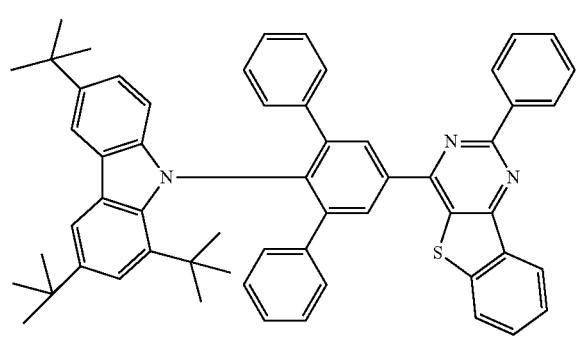
541
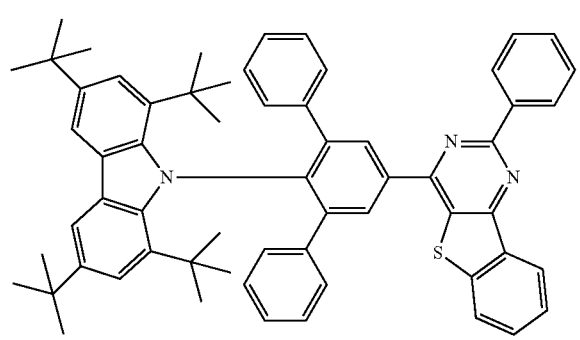
542
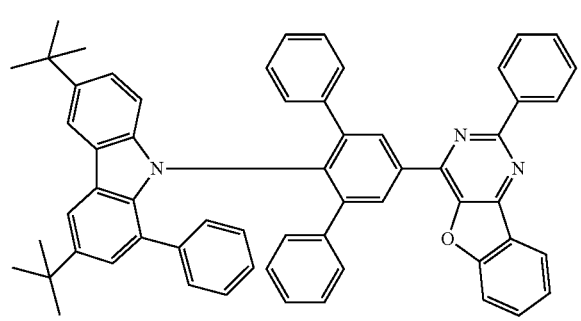
543
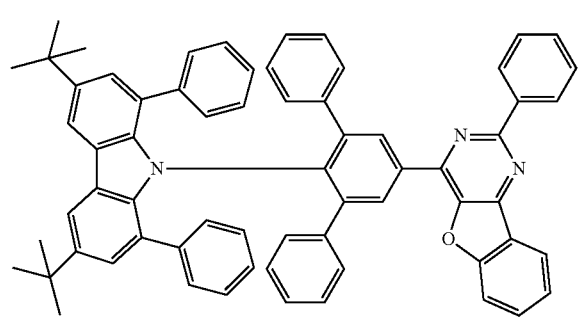

544
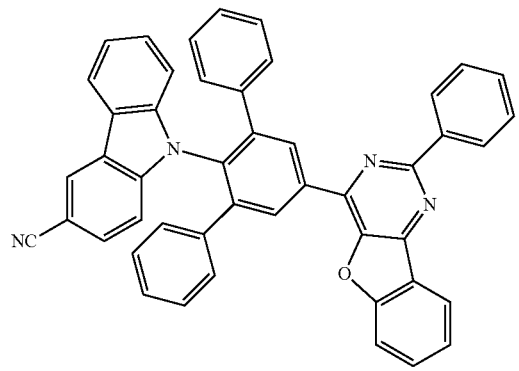
545
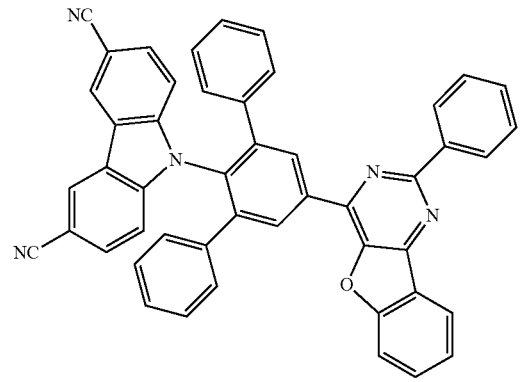
546
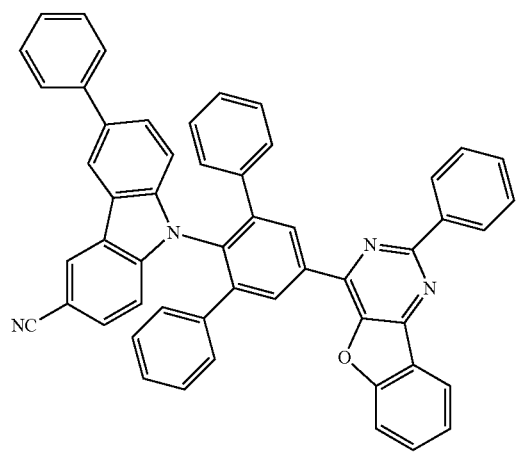
547
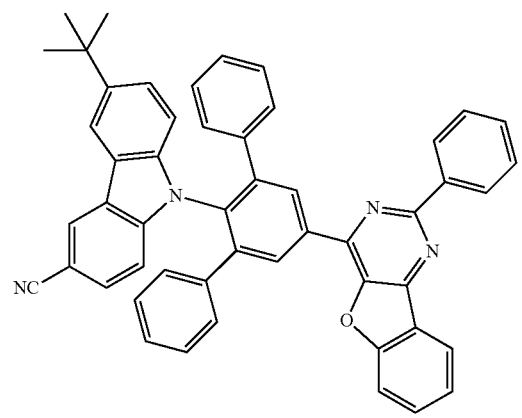
548
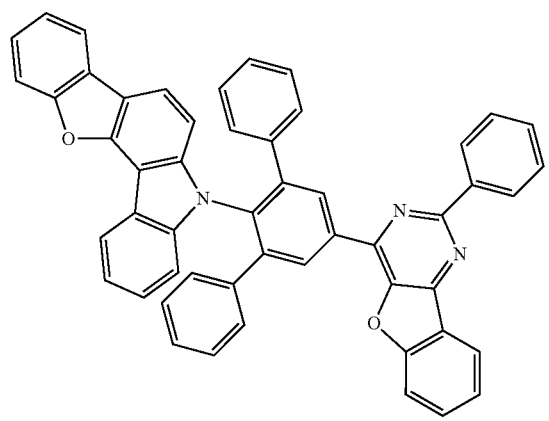
549
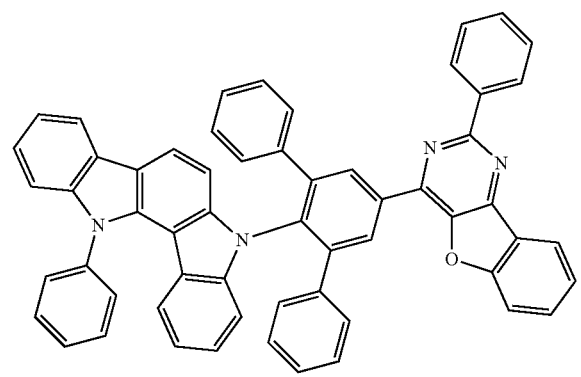

550
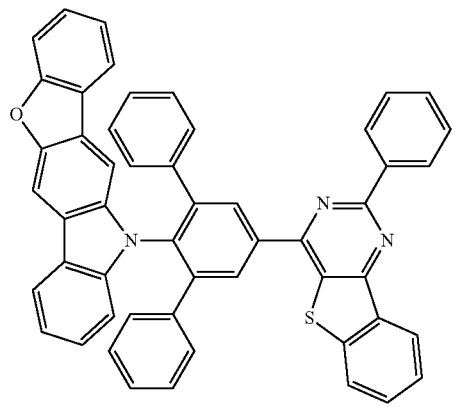
551
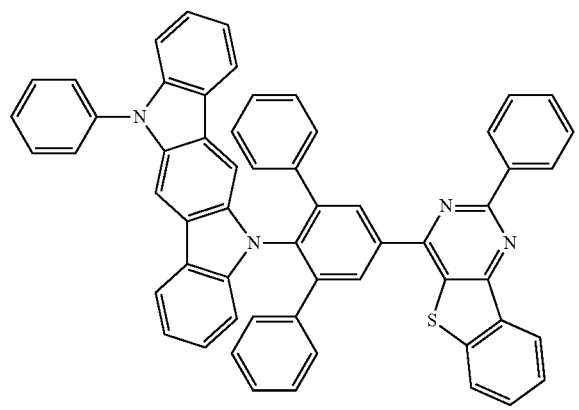
552
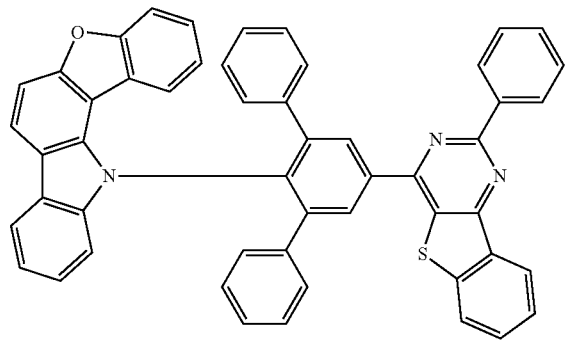
553
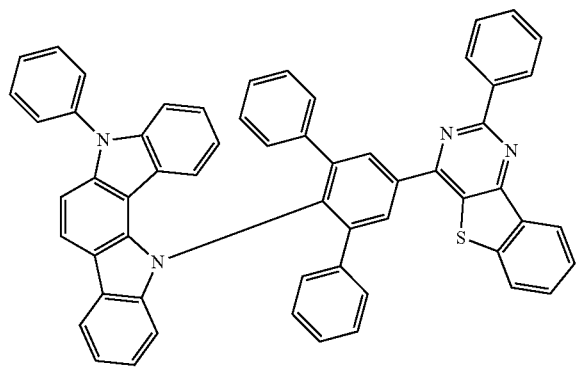
-continued
554
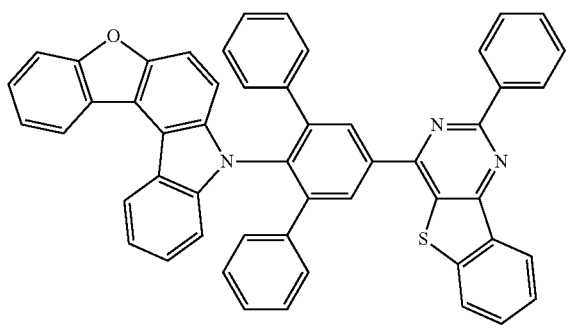
555
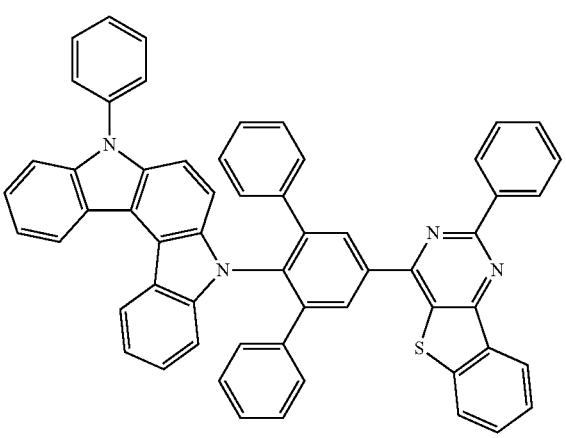
556
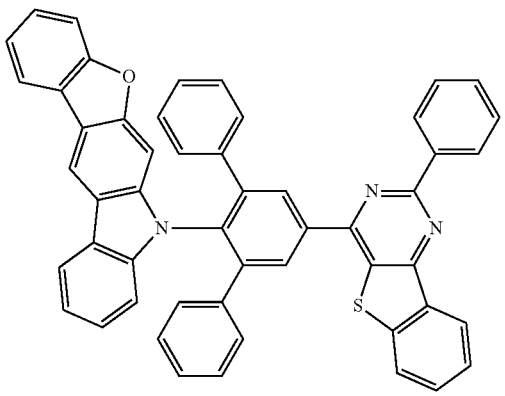
557
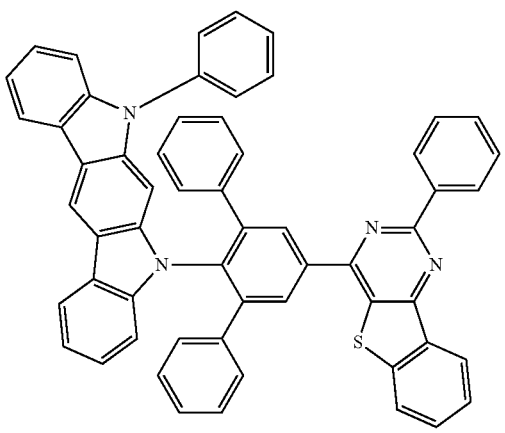

357
-continued
558
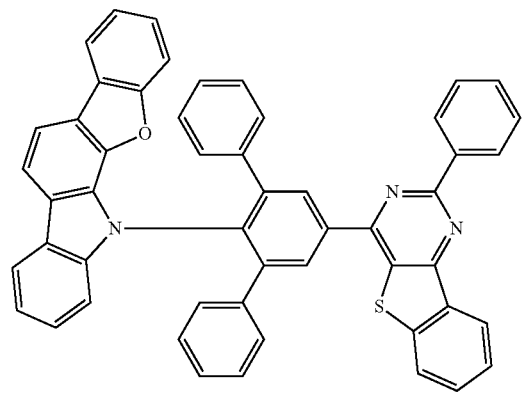
559
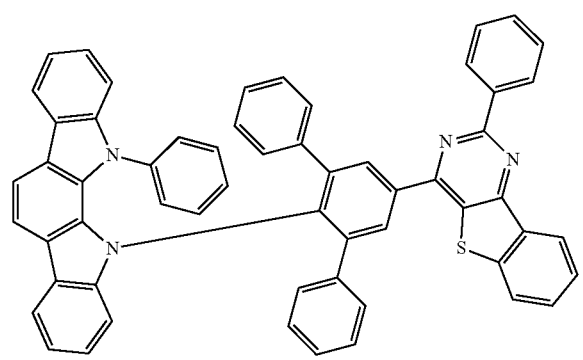
560
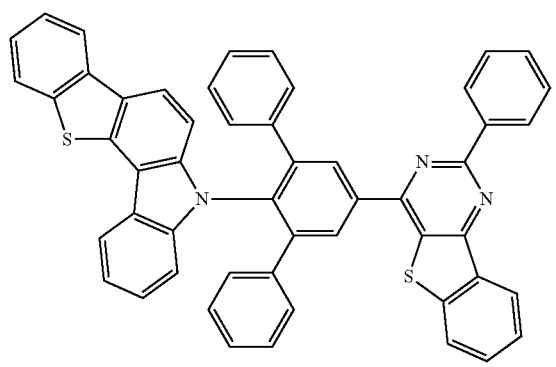
561
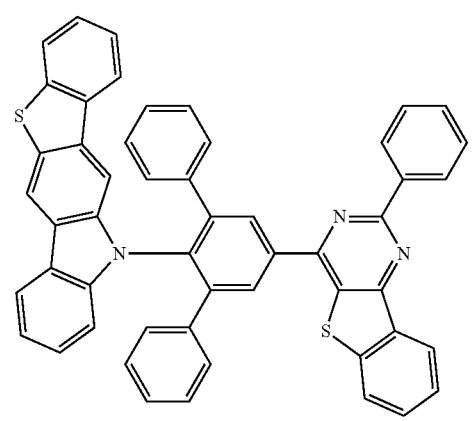
358
-continued
562
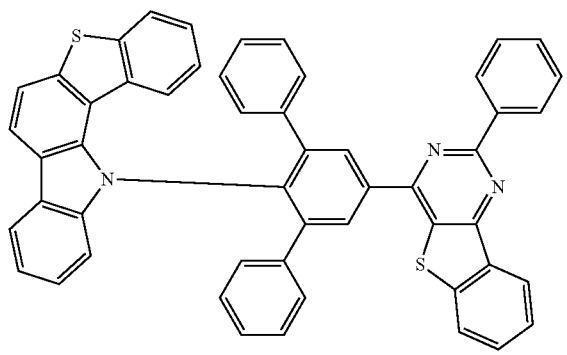
563
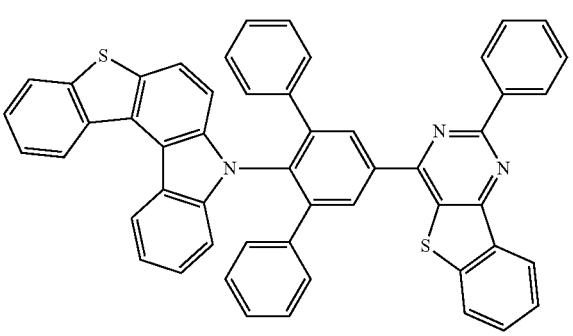
564
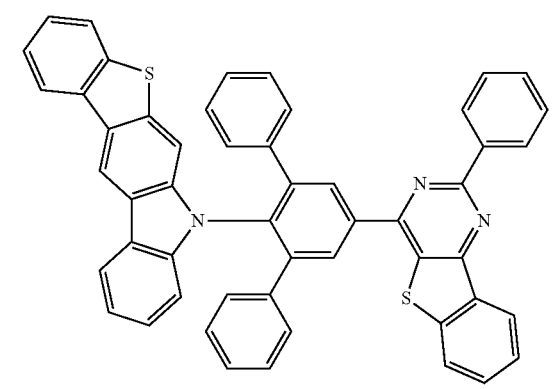
565
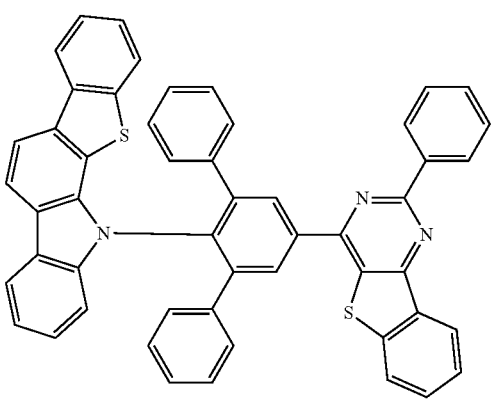

566
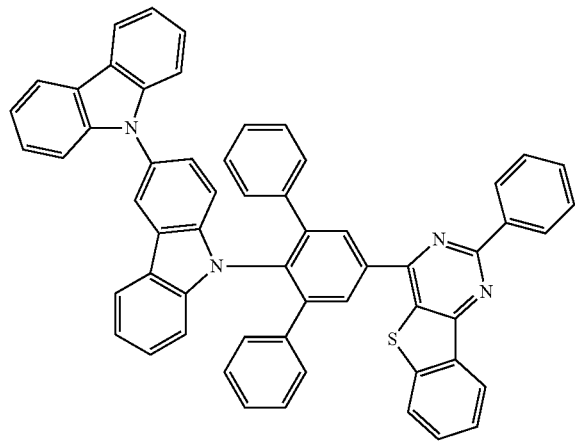
567
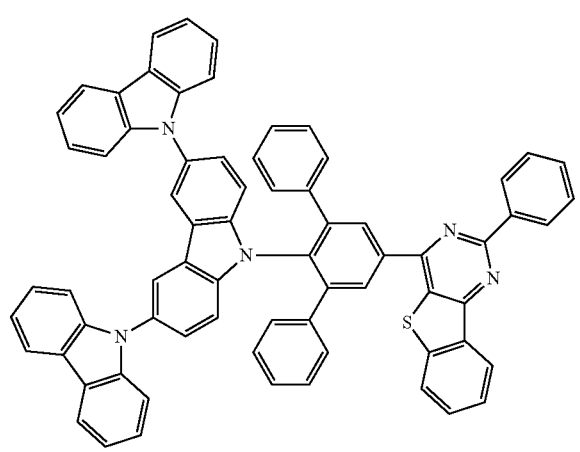
568
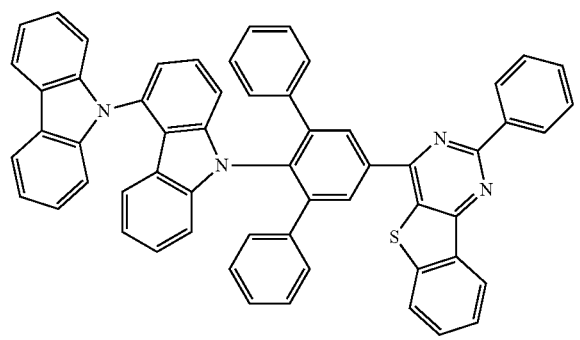
569
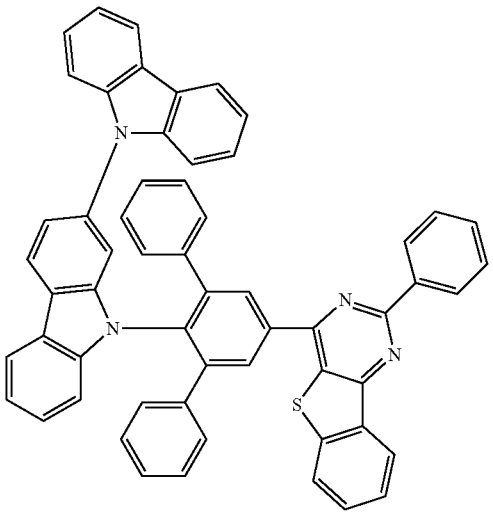
570
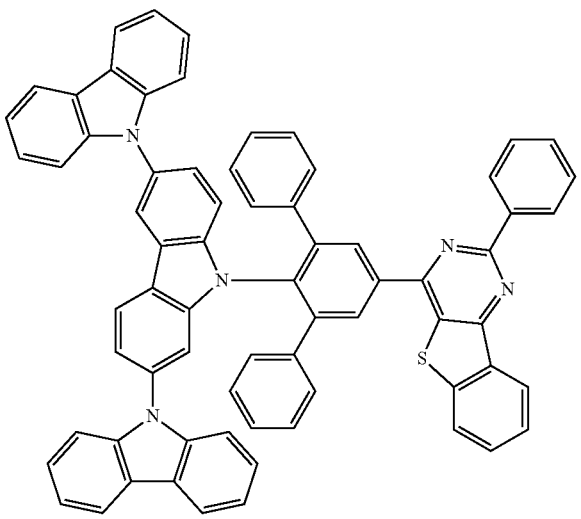
571
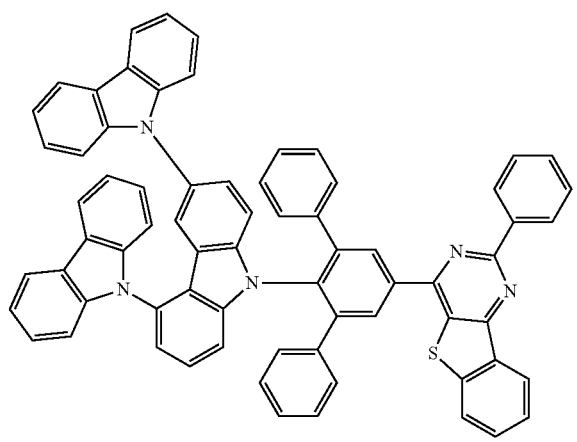

-continued
572
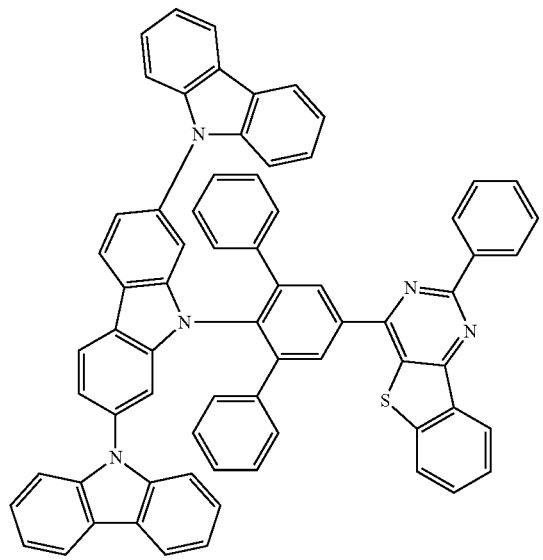
573
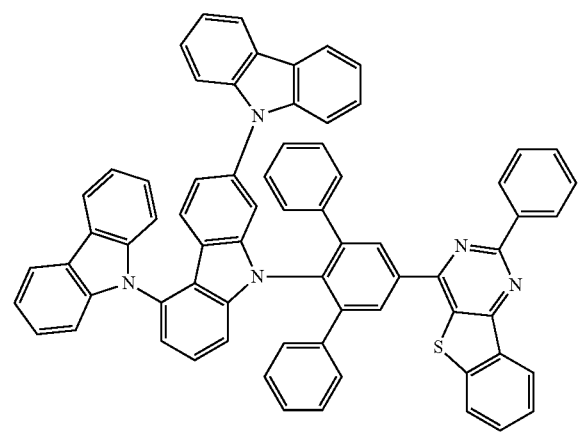
574
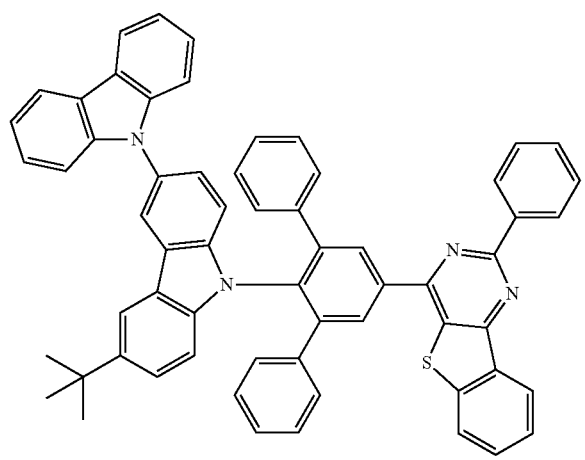
-continued
575
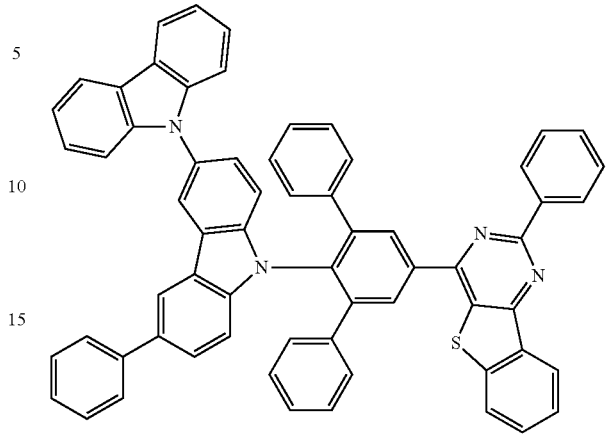
576
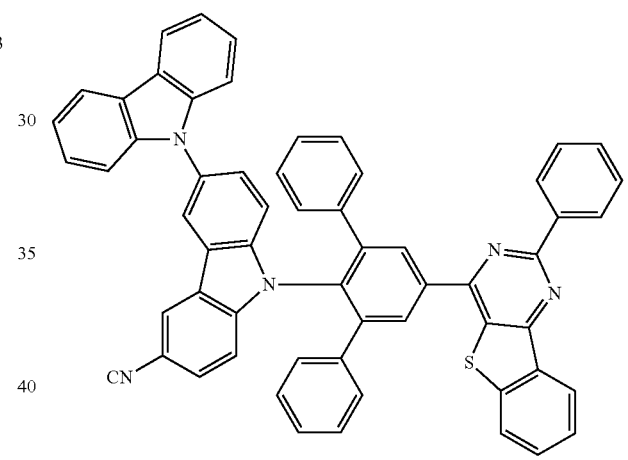
577
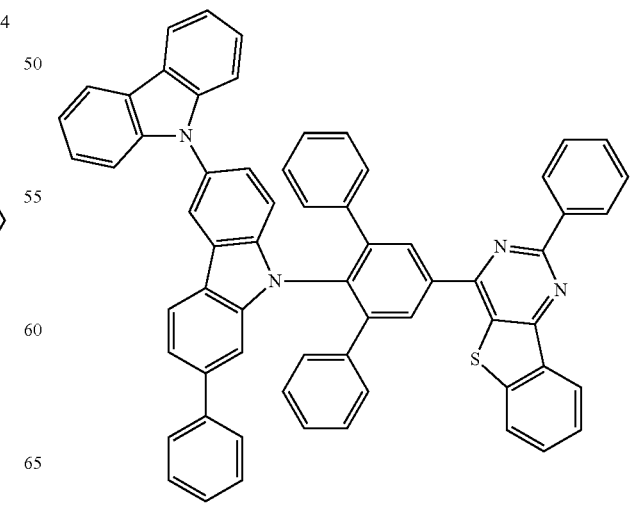

-continued
578
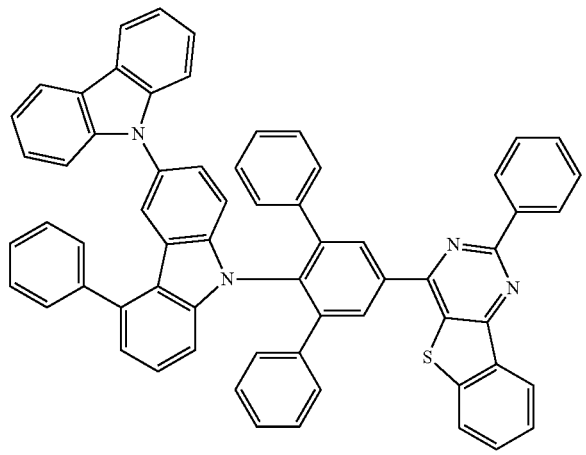
579
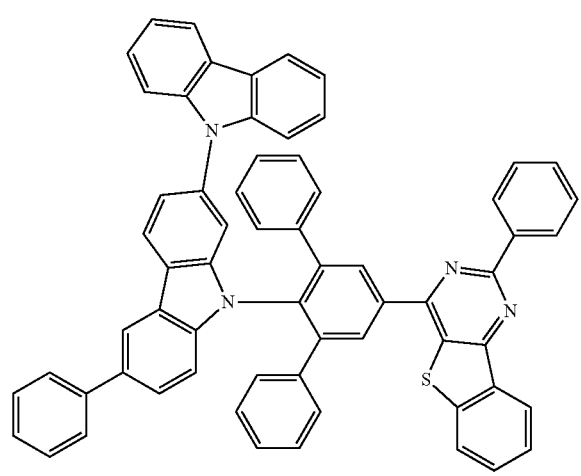
580
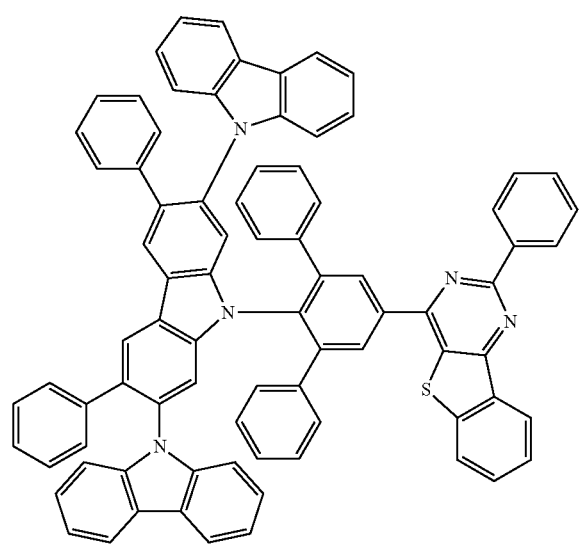
-continued
581
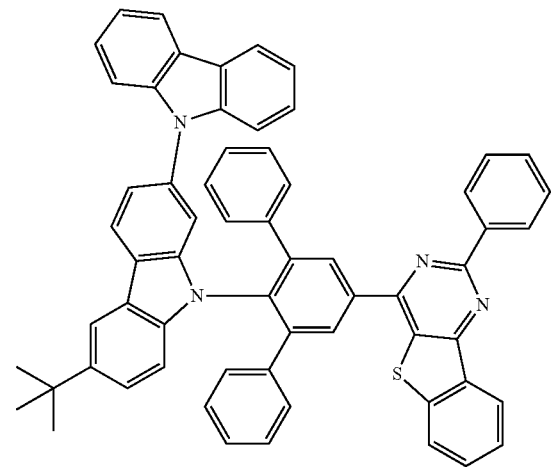
582
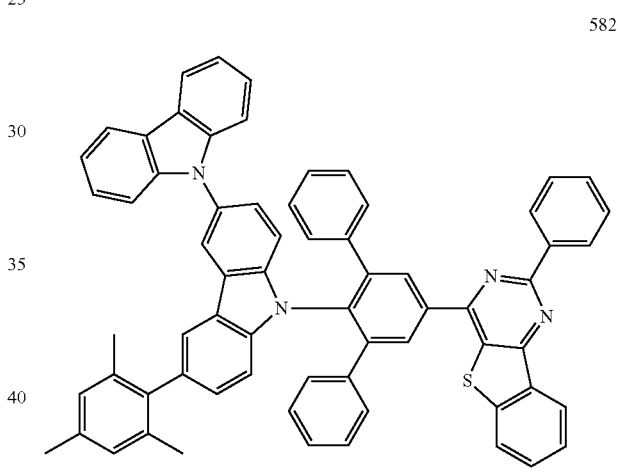
583
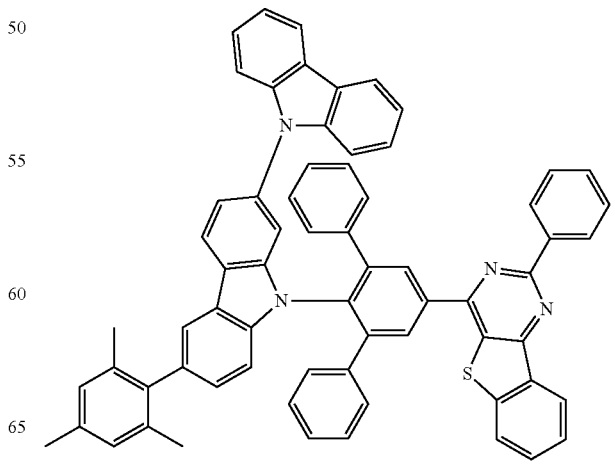

365
-continued
584
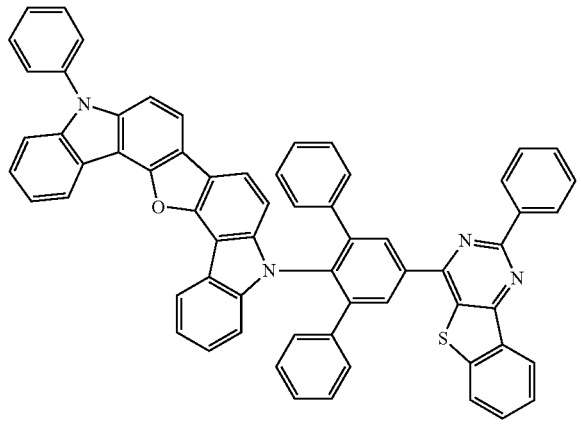
585
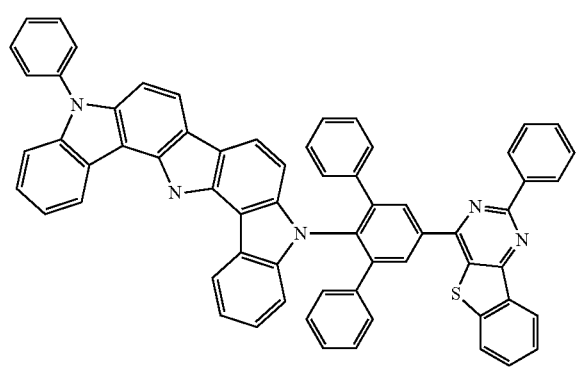
586
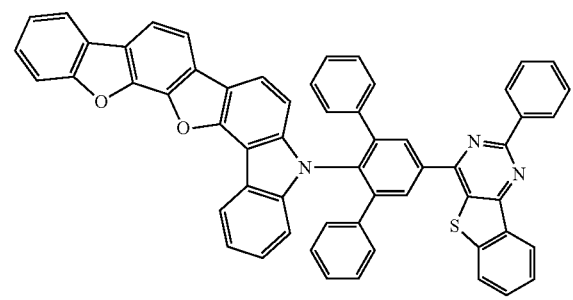
587
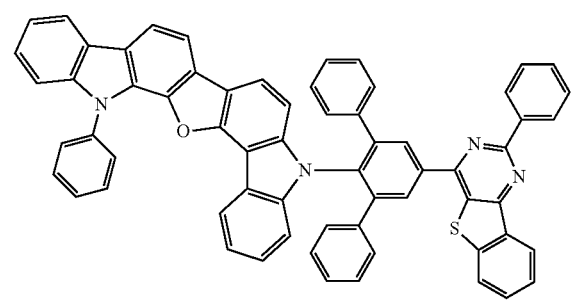
366
-continued
588
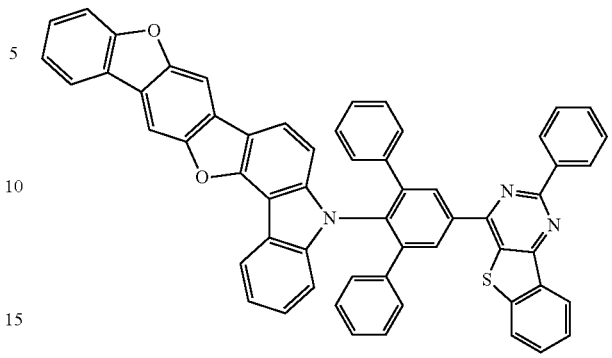
589
590

367
-continued
591
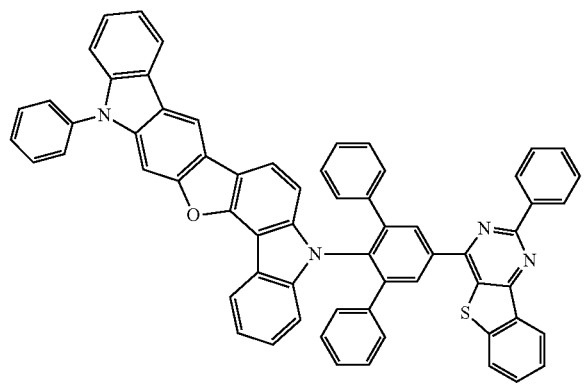
592
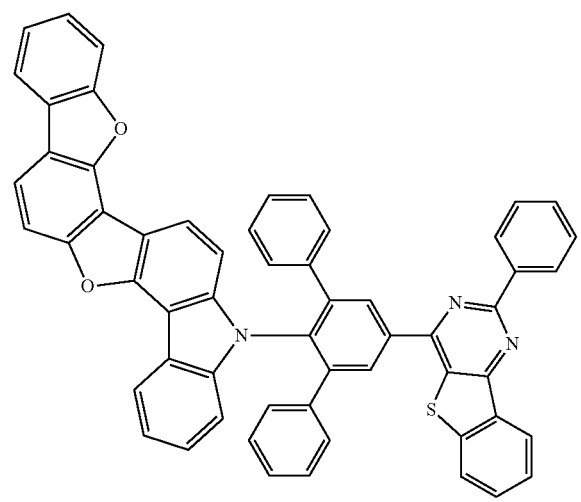
593
368
-continued
594
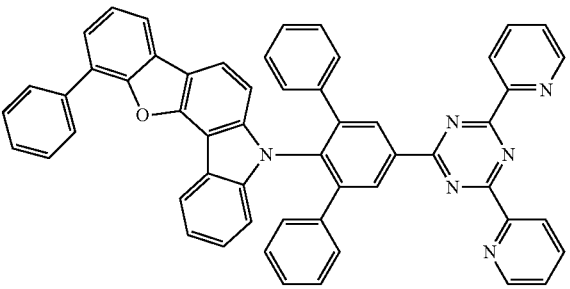
595
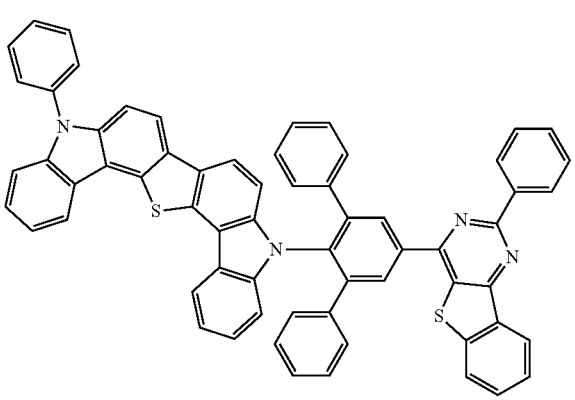
596
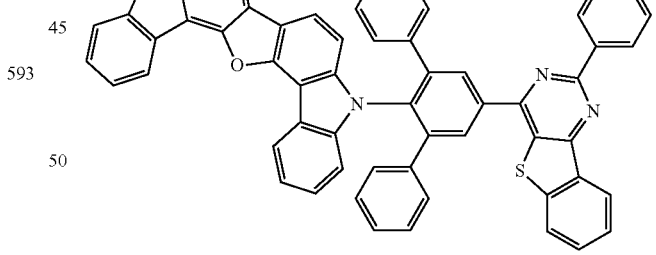
597
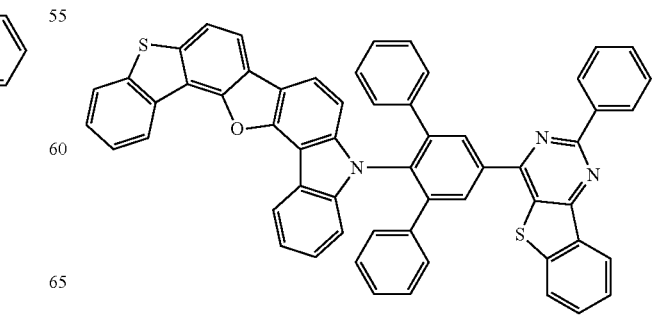

US 11,569,452 B2
369
-continued
598
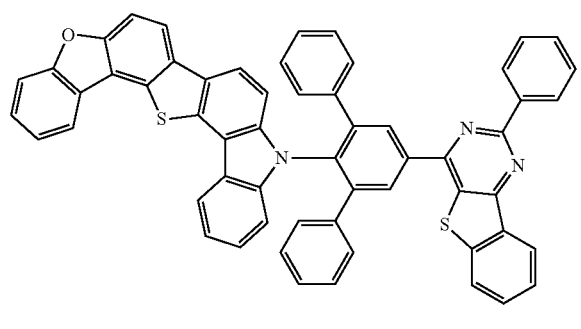
599
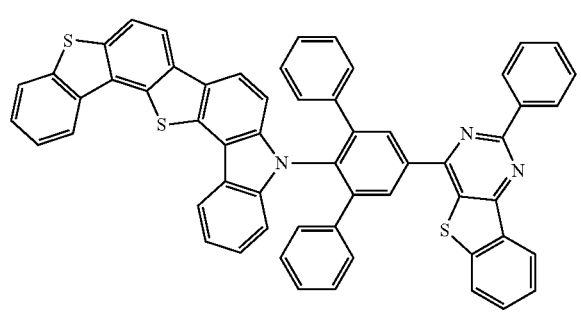
600
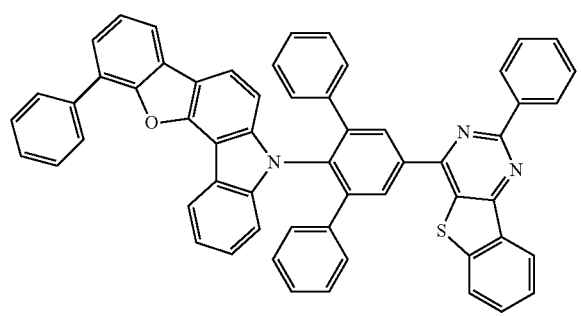
370
-continued
602
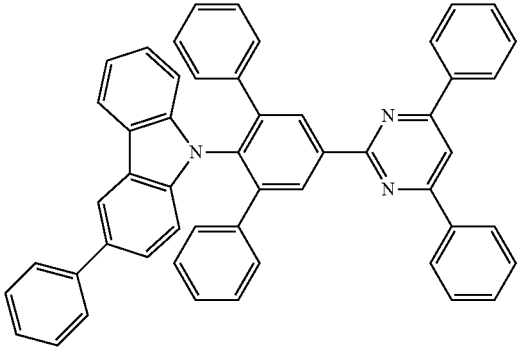
603
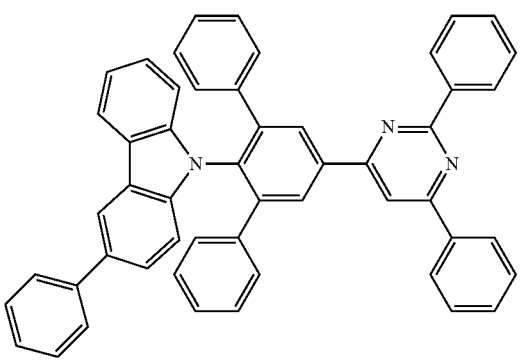
604
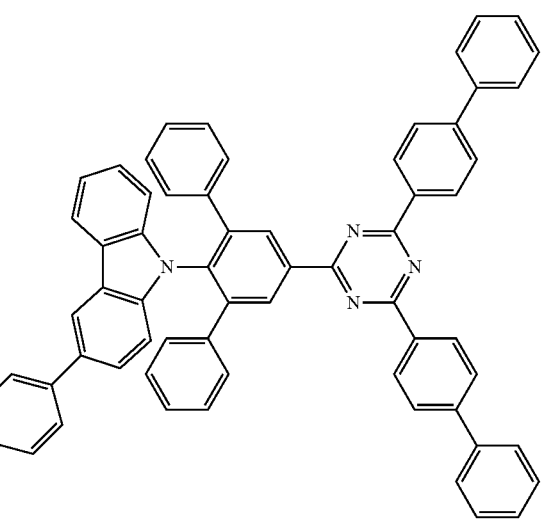
601

605
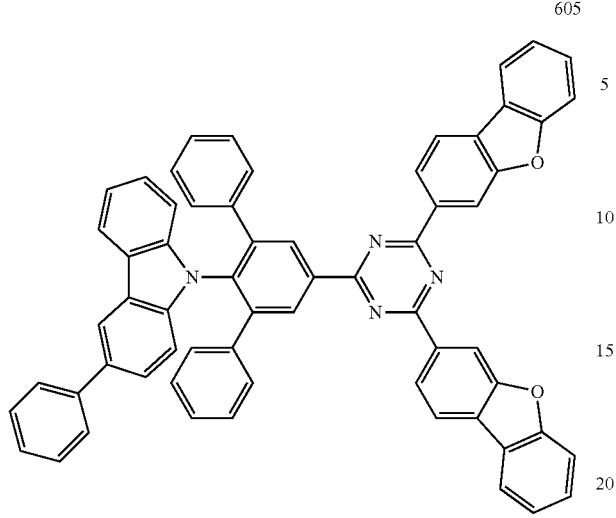
606
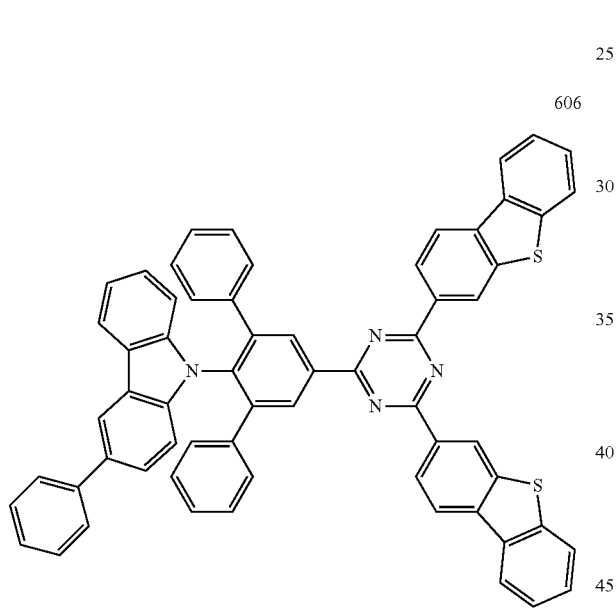
607
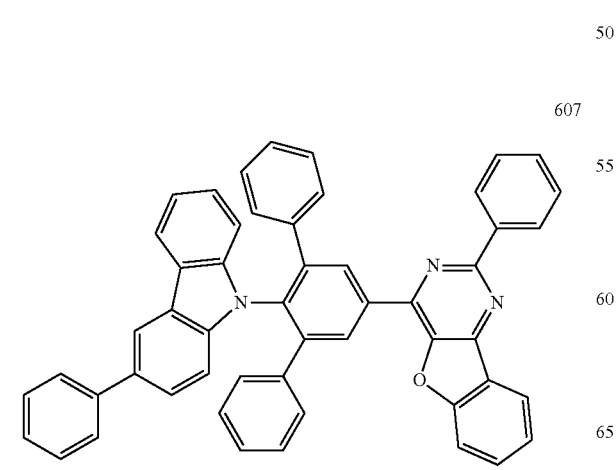
608
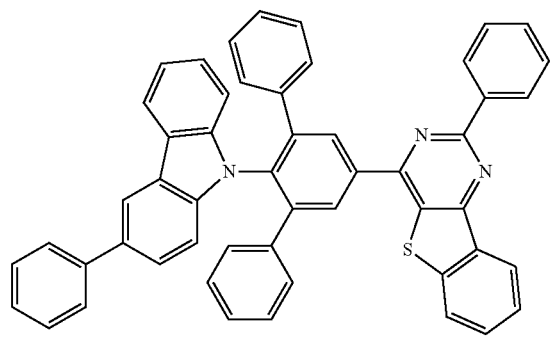
609
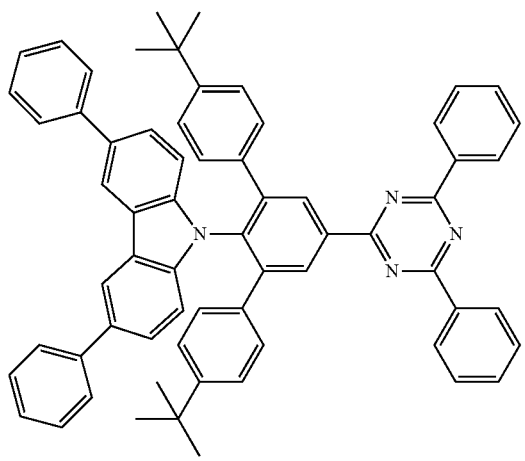
610
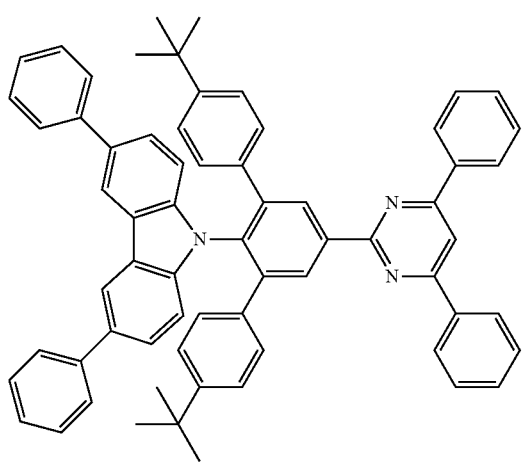

373
-continued
611
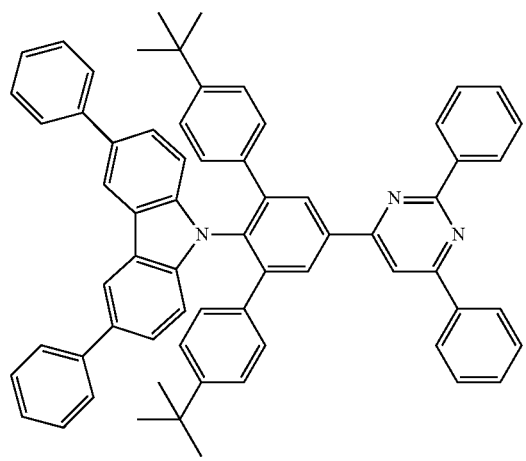
612
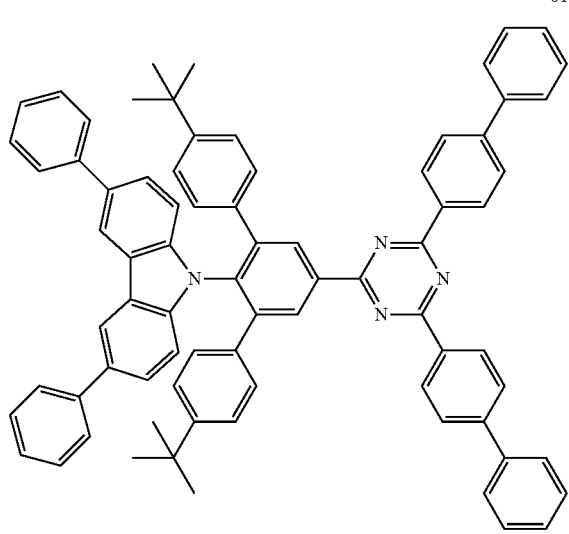
613
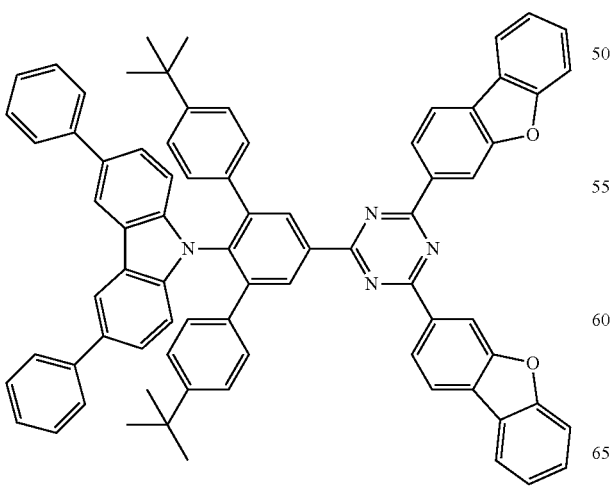
374
-continued
614
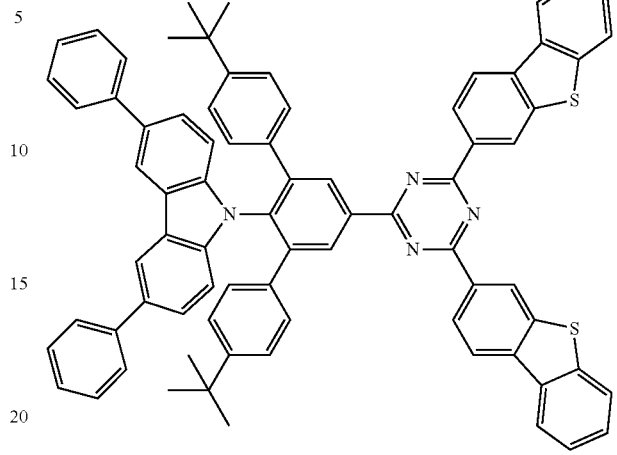
615
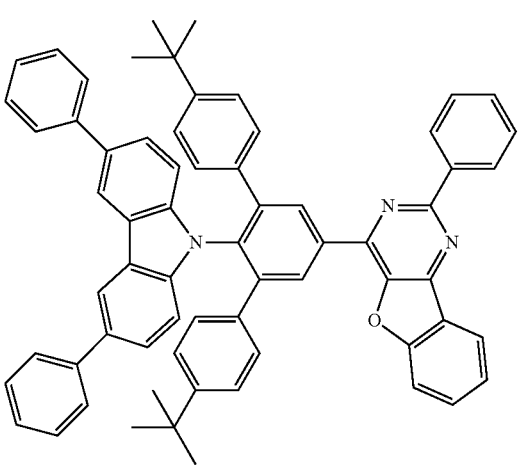
616
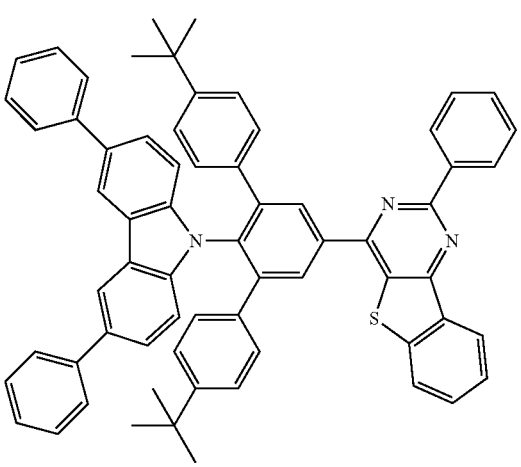

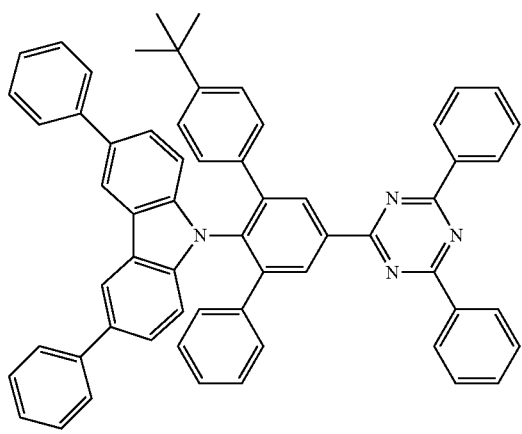
617
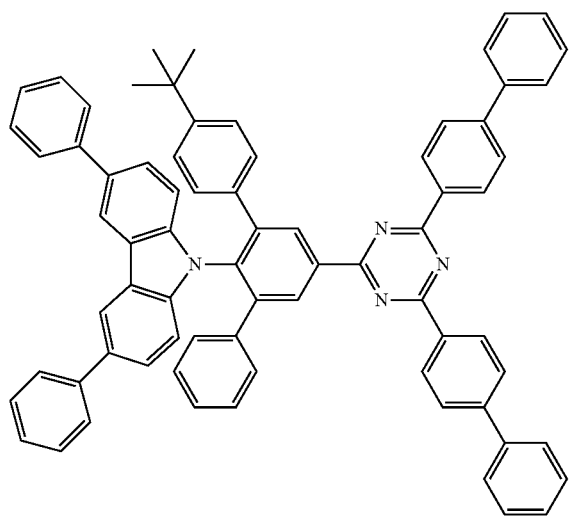
620
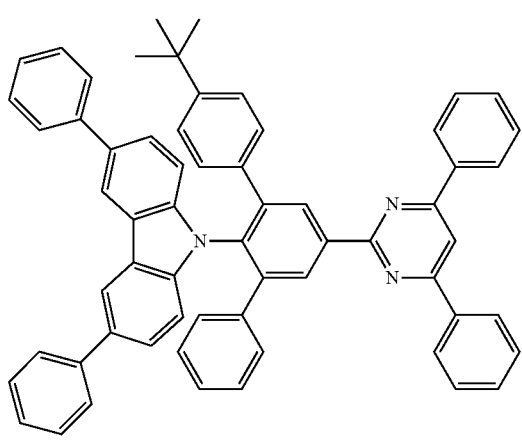
618
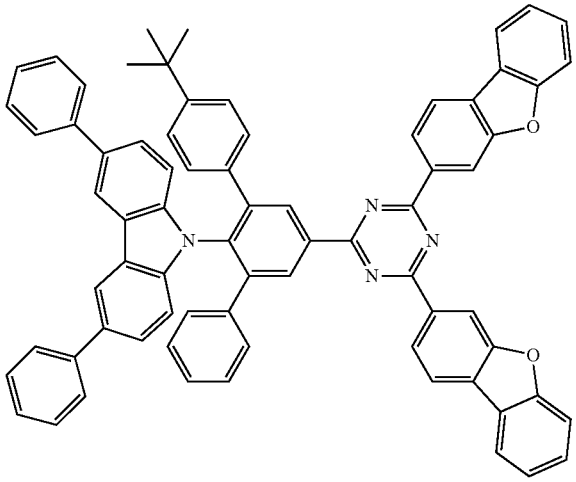
621
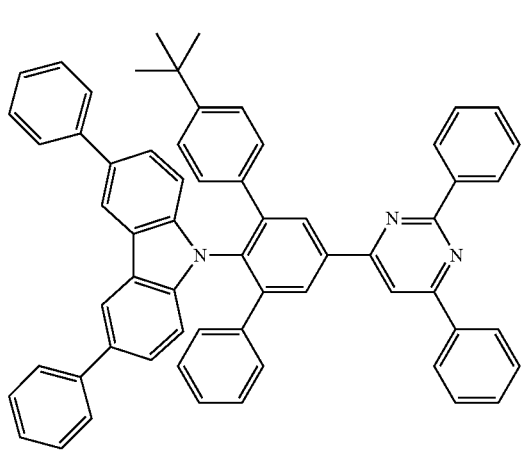
619
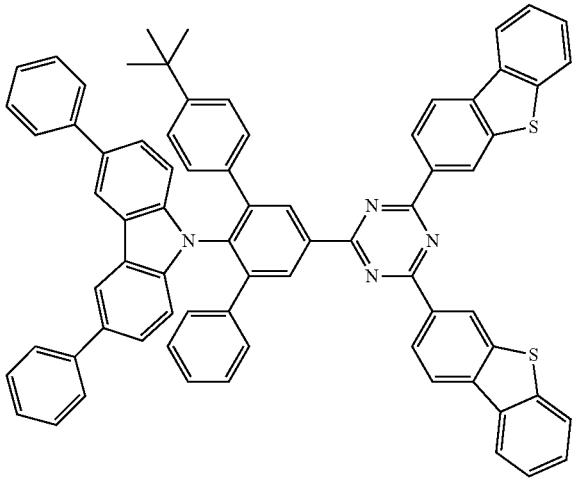
622

623
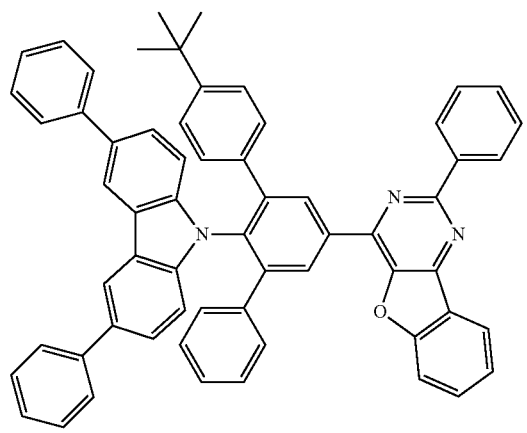
624
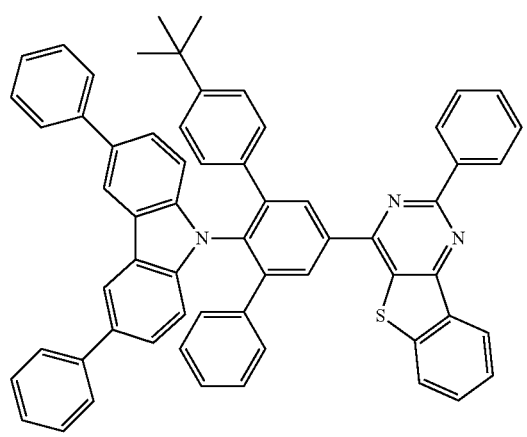
625
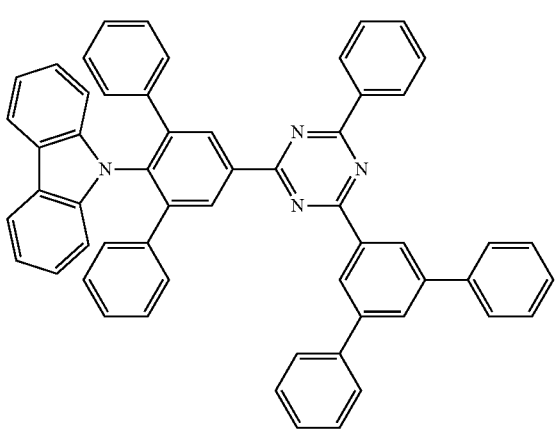
626
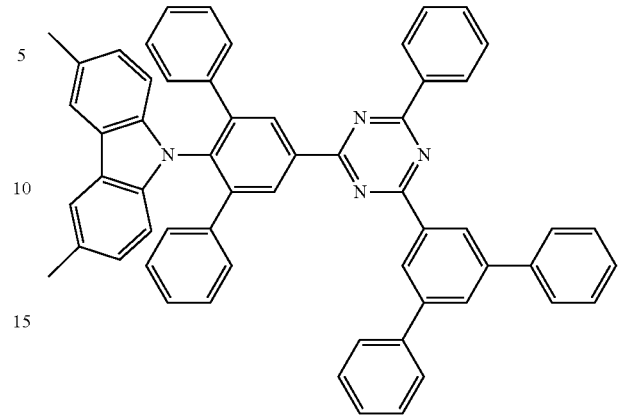
627
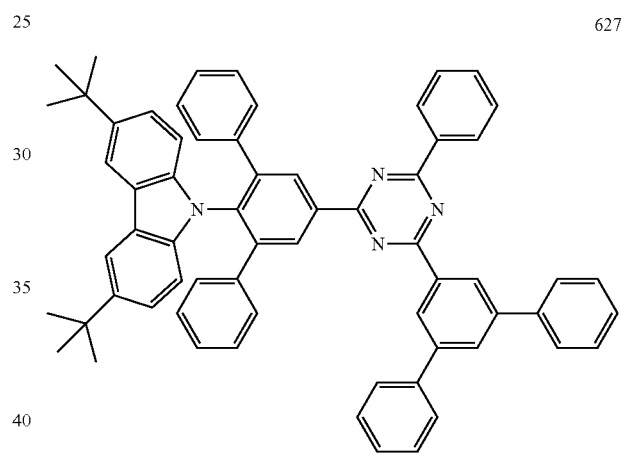
628
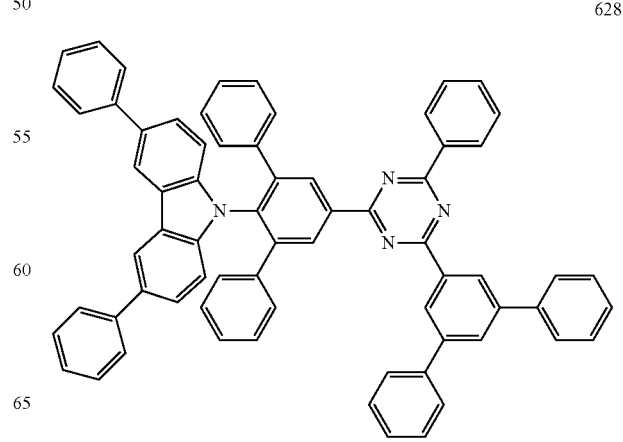

379
-continued
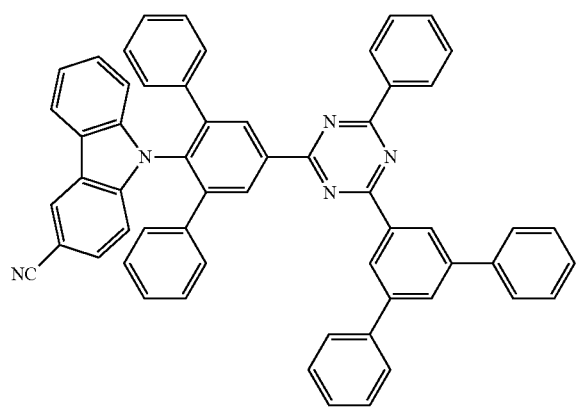
629
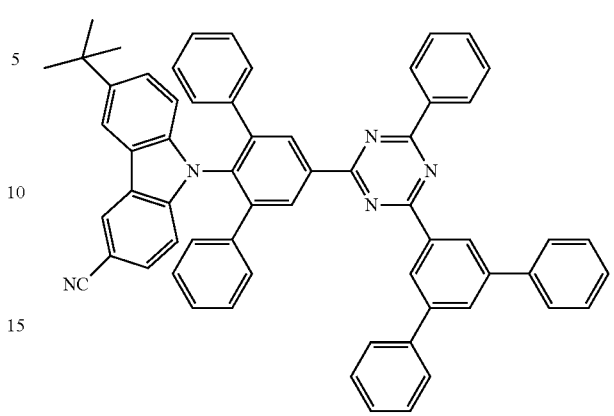
632
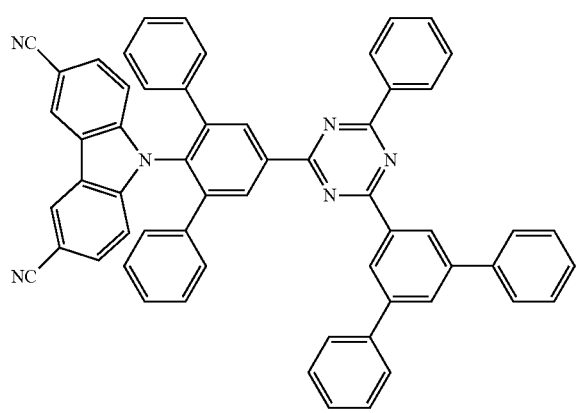
630
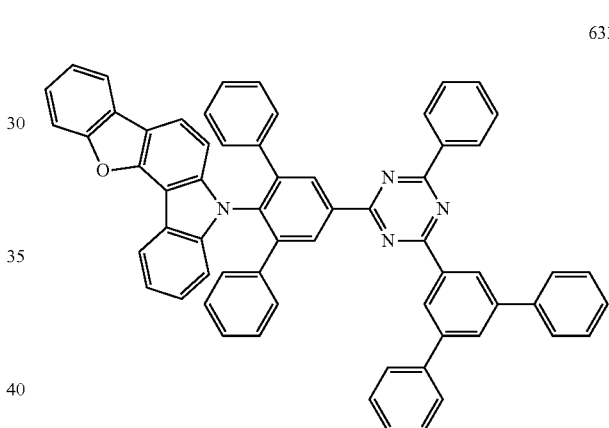
633
380
-continued
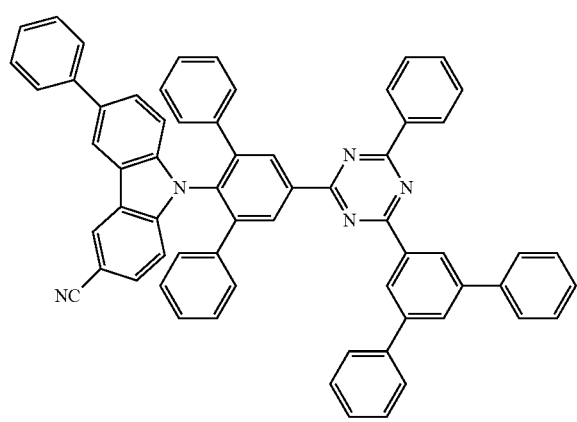
631
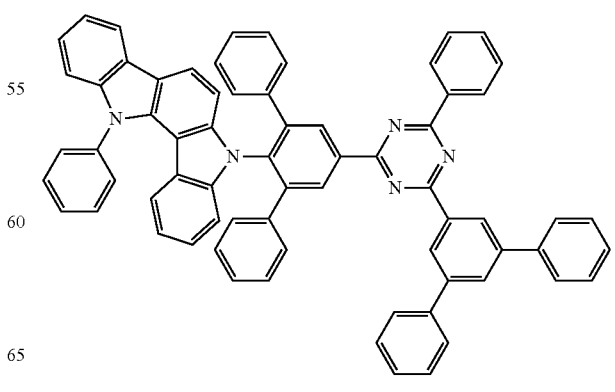
634

-continued
635
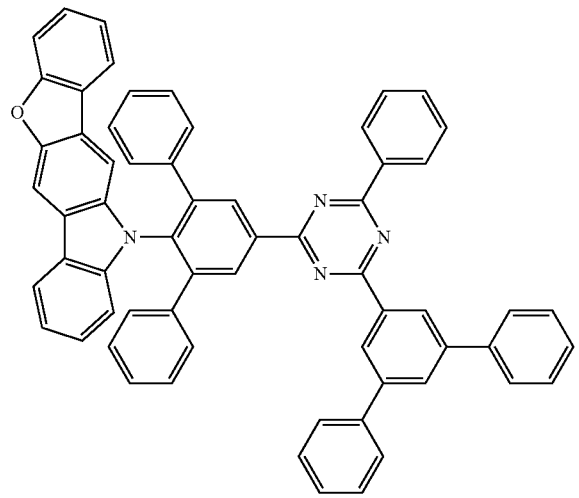
636
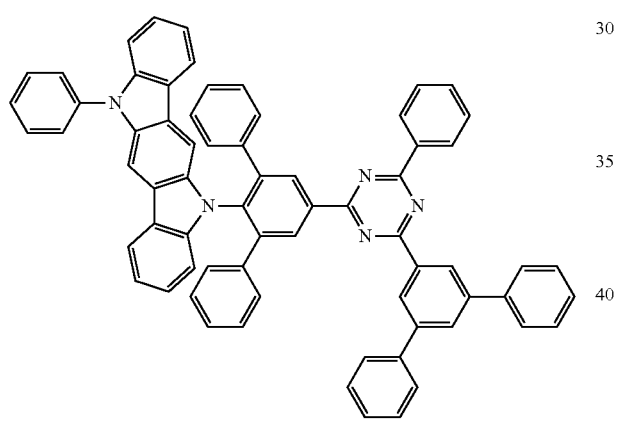
637
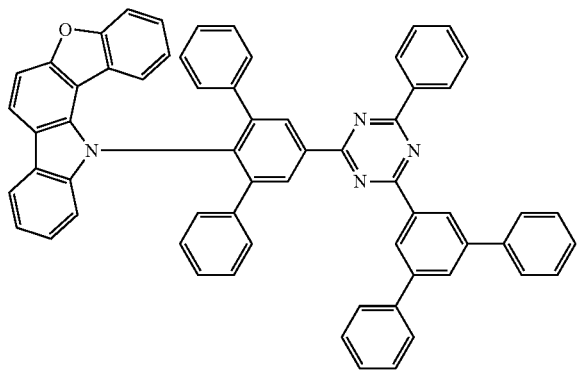
-continued
638
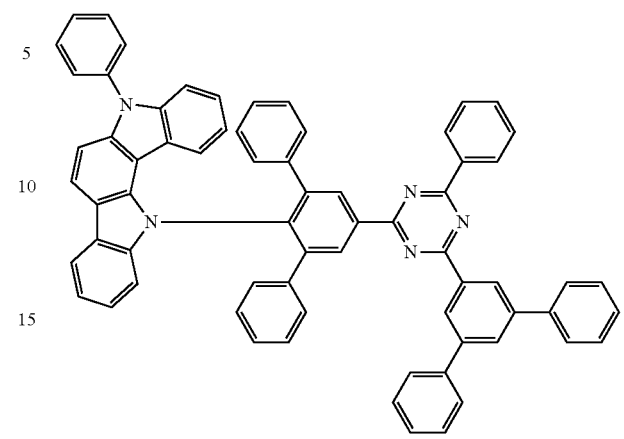
639
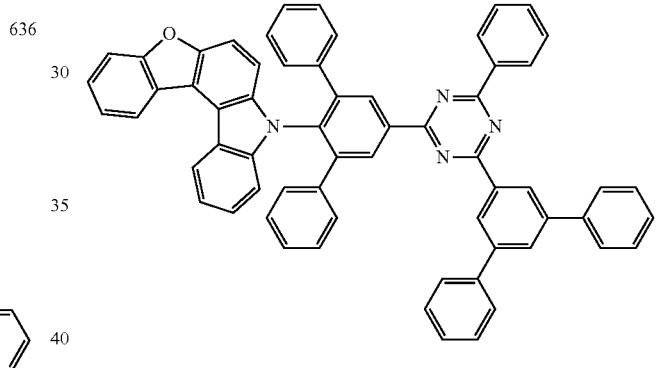
640
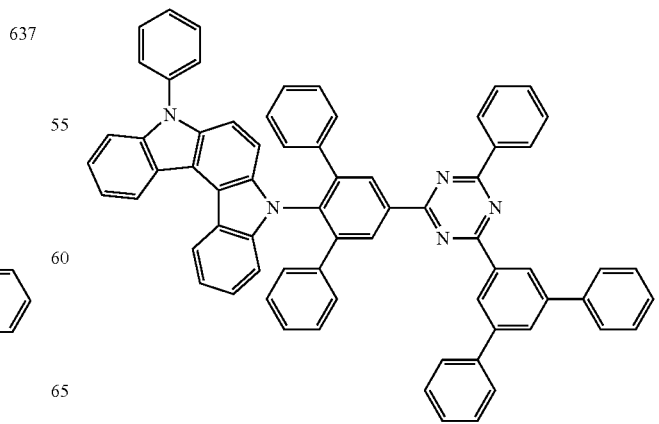

383
-continued
641
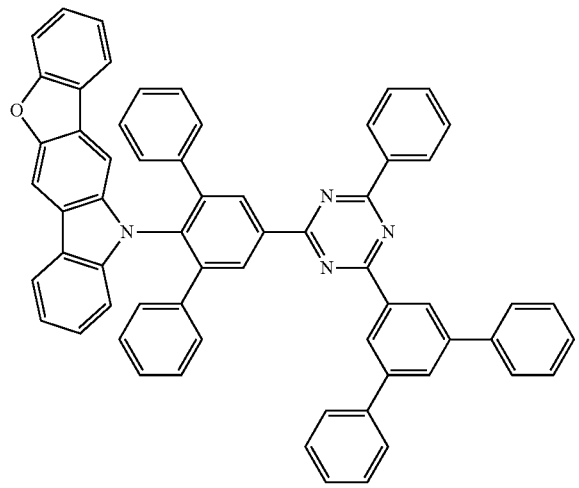
642
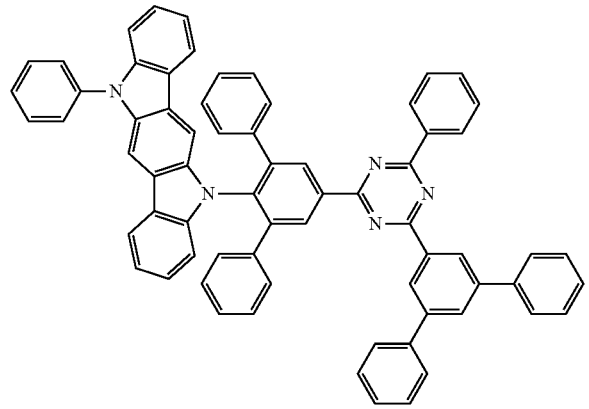
643
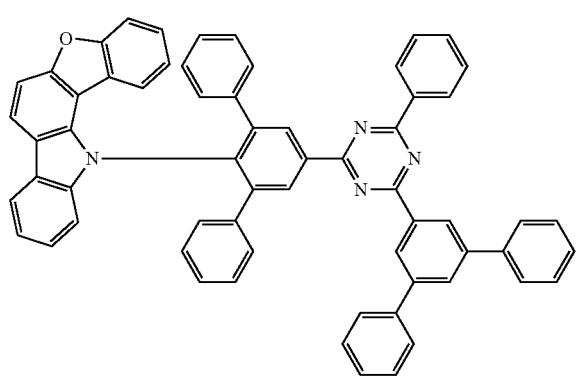
384
-continued
644
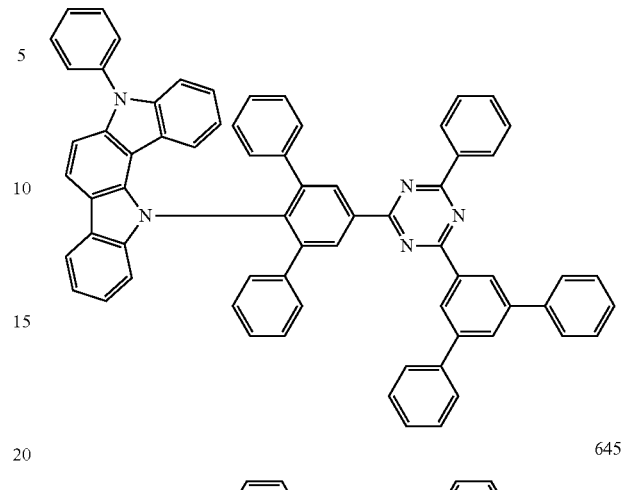
645
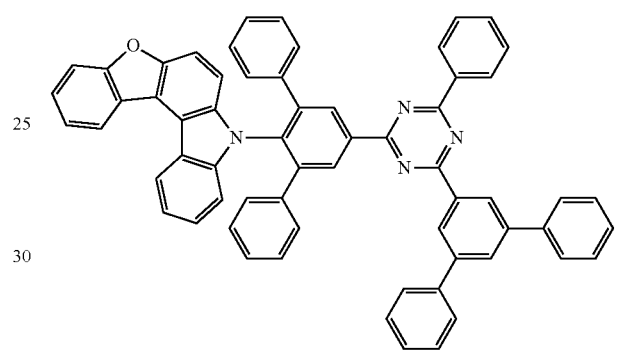
646
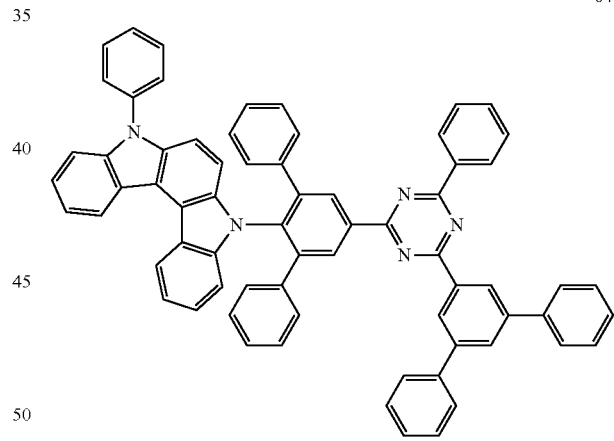
647
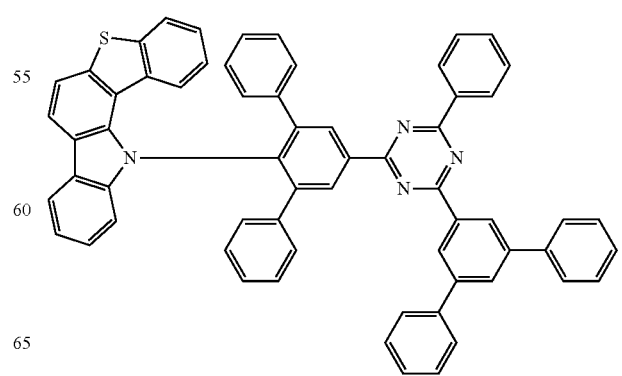

385
-continued
648
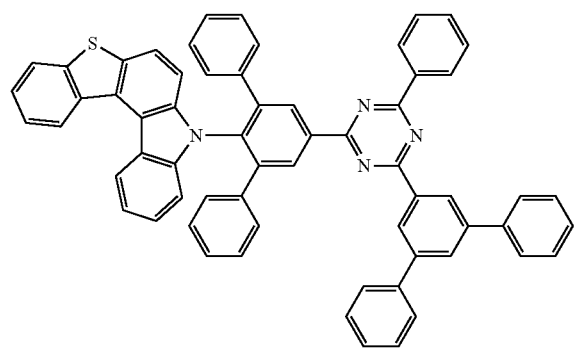
649
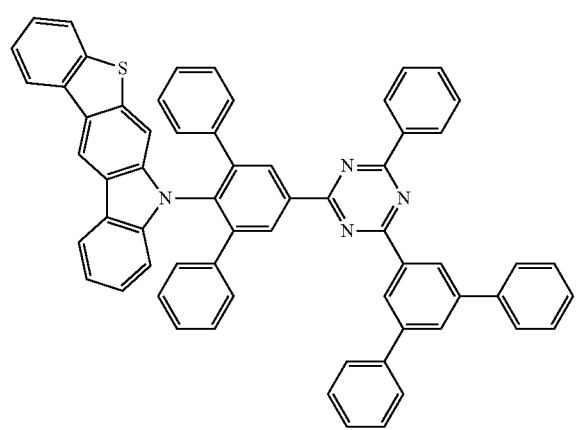
650
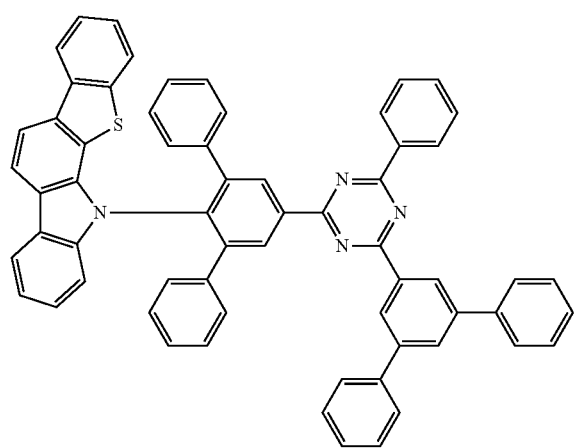
386
-continued
651
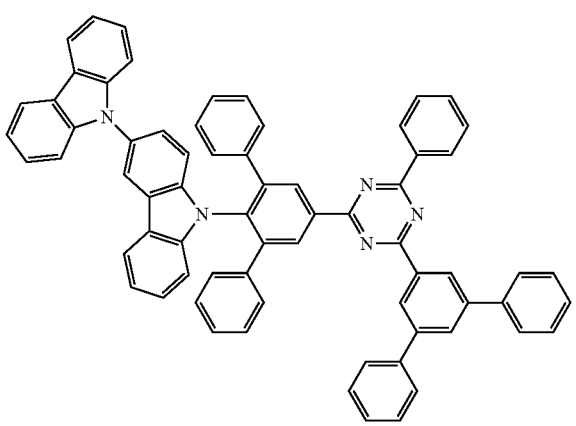
652
653
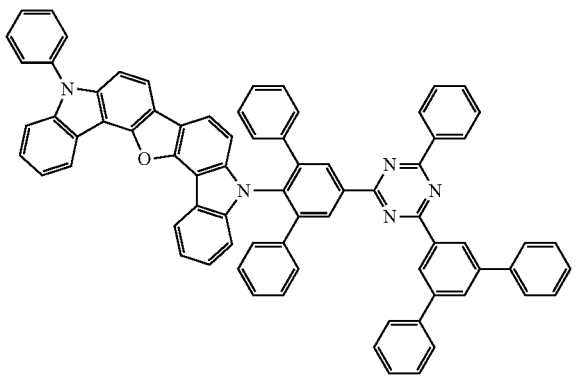

387
-continued
654
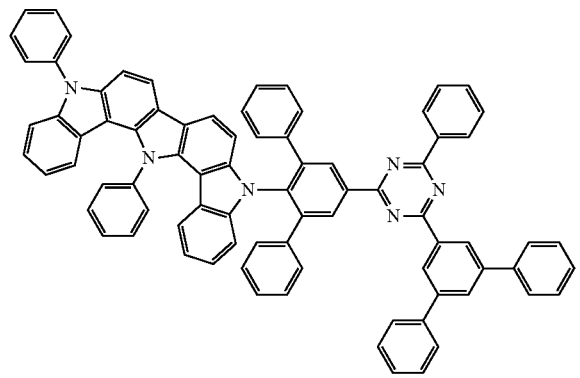
655
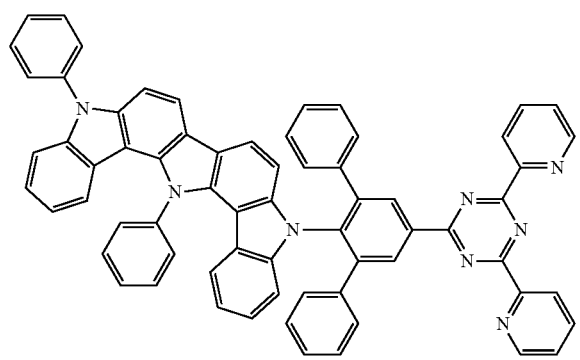
656
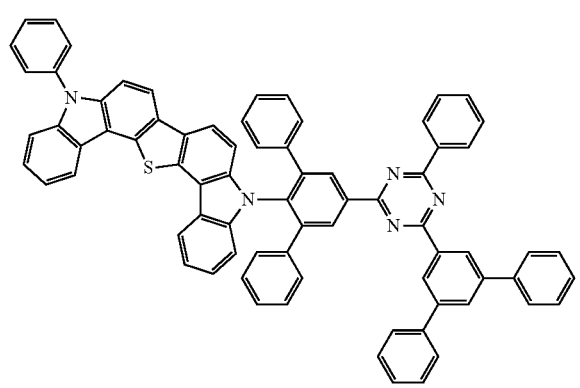
657
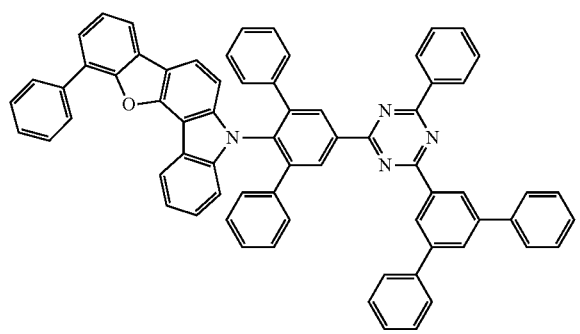
388
-continued
658
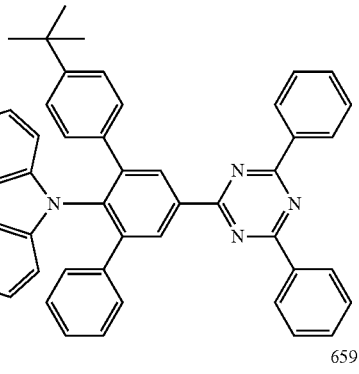
659
660
661

389
-continued
662
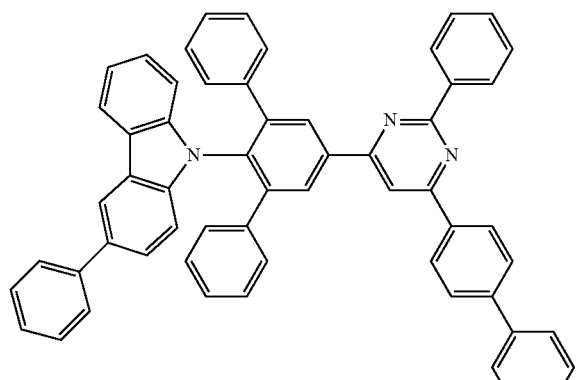
663
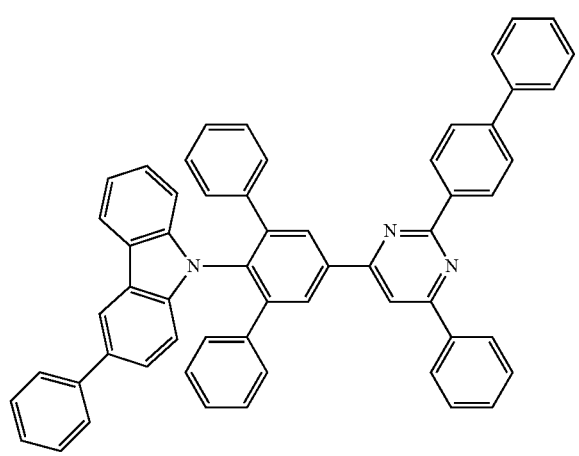
664
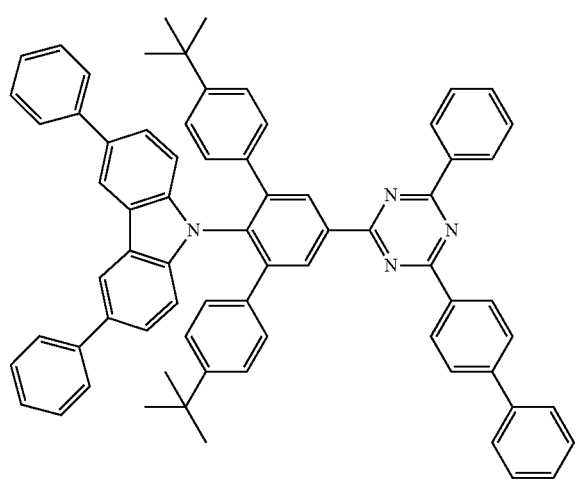
390
-continued
665
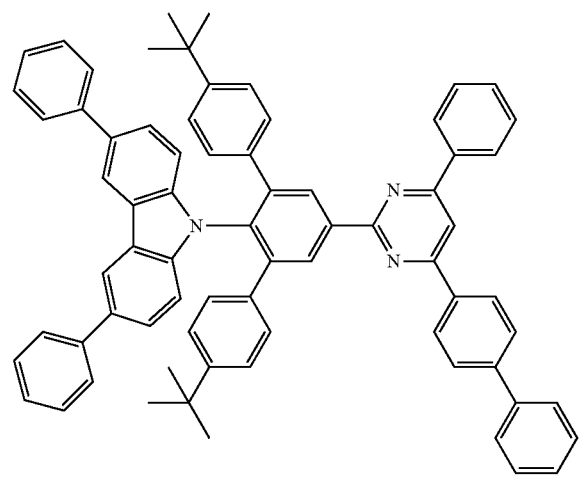
666
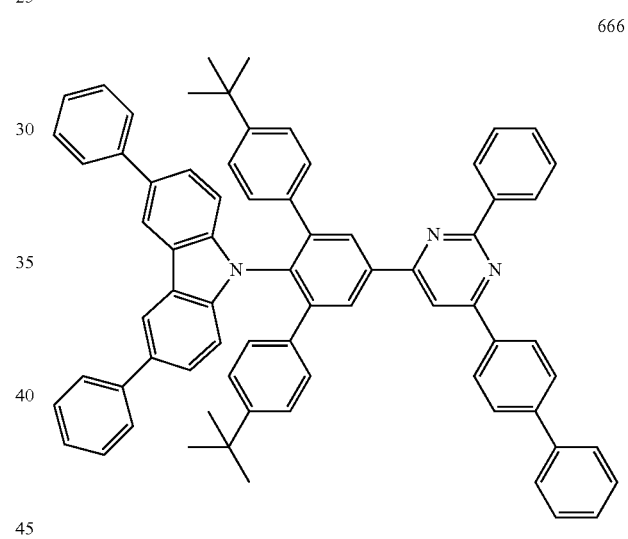
667
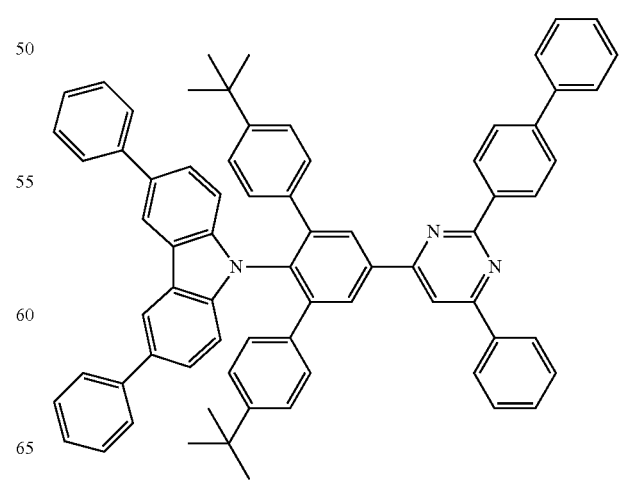

391
-continued
668
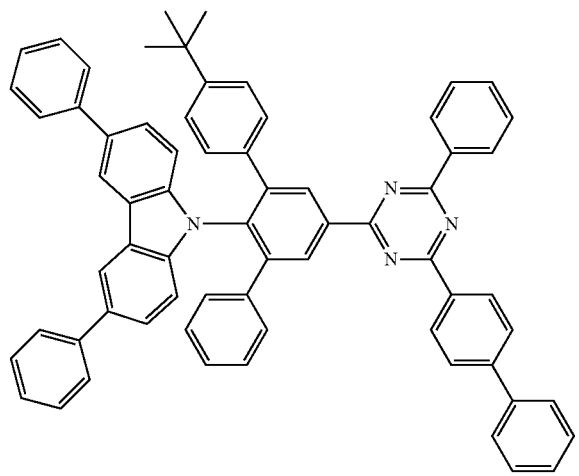
669
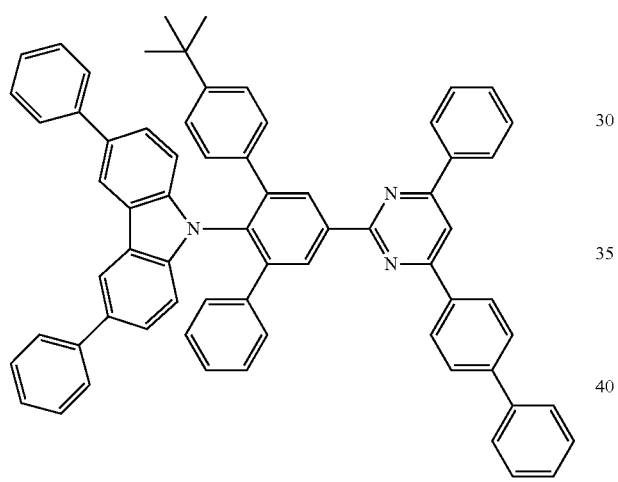
670
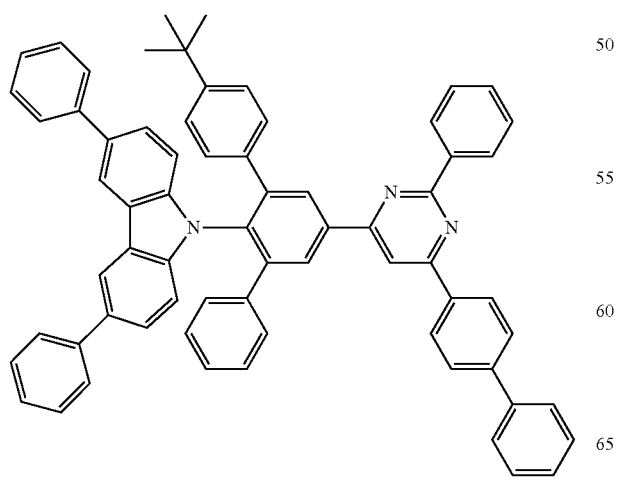
392
-continued
671
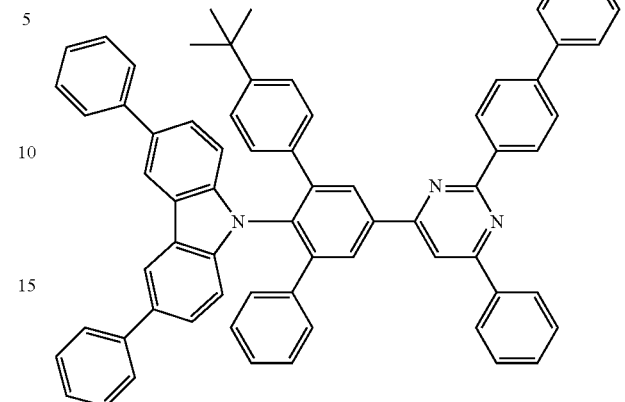
672
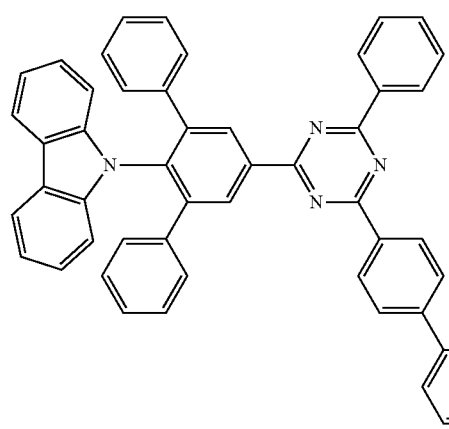
673
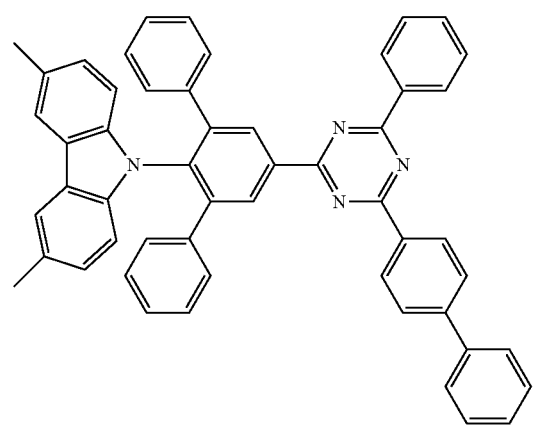

393
-continued
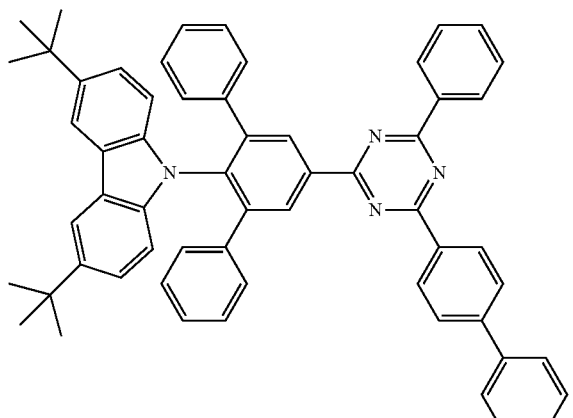
674
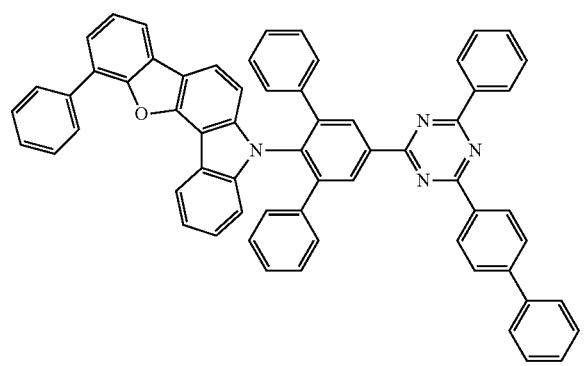
675
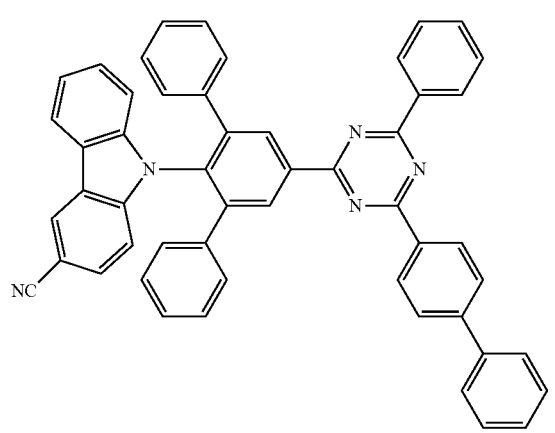
676
394
-continued
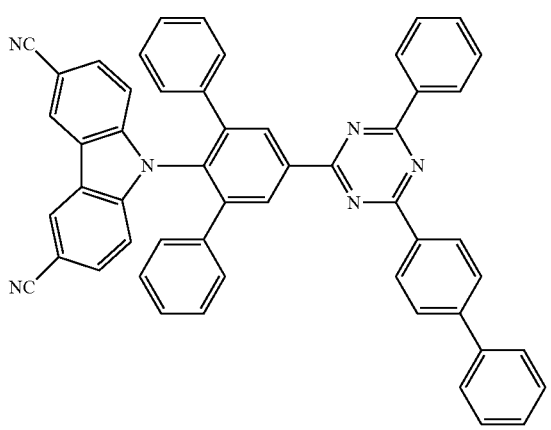
677
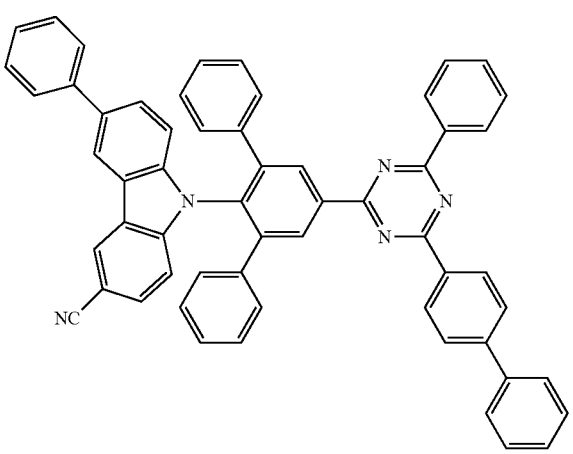
678
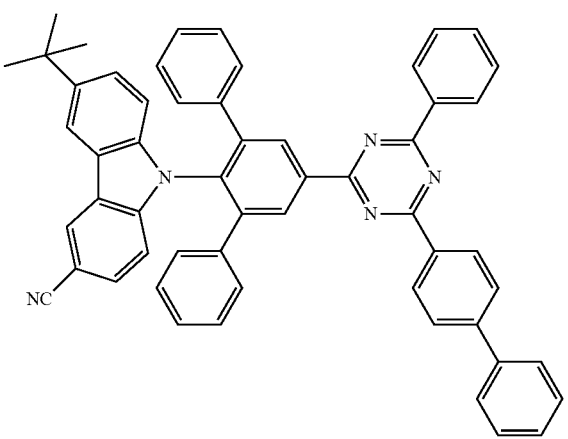
679

680
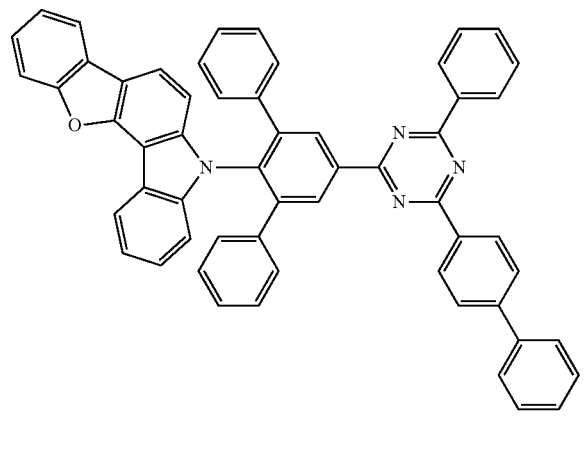
681
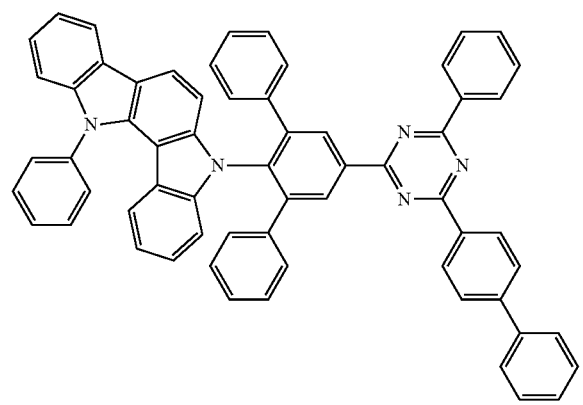
682
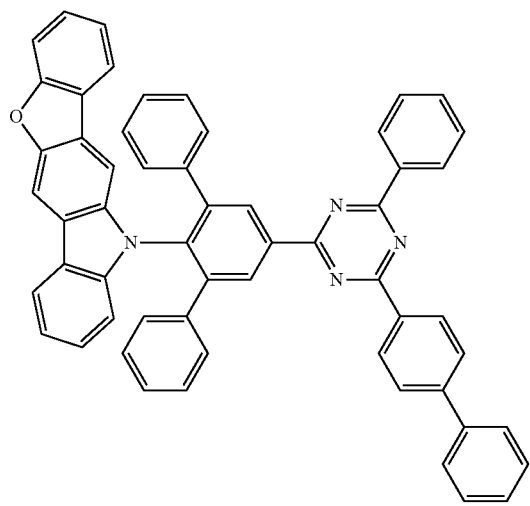
683
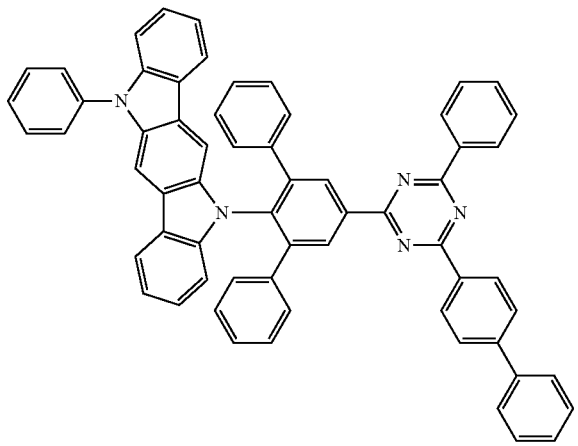
684
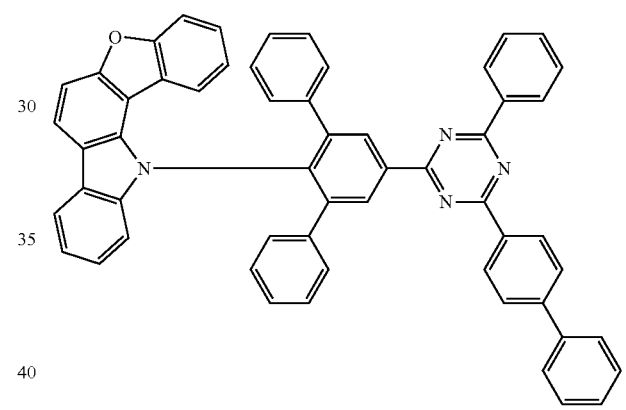
685
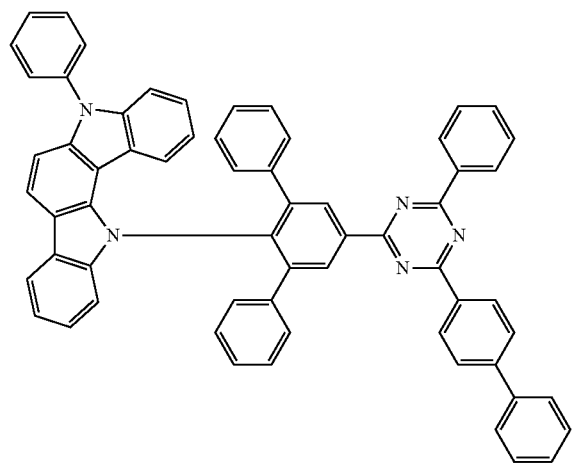

397
-continued
686
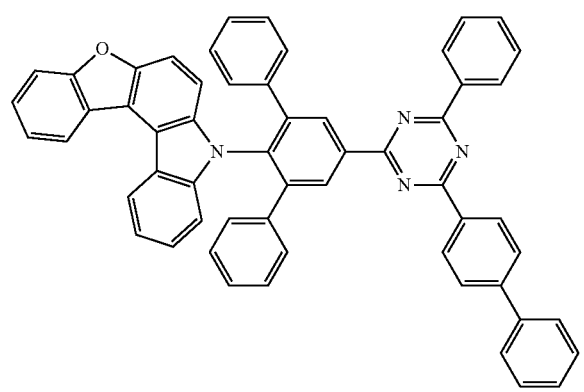
687
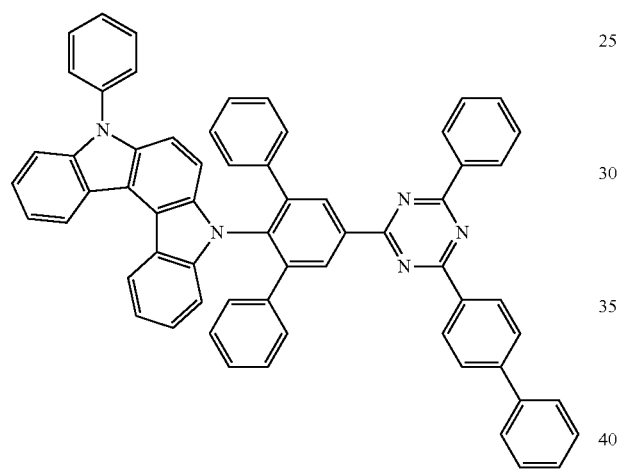
688
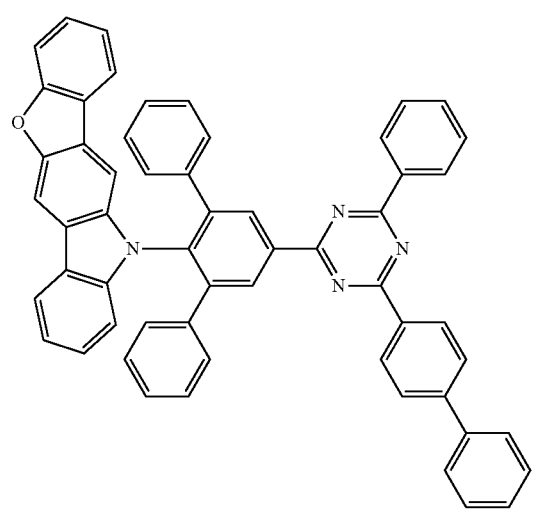
398
-continued
689
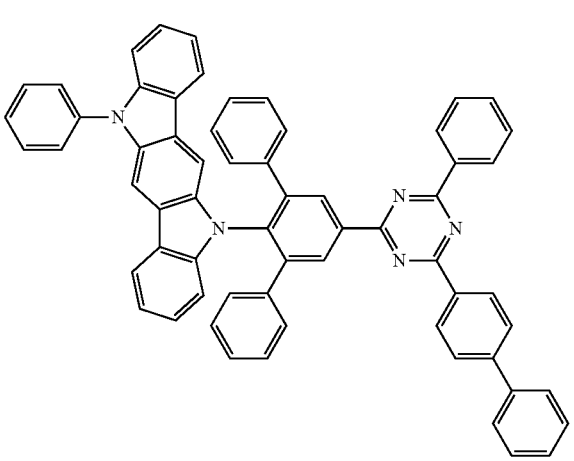
690
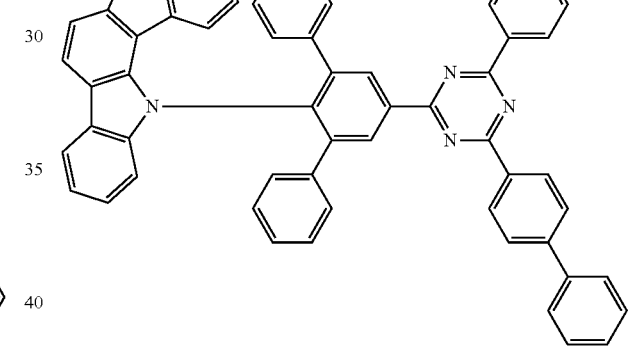
691
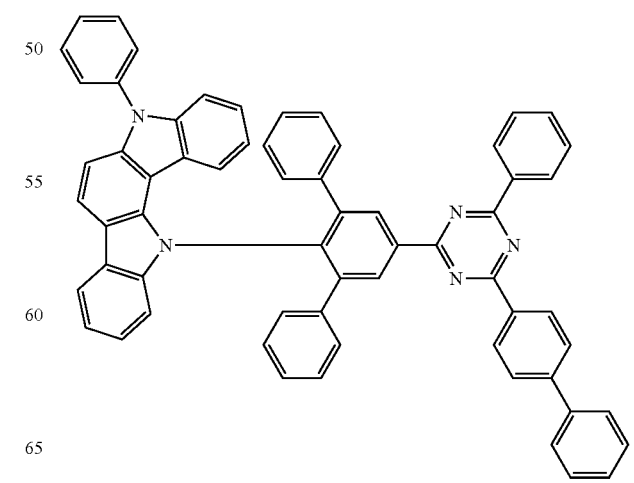

-continued
692
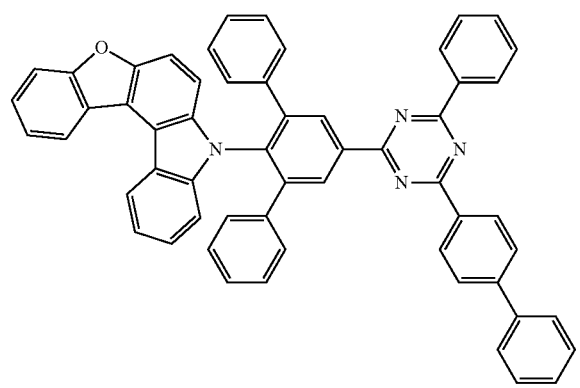
693
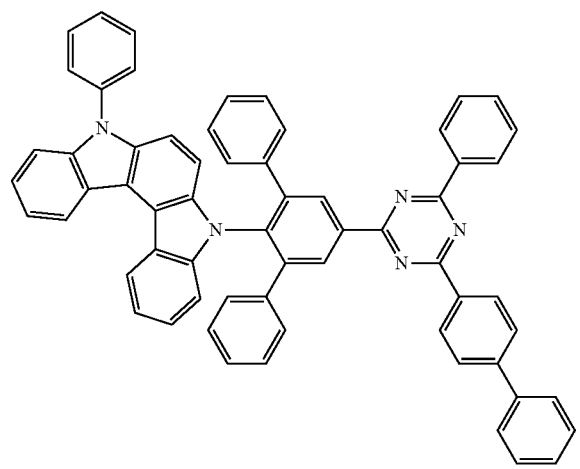
694
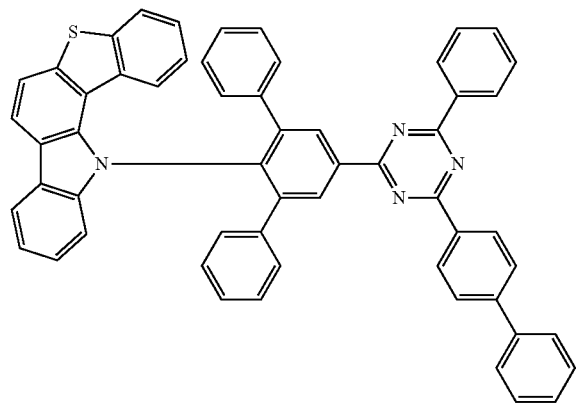
-continued
695
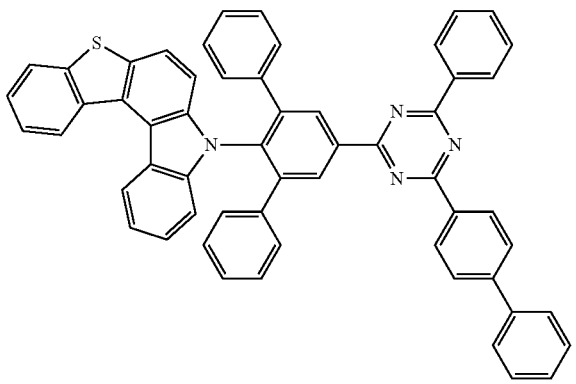
696
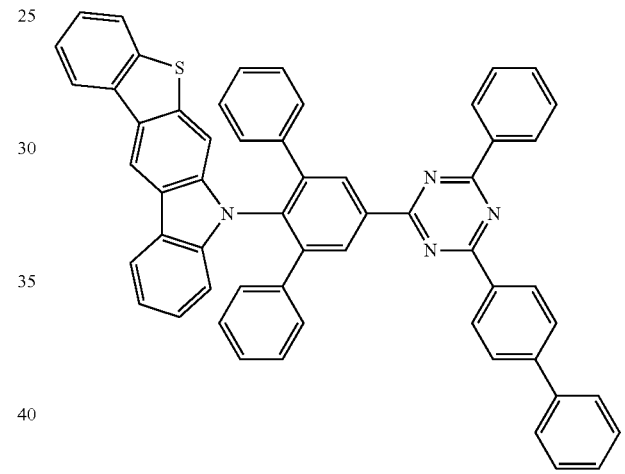
697
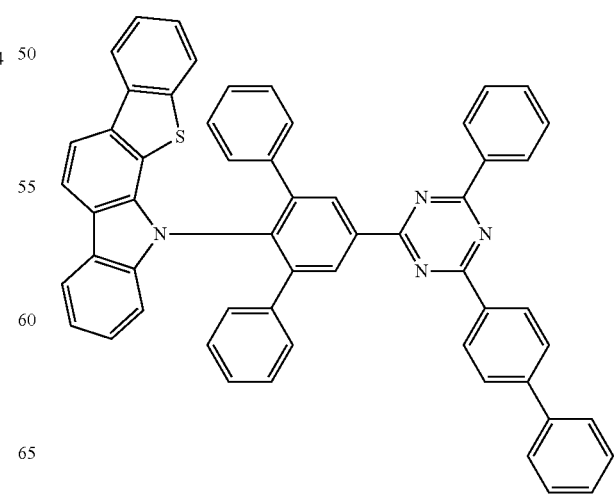

401
-continued
698
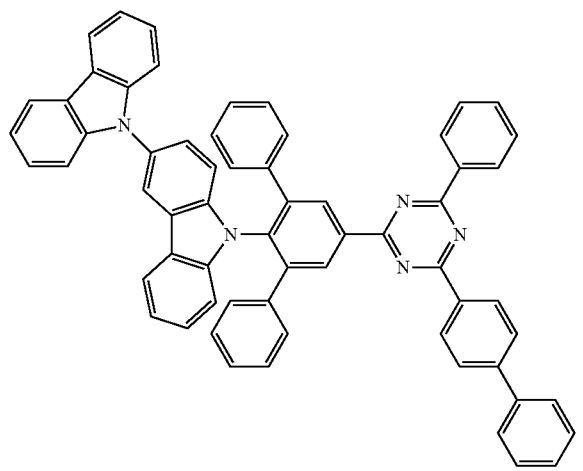
699
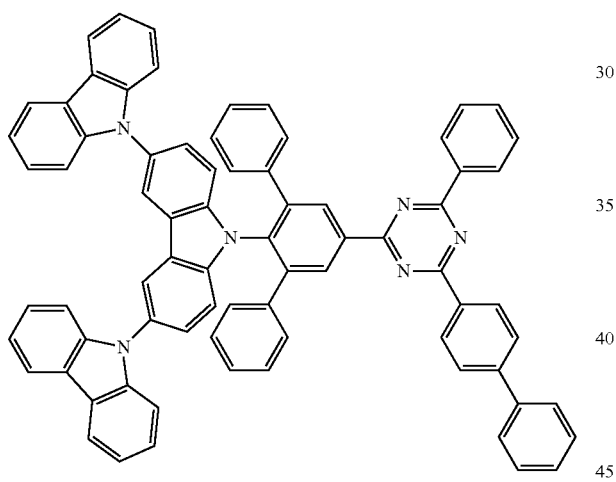
700
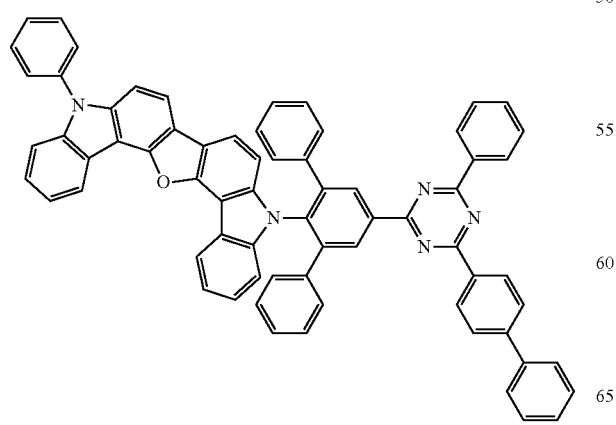
402
-continued
701
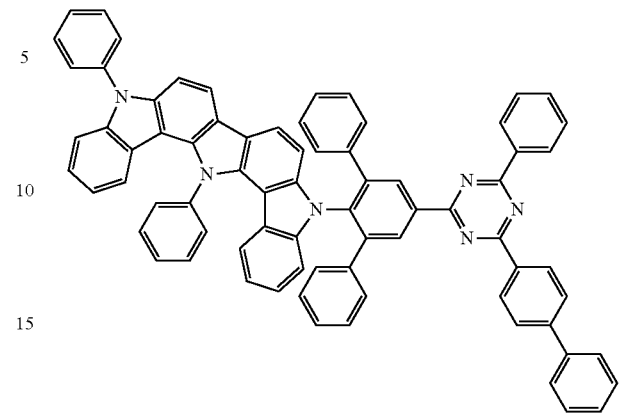
702
703
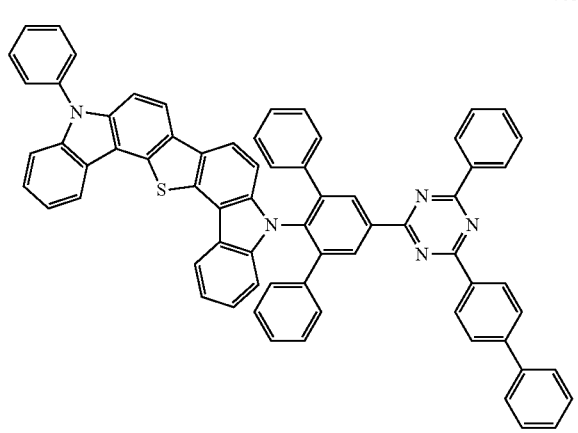

403
-continued
704
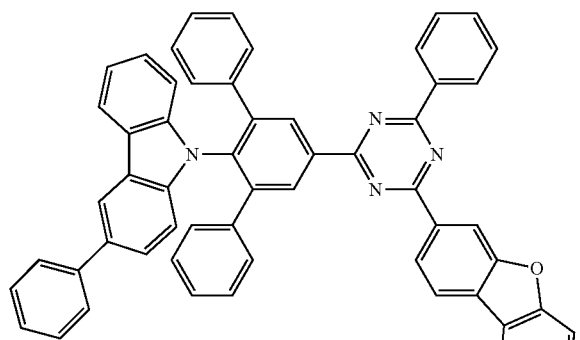
705
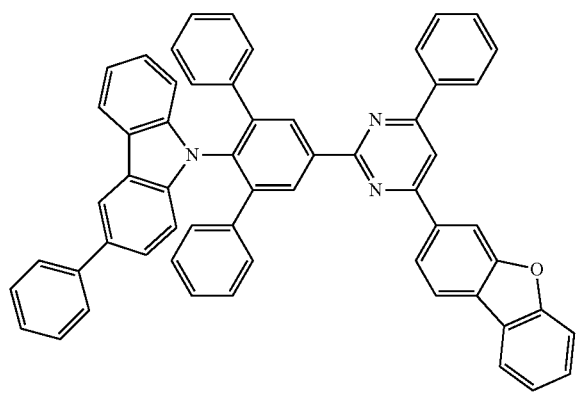
706
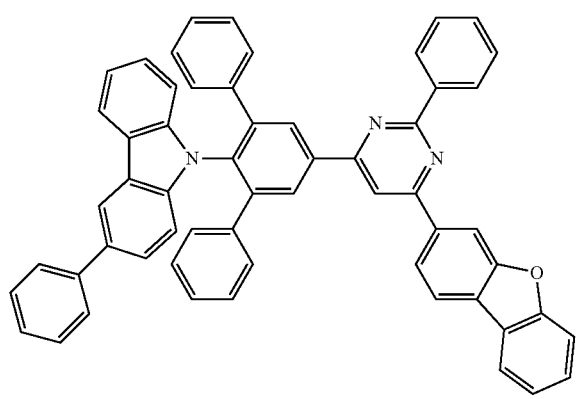
404
-continued
707
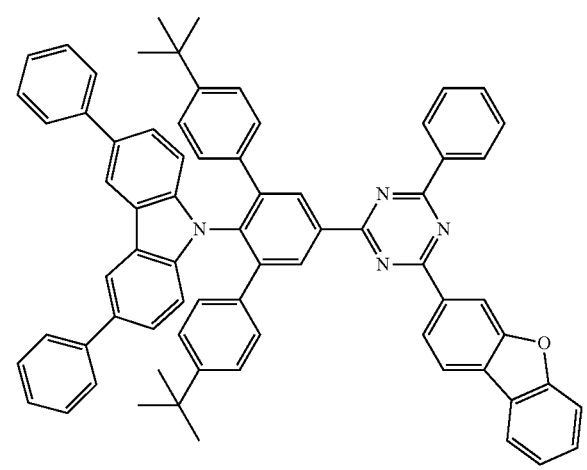
708
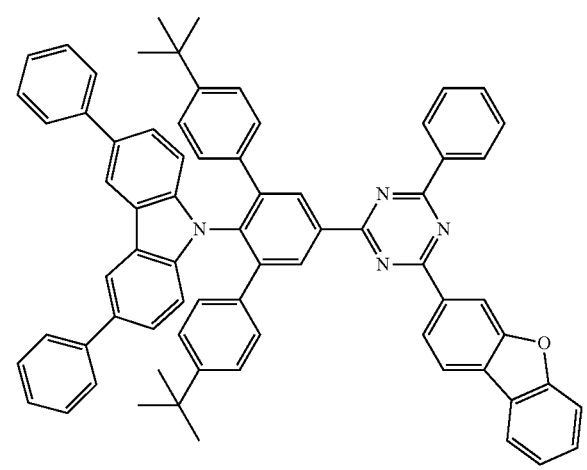
709
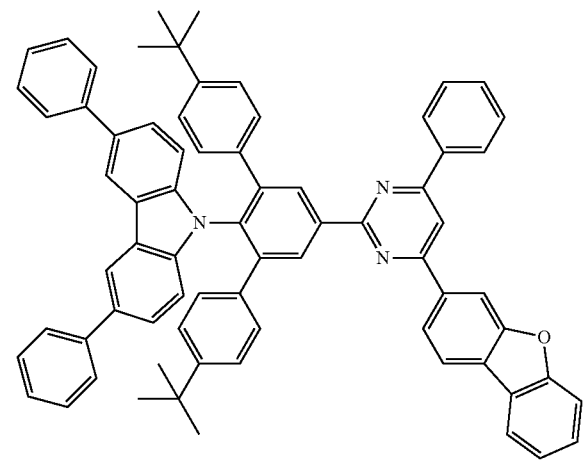

405
-continued
406
-continued
710
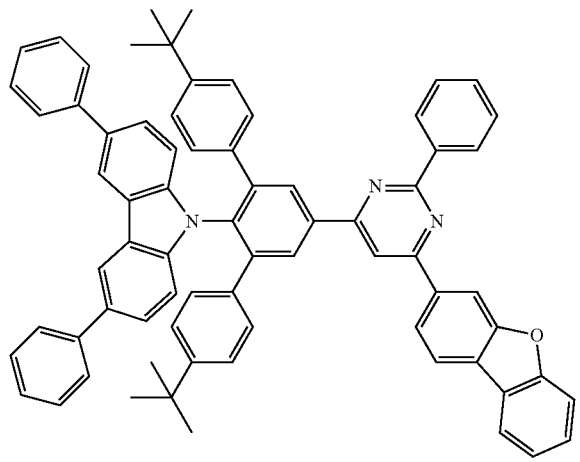
713
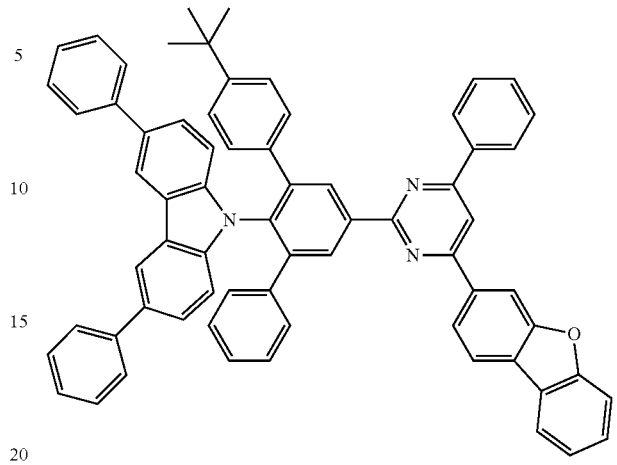
711
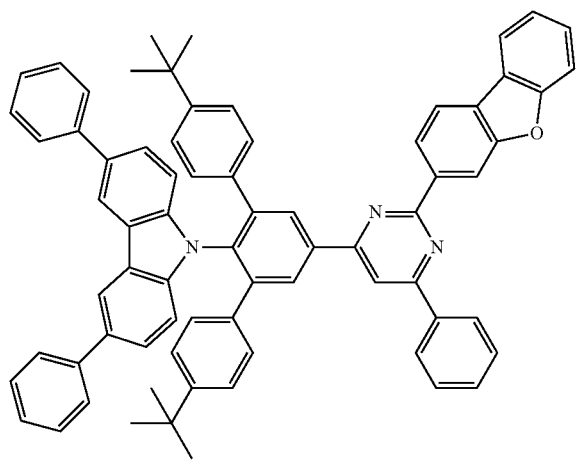
714
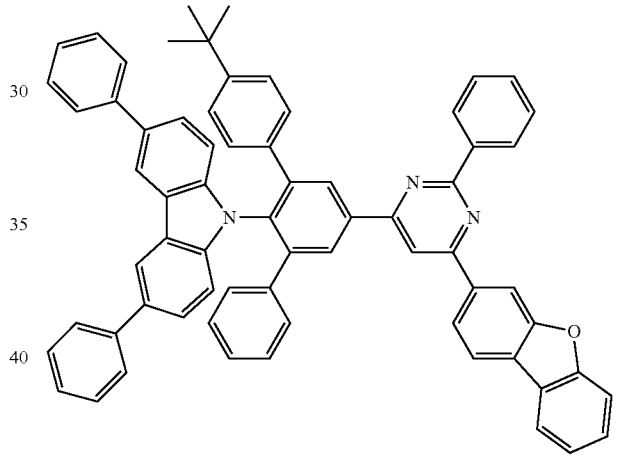
712
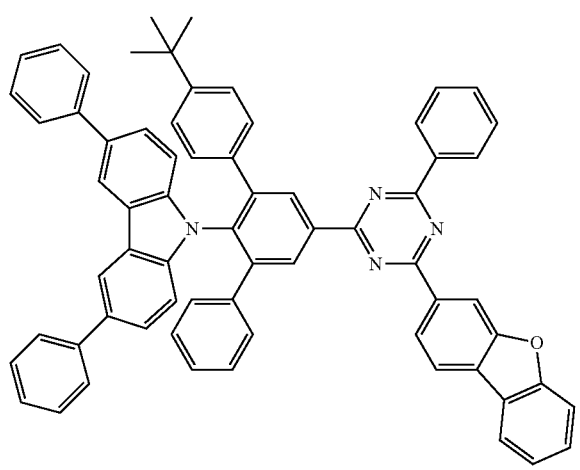
715
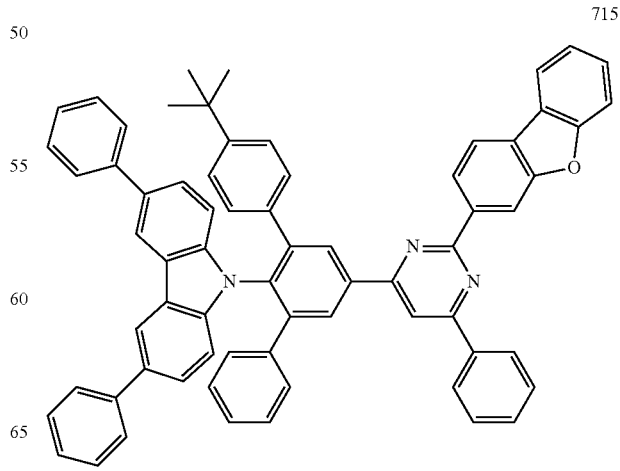

-continued
716
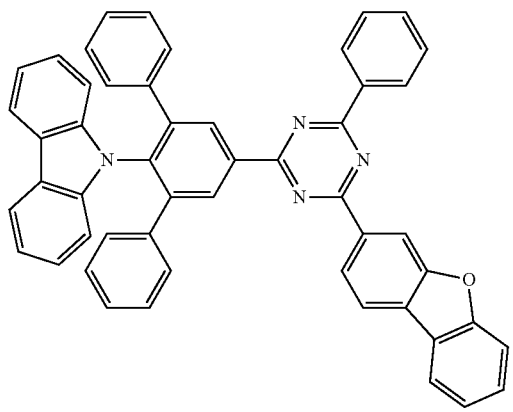
717
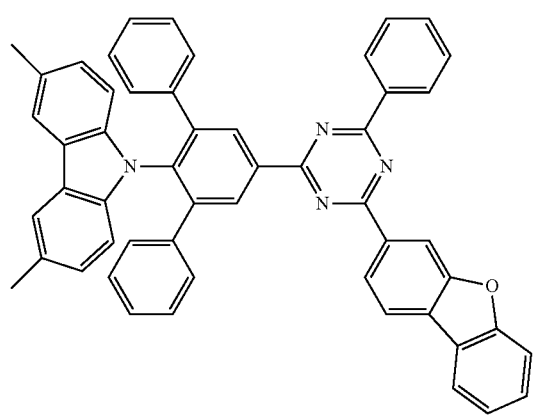
718
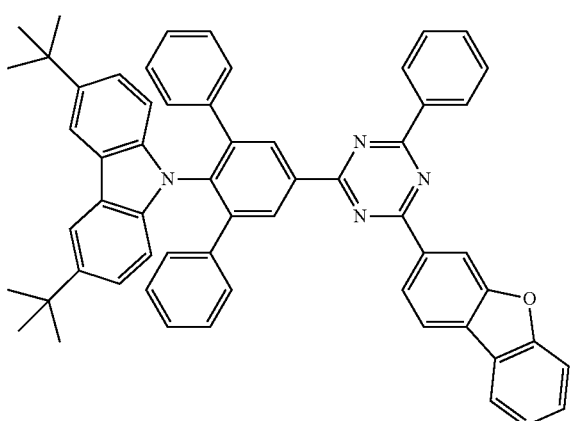
719
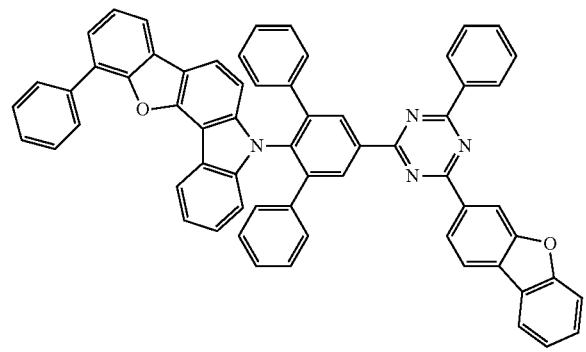
-continued
720
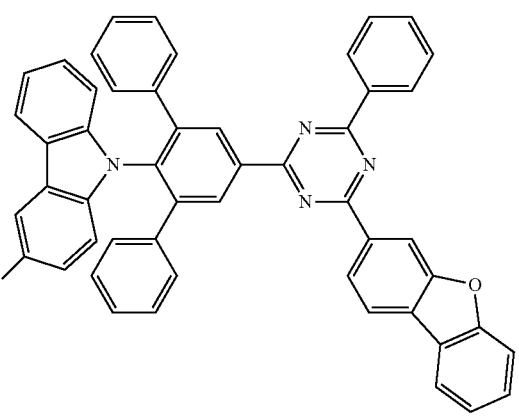
721
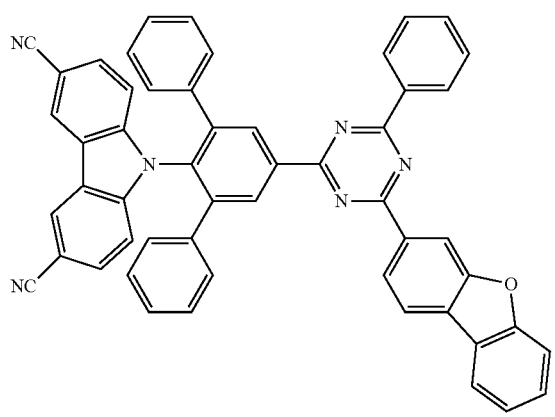
722
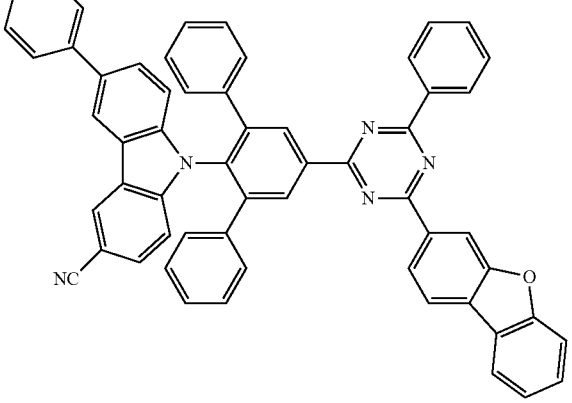

409
-continued
723
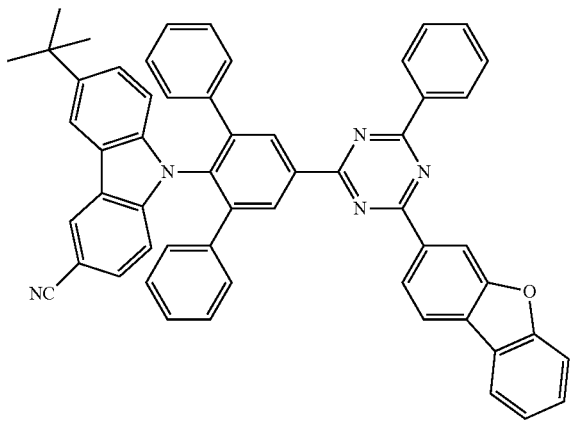
724
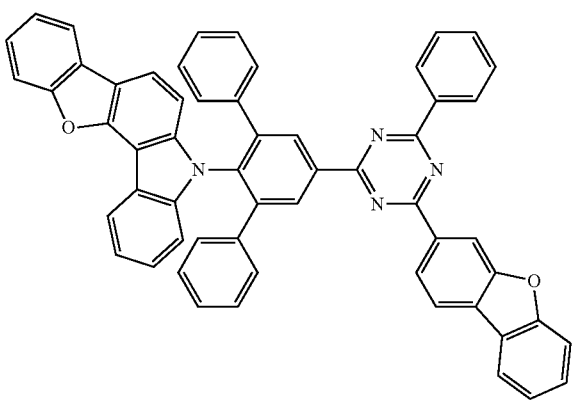
725
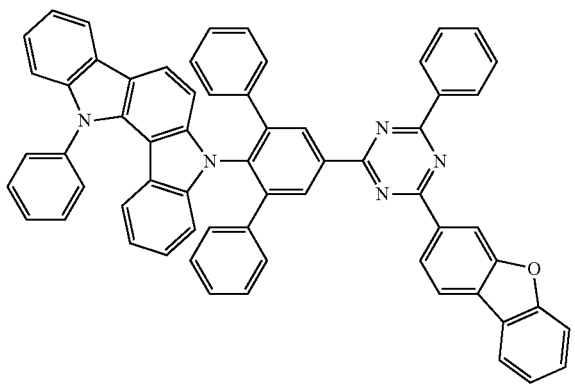
410
-continued
726
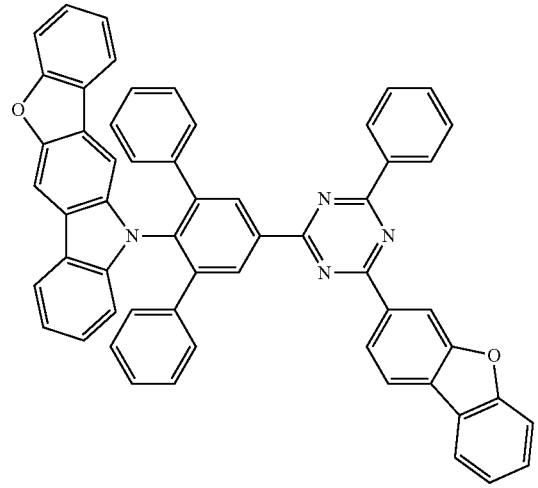
727
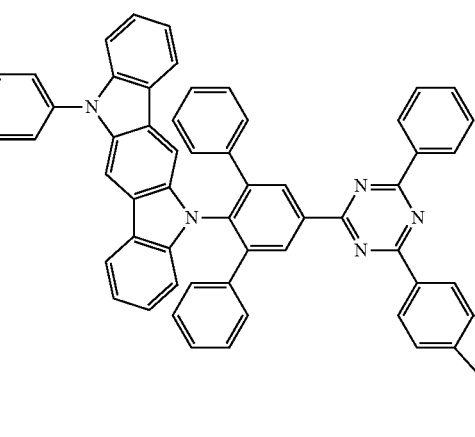
728
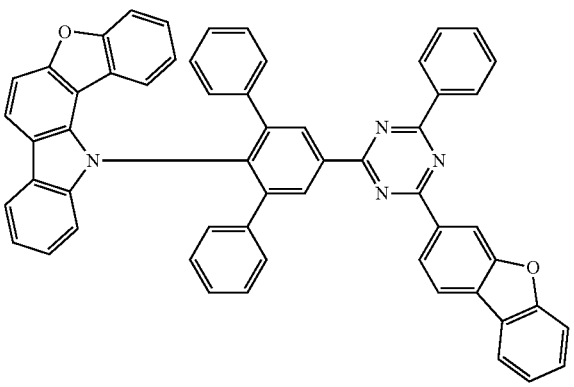

411
-continued
729
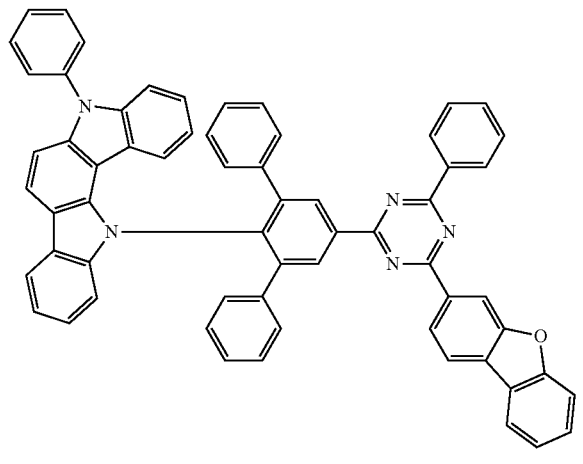
730
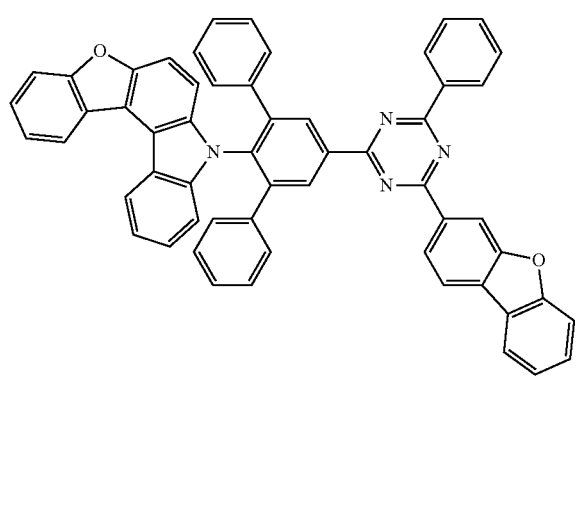
731
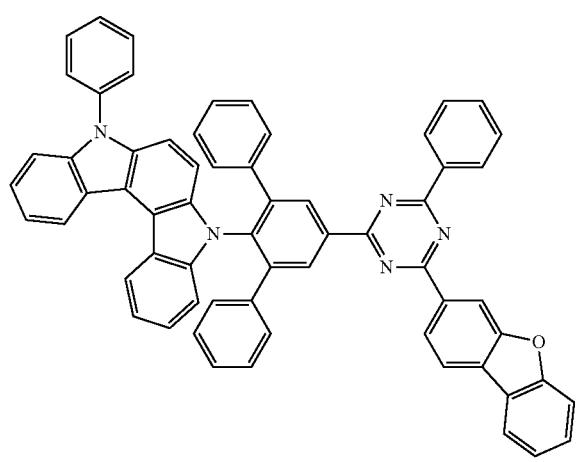
412
-continued
732
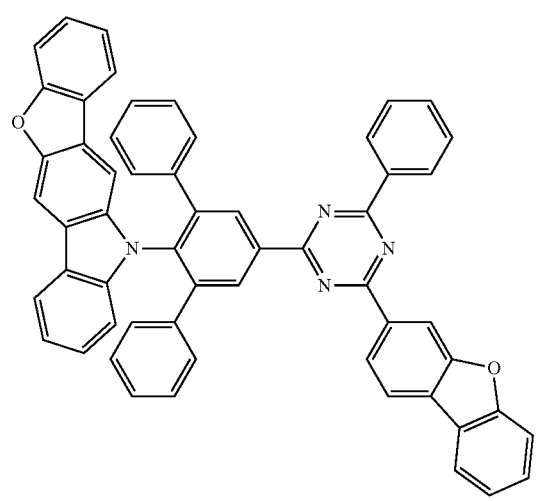
733
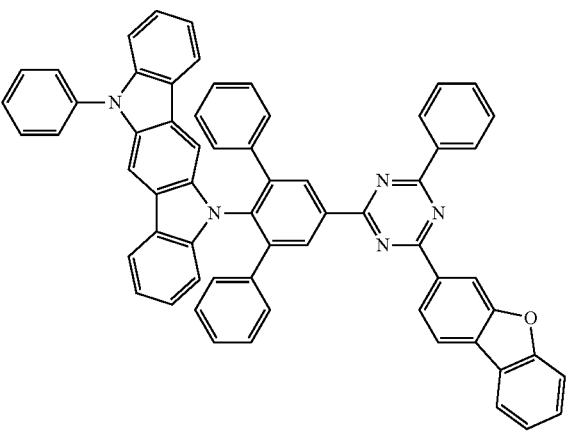
734
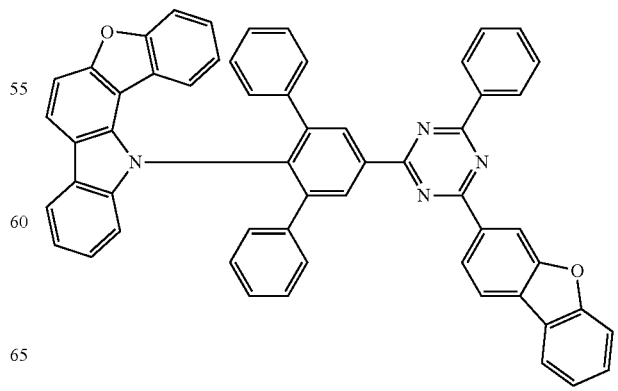

735
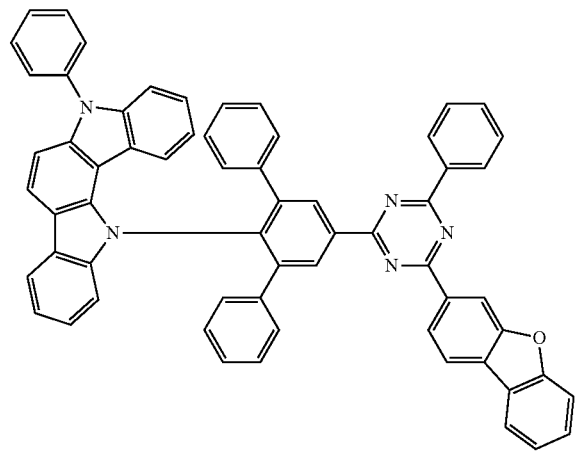
736
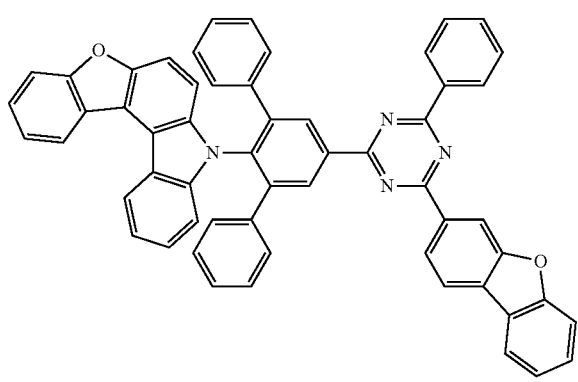
737
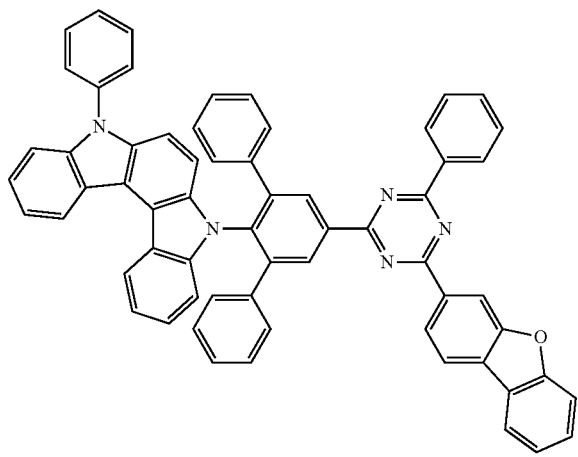
738
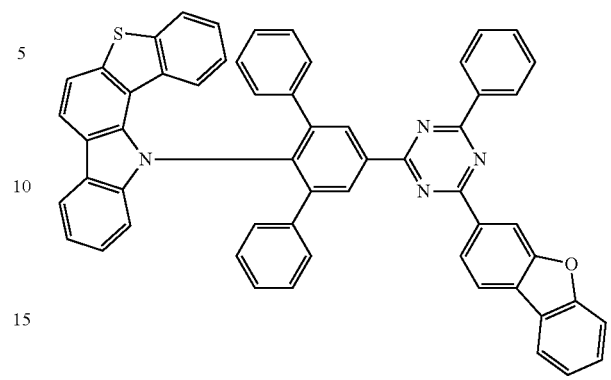
739
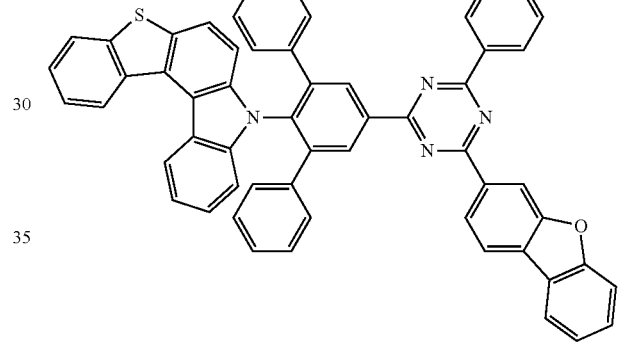
740
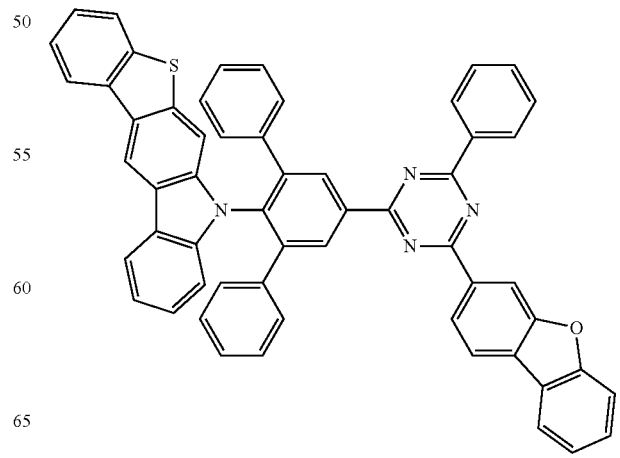

415
-continued
741
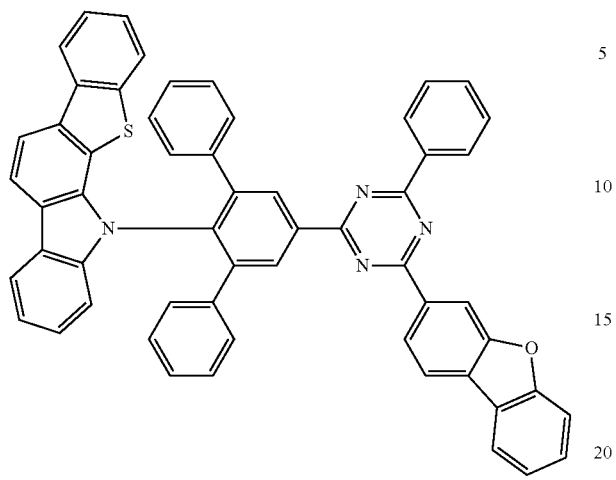
742
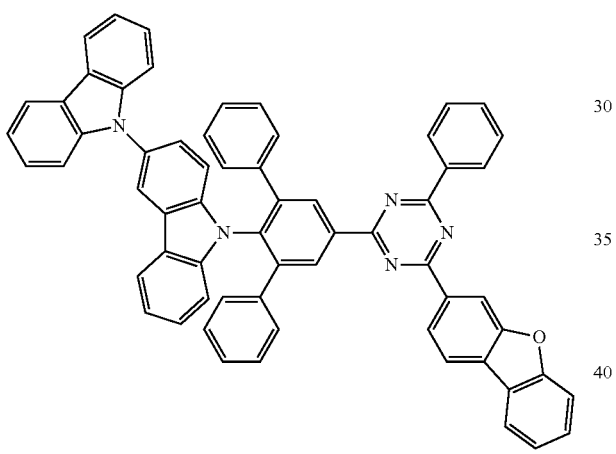
743
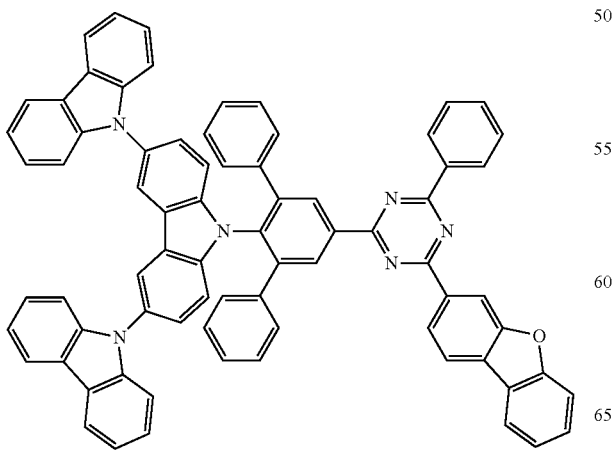
416
-continued
744
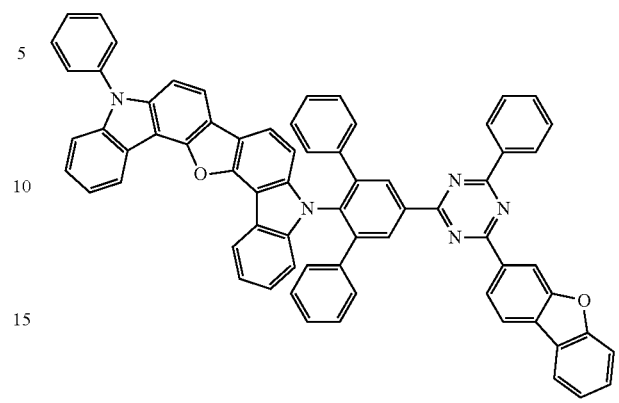
745
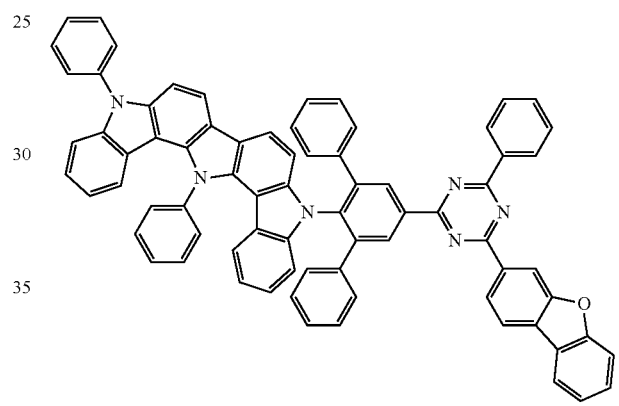
746
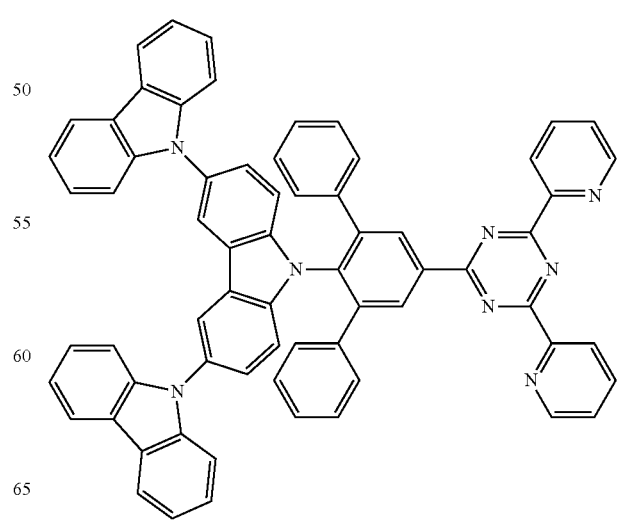

417
-continued
747
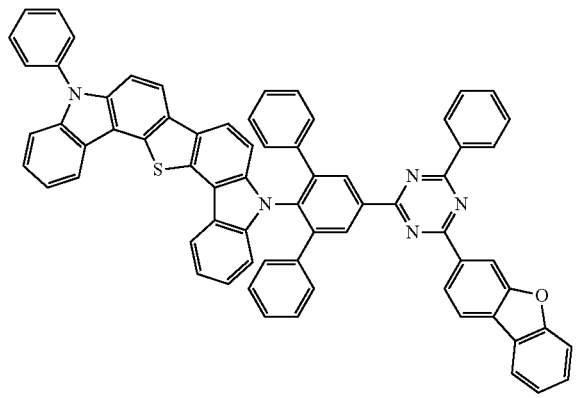
748
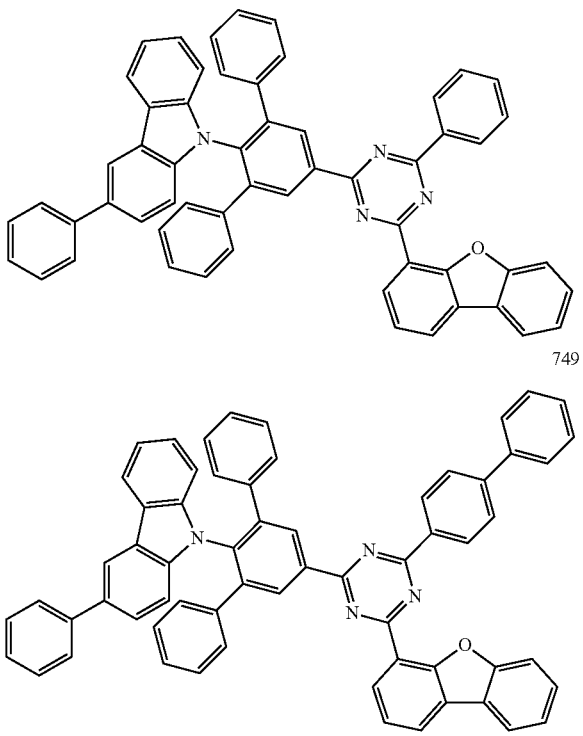
749
750
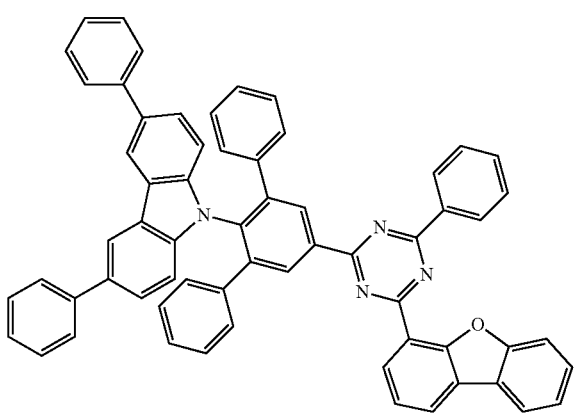
418
-continued
751
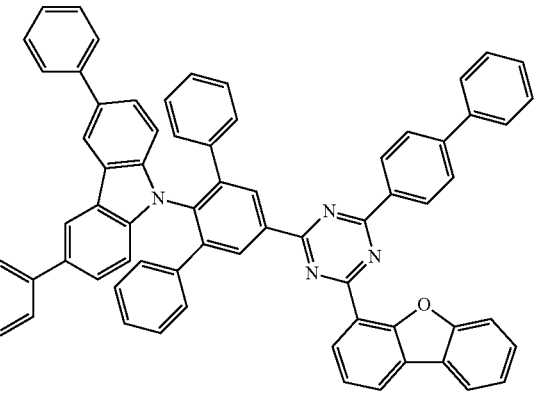
752
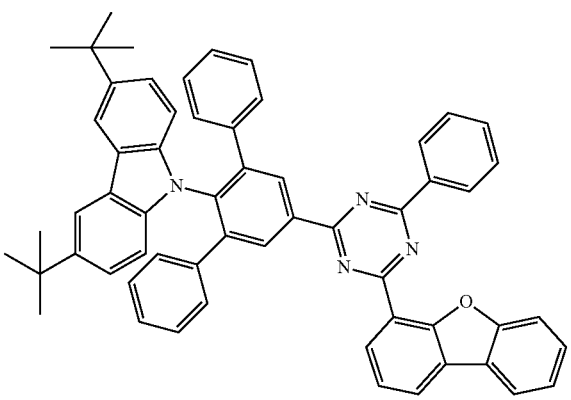
753
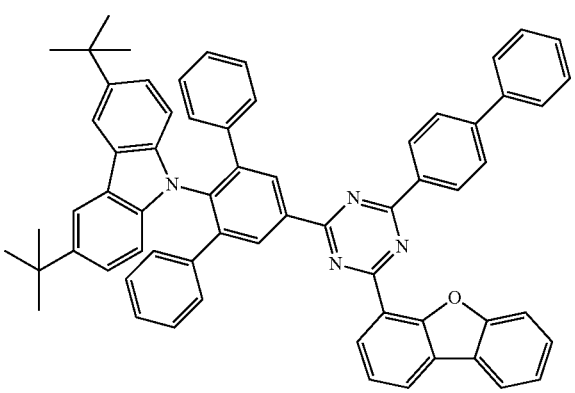

-continued
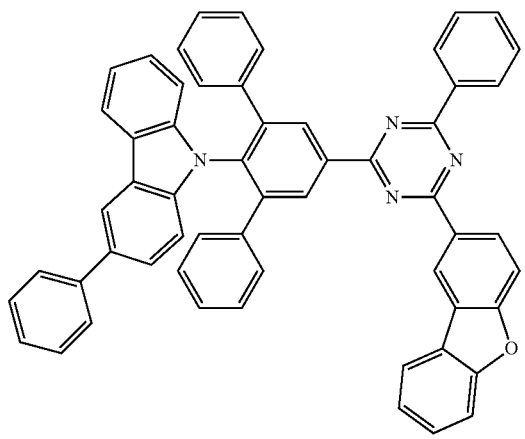
754
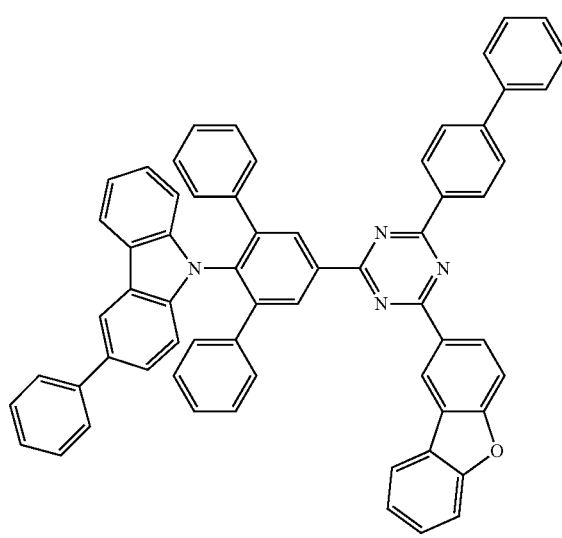
755
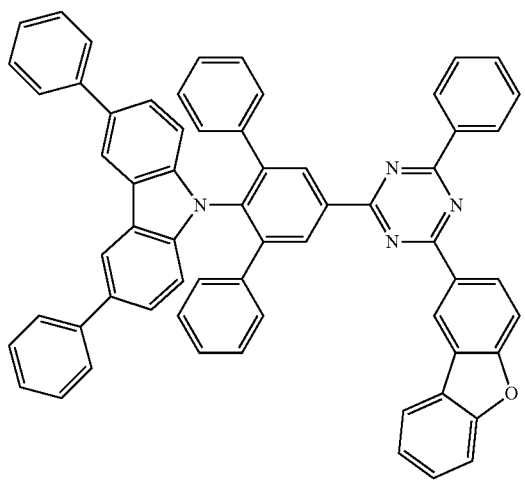
756
-continued
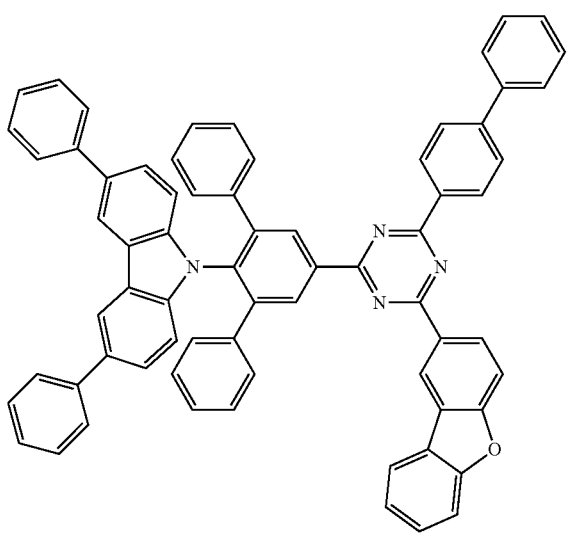
757
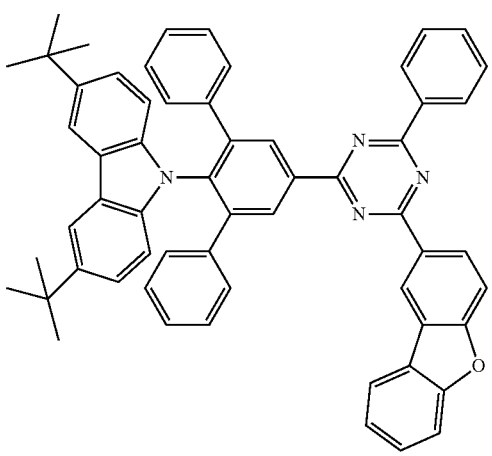
758
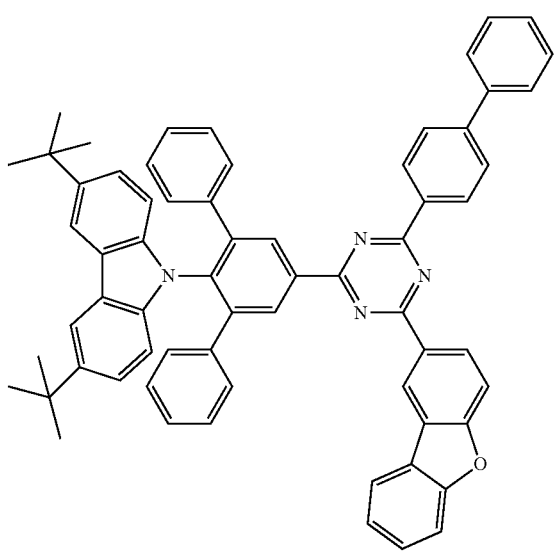
759

421
-continued
760
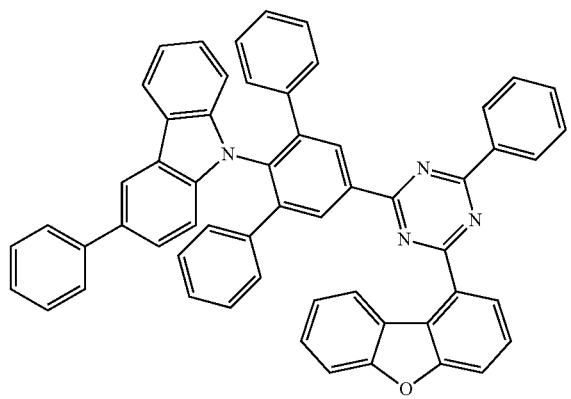
761
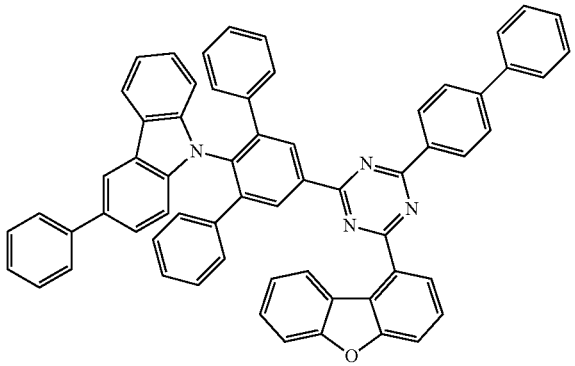
762
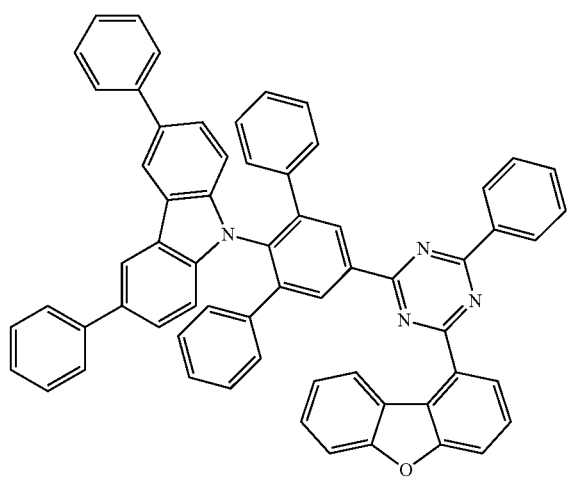
422
-continued
763
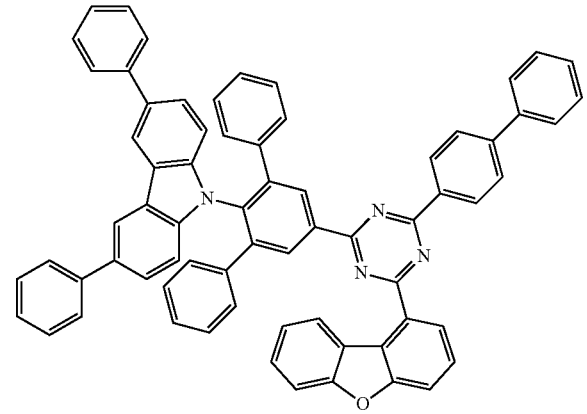
764
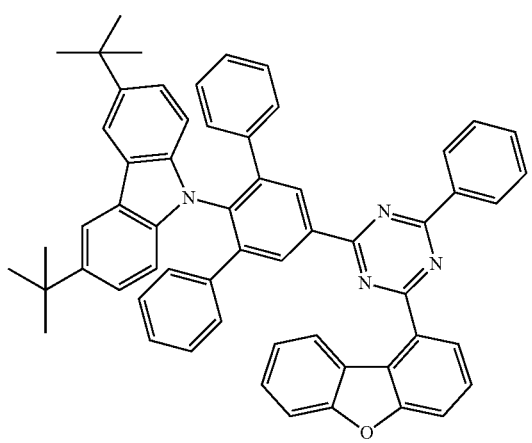
765
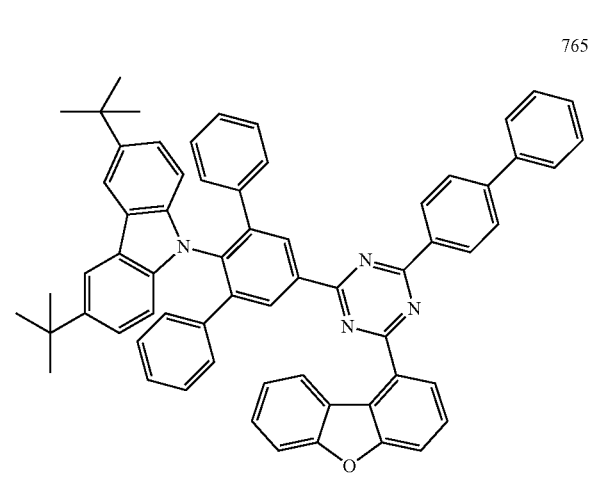

766
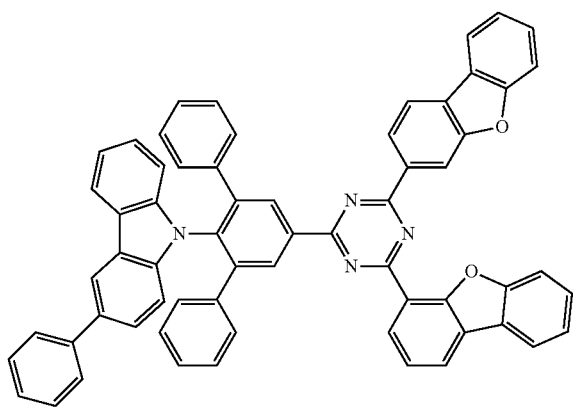
767
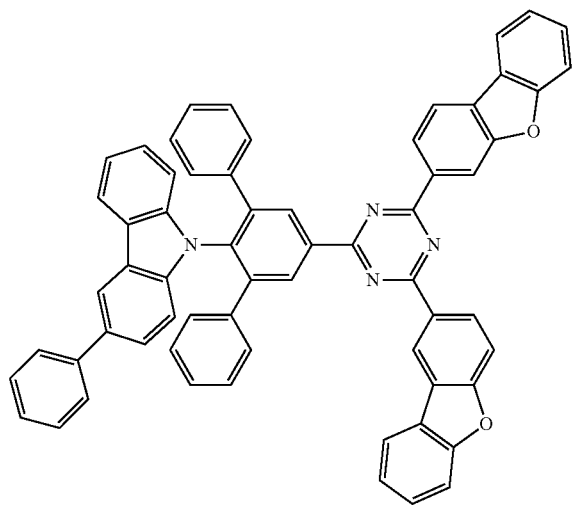
768
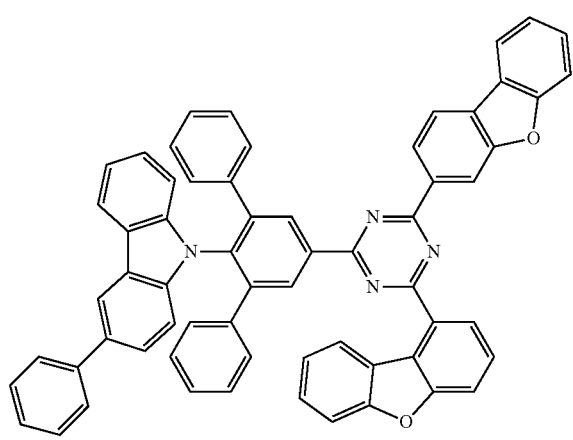
769
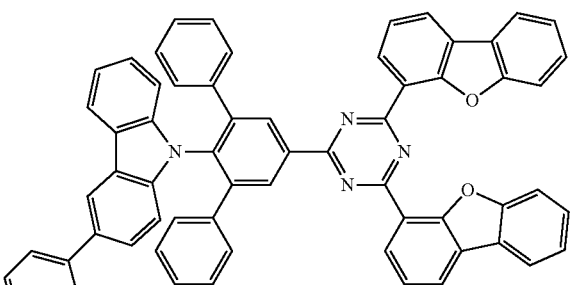
770
771
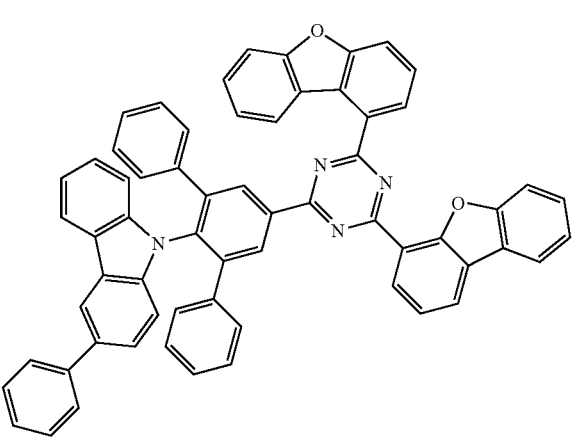

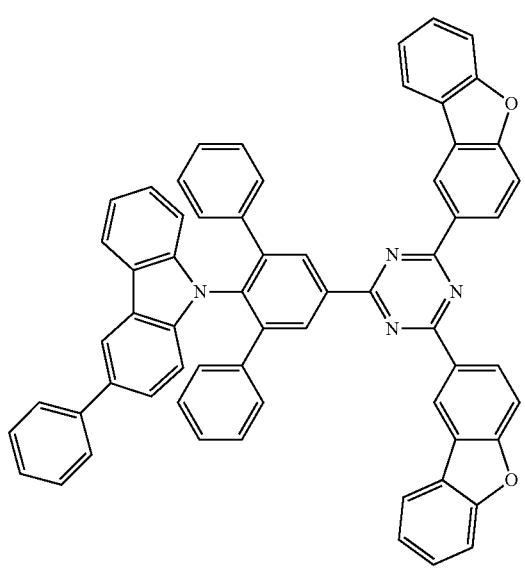
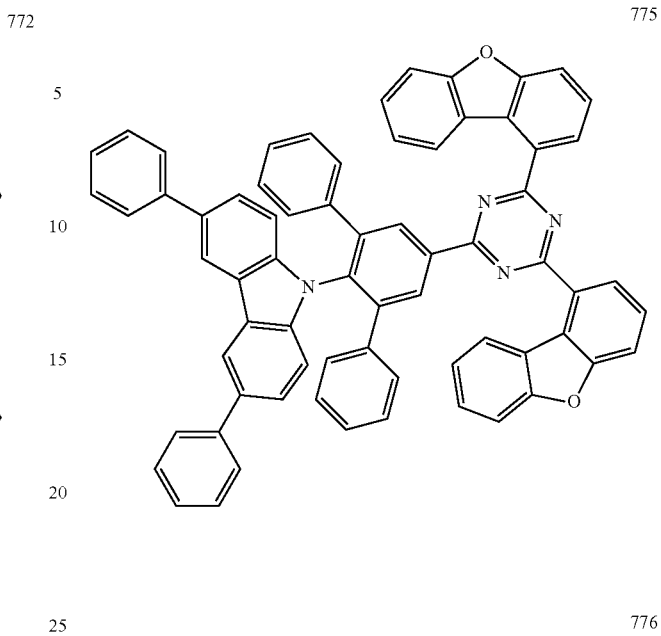

778
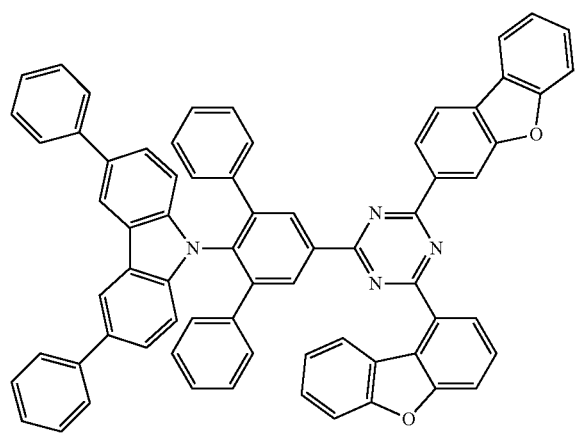
779
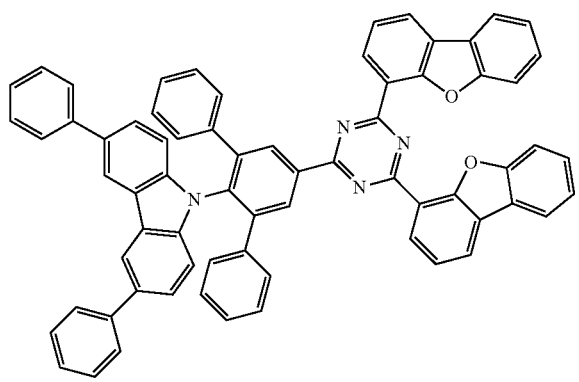
780
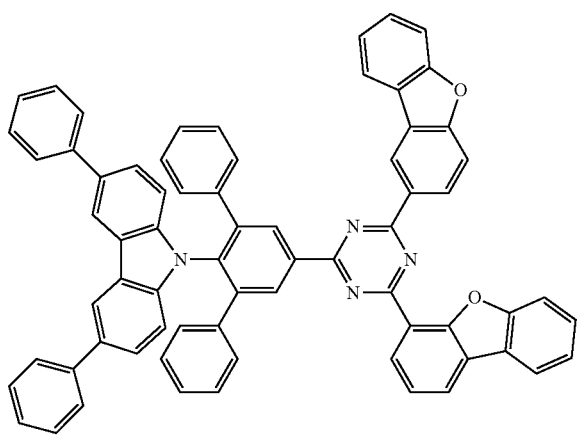
781
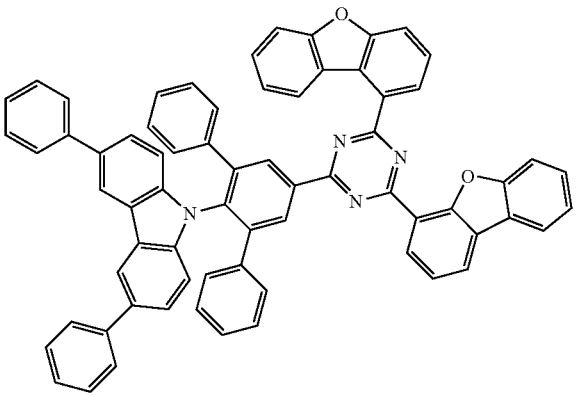
782
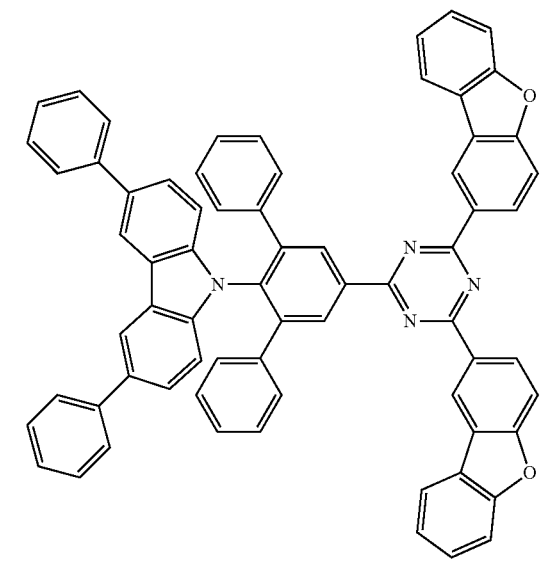
783
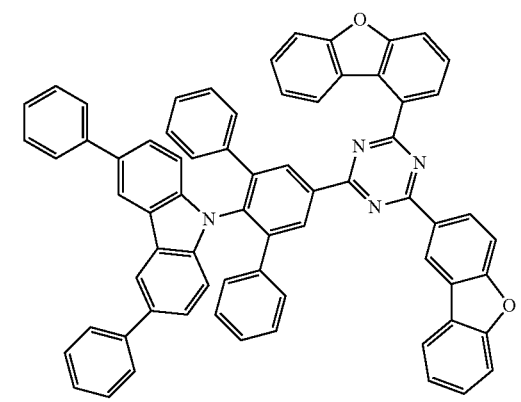

429
-continued
784
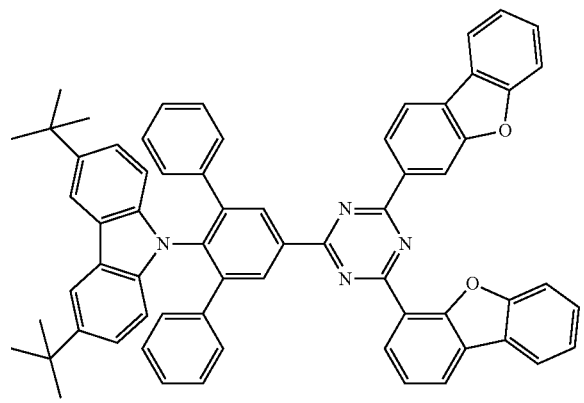
785
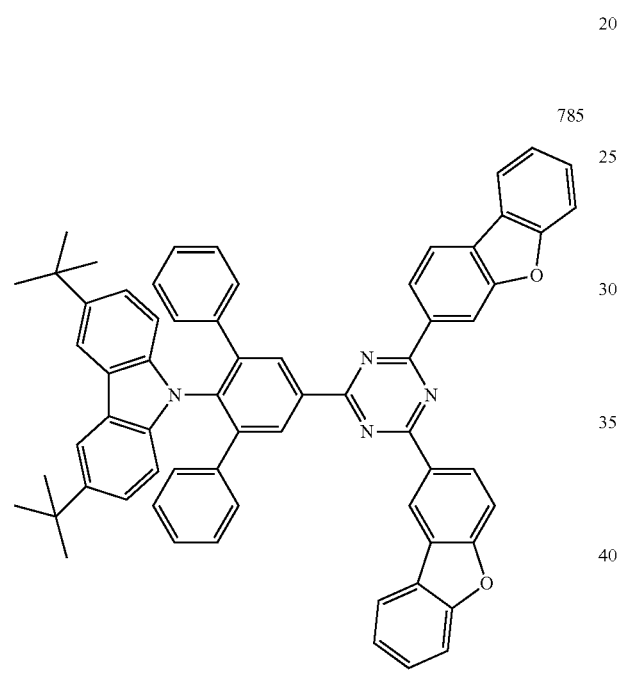
786
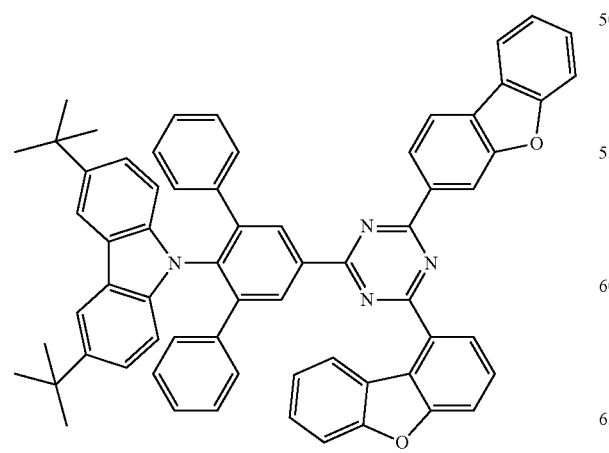
430
-continued
787
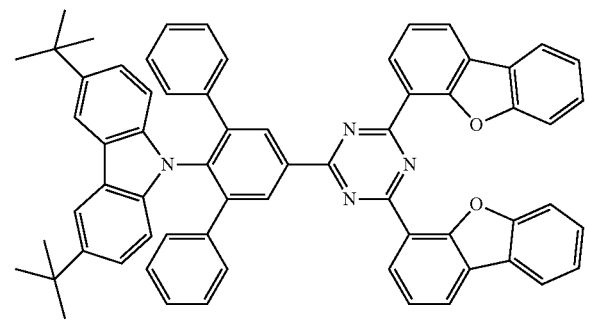
788
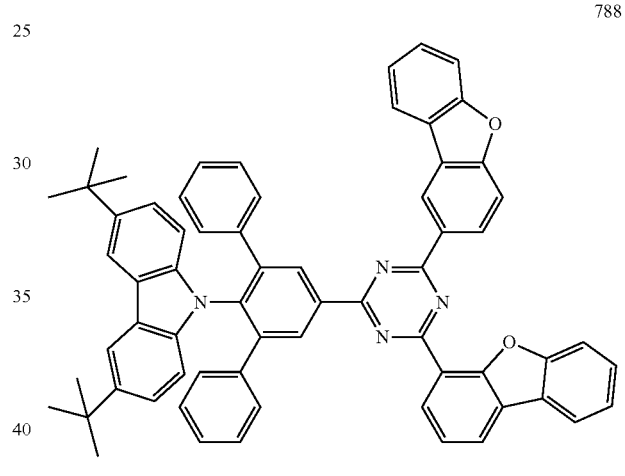
789
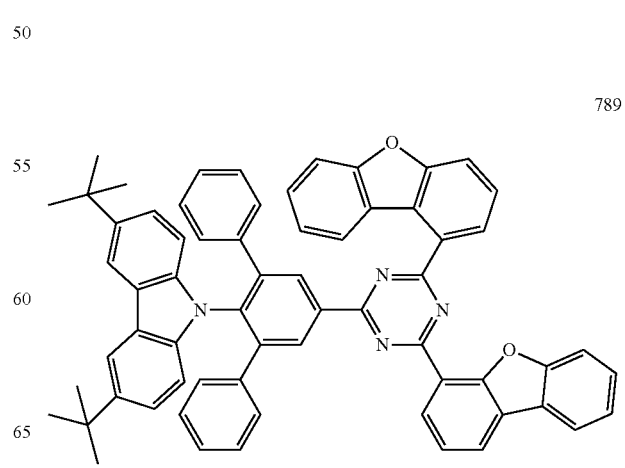

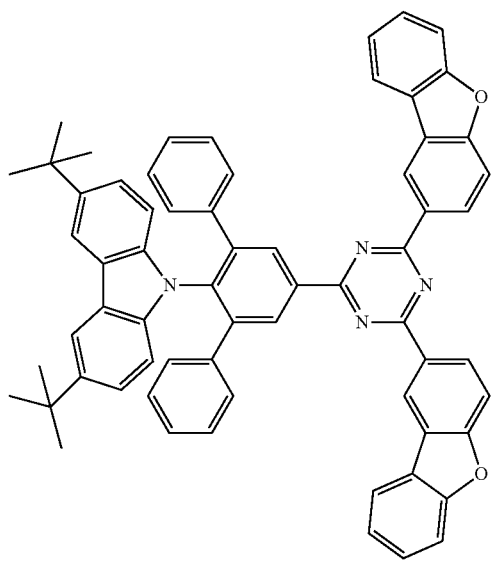
790
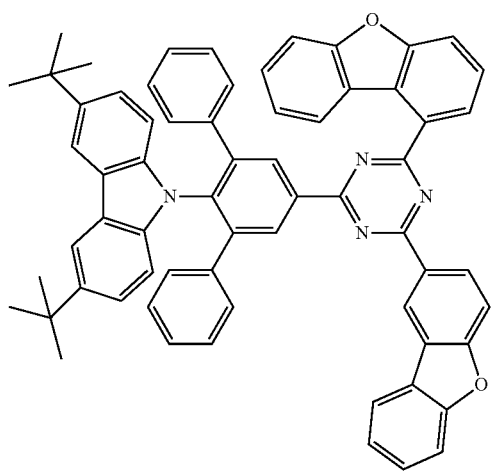
791
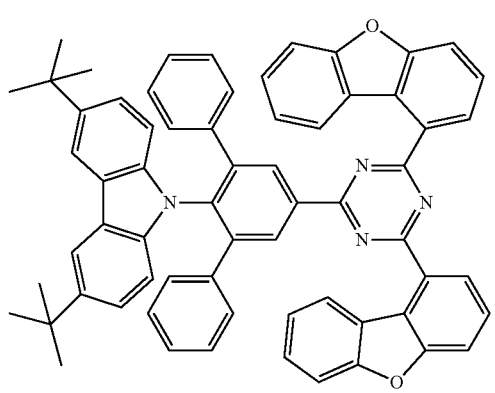
792
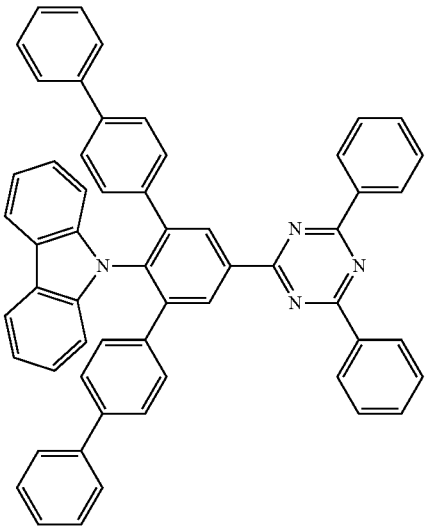
793
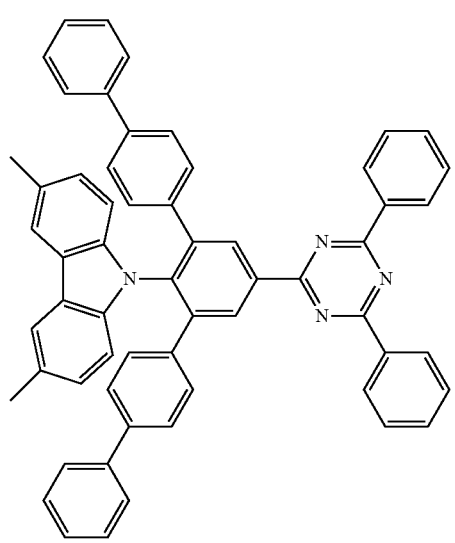
794
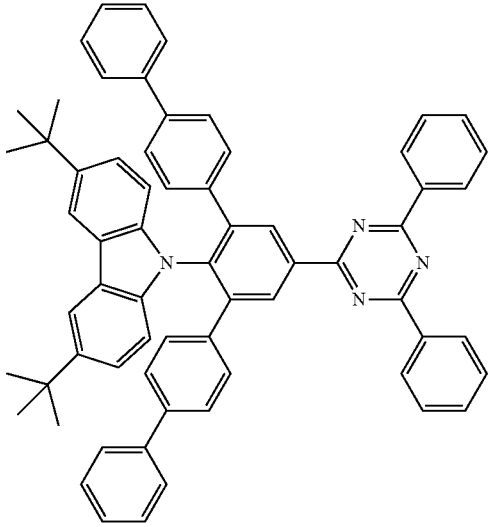
795

796 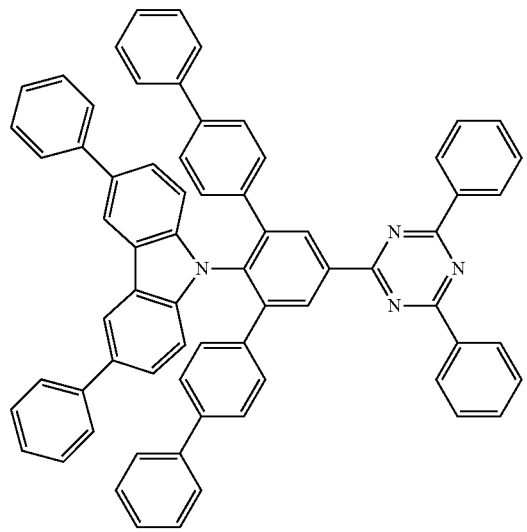
797 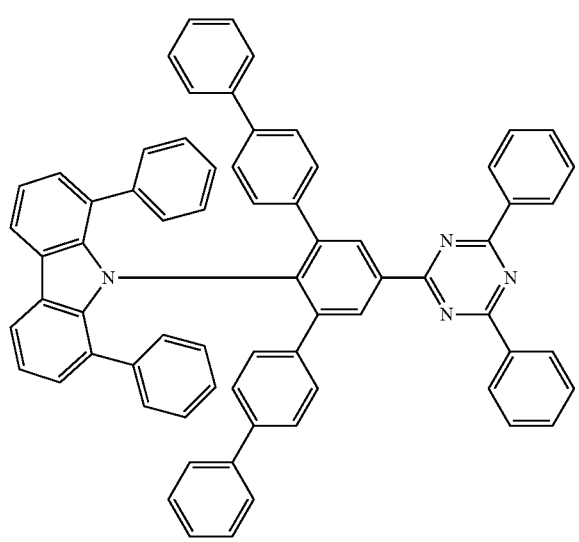
798 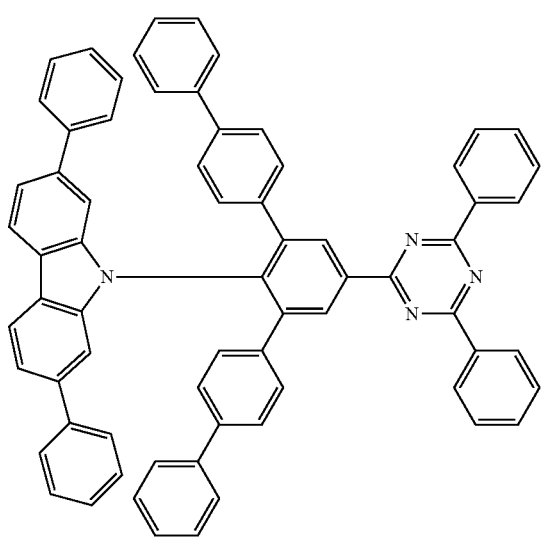
799 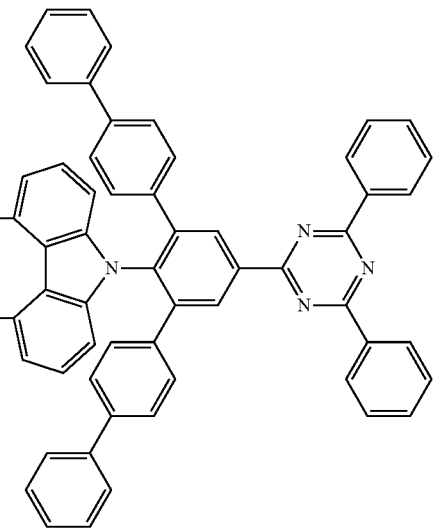
800 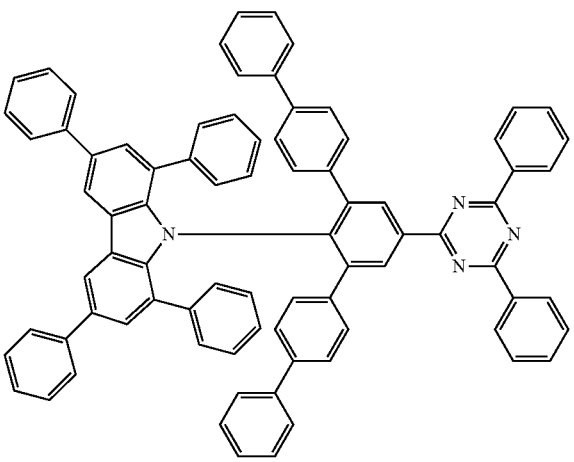
801 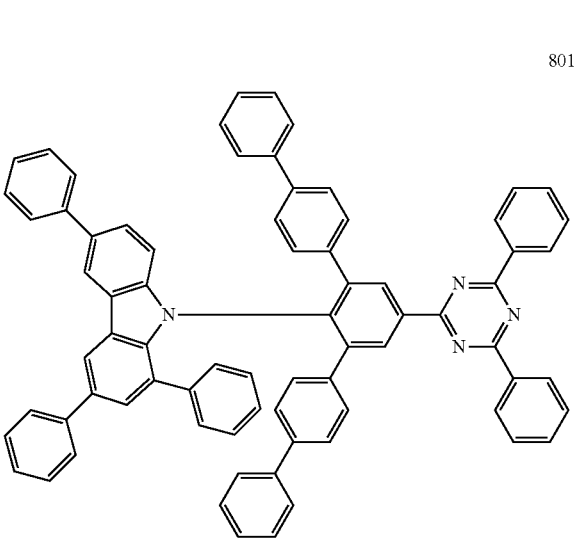

-continued
802
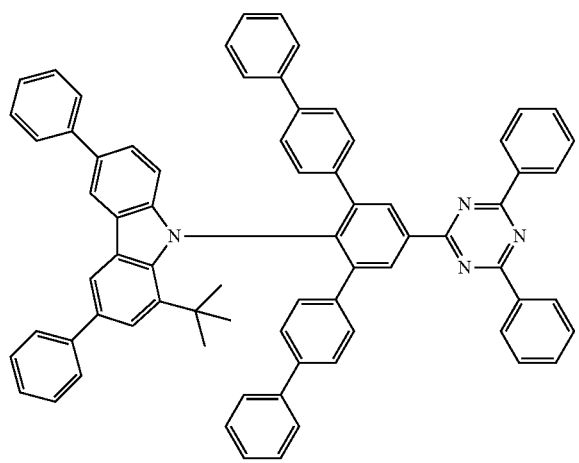
803
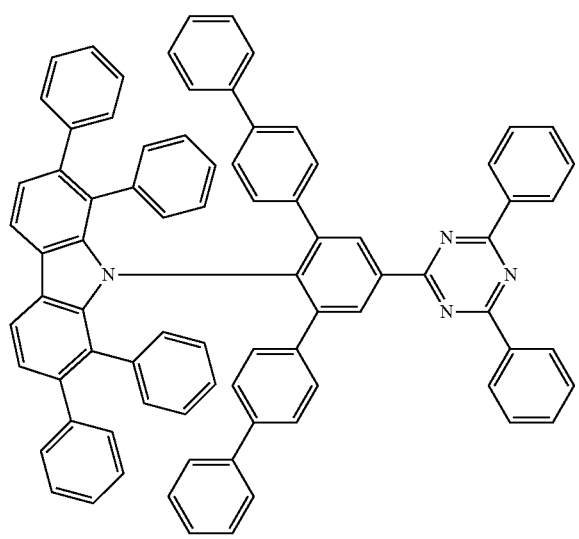
804
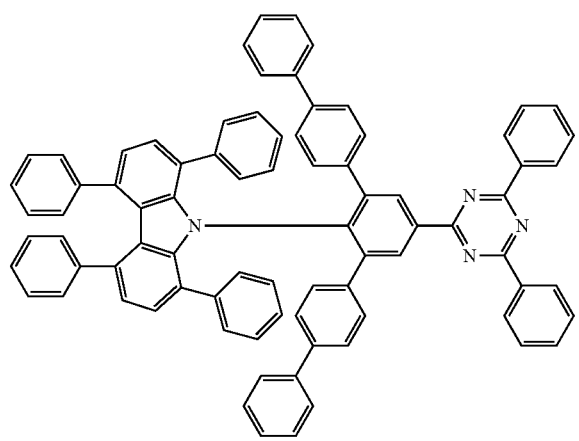
-continued
805
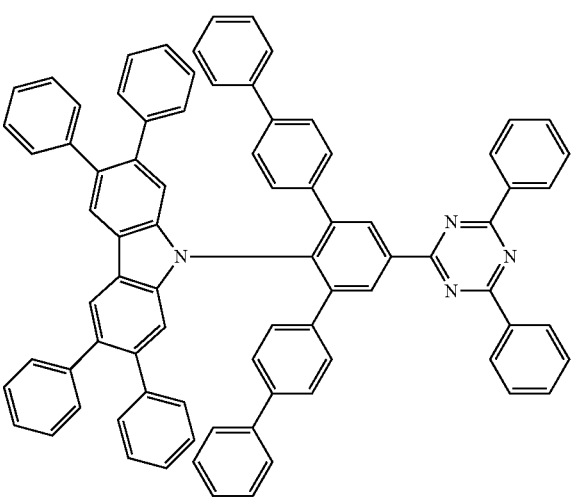
806
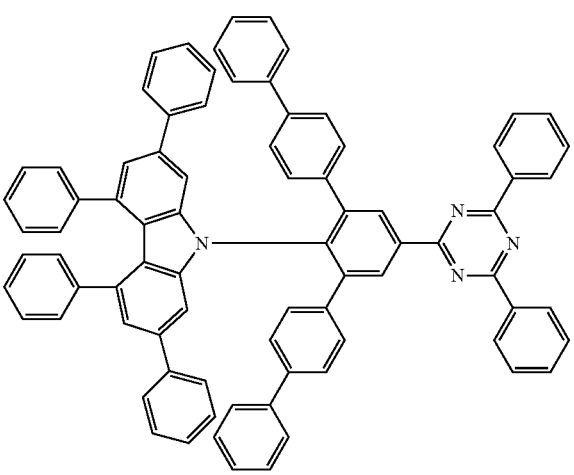
807
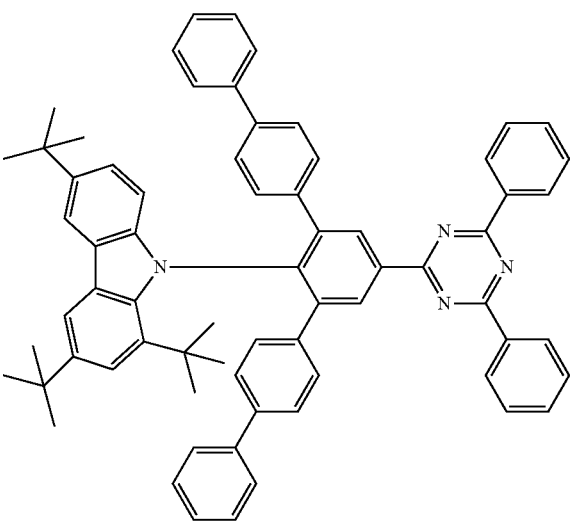

808
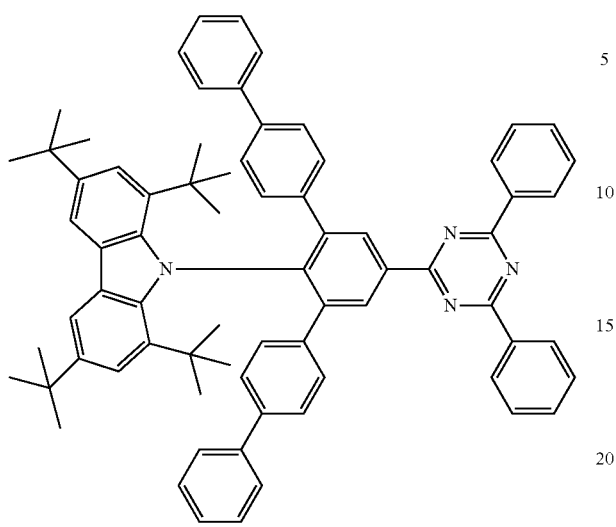
809
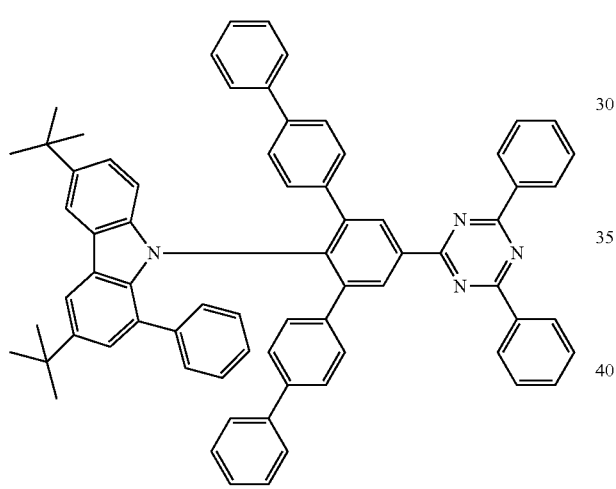
810
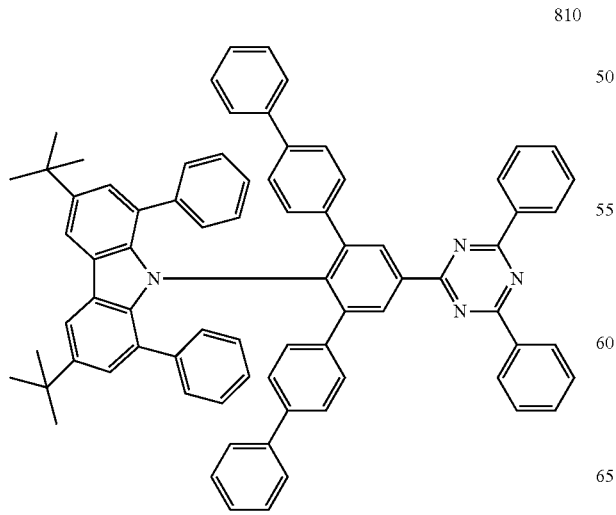
811
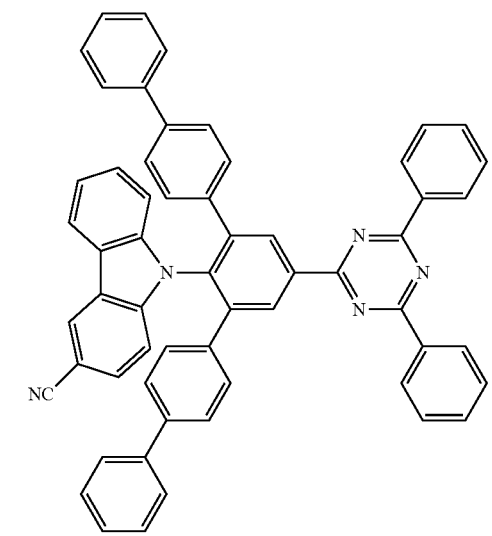
812
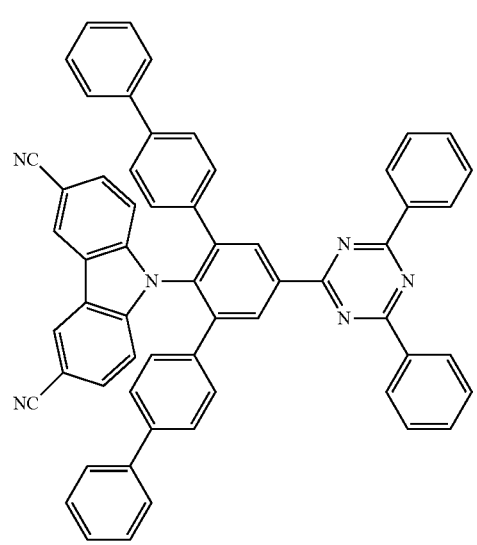
813
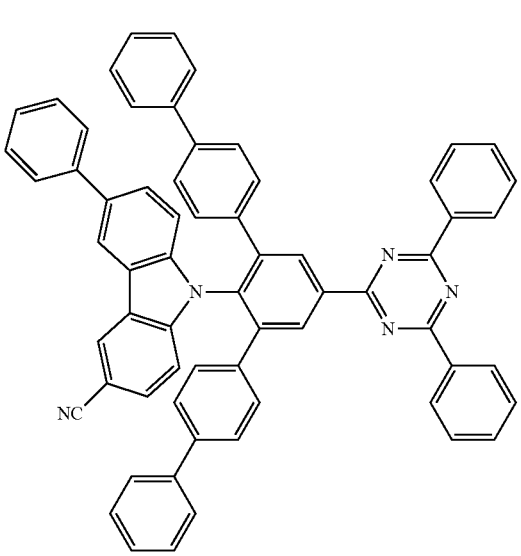

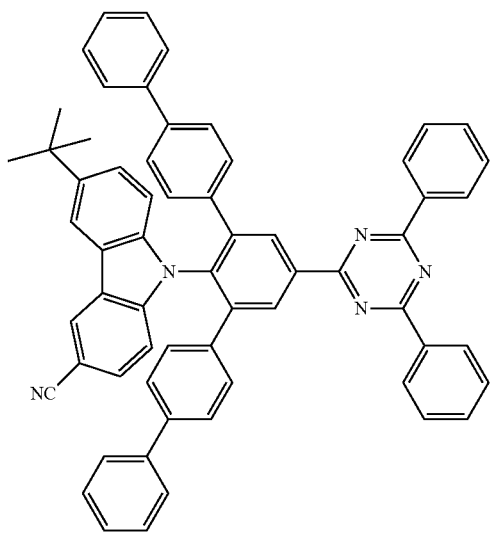
814
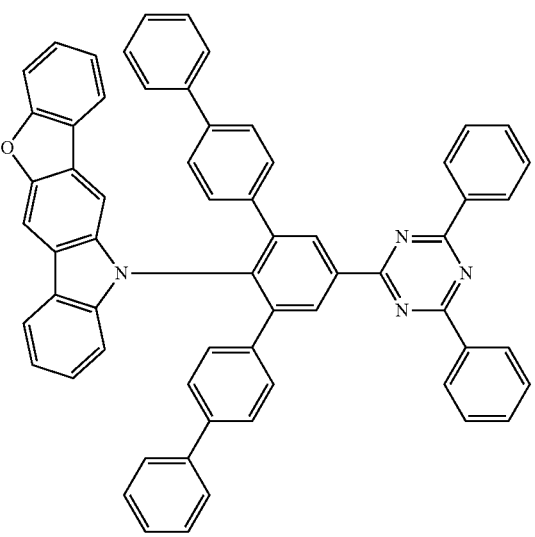
817
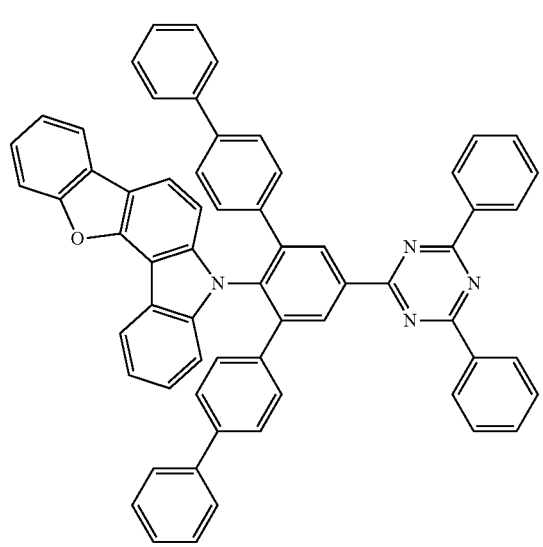
815
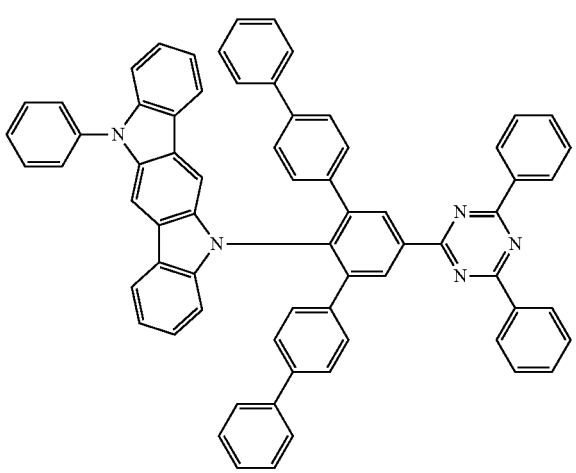
818
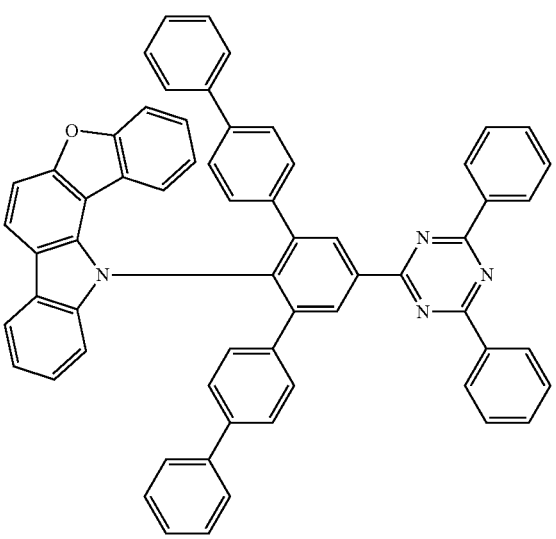
819

820
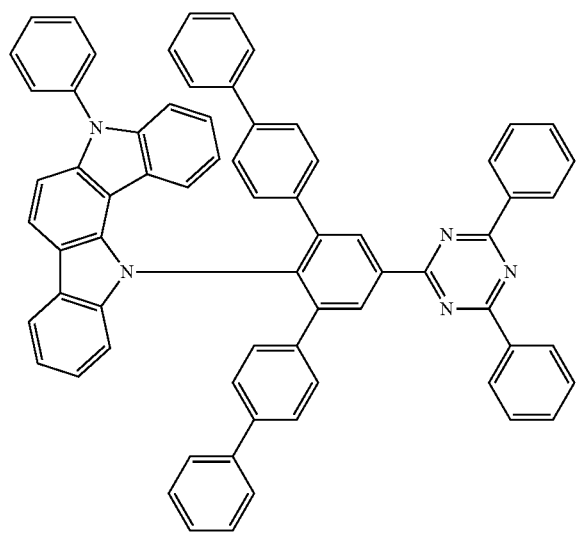
821
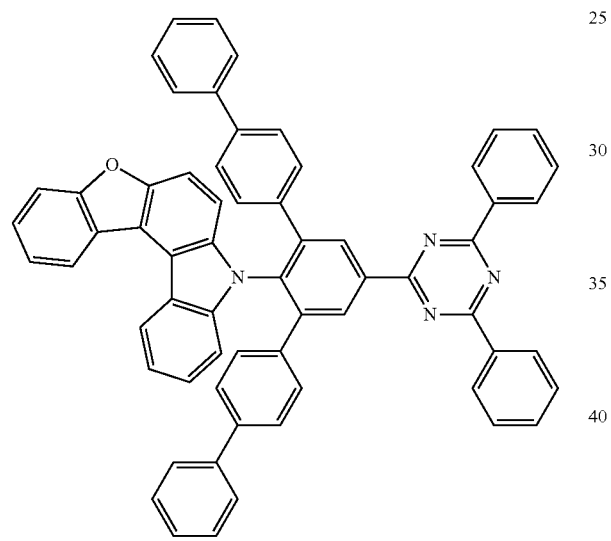
822
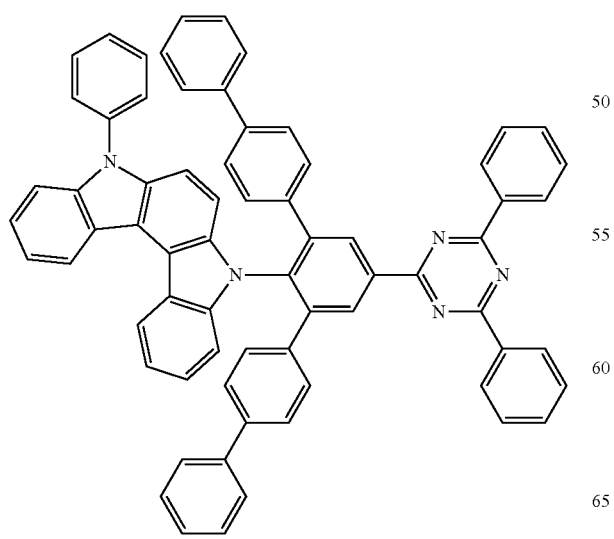
823
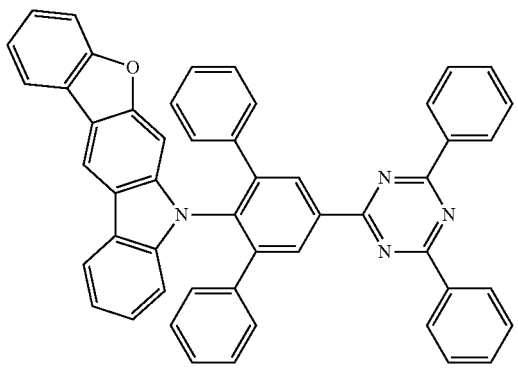
824
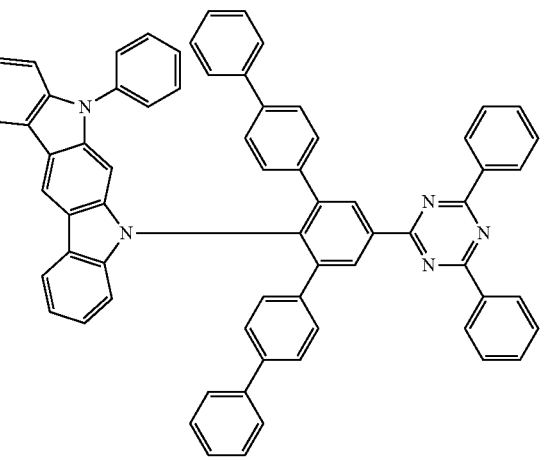
825
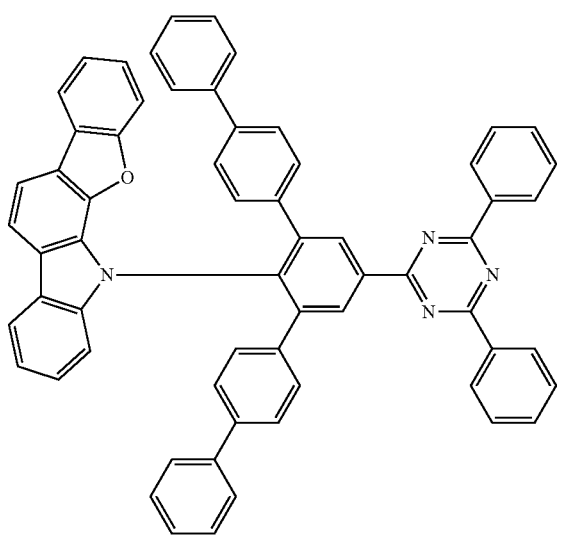

826
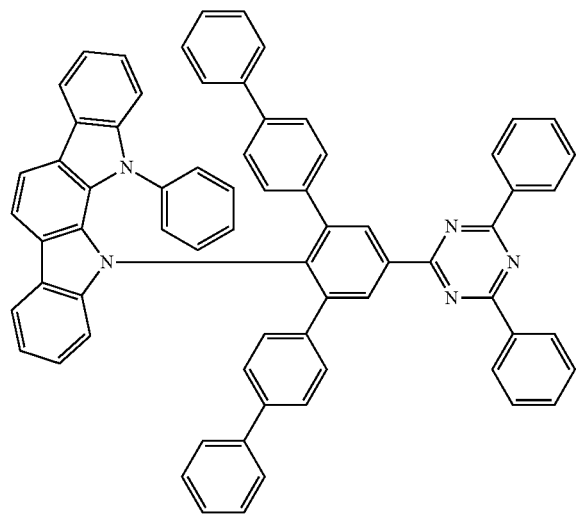
827
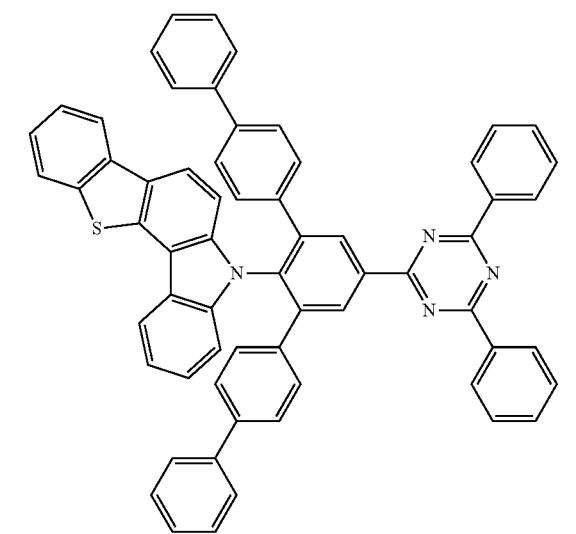
828
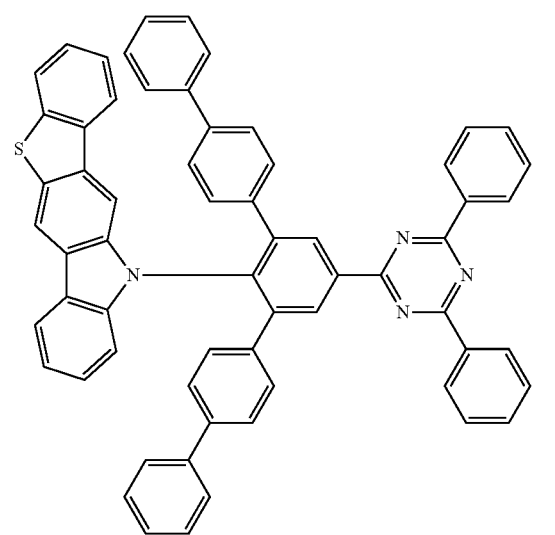
829
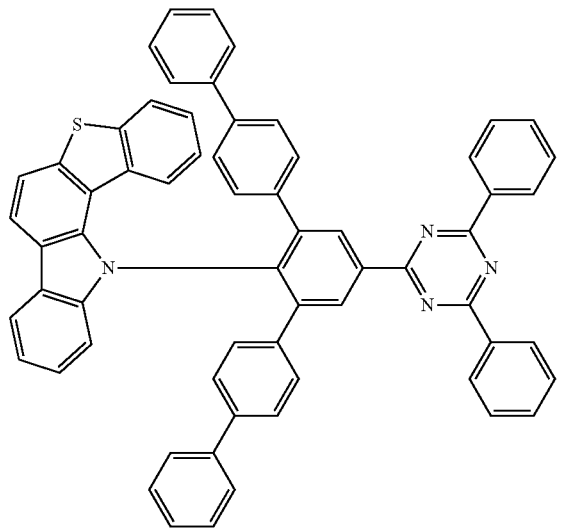
830
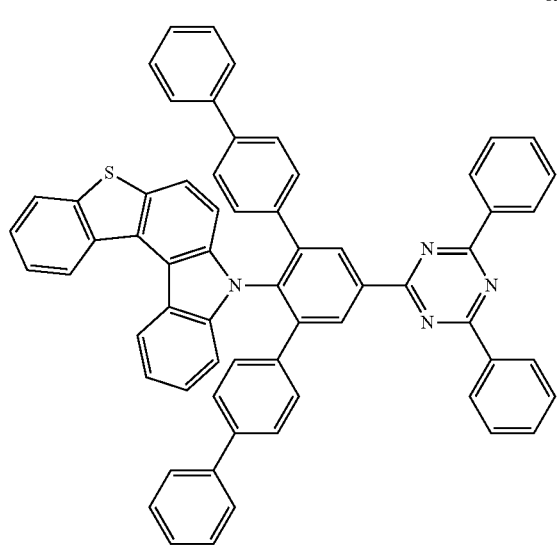
831
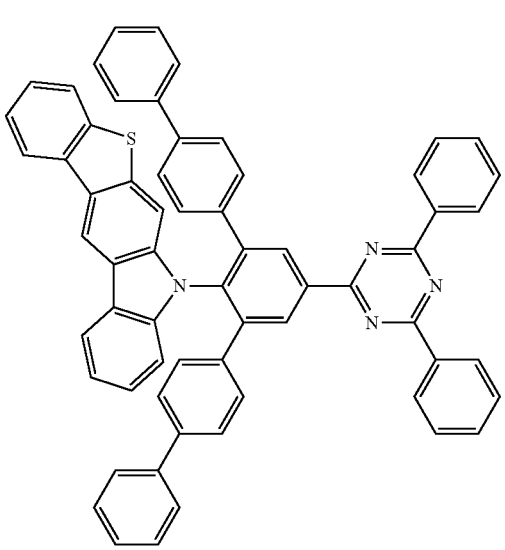

832
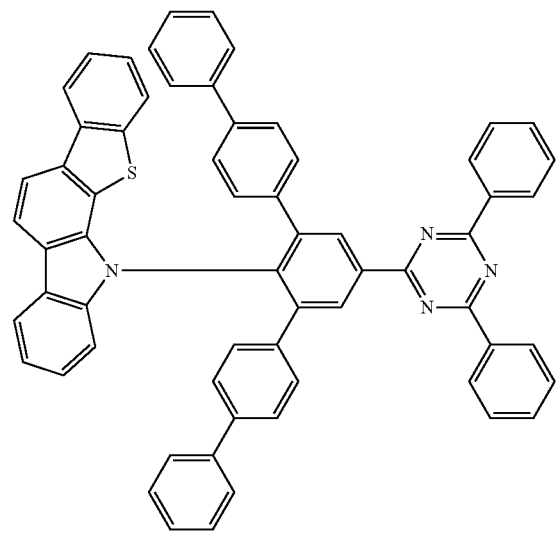
833
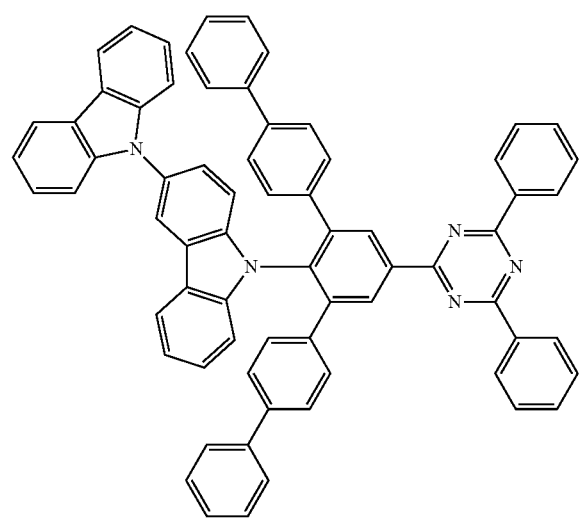
834
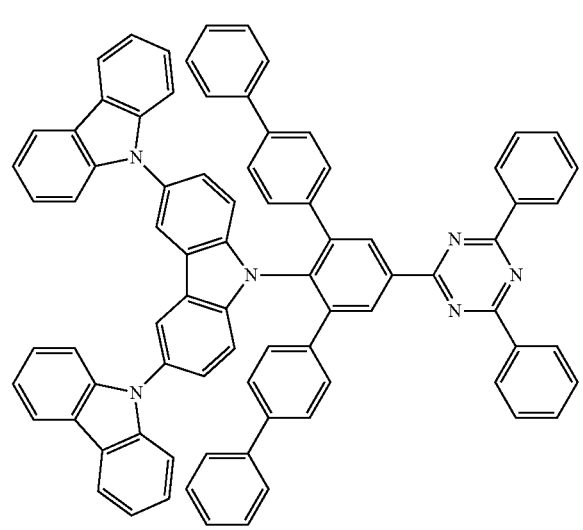
835
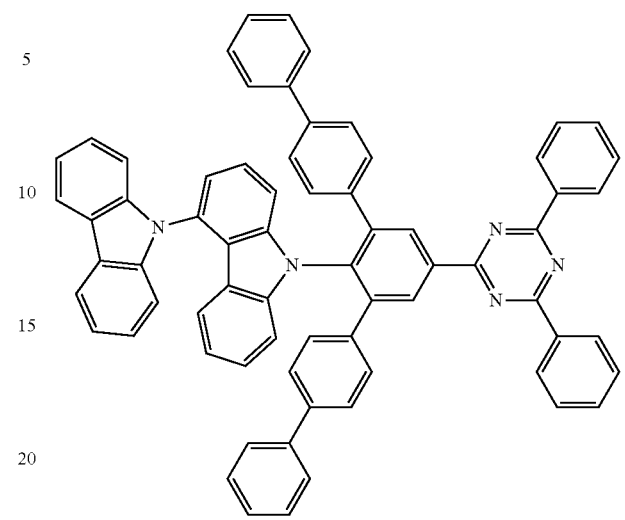
836
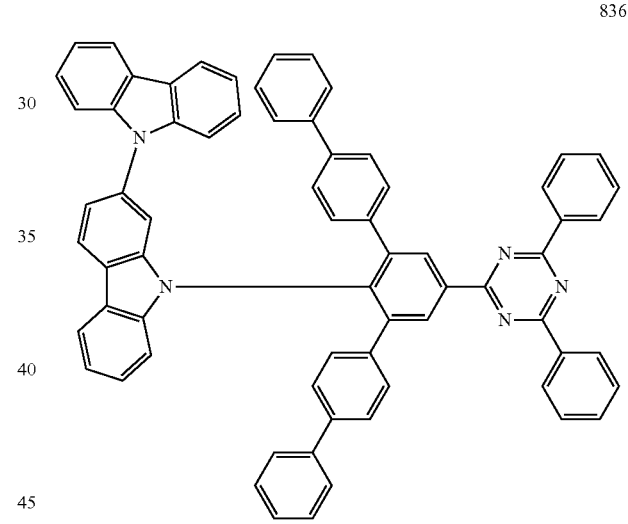
837
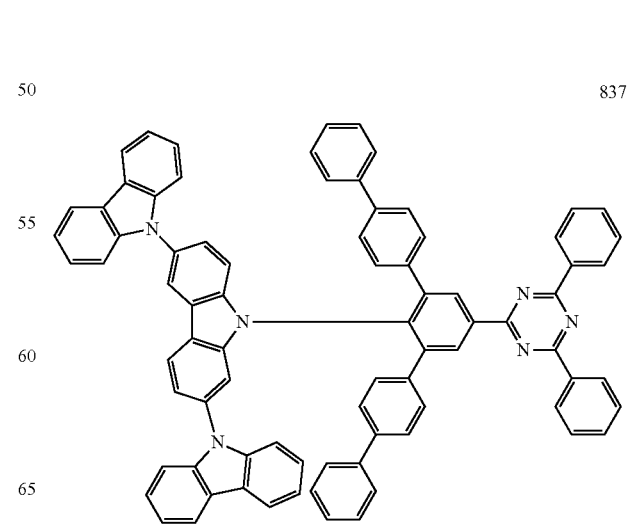

838
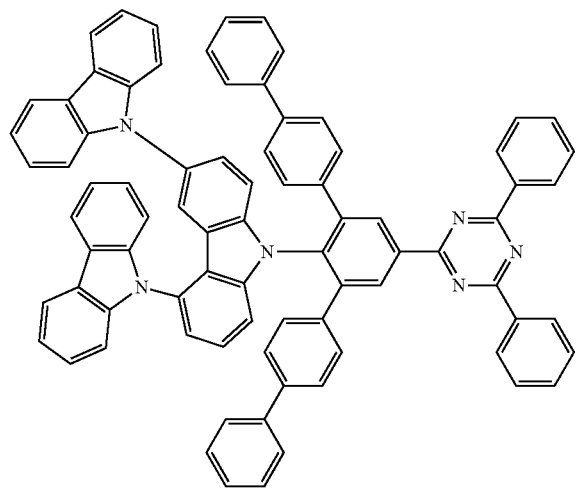
839
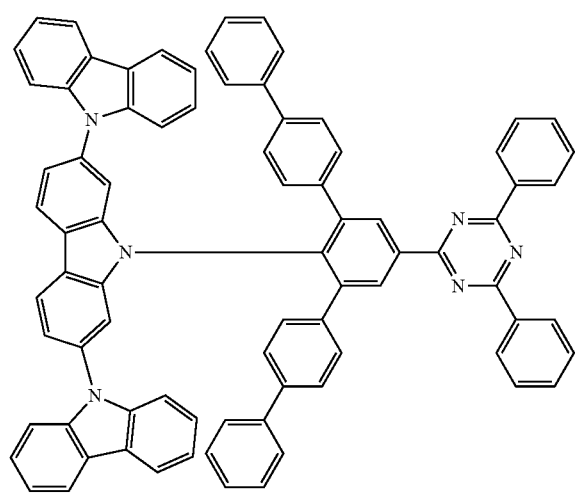
840
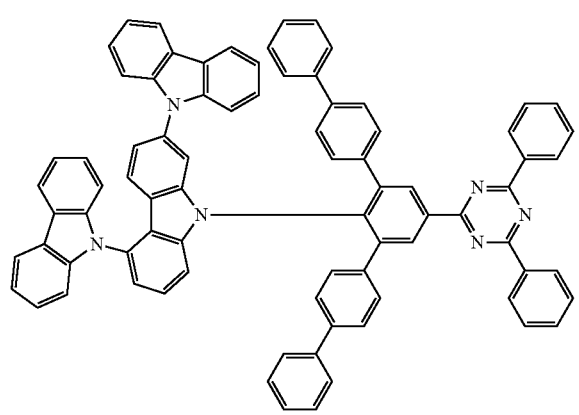
841
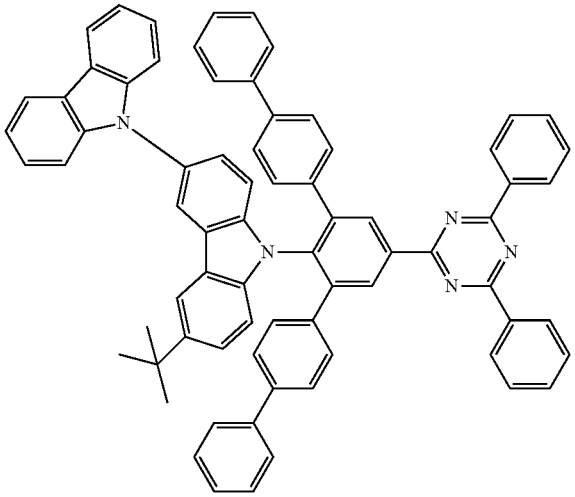
842
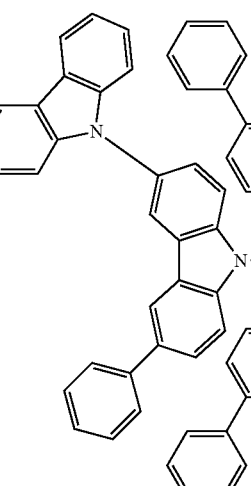
843
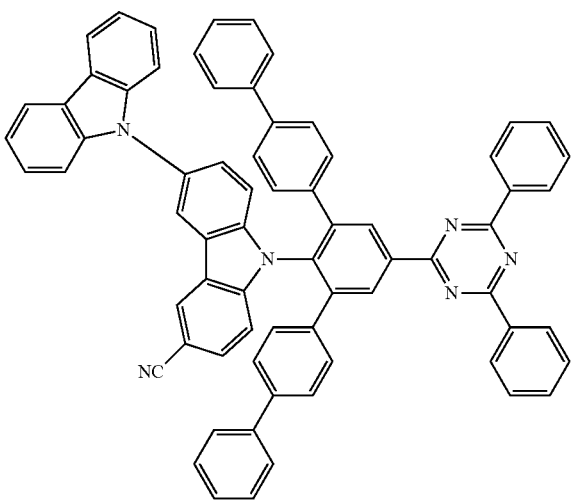

844
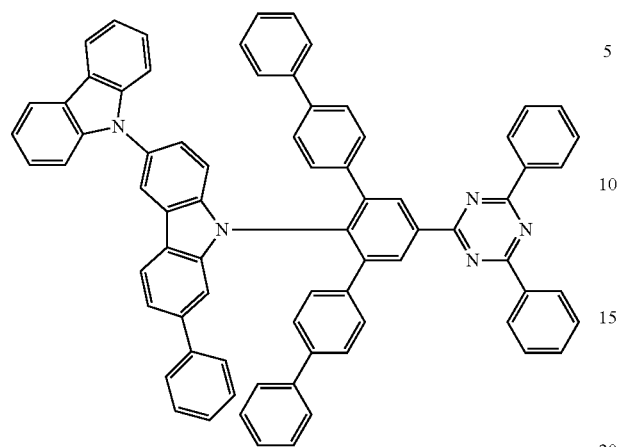
845
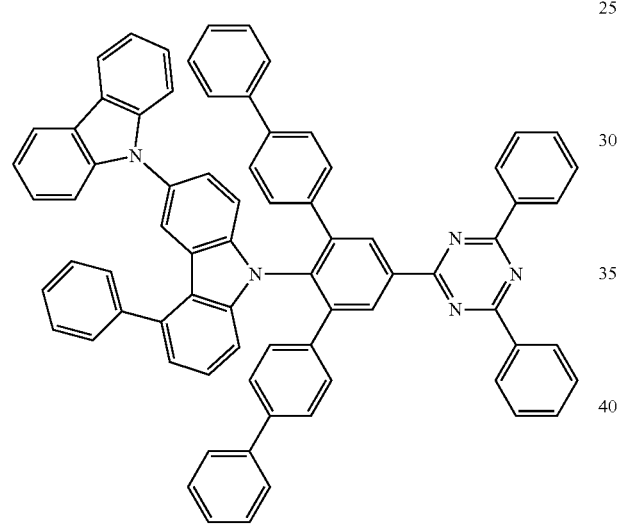
846
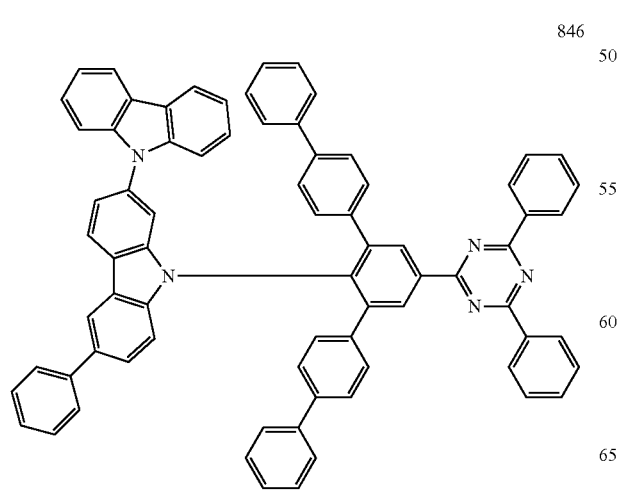
847
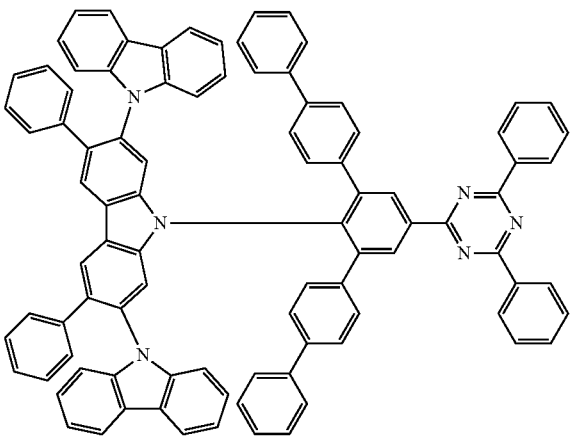
848
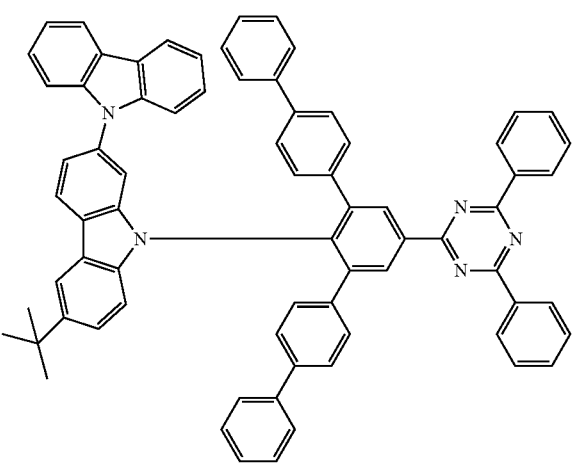

-continued
849
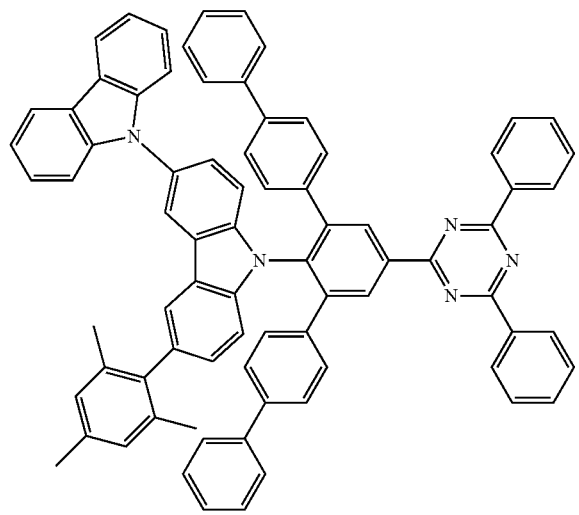
850
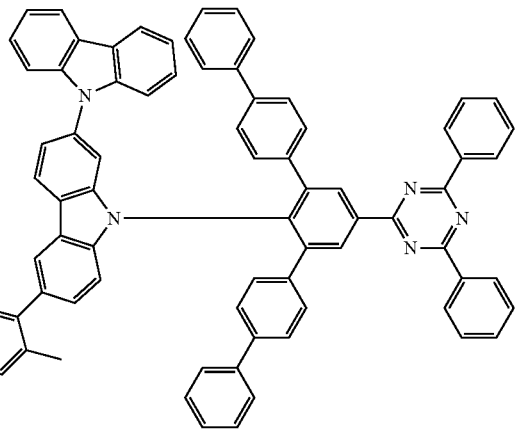
851
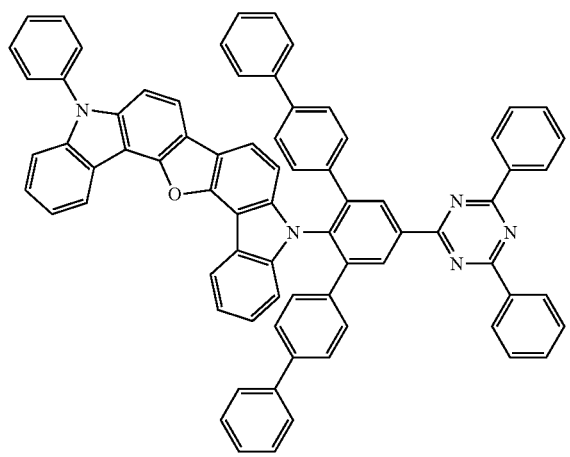
852
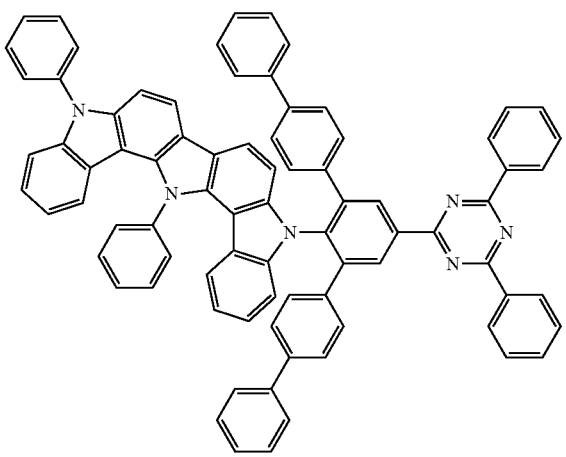
853
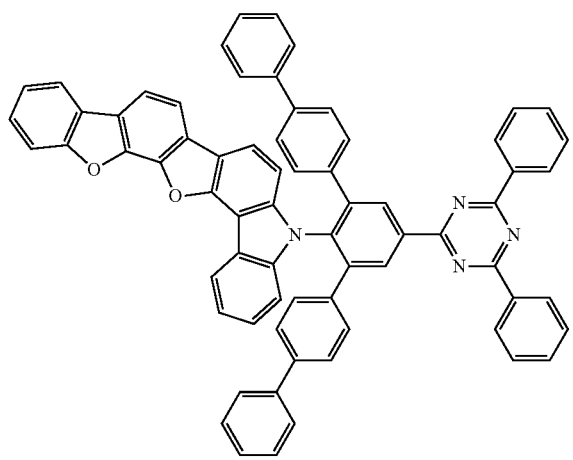
854
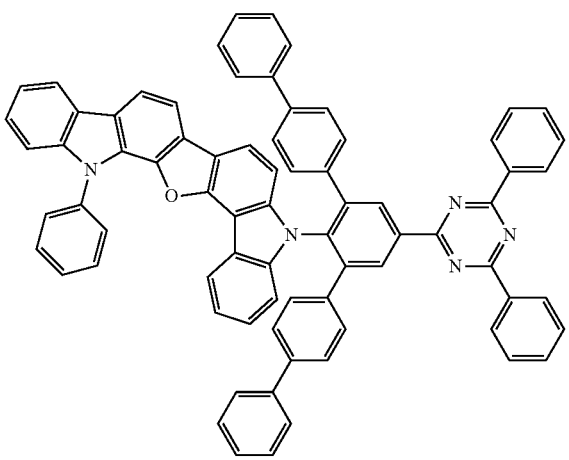

855
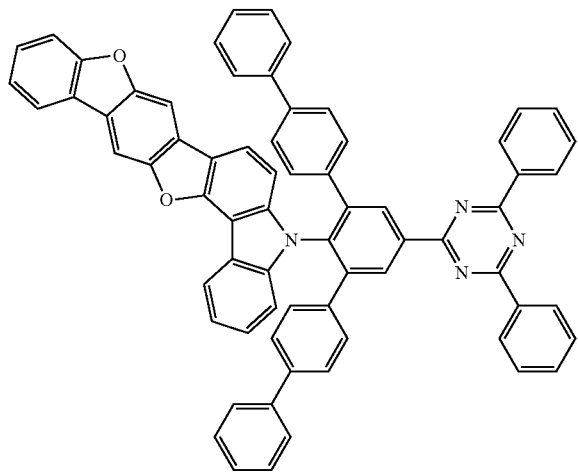
856
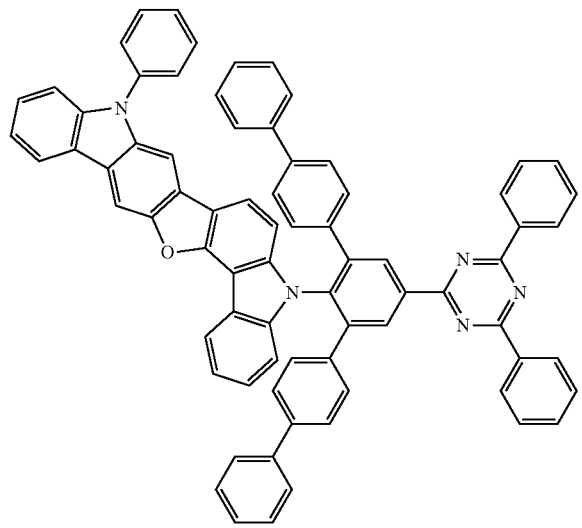
857
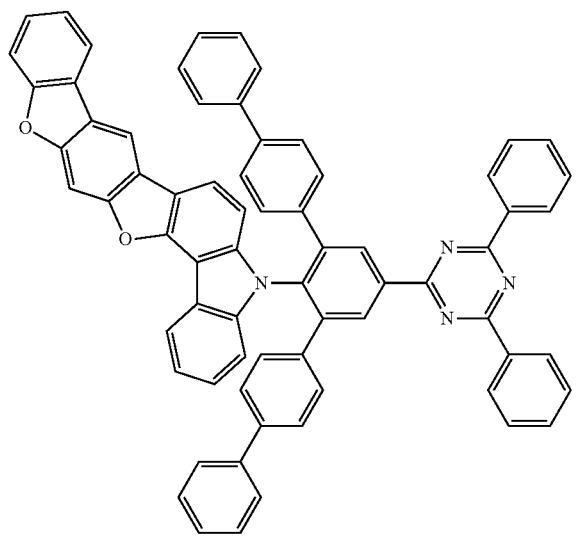
858
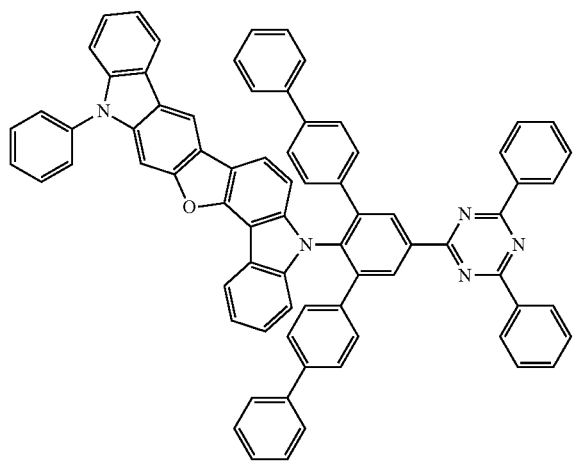

859
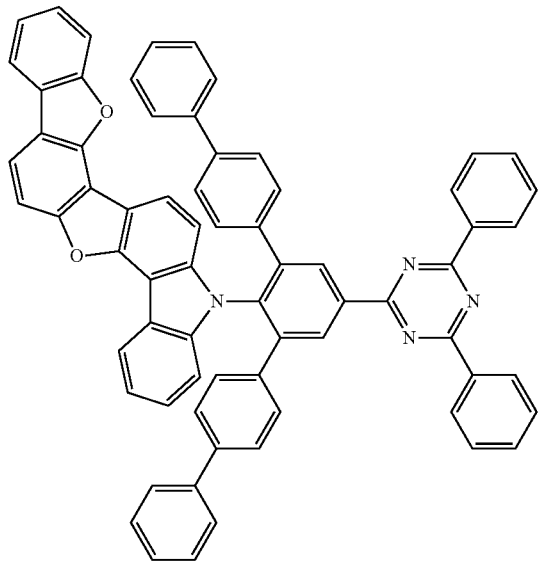
860
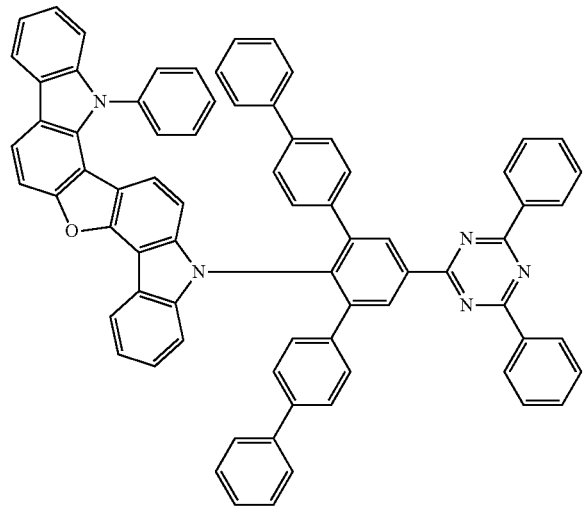
861
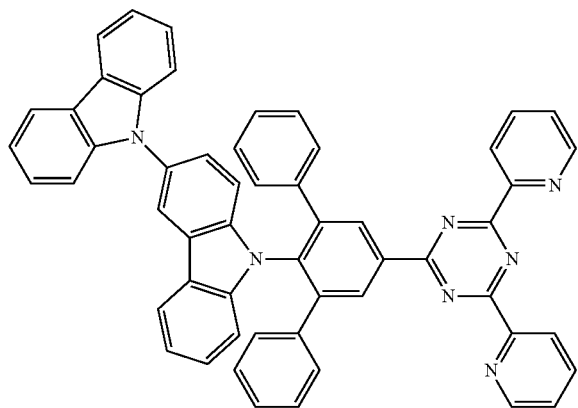
862
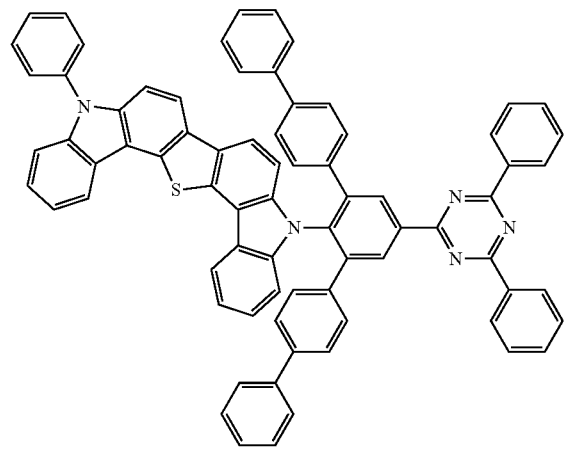
863
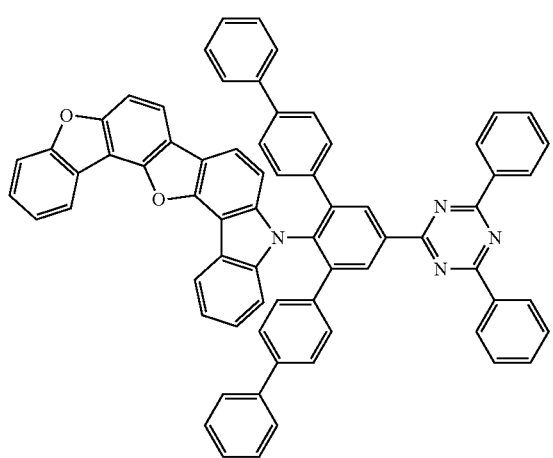
864
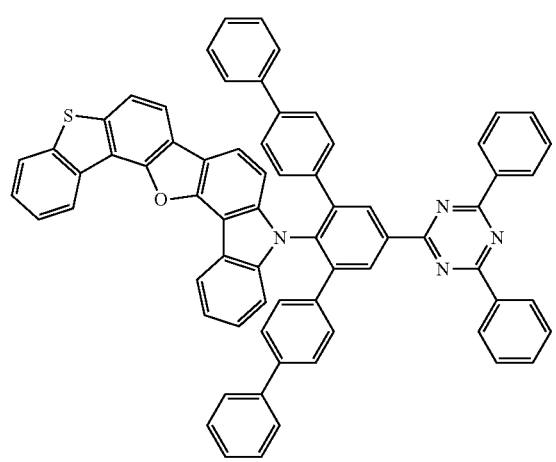

-continued
865
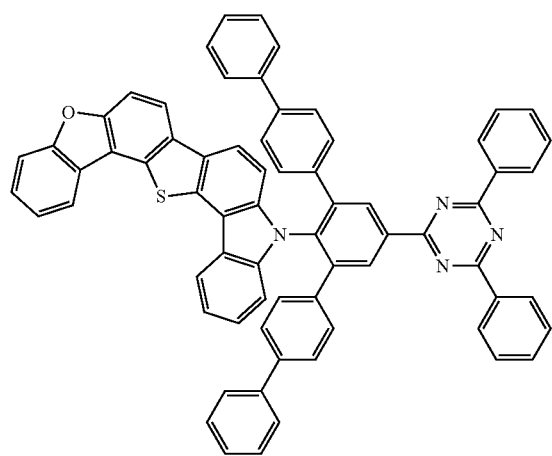
866
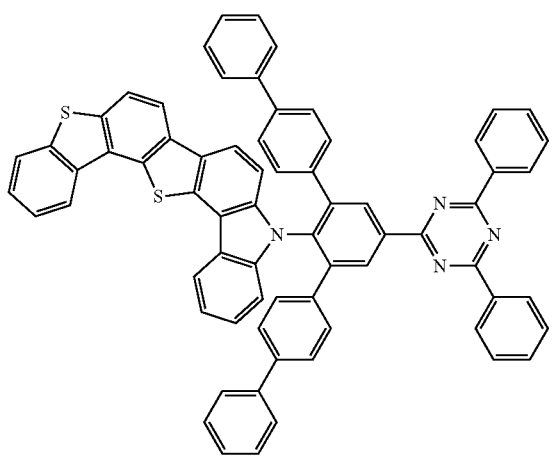
867
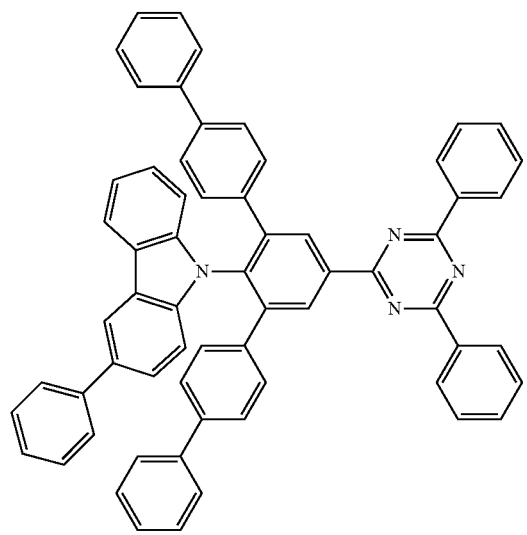
868
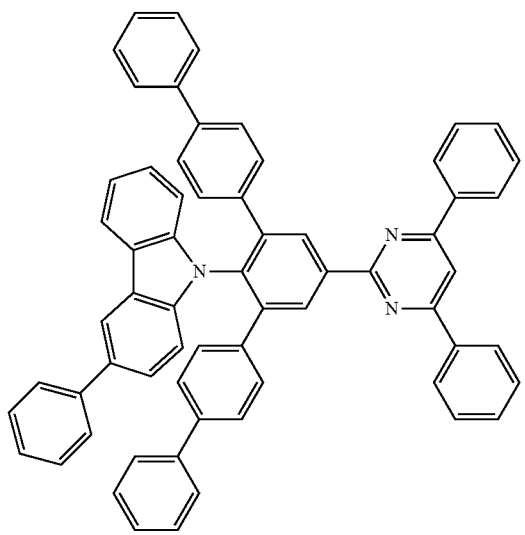
869
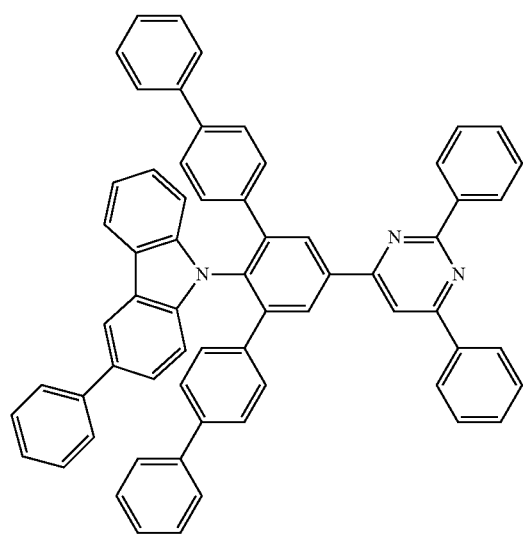
870
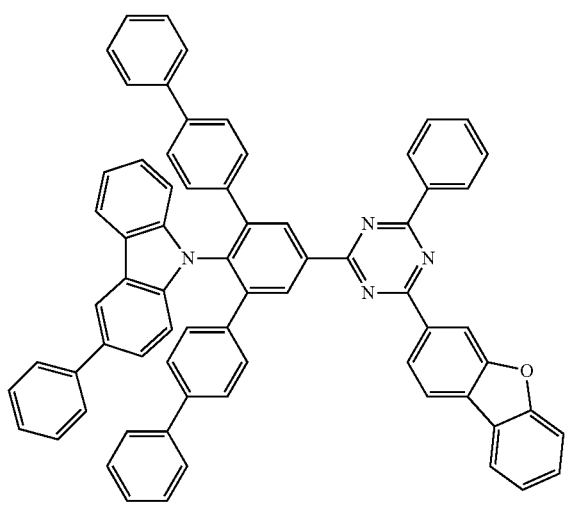

-continued
871
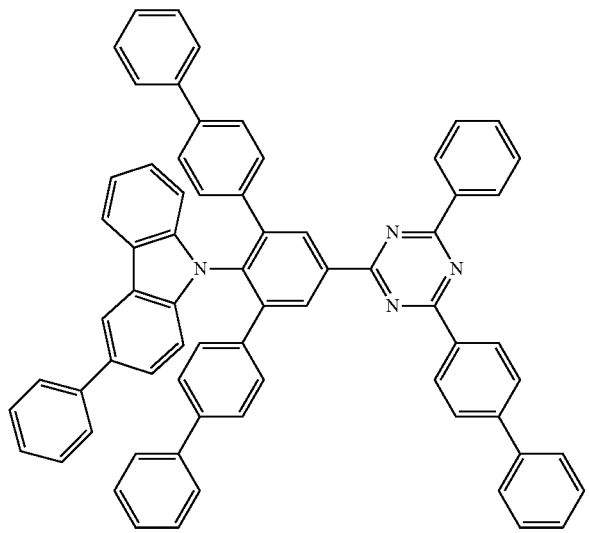
872
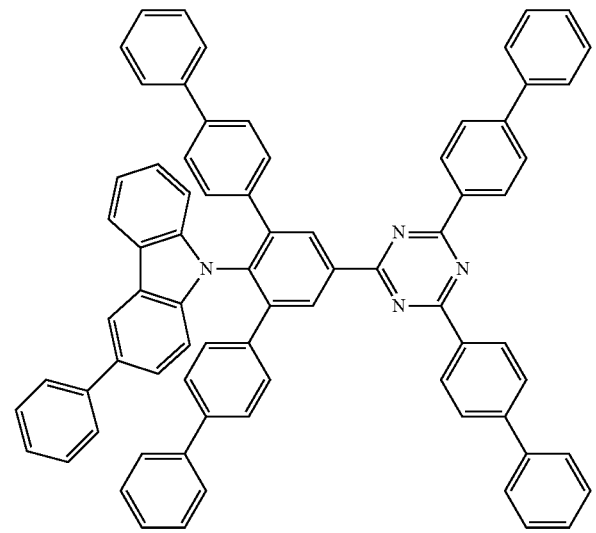
873
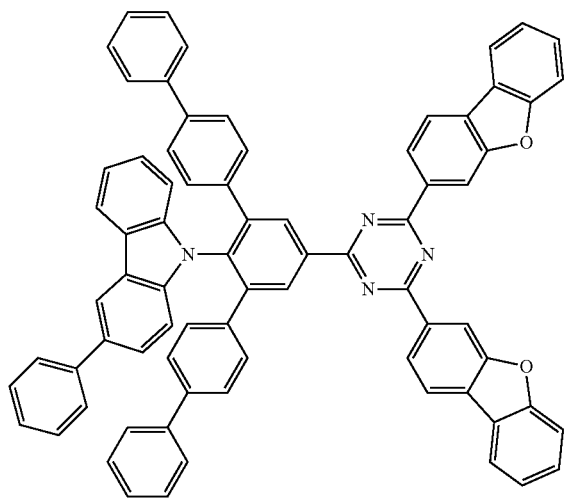
874
875
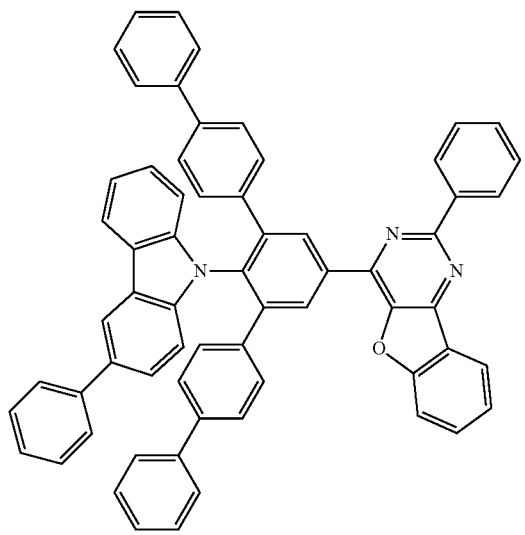
876
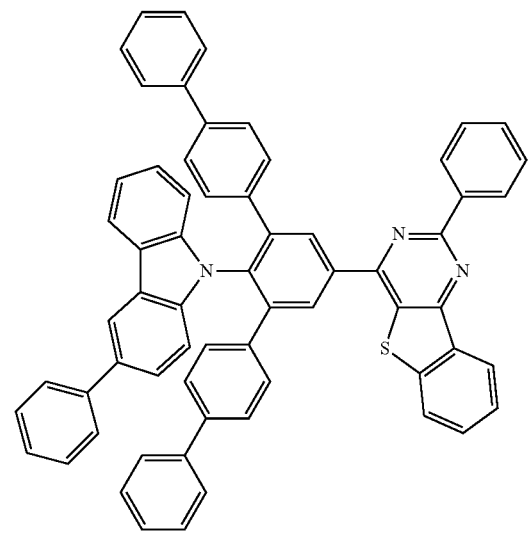

461                                         462
-continued
877
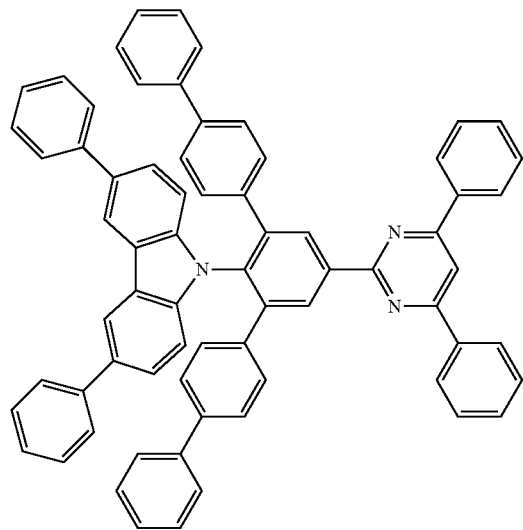
878
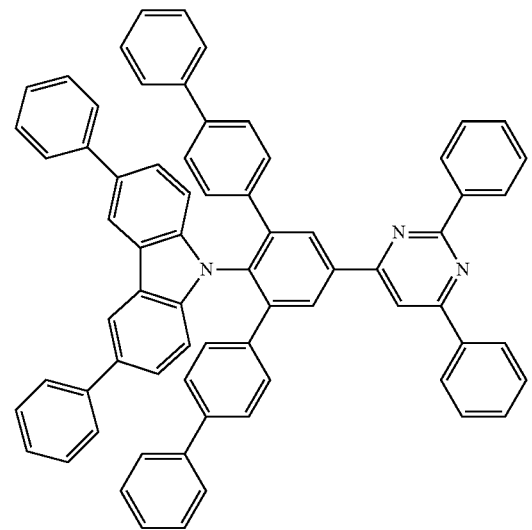
879
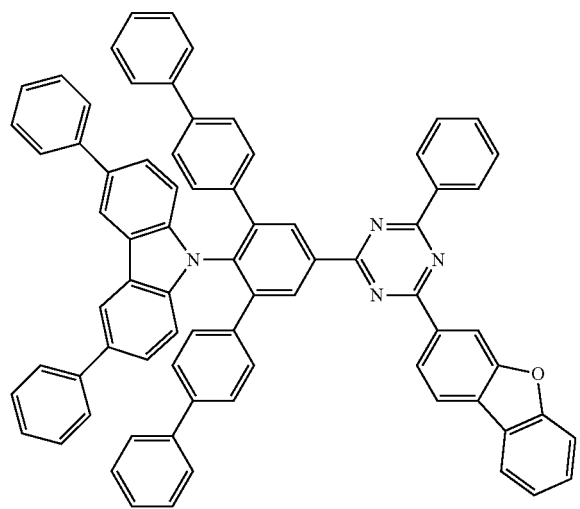
880
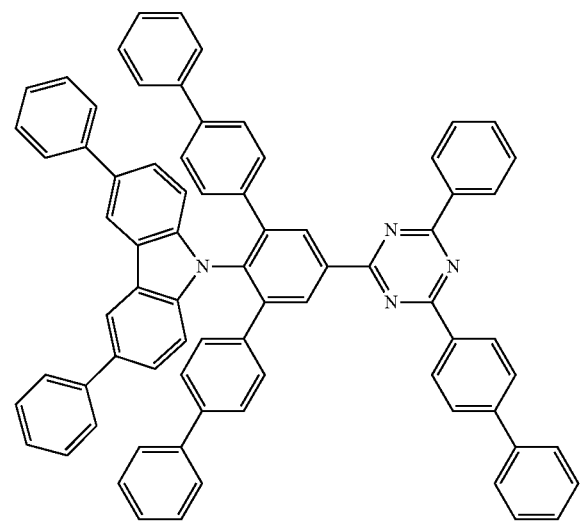
881
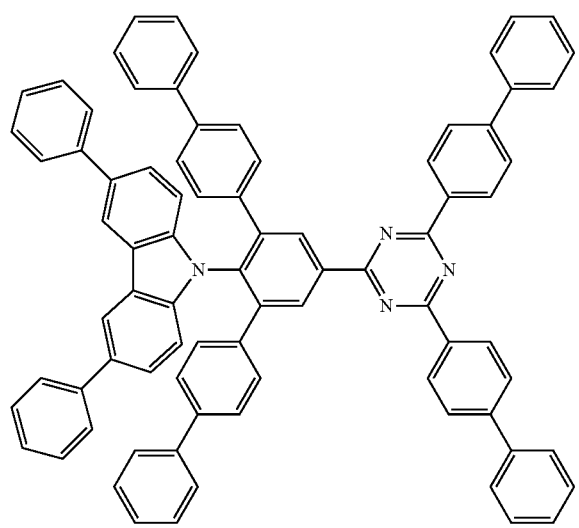
882
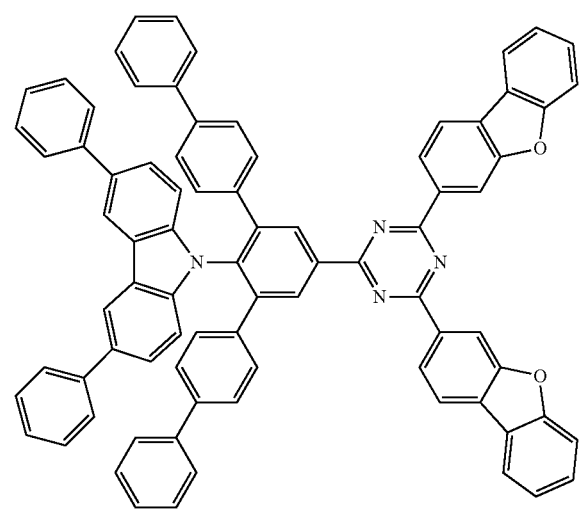

-continued
883
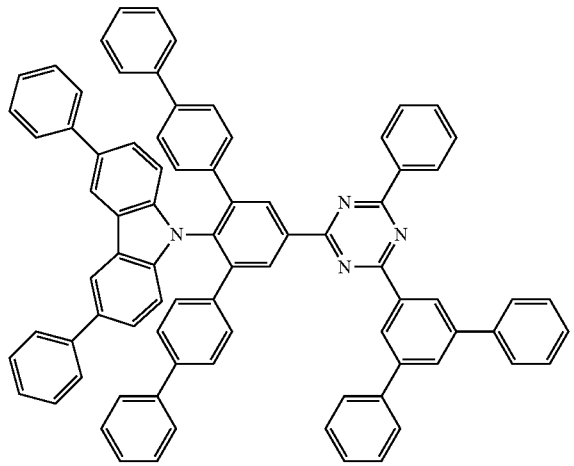
884
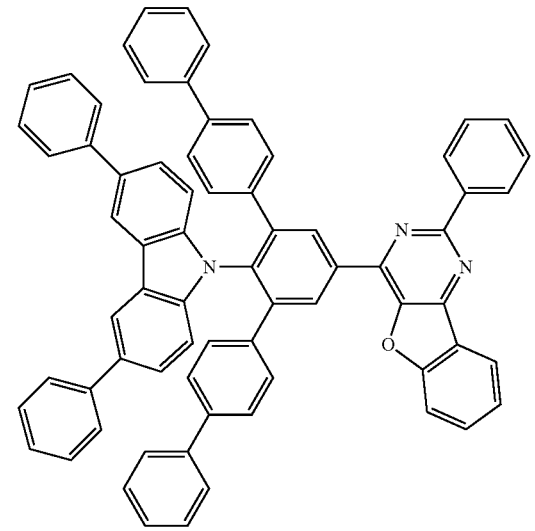
885
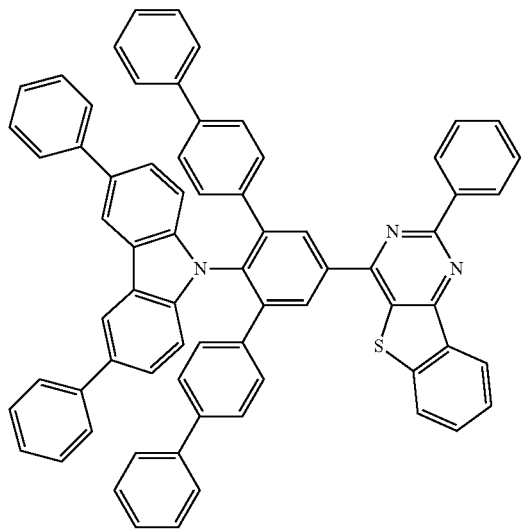
886
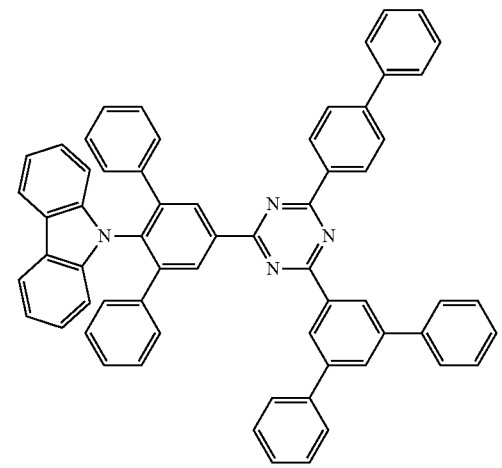
887
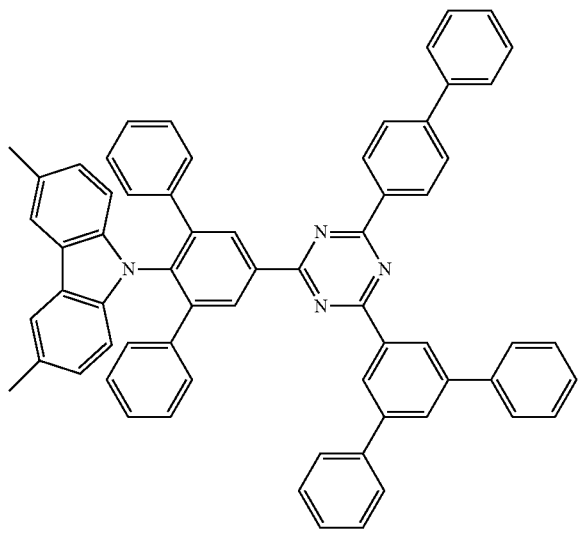
888
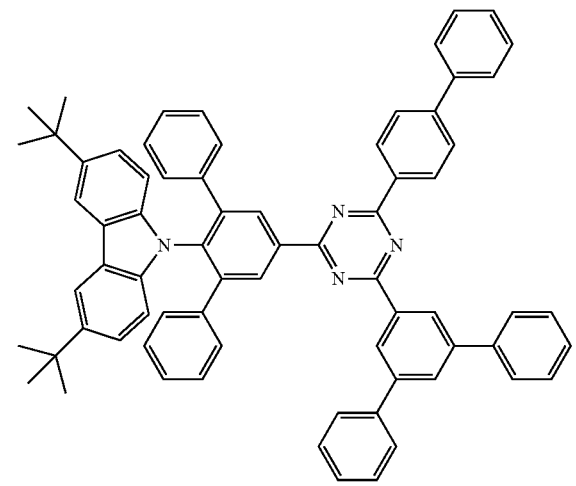

-continued
889
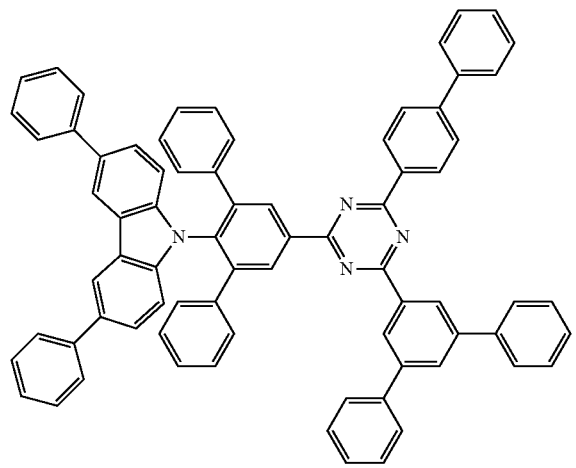
890
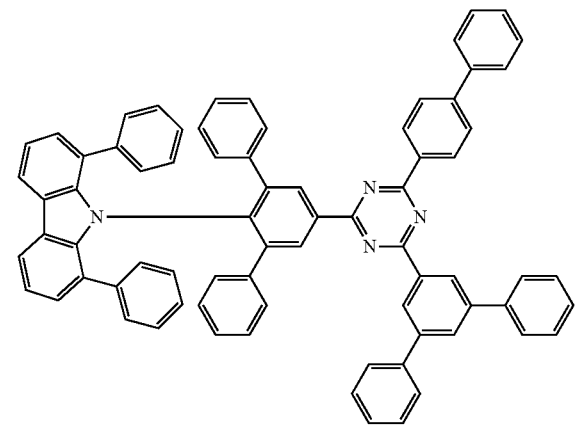
891
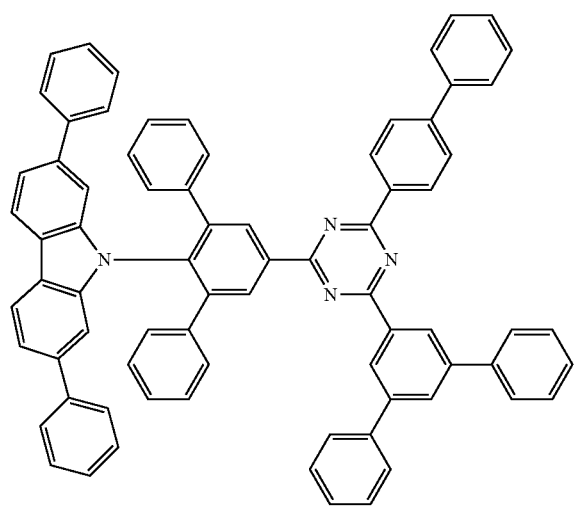
892
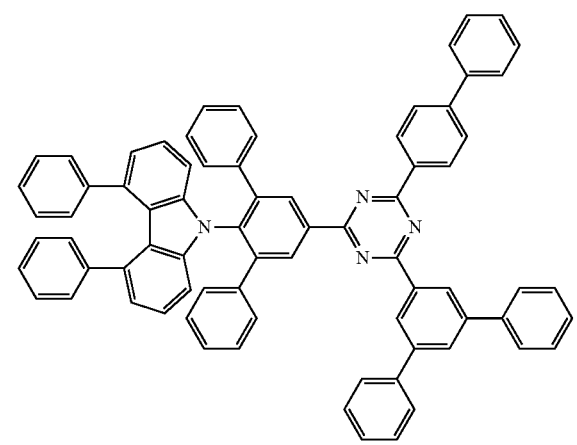
893
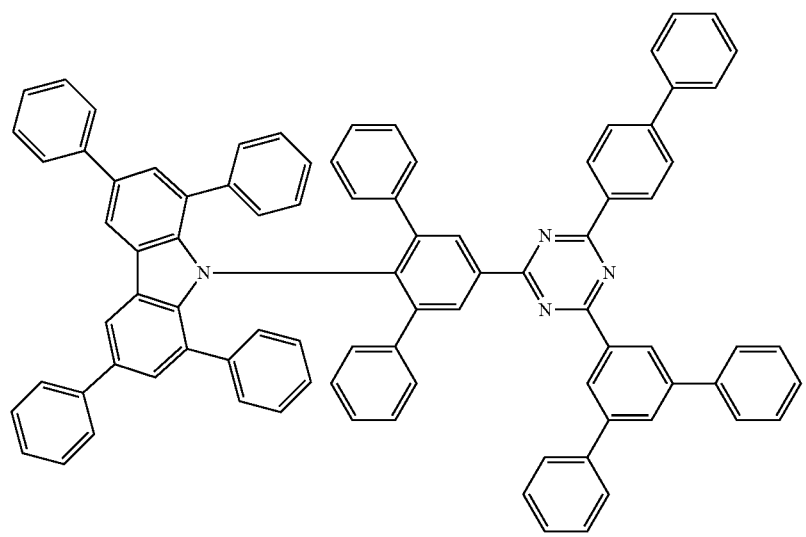

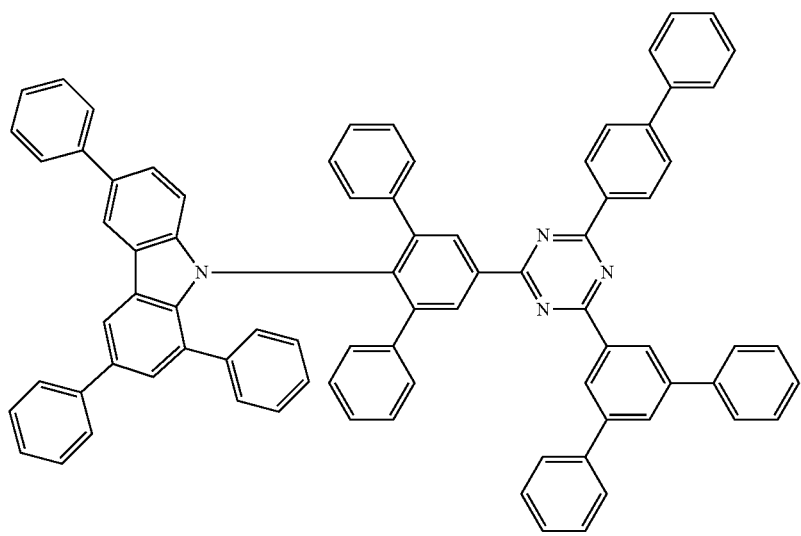
894
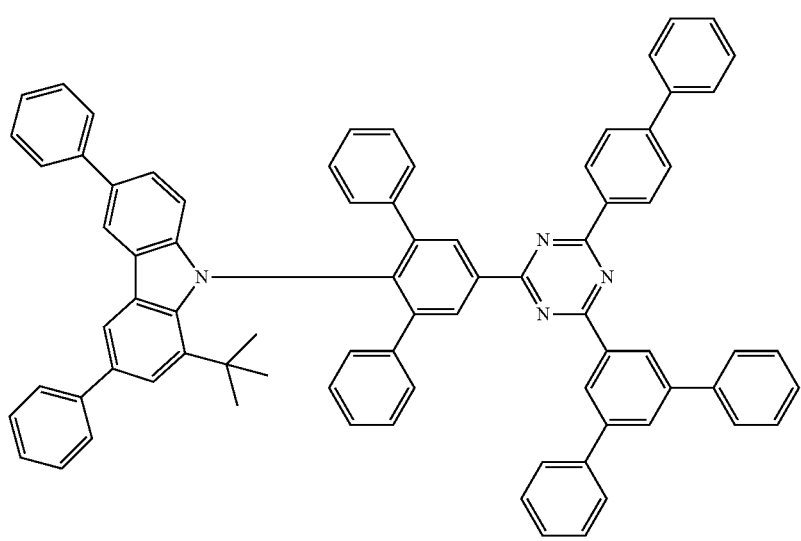
895
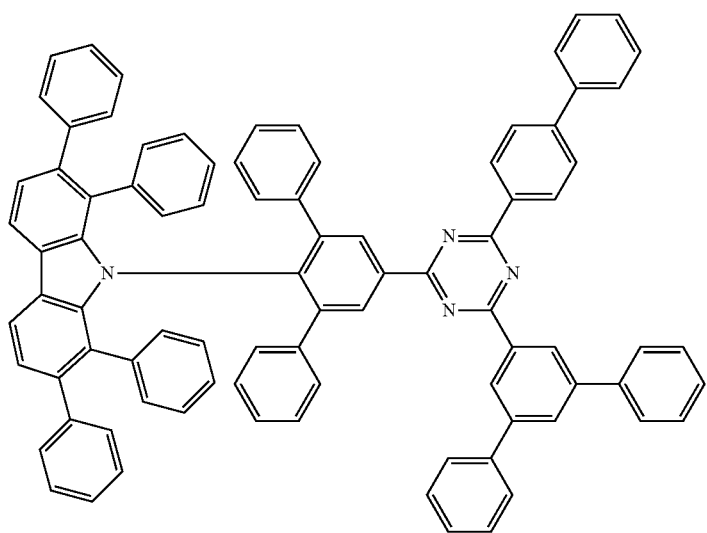
896

-continued
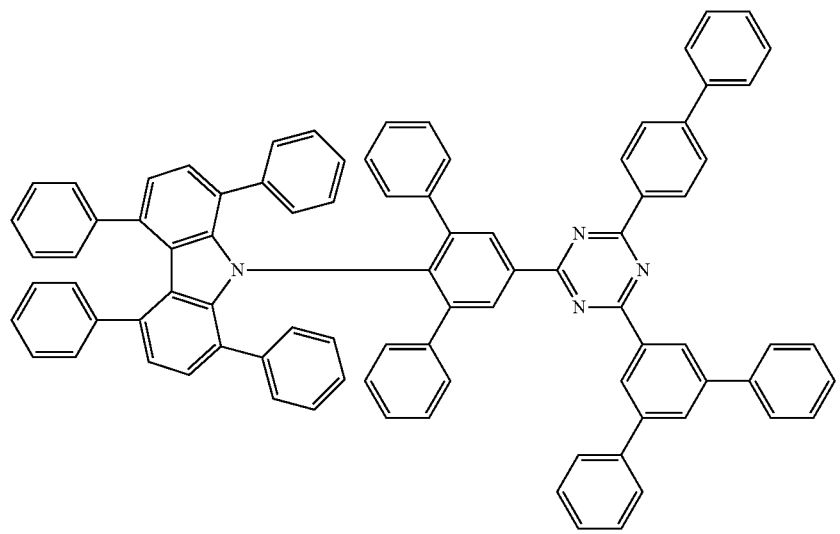
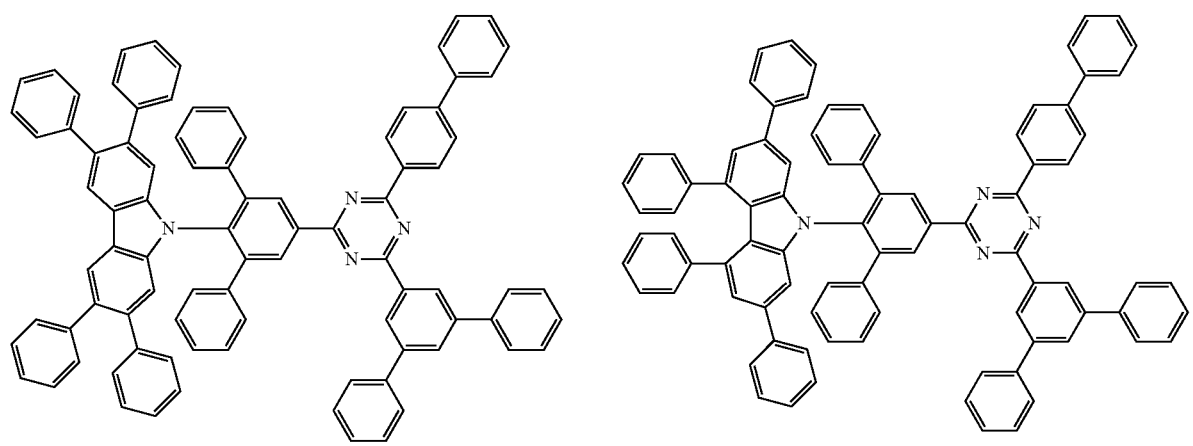
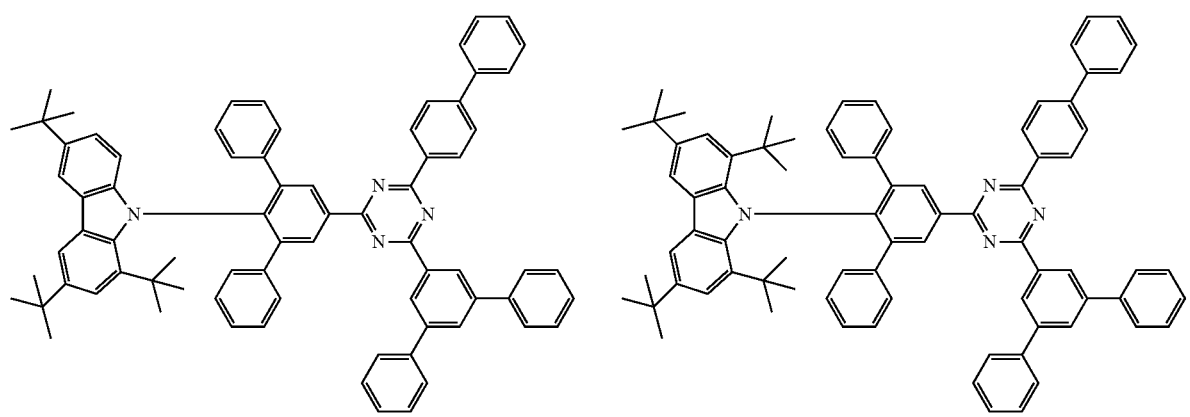

-continued
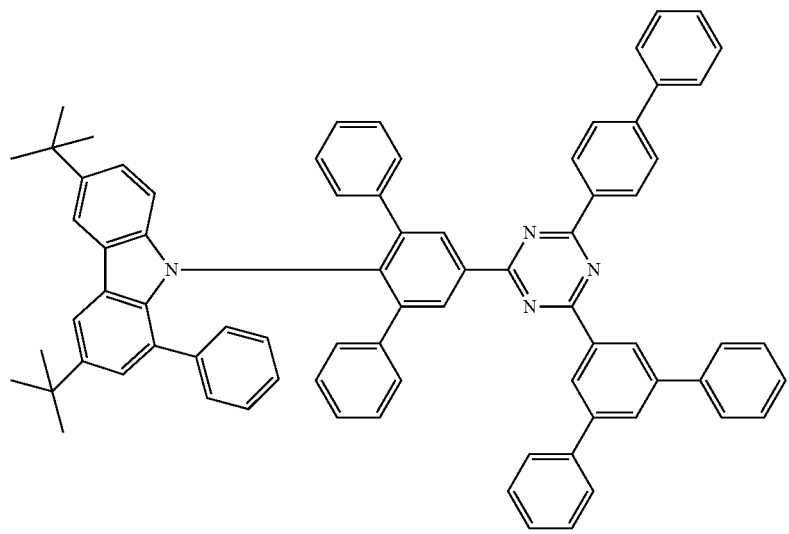
902
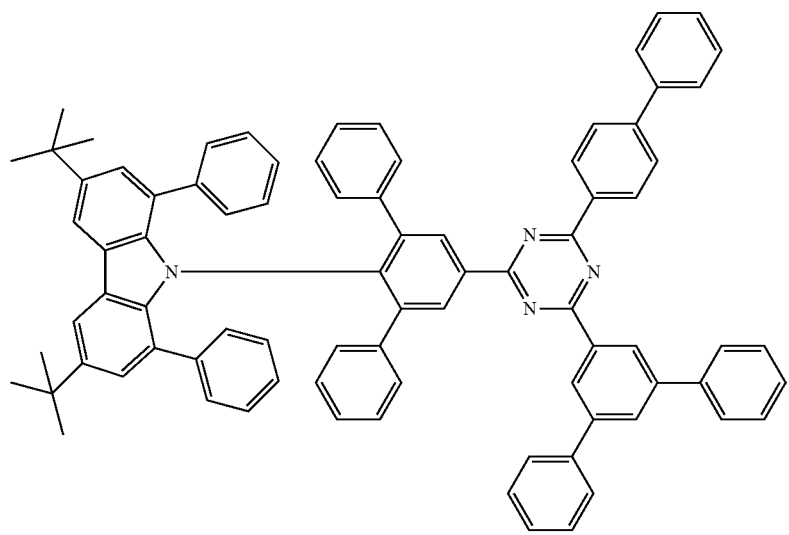
903
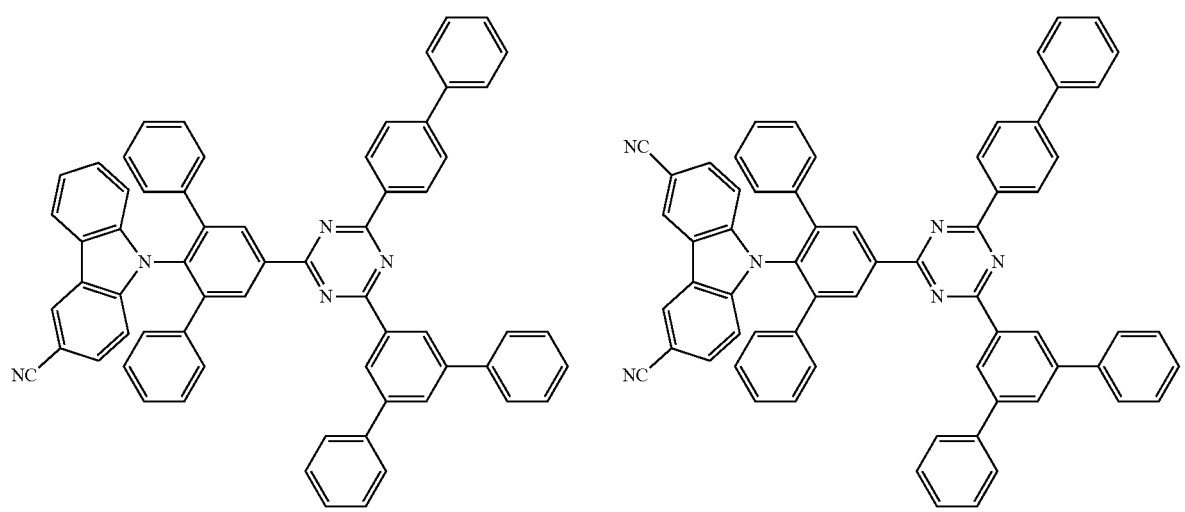
904 905

-continued
906
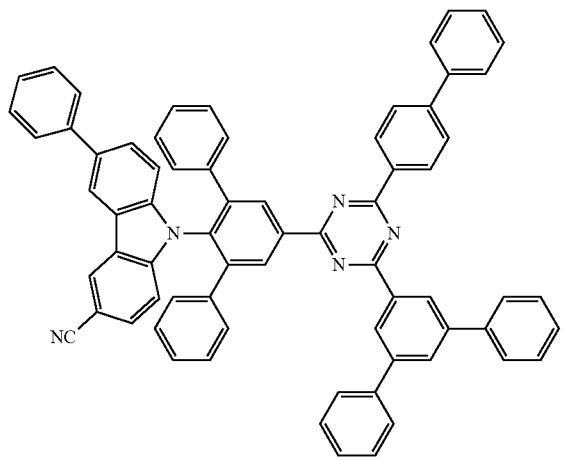
907
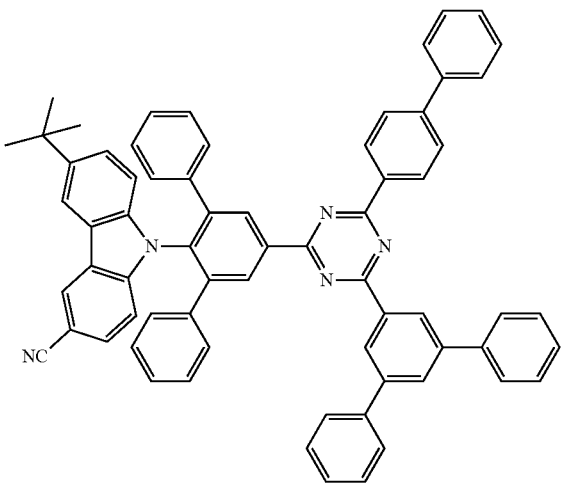
908
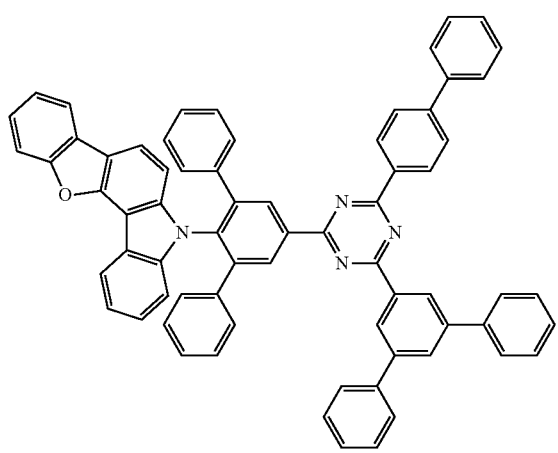
909
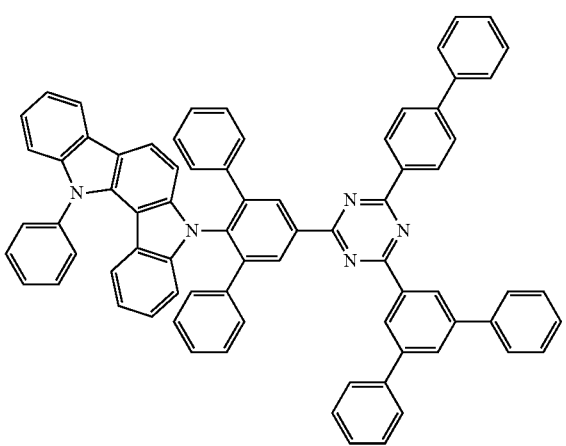
910
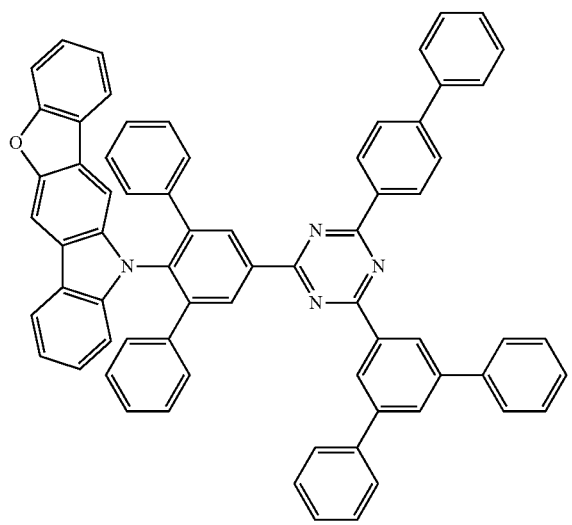
911
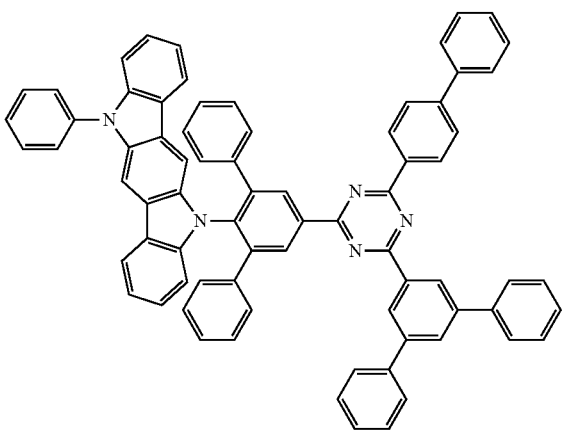

-continued
912
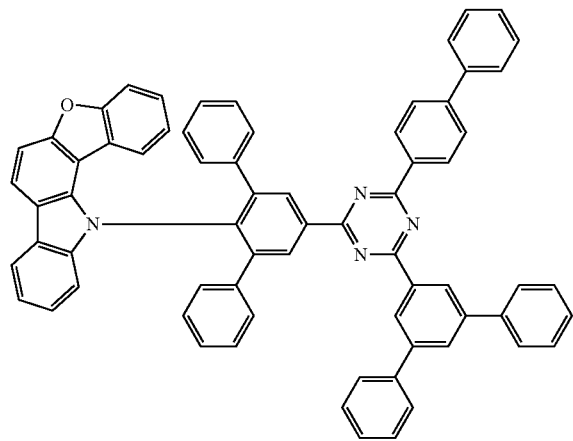
913
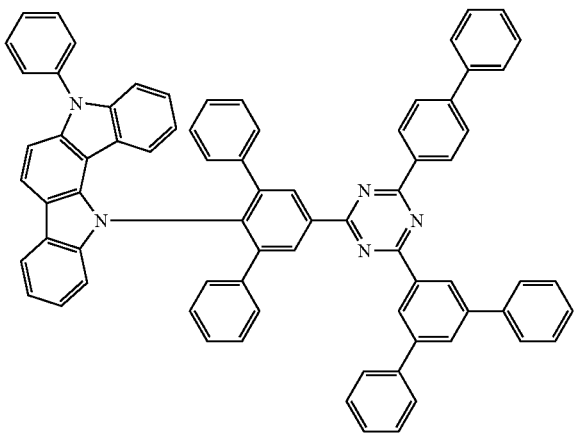
914
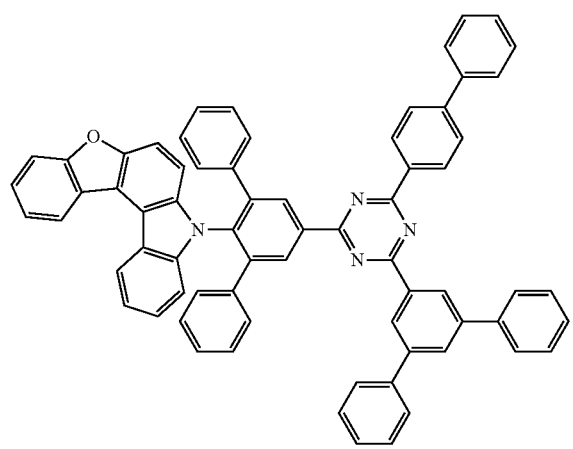
915
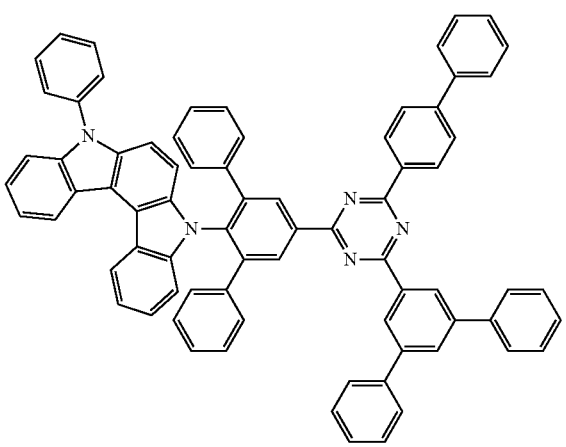
916
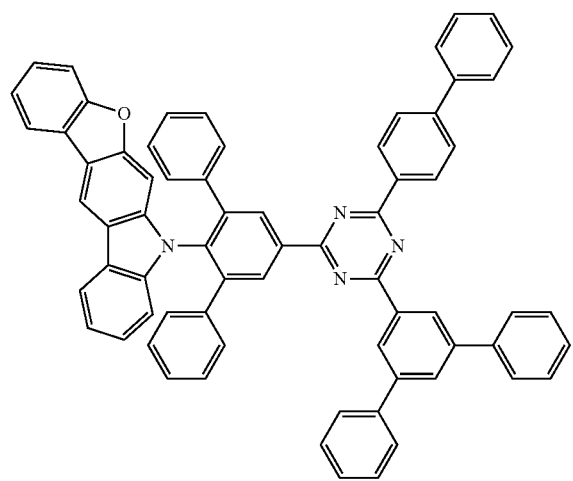
917
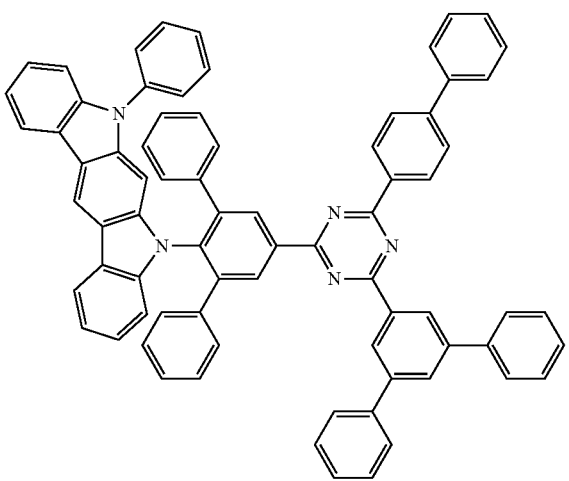

-continued
477
918
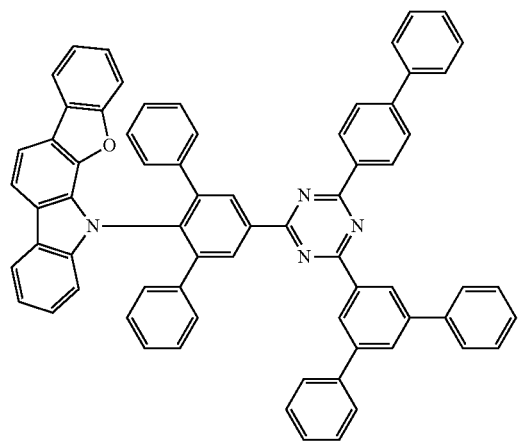
920
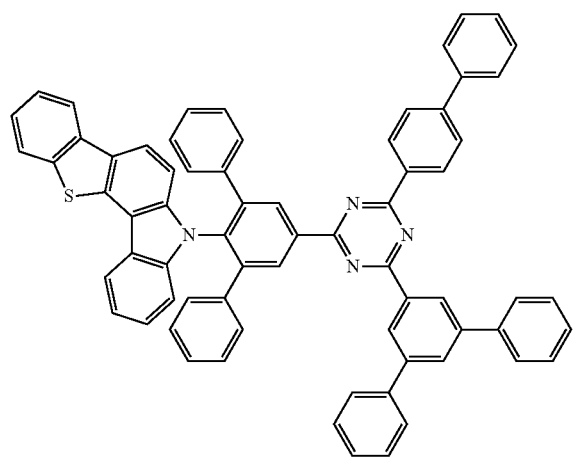
922
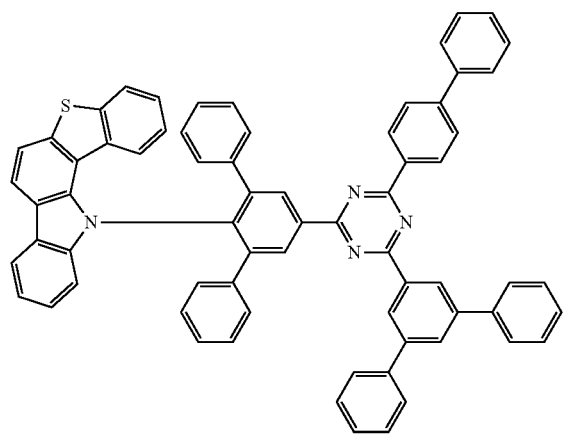
478
919
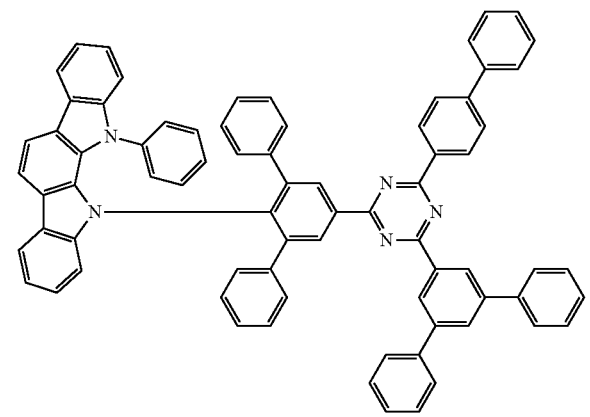
921
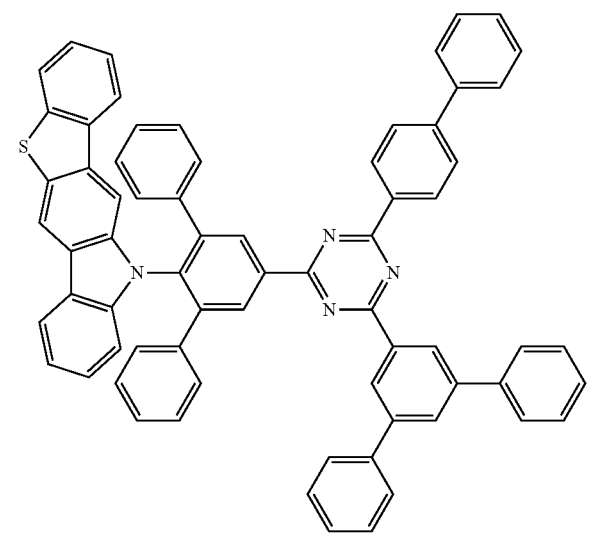
923
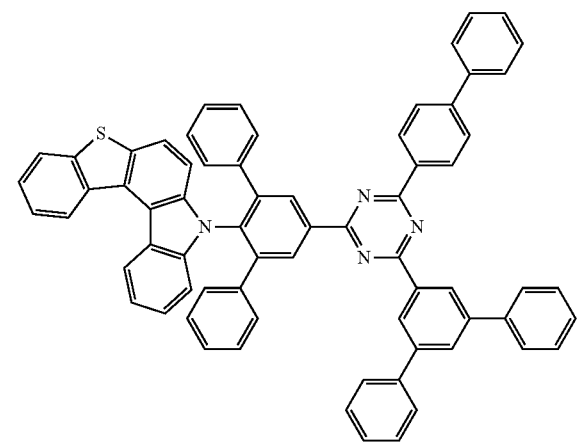

-continued
924
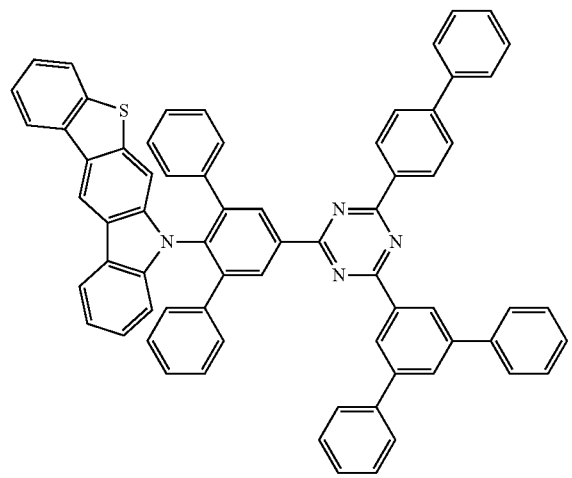
925
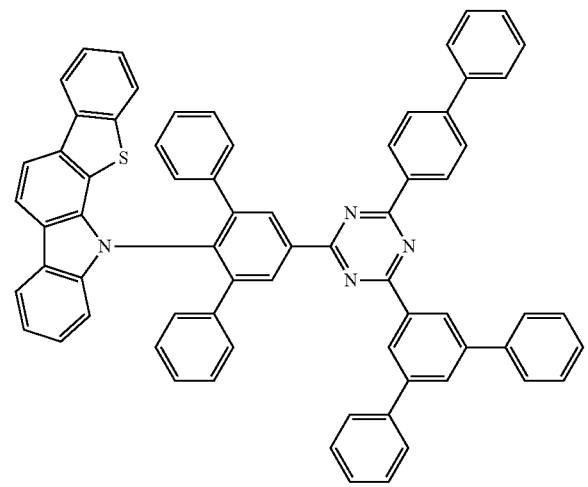
926
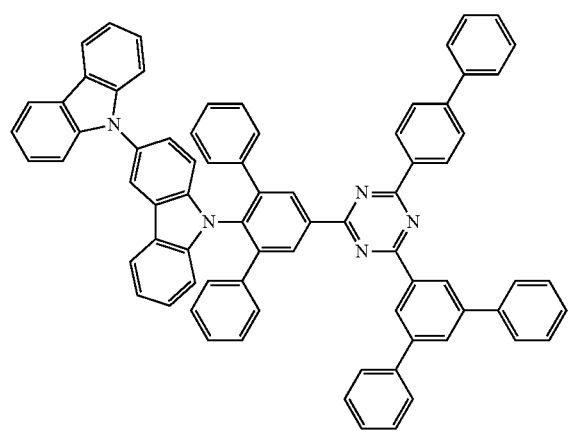
927
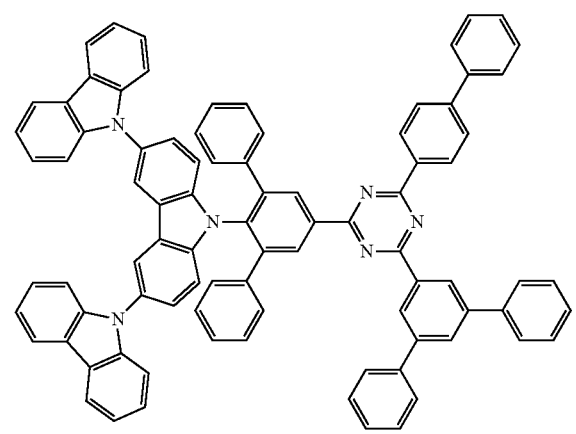
928
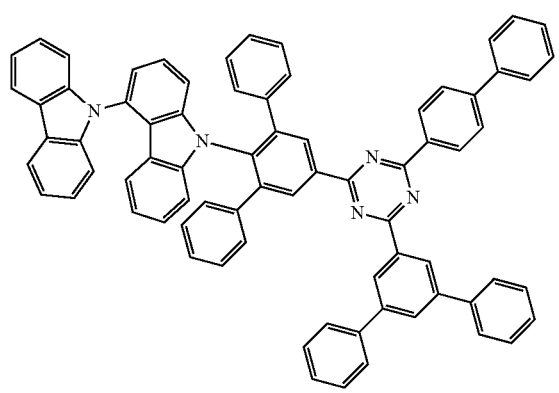
929
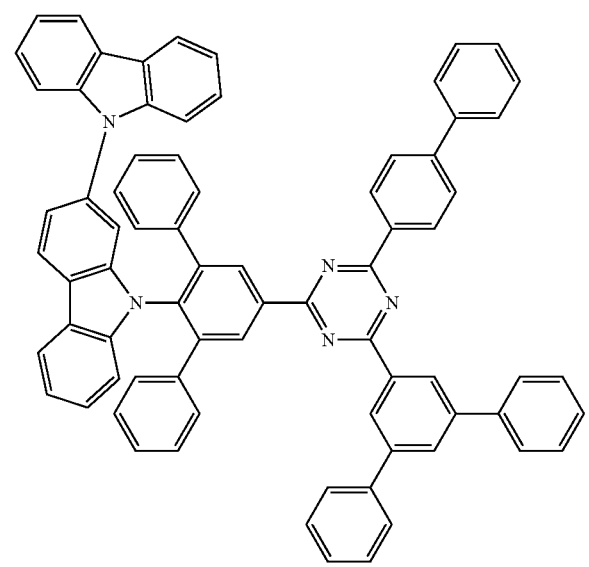

-continued
930
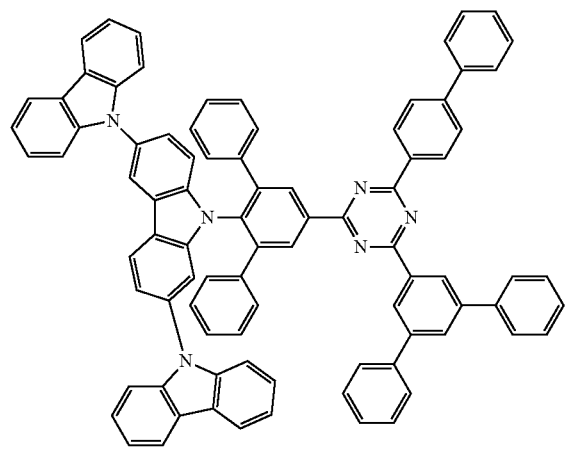
931
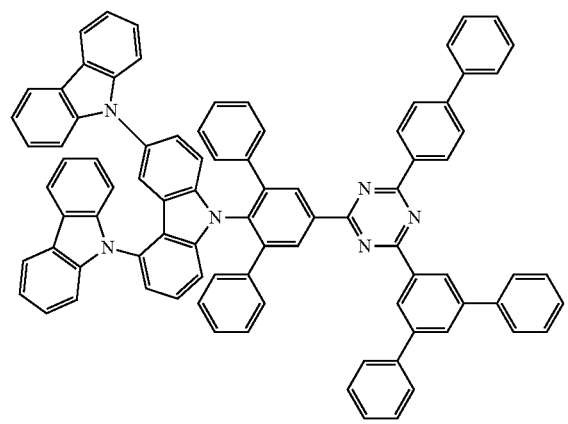
932
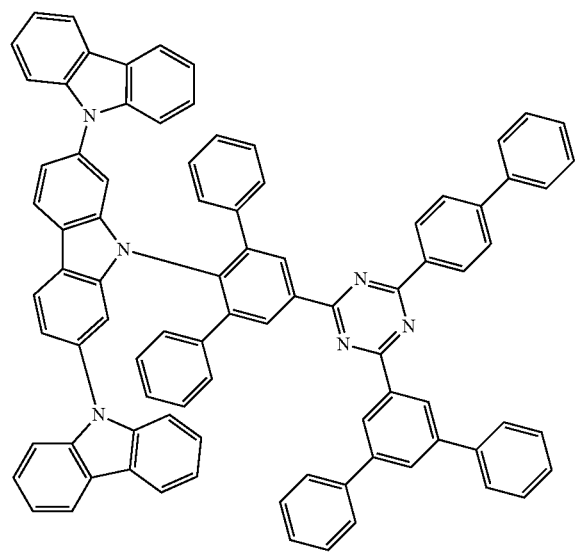
933
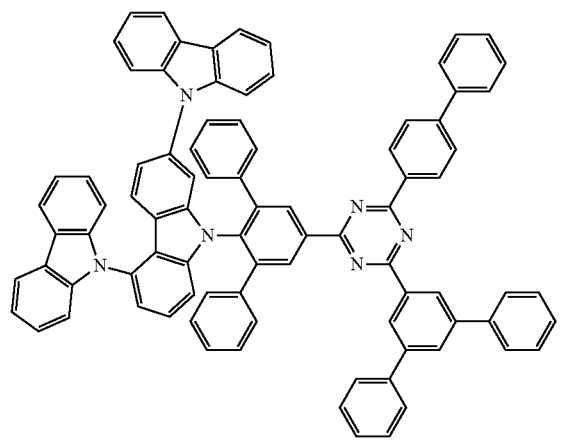
934
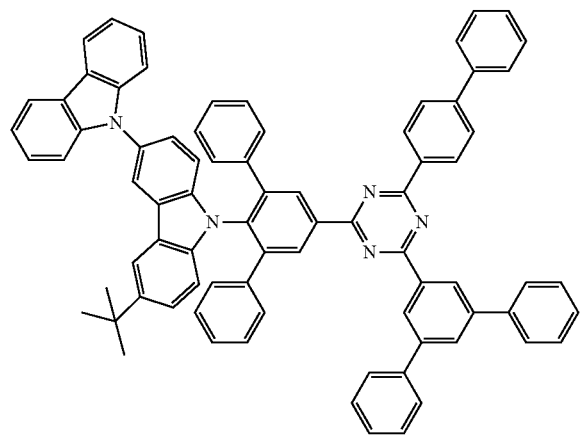
935
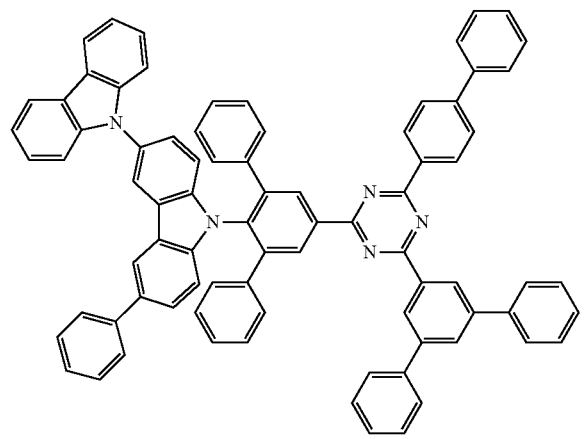

-continued
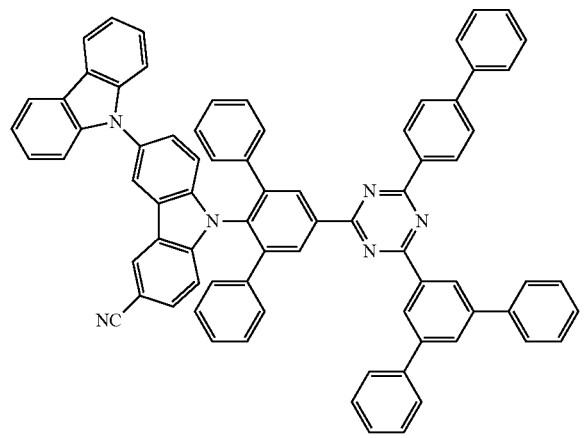
936
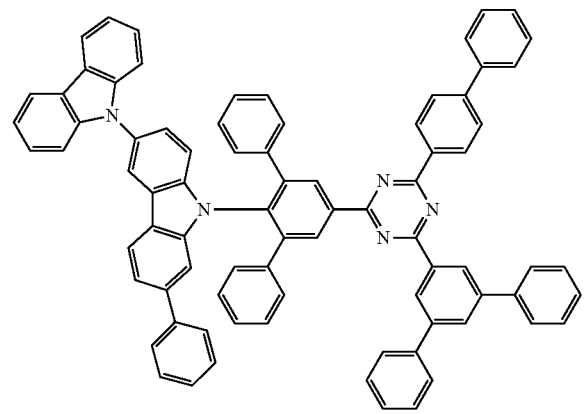
937
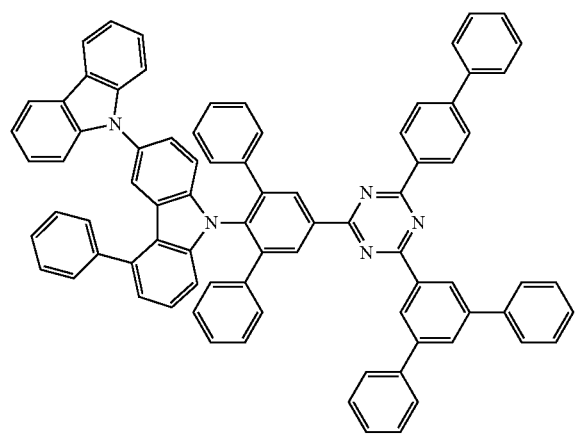
938
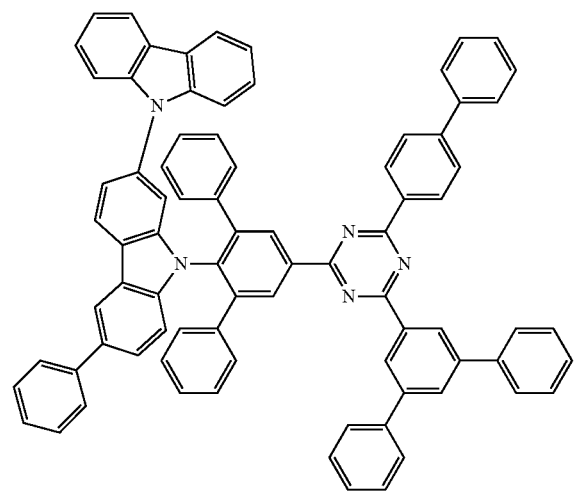
939
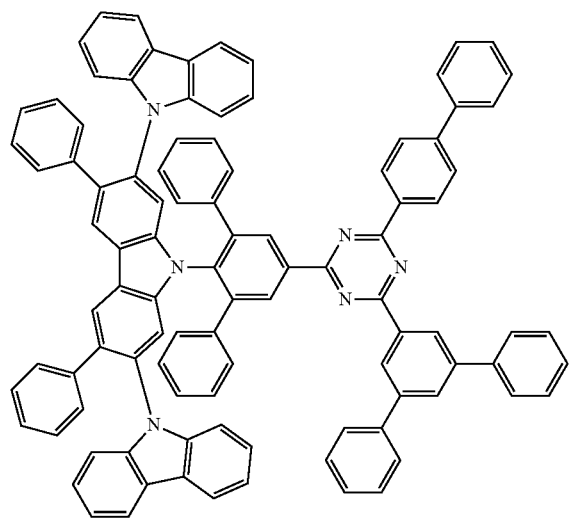
940
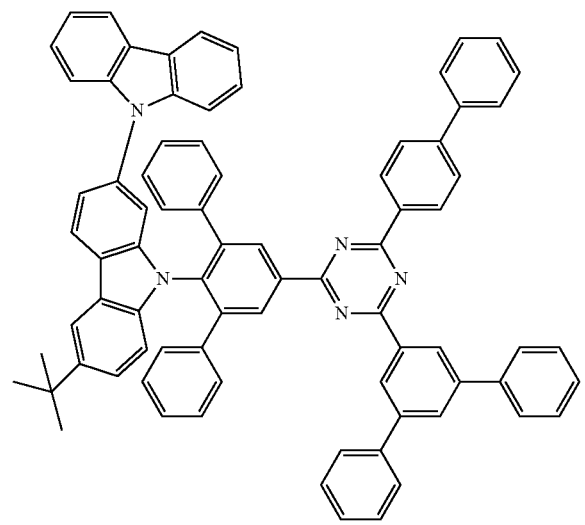
941

-continued
942
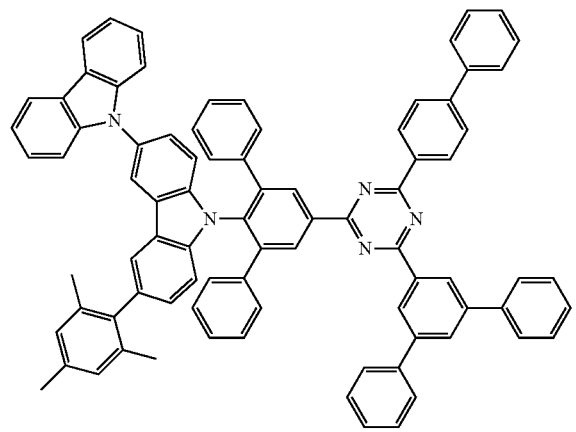
943
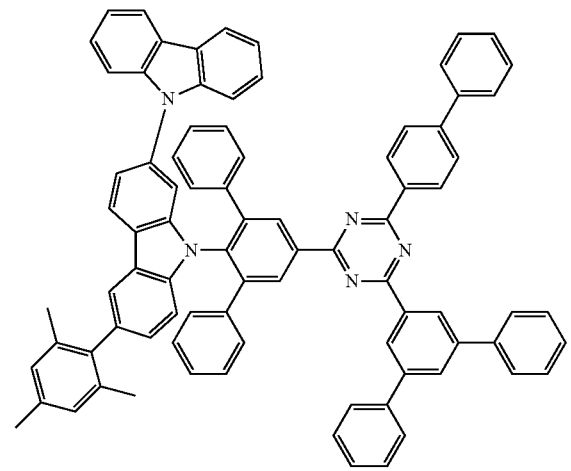
944
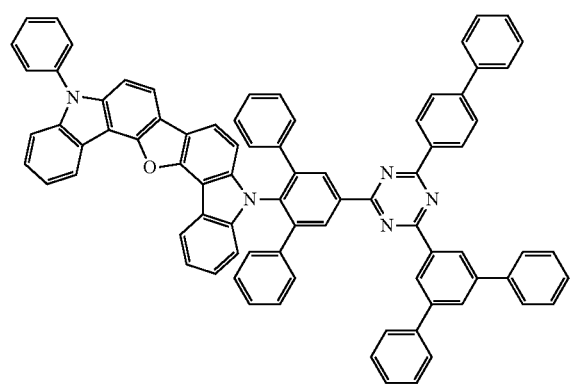
945
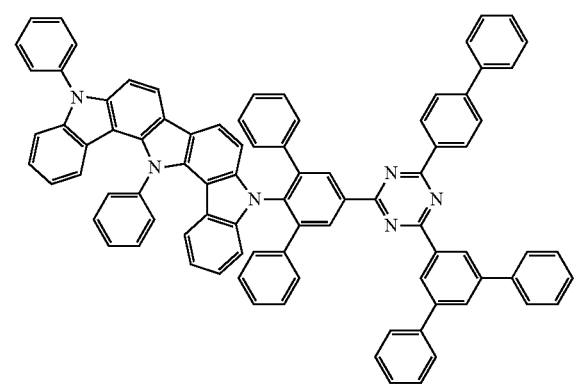
946
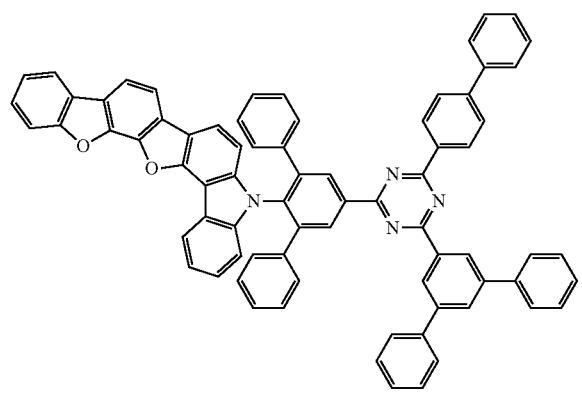
947
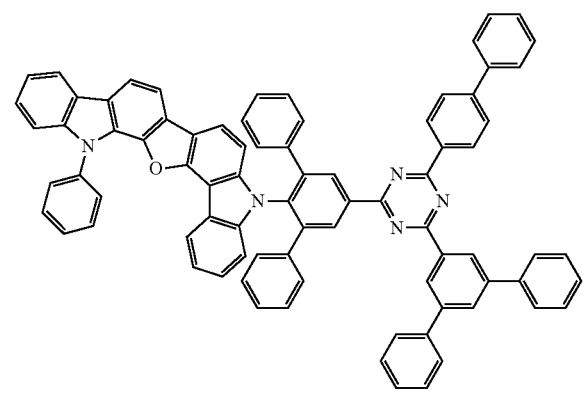

948
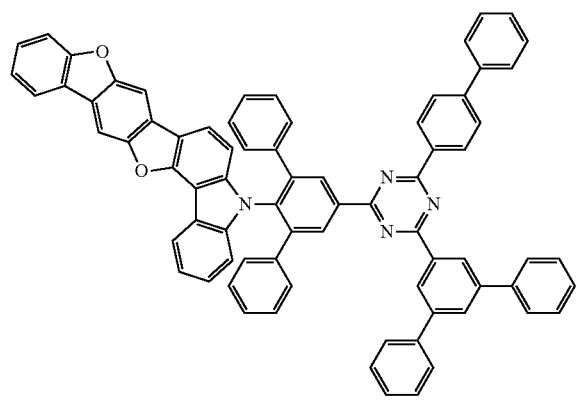
949
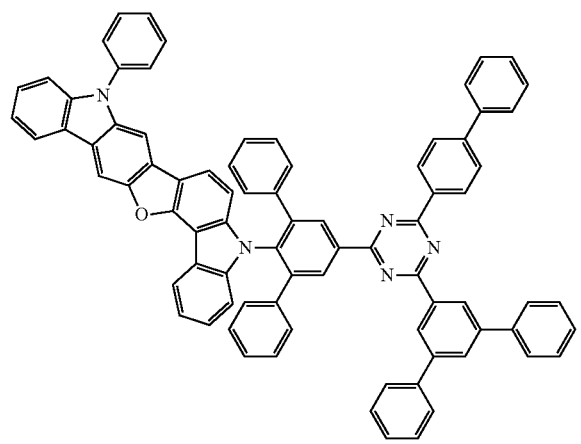
950
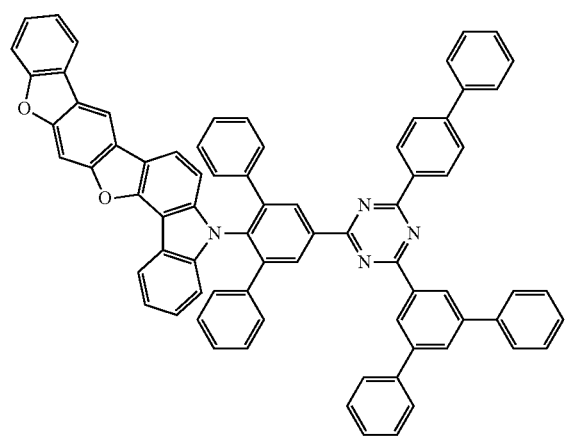
951
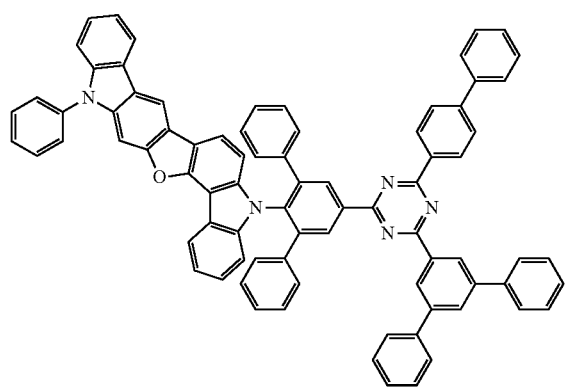
952
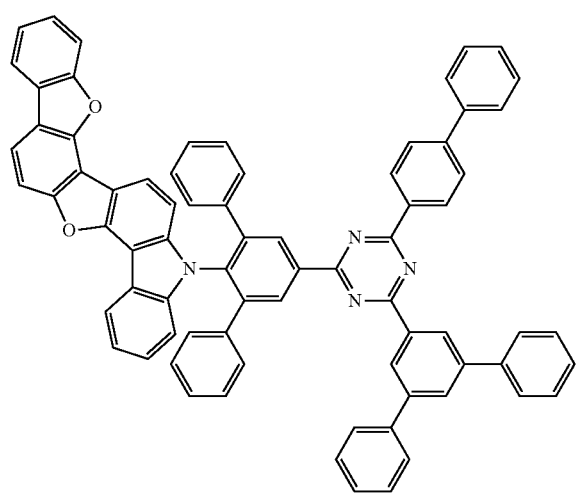
953
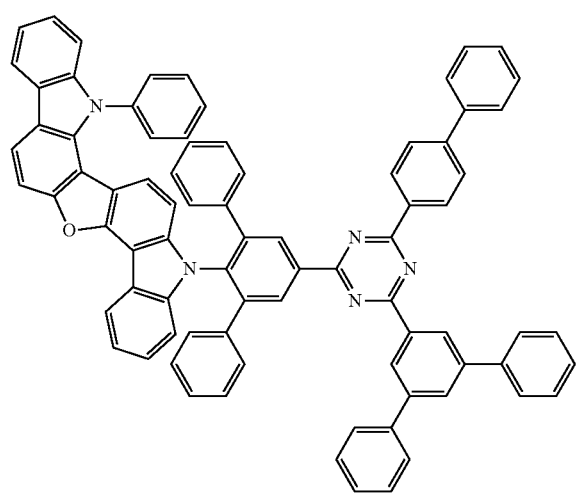

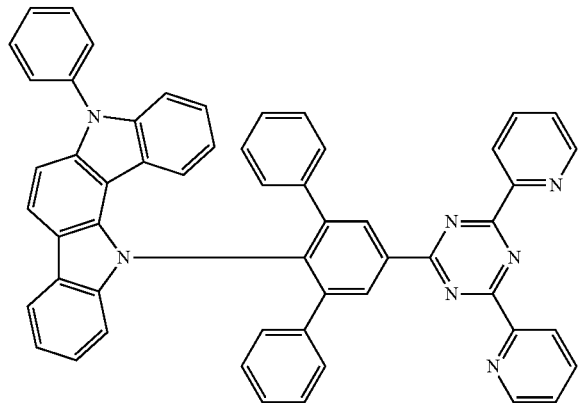
954
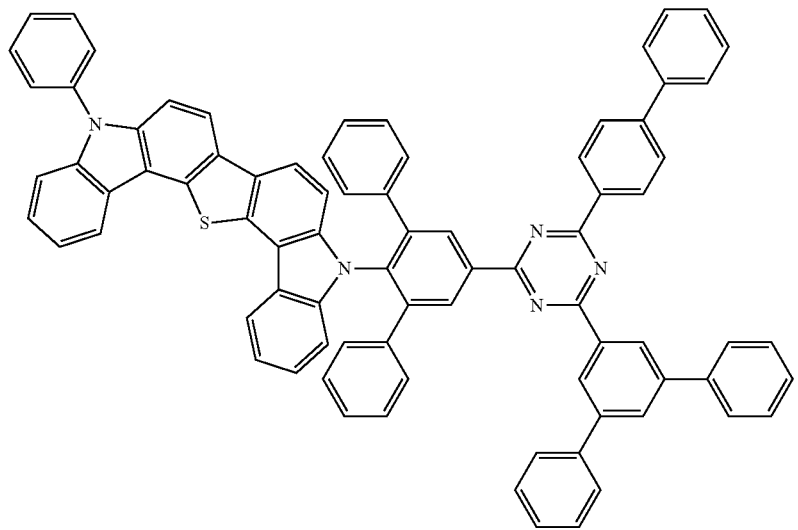
955
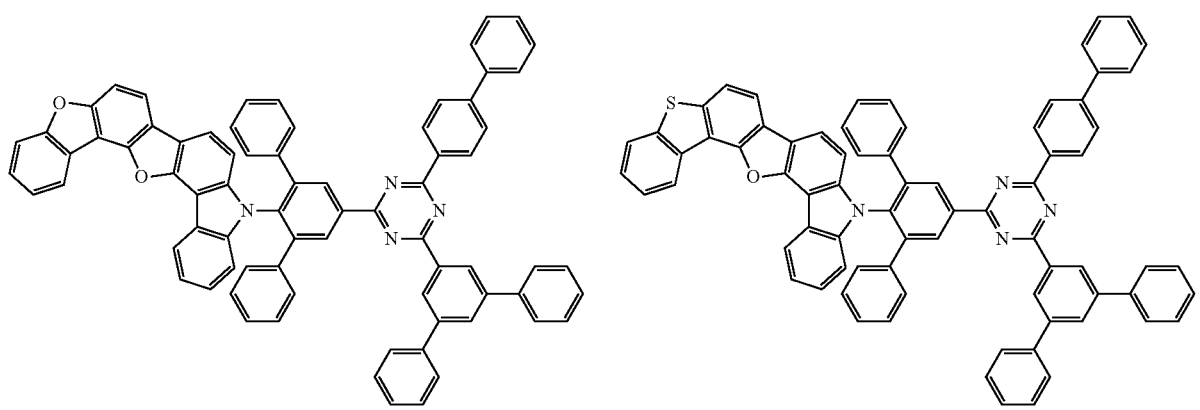
956 957

-continued
958
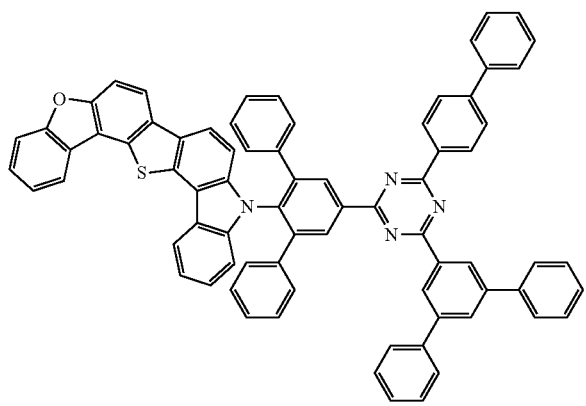
959
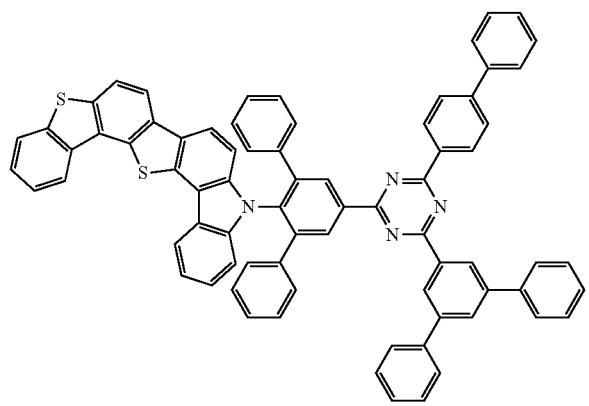
960
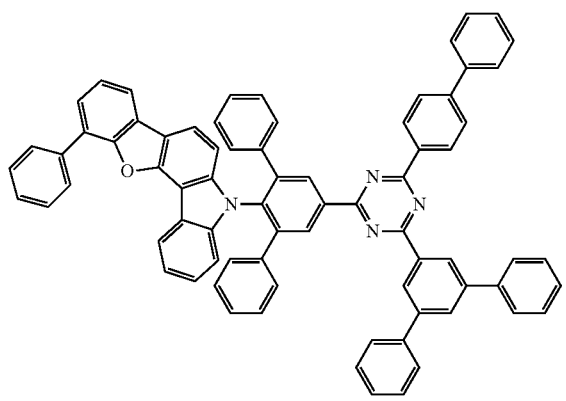
961
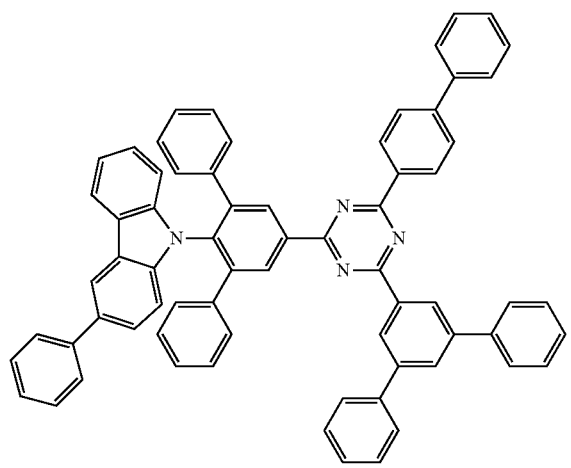
962
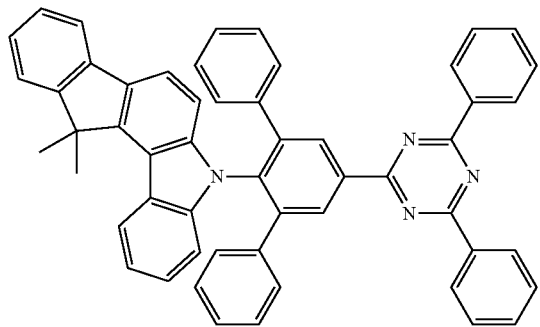
963
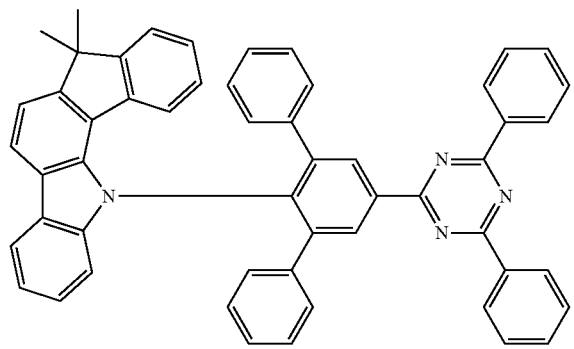

964
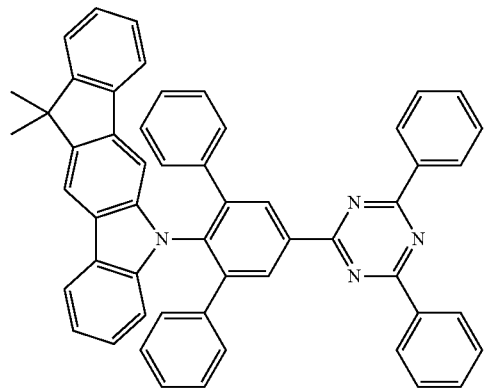
965
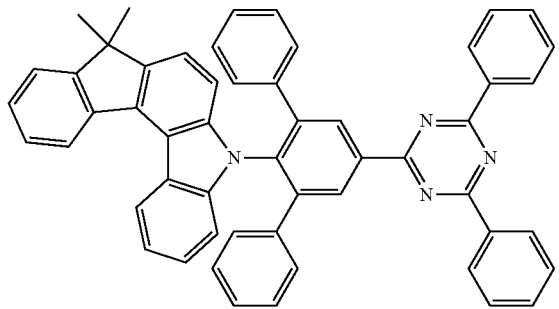
966
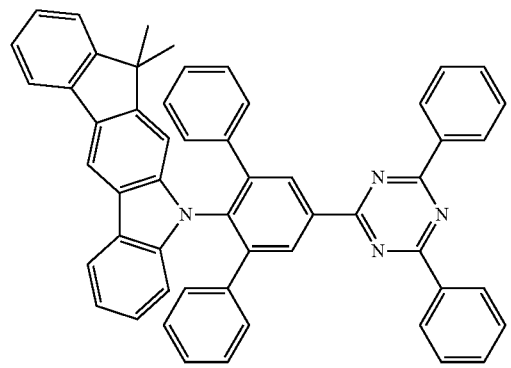
967
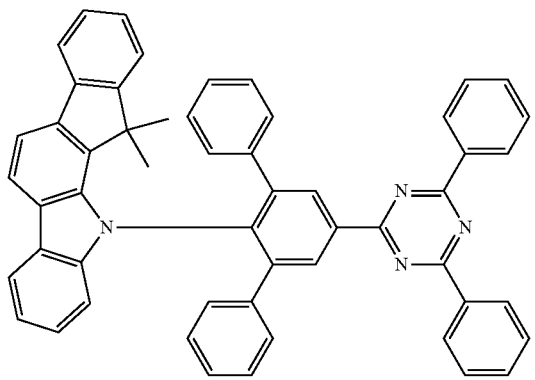
968
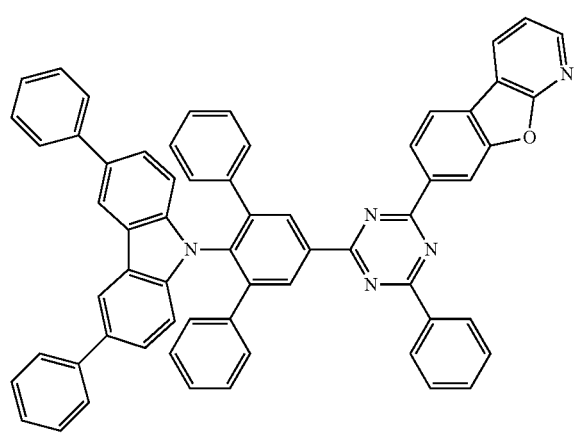
969
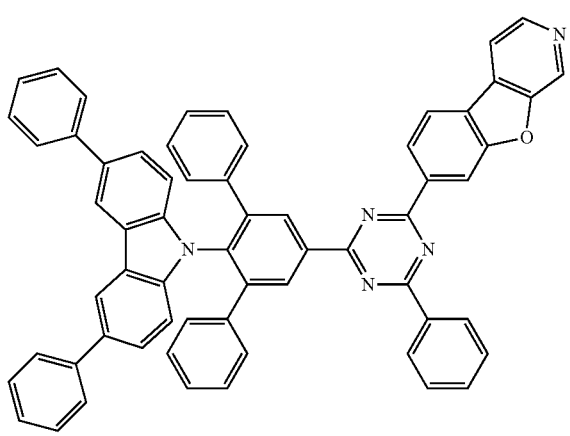

-continued
970
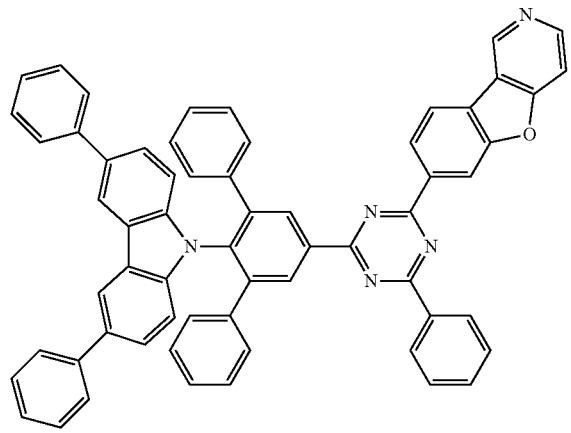
971
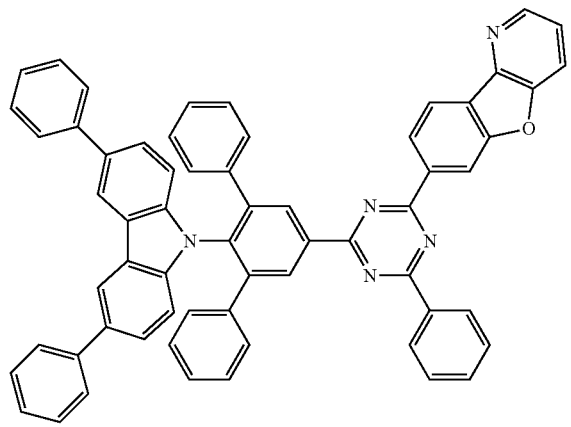
972
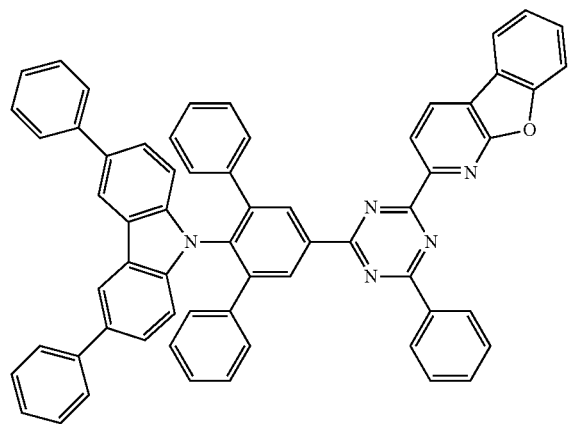
973
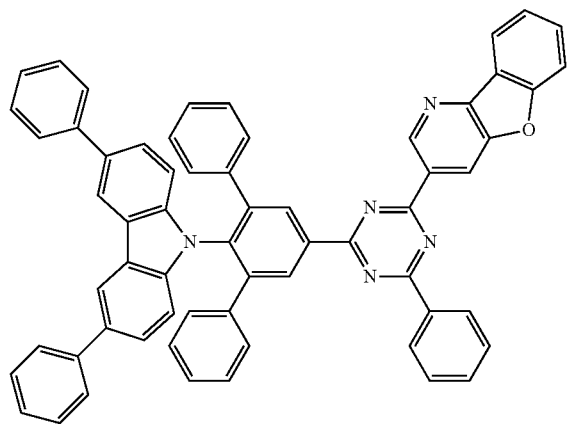
974
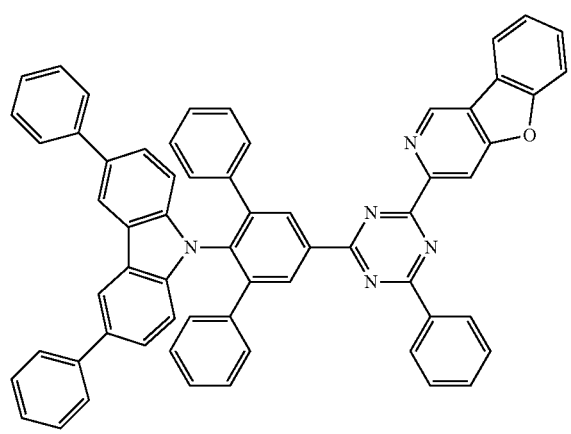
975
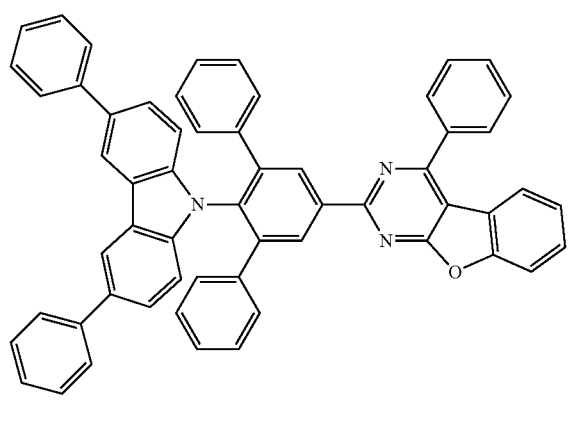

-continued
976
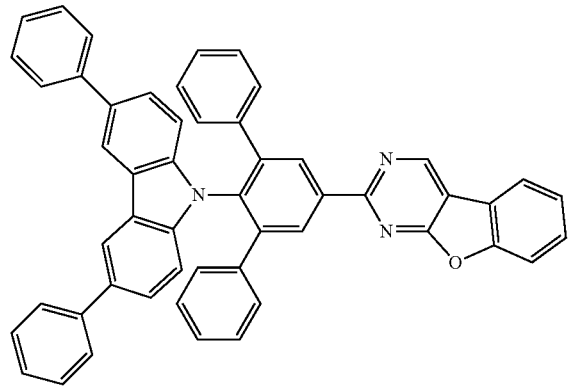
977
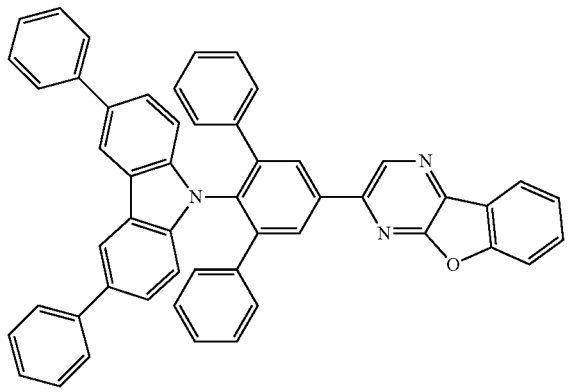
978
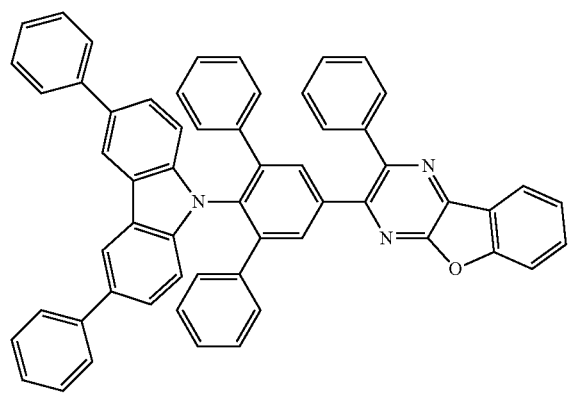
979
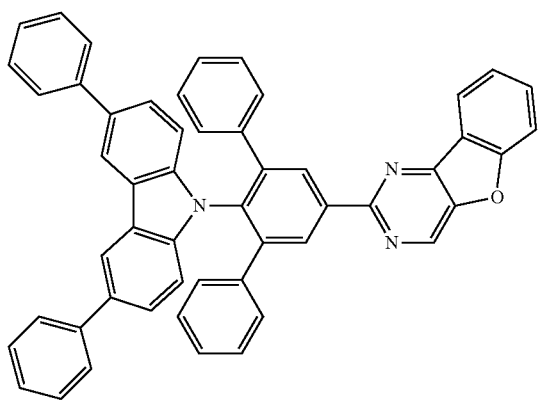
980
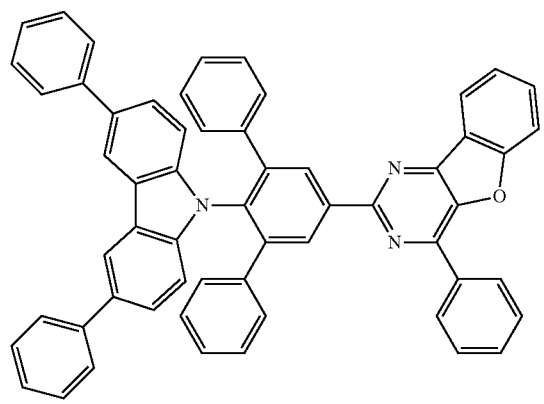
981
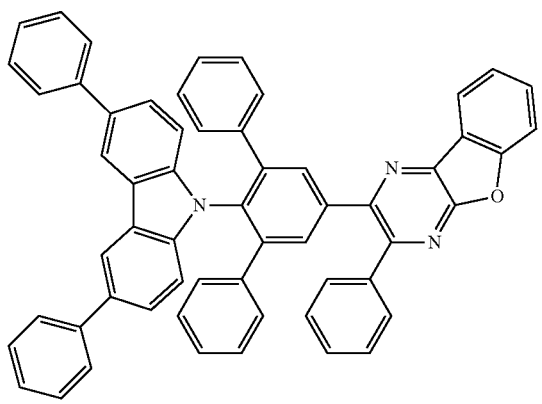
982
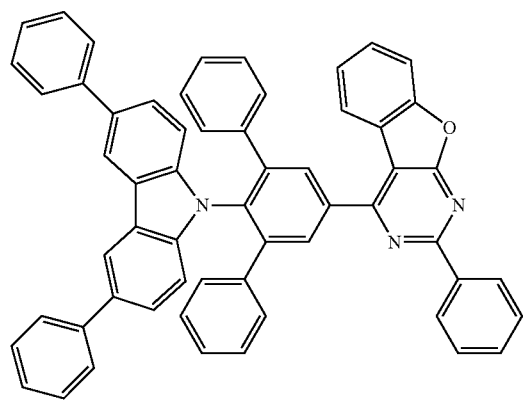
983
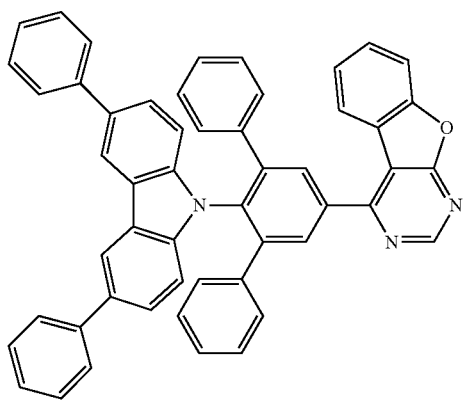

-continued
| 984 | 985 |
|---|---|
| 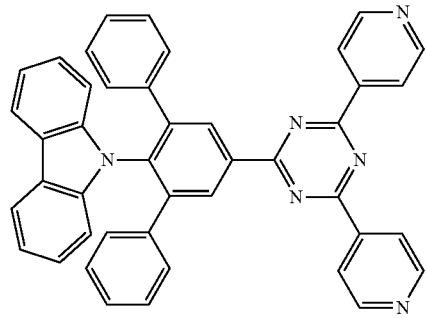 | 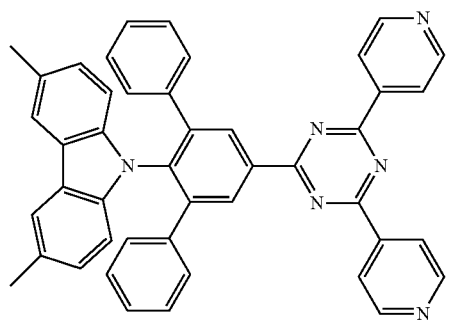 |
| 986 | 987 |
| 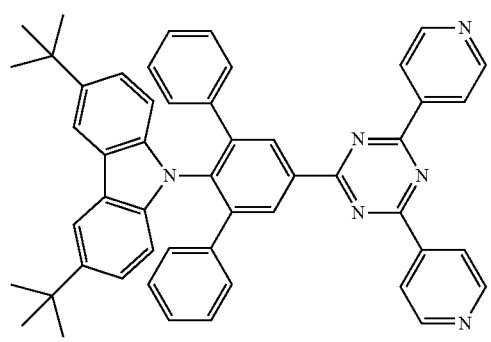 | 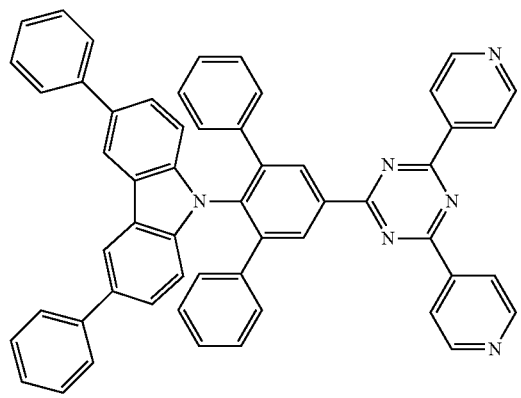 |
| 988 | 989 |
| 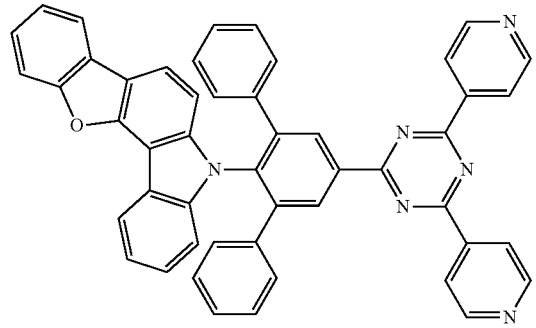 | 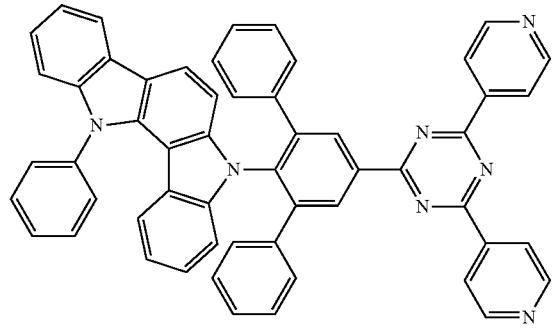 |
| 990 | 991 |
| 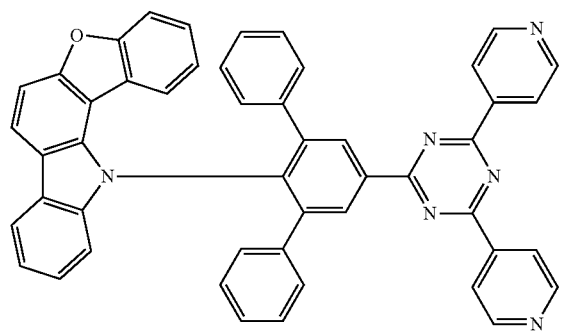 | 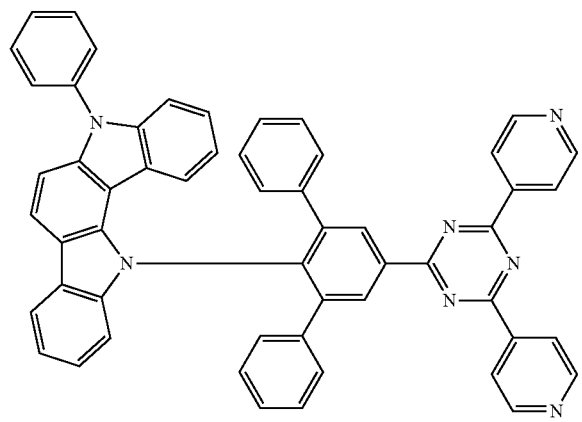 |

-continued
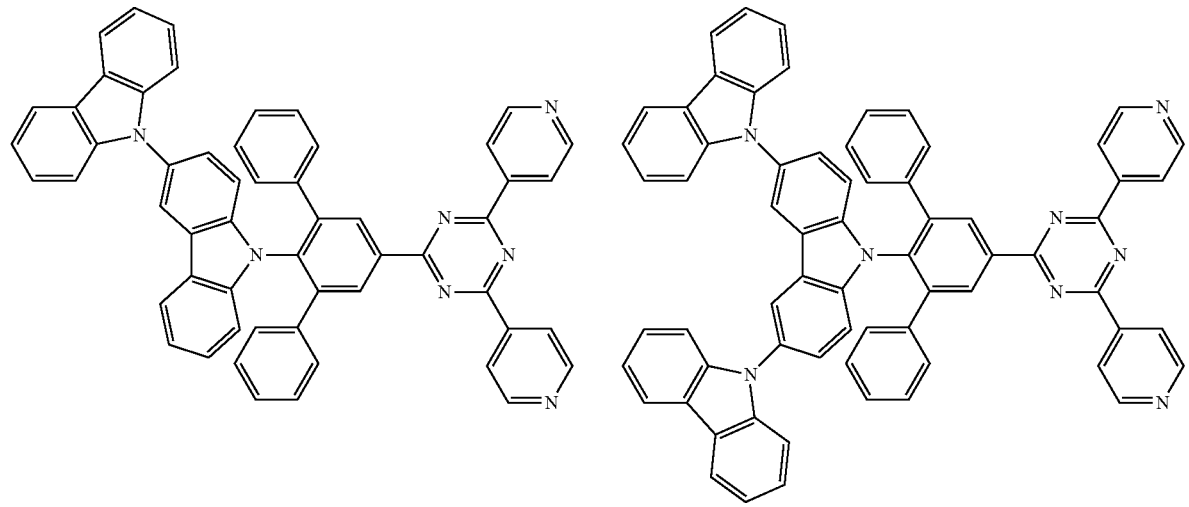
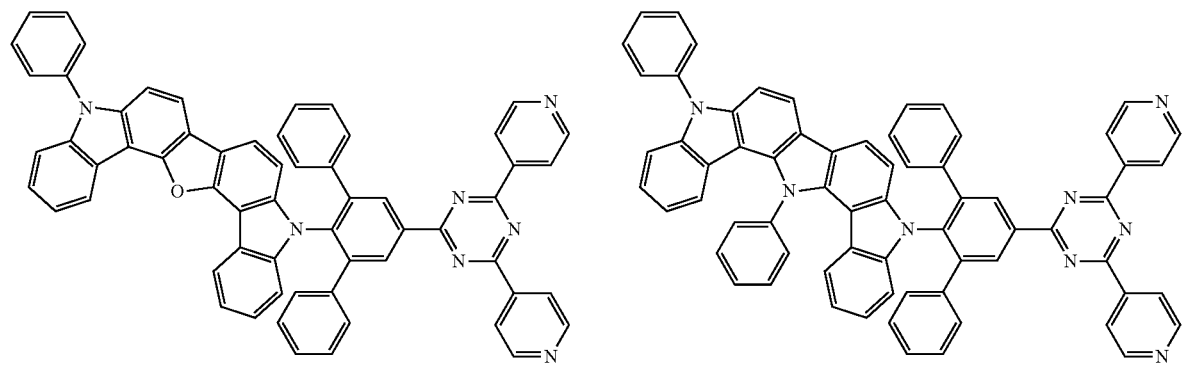
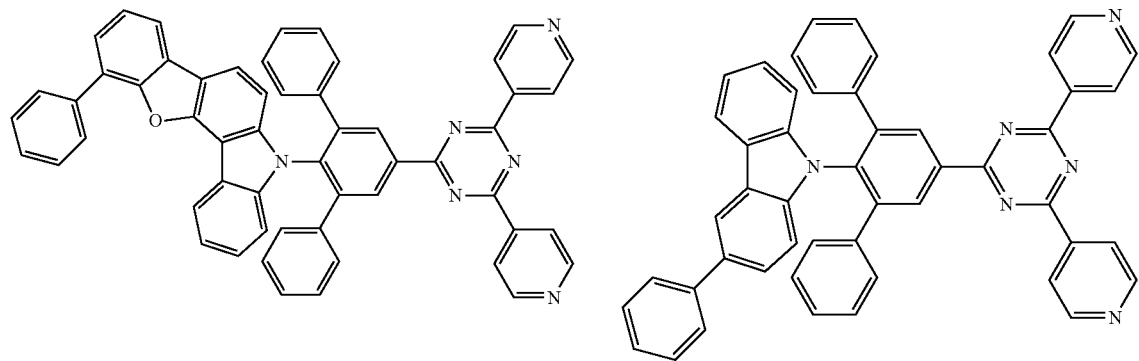

-continued
| 998 | 999 |
|---|---|
| 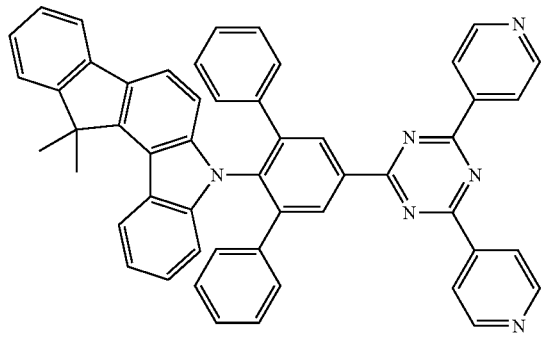 | 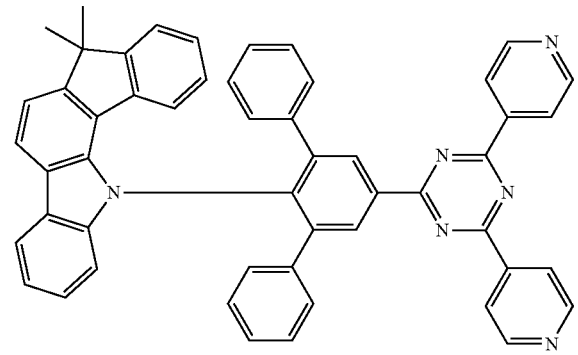 |
| 1000 | 1001 |
| 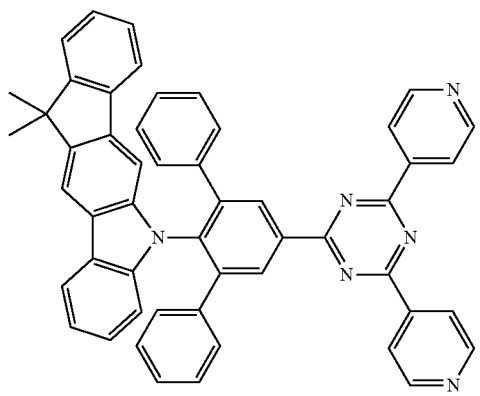 | 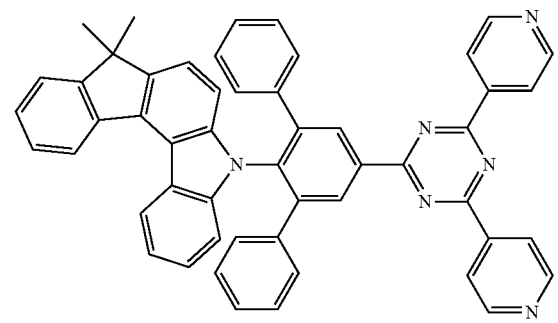 |
| 1002 | 1003 |
| 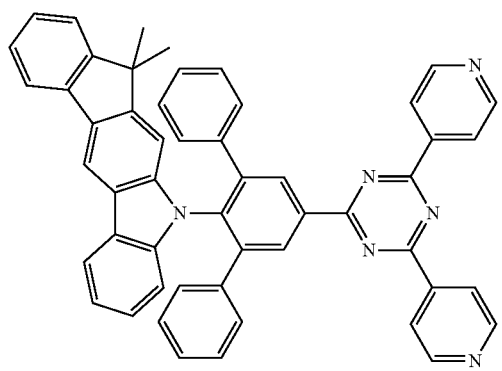 | 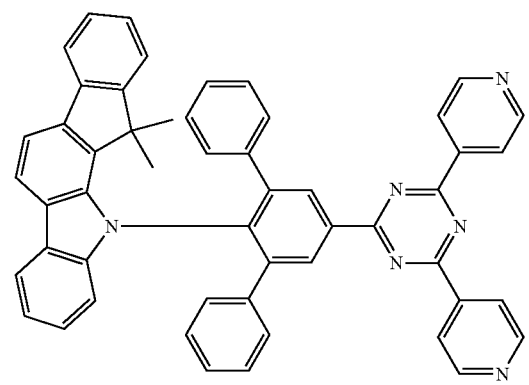 |
| 1004 | 1005 |
| 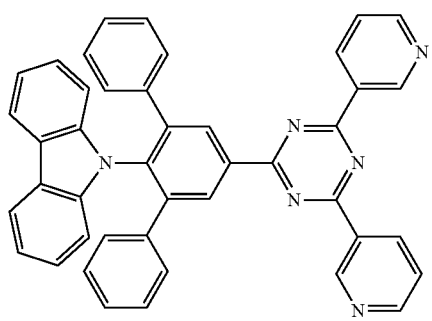 | 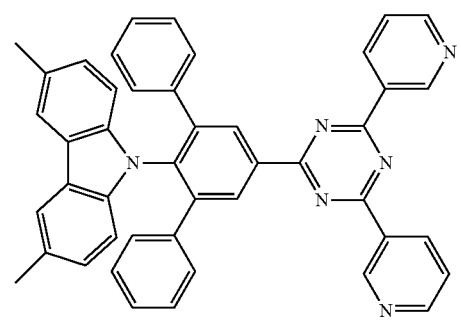 |

-continued

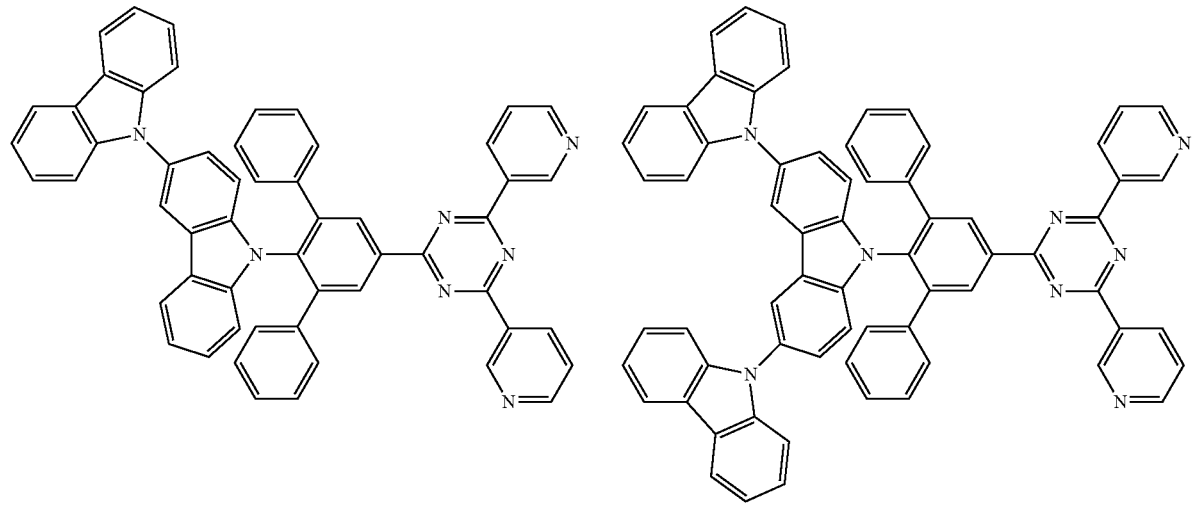
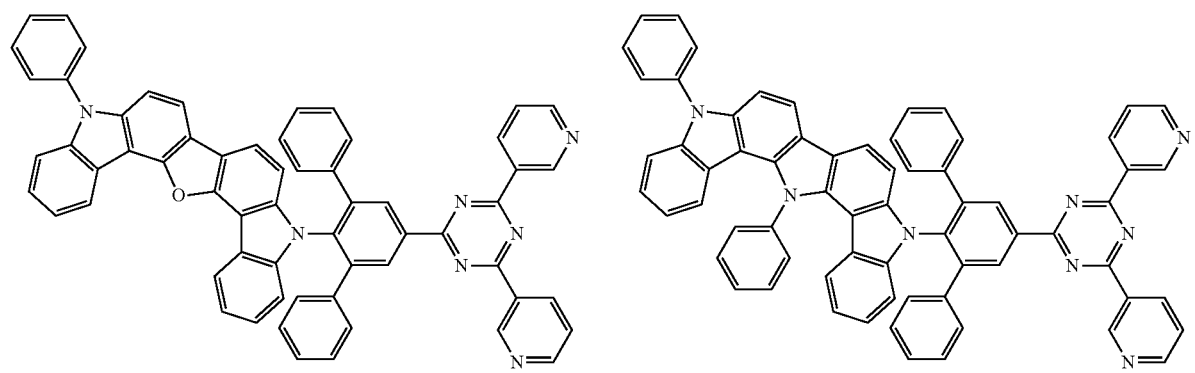
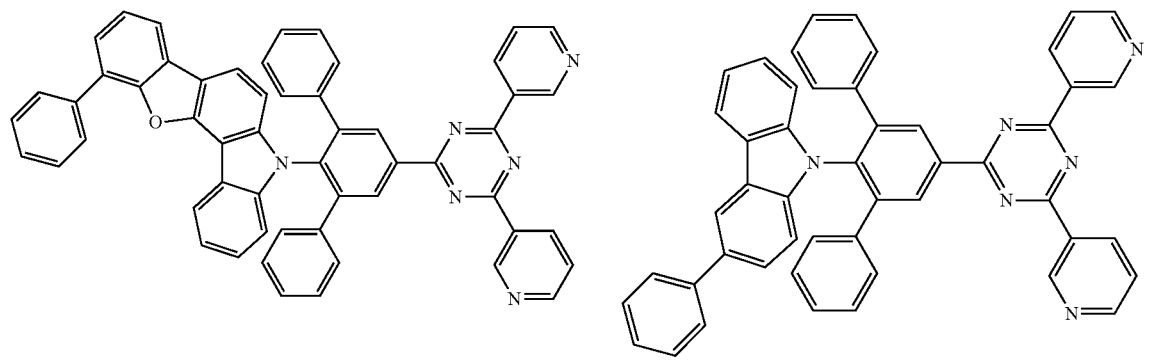

-continued
1018
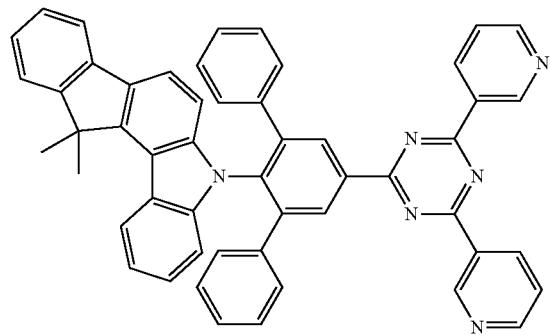
1019
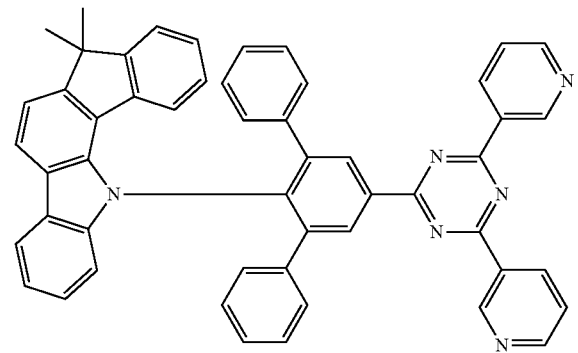
1020
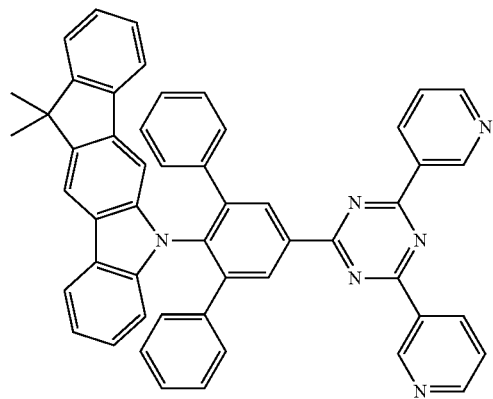
1021
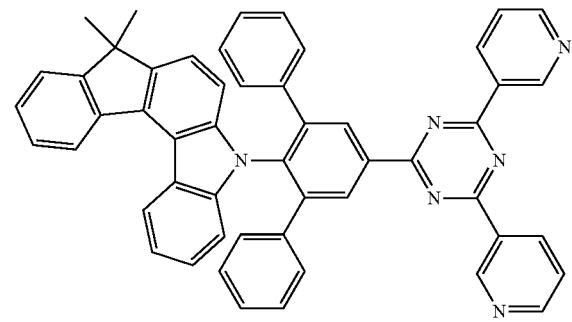
1022
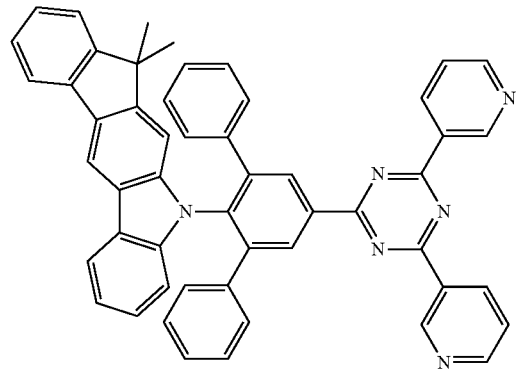
1023
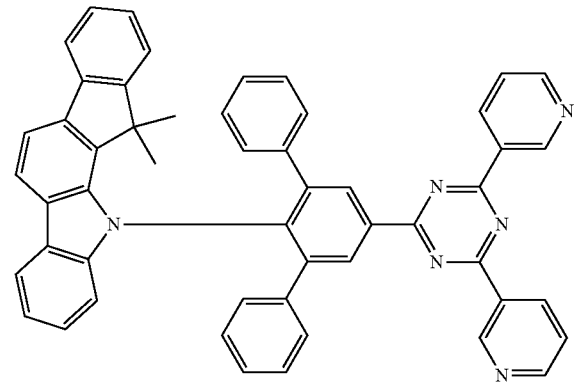
1024
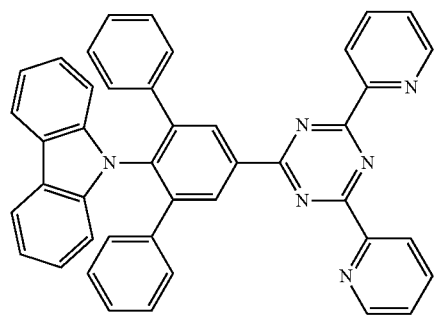
1025
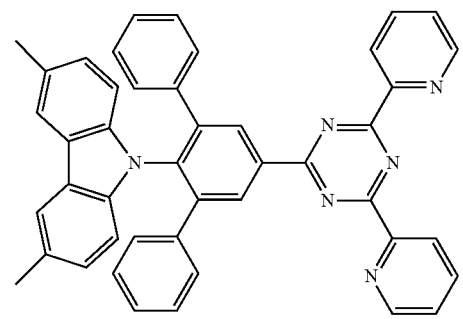

-continued
1026
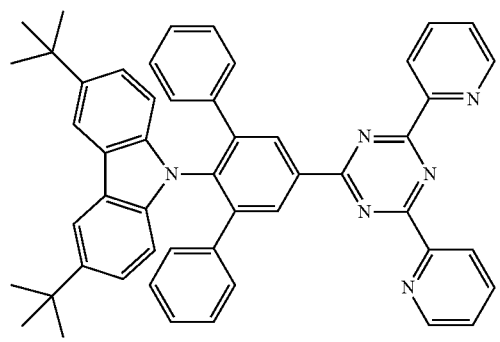
1027
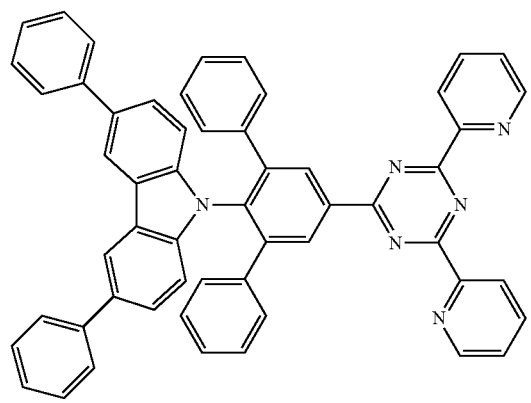
1028
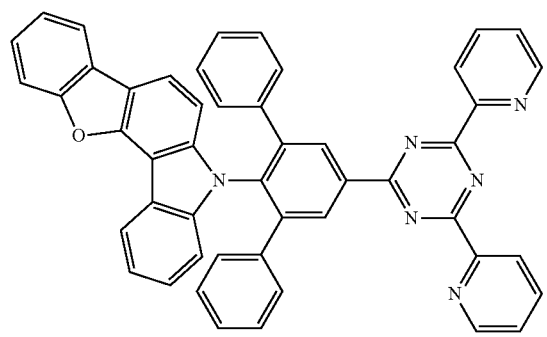
1029
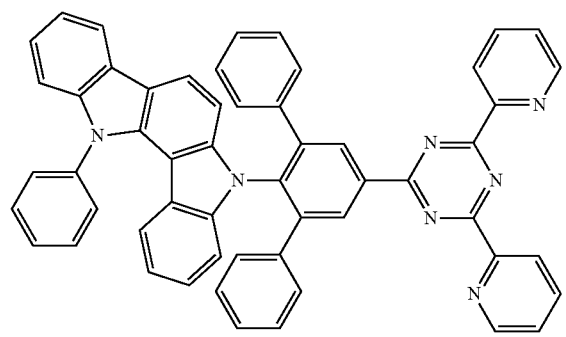
1030
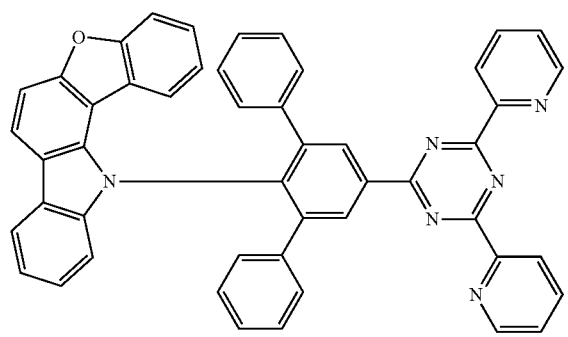
TD1
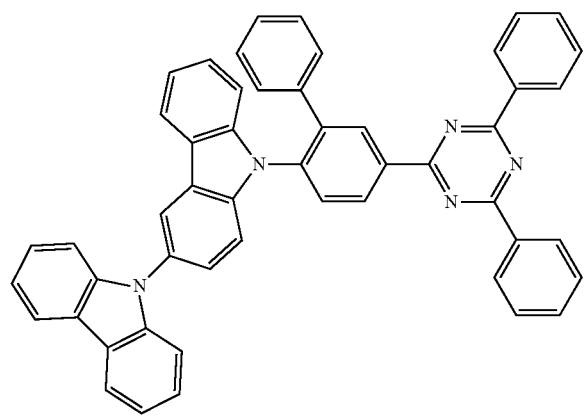
TD2
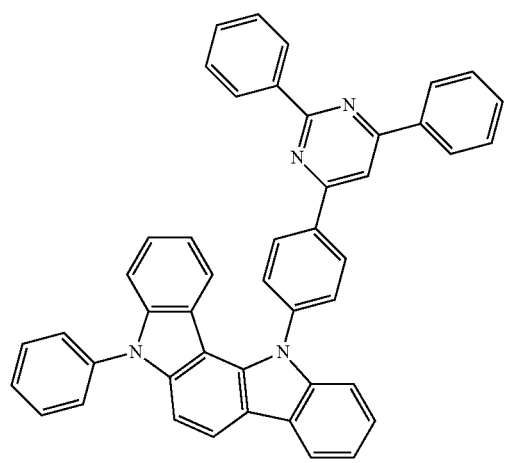
TD3
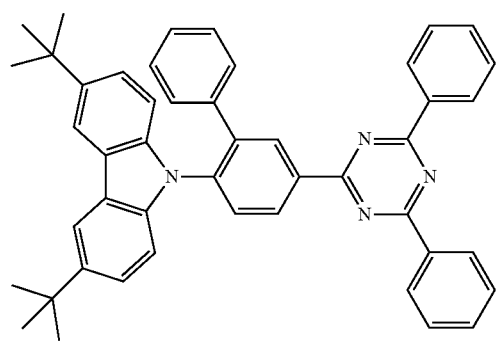

TD4

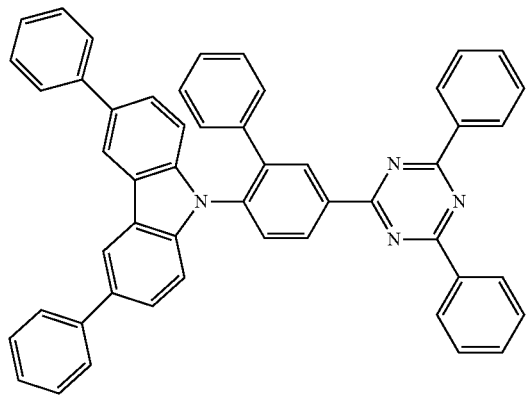

The emission layer including the host and the thermally activated delayed fluorescence emitter may not include a transition metal-containing organometallic compound. That is, the emission layer is clearly distinguished from a phosphorescence layer which includes a transition metal-containing organometallic compound and emits phosphorescence from the transition metal-containing organometallic compound.

A portion of delayed fluorescence components emitted by the thermally activated delayed fluorescence emitter in total luminescence components emitted by the emission layer including the host and the thermally activated delayed fluorescence emitter may be about 90% or more, about 92% or more, about 94% or more, about 96% or more, or about 98% or more.

The emission layer may emit red light, green light, and/or blue light in various ways according to a maximum emission wavelength of the thermally activated delayed fluorescence emitter.

In one embodiment, the light emitted by the thermally activated delayed fluorescence emitter in the emission layer may be blue light, but embodiments of the present disclosure are not limited thereto.

An amount of the thermally activated delayed fluorescence emitter in the emission layer may be in a range of about 0.01 parts by weight to about 30 parts by weight based on 100 parts by weight of the host, but embodiments of the present disclosure are not limited thereto. When the amount of fluorescence emitted by the thermally activated delayed fluorescence emitter is within the range above, a high-quality organic light-emitting device without density extinction phenomenon may be realized.

In one embodiment, the emission layer may include the host and the thermally activated delayed fluorescence emitter, but may not include a phosphorescent compound (for example, a transition metal-containing organometallic compound). Thus, the organic light-emitting device including the emission layer may emit not phosphorescence, but delayed fluorescence, thereby having both a high efficiency and a long lifespan.

According to one or more exemplary embodiments, the host in the emission layer may include a first material and a second material. The first material and the second material may be different from each other, and the second material may include the compound represented by Formula 1, the compound represented by Formula 2, or a combination thereof. Formulae 1 and 2 are each independently the same as described herein.

The first material may be a hole transport material. In an exemplary embodiment, the first material may not include an electron transport moiety.

In an exemplary embodiment, the first material may not include a cyano group, a π electron-depleted nitrogen-containing cyclic group, and a group represented by the following formulae:

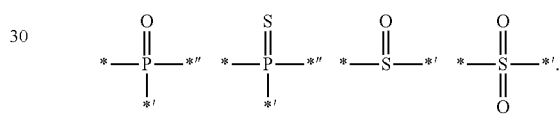

In the formulae above, *, *', and *" each indicate a binding site to a neighboring atom.

In one embodiment, the first material may include at least one π electron-depleted nitrogen-free cyclic group, and may not include an electron transport moiety.

In one or more embodiments, the first material may include at least one carbazole group.

In one or more embodiments, the first material may include two or more carbazole groups, but embodiments of the present disclosure are not limited thereto.

In one or more embodiments, the first material may include a benzene group not including a cyano group and a carbazole group not including a cyano group.

In one or more embodiments, the first material may have an absolute value of a lowest unoccupied molecular orbital (LUMO) energy level of greater than or equal to about 0.90 eV to less than or equal to about 1.20 eV, and an absolute value of a highest occupied molecular orbital (HOMO) energy level of greater than or equal to about 5.20 eV to less than or equal to about 5.60 eV.

When the first material has the HOMO energy level and the LUMO energy level within the ranges above, the movement of charges and/or excitons in the emission layer and the energy flow may be smoothly performed, thereby realizing the organic light-emitting device having a high luminescence efficiency and a long lifespan.

In one or more embodiments, the first material may include a compound represented by Formula H-1(1), a compound represented by Formula H-1(2), a compound represented by Formula H-1(3), or a combination thereof:

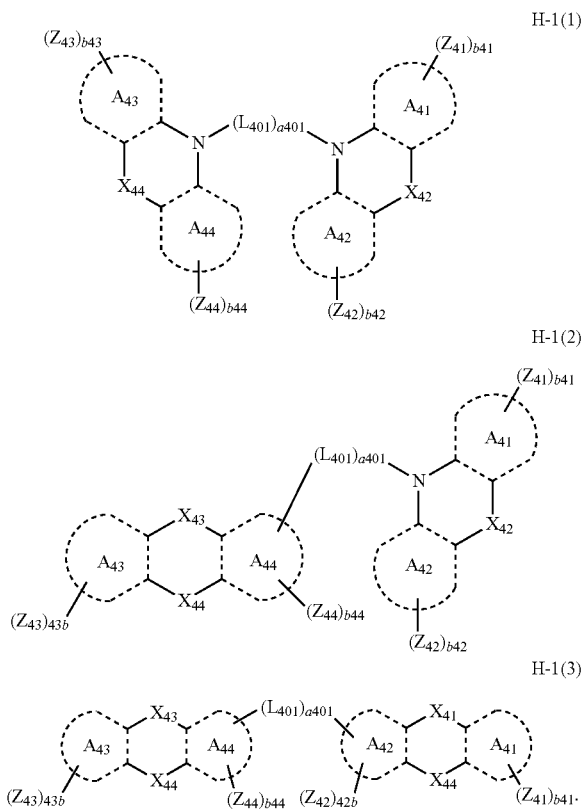

In Formulae H-1(1) to H-1(3), ring $A_{41}$ to ring $A_{44}$ may each independently be a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group.

In an exemplary embodiment, ring $A_{41}$ to ring $A_{44}$ may each independently be a benzene group, a fluorene group, a carbazole group, a dibenzofuran group, a dibenzothiophene group, or a dibenzosilole group, wherein ring $A_{41}$, ring $A_{42}$, or a combination thereof may be a benzene group, and ring $A_{43}$, ring $A_{44}$, or a combination thereof may be a benzene group.

In Formulae H-1(1) to H-1(3),
$X_{41}$ may be N-[$(L_{411})_{c411}$-$Z_{411}$], $C(Z_{415})(Z_{416})$, O, or S,
$X_{42}$ may be a single bond, N-[$(L_{412})_{c412}$-$Z_{412}$], $C(Z_{417})(Z_{418})$, O, or S,
$X_{43}$ may be N-[$(L_{413})_{c413}$-$Z_{413}$], $C(Z_{419})(Z_{420})$, O, or S, and
$X_{44}$ may be a single bond, N-[$(L_{414})_{c414}$-$Z_{414}$], $C(Z_{421})(Z_{422})$, O, or S.

$L_{401}$ and $L_{411}$ to $L_{414}$ may each independently be:
a single bond; or
a π electron-depleted nitrogen-free cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{20}$ alkyl)phenyl group, $-Si(Q_{401})(Q_{402})(Q_{403})$, or any combination thereof (for example, a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, $-Si(Q_{401})(Q_{402})(Q_{403})$, or any combination thereof).

a401 and c411 to c414 each indicate the number of $L_{401}$ and the number of each of $L_{411}$ to $L_{414}$, respectively, and may each independently be an integer from 1 to 10 (for example, an integer from 1 to 5), wherein, when a401 is two or more, two or more $L_{401}$ may be identical to or different from each other, when c411 is two or more, two or more $L_{411}$ may be identical to or different from each other, when c412 is two or more, two or more $L_{412}$ may be identical to or different from each other, when c413 is two or more, two or more $L_{413}$ may be identical to or different from each other, and when c414 is two or more, two or more $L_{414}$ may be identical to or different from each other.

$Z_{41}$ to $Z_{44}$ and $Z_{411}$ to $Z_{422}$ may each independently be:
hydrogen, deuterium, a $C_1$-$C_{20}$ alkyl group, or a $C_1$-$C_{20}$ alkoxy group; or
a π electron-depleted nitrogen-free cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{20}$ alkyl)phenyl group, $-Si(Q_{401})(Q_{402})(Q_{403})$, or any combination thereof (for example, a phenyl group, a biphenyl group, a terphenyl group, a tetraphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, an isoindolyl group, an indolyl group, a furanyl group, a thiophenyl group, a benzofuranyl group, a benzothiophenyl group, a benzosilolyl group, a benzocarbazolyl group, a dibenzocarbazolyl group, a dibenzofuranyl group, a dibenzothiophenyl group, a carbazolyl group, a dibenzosilolyl group, an indeno carbazolyl group, an indolocarbazolyl group, a benzofurocarbazolyl group, a benzothienocarbazolyl group, a benzosilolocarbazolyl group, an acridinyl group or a dihydroacridinyl group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, $-Si(Q_{401})(Q_{402})(Q_{403})$, or any combination thereof).

b41 to b44 each indicate the number of $Z_{41}$ to the number of $Z_{44}$, respectively, and may each independently be 1, 2, 3, or 4.

$Q_{401}$ to $Q_{403}$ may each independently be hydrogen, deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, or a tetraphenyl group.

In one embodiment, in Formulae H-1(1) to H-1(3), $L_{401}$ and $L_{411}$ to $L_{414}$ may each independently be:

a single bond; or a benzene group, a fluorene group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, an acridine group, or a dihydroacridine group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{10}$ alkyl)phenyl group, or any combination thereof, $Z_{41}$ to $Z_{44}$ and $Z_{411}$ to $Z_{422}$ may each independently be:

hydrogen, deuterium, a $C_1$-$C_{10}$ alkyl group, or a $C_1$-$C_{10}$ alkoxy group; or a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indeno carbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{10}$ alkyl)phenyl group, or any combination thereof but embodiments of the present disclosure are not limited thereto.

In one embodiment, the first material may include at least one of Compounds H1 to H32, but embodiments of the present disclosure are not limited thereto:

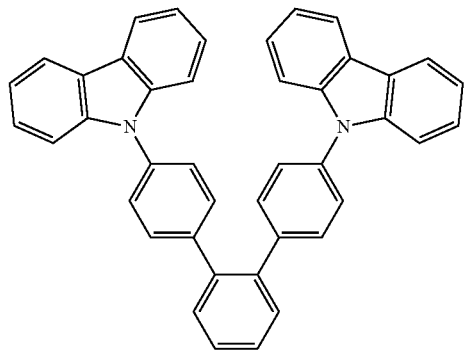

H1

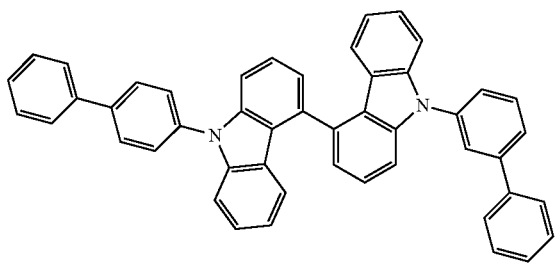

H2

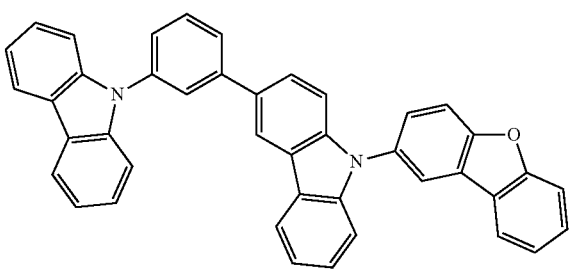

H3

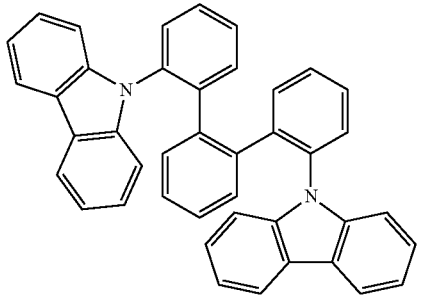

H4

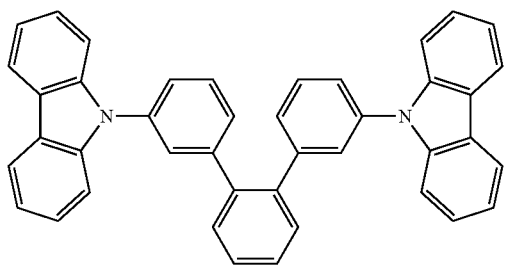

H5

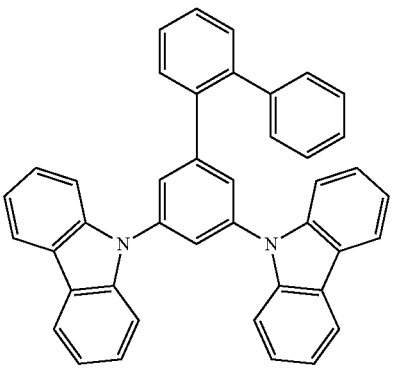

H6

-continued
H7
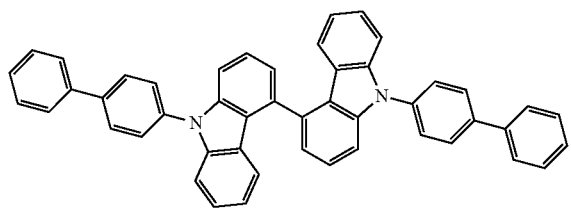
H8
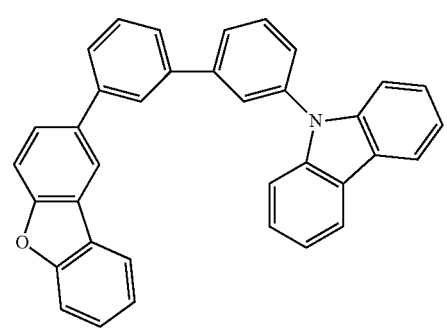
H9
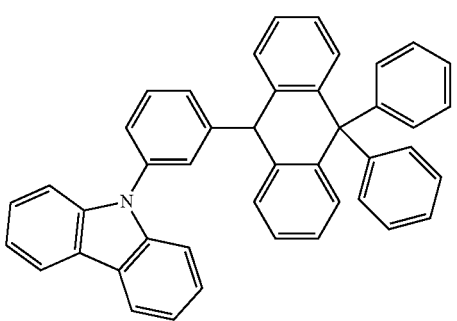
H10
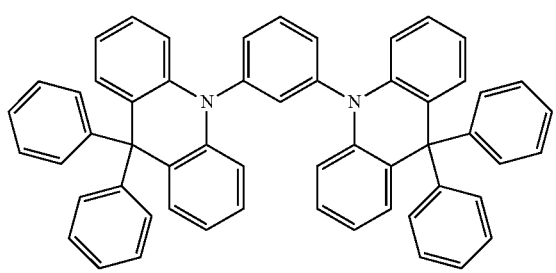
H11
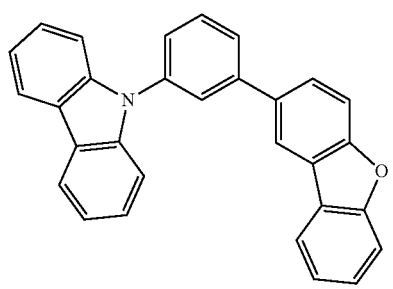
-continued
H12
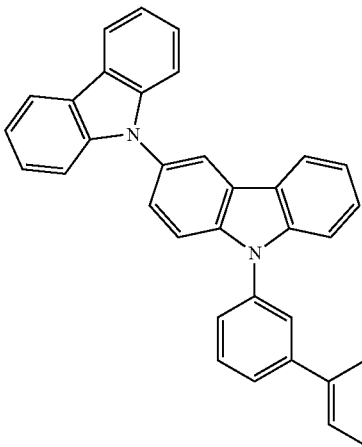
H13
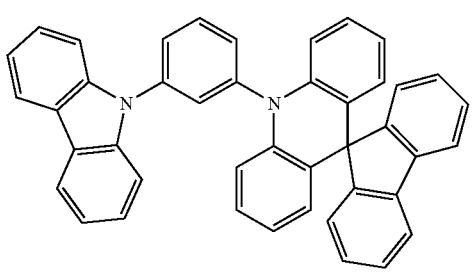
H14
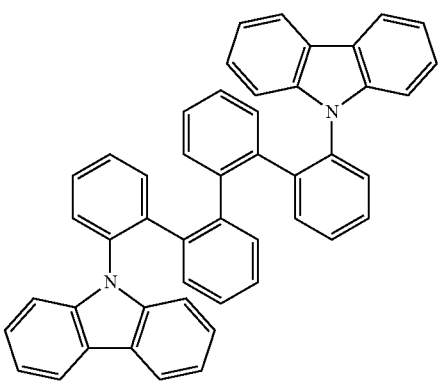
H15
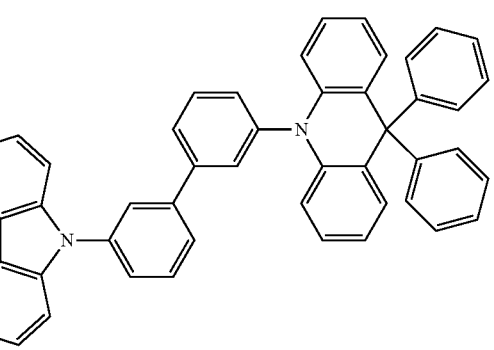

H16 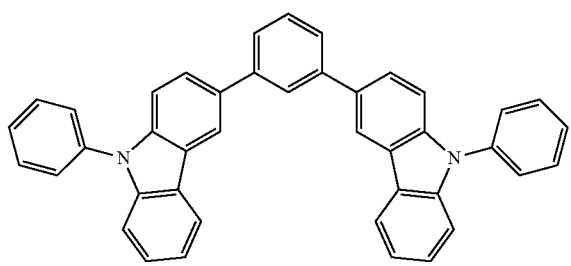
H17 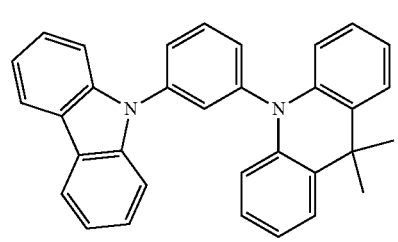
H18 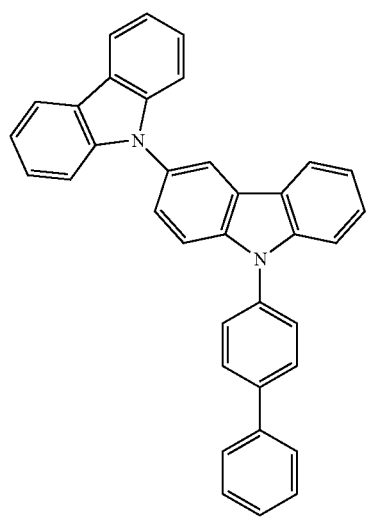
H19 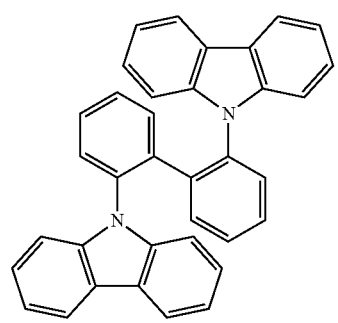
H20 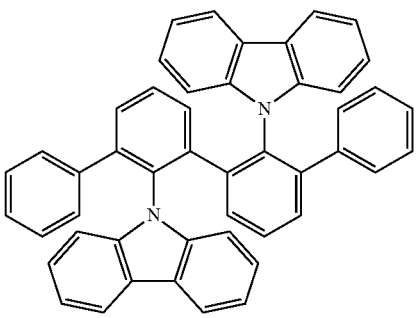
H21 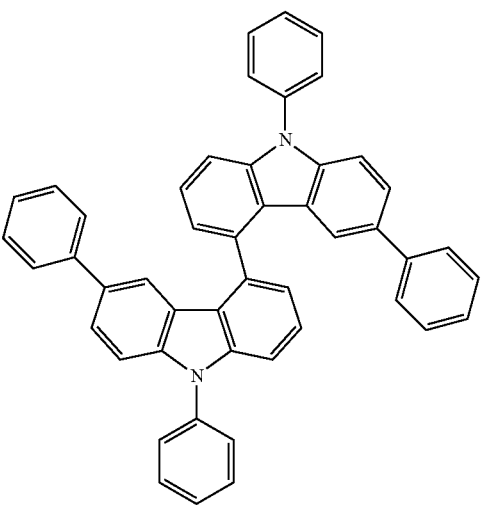
H22 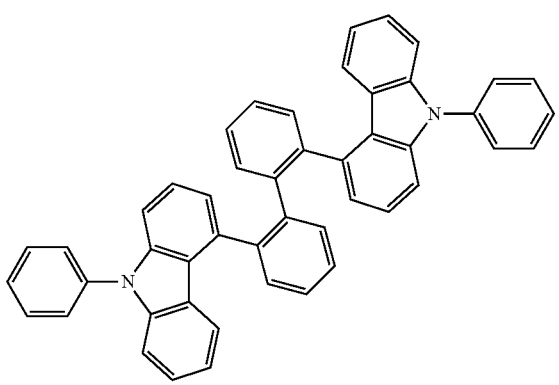

-continued
H23
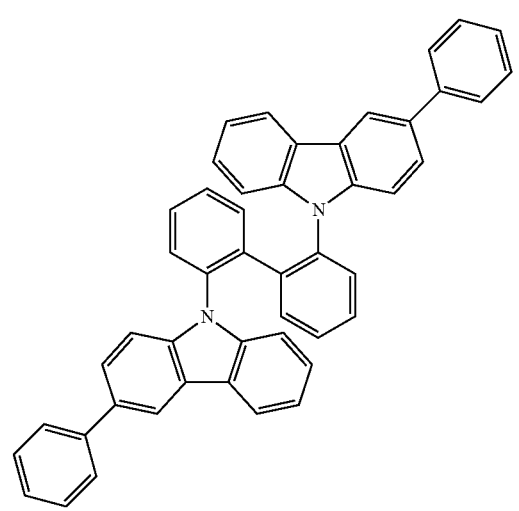
H24
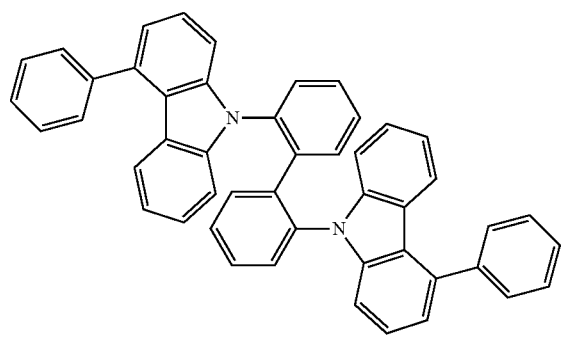
H25
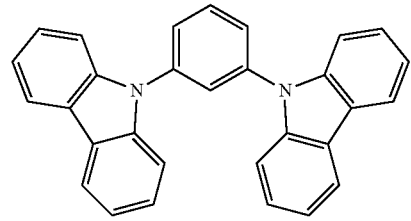
H26
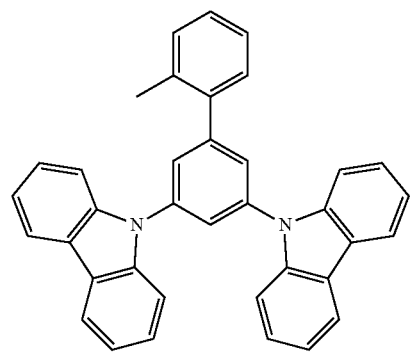
-continued
H27
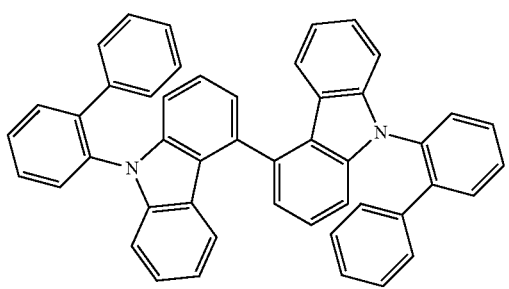
H28
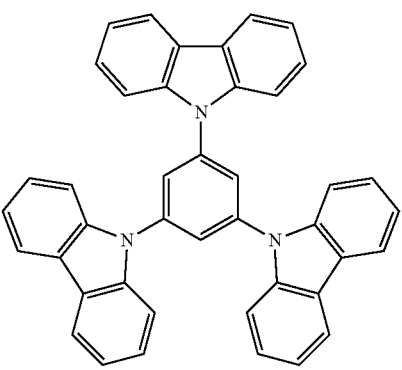
H29
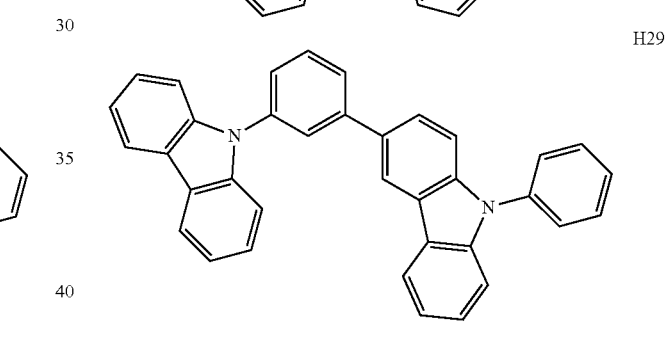
H30
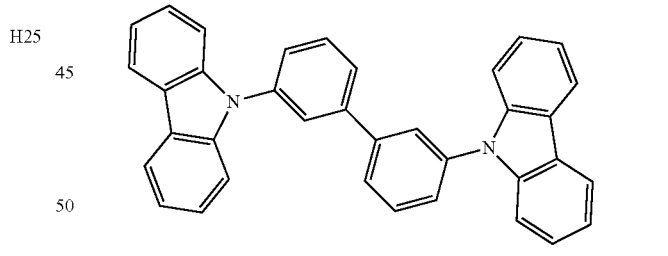
H31
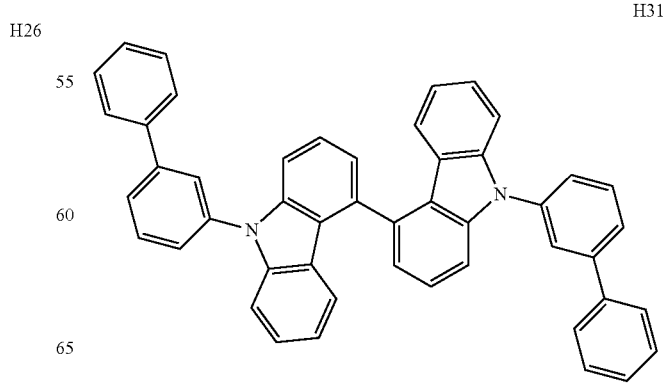

H32

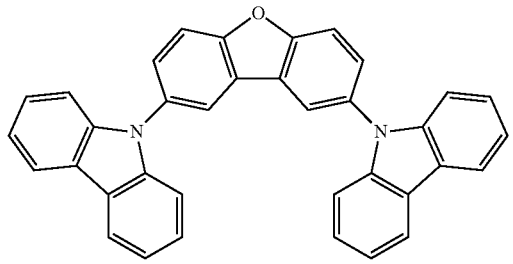

In one embodiment, the first material may not be an amine compound.

In one or more embodiments, the first material may not be 1,3-bis(9-carbazolyl)benzene (mCP), tris(4-carbazoyl-9-ylphenyl)amine (TCTA), 4,4'-bis(N-carbazolyl)-1,1'-biphenyl (CBP), 3,3-bis(carbazol-9-yl)biphenyl (mCBP), N,N'-di(1-naphthyl)-N,N'-diphenyl-(1,1'-biphenyl)-4,4'-diamine (NPB), 4,4',4"-tris[phenyl(m-tolyl)amino]triphenylamine (m-MTDATA), or N,N'-bis(3-methylphenyl)-N,N'-diphenylbenzidine (TPD).

FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be a material with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), or zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. In an exemplary embodiment, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods such as vacuum deposition, spin coating, casting, or Langmuir-Blodgett (LB) deposition.

When a hole injection layer is formed by vacuum deposition, the deposition conditions may vary according to a compound that is used to form the hole injection layer, and the structure and thermal characteristics of the hole injection layer. In an exemplary embodiment, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. In an exemplary embodiment, a coating speed may be from about 2,000 rpm to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201 below, a compound represented by Formula 202, or a combination thereof:

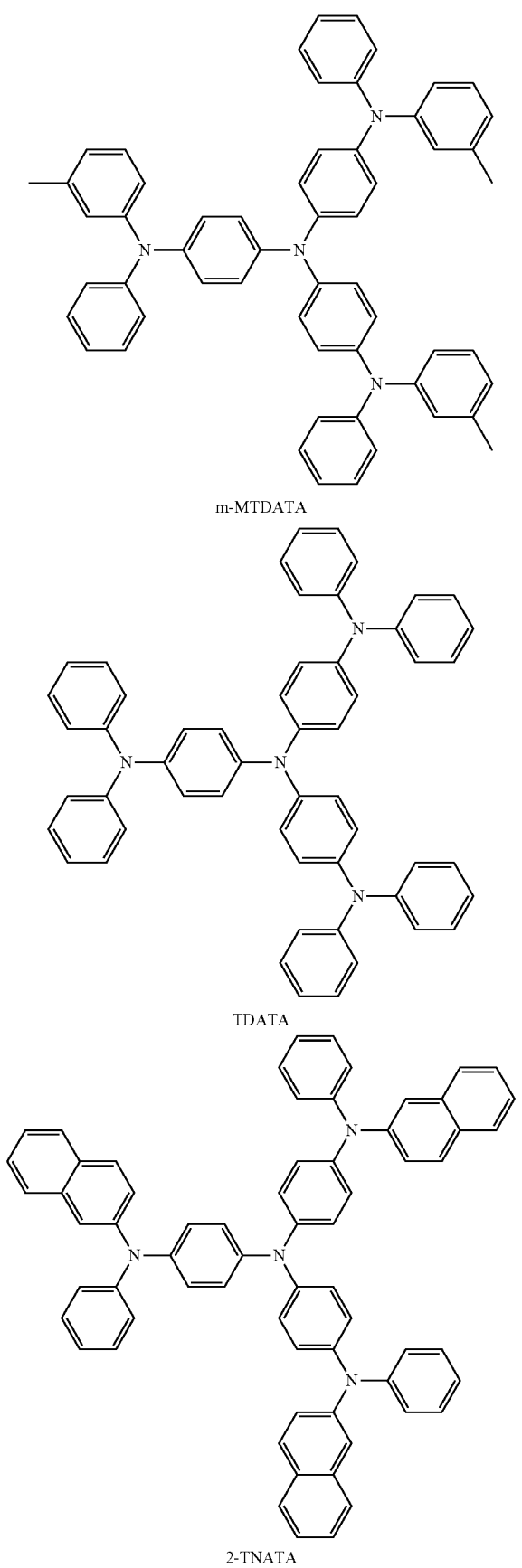
m-MTDATA
TDATA
2-TNATA
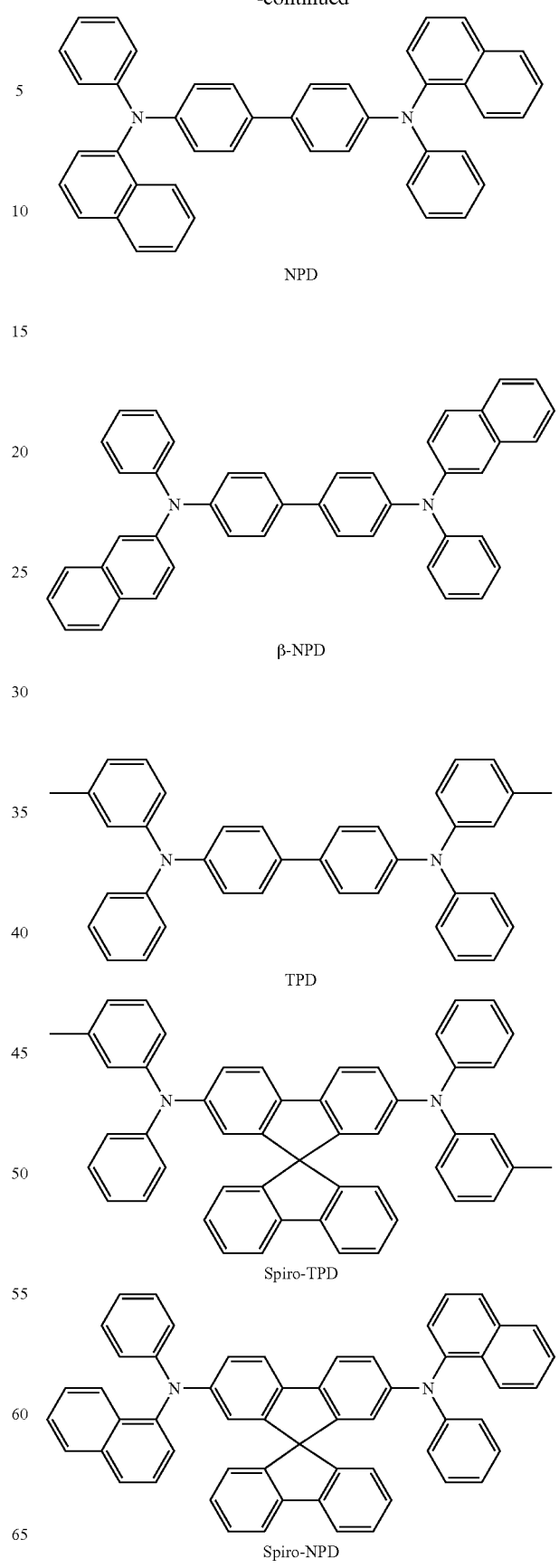
NPD
β-NPD
TPD
Spiro-TPD
Spiro-NPD

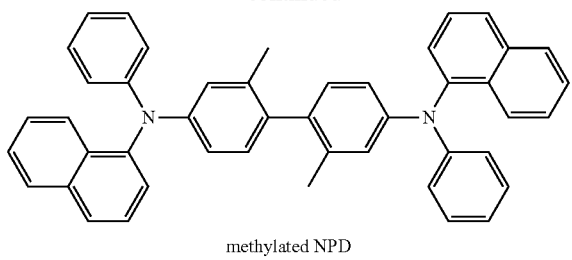

methylated NPD

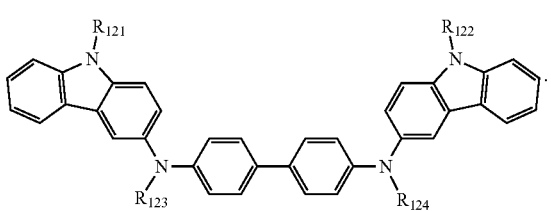

Formula 202

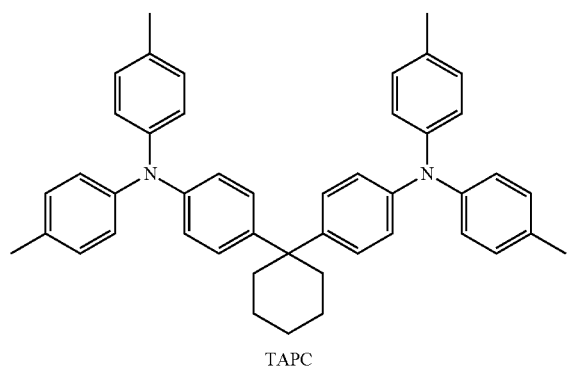

TAPC

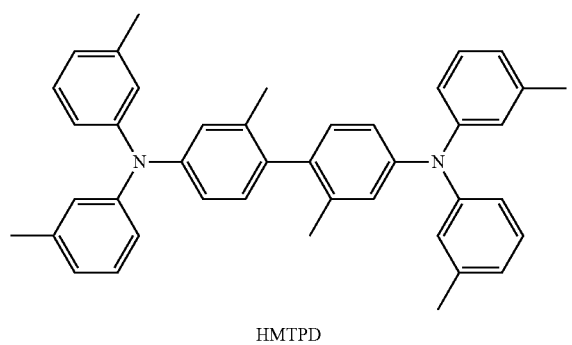

HMTPD

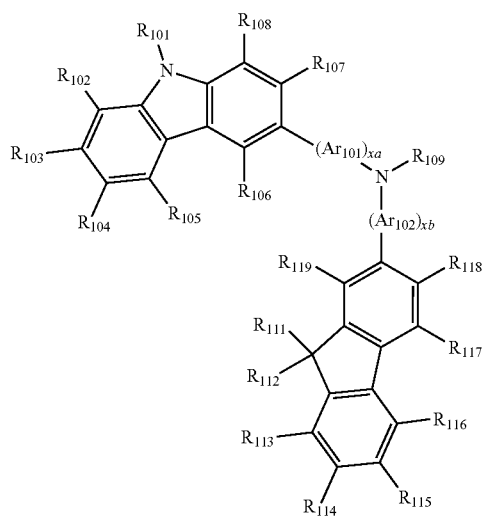

Formula 201

In Formula 201, $Ar_{101}$ and $Ar_{102}$ may each independently be:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof.

In Formula 201, xa and xb may each independently be an integer from 0 to 5, or may be 0, 1, or 2. In an exemplary embodiment, xa is 1 and xb is 0, but xa and xb are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a C$_1$-C$_{10}$ alkyl group or a C$_1$-C$_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, or any combination thereof;

a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, or any combination thereof, but embodiments of the present disclosure are not limited thereto.

In Formula 201, R$_{109}$ may be:

a phenyl group, a naphthyl group, an anthracenyl group, or a pyridinyl group; or a phenyl group, a naphthyl group, an anthracenyl group, or a pyridinyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, an anthracenyl group, a pyridinyl group, or any combination thereof.

According to an embodiment, the compound represented by Formula 201 may be represented by Formula 201A, but embodiments of the present disclosure are not limited thereto:

Formula 201A

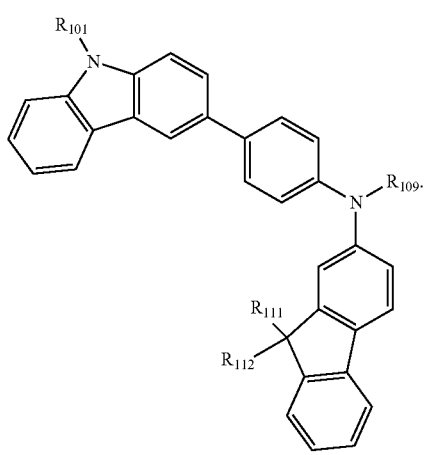

In Formula 201A, R$_{101}$, R$_{111}$, R$_{112}$, and R$_{109}$ are each independently the same as described herein.

In an exemplary embodiment, the compound represented by Formula 201 and the compound represented by Formula 202 may include Compounds HT1 to HT20, but embodiments of the present disclosure are not limited thereto:

HT1

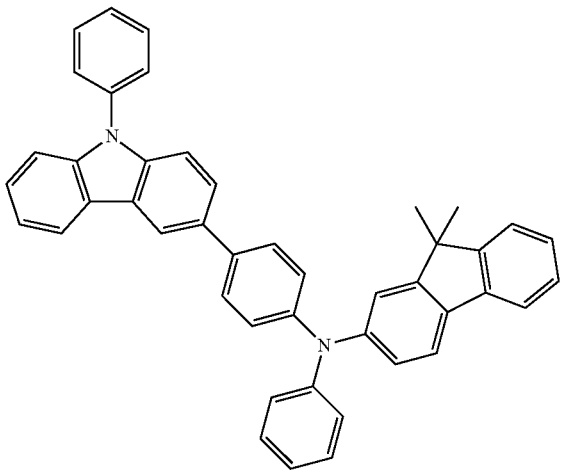

HT2

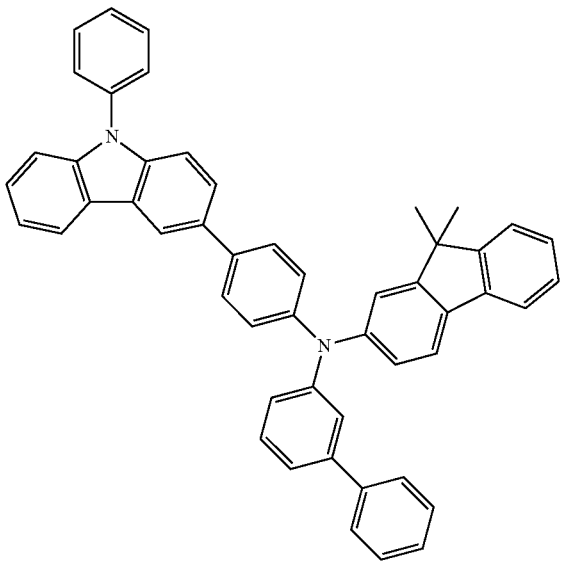

533
-continued
534
-continued
HT3
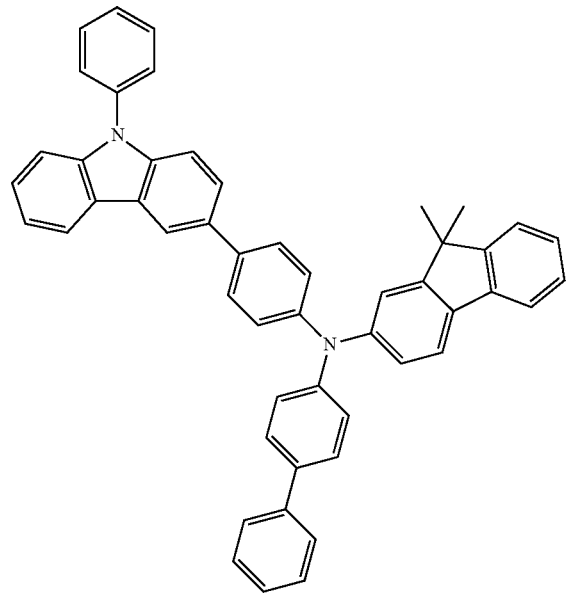
HT5
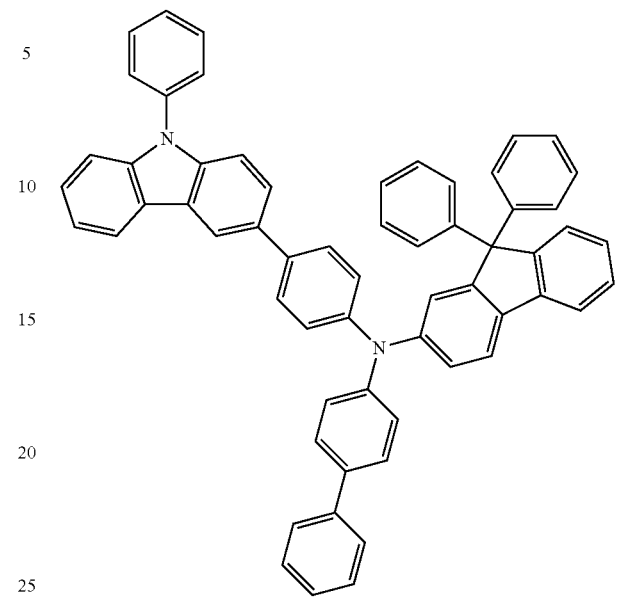
HT4
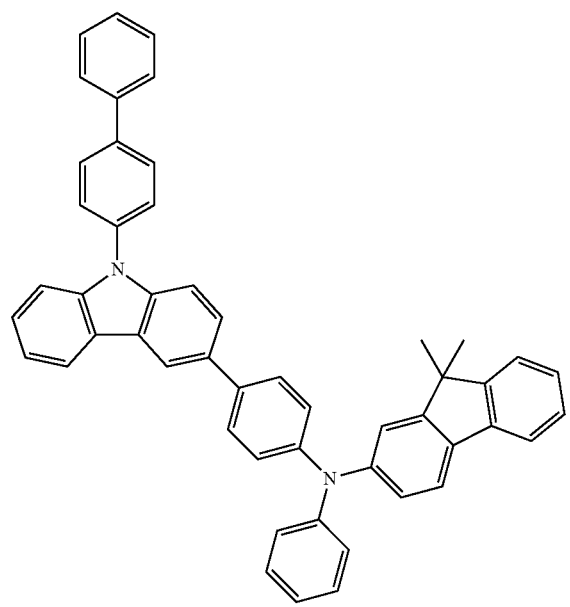
HT6
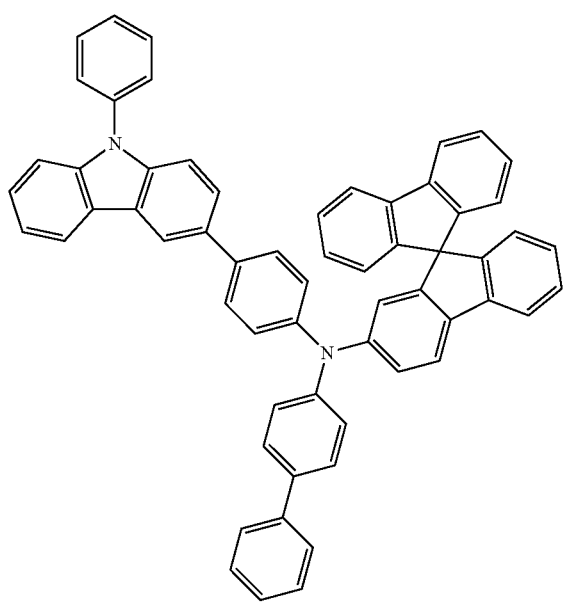

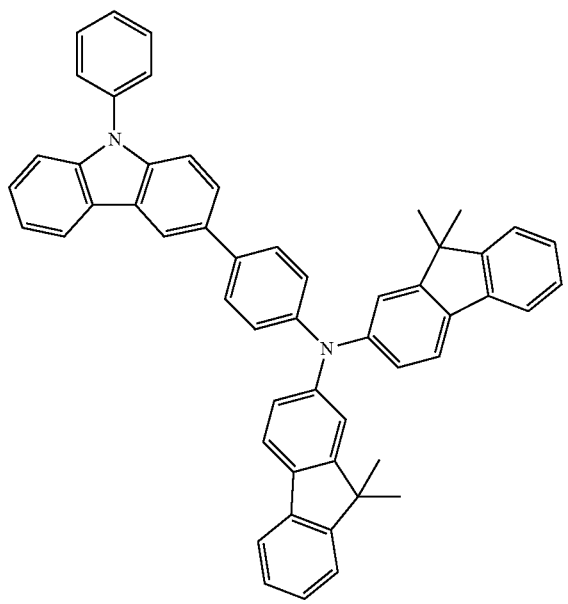
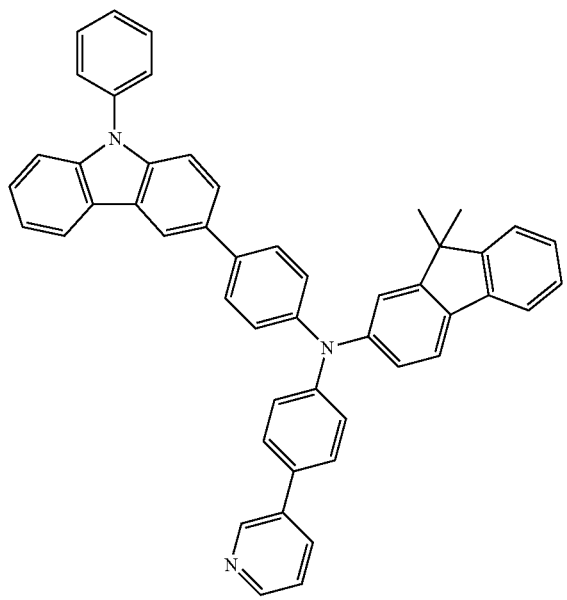

HT12
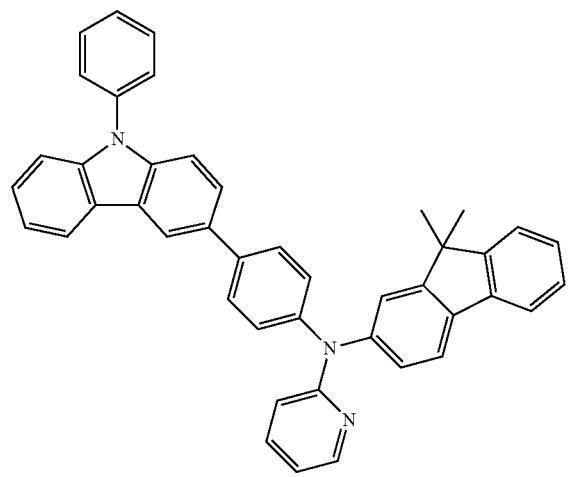
HT13
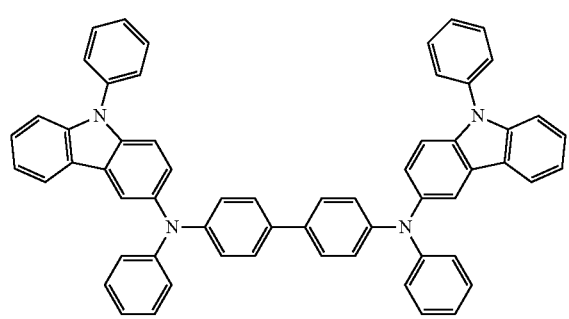
HT14
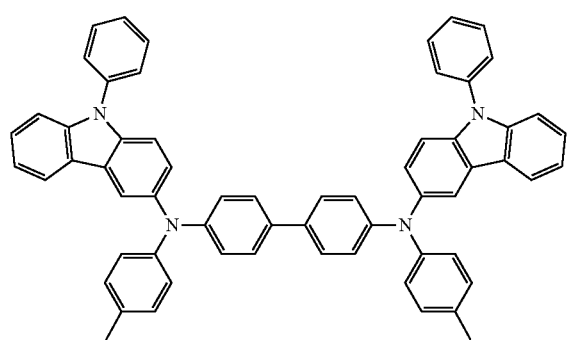
HT15
HT16
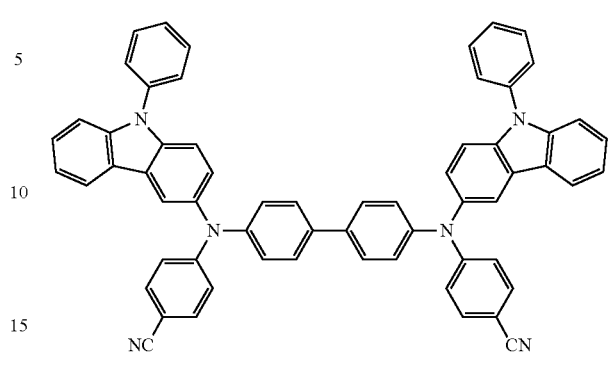
HT17
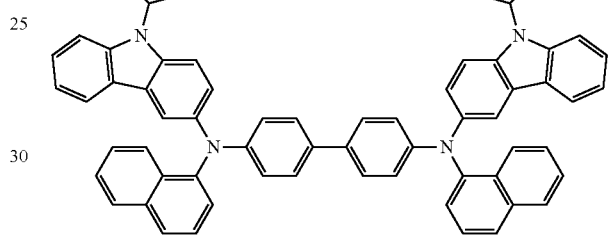
HT18
HT19
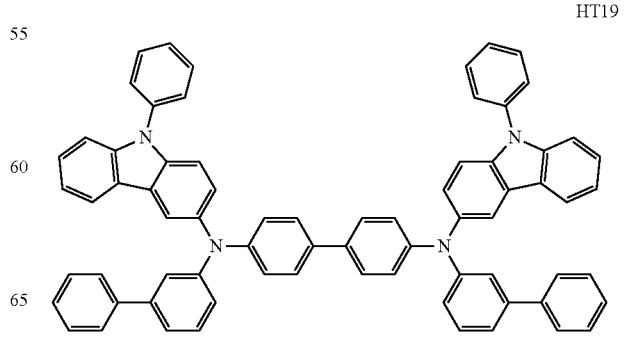

-continued

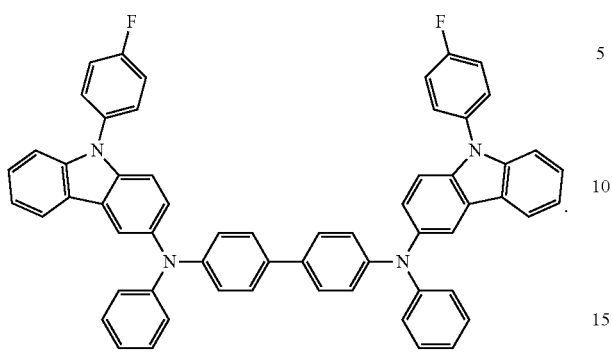

HT20

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, or a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or Compound HT-D2 below, but are not limited thereto:

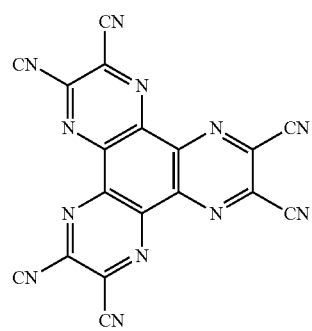

HT-D1

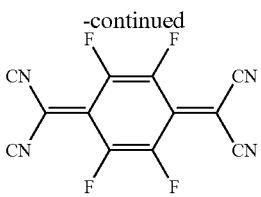

F4-TCNQ

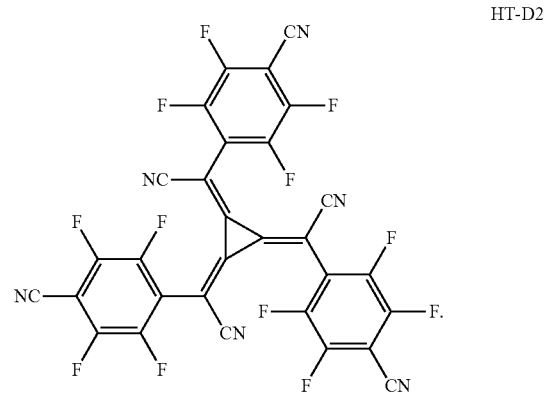

HT-D2

The hole transport region may include a buffer layer.

Also, the buffer layer may compensate for an optical resonance distance according to a wavelength of light emitted from the emission layer, and thus, efficiency of a formed organic light-emitting device may be improved.

The electron transport region may further include an electron blocking layer. The electron blocking layer may include, for example, mCP, but a material therefor is not limited thereto:

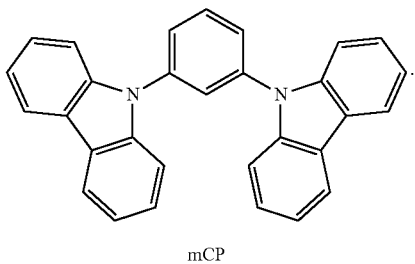 [SMILES: c1cc(-n2c3ccccc3c3ccccc32)cc(-n2c3ccccc3c3ccccc32)c1]

mCP

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and/or a blue emission layer. In one or more embodiments, due to a stacked structure including a red emission layer, a green emission layer, and/or a blue emission layer, the emission layer may emit white light.

The emission layer may include the host and the thermally activated delayed fluorescence emitter, wherein the host and the thermally activated delayed fluorescence emitter are each independently the same as described herein.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

In an exemplary embodiment, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, Bphen, or any combination thereof, but may also include other materials:

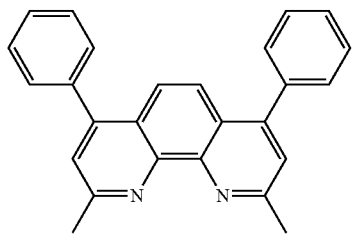

BCP

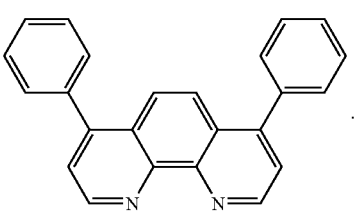

Bphen

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include BCP, Bphen, $Alq_3$, BAlq, TAZ, NTAZ, or any combination thereof:

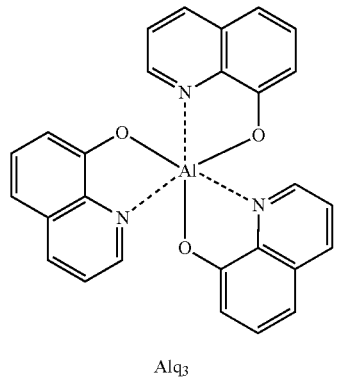

$Alq_3$

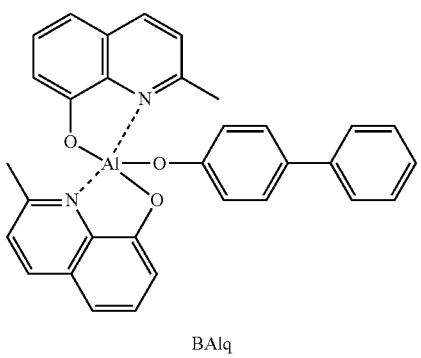

BAlq

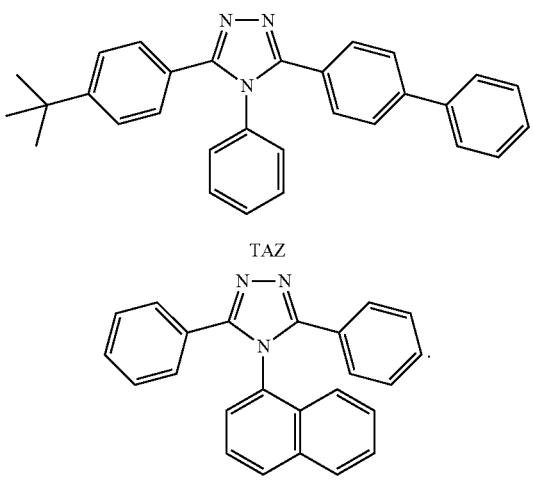

TAZ

NTAZ

In one or more embodiments, the electron transport layer may include a compound of ET1 to ET25, but are not limited thereto:
ET1
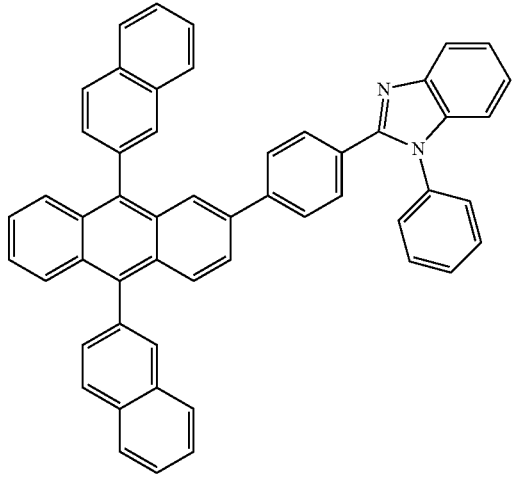
ET2
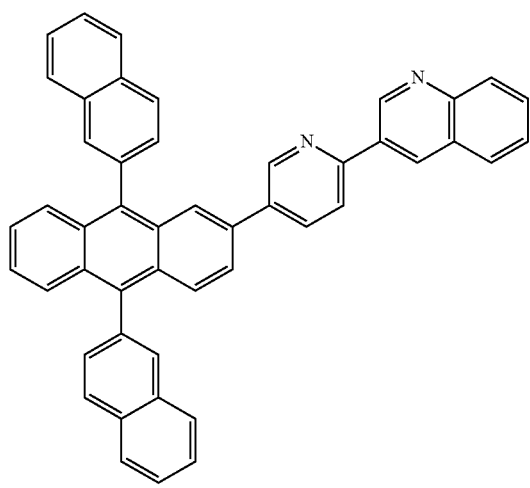
ET3
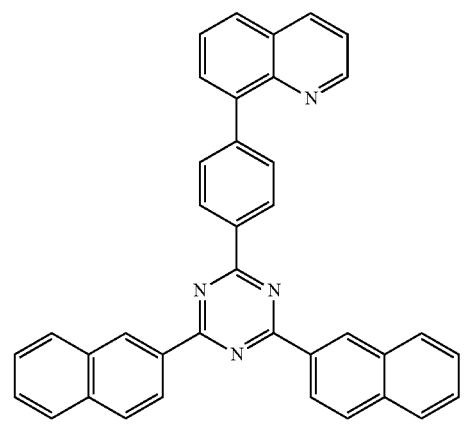
ET4
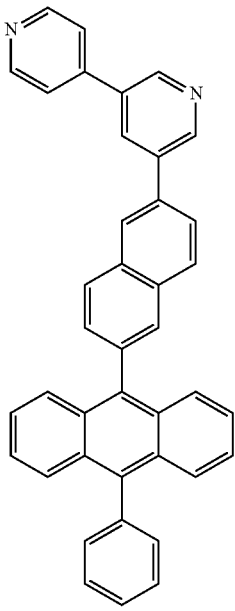
ET5
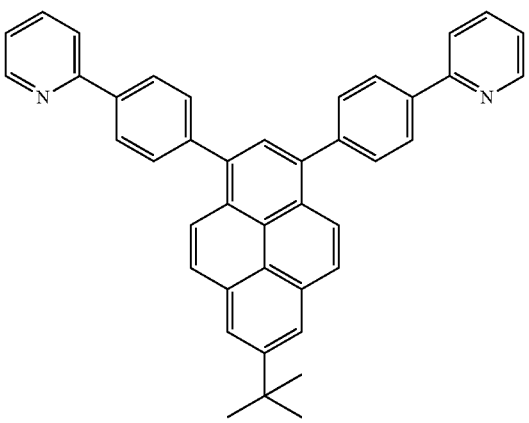
ET6
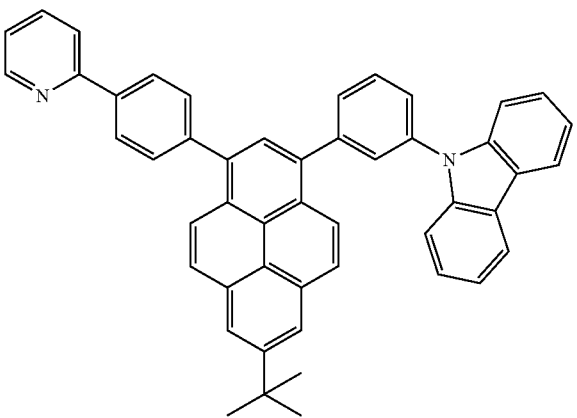

545
-continued
ET7
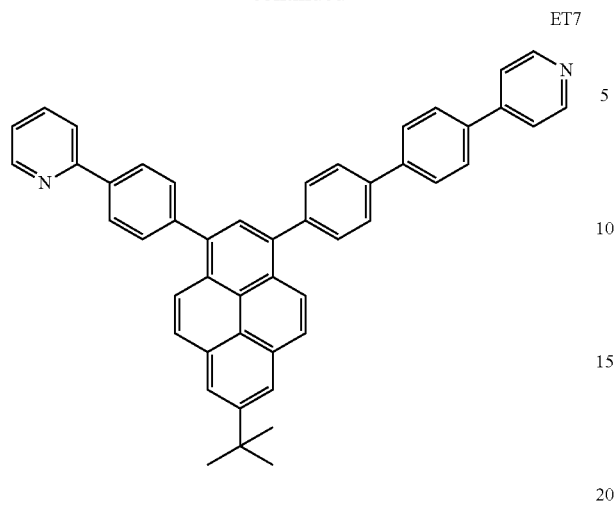
ET8
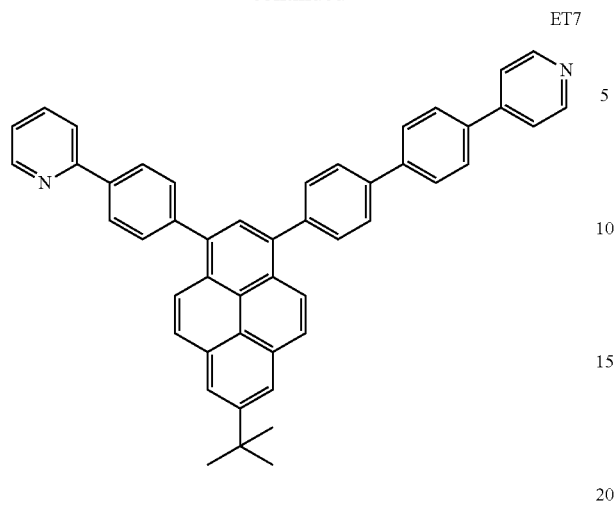
ET9
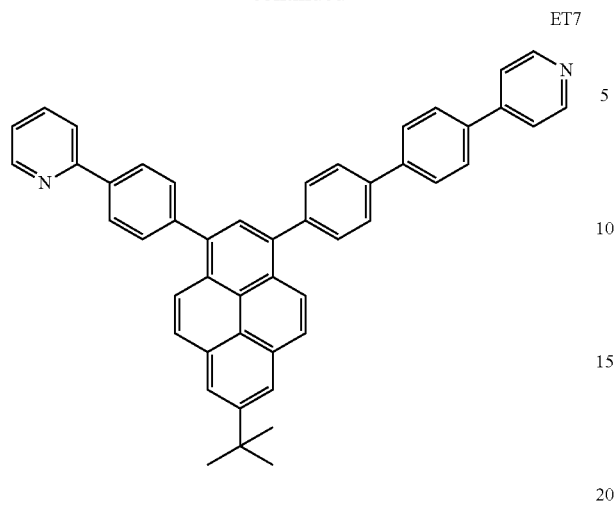
546
-continued
ET10
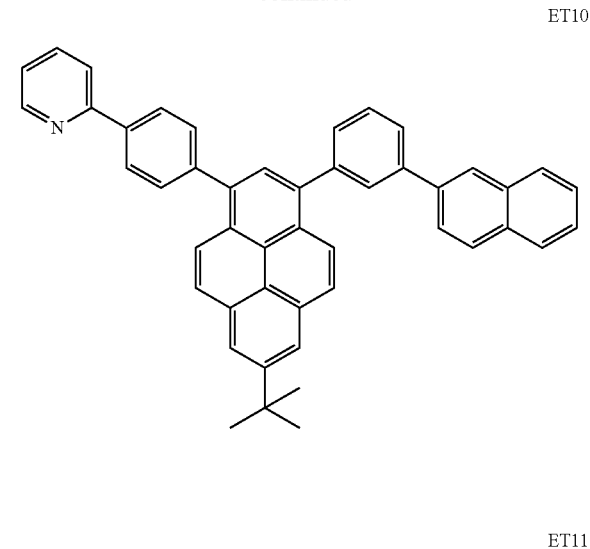
ET11
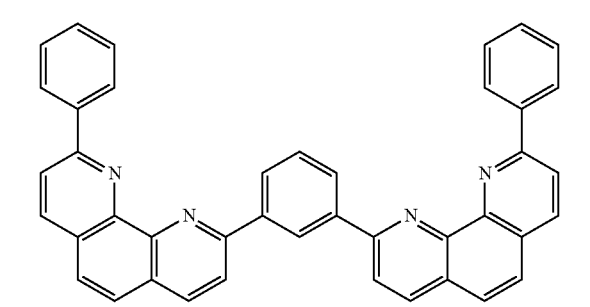
ET12
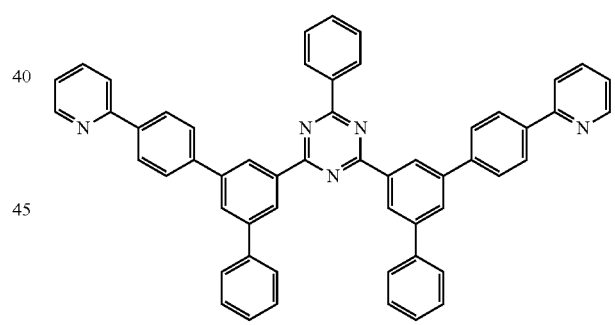
ET13
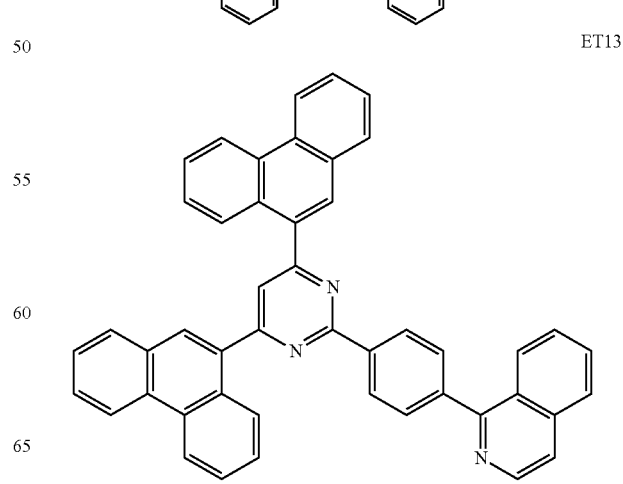

ET14
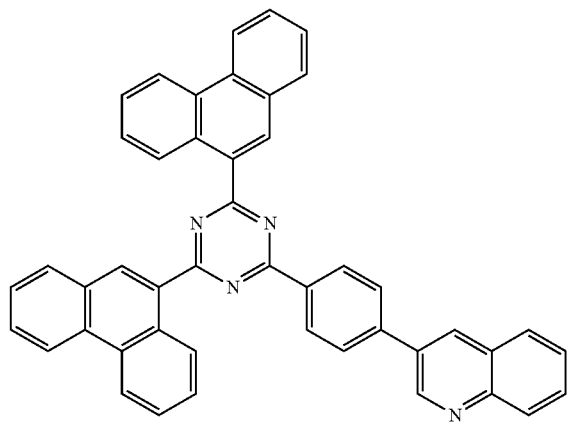
ET18
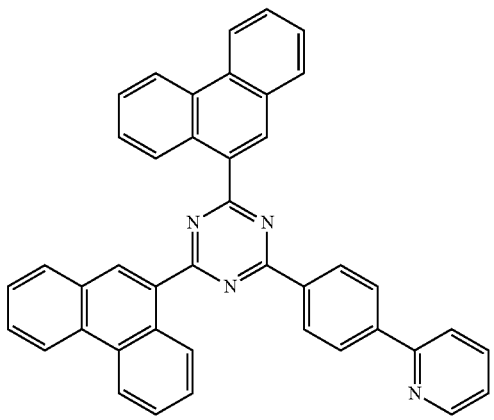
ET15
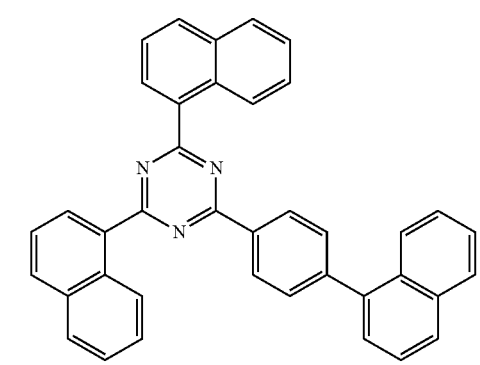
ET19
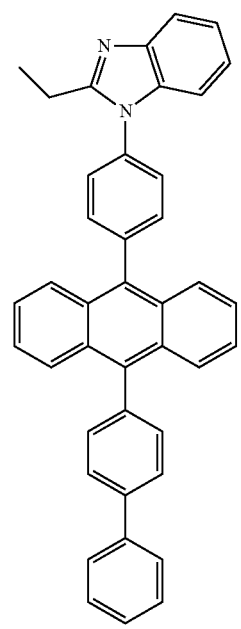
ET16
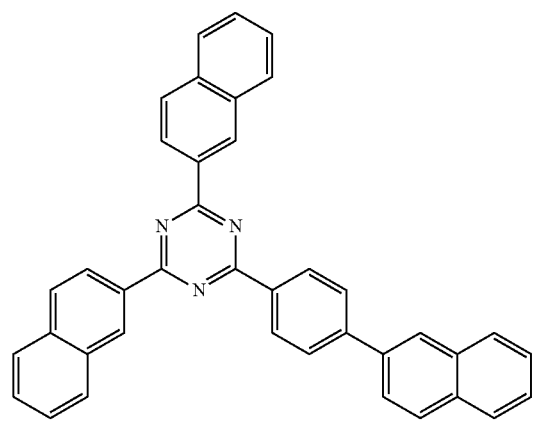
ET17
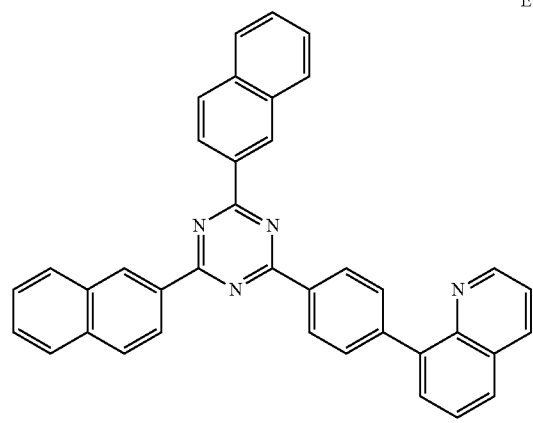
ET20
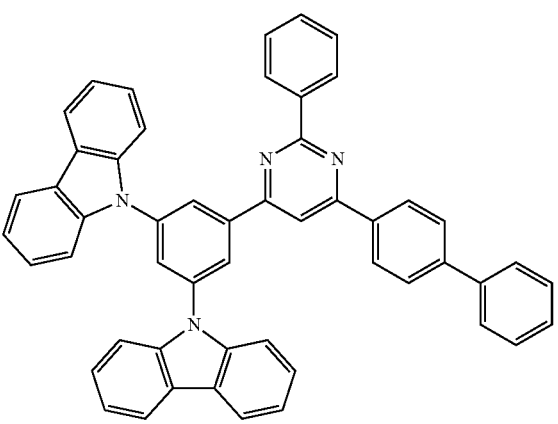

ET21
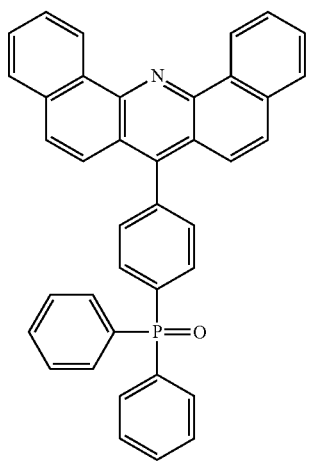

ET22
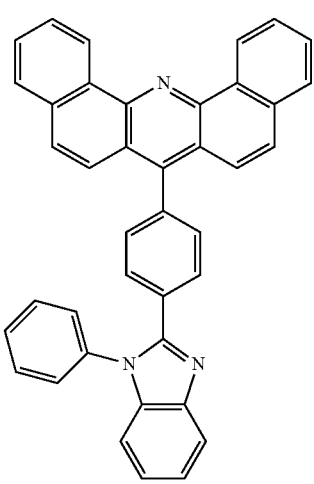

ET23
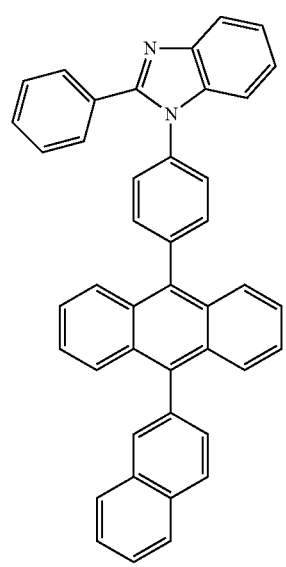

ET24
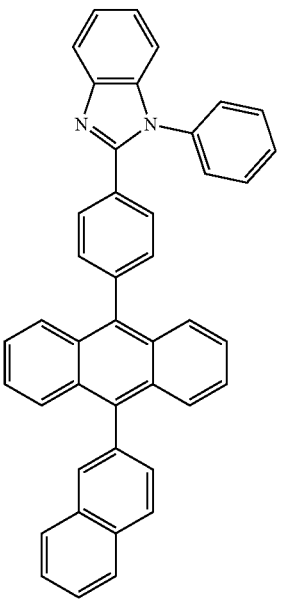

ET25
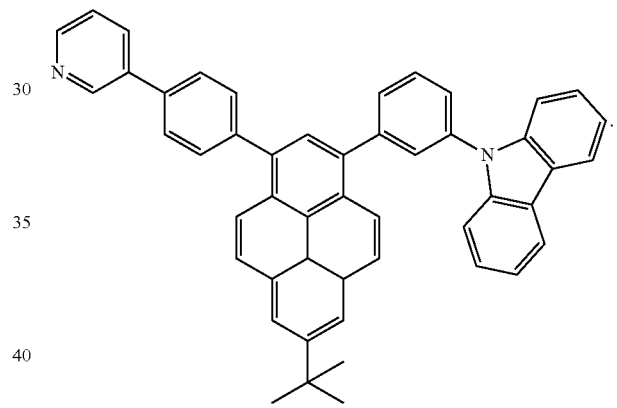

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1
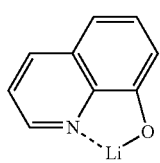

ET-D2

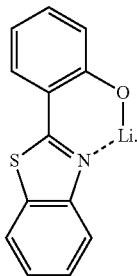

The electron transport region may include an electron injection layer that promotes the flow of electrons from the second electrode 19 thereinto.

The electron injection layer may include LiF, NaCl, CsF, $Li_2O$, BaO, or any combination thereof.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be a metal, an alloy, an electrically conductive compound, or a combination thereof, which have a relatively low work function. In an exemplary embodiment, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to FIG. 1, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an isopropyloxy group.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having N, O, P, Si, Se or S as a ring-forming atom and 2 to 10 carbon atoms, and non-limiting examples thereof include a tetrahydrofuranyl group and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and a carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has N, O, P, Si, Se, or S as a ring-forming atom, 2 to 10 carbon atoms, and at least one carbon-carbon double bond in its ring. Non-limiting examples of the $C_2$-$C_{10}$ heterocycloalkenyl group include a 2,3-dihydrofuranyl group, and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a heterocyclic aromatic system that has N, O, P, Si, Se, or S as a ring-forming atom, and 2 to 60 carbon atoms. The term "$C_2$-$C_{60}$ heteroarylene group," as used herein refers to a divalent group having a heterocyclic aromatic system that has an N, O, P, Si, Se, or S as a ring-forming atom, and 2 to 60 carbon atoms. Non-limiting examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —SA103 (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as ring-forming atoms, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, an N, O, P, Si, Se, or S, other than carbon atoms (for example, the number of carbon atoms may be in a range of 2 to 60), as ring-forming atoms, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In the present specification, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), or any combination thereof; or —Si($Q_{31}$)($Q_{32}$)($Q_{33}$), —N($Q_{34}$)($Q_{35}$), or —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ may each independently be hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

The term "room temperature" as used herein refers to about 25° C.

The term "a biphenyl group, a terphenyl group, or a tetraphenyl group" as used herein each refer to a monovalent group linked to two, three, or four benzene groups, respectively, via a single bond.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1

Synthesis of Compound EH1

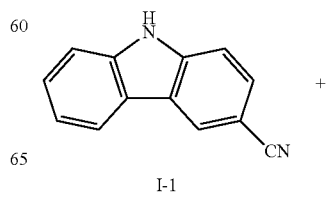

I-1

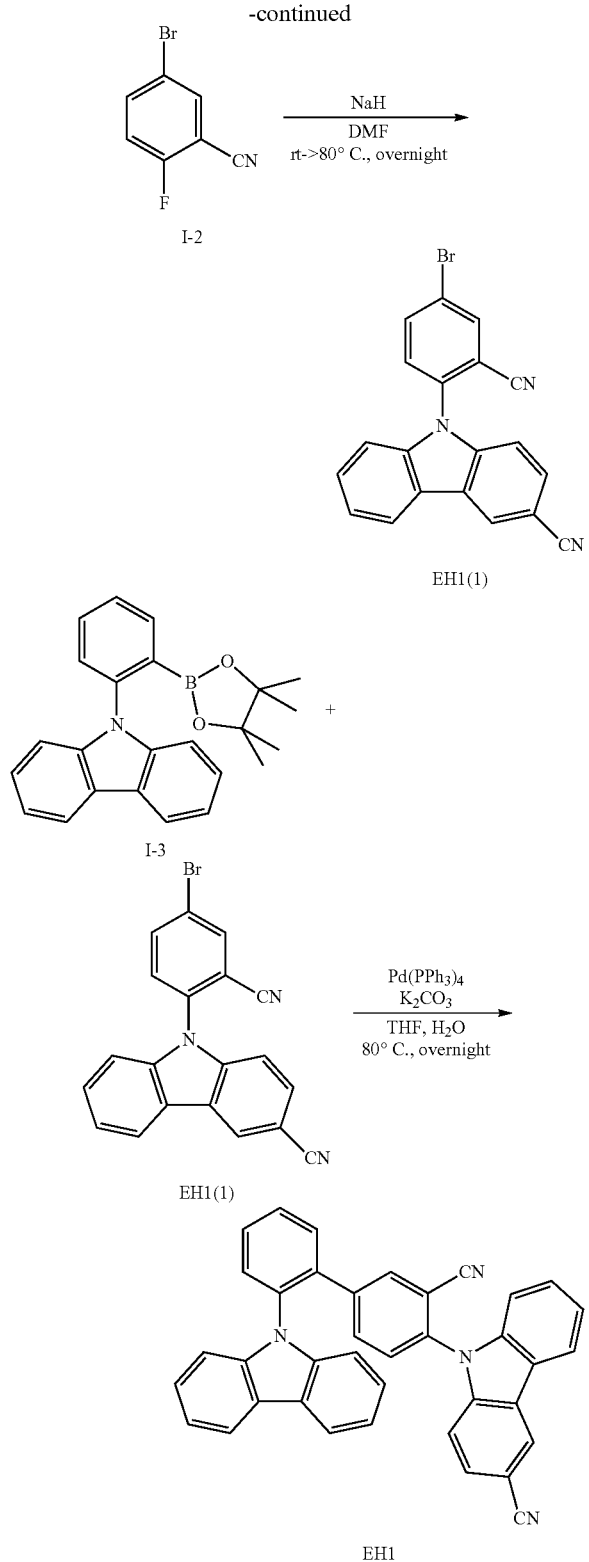

solution at room temperature (resulting in the production of hydrogen). Afterwards, the resulting mixed solution was stirred at room temperature for 15 minutes, and then, 11.0 g (55 mmol, ~1.2 eq) of Compound I-2 was added thereto at once. The temperature was slowly raised up to 80° C., and the resulting mixed solution was stirred overnight. The temperature of the mixed solution thus obtained was cooled to room temperature, and excess water was poured into the mixture to precipitate a solid product. 50 ml of ethyl acetate was added to the mixed solution which was then stirred. A solid product obtained by filtration was washed with 50 ml of ethyl acetate, and a resulting product obtained therefrom was dried without further purification, thereby obtaining 12 g (purity of 99.88% by LC-MS) of a white solid product, Intermediate EH1(1).

Synthesis of Compound EH1

16 g (43 mmol, 1 eq) of Intermediate EH1(1), 31.7 g (86 mmol, 2 eq) of Compound I-3, 23.8 g (172 mmol, 4 eq) of potassium carbonate ($K_2CO_3$), and 2.3 g (2 mmol, 0.05 eq) of $Pd(PPh_3)_4$ were added to a mixed solution of 110 ml of tetrahydrofuran (THF) and 85 ml of water, and the resulting mixed solution was stirred at a temperature of 85° C. overnight (by using a pressure reactor). The mixed solution thus obtained was cooled to room temperature, and the reaction mixture was extracted with ethyl acetate. The resulting organic layer was dried by using $MgSO_4$, filtered, and concentrated in vacuo to remove the solvent. A resulting product obtained therefrom was separated and purified by silica gel column chromatography, thereby obtaining 13 g of Compound EH1 (purity of 99.95% by LC-MS).

LC-Mass Cal.: 534.18 g/mol, Measured.: M+1=535.18 g/mol

Synthesis Example 2

Synthesis of Compound EH2

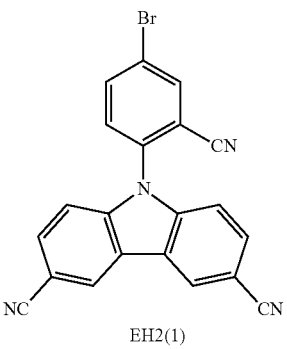

Synthesis of Intermediate EH1(1)

In a 500 ml round-bottom flask in a water bath at room temperature, 8.8 g (46 mmol) of 3-cyanide carbazole (Compound I-1) was mixed with 250 ml of N,N-dimethylformamide (DMF), and 1.84 g (46 mmol, 1 eq) of 60 wt % sodium hydride (NaH) in mineral oil was slowly added to the mixed

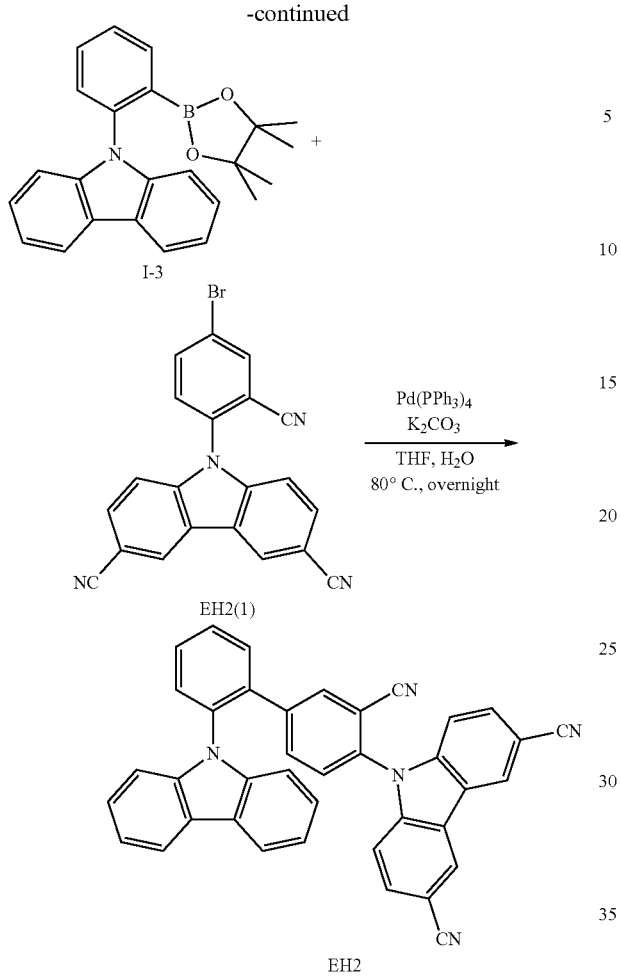

Synthesis of Intermediate EH2(1)

In a 500 ml round-bottom flask in a water bath at room temperature, 17.4 g (80 mmol) of 3,6-dicyanide carbazole (Compound I-4) was mixed with 200 ml of N,N-dimethylformamide (DMF), and 3.6 g (90 mmol, 1 eq) of 60 wt % sodium hydride (NaH) in mineral oil was slowly added to the mixed solution at room temperature (resulting in the production of hydrogen). Here, 150 ml of N,N-dimethylformamide (DMF) was used to wash out the solid products attached to a container wall. Afterwards, the mixed solution containing the washed solid products was stirred for 10 minutes at room temperature, and 20 g (100 mmol, ~1.25 eq) of Compound I-2 was added thereto at once. The temperature was slowly raised up to 80° C., and the resulting mixed solution was stirred overnight. The mixed solution thus obtained was cooled to room temperature, and excess water was poured into the mixture to precipitate a solid product. 50 ml of ethyl acetate was added to the mixed solution which was then stirred. A solid product obtained by filtration was washed with 50 ml of ethyl acetate, and a resulting product obtained therefrom was dried without further purification, thereby obtaining 30 g (purity of 99.69%) of Intermediate EH2(1).

Synthesis of Compound EH2

16 g (40 mmol, 1 eq) of Intermediate EH2(1), 22.2 g (60 mmol, 1.5 eq) of Compound I-3, 16.8 g (120 mmol, 3 eq) of potassium carbonate ($K_2CO_3$), and 2.2 g (2 mmol, 0.05 eq) of $Pd(PPh_3)_4$ were added to a mixed solution of 300 ml of tetrahydrofuran (THF) and 75 ml of water, and the resulting mixed solution was stirred at a temperature of 85° C. overnight (by using a pressure reactor). The mixed solution thus obtained was cooled to room temperature, and the reaction mixture was extracted with ethyl acetate. The resulting organic layer was dried by using $MgSO_4$, filtered, and concentrated in vacuo to remove the solvent. A resulting product obtained therefrom was separated and purified by silica gel column chromatography, thereby obtaining 13 g (purity of 99.90% by LC-MS) of Compound EH2.

LC-Mass Cal.: 559.18 g/mol, Measured.: M+1=560.18 g/mol

Synthesis Example 3

Synthesis of Compound EH14

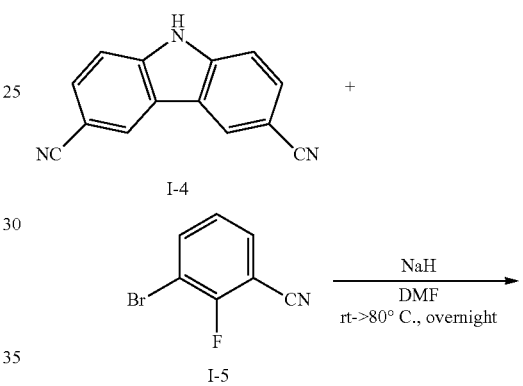

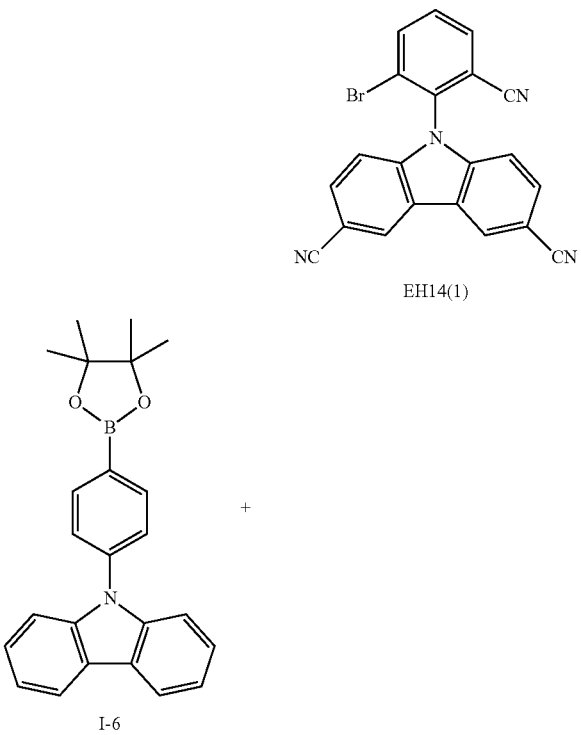

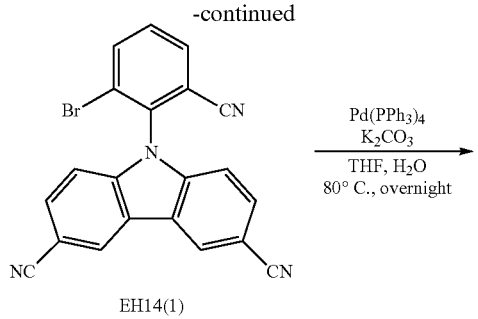

EH14(1)

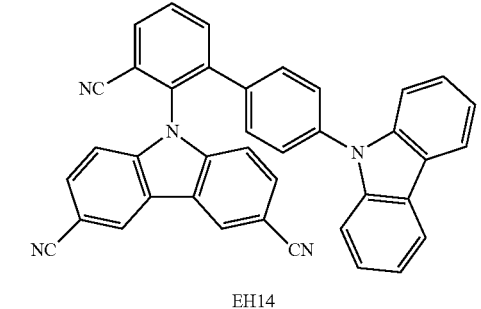

EH14

Synthesis of Intermediate EH14(1)

In a 500 ml round-bottom flask in a water bath at room temperature, 8.2 g (38 mmol) of 3,6-dicyanide carbazole (Compound I-4) was mixed with 150 ml of N,N-dimethylformamide (DMF), and 1.5 g (38 mmol, 1 eq) of 60 wt % sodium hydride (NaH) in mineral oil was slowly added to the mixed solution at room temperature (resulting in the production of hydrogen). Here, 100 ml of N,N-dimethylformamide (DMF) was used to wash out the solid products attached to a container wall. Afterwards, the mixed solution containing the washed solid products was stirred for 10 minutes at room temperature, and 9.1 g (45 mmol, ~1.2 eq) of Compound I-5 was added thereto at once. The temperature was slowly raised up to 80° C., and the resulting mixed solution was stirred overnight. The mixed solution thus obtained was cooled to room temperature, and excess water was poured into the mixture to precipitate a solid product. 50 ml of ethyl acetate was added to the mixed solution which was then stirred. A solid product obtained by filtration was washed with 50 ml of ethyl acetate, and a resulting product obtained therefrom was dried without further purification, thereby obtaining 7.2 g (purity of 99.56% by LC-MS) of Intermediate EH14(1).

Synthesis of Compound EH14

7.1 g (18 mmol, 1 eq) of Intermediate EH14(1), 13.2 g (36 mmol, 2 eq) of Compound I-6, 7.4 g (54 mmol, 3 eq) of potassium carbonate ($K_2CO_3$), and 1.0 g (0.9 mmol, 0.05 eq) of $Pd(PPh_3)_4$ were added to a mixed solution of 50 ml of tetrahydrofuran (THF) and 25 ml of water, and the resulting mixed solution was stirred at a temperature of 85° C. overnight (by using a pressure reactor). The mixed solution thus obtained was cooled to room temperature, and the reaction mixture was extracted with ethyl acetate. The resulting organic layer was dried by using $MgSO_4$, filtered, and concentrated in vacuum to remove the solvent. A resulting product obtained therefrom was separated and purified by silica gel column chromatography, thereby obtaining 3.4 g (purity of 99.96% by LC-MS) of Compound EH14.

LC-Mass Cal.: 559.18 g/mol, Measured.: M+1=560.18 g/mol

Evaluation Example 1

Measurement of Dipole Moment

The electrostatic potential fitting (ESP) charge of each atom of Compounds EH1, EH2, EH14, and A to C and the distance between atoms were obtained by using a Density Functional Theory (DFT) method of a Jaguar program (that is structurally optimized at a level of B3LYP, 6-31G (d,p), and then, the dipole moment of the relevant compounds. The results are shown in Table 1.

TABLE 1

| Compound No. | Dipole moment (debye) |
| --- | --- |
| EH1 | 9.89 |
| EH2 | 12.66 |
| EH14 | 11.05 |
| A (DPEOP) | 8.05 |
| B | 5.30 |
| C | 3.40 |

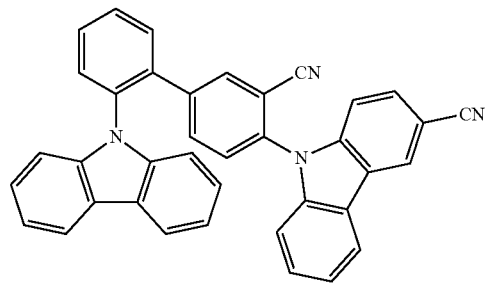

EH1

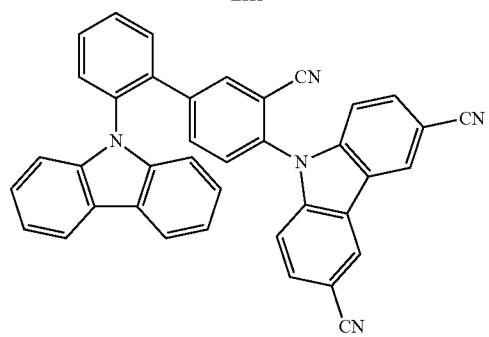

EH2

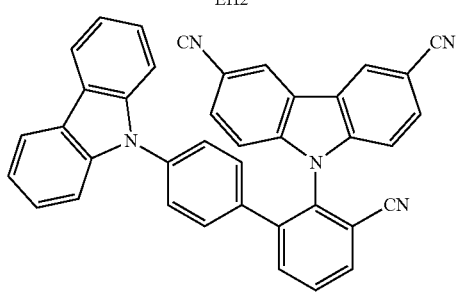

EH14

-continued

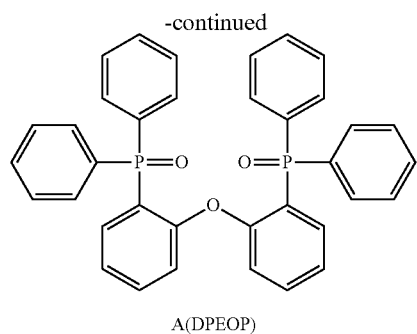

A(DPEOP)

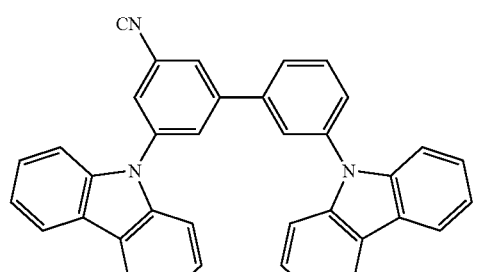

B

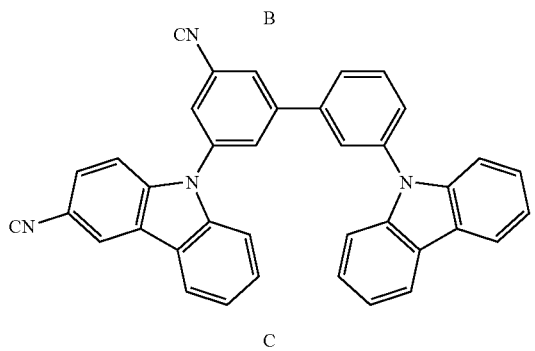

C

Evaluation Example 2

Evaluation of Maximum Emission Wavelength and Ratio of Delayed Fluorescence Components (1) Film Preparation A quartz substrate washed with chloroform and pure water was prepared, and then, Compound EH1 and Compound TD1 were vacuum-(co)-deposited at a volume ratio of 85:15 on the quartz substrate at a vacuum degree of $10^{-7}$ torr, thereby preparing a film having a thickness of 50 nm.

(2) Evaluation of Maximum Emission Wavelength

A photoluminescence (PL) spectrum of the film prepared according to the description above was measured by using an ISC PC1 spectrofluorometer equipped with a xenon lamp, and based on the PL spectrum, a maximum emission wavelength (peak emission wavelength) of the emission from the film was evaluated.

(3) Evaluation of Ratio of Delayed Fluorescence Components

A PL spectrum of the film prepared according to the description above was evaluated at room temperature by using a PicoQuant TRPL measurement system FluoTime 300 and a PicoQuant pumping source PLS340 (excitation wavelength=340 nm, spectral width=20 nm), a wavelength of a main peak of the spectrum was determined, and PLS340 repeatedly measured the number of photons emitted from the film at the wavelength of the main peak due to a photon pulse (pulse width=500 ps) applied to the film according to time based on time-correlated single photon counting (TCSPC), thereby obtaining a sufficiently fittable TRPL curve. $T_{decay}$(Ex) (decay time) of the film was obtained by fitting two or more exponential decay functions to the result obtained therefrom. The function used for fitting is expressed by Equation 1, and the greatest value of $T_{decay}$ obtained from each exponential decay function used for fitting was taken as $T_{decay}$(Ex), whereas the remaining $T_{decay}$ values were used to determine the lifetime of the decay of normal fluorescence. At this time, a baseline or background signal curve was obtained by repeating the same measurement once more for the same measurement time as the measurement time for obtaining the TRPL curve in a dark state (a state in which a pumping signal applied to the predetermined film was blocked), and the baseline or background signal curve was used for fitting as a baseline.

Next, by calculating the ratio of the integral value of the total luminescence intensity of time to the value obtained by integrating the exponential decay curve (intensity change with time) determined by $T_{decay}$(Ex) over time, the ratio of delayed fluorescence components to the total luminescence components was evaluated.

$$f(t) = \sum_{i=1}^{n} A_i \exp(-t/T_{decay,i})$$ Equation 1

(4) Compilation of Table 2

Compounds listed in Table 2 were used in a volume ratio of 85:15 in the film preparation according to step (1) to form a film. Then, steps (2) and (3) were repeated to evaluate the maximum emission wavelength of each film and the ratio of the delayed fluorescence components, and the results are summarized in Table 2.

TABLE 2

| Film composition | Maximum emission wavelength ($\lambda_{max}$) (nm) | Ratio of delayed fluorescence components to total luminescence components (%) |
|---|---|---|
| EH1:TD1 | 465 | 65.3 |
| EH2:TD1 | 467 | 37.8 |
| EH14:TD1 | 475 | 61.3 |
| A (DPEOP):TD1 | 470 | 58.8 |
| B:TD1 | 457 | 10.3 |
| C:TD1 | 460 | 10.4 |
| EH1:TD2 | 450 | 22.8 |
| EH2:TD2 | 452 | 14.0 |
| A (DPEOP):TD2 | 459 | 81.3 |
| B:TD2 | 447 | 6.1 |
| C:TD2 | 445 | 2.5 |

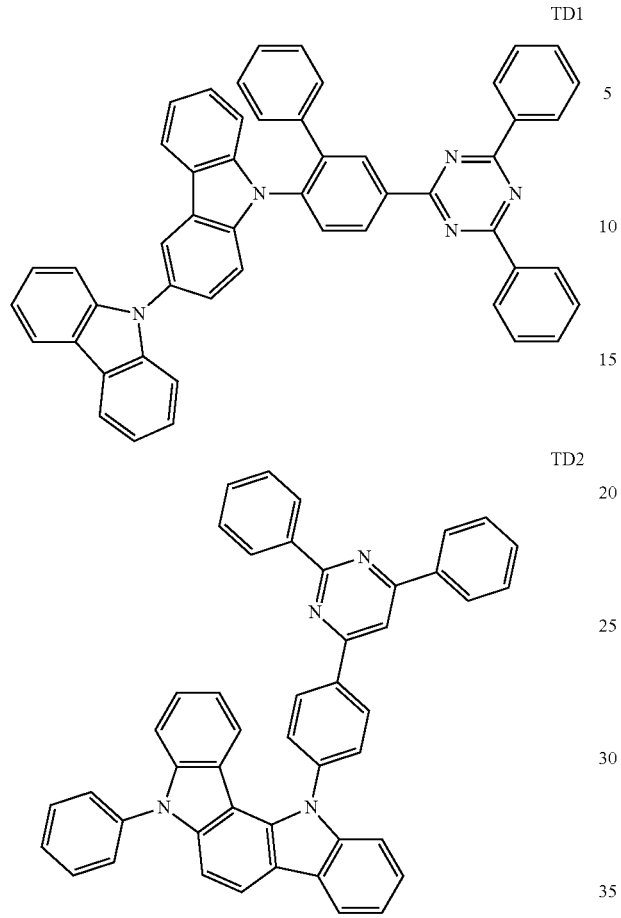

TD1

TD2

Referring to Table 2, it was confirmed that the films each including Compounds EH1, EH2, and EH14 had a higher ratio of delayed fluorescence components to total luminescence components than the films each including Compounds A and B.

Example 1-1

A glass substrate on which an indium tin oxide (ITO) electrode (also referred to as a first electrode or an anode) was formed to a thickness of 1,500 Å was washed by using distilled water and ultrasonic waves. When the washing with distilled water was completed, sonification washing was performed using a solvent, such as isopropyl alcohol, acetone, or methanol. The washed substrate was dried and then transferred to a plasma washer, and the resultant substrate was washed with oxygen plasma for 5 minutes and then, transferred to a vacuum depositing device.

Compound HT3 and Compound HT-D2 were co-deposited on the ITO electrode on the glass substrate to form a hole injection layer having a thickness of 100 Å. Then, Compound HT3 was deposited on the hole injection layer to form a hole transport layer having a thickness of 1,350 Å, and mCP was deposited on the hole transport layer to form an electron blocking layer having a thickness of 100 Å, thereby forming a hole transport region.

The host and the delayed fluorescence emitter were co-deposited at a volume ratio of 85:15 on the hole transport region to form an emission layer having a thickness of 300 Å. The configurations of the host and the delayed fluorescence emitter are provided in Table 3.

Compound BCP was vacuum-deposited on the emission layer to form a hole blocking layer having a thickness of 100 Å, Compound ET3 and Liq were vacuum deposited together on the hole blocking layer to form an electron transport layer having a thickness of 300 Å, and then, Liq was deposited on the electron transport layer to form an electron injection layer having a thickness of 10 Å, and an Al second electrode (cathode) having a thickness of 1,000 Å was formed on the electron injection layer to complete the manufacturing of an organic light-emitting device.

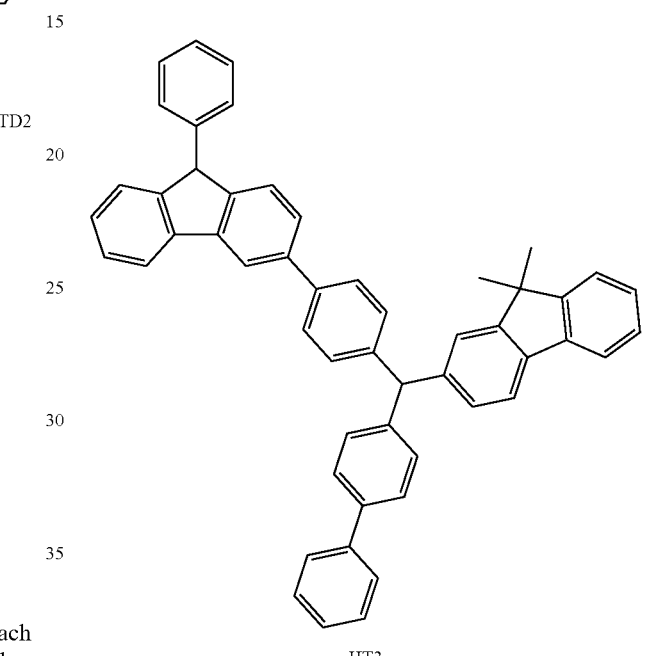

HT3

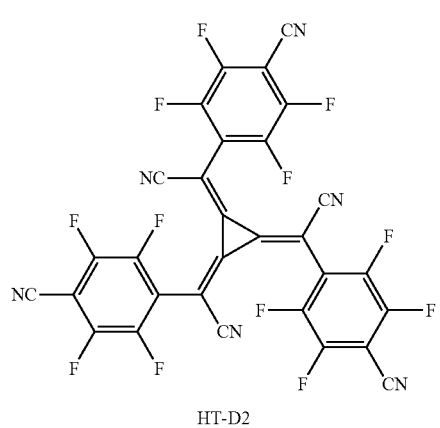

HT-D2

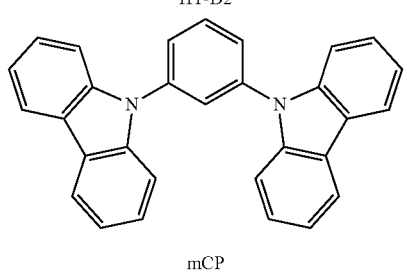

mCP

-continued

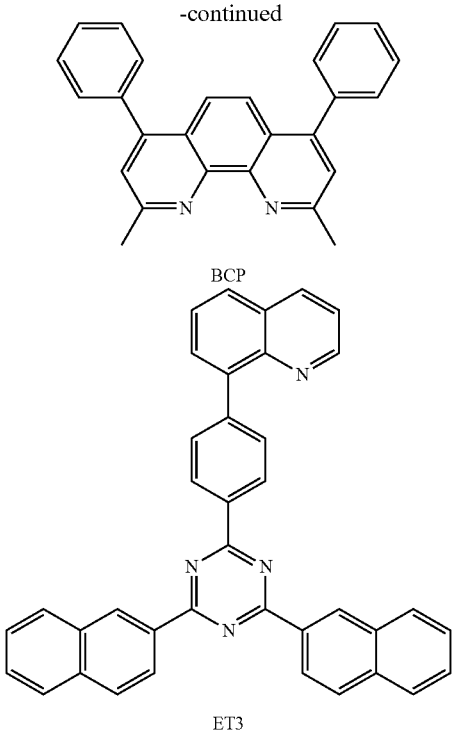

BCP

ET3

Examples 1-1 to 1-3, Comparative Examples 1-A to 1-D, Examples 2-1 and 2-2, Comparative Example 2-A to 2-C, Example 3-1, and Comparative Example 3-C Organic light-emitting devices were manufactured in the same manner as in Example 1-1, except that the configuration of the emission layer was changed to the configurations provided in Tables 3 to 6.

Evaluation Example 3

Evaluation of Data About Organic Light-Emitting Devices

For each of the organic light-emitting devices of Examples 1-1 to 1-3, Comparative Examples 1-A to 1-D, Examples 2-1 and 2-2, Comparative Examples 2-A to 2-C, Example 3-1, and Comparative Example 3-C, CIEy coordinates, an external quantum efficiency (EQE) at 500 cd/m$^2$, a maximum emission wavelength ($\lambda_{max}$, nm), and/or a lifespan ($T_{80}$) were measured by using a current-voltage meter (KEITHLEY 2400) and a luminance meter (MINOLTA Cs-1000A), and the results are summarized in Tables 3 to 6. Here, the lifespan ($T_{80}$, at 500cd/m$^2$) data indicate an amount of time (hr) that lapsed when luminance was 80% of initial luminance (100%).

TABLE 3

| No. | Host | Delayed fluorescence emitter | CIEy | EQE at 500 cd/m$^2$ (%) | Maximum emission wavelength ($\lambda_{max}$) (nm) | Lifespan ($T_{80}$) at 500 cd/m$^2$ (hr) |
|---|---|---|---|---|---|---|
| Example 1-1 | EH1 | TD1 | 0.272 | 8.0 | 470 | 12.55 |
| Example 1-2 | EH2 | TD1 | 0.310 | 8.9 | 475 | 11.46 |
| Comparative Example 1-A | A | TD1 | 0.294 | 9.7 | 475 | 0.13 |
| Comparative Example 1-B | B | TD1 | 0.179 | 6.0 | 453 | 7.27 |
| Comparative Example 1-D | D | TD1 | 0.254 | 8.8 | 466 | 7.83 |

TABLE 4

| No. | Host | Delayed fluorescence emitter | CIEy | EQE at 500 cd/m$^2$ (%) | Maximum emission wavelength ($\lambda_{max}$) (nm) |
|---|---|---|---|---|---|
| Example 1-3 | EH14 | TD1 | 0.348 | 11.1 | 484 |
| Comparative Example 1-C | C | TD1 | 0.231 | 7.3 | 461 |

TABLE 5

| No. | Host | Delayed fluorescence emitter | CIEy | EQE at 500 cd/m$^2$ (%) | Maximum emission wavelength ($\lambda_{max}$) (nm) | Lifespan ($T_{80}$) at 500 cd/m$^2$ (hr) |
|---|---|---|---|---|---|---|
| Example 2-1 | EH1 | TD2 | 0.195 | 3.9 | 448 | 3.25 |
| Example 2-2 | EH2 | TD2 | 0.213 | 3.7 | 454 | 1.93 |
| Comparative Example 2-A | A | TD2 | 0.230 | 5.7 | 458 | 0.10 |
| Comparative Example 2-B | B | TD2 | 0.117 | 3.8 | 452 | 1.03 |
| Comparative Example 2-C | C | TD2 | 0.131 | 2.9 | 444 | 1.45 |

TABLE 6

| | Host | | | | | | | |
|---|---|---|---|---|---|---|---|---|
| No. | First material | Second material | Volume ratio of first material and second material | Delayed fluorescence emitter | CIEy | EQE at 500 cd/m$^2$ (%) | Maximum emission wavelength ($\lambda_{max}$) (nm) | Lifespan ($T_{80}$) at 500 cd/m$^2$ (hr) |
| Example 3-1 | H19 | EH14 | 1:9 | TD1 | 0.340 | 10.4 | 480 | 28.60 |
| Comparative Example 3-C | H19 | C | 1:9 | TD1 | 0.235 | 7.0 | 461 | 20.94 |

EH1
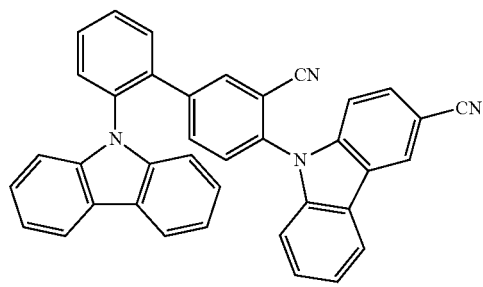
EH2
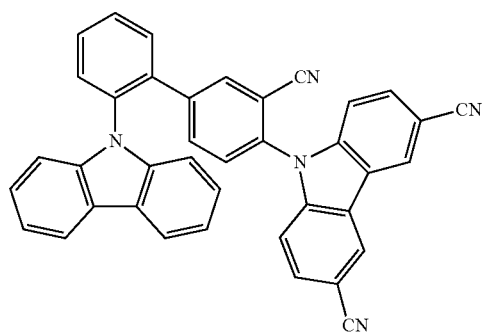
EH14
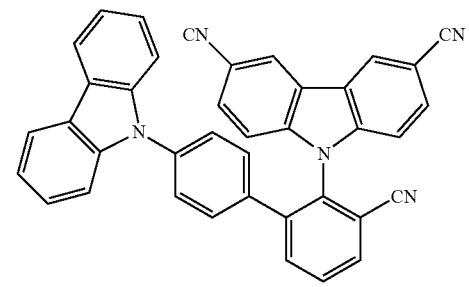
A(DPEOP)
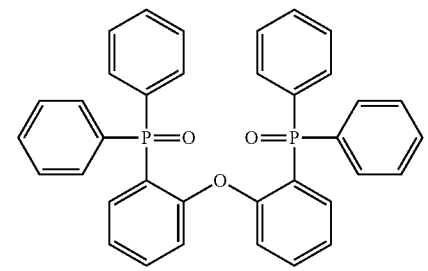
B
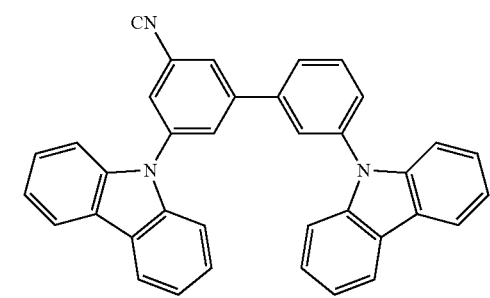
C
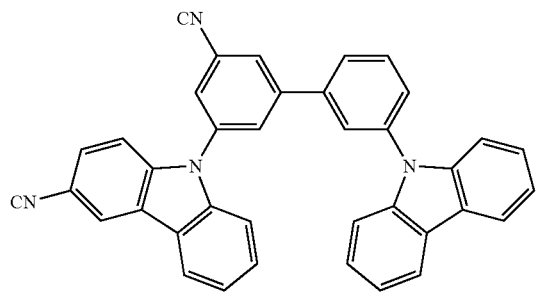
D
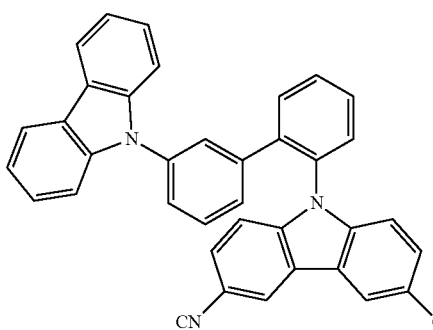
H19
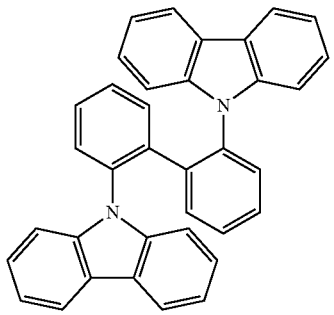
TD1
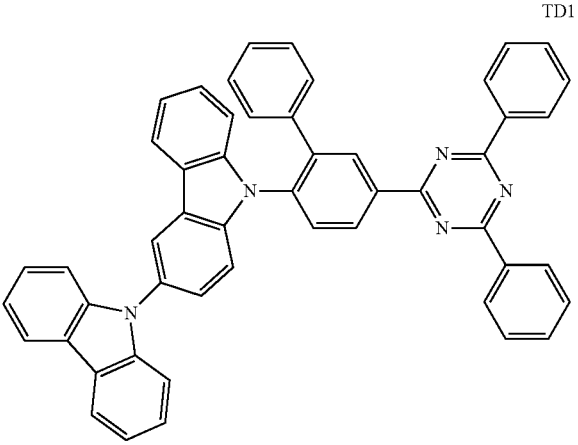

-continued

TD2

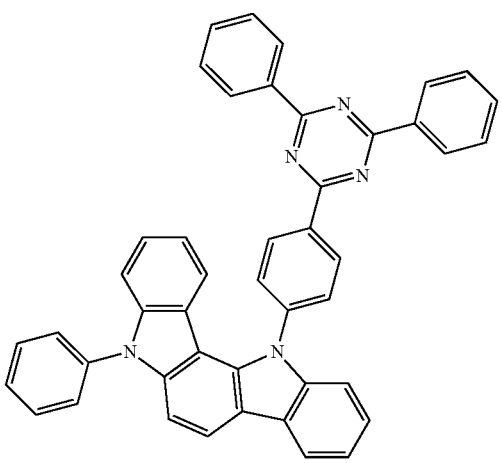

Accordingly, 1) referring to Table 3, it was confirmed that the organic light-emitting devices of Examples 1-1 and 1-2 had improved lifespan compared to the organic light-emitting devices of Comparative Examples 1-A and 1-D, and had improved EQEs and lifespans compared to the organic light-emitting device of Comparative Example 1-B;

2) referring to Table 4, it was confirmed that the organic light-emitting device of Example 1-3 had a better EQE than the organic light-emitting device of Comparative Example 1-C;

3) referring to Table 5, it was confirmed that the organic light-emitting devices of Examples 2-1 and 2-2 had better lifespans than the organic light-emitting devices of Comparative Examples 2-A and 2-B, and had improved EQEs and lifespans than the organic light-emitting device of Comparative Example 2-C; and 4) referring to Table 6, it was confirmed that the organic light-emitting device of Example 3-1 had an improved EQE and lifespan than the organic light-emitting device of Comparative Example 3-C.

Here, as shown in Table 2, the ratio of the delayed fluorescence components to the total luminescence components (in film) in Compound A was high. In this regard, as shown in Tables 3 to 5, the organic light-emitting devices of Comparative Examples 1-A and 2-A each including Compound A was found to have poor lifespan data, whereas the organic light-emitting devices of Examples 1-1 to 1-3, 2-1, 2-2, and 3-1 each emitted delayed fluorescence with a high efficiency and also simultaneously had a long lifespan.

According to the one or more embodiments, the organic light-emitting device may emit delayed fluorescence with a high efficiency and also simultaneously have a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An organic light-emitting device comprising:
a first electrode;
a second electrode facing the first electrode; and
an emission layer disposed between the first electrode and the second electrode,
wherein the emission layer comprises a host and a thermally activated delayed fluorescence emitter,
wherein the emission layer does not comprise a transition metal-containing organometallic compound, and
the host comprises a compound represented by Formula 1, a compound represented by Formula 2, or a combination thereof:

Formula 1

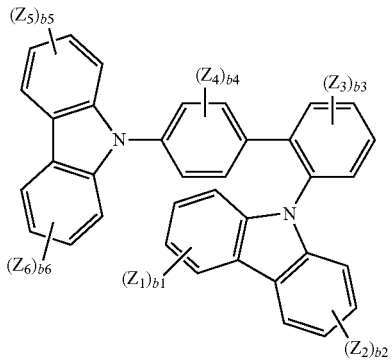

Formula 2

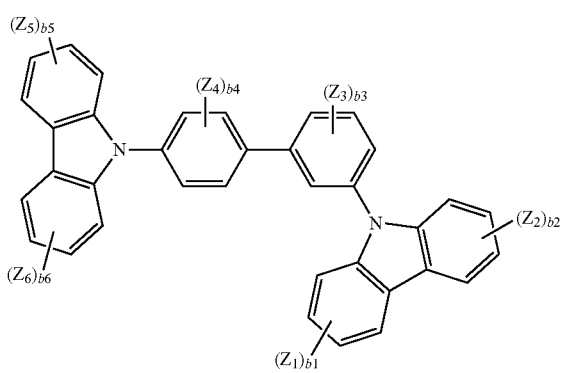

wherein, in Formulae 1 and 2,
$Z_1$ to $Z_6$ are each independently:
hydrogen, deuterium, —F, —Cl, —Br, —I, or a cyano group; or
a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof,
b1 to b6 are each independently 1, 2, 3, or 4, and
in Formulae 1 and 2, at least one of, i) $Z_1$ in the number of b1, ii) $Z_2$ in the number of b2, iii) $Z_3$ in the number of b3, iv) $Z_4$ in the number of b4, v) $Z_5$ in the number of b5, and vi) $R_6$ in the number of b6 is a cyano group.

2. The organic light-emitting device of claim 1, wherein $Z_1$ to $Z_6$ are each independently:
hydrogen, deuterium, or a cyano group; or
a $C_1$-$C_{10}$ alkyl group, a phenyl group, a biphenyl group, a terphenyl group, a dibenzofuranyl group, or a dibenzothiophenyl group, each unsubstituted or substituted with deuterium, a cyano group, a $C_1$-$C_{10}$ alkyl group, a phenyl group, a biphenyl group, or any combination thereof, and b1 to b6 are each independently 0, 1, or 2.

3. The organic light-emitting device of claim 1, wherein the number of a cyano group included in the compound represented by Formula 1 and the number of a cyano group included in the compound represented by Formula 2 are each independently 1, 2, 3, or 4.

4. The organic light-emitting device of claim 1, wherein in Formulae 1 and 2, at least one of, i) $Z_1$ in the number of b1 and ii) $Z_2$ in the number of b2 is a cyano group, at least one of, i) $Z_3$ in the number of b3 and ii) $Z_4$ in the number of b4 is a cyano group, at least one of, i) $Z_5$ in the number of b5 and ii) $Z_6$ in the number of b6 is a cyano group, at least one of, i) $Z_1$ in the number of b1 and ii) $Z_2$ in the number of b2 is a cyano group, and at least one of, i) $Z_3$ in the number of b3 and ii) $Z_4$ in the number of b4 is a cyano group, at least one of, i) $Z_1$ in the number of b1 and ii) $Z_2$ in the number of b2 is a cyano group, and at least one of, i) $Z_5$ in the number of b5 and ii) $Z_6$ in the number of b6 is a cyano group, at least one of, i) $Z_3$ in the number of b3 and ii) $Z_4$ in the number of b4 is a cyano group, and at least one of, i) $Z_5$ in the number of b5 and ii) $Z_6$ in the number of b6 is a cyano group, or at least one of, i) $Z_1$ in the number of b1 and ii) $Z_2$ in the number of b2 is a cyano group, at least one of, i) $Z_3$ in the number of b3 and ii) $Z_4$ in the number of b4 is a cyano group, and at least one of, i) $Z_5$ in the number of b5 and ii) $Z_6$ in the number of b6 is a cyano group.

5. The organic light-emitting device of claim 1, wherein a group represented by

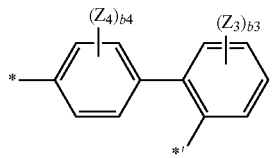

in Formula 1 is a group represented by one of Formulae PO1 to PO25, a group represented by

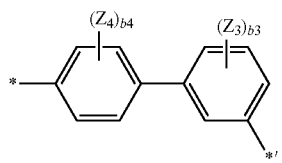

in Formula 2 is a group represented by one of Formulae PM1 to PM25:

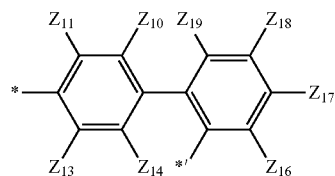
PO1

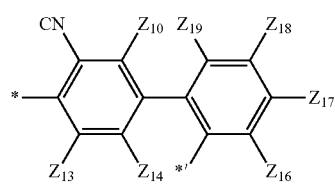
PO2

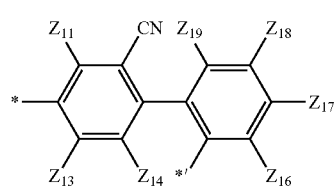
PO3

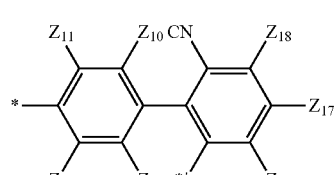
PO4

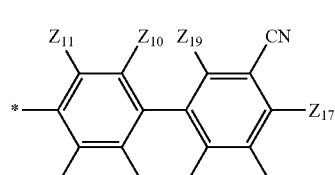
PO5

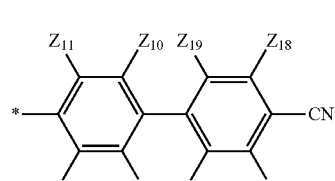
PO6

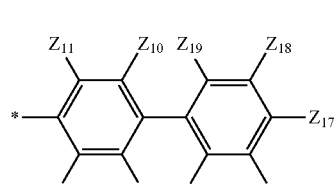
PO7

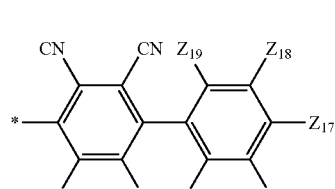
PO8

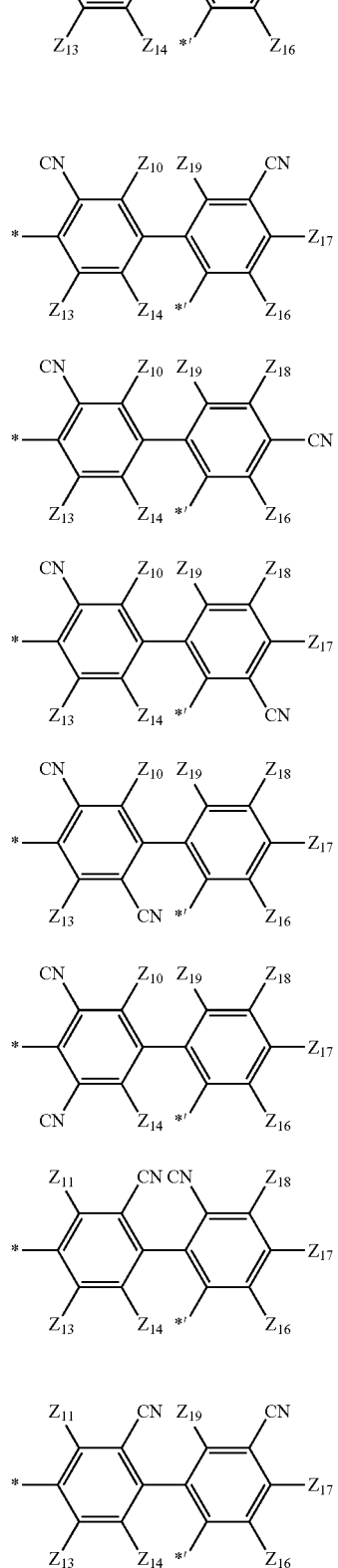

PO25
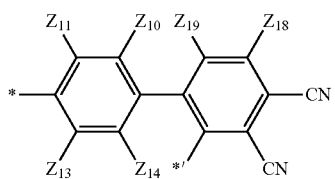
PM1
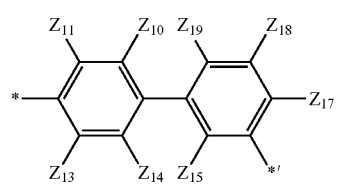
PM2
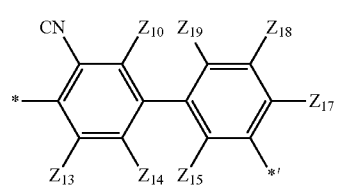
PM3
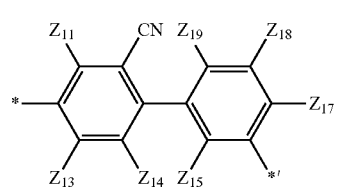
PM4
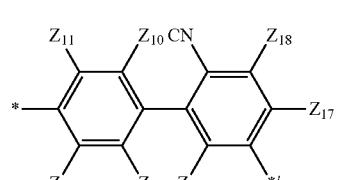
PM5
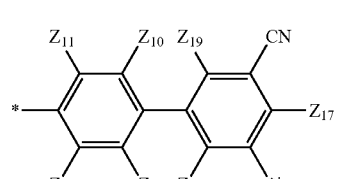
PM6
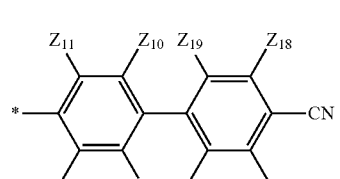
PM7
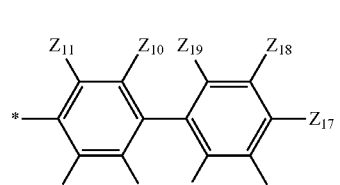
PM8
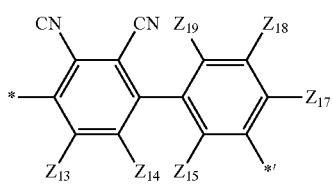
PM9
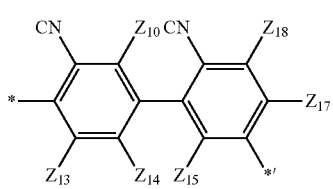
PM10
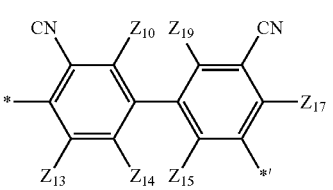
PM11
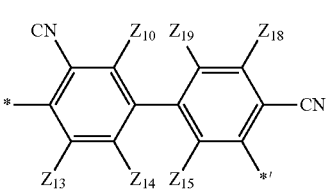
PM12
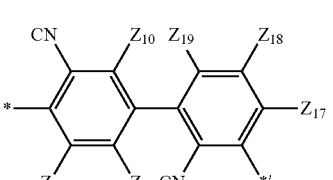
PM13
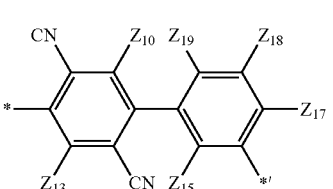
PM14
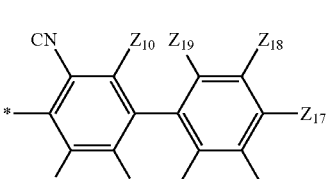
PM15
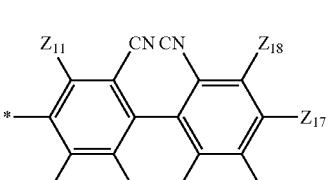

-continued

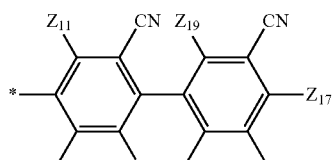
PM16

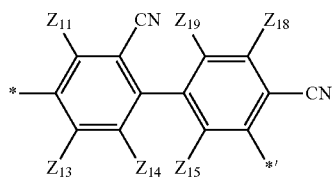
PM17

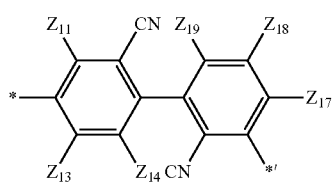
PM18

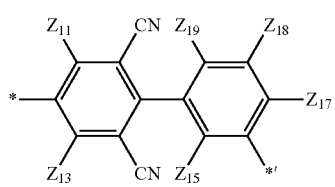
PM19

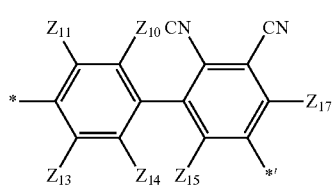
PM20

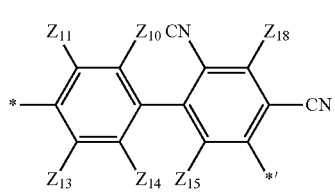
PM21

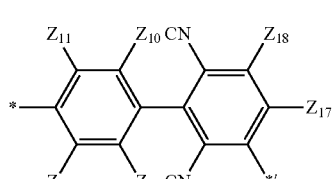
PM22

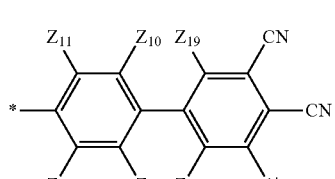
PM23

-continued

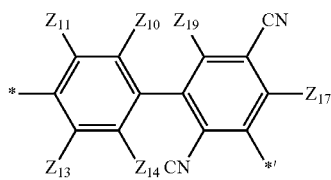
PM24

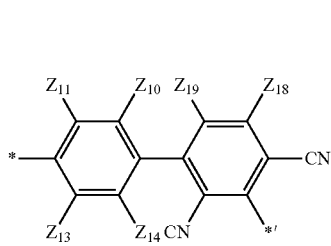
PM25 wherein, in Formulae PO1 to PO25 and PM1 to PM25, $Z_{10}$ to $Z_{19}$ are each independently:

hydrogen, deuterium, —F, —Cl, —Br, —I, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof, and

* and *' each indicate a binding site to a neighboring nitrogen atom.

6. The organic light-emitting device of claim 1, wherein a group represented by

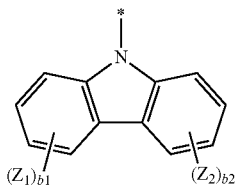

in Formulae 1 and 2 is a group represented by one of Formulae A1-1 to A1-3, a group represented by

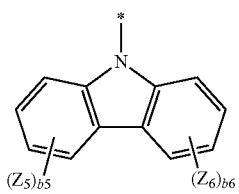

in Formulae 1 and 2 is a group represented by one of Formulae A2-1 to A2-3:

A1-1
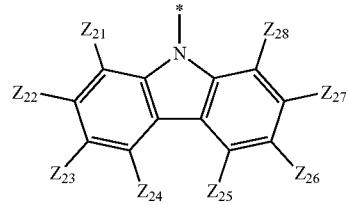

A1-2
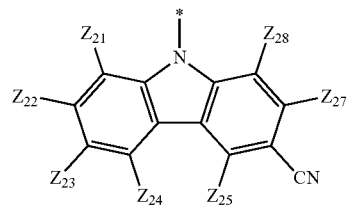

A1-3
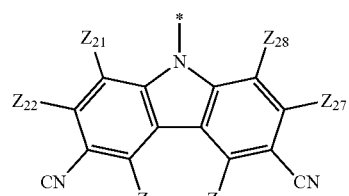

A2-1
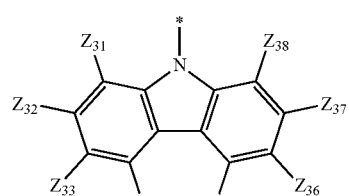

A2-2
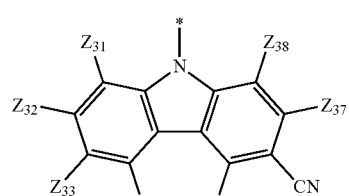

A2-3
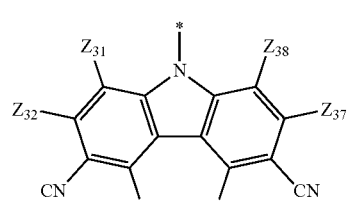

wherein, in Formulae A1-1 to A1-3 and A2-1 to A2-3, $Z_{21}$ to $Z_{28}$ and $Z_{31}$ to $Z_{38}$ are each independently:
hydrogen, deuterium, —F, —Cl, —Br, —I, or a cyano group; or
a $C_1$-$C_{20}$ alkyl group, a phenyl group, a biphenyl group, a terphenyl group, a dibenzofuranyl group, or a dibenzothiophenyl group, each unsubstituted or substituted with deuterium, —F, —Cl, —Br, —I, a cyano group, a $C_1$-$C_{20}$ alkyl group, a phenyl group, a biphenyl group, or any combination thereof, and

* and *' each indicate a binding site to a neighboring atom.

7. The organic light-emitting device of claim 1, wherein the host comprises at least one of Compounds EH1 to EH15:

EH1
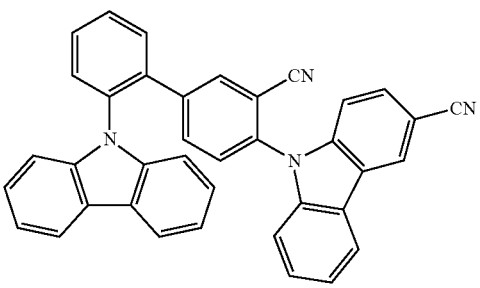

EH2
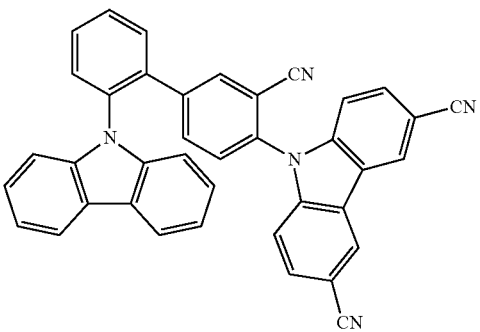

EH3
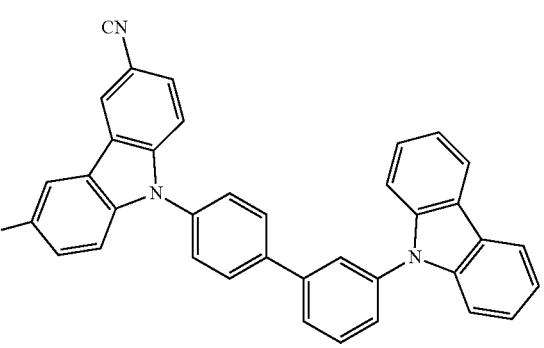

EH4
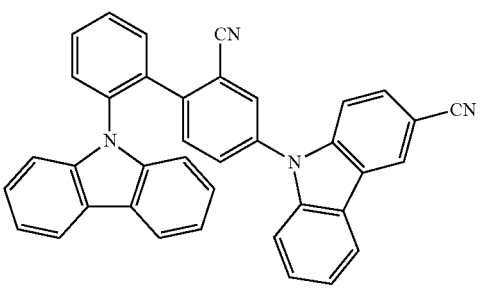

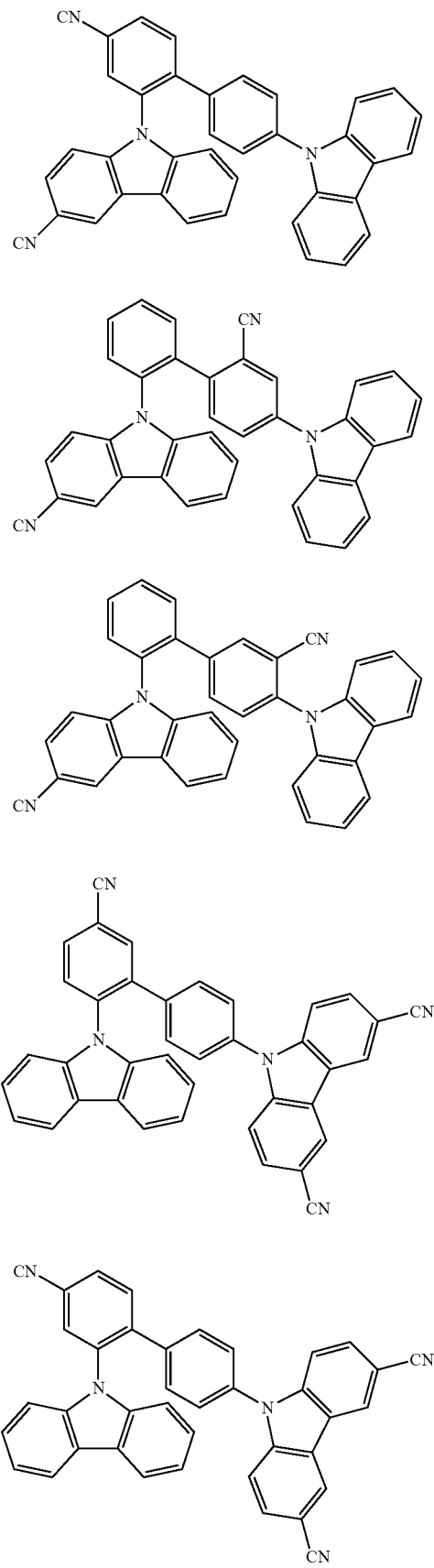
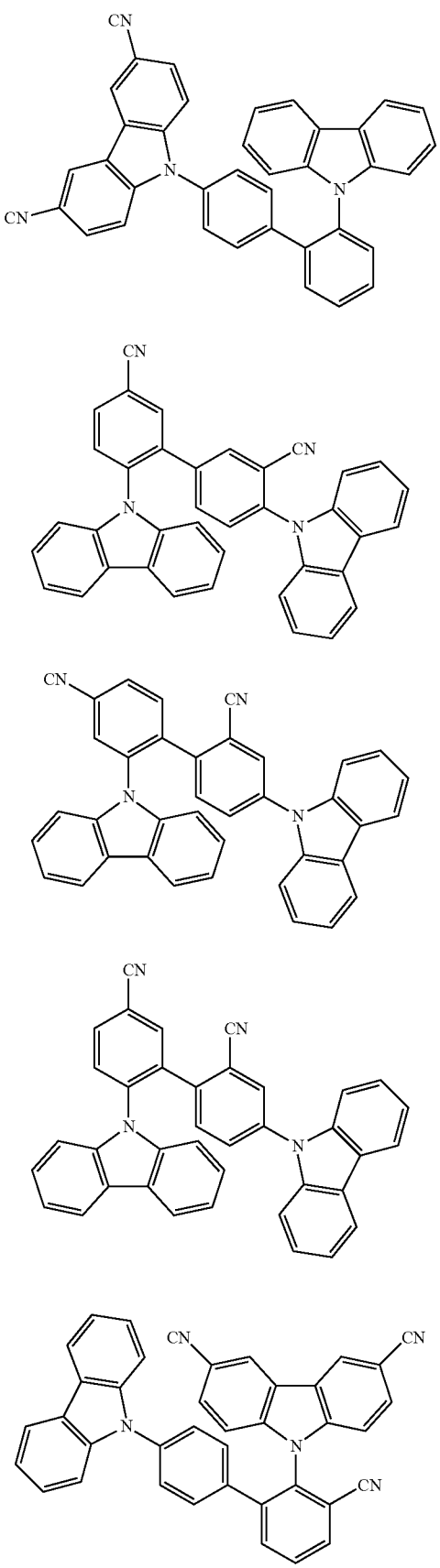

EH15

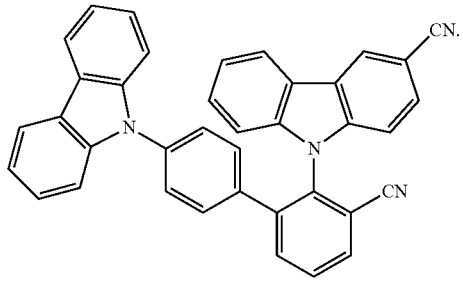

8. The organic light-emitting device of claim 1, wherein the compound represented by Formula 1 and the compound represented by Formula 2 each have a dipole moment of about 6.4 debye or more.

9. The organic light-emitting device of claim 1, wherein a difference between a triplet energy level of the thermally activated delayed fluorescence emitter and a singlet energy level of the thermally activated delayed fluorescence emitter is greater than or equal to about 0 eV to less than or equal to about 0.5 eV, and the triplet energy level and the singlet energy level are each evaluated by using a density functional theory method of a Gaussian program that is structurally optimized at a level of B3LYP/6-31 G(d,p).

10. The organic light-emitting device of claim 1, wherein the thermally activated delayed fluorescence emitter comprises a compound represented by Formula 11:

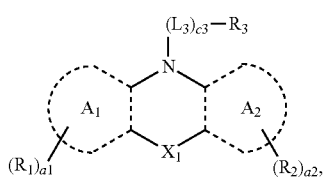

Formula 11 wherein, in Formula 11, $X_1$ is a single bond, N-[$(L_4)_{c4}$-$R_4$], C($R_5$)($R_6$), O, or S, $A_1$ and $A_2$ are each independently a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group, $L_3$ and $L_4$ are each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, c3 and c4 are each independently an integer from 0 to 4, $R_1$ to $R_5$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), a1 and a2 are each independently an integer from 0 to 10, a substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group is:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof;

a $C_1$-$C_{60}$ alkyl group, a $C_2$-$C_{60}$ alkenyl group, a $C_2$-$C_{60}$ alkynyl group, a $C_1$-$C_{60}$ alkoxy group, or a combination thereof, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), or any combination thereof;

—Si($Q_{31}$)($Q_{32}$)($Q_{33}$), —N($Q_{34}$)($Q_{35}$), —B($Q_{36}$)($Q_{37}$), or a combination thereof, and $Q_1$ to $Q_7$, $Q_{11}$ to $Q_{17}$, $Q_{21}$ to $Q_{27}$, and $Q_{31}$ to $Q_{37}$ are each independently hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

11. The organic light-emitting device of claim 10, wherein $R_3$ comprises at least one π electron-depleted nitrogen-containing cyclic group.

12. The organic light-emitting device of claim 10, wherein $R_3$ is:

a group represented by Formula 13(1) or a group represented by Formula 13(2);

a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group; or a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, or an indolocarbazolyl group, each substituted with deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, —Si($Q_{31}$)($Q_{32}$)($Q_{33}$), or any combination thereof, and $Q_{31}$ to $Q_{33}$ are each independently a $C_1$-$C_{10}$ alkyl group, a $C_1$-$C_{10}$ alkoxy group, a phenyl group, a biphenyl group, a terphenyl group, or a naphthyl group:

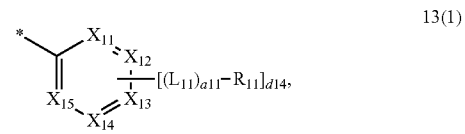

13(1)

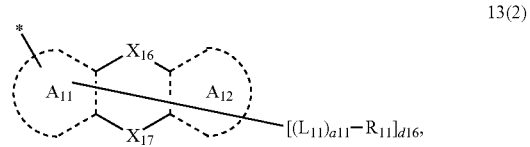

13(2)

wherein, in Formulae 13(1) and 13(2), $X_{11}$ to $X_{15}$ are each independently C or N, wherein at least one of $X_{11}$ to $X_{15}$ is N, $A_{11}$ and $A_{12}$ are each independently a benzene group, a naphthalene group, a pyridine group, a pyrazine group, a pyrimidine group, a pyridazine group, a quinoline group, an isoquinoline group, a quinoxaline group, or a quinazoline group, wherein $A_{11}$, $A_{12}$, or a combination thereof is a pyridine group, a pyrazine group, a pyrimidine group, a pyridazine group, a quinoline group, an isoquinoline group, a quinoxaline group, or a quinazoline group, $X_{16}$ is N-[($L_{12}$)$_{a12}$-$R_{12}$], C($R_{14}$)($R_{15}$), O, or S, $X_{17}$ is a single bond, N-[($L_{13}$)$_{a13}$-$R_{13}$], C($R_{16}$)($R_{17}$), O, or S, d16 is an integer from 0 to 6, d14 is an integer from 0 to 4, and

* indicates a binding site to a neighboring atom.

13. The organic light-emitting device of claim 10, wherein the thermally activated delayed fluorescence emitter comprises a compound represented by one of Formulae 11-1 to 11-7:

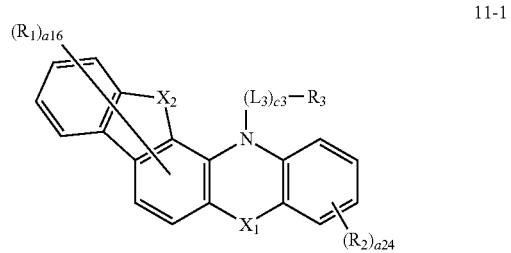

11-1

-continued

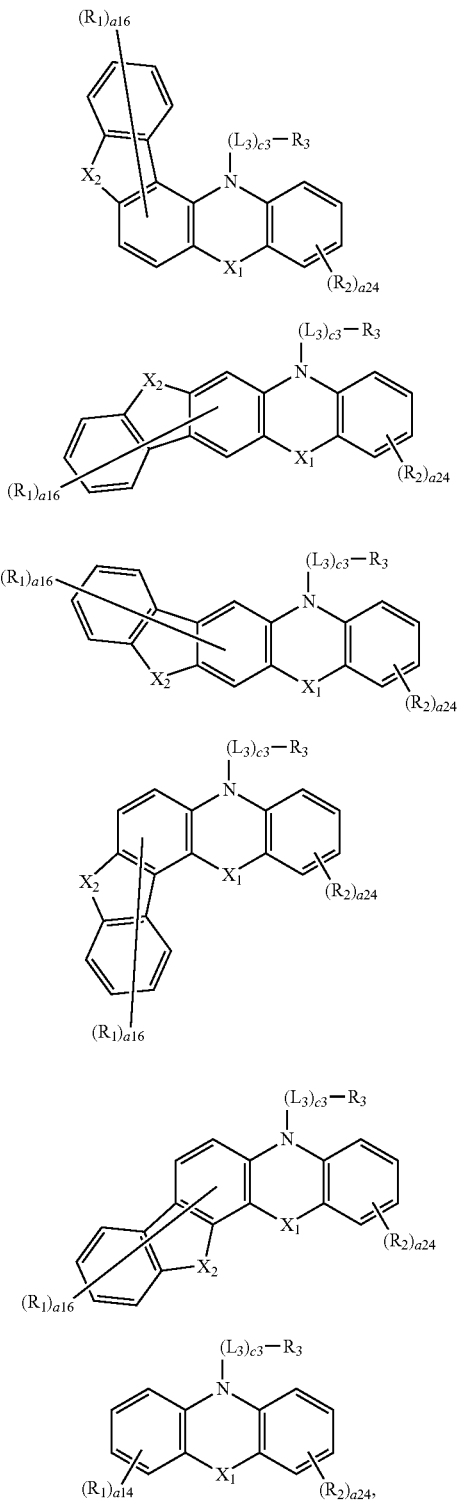

11-2

11-3

11-4

11-5

11-6

11-7 wherein, in Formulae 11-1 to 11-7,
$X_2$ is $N\text{-}[(L_5)_{c5}\text{-}R_7]$, $C(R_8)(R_9)$, O, or S,
$L_5$ and c5 are each independently defined the same as $L_3$ and c3, respectively, in claim 10,
$R_7$ is defined the same as $R_3$ in claim 10,
$R_8$ and $R_9$ are each independently defined the same as $R_5$ and $R_6$, respectively, in claim 10, a16 is an integer from 0 to 6, and
a14 and a24 are each independently an integer from 0 to 4.

14. The organic light-emitting device of claim 1, wherein the light emitted by the thermally activated delayed fluorescence emitter in the emission layer is blue light.

15. The organic light-emitting device of claim 1, wherein an amount of the thermally activated delayed fluorescence emitter is in a range of about 0.01 parts by weight to about 30 parts by weight based on 100 parts by weight of the host.

16. The organic light-emitting device of claim 1, wherein the host comprises a first material and a second material, the first material and the second material are different from each other, and
the second material comprises the compound represented by Formula 1, the compound represented by Formula 2, or a combination thereof.

17. The organic light-emitting device of claim 16, wherein the first material comprises at least one π electron-depleted nitrogen-free cyclic group, and does not comprise an electron transport moiety.

18. The organic light-emitting device of claim 16, wherein the first material comprises a benzene group not including a cyano group and a carbazole group not including a cyano group.

19. The organic light-emitting device of claim 16, wherein the first material comprises a compound represented by Formula H-1(1), a compound represented by Formula H-1(2), a compound represented by Formula H-1(3), or any combination thereof:

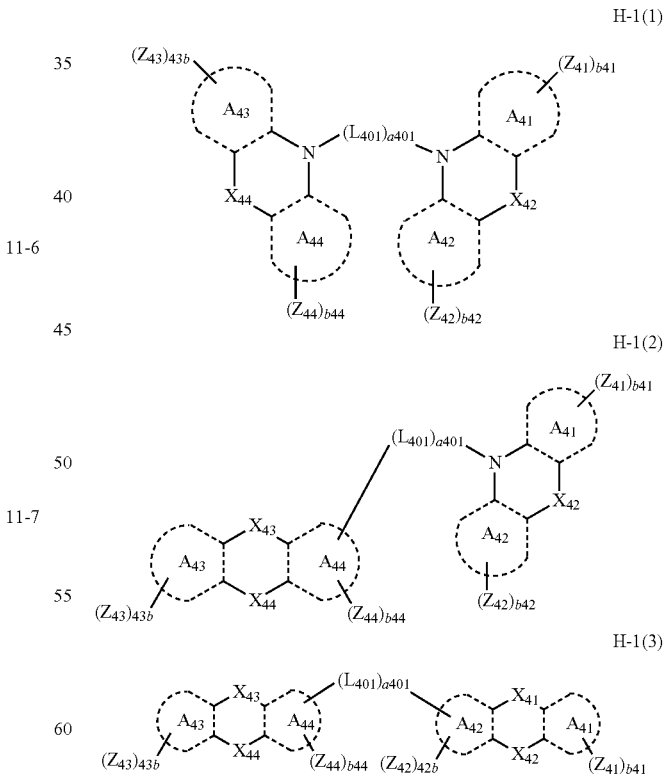

wherein, in Formulae H-1(1) to H-1(3),
ring $A_{41}$ to ring $A_{44}$ are each independently a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group, $X_{41}$ is $N-[(L_{411})_{c411}-Z_{411}]$, $C(Z_{415})(Z_{416})$, O, or S, $X_{42}$ is a single bond, $N-[(L_{412})_{c412}-Z_{412}]$, $C(Z_{417})(Z_{418})$, O, or S, $X_{43}$ is $N-[(L_{413})_{c413}-Z_{413}]$, $C(Z_{419})(Z_{420})$, O, or S, $X_{44}$ is a single bond, $N-[(L_{414})_{c414}-Z_{414}]$, $C(Z_{421})(Z_{422})$, O, or S, $L_{401}$ and $L_{411}$ to $L_{414}$ are each independently:

a single bond; or a π electron-depleted nitrogen-free cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{20}$ alkyl)phenyl group, —$Si(Q_{401})(Q_{402})(Q_{403})$, or any combination thereof, a401 and c411 to c414 are each independently an integer from 1 to 10, wherein, when a401 is two or more, two or more $L_{401}$ are identical to or different from each other, when c411 is two or more, two or more $L_{411}$ are identical to or different from each other, when c412 is two or more, two or more $L_{412}$ are identical to or different from each other, when c413 is two or more, two or more $L_{413}$ are identical to or different from each other, and when c414 is two or more, two or more $L_{414}$ are identical to or different from each other, $Z_{41}$ to $Z_{44}$ and $Z_{411}$ to $Z_{422}$ are each independently:

hydrogen, deuterium, a $C_1$-$C_{20}$ alkyl group, or a $C_1$-$C_{20}$ alkoxy group; or a π electron-depleted nitrogen-free cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, a ($C_1$-$C_{20}$ alkyl)phenyl group, —$Si(Q_{401})(Q_{402})(Q_{403})$, or any combination thereof, b41 to b44 are each independently 1, 2, 3, or 4, and $Q_{401}$ to $Q_{403}$ are each independently hydrogen, deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, or a tetraphenyl group.

\* \* \* \* \*